United States Patent
Vepachedu et al.

(10) Patent No.: US 11,478,467 B2
(45) Date of Patent: Oct. 25, 2022

(54) TARGETED DRUG RESCUE WITH NOVEL COMPOSITIONS, COMBINATIONS, AND METHODS THEREOF

(71) Applicants: Sreenivasarao Vepachedu, Vernon Hills, IL (US); EXCIVA GmbH, Vernon Hills, IL (US)

(72) Inventors: Sreenivasarao Vepachedu, Vernon Hills, IL (US); Hans J Moebius, Wollerau (CH); Anton Bespalov, Heidelberg (DE)

( * ) Notice: Subject to any disclaimer, the term of this patent is extended or adjusted under 35 U.S.C. 154(b) by 0 days.

(21) Appl. No.: 16/672,517

(22) PCT Filed: May 3, 2018

(86) PCT No.: PCT/US2018/030978
§ 371 (c)(1),
(2) Date: Nov. 3, 2019

(87) PCT Pub. No.: WO2018/204713
PCT Pub. Date: Nov. 8, 2018

(65) Prior Publication Data
US 2020/0069674 A1 Mar. 5, 2020

Related U.S. Application Data

(60) Provisional application No. 62/636,171, filed on Feb. 28, 2018, provisional application No. 62/636,099, filed on Feb. 27, 2018, provisional application No. 62/635,554, filed on Feb. 27, 2018, provisional application No. 62/501,696, filed on May 4, 2017.

(30) Foreign Application Priority Data

Aug. 28, 2017 (TW) ................. 106129169

(51) Int. Cl.
| | | |
|---|---|---|
| A61K 31/4748 | (2006.01) | |
| A61K 31/662 | (2006.01) | |
| A61K 31/222 | (2006.01) | |
| A61K 31/225 | (2006.01) | |

(52) U.S. Cl.
CPC ........ *A61K 31/4748* (2013.01); *A61K 31/222* (2013.01); *A61K 31/225* (2013.01); *A61K 31/662* (2013.01)

(58) Field of Classification Search
CPC .. A61K 31/225; A61K 31/222; A61K 31/662; A61K 31/4748
See application file for complete search history.

(56) References Cited

U.S. PATENT DOCUMENTS

| | | | |
|---|---|---|---|
| 4,241,065 A | 12/1980 | Boswel | |
| 6,093,747 A * | 7/2000 | Gacsalyi | A61P 25/22 514/650 |
| 6,207,674 B1 | 3/2001 | Smith | |
| 6,335,371 B1 | 1/2002 | Maki-Ikola | |
| 6,335,372 B1 | 1/2002 | Maki-Ikola | |
| 6,589,996 B2 | 7/2003 | Maki-Ikola | |
| 8,227,484 B2 | 7/2012 | Yakatan | |
| 8,263,125 B2 * | 9/2012 | Vaya | A61K 9/2077 424/469 |
| 9,486,453 B2 | 11/2016 | Javitt | |
| 9,592,288 B2 * | 3/2017 | Schultz | A61K 39/3955 |
| 10,022,355 B2 | 7/2018 | Friedhoff | |
| 11,103,499 B2 * | 8/2021 | Vepachedu | A61P 25/00 |
| 2002/0099098 A1 | 7/2002 | Maki-Ikola | |
| 2002/0132858 A1 | 9/2002 | Maki-Ikola | |

(Continued)

FOREIGN PATENT DOCUMENTS

WO WO2009006194 A1 1/2009

OTHER PUBLICATIONS

Weinbroum et al., "The role of dextromethorphan in pain control", 2000, Can. J. Anaesth., 47(6), pp. 585-596. (DOI: 10.1007/BF03018952) (Year: 2000).*

(Continued)

*Primary Examiner* — My-Chau T. Tran
(74) *Attorney, Agent, or Firm* — Sreenivasarao Vepachedu

(57) ABSTRACT

Compounds of Formula I, pharmaceutically acceptable salts thereof, enantiomers thereof, metabolites thereof, derivatives thereof, prodrugs thereof, acid addition salts thereof, pharmaceutically acceptable salts thereof, or N-oxides thereof; or a combination thereof; processes and intermediates for preparation thereof, compositions thereof, and uses thereof; are provided. Pharmaceutical compositions comprising a compound of Formula I, or enantiomers thereof, metabolites thereof, derivatives thereof, prodrugs thereof, acid addition salts thereof, pharmaceutically acceptable salts thereof, or N-oxides thereof; or a combination thereof; wherein the compound is a double and/or triple agent or ligand for CYP2D6, 5-HT2A, and/or 5HT2C receptors, and/or acetylcholinesterase are provided.

FORMULA I

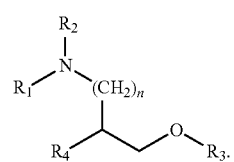

11 Claims, 14 Drawing Sheets

(56) References Cited

U.S. PATENT DOCUMENTS

| | | | |
|---|---|---|---|
| 2002/0156068 | A1 | 10/2002 | Behan |
| 2002/0173505 | A1 | 11/2002 | Skogvall |
| 2003/0032636 | A1 | 2/2003 | Cremers |
| 2004/0082665 | A1 | 4/2004 | Maki-Ikola |
| 2004/0171696 | A1 | 9/2004 | Gacsalyi |
| 2006/0258745 | A1 | 11/2006 | Fekete |
| 2006/0258750 | A1 | 11/2006 | Gacsalyi |
| 2007/0099947 | A1 | 5/2007 | Dean |
| 2007/0105843 | A1 | 5/2007 | Cremers |
| 2007/0244102 | A1 | 10/2007 | Gacsalyi |
| 2009/0124606 | A1 | 5/2009 | Gacsalyi |
| 2009/0176808 | A1 | 7/2009 | Cremers |
| 2010/0004278 | A1 | 1/2010 | Singh |
| 2010/0074955 | A1 | 3/2010 | Buschmann |
| 2019/0046506 | A1 | 2/2019 | Friedhoff |
| 2019/0111047 | A1 | 4/2019 | Siffert |
| 2020/0261442 | A1* | 8/2020 | Vepachedu .......... A61K 31/222 |
| 2021/0228508 | A1* | 7/2021 | Vepachedu ............. A61P 25/28 |

OTHER PUBLICATIONS

Obata et al., "Antinociception in rat by sarpogrelate, a selective 5-HT2A receptor antagonist, is peripheral", 2000, European Journal of Pharmacology, 404(1-2), pp. 95-102. (Year: 2000).*

Laine et al., "Effect of the novel anxiolytic drug deramciclane on cytochrome P450 2D6 activity as measured by desipramine pharmacokinetics", 2004, Eur. J. Clin. Pharmacol., 59(12), pp. 893-898. (DOI 10.1007/s00228-003-0714-z). (Year: 2004).*

Gupta et al., "Salts of Therapeutic Agents: Chemical, Physicochemical, and Biological Considerations", 2018, Molecules, 23(7), pp. 1-15. (doi:10.3390/molecules23071719). (Year: 2018).*

* cited by examiner

FIGURE 2A STAGE 1 ANALYSIS
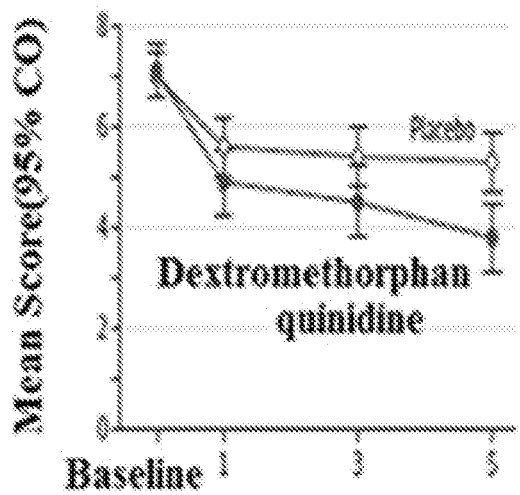
FIGURE 2B STAGE 2 ANALYSIS
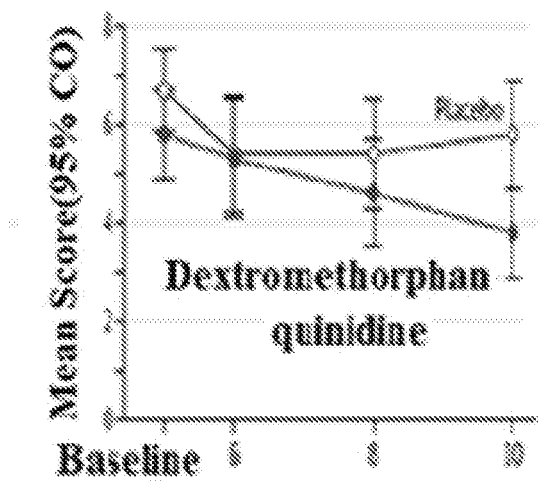
FIGURE 2C STAGE 3 (10 wk) ANALYSIS
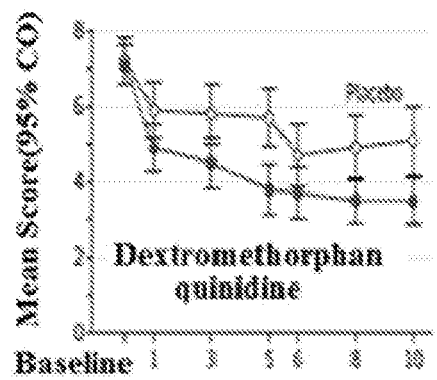

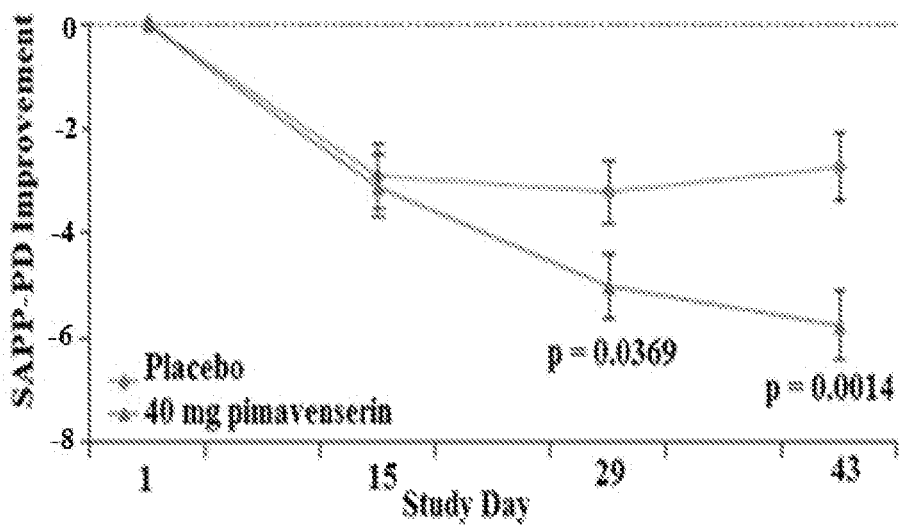
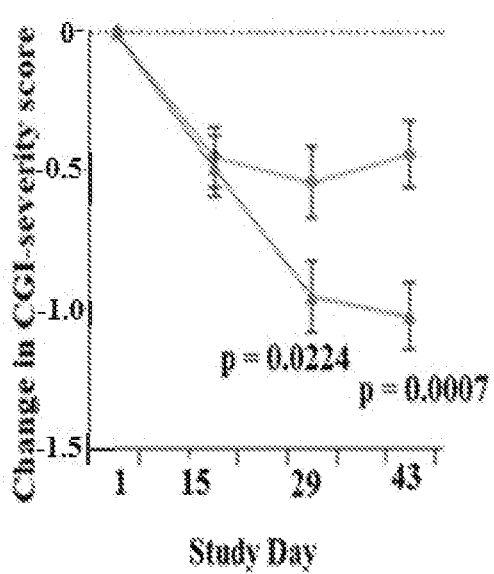
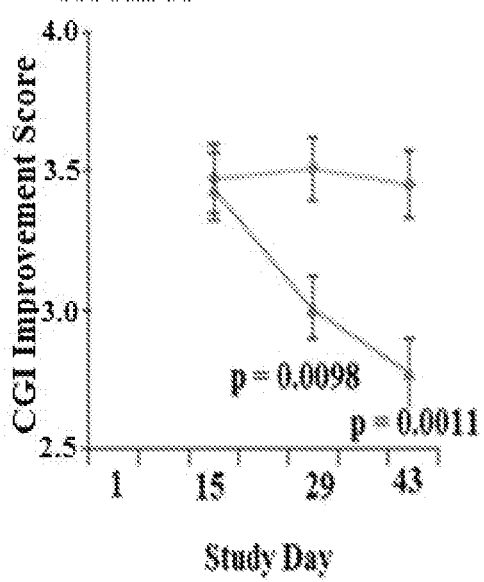

TARGETED DRUG RESCUE WITH NOVEL COMPOSITIONS, COMBINATIONS, AND METHODS THEREOF

TECHNICAL FIELD

This disclosure relates to Targeted Drug Rescue (TDR)™ with novel compositions, combinations, therapeutic formulations, symptomatic and disease-modifying treatments, therapies, kits thereof, and methods thereof.

BACKGROUND

Excess weight changes the body, increasing certain hormones and levels of inflammation that can lead to metabolic disorders, cancer, and brain disorders, including developmental, psychiatric and neurodegenerative diseases, which represent an enormous disease burden, regarding human suffering and economic cost, and causing the rapid rise in healthcare spending. Diseases affecting the brain and central nervous system represent one of the largest global healthcare challenges and greatest medical needs due to the devastating personal and economic consequences for patients, caregivers and society. An estimated 55 million people worldwide suffer from neurodegenerative diseases with no currently approved disease-modifying therapies available. As modern therapeutic interventions increase life expectancy, the number of patients suffering from these diseases is expected to double every 20 years. Just nine of the most common neurological diseases such as Alzheimer's disease and other dementias, low back pain, stroke, traumatic brain injury, migraine, epilepsy, multiple sclerosis, spinal cord injury, and Parkinson's disease is staggering, totaling $789 billion in 2014 dollars, currently estimated at $818 billion, and estimated to be more than $1 trillion by 2030. Total European 2010 cost of brain disorders was €798 billion, of which direct health care cost 37%, direct non-medical cost 23%, and indirect cost 40% (Oleson et al., The economic cost of brain disorders in Europe, EJN, 19, 1, 155-162 (2012).

Progress in specifically addressing therapeutic needs in dementia has been slow in the past two decades, and all development projects in Alzheimer's Disease have failed since the approval of memantine by the EMA (2002) and the FDA (2003). Rather than insisting on "treatment" indications, regulators have addressed the persisting high medical need by opening up the range of approvable medications to therapies with syndromal indication labels. Such a syndromal indication label could cover, e.g., Behavioral and Psychiatric Symptoms in Dementia (BPSD), sub-syndromal indications like aggression or apathy in Alzheimer's Disease, hallucinations and delusions in Parkinson's Disease Dementia (PDD). Accordingly, there is need for development of such new therapies with syndromal indication labels for novel compositions, combinations, therapeutic formulations, symptomatic and disease-modifying treatments, and therapies using EXCIVA TDR™ technology.

SUMMARY OF THE INVENTION

Various embodiments of the disclosure relate to Targeted Drug Rescue (TDR)™ with novel compositions, combinations, therapeutic formulations, symptomatic and disease-modifying treatments, therapies, kits thereof, and methods of making such compositions, combinations, therapeutic formulations, treatments, therapies, and kits comprising biologics, chemicals, nutritionals, pharmaceuticals, compositions, treatments, therapies, cures, prophylactics, supplements, and formulations; including allopathic, alternative, ayurvedic, herbal, holistic, homeopathic, natural, medicinal, pharmaceutical, unnatural agents, adjuvants, aids, brews, chemicals, compositions, combinations, concoctions, drugs, elements, extracts, extractions, formulations, kits, mechanisms, medications, medicines, mixtures, potions, preparations, prophylactics, recipes, solutes, solutions, solvents, substances, systems, teas, therapies, tinctures, and treatments; biologics and vaccines; cures; diagnostic kits, reagents and assays; dietary, gastronomical, and nutritional agents, potions, and supplements; healthcare products; and neutraceuticals; and related products and services thereof; for administering, cleansing, curing, diagnosing, healing, disinfecting, medicating, preventing, and treating the acute or chronic situations namely: addictions, conditions, deficiencies, disabilities, diseases, disorders, dysfunctions, infections, problems, poisonings, pollutions, and maladies thereof; due to and related to, namely, accidental, allergic, auditory, anti-cancer, cardiovascular, cardiopulmonary, chemotherapeutic, cognitive, congenital, dermatological, endocrinal, gastrointestinal, genetical, genital, genitourinary, hereditary, hormonal, hepatological, immunological, incidental, intellectual, karmic, lymphatic, metabolic, mental, muscular, musculoskeletal, neurological, oncological, optical, ophthalmic, osteological, osteopathic, psychiatric, psychological, psychopathic, psychosomatic, physical, physiological, respiratory, reproductive, sexual, skeletal, urological, virtual, and visual functions, systems, and causes thereof.

In various embodiments, the invention is a composition comprising a combination of one or more agents, each having a unique Therapeutic Mode of Action (TMA), wherein the agent is NMDA Receptor Antagonist, 5-HT$_{2A}$ Receptor Antagonist, 5-HT$_{2A}$ Receptor Inverse Agonist, 5-HT$_{2C}$ Receptor Antagonist, and/or CYP2D6 Inhibitor.

An embodiment of the invention is a composition comprising a compound of Formula I:

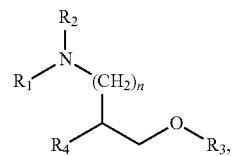

Formula I wherein, $R_1$ and $R_2$ are independently H, substituted or unsubstituted $C_{1-10}$ alkyl, substituted or unsubstituted $C_{5-10}$ aryl, substituted or unsubstituted $C_{3-10}$ cycloalkyl-$C_{5-10}$ aryl, substituted or unsubstituted $C_{4-10}$ bicycloalkyl, substituted or unsubstituted $C_{4-10}$ bicycloalkyl-$C_{5-10}$ aryl, substituted or unsubstituted $C_{4-10}$ bicycloalkyl-$C_{5-10}$ heteroaryl, substituted or unsubstituted $C_{4-10}$ tricycloalkyl, substituted or unsubstituted $C_{4-10}$ tricycloalkyl-$C_{5-10}$ aryl, substituted or unsubstituted $C_{4-10}$ tricycloalkyl-$C_{5-10}$ heteroaryl, or substituted or unsubstituted $C_{5-10}$ heteroaryl, or $R_1$ and $R_2$ together with the nitrogen form a saturated or unsaturated heterocycle having one or more hetero atoms selected from N, O, and S; $R_3$ is independently H, substituted or unsubstituted $C_{1-10}$ alkyl, substituted or unsubstituted $C_{5-10}$ aryl, substituted or unsubstituted $C_{5-10}$ heteroaryl, substituted or unsubstituted $C_{3-10}$ cycloalkyl-$C_{5-10}$ aryl, substituted or unsubstituted $C_{4-10}$ bicycloalkyl, substituted or unsubstituted $C_{4-10}$ bicycloalkyl-$C_{5-10}$ aryl, substituted or unsubstituted $C_{4-10}$ bicycloalkyl-$C_{5-10}$ heteroaryl, substituted or unsubstituted $C_{4-10}$ bicycloalkyl-$C_{1-10}$-alkyl-$C_{5-10}$ aryl, substituted or unsubstituted $C_{4-10}$ bicycloalkyl-$C_{1-10}$-alkyl-$C_{5-10}$heteroaryl, substituted or unsubstituted $C_{4-10}$ tricycloalkyl, substituted or unsubstituted $C_{4-10}$tricycloalkyl-$C_{1-10}$-alkyl-$C_{5-10}$ aryl, substituted or unsubstituted $C_{4-10}$ tricycloalkyl-$C_{1-10}$-alkyl-$C_{5-10}$ heteroaryl, substituted or unsubstituted $C_{4-10}$ tricycloalkyl-$C_{5-10}$ aryl, substituted or unsubstituted $C_{4-10}$ tricycloalkyl-$C_{5-10}$ heteroaryl, or substituted or unsubstituted $C_{5-10}$ heteroaryl, or substituted or unsubstituted $C_{5-10}$ heteroaryl;

n is an integer from 0 to 5; $R_4$ is H, NH—$R_5$, S—$R_5$, —OH, O—$R_5$, —CO—$R_5$, —O—CO—$R_5$, or —CO—O—$R_5$, wherein $R_5$ is an acyl radical; or $R_5$ and $R_2$ form a heterocycle; or enantiomers thereof, metabolites thereof, derivatives thereof, and/or prodrugs thereof, pharmaceutically acceptable salts thereof, N-oxides thereof, or a combination thereof.

Some embodiments include a composition comprising an effective amount of: 1) a composition comprising a compound of Formula I, as defined above, enantiomers thereof, metabolites thereof, derivatives thereof, and/or prodrugs thereof, pharmaceutically acceptable salts thereof, N-oxides thereof, or a combination thereof; or 2) a compound of Formula II

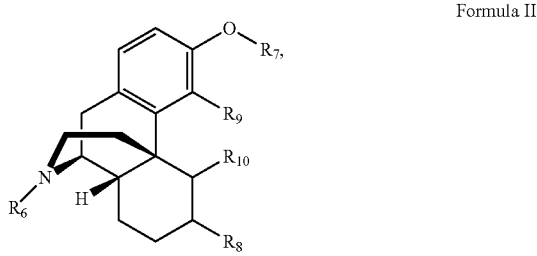

Formula II wherein, $R_6$, $R_7$, and $R_8$ are independently H, D, $C_{1-10}$-alkyl, halo $C_{1-10}$-alkyl wherein halogen is F, Cl, or Br; $R_9$ and $R_{10}$ are independently H; $C_{1-10}$-alkyl; halo $C_{1-10}$-alkyl wherein halogen is F, Cl, or Br; OH; or $R_9$ and $R_{10}$ together form a five-membered heterocycle wherein the hetero atom is O, S, or N; enantiomers, metabolites, derivatives, prodrugs, salts, diastereomers, pharmaceutically acceptable salts, or N-oxides thereof, or a combination thereof; or 3) a combination of 1 and 2; or a combinations thereof.

Some embodiments include a method of treating a disease or disorder in a subject in need thereof comprising an effective amount of: 1) a composition comprising a compound of Formula I, as defined above; enantiomers thereof, metabolites thereof, derivatives thereof, and/or prodrugs thereof, pharmaceutically acceptable salts thereof, N-oxides thereof, or a combination thereof; or 2) a compound of Formula II, as defined above, enantiomers, metabolites, derivatives, prodrugs, salts, diastereomers, pharmaceutically acceptable salts, or N-oxides thereof, or a combination thereof; or 3) a combination of 1 and 2.

Some embodiments include a method of treating a disease or disorder in a subject in need thereof comprising an effective amount of a composition comprising dextromethorphan, enantiomers, metabolites, derivatives, or prodrugs thereof, or a combination thereof; salts and diastereomers thereof, pharmaceutically acceptable salts thereof, N-oxides thereof, processes and intermediates for preparation thereof, compositions thereof, and uses thereof.

In an embodiment, the method is a method of decreasing the number of doses and/or total daily dose of the compound of Formula II that can be administered while increasing efficacy and safeguarding tolerability and safety; a method of reducing an adverse event associated with treatment by the compound of Formula II, wherein the subject is at risk of experiencing the adverse event as a result being treated with the compound of Formula II; a method of decreasing metabolites of the compound of Formula II plasma levels, a method of treating a neurological disorder, a method of increasing the compound of Formula II plasma levels in a subject in need of treatment with the compound of Formula II, wherein the subject is an extensive metabolizer of the compound of Formula II; a method of inhibiting the metabolism of the compound of Formula II; a method of increasing the metabolic lifetime of the compound of Formula II; a method of correcting extensive metabolism of the compound of Formula II; a method of improving the antitussive properties of the compound of Formula II; a method of treating cough. Another embodiment is the method, wherein the disease or disorder is a neurological disorder, wherein the composition is administered at least once a day for at least 1 day, 2 days, 3 days, 4 days, 5 days, 6 days, 7 days, or 8 days.

Some embodiments include a method of treating a neurological disorder comprising administering about 5 mg/day to about 600 mg/day, about 5 mg/day to about 300 mg/day, about 5 mg/day to about 400 mg/day, about 5 mg/day to about 500 mg/day, about 5 mg/day to about 600 mg/day, about 5 mg/day to about 1,000 mg/day, about 50 mg/day to about 1000 mg/day, about 100 mg/day to about 1000 mg/day, about 150 mg/day to about 1000 mg/day, about 150 mg/day to about 5000 mg/day, about 150 mg/day to about 300 mg/day, or about 150 mg/day to about 100 mg/day, or an amount as required of a compound of Formula I, and about 0.1 mg/day to about 1 mg/day, about 0.5 mg/day to about 15 mg/day, about 15 mg/day to about 60 mg/day, about 15 mg/day to about 120 mg/day, about 0.1 mg/day to about 200 mg/day, or an amount as required of the compound of Formula II to a subject in need thereof.

Another embodiment is a pharmaceutical composition comprising the compound of Formula II and one or more agents selected from the group comprising 5-HT2A receptor antagonist/inverse agonist, and CYP2D6 inhibitor. In another embodiment, the agent is an agent having properties of both 5-HT2A receptor antagonist/inverse agonist and CYP2D6 inhibitor. In another embodiment, the agent is a dual agent (DA) having properties of both 5-HT2A receptor inverse agonist and CYP2D6 inhibitor. In another embodiment, the DA is a compound of Formula I.

BRIEF DESCRIPTION OF FIGURES

FIGS. 2A, 2B, and 2C represent Mean Neuropsychiatric Inventory Agitation/Aggression Domain Scores by Stage and Visit for Patients Included in the Sequential Parallel Comparison Design and 10-Week Analyses. A, Stage 1 (weeks 1-5); B, stage 2 (weeks 6-10) for placebo nonresponders rerandomized after stage 1; C, 10-week results (the 10-week secondary analysis includes only patients who continued the same treatment assignment throughout study participation; ie, were randomized to receive only dextromethorphan-quinidine or only placebo [excludes patients who were rerandomized from placebo to dextromethorphan-quinidine in stage 2], thus simulating a parallel-group design). Analysis-of-covariance models with treatment as fixed effect and baseline as covariate were used to compare mean change from baseline between groups at each time point. Baseline for stage 2 is the patients' scores at the start of stage 2. Least squares mean treatment differences are as follows: for stage 1, week 1, −0.8 (95% CI, −1.5 to −0.03; P=0.04), week 3, −1.0 (95% CI, −1.8 to −0.2; P=0.01), and week 5, −1.5 (95% CI, −2.3 to −0.7; P<0.001); for stage 2, week 6, 0.7 (95% CI, −0.4 to 1.9; P=0.19), week 8, −0.1 (95% CI, −1.3 to 1.2; P=0.93), and week 10, −1.6 (95% CI, −2.9 to −0.3; P=0.02); for 10-week analysis, week 1, −0.9 (95% CI, −1.8 to −0.04; P=0.047), week 3, −1.3 (95% CI, −2.2 to −0.3; P=0.01), week 5, −1.8 (95% CI, −2.7 to −0.9; P<0.001), week 6, −0.9 (95% CI, −2.0 to 0.1; P=0.06), week 8, −1.3 (95% CI, −2.4 to −0.3; P=0.01), and week 10, −1.8 (95% CI, −2.8 to −0.7; P=0.003). a Observed cases (Cummings et al., Effect of dextromethorphan quinidine on agitation in patients with Alzheimer Disease dementia: a randomized clinical trial. JAMA 314(12):1242-1254 (2015), incorporated in entirety by reference).

FIGS. 3A, 3B, and 3C show treatment effects on psychosis severity reduction in the 6 week study period in the full analysis set. The full analysis set includes all patients who received ≥1 dose and had a SAPS assessment at baseline and at least one afterward. Data points show least squares means (standard error). (A) SAPS-PD improvement. (B) Change in CGI-severity score. (C) CGI-improvement scores. SAPS=scale for assessment of positive symptoms. CGI=clinical global impression (Cummings et al., Pimavanserin for patients with Parkinson's disease psychosis: a randomized, placebo-controlled phase 3 trial. Lancet, 383 (9916):533-40 (8 Feb. 2014), incorporated in entirety by reference).

DETAILED DESCRIPTION OF THE INVENTION

Figure 1A:
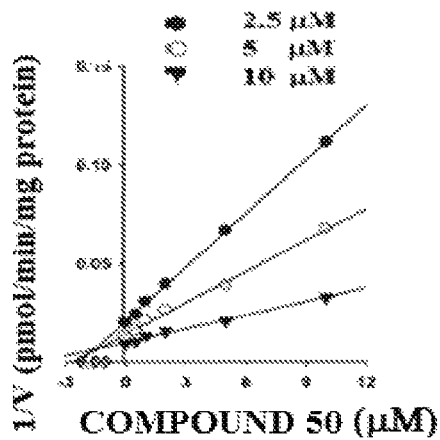
FIGS. 1A, 1B, and 1C represent Dixon plots to determine Ki values for CYP2D6 of compounds of Formula I exemplified by Sarpogrelate and M−1, and quinidine. The concentrations of dextromethorphan were determined 2.5 (filled circles), 5 (open circles), and 10 (triangles) mM, respectively. V represents formation rate of dextrorphan (pmol/min/mg protein). Data are the mean values of triplicate determinations. The solid lines of a compound of Formula I, exemplified by Sarpogrelate and M−1, and quinidine fit well to all competitive inhibition types (Cho et al., Effect of the potent CYP2D6 inhibitor on the pharmacokinetics and pharmacodynamics of metoprolol in healthy male Korean volunteers. Xenobiotica, 45(3):256-63 (2015 March), incorporated in entirety by reference).

Various embodiments of the inventive Targeted Drug Rescue (TDR)™ comprising novel compositions, and combinations, therapeutic formulations, symptomatic and disease-modifying treatments, therapies, kits thereof, and methods of making such compositions, combinations, therapeutic formulations, treatments, therapies, and kits comprising biologics, chemicals, nutritionals, pharmaceuticals, compositions, treatments, therapies, cures, prophylactics, supplements, and formulations, including the disclosures of U.S. patent application 62/501,693 filed May 4, 2017, PCT/US2017/048748 filed Aug. 25, 2017 published WO 2018/039642 A1 Mar. 1, 2018, TW 106129169 filed Aug. 28, 2017, U.S. 62/634,162 filed Feb. 22, 2018, U.S. 62/636,171 filed Feb. 22, 2018, U.S. 62/635,554 filed Feb. 27, 2018, and U.S. 62/636,099 filed Feb. 27, 2018, all of which are incorporated by reference.

An embodiment of the invention is a composition comprising a compound of formula I:

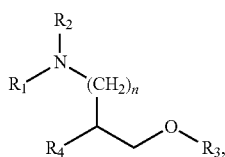

Formula I wherein, $R_1$ and $R_2$ are independently H, substituted or unsubstituted $C_{1-10}$ alkyl, substituted or unsubstituted $C_{5-10}$ aryl, substituted or unsubstituted $C_{3-10}$ cycloalkyl-$C_{5-10}$ aryl, substituted or unsubstituted $C_{4-10}$ bicycloalkyl, substituted or unsubstituted $C_{4-10}$ bicycloalkyl-$C_{5-10}$ aryl, substituted or unsubstituted $C_{4-10}$ bicycloalkyl-$C_{5-10}$ heteroaryl, or substituted or unsubstituted $C_{5-10}$ heteroaryl, or $R_1$ and $R_2$ together with the nitrogen form a saturated or unsaturated heterocycle having one or more hetero atoms selected from N, O, and S;

$R_3$ is independently H, substituted or unsubstituted $C_{1-10}$ alkyl, substituted or unsubstituted $C_{5-10}$ aryl, substituted or unsubstituted $C_{5-10}$ heteroaryl, substituted or unsubstituted $C_{3-10}$ cycloalkyl-$C_{5-10}$ aryl, substituted or unsubstituted $C_{4-10}$ bicycloalkyl, substituted or unsubstituted $C_{4-10}$ bicycloalkyl-$C_{5-10}$ aryl, substituted or unsubstituted $C_{4-10}$ bicycloalkyl-$C_{5-10}$ heteroaryl or substituted or unsubstituted $C_{5-10}$ heteroaryl; n is an integer from 0 to 5; $R_4$ is H, NH—$R_5$, S—$R_5$, —OH, O—$R_5$, —CO—$R_5$, —O—CO—$R_5$, or —CO—O—$R_5$, wherein $R_5$ is an acyl radical; or $R_5$ and $R_2$ form a heterocycle; or enantiomers thereof, metabolites thereof, derivatives thereof, and/or prodrugs thereof, pharmaceutically acceptable salts thereof, N-oxides thereof, or a combination thereof.

An embodiment is a compound of Formula I, wherein the substituted or unsubstituted $C_{4-10}$ cycloalkyl is cyclopropyl, cyclobutyl, cyclopentyl, cyclohexyl, cycloheptyl, cyclooctyl, cyclononyl, or cyclodecyl radical. In another embodiment, the cycloalkyl comprises one or more heteroatoms N, S, or O.

Another embodiment is a compound of Formula I, wherein the substituted or unsubstituted $C_{3-10}$ bicycloalkyl is bicyclobutyl, bicyclopentyl, bicyclohexyl, bicycloheptyl, bicyclooctyl, bicyclononyl, or bicyclodecyl radical. In another embodiment, the bicycloalkyl comprises one or more heteroatoms N, S, or O.

Another embodiment is a compound of Formula I, wherein the aryl is phenyl, naphtyl, anthracenyl, or phenanthrenyl.

In another embodiment, the compound is a compound of Formula I wherein R5 is an acyl radical selected from the group consisting of mono, di, and tri carboxylic acid radicals.

In another embodiment, the compound is a compound of Formula I wherein R5 is an acyl radical selected from the group consisting of acetate, acetyl salicylate, adipate, N-acyl-aspartate, aspartate, butyrate, caprate, caproate, caprylate, enanthate, formate, fumarate, N-acyl-glutarate, glutarate, isophthallate, maleate, malonate, methionate, N-acyl-methionate oxalate, pelargonate, pimelate, propionate, phthallate, salicylate, sebacate, succinate, terephthallate, tyrosinate, N-acyl-tyrosinate, tryptophanate, N-acyl-tryptophanate, and valerate.

Another embodiment is a compound of Formula II,

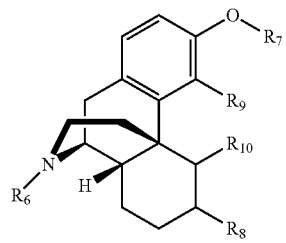

Formula IIa

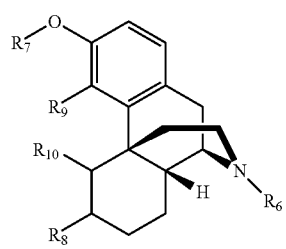

Formula IIb wherein, $R_6$, $R_7$, and $R_8$ are independently H, D, $C_{1-10}$-alkyl, halo $C_{1-10}$-alkyl wherein halogen is F, Cl, or Br; $R_9$ and $R_{10}$ are independently H; $C_{1-10}$-alkyl; halo $C_{1-10}$-alkyl wherein halogen is F, Cl, or Br; OH; or $R_9$ and $R_{10}$ together form a five-membered heterocycle wherein the hetero atom is O, S, or N.

Another embodiment is a compound of Formula I, wherein R5 and R2 form a heterocycle selected from the radicals such as morpholine, dihydrooxazine, oxazine, piperazine, dihydropiperzine, and tetrahydropirazine. Compounds of this embodiment include, but not limited to, the following compounds 10-24:

Compound 10
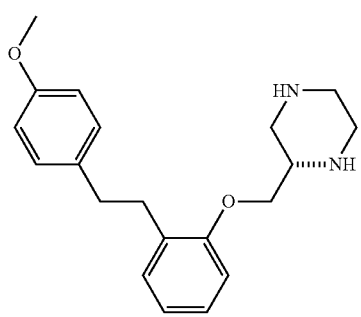
Compound 11
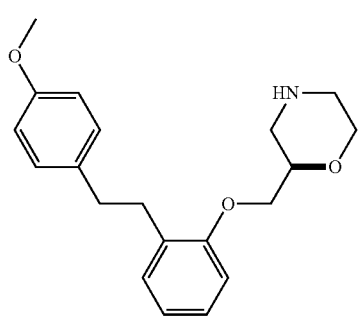
Compound 12
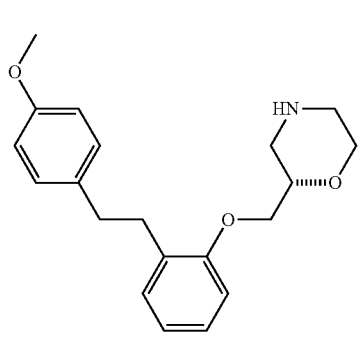
Compound 13
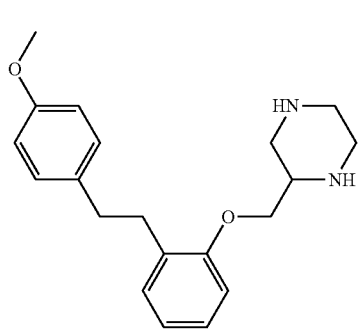
Compound 14
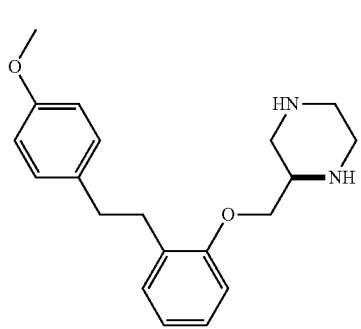
Compound 15
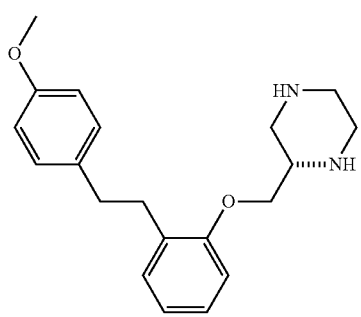
Compound 16
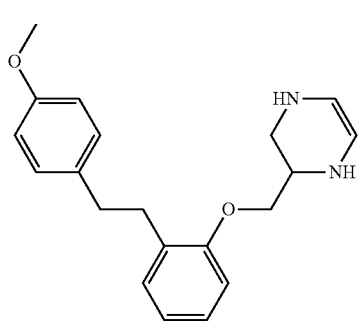
Compound 17
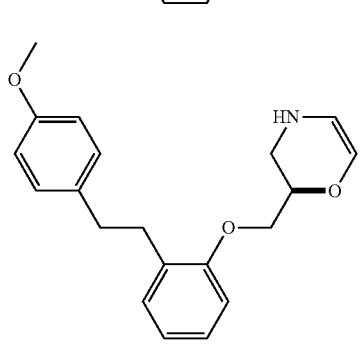
Formula Ia
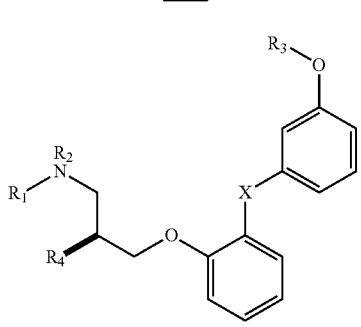
Pure Enantiomer
Compound 18
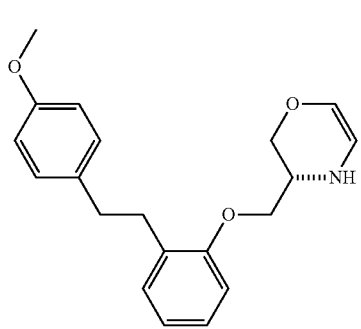

Compound 19
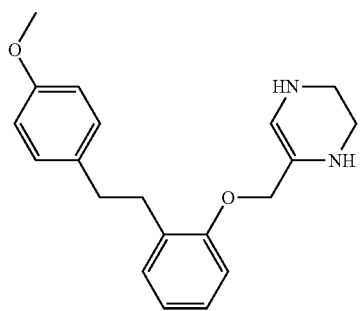

Compound 20
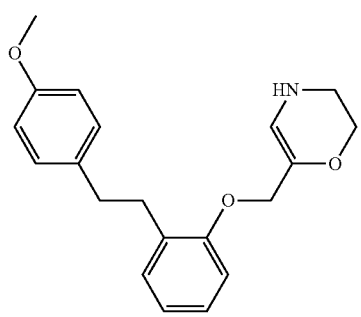

Compound 21
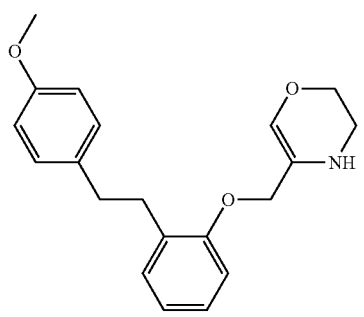

Compound 22
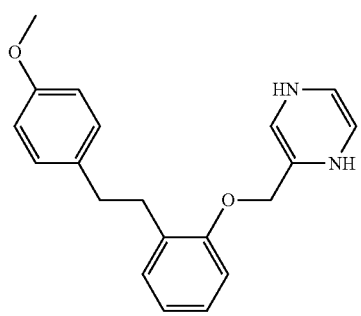

Compound 23
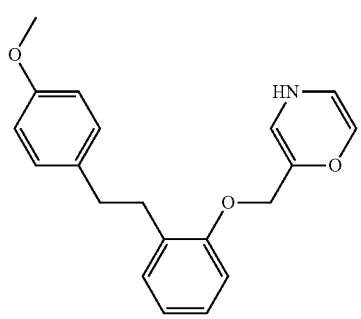

Compound 24
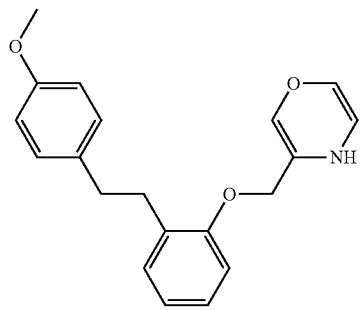

Formula Ib
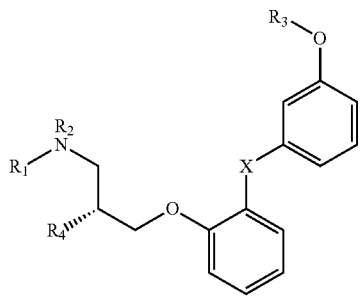

Pure Enantiomer

Another embodiment is a pure enantiomer of Formula I selected from Formula Ia or Ib.

In another embodiment, the compound of Formula I, wherein $R_1$, $R_2$, and $R_3$ are methyl, provided X is not ethyl.

In another embodiment, the composition comprising Formula I is sarpogrelate (SARPO), wherein $R_1$, $R_2$, and $R_3$ are methyl, X is ethyl, and $R_4$ is succinoyl radical, having the following compounds SGL, SGL-E1, and SGL-E2.

In another embodiment, the composition comprising formula I is sarpogrelate metabolite M1, wherein $R_1$, $R_2$, and $R_3$ are methyl, X is ethyl, and $R_4$ is OH, having the following compounds M1, M1-E1, and M1-E2.

In another embodiment, the composition comprising formula I is sarpogrelate metabolite M1, wherein $R_1$ and $R_2$ together with the nitrogen form a saturated or unsaturated heterocycle having one or more hetero atoms selected from N, O, and S; and $R_3$ is methyl, X is ethyl, and R4 is OH. In another embodiment, the heterocycle is a five-membered ring. Another embodiment is where the heterocycle is a six-membered ring. In another embodiment, the heterocycle is saturated. Another embodiment has the unsaturated heterocycle. In one embodiment the heterocycle has one hetero atom. In another, the heterocycle has two hetero atoms.

In another embodiment, the compound of formula I, wherein the heterocycle formed from $R_1$ and $R_2$ together with the nitrogen is selected from the heterocycles listed below:

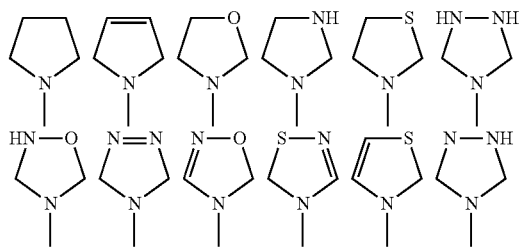

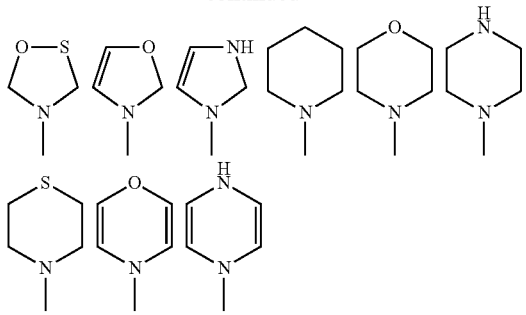

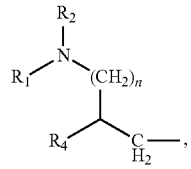

The term "DEX" represents a compound of Formula II, such as dextromethorphan, enantiomers thereof, metabolites thereof, derivatives thereof, and/or prodrugs thereof, or a combination thereof. Derivatives include, but not limited to, deuterated derivatives, e.g., DEX-H3, DEX-D3, DO, and DO-D3.

The term "SARPO," represents one or more compounds selected from the group consisting of sarpogrelate (SGL), enantiomers thereof, a metabolite thereof, M1, SG1, SG2, SMG1, SMG2, SMG3, a derivative thereof, a prodrug thereof, and a combination thereof.

The term SARPODEX™ represents a combination of DEX and a compound of Formula I. An embodiment of the invention is a composition comprising a compound of formula I and dextromethorphan. An embodiment of the invention is a composition comprising a compound of formula I and DEX-H3, DEX-D3, DO, or DO-D3. An embodiment of the invention is a composition comprising: M1, M1-E1, M1-E2, SGL, SGL-E1, or SGL-E2; and DEX-H3, DEX-D3, DO, or DO-D3.

The term DERADEX™ or DERAPHAN™ represents a combination of DEX and a compound of Formula I, wherein the compound is a derivative of bicyclo[2.2.1]heptanol having the Formula I:

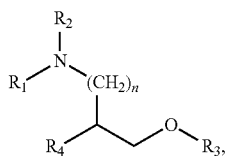

Formula I wherein $R_3$ is a bicyclic system and the rest of the Formula I represented by $R_7$: as shown in Formula If

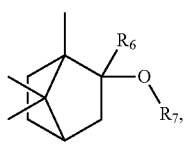

Formula If wherein, $R_6$ is H, substituted or unsubstituted —$C_{1-10}$ alkyl, substituted or unsubstituted —$C_{3-10}$ cycloalkyl, substituted or unsubstituted —$C_{5-10}$ aryl, substituted or unsubstituted —$C_{1-10}$ alkyl-$C_{5-10}$ aryl, substituted or unsubstituted —$C_{5-10}$ heteroaryl, or substituted or unsubstituted —$C_{1-10}$ alkyl-$C_{5-10}$ heteroaryl; $R_7$ is —$C_{1-10}$alkyl-X—$(Y)_n$, —$C_{3-10}$ cycloalkyl-X—$(Y)_m$, —$C_{5-10}$ aryl-X—$(Y)_m$, or —$C_{5-10}$ heteroaryl-X—$(Y)_m$; wherein X is a bond, N, O, S, —$C_{1-10}$ alkyl, —$C_{3-10}$ cycloalkyl, —$C_{5-10}$ aryl, —CO—$C_{1-10}$ alkyl, —CO—$C_{3-10}$ cycloalkyl, —COC$_{5-10}$ aryl, —CO—$C_{5-10}$ heteroaryl, —CO—NH—$C_{1-10}$ alkyl, —CO—NH—$C_{3-10}$ cycloalkyl, —CO—NH—$C_{5-10}$ aryl, or —CO—NH—$C_{5-10}$ heteroaryl; Y is H, $C_{1-10}$ alkyl, $C_{3-10}$ cycloalkyl, $C_{5-10}$ aryl, —CO—$C_{1-10}$ alkyl, —CO—$C_{3-10}$ cycloalkyl, —COC$_{5-10}$ aryl, CO—$C_{5-10}$ heteroaryl, —CO—NH—$C_{1-10}$ alkyl, —CO—NH—$C_{3-10}$ cycloalkyl, —CO—NH—$C_{5-10}$ aryl, or —CO—NH—$C_{5-10}$ heteroaryl; and m is an integer 1 or 2; or pharmaceutically acceptable salts or N-oxides thereof; or prodrugs thereof.

The term DERATINE™ represents a combination of an NMDA receptor antagonist and and a compound of Formula I, as defined above.

The term SARPOTINE™ represents a combination of an NMDA receptor antagonist and and a compound of Formula I, as defined above.

An embodiment of the invention is a composition comprising a compound of Formula I and DEX-H3, DEX-D3, DO, or DO-D3.

In another embodiment, a compound of Formula I or analogs can be made using the following carboxylic acids: Malic Acid HO$_2$C—CH$_2$—CH(OH)—CO$_2$H (Compounds 25-29), Methionine H$_3$C—S—(CH$_2$)$_2$—CH(NH$_2$)—CO$_2$H (Compounds 30-34), Phthallic Acid C$_6$H$_4$(CO$_2$H)$_2$ (Compounds 35-37), Malonic Acid HO$_2$C—CH$_2$—CO$_2$H (Compounds 38-40), Tyrosine HO—C$_6$H4-CH$_2$—CH(NH$_2$)—CO$_2$H (Compounds 41-43), Tryptophan C$_8$H$_6$N—CH$_2$—CH(NH$_2$)—CO$_2$H (Compounds 44-46), Maleic Acid HO$_2$C—CH=CH—CO$_2$H (Compounds 47-49), Succinic Acid HO$_2$C—(CH$_2$)$_2$—CO$_2$H (Compounds 50-52), Glutaric acid HO$_2$C—(CH$_2$)$_3$—CO$_2$H (Compounds 53-55), Adipic Acid HO$_2$C—(CH$_2$)$_4$—CO$_2$H (Compounds 56-58), Pimelic acid HO$_2$C—(CH$_2$)$_5$—CO$_2$H (Compounds 59-61), Sebacic acid HO$_2$C—(CH$_2$)$_6$—CO$_2$H (Compounds 62-64), Formic acid HCO$_2$H (Compounds 65-67), Acetic acid CH$_3$CO$_2$H (Compounds 68-70), Propionic acid CH$_3$CH$_2$CO$_2$H (Compounds 71-73), Butyric acid CH$_3$(CH$_2$)$_2$CO$_2$H (Compounds 74-76), Valeric acid CH$_3$(CH$_2$)$_3$CO$_2$H (Compounds 77-79), Caproic acid CH$_3$(CH$_2$)$_4$CO$_2$H (Compounds 80-82), Enanthic acid CH$_3$(CH$_2$)$_6$CO$_2$H (Compounds 83-85), Caprylic acid CH$_3$(CH$_2$)$_6$CO$_2$H (Compounds 86-88), Pelargonic acid CH$_3$(CH$_2$)$_7$CO$_2$H (Compounds 89-91), Capric acid CH$_3$(CH$_2$)$_8$CO$_2$H (Compounds 92-94), Oxalic Acid HO—CO—CO$_2$H (Compounds 95-97), Isophthallic Acid C$_6$H$_4$(CO$_2$H)$_2$ (Compounds 98-100), Terephthallic Acid C$_6$H$_4$(CO$_2$H)$_2$ (Compounds 101-103), Salicylic Acid HO—C$_6$H$_4$—CO$_2$H (Compounds 104-106), Acetyl Salicylic Acid CH$_3$—CO—O—C$_6$H$_4$—CO$_2$H (Compounds 107-109).

An embodiment of the invention is a compound of formula I, wherein the compound is sarpomalate, wherein $R_1$, $R_2$, and $R_3$ are methyl, X is ethyl, and R4 is malate; compounds 25-29. An embodiment of the invention is a compound of formula I, wherein the compound is sarpomethionate, wherein $R_1$, $R_2$, and $R_3$ are methyl, X is ethyl, and R4 is methionate; compounds 30-34. An embodiment of the invention is a compound of formula I, wherein the compound is sarpophthallate, wherein $R_1$, $R_2$, and $R_3$ are methyl, X is ethyl, and R4 is phthalate; compounds 35-37. An embodiment of the invention is a compound of formula I, wherein the compound is sarpomalonate, wherein $R_1$, $R_2$, and $R_3$ are methyl, X is ethyl, and R4 is malonate' compounds 38-40. An embodiment of the invention is a compound of formula I, wherein the compound is sarpotyrosinate, wherein $R_1$, $R_2$, and $R_3$ are methyl, X is ethyl, and R4 is tyrosinate; compounds 41-43. An embodiment of the invention is a compound of formula I, wherein the compound is sarpotryptophanate, wherein $R_1$, $R_2$, and $R_3$ are methyl, X is ethyl, and R4 is tryptophanate; compounds 44-46. In an embodiment, the composition is a combination of DEX and at least one compound selected from compounds 10-46, SGL, SGL-E1, SGL-E2, M1, M1-E1, M1-E2. An embodiment of the invention is a composition comprising a compound of formula I, wherein the compound is sarpogrelate, and dextromethorphan.

An embodiment of the invention is a composition comprising a compound of formula I, wherein the compound is sarpogrelate, and dextromethorphan, wherein sarpogrelate and dextromethorphan form diastereomeric mixture.

Compound 25

Compound 26

Compound 27

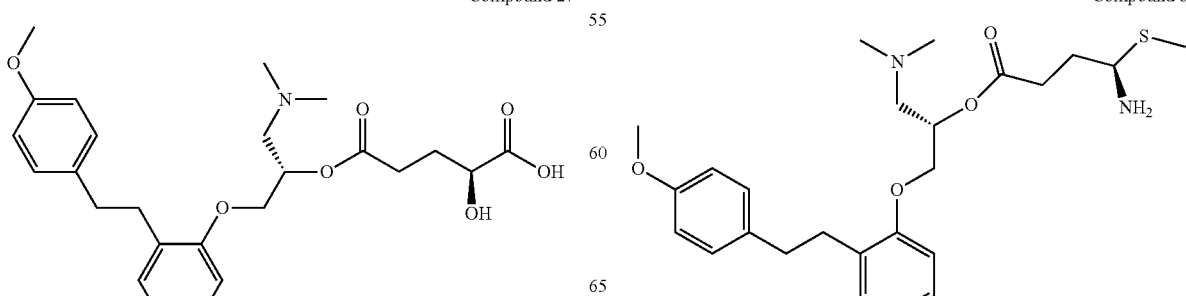

Compound 28

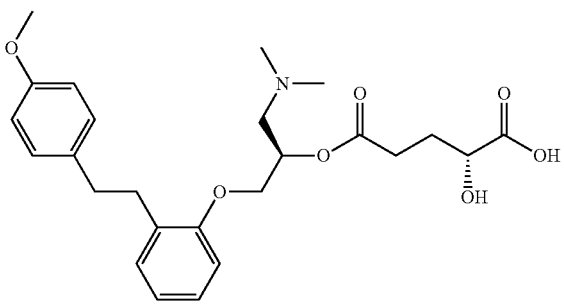

Compound 29

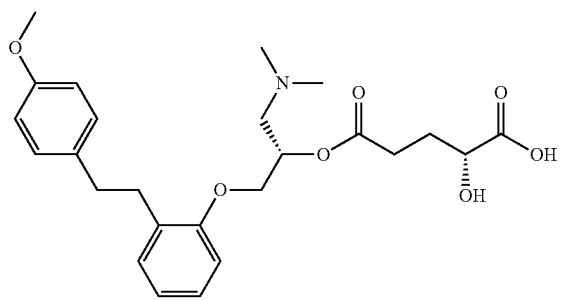

Compound 30

Compound 31

Compound 32

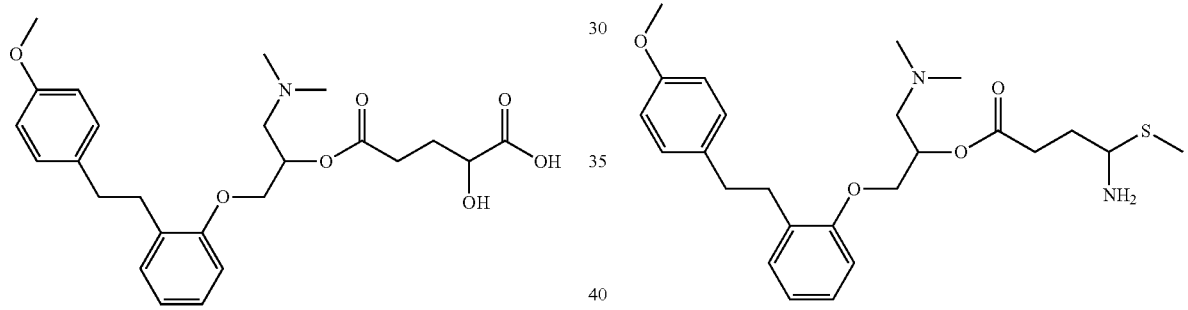

Compound 33

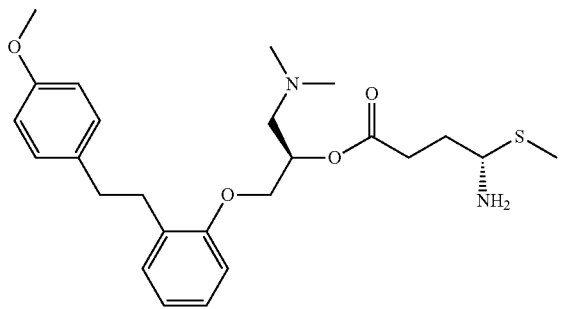

Compound 34

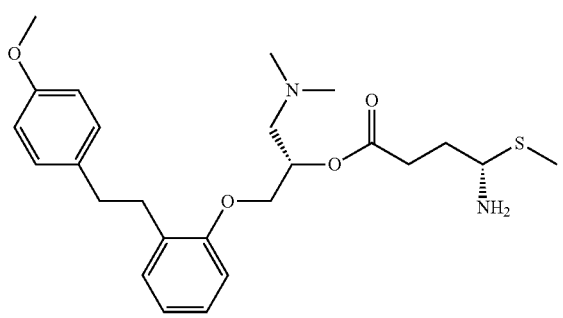

Compound 35

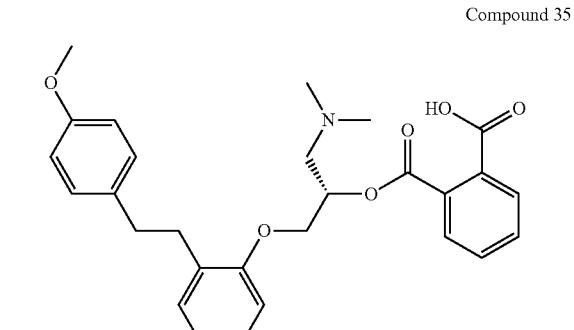

Compound 36

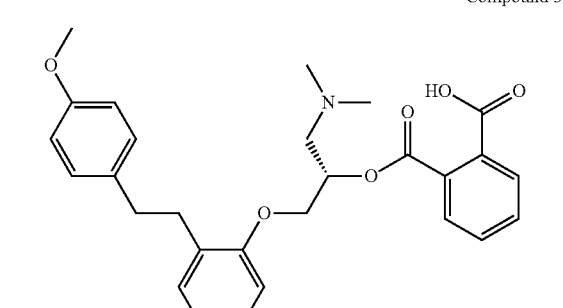

Compound 37

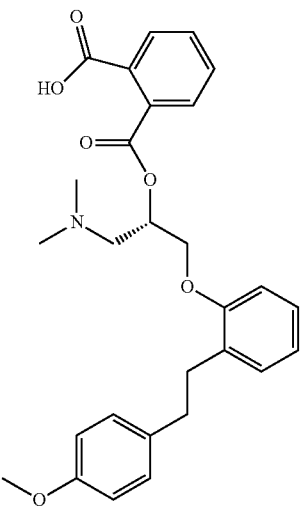

An embodiment of the invention is a composition comprising a compound of formula I, wherein the compound is sarpogrelate, and dextromethorphan, wherein sarpogrelate and dextromethorphan form a salt, wherein the salt is a diastereomeric mixture. An embodiment of the invention is a composition comprising a compound of formula I, wherein the compound is sarpogrelate, and dextromethorphan, wherein sarpogrelate and dextromethorphan form a salt, wherein the salt is a pure diastereomer. An embodiment of the invention is a composition comprising a compound of formula I, wherein the compound is sarpogrelate metabolite M1, and dextromethorphan. An embodiment of the invention is a composition comprising dextromethorphan and a compound of formula I, wherein the compound is sarpomalate, forming a salt comprising diastereomeric mixture or a pure diastereomer thereof. An embodiment of the invention is a composition comprising a compound of formula I, wherein the compound is sarpomethionate, and dextromethorphan, forming a salt comprising diastereomeric mixture or a pure diastereomer thereof. An embodiment of the invention is a composition comprising a compound of formula I, wherein the compound is sarpophthallate, and dextromethorphan, forming a salt comprising diastereomeric mixture or a pure diastereomer thereof. An embodiment of the invention is a composition comprising a compound of formula I, wherein the compound is sarpomalonate, and dextromethorphan, forming a salt comprising diastereomeric mixture or a pure diastereomer thereof. An embodiment of the invention is a composition comprising a compound of formula I, wherein the compound is sarpotyrosinate, and dextromethorphan, forming a salt comprising diastereomeric mixture or a pure diastereomer thereof. An embodiment of the invention is a composition comprising a compound of formula I, wherein the compound is sarpotryptophanate, and dextromethorphan, forming a salt comprising diastereomeric mixture or a pure diastereomer thereof.

An embodiment of the invention is a composition comprising a compound of formula I, wherein the compound is SGL, and dextromethorphan HCl, forming a salt comprising diastereomeric mixture or a pure diastereomer thereof. An embodiment of the invention is a composition comprising a compound of formula I, wherein the compound is SGL, and dextromethorphan HBr, forming a salt comprising diastereomeric mixture or a pure diastereomer thereof. An embodiment of the invention is a composition comprising a compound selected from the group consisting of SGL, enantiomers thereof, a metabolite thereof, M1, SG1, SG2, SMG1, SMG2, SMG3, a derivative thereof, a prodrug thereof, and a combination thereof. An embodiment of the invention is a composition comprising a compound selected from the group consisting of SGL, enantiomers thereof, a metabolite thereof, M1, SG1, SG2, SMG1, SMG2, SMG3, a derivative thereof, a prodrug thereof, and a combination thereof, and dextromethorphan.

Another embodiment is a compound of Formula 1, wherein the Ra and R2 form a five- or six-membered heterocyclic moiety, exemplary compounds are compounds 110-145. An embodiment of the invention is a composition comprising a compound selected from the group consisting of SGL, enantiomers thereof, a metabolite thereof, M1, SG1, SG2, SMG1, SMG2, SMG3, a derivative thereof, a prodrug thereof, and a combination thereof, and dextromethorphan.

Compound 38

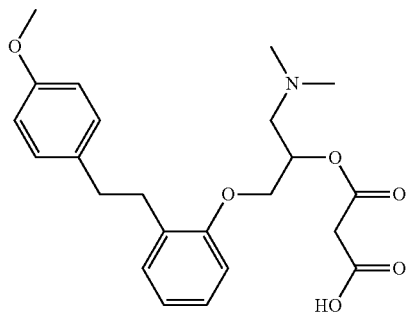

Compound 39

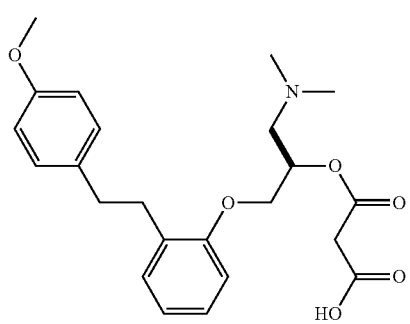

Compound 40

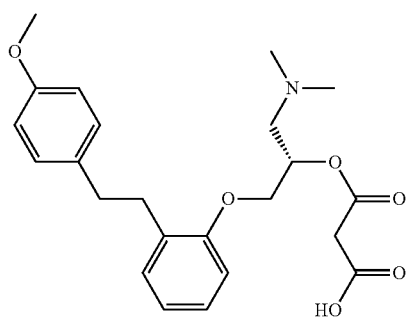

Compound 41

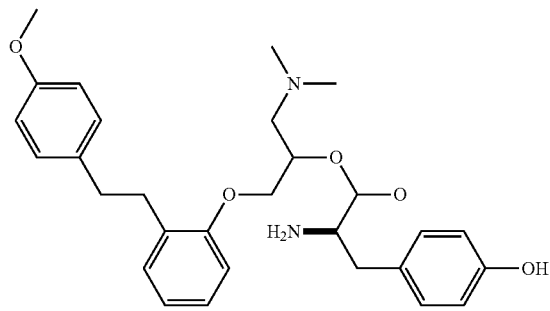

Compound 42

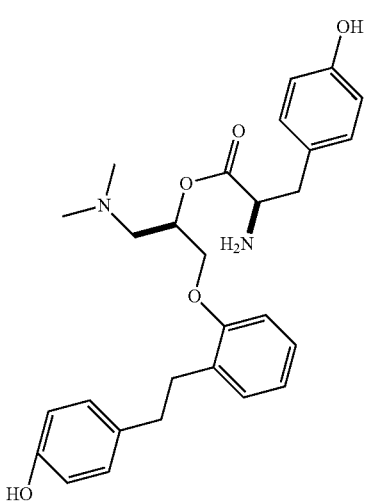

Compound 43

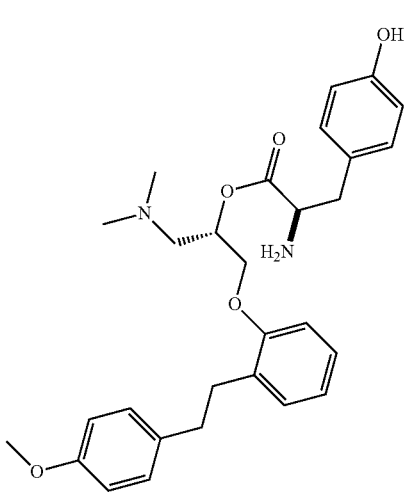

Compound 44
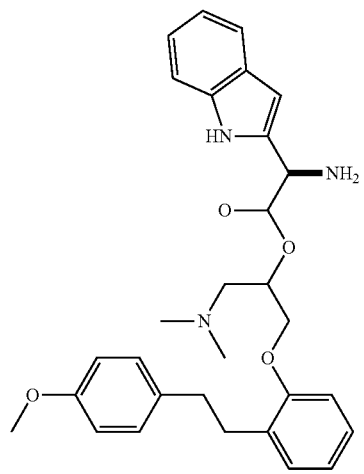
Compound 45
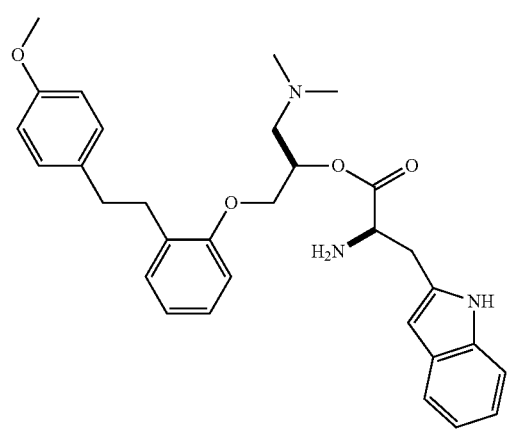
Compound 46
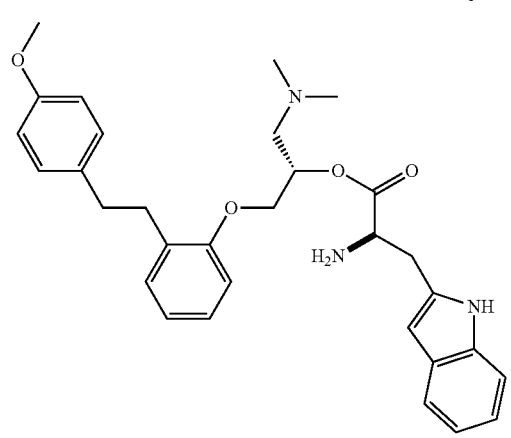
Compound 47
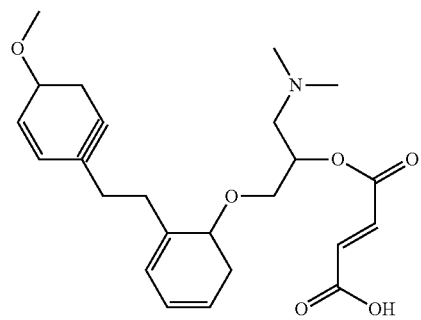
Compound 48
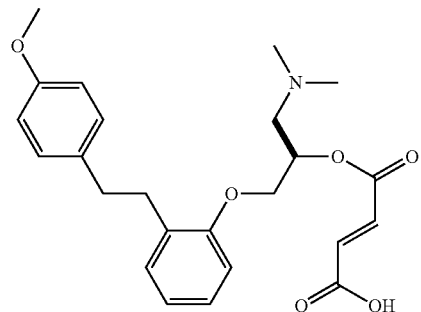
Compound 49
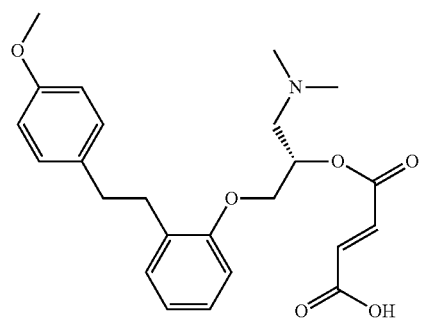
Compound 50
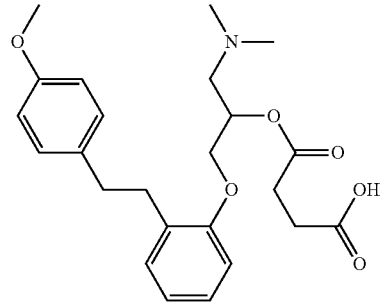
Compound 51
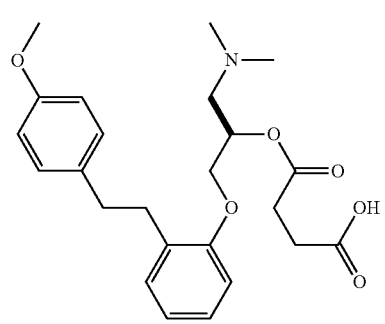

Compound 52
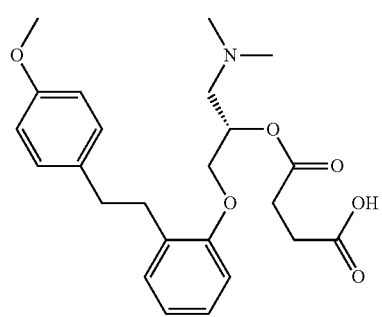
Compound 53
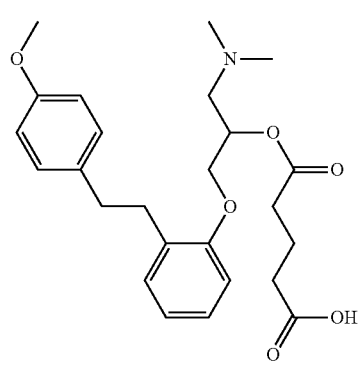
Compound 54
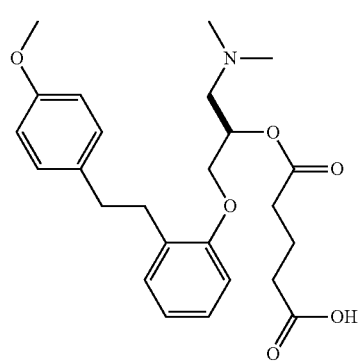
Compound 55
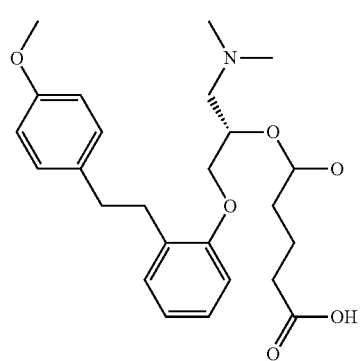
Compound 56
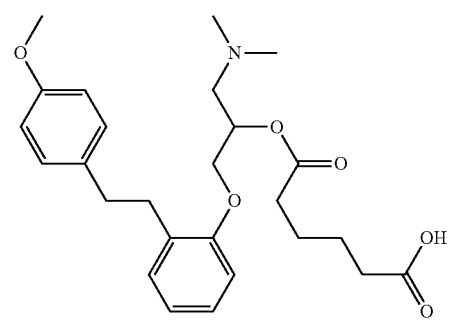
Compound 57
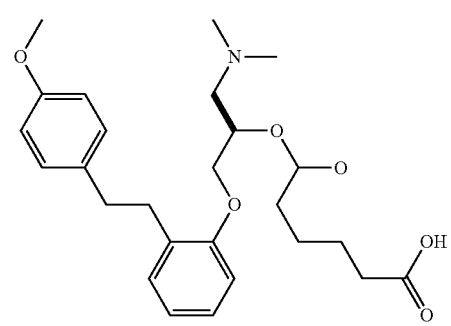
Compound 58
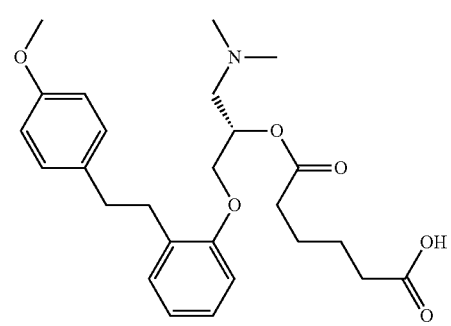
Compound 59
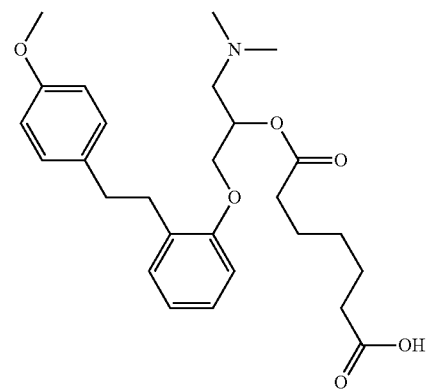

Compound 60
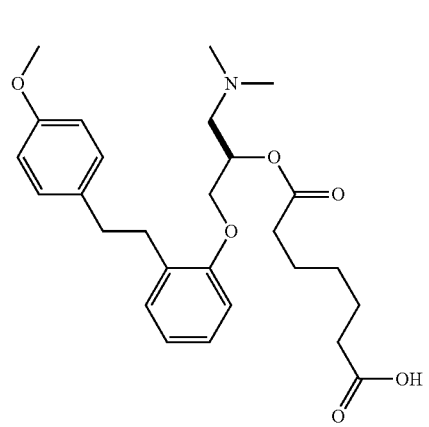
Compound 61
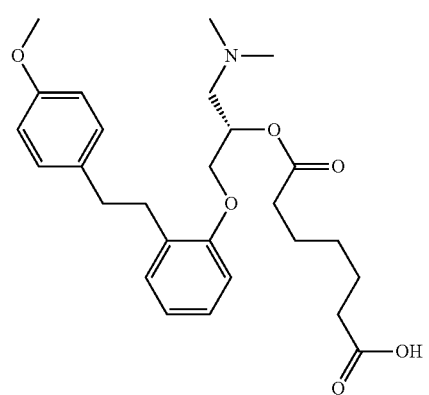
Compound 62
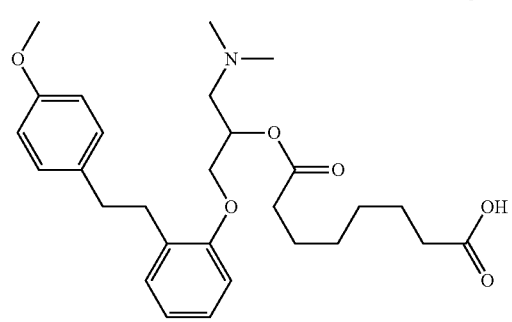
Compound 63
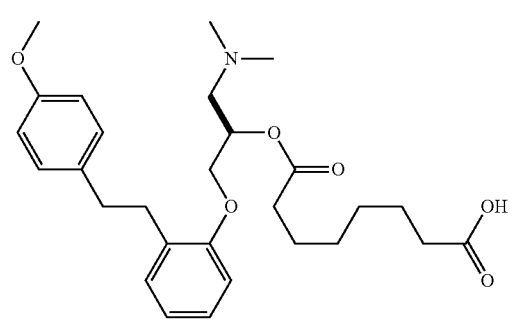
Compound 64
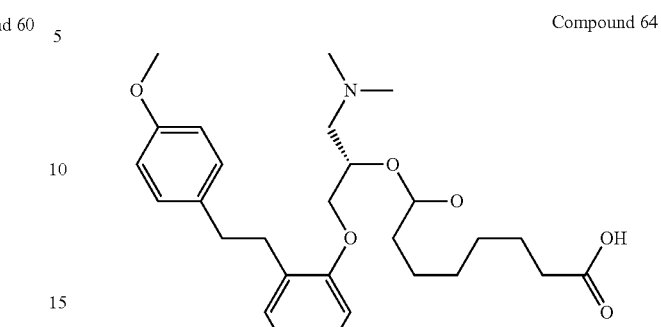
Compound 65
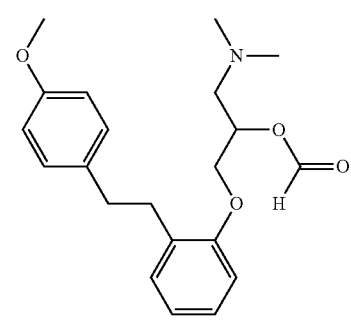
Compound 66
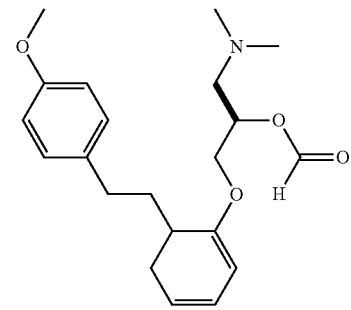
Compound 67
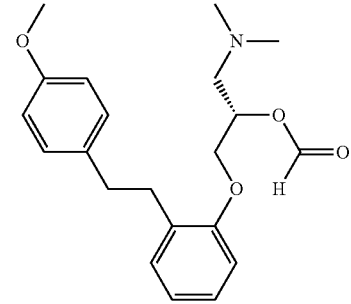
Compound 68
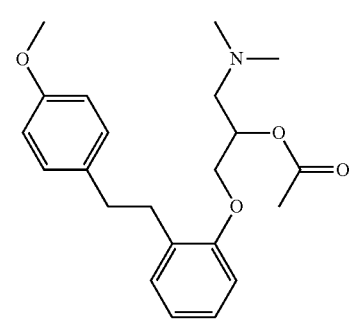

-continued
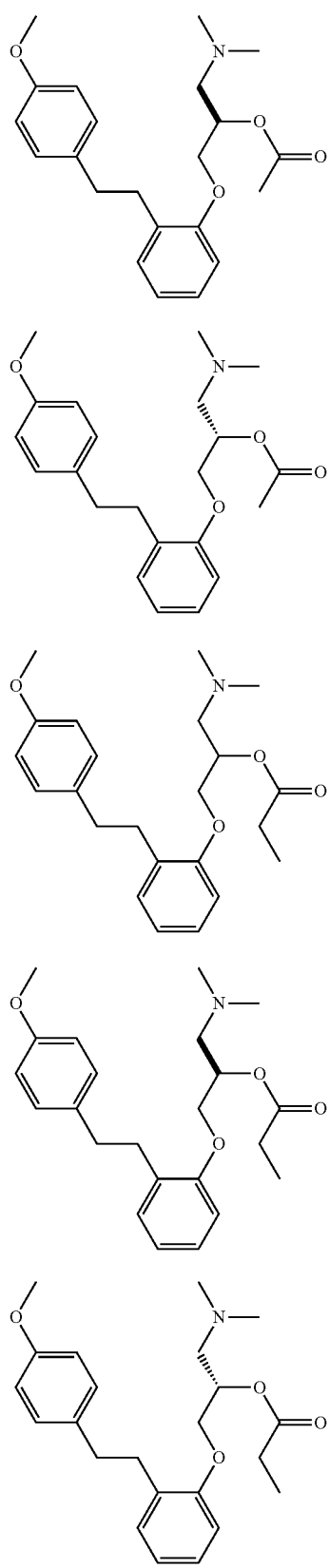
Compound 69
Compound 70
Compound 71
Compound 72
Compound 73
-continued
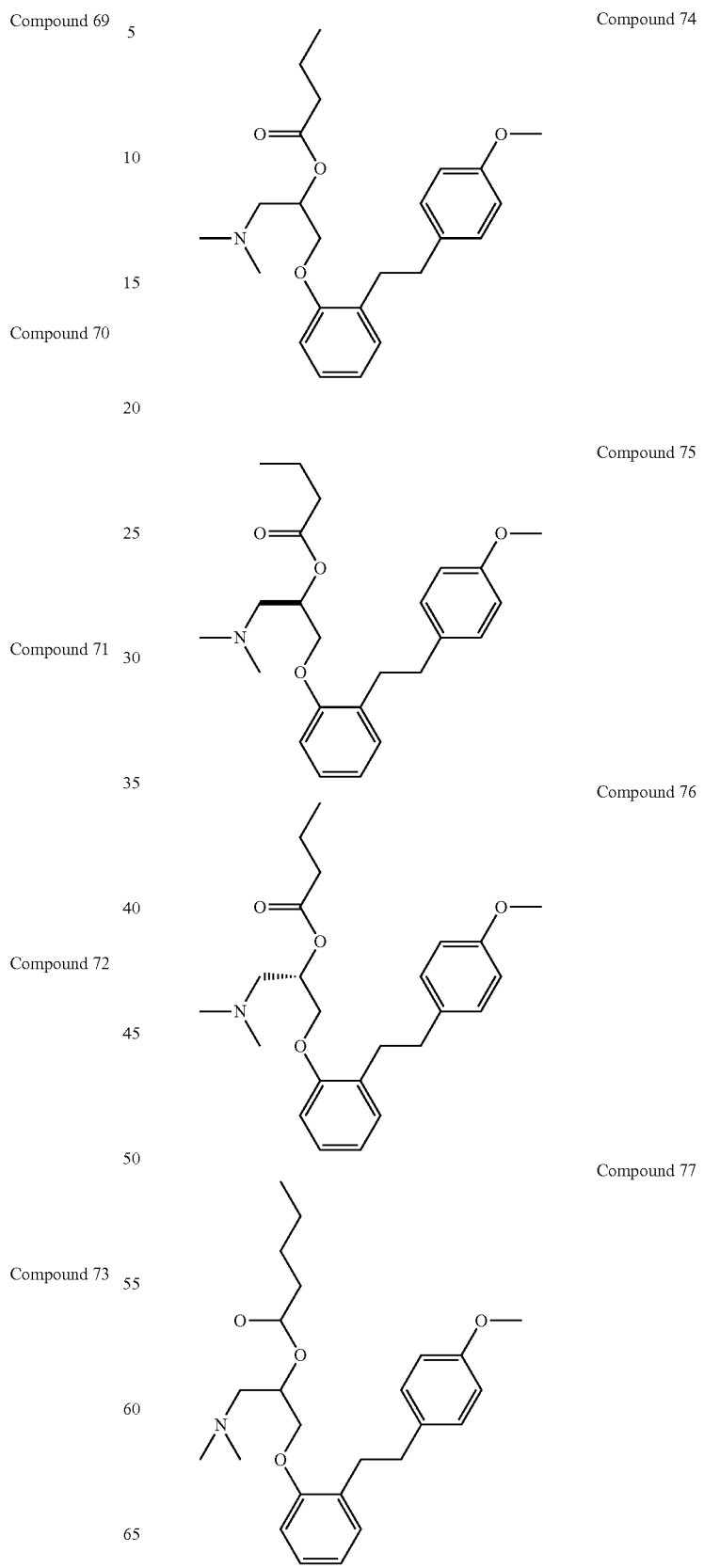
Compound 74
Compound 75
Compound 76
Compound 77

Compound 78
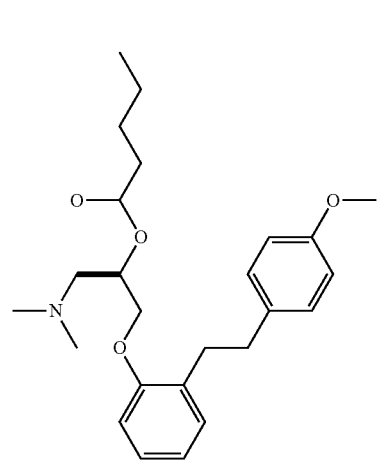
Compound 81
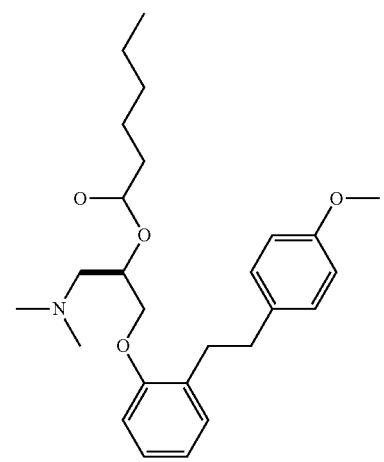
Compound 79
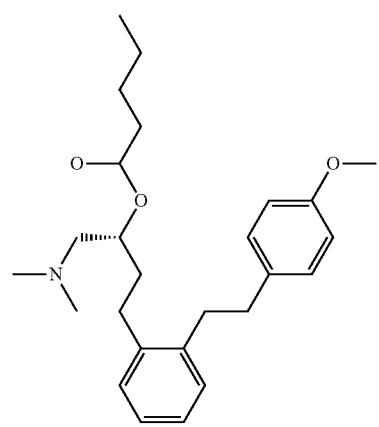
Compound 82
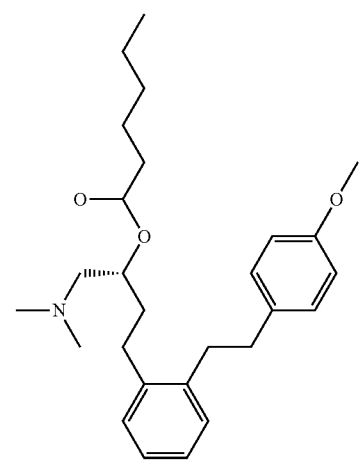
Compound 80
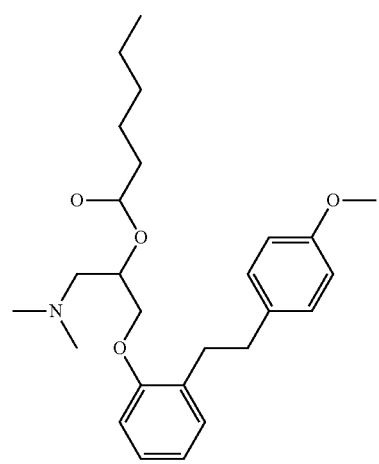
Compound 83
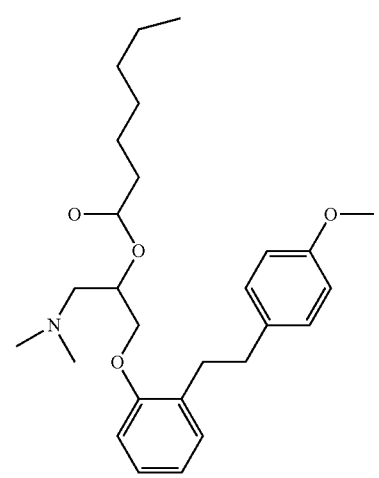

Compound 84
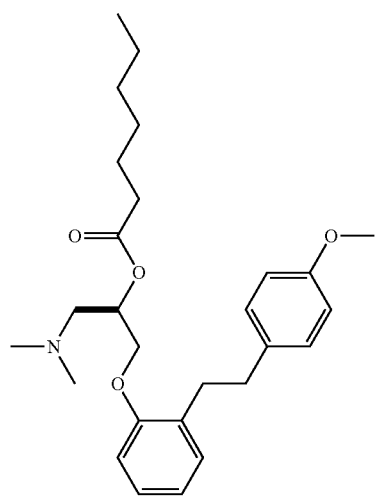
Compound 85
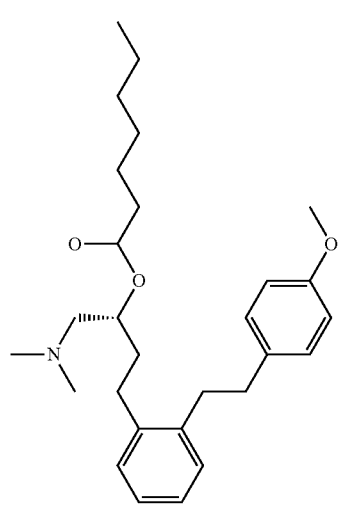
Compound 86
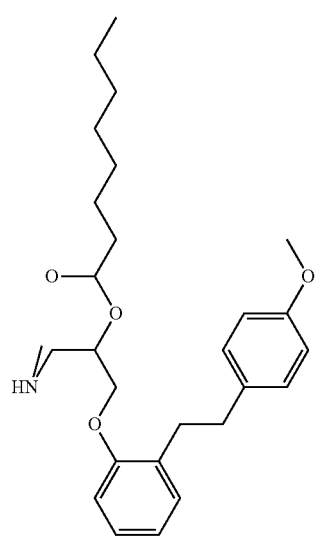
Compound 87
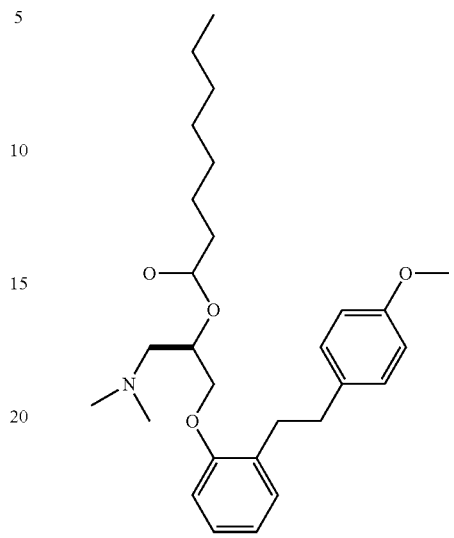
Compound 88
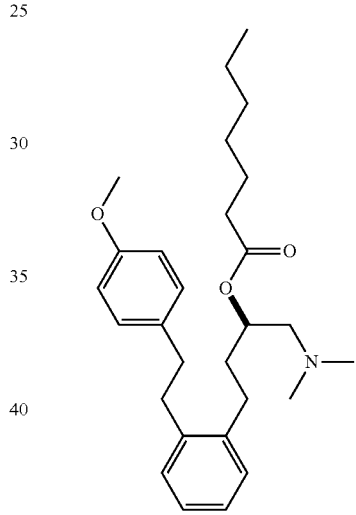
Compound 89
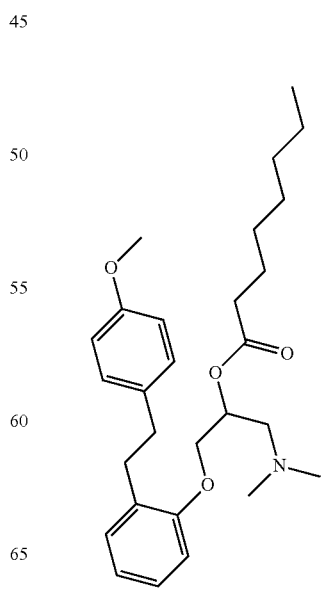

Compound 90
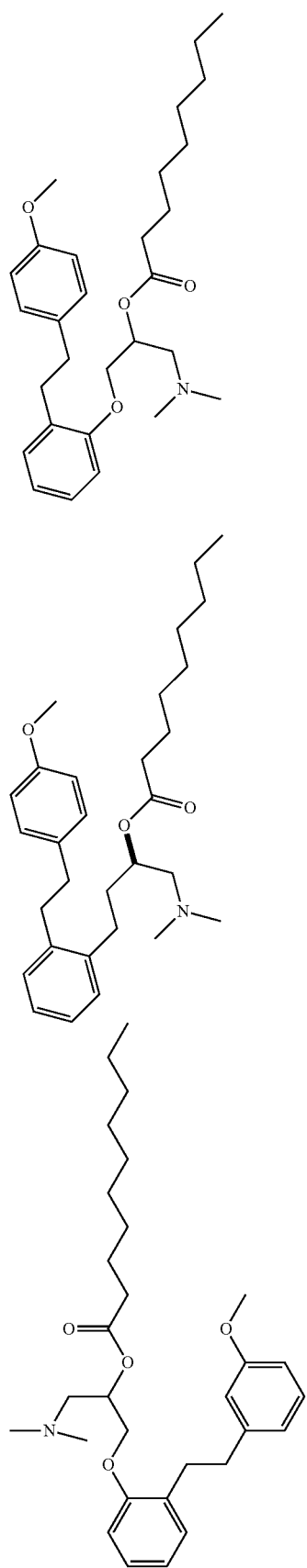
Compound 91
Compound 92
Compound 93
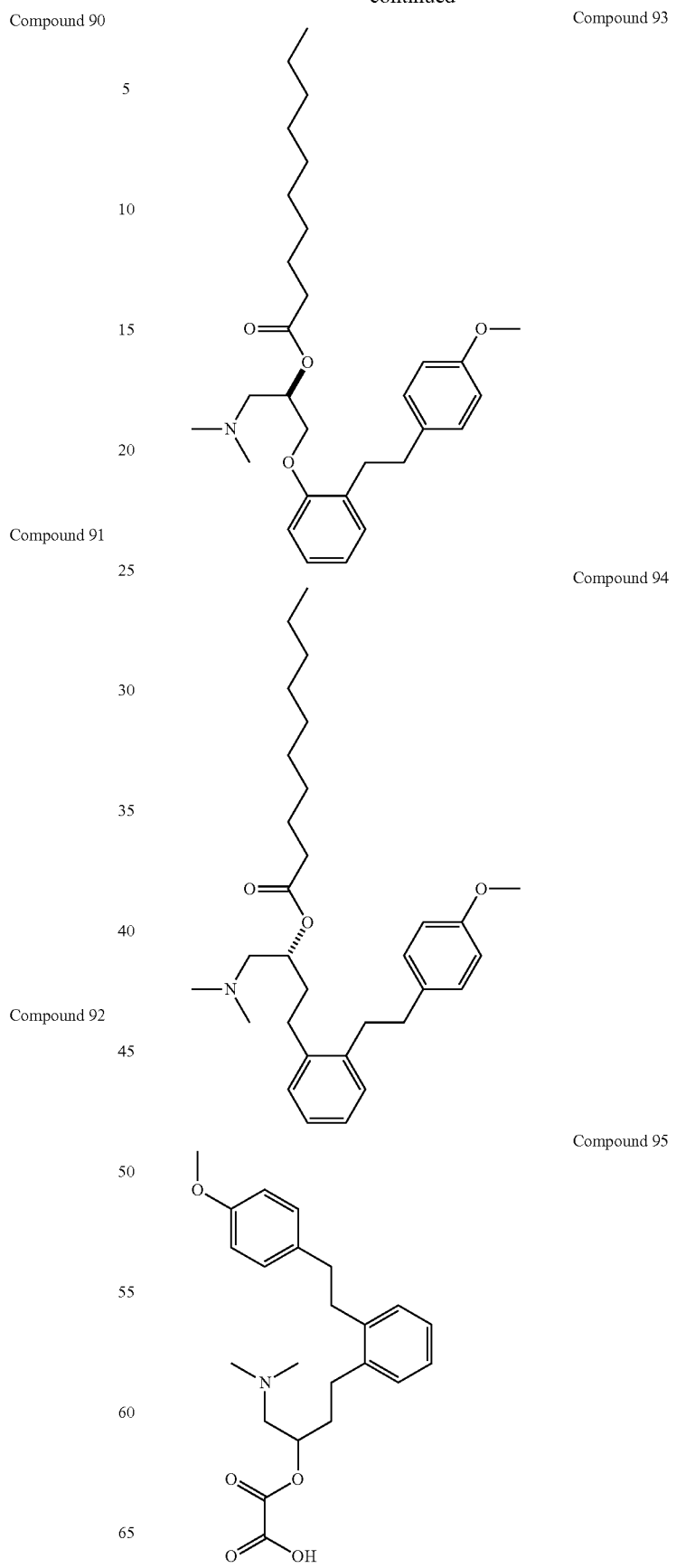
Compound 94
Compound 95

Compound 96
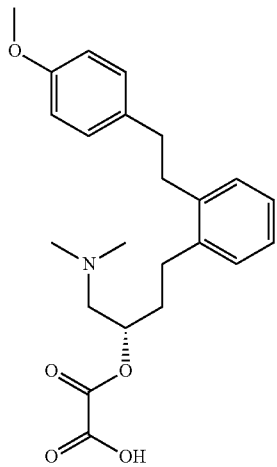
Compound 97
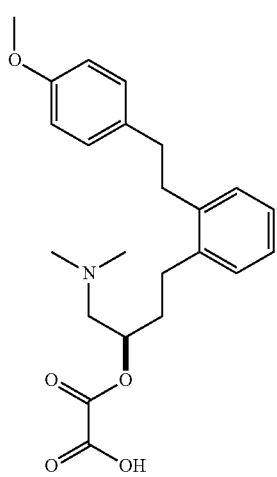
Compound 104
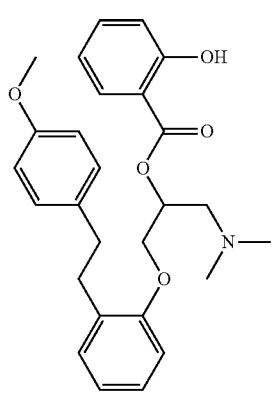
Compound 98
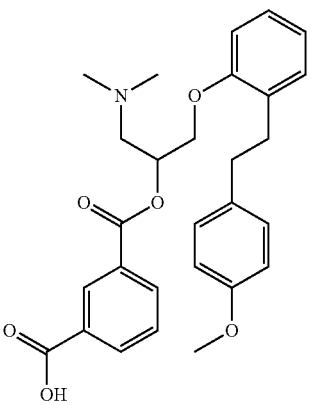
Compound 99
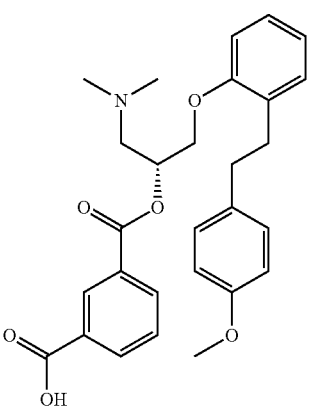
Compound 100
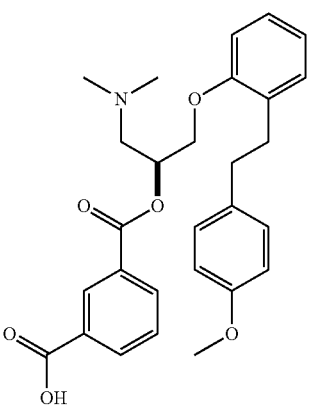
Compound 101
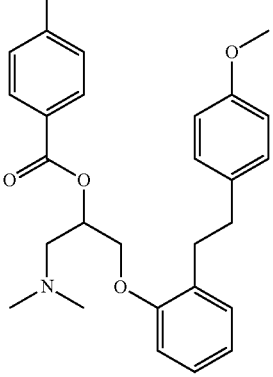

Compound 102
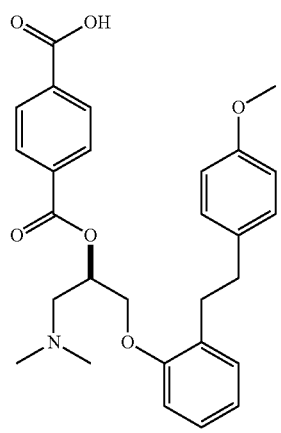
Compound 103
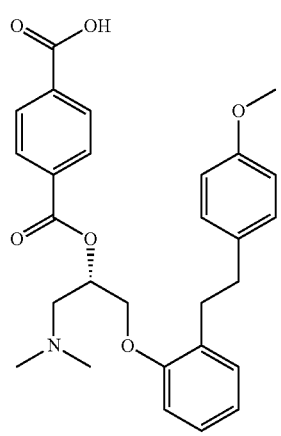
Compound 105
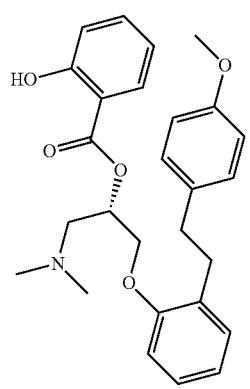
Compound 106
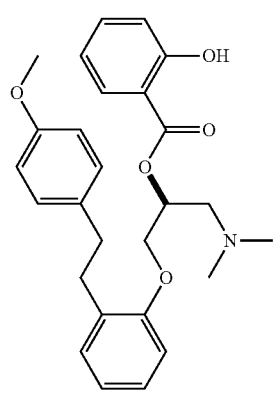
Compound 107
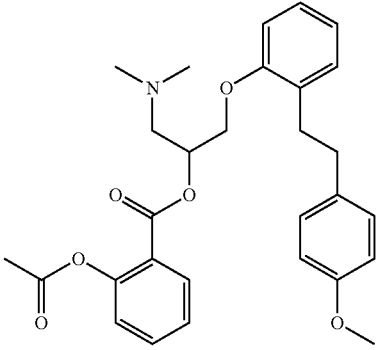
Compound 108
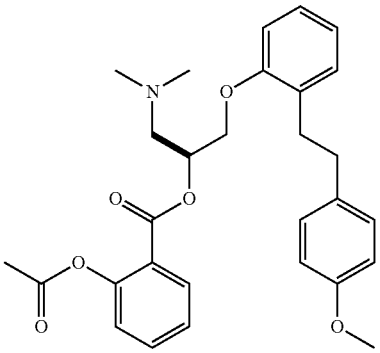
Compound 109
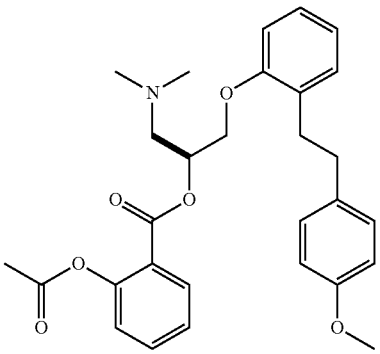
Compound 110
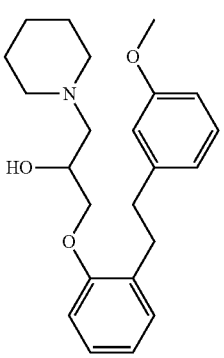

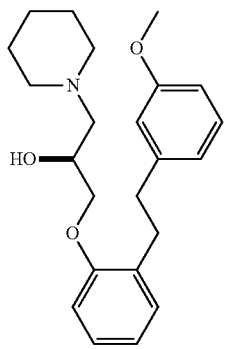
Compound 111
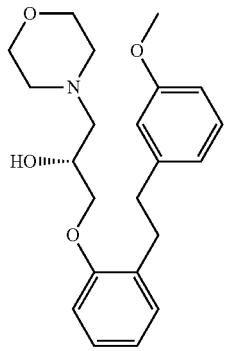
Compound 115
Compound 112
Compound 116
Compound 113
Compound 117
Compound 114
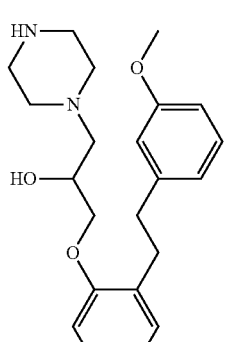
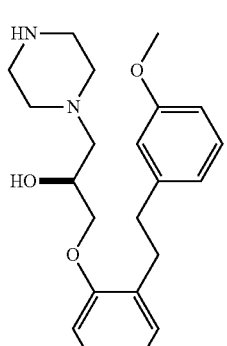
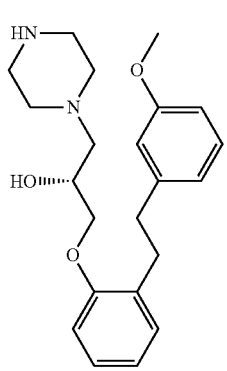
Compound 118

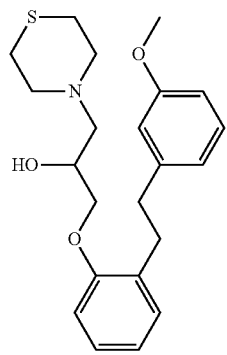 Compound 119
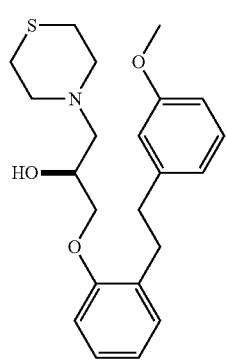 Compound 120
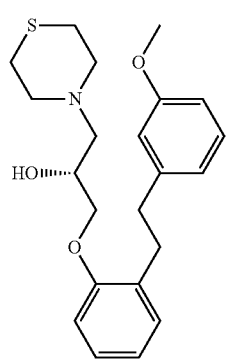 Compound 121
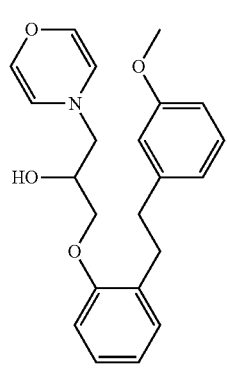 Compound 122
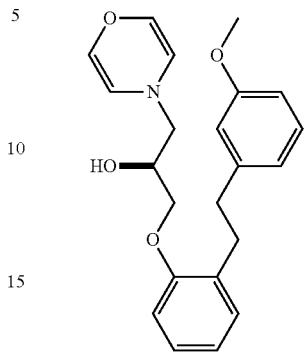 Compound 123
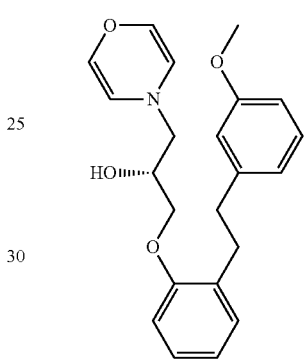 Compound 124
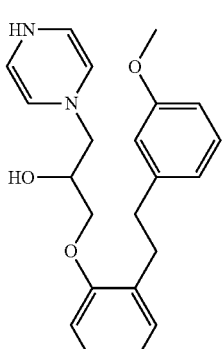 Compound 125
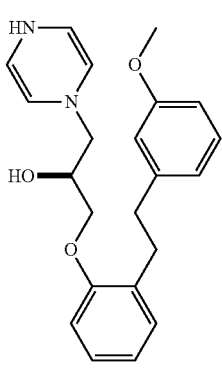 Compound 126

Compound 127
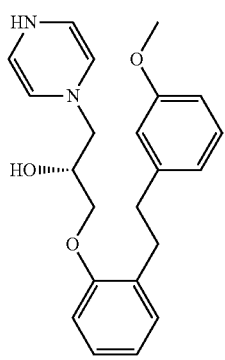
Compound 131
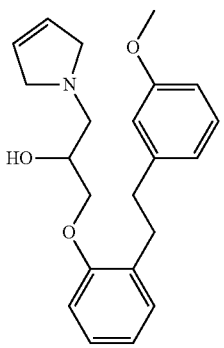
Compound 128
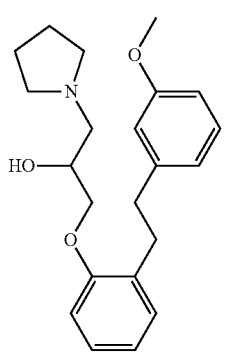
Compound 132
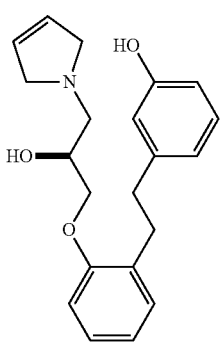
Compound 129
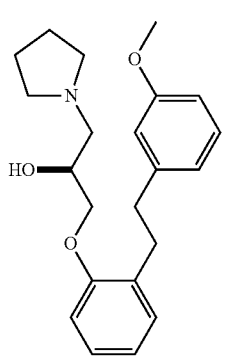
Compound 133
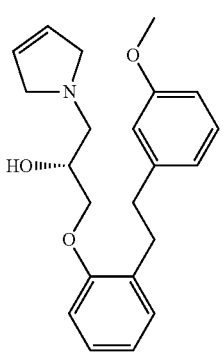
Compound 130
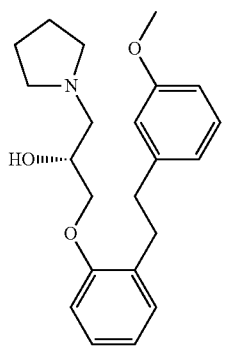
Compound 134
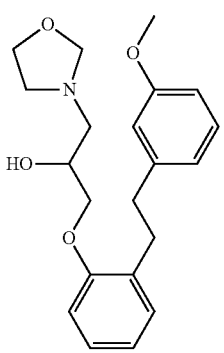

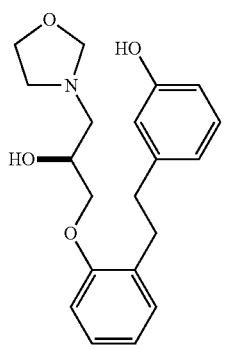
Compound 135
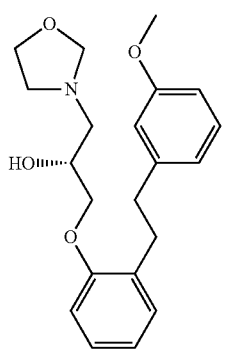
Compound 136
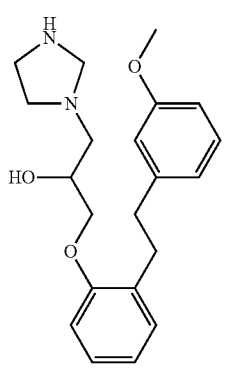
Compound 137
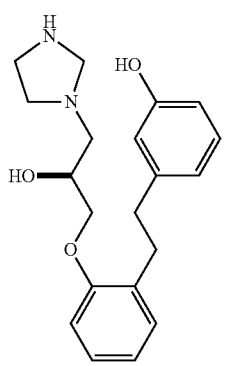
Compound 138
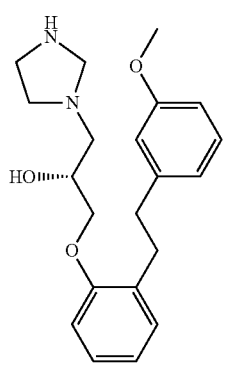
Compound 139
Compound 140
Compound 141
Compound 142

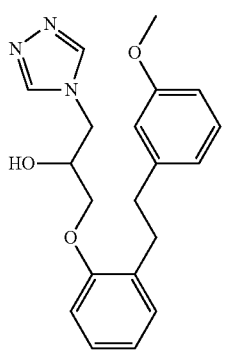
Compound 143
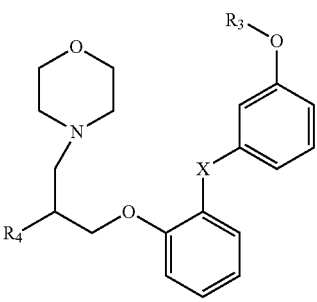
Formula Id
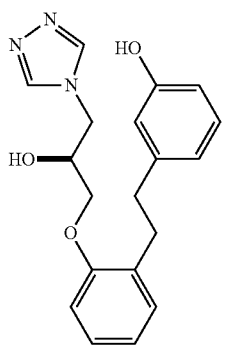
Compound 144
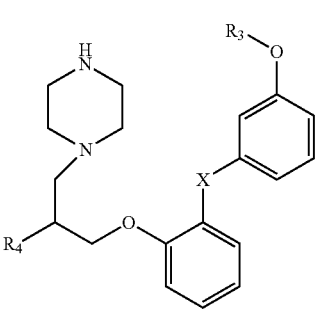
Formula Ie
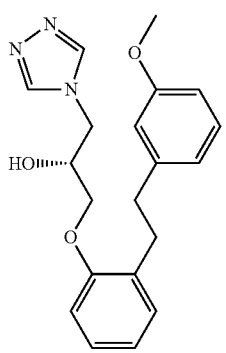
Compound 145
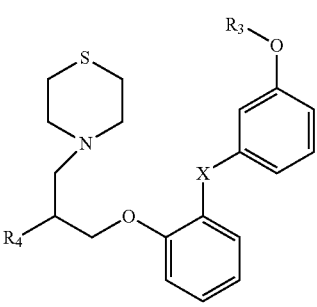
Formula If
In another embodiment, examples of the compound of formula I, wherein the heterocycle formed from $R_1$ and $R_2$ together with the nitrogen, represented by the compounds having Formulae Ic-Is comprising saturated (shown below) and unsaturated heterocycles:
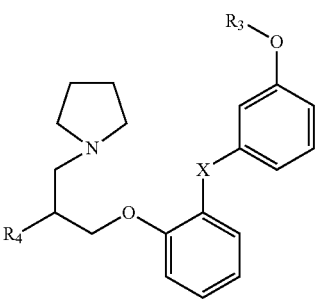
Formula Ig
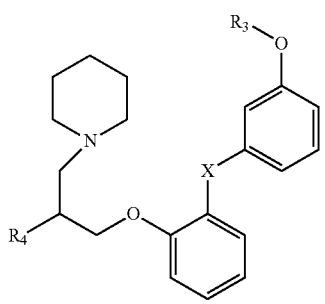
Formula Ic
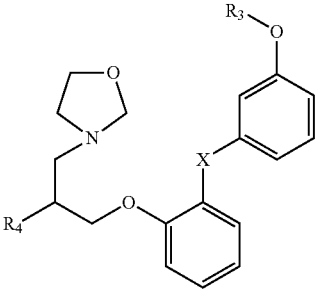
Formula Ih

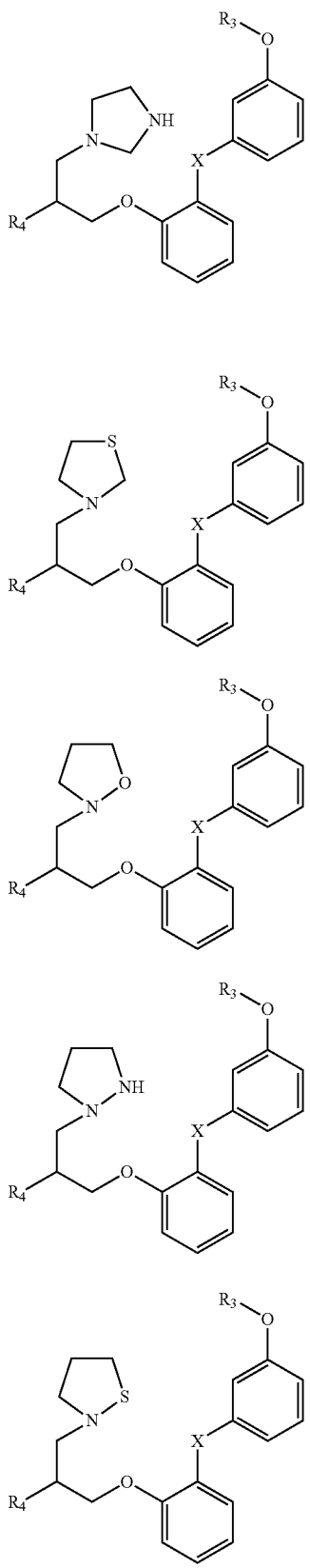
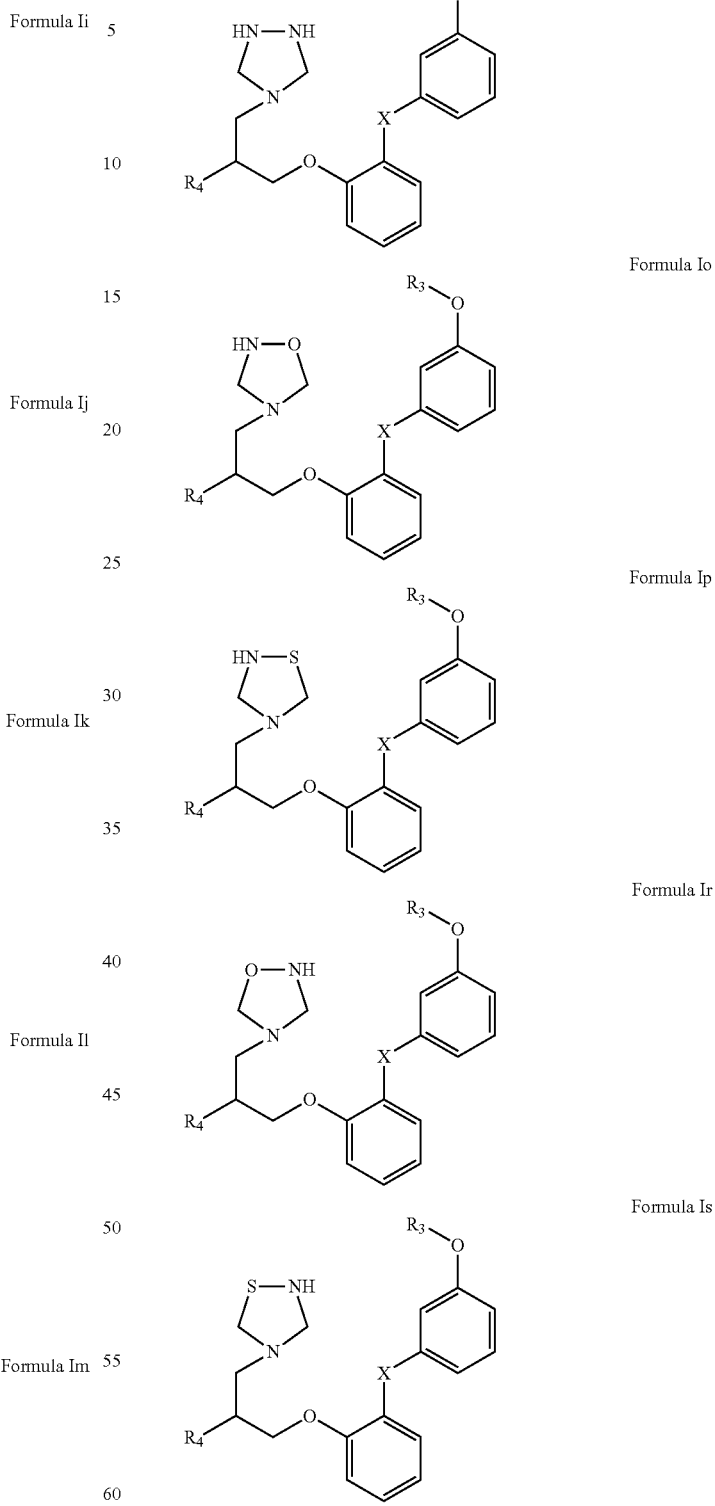
In another embodiment, the compound is a compound of Formulae Ic-Is, wherein the 5-membered heterocycle is unsaturated.
In another embodiment, the composition comprises DEX and a compound of formula I and/or prehexiline, flecainide, quinidine, (R)-propaphenone, (S)-propaphenone, isoniazid, (R)fluoxetine, (S)fluoxetine, nefazodone, paroxetine, ketoconazole, chloroquine, oxamniquine, primaquine, quinine, acetbutolol, betaxolol, bufuralol, oxprenolol, pindolol, propranolol, budipine, simvastatin, fluvastatin, lovastatin, pravastatin, perazine, ajamlicine, corynanthine, lobeline, or derivatives thereof.

In another embodiment, the composition comprising formula I, wherein $R_1$, $R_2$, and $R_3$ are methyl, X is ethyl, and R4 is OH, represented by the following compounds M1, M1-E1, and M1-E2.

Compound 146

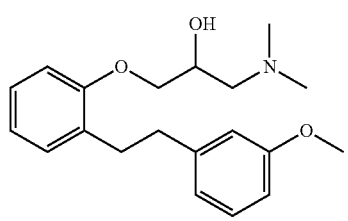

Racemate M1
1-(dimethylamino)-3-(2-(3-methoxyphenethyl)phenoxy)propan-2-ol

Compound 147

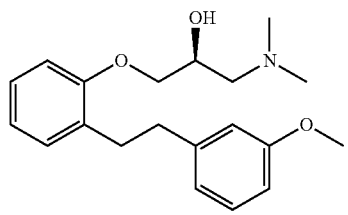

Enantiomer (M1-E1)
(S)-1-(dimethylamino)-3-(2-(3-methoxyphenethyl)phenoxy)propan-2-ol Compound 148

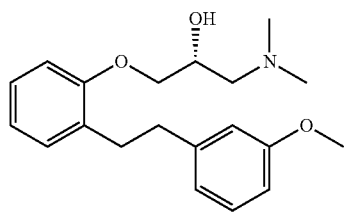

Enantiomer 2 (M1L-E2)
(R)-1-(dimethylamino)-3-(2-(3-methoxyphenethyl)phenoxy)propan-2-ol Compound 50

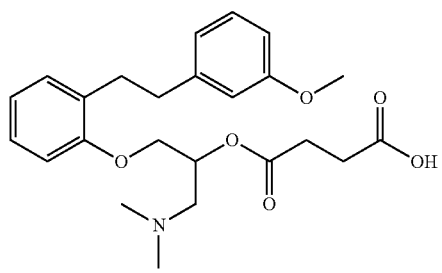

Sarpogrelate Racemate (SGL)
4-((1-(dimethylamino)-3-(2-(3-methoxyphenethyl)phenoxy)propan-2-yl)oxy)-4-oxobutanoic acid Compound 51

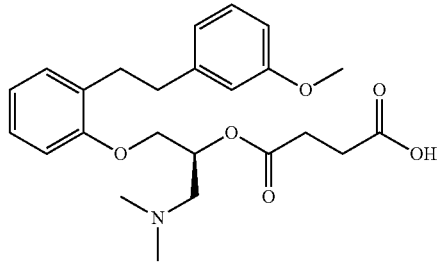

Sarpogrelate Enantiomer (SGL-E1)
(S)-4-((1-(dimethylamino)-3-(2-(3-methoxyphenethyl)phenoxy)propan-2-yl)oxy)-4-oxobutanoic acid Compound 52

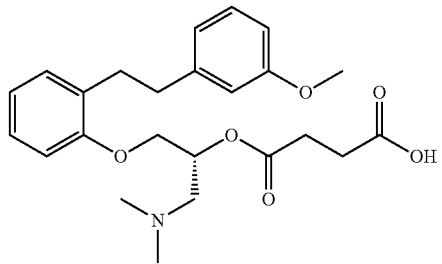

Sarpogrelate Enantiomer (SGL-E2)
(R)-4-((1-(dimethylamino)-3-(2-(3-methoxyphenethyl)phenoxy)propan-2-yl)oxy)-4-oxobutanoic acid In another embodiment, the composition comprising formula I, wherein $R_1$, $R_2$, and $R_3$ are methyl, X is ethyl, and R4 is succinoyl radical, represented by the following compounds SGL, SGL-E1, and SGL-E2.

In one embodiment, the composition comprises a formula I, wherein $R_5$ is —O(CO)—CH2-CH$_2$—(CO)O—Y, wherein an alkyl, cycloalkyl, aryl, heteroaryl, -akenyl-aryl, -aralkyl, alkyl-ONO$_2$, cycloalkyl-ONO$_2$, aryl-ONO$_2$, heteroaryl-ONO$_2$, -akenyl-aryl-ONO$_2$, and -aralkyl-ONO$_2$, as exemplified, but not limited to, the following: 1-(dimethylamino)-3-(2-(3-methoxyphenethyl)phenoxy)propan-2-yl methyl succinate, 1-(dimethylamino)-3-(2-(3-methoxyphenethyl)phenoxy)propan-2-yl ((nitrooxy)methyl) succinate, 1-(dimethylamino)-3-(2-(3-methoxyphenethyl) phenoxy) propan-2-yl (2-(nitrooxy)ethyl) succinate, 1-(dimethyl amino)-3-(2-(3-methoxyphenethyl)phenoxy)propan-2-yl(3-(nitrooxy)propyl)succinate, 1-(dimethyl amino)-3-(2-(3-methoxyphenethyl) phenoxy)propan-2-yl (4-(nitrooxy) butyl) succinate, 4-((1-(dimethylamino)-3-(2-(3-methoxyphenethyl) phenoxy)propan-2-yl)oxy)-4-oxobutanoic nitric anhydride, etc.

Compound 177
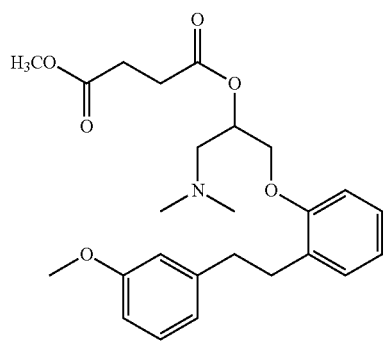
Compound 178
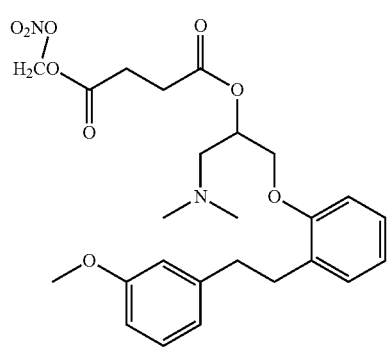
Compound 179
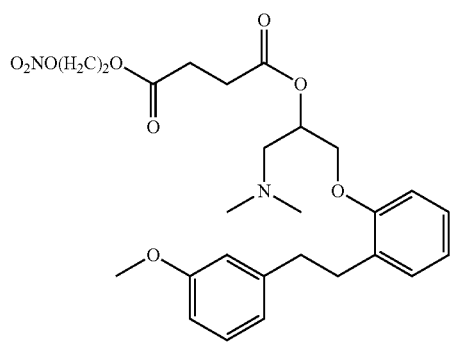
Compound 180
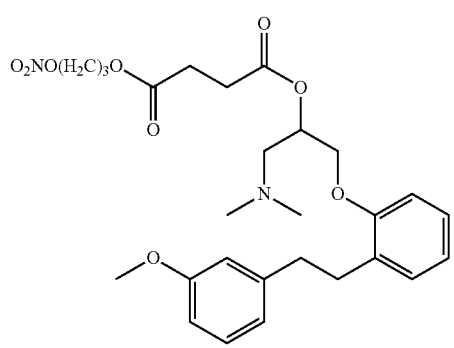
Compound 181
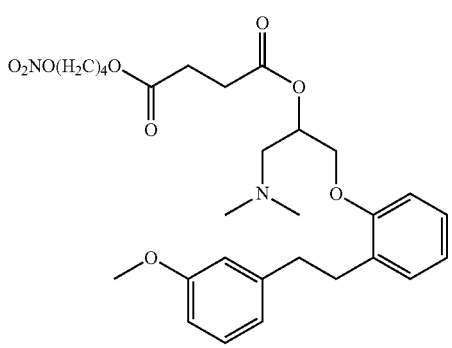
Compound 182
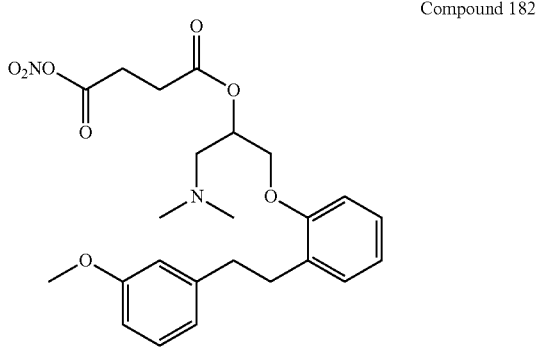
Compound 149
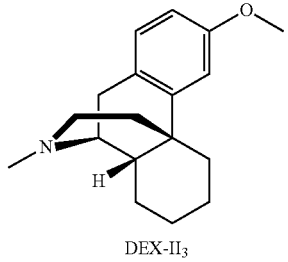
DEX-II$_3$
Compound 150
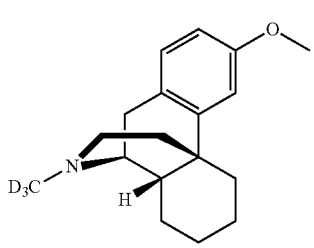
DEX-D$_3$
Compound 151
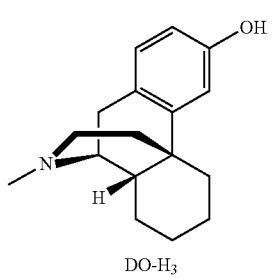
DO-H$_3$ -continued

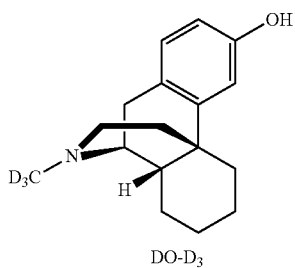
DO-D₃

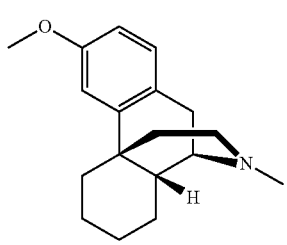

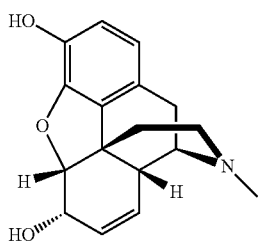

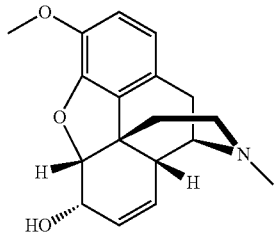

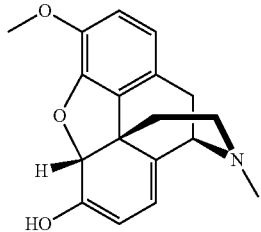

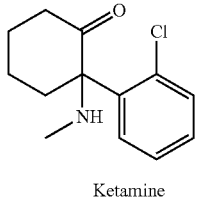
Ketamine

Compound 153

Compound 154

Compound 155

Compound 156

Compound 157

Compound 159

-continued

Compound 160
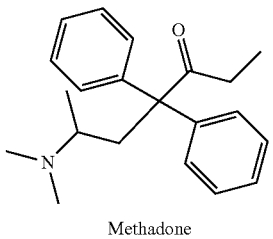
Methadone

Compound 161
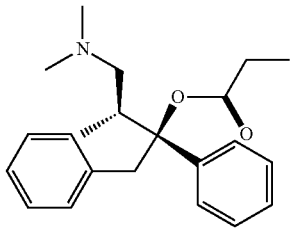
Dextro-propoxyphene

Compound 162
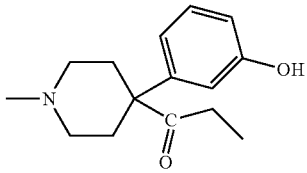
Ketobemidone

Compound 898
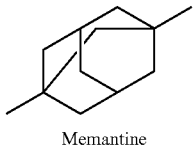
Memantine

Compound 899
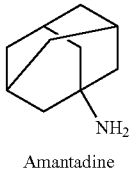
Amantadine

In one embodiment, the composition comprises DEX-H₃, DEX-D₃, DO, DO-D₃, levomethorphan, morphine, codeine, thebaine, benzocaine, ketamine, methadone, memantine (3,5-dimethyladamantan-1-amine), amantadine, dextropropoxyphene ((2R)-4-(dimethylamino)-3-methyl-1,2-diphenylbutan-2-yl propionate), ketobemidone (1-(4-(3-hydroxyphenyl)-1-methylpiperidin-4-yl)propan-1-one), tropane alkaloids such as cocaine, atropine, scopolamine, etc.

In another embodiment, the composition comprises a combination of a compound of Formula I and a compound of Formula II comprising DEX-H₃, DEX-D₃, DO, DO-D₃, levomethorphan, morphine, codeine, thebaine, or benzocaine; and/or ketamine, methadone, memantine, amantadine, dextropropoxyphene, ketobemidone, cocaine, atropine, or scopolamine.

In another embodiment, the composition comprises a combination of a compound of Formula I and ketamine, methadone, memantine, amantadine, dextropropoxyphene, ketobemidone, cocaine, atropine, or scopolamine, wherein the compound of Formula I is racemic compound 50 (sarpogrelate), racemic compound 146 (M1), or compound 829 (deramciclane). In another embodiment, the composition comprises memantine. In another embodiment, the composition comprises sarpogrelate and memantine. In another embodiment, the composition comprises enatimerically pure S-compound 51 (S-sarpogrelate) and R-compound 52 (R-sarpogrelate)) and memantine. In another embodiment, the composition comprises enatimerically pure S-compound 147 (S-M1), R-compound 148 (R-M1), and memantine. In another embodiment, the composition comprises enantiomerically pure deramciclane and memantine.

In another embodiment, the compound of the invention is a compound Formula I, wherein, R1, R2, and R3 are independently substituted with one, two or three halogens, wherein the halogen is F, Cl, or Br. Examples of fluorine derivatives of Formula I:

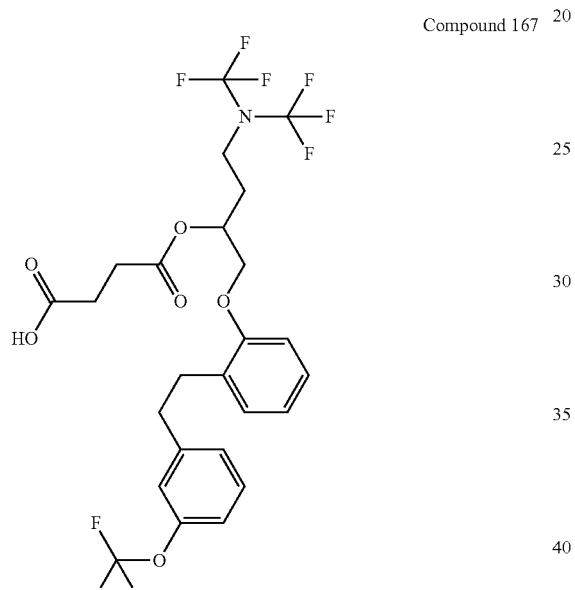

Compound 167

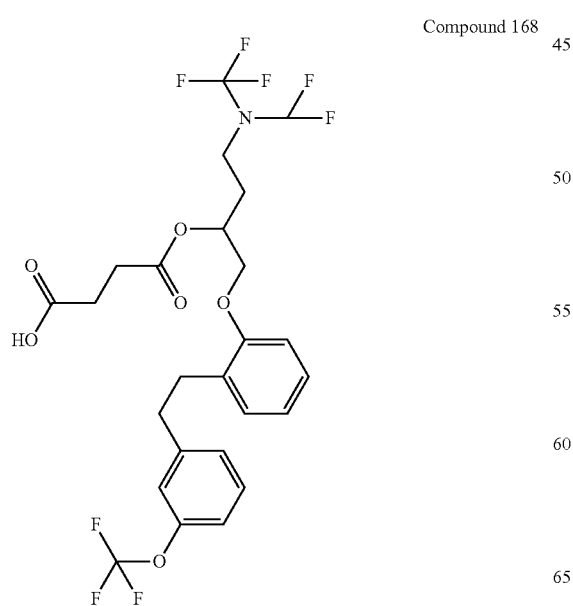

Compound 168

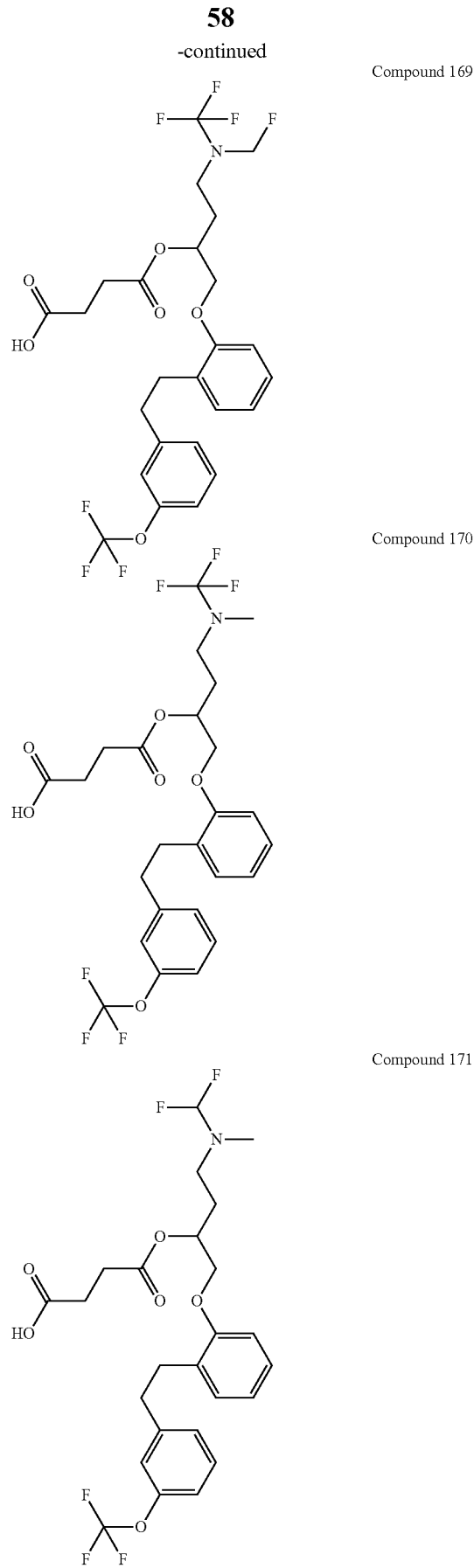

Compound 169

Compound 170

Compound 171

Compound 172

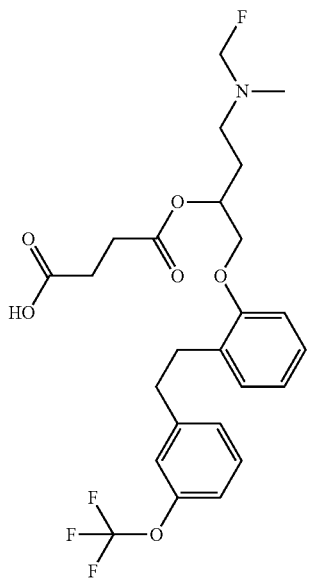

Compound 173

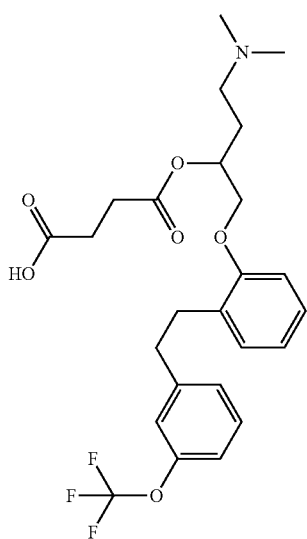

Compound 174

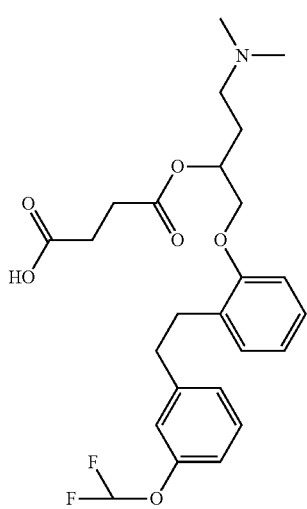

Compound 175

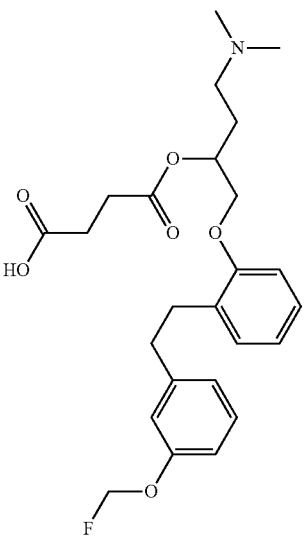

In another embodiment, a compound of Formula I or analogs can be made using the following carboxylic acids: difluorosuccinic acid, $HO_2C-CF_2-CH_2-CO_2H$ (201-206), trifluorosuccinic acid, $HO_2C-CF_2-CHF-CO_2H$ (207-212), tetrafluorosuccinic acid, $HO_2C-(CF_2)_2-CO_2H$, difluorosuccinic acid (213-215), $HO_2C-CHF-CHF-CO_2H$ (216-219), difluoroglutaric acid, $HO_2C-(CH_2)_2-CF_2-CO_2H$ (219-221), difluoroglutaric acid, $HO_2C-CF_2-(CH_2)_2-CO_2H$ (222-225), difluoroacetic acid, $HO_2C-CF_2H$ (226-228), and trifluoroacetic acid, $HO_2C-CF_3$ (229-231).

Compounds 201-203

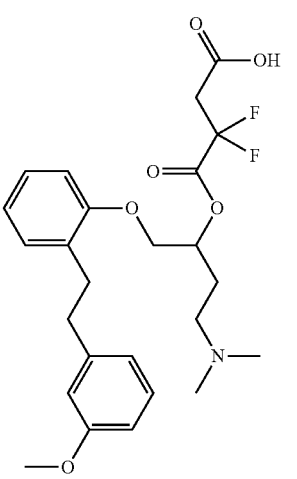

Compounds 204-206
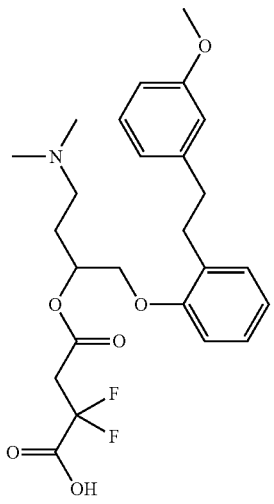
Compounds 207-209
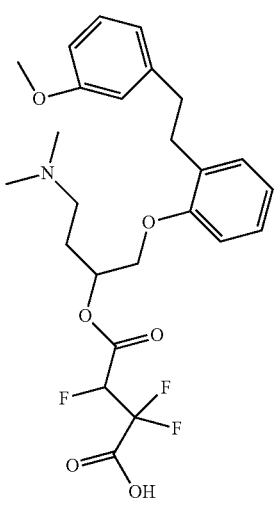
Compounds 210-212
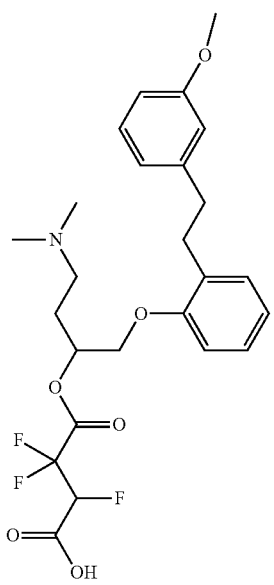
Compounds 216-218
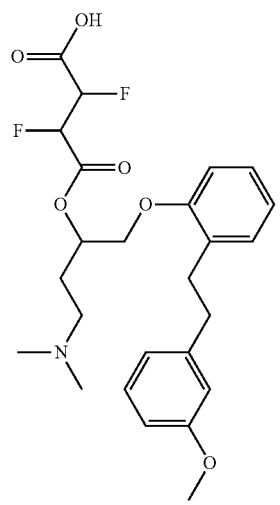
Compounds 213-215
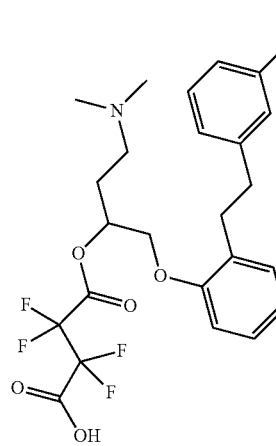
Compounds 219-221
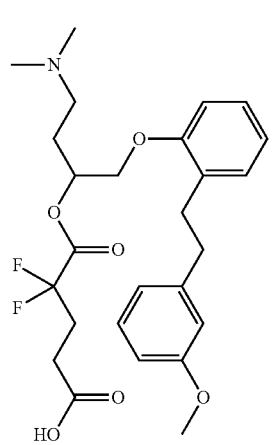

Compounds 222-224

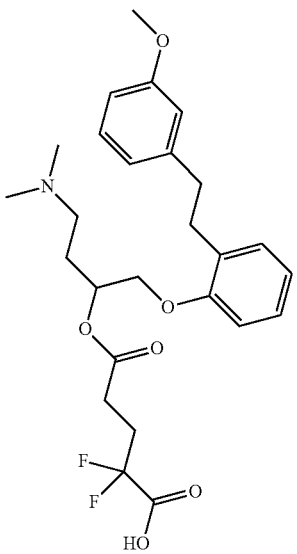

Compounds 226-228

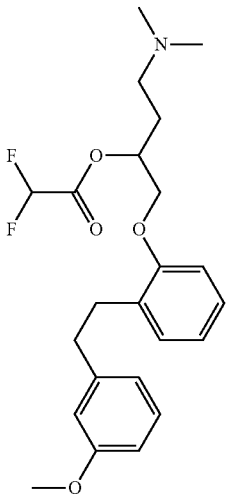

Compounds 229-231

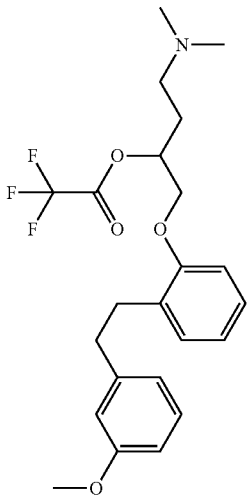

In another embodiment, a compound of Formula I is Formula Ic or Formula Id, as defined above, and derivatives thereof comprising acid addition salts selected from: acetate, acetyl salicylate, adipate, aspartate, butyrate, caprate, caproate, caprylate, enanthate, formate, fumarate, glutamate glutarate, isophthallate, maleate, malonate, methionate, oxalate, pelargonate, pimelate, propionate, phthallate, salicylate, sebacate, succinate, terephthallate, tyrosinate, tryptophanate, valerate, N-acyl-aspartate, N-acyl-glutamate, N-acyl-tyrosinate, N-acyl-tryptophanate, N-acyl-methionate, citrate, galactonate, glucaric acid (saccharic acid), mannonate, mucate, rhamnonate, and tartrate.

In another embodiment, a compound of Formula I is Formula Ic or Formula Id, as defined above, and derivatives thereof comprising acid addition salts formed from di and tri carboxylic acids selected from: adipic acid, aspartic acid, N-acyl aspartic acid, citric acid, fumaric acid, galactonic acid, glutaric acid, glutamic acid, N-acyl glutamic acid, glucaric acid (saccharic acid), malic acid, maleic acid, mannonic acid, mucic acid, oxalic acid, pimelic acid, phthallic acid, isophthallic acid, terephthallic acid, rhamnonic acid, sebacic acid, succinic acid, and tartaric acid.

Another embodiment is a composition comprising a derivative of a compound of Formula Ic or Formula Id, and a derivative of a compound of Formula II, wherein the derivative of Formula Ic, Formula Id, and Formula II thereof is independently an acid addition salt: hydrogen acetate, hydrogen acetyl salicylate, hydrogen adipate, hydrogen aspartate, hydrogen butyrate, hydrogen caprate, hydrogen caproate, hydrogen caprylate, hydrogen enanthate, hydrogen formate, hydrogen fumarate, hydrogen glutamate, hydrogen glutarate, hydrogen isophthallate, hydrogen maleate, hydrogen malonate, hydrogen methionate, hydrogen oxalate, hydrogen pelargonate, hydrogen pimelate, hydrogen propionate, hydrogen phthallate, hydrogen salicylate, hydrogen sebacate, hydrogen succinate, hydrogen terephthallate, hydrogen tyrosinate, hydrogen tryptophanate, hydrogen valerate, hydrogen N-acyl-aspartate, hydrogen N-acyl-glutamate, hydrogen N-acyl-tyrosinate, hydrogen N-acyl-tryptophanate, hydrogen N-acyl-methionate, hydrogen citrate, hydrogen galactonate, hydrogen glucaric acid (saccharic acid), hydrogen mannonate, hydrogen mucate, hydrogen rhamnonate, and hydrogen tartrate.

Another embodiment is a composition comprising an acid addition salt of dextromethorphan and M1 selected from: dextromethorphan and M1 dihydrogen adipate, dextromethorphan and M1 dihydrogen aspartate, dextromethorphan and M1 dihydrogen fumarate, dextromethorphan and M1 dihydrogen glutamate, dextromethorphan and M1 dihydrogen glutarate, dextromethorphan and M1 dihydrogen isophthallate, dextromethorphan and M1 dihydrogen maleate, dextromethorphan and M1 dihydrogen malonate, dextromethorphan and M1 dihydrogen oxalate, dextromethorphan and M1 dihydrogen pimelate, dextromethorphan and M1 dihydrogen phthallate, dextromethorphan and M1 dihydrogen sebacate, dextromethorphan and M1 dihydrogen succinate, dextromethorphan and M1 dihydrogen terephthallate, dextromethorphan and M1 dihydrogen N-acyl-aspartate, dextromethorphan and M1 dihydrogen N-acyl-glutamate, dextromethorphan and M1 dihydrogen citrate, dextromethorphan and M1 dihydrogen galactonate, dextromethorphan and M1 dihydrogen glucarate, dextromethorphan and M1 di hydrogen saccharate, dextromethorphan and M1 dihydrogen mannonate, dextromethorphan and M1 dihydrogen mucate, dextromethorphan and M1 dihydrogen rhamnonate, and dextromethorphan and M1 dihydrogen tartrate.

In another embodiment, a compound of Formula I is Formula Ic or Formula Id, as defined above, and fluoro derivatives thereof. In another embodiment, a compound of Formula I is a compound of Formula Ic or Formula Id, wherein the compound is Fluoro Derivative (FD) of Formula Ic (FDIc) or Formula Id (FDId), selected from compounds 221-269, and dextromethorphan or a compound of Formula II as defined above.

Another embodiment is a composition comprising an acid addition salt of dextromethorphan and FDIc selected from: dextromethorphan and FDIc dihydrogen adipate, dextromethorphan and FDIc dihydrogen aspartate, dextromethorphan and FDIc dihydrogen fumarate, dextromethorphan and FDIc dihydrogen glutamate, dextromethorphan and FDIc dihydrogen glutarate, dextromethorphan and FDIc dihydrogen isophthallate, dextromethorphan and FDIc dihydrogen maleate, dextromethorphan and FDIc dihydrogen malonate, dextromethorphan and FDIc dihydrogen oxalate, dextromethorphan and FDIc dihydrogen pimelate, dextromethorphan and FDIc dihydrogen phthallate, dextromethorphan and FDIc dihydrogen sebacate, dextromethorphan and FDIc dihydrogen succinate, dextromethorphan and FDIc dihydrogen terephthallate, dextromethorphan and FDIc dihydrogen N-acyl-aspartate, dextromethorphan and FDIc dihydrogen N-acyl-glutamate, dextromethorphan and FDIc dihydrogen citrate, dextromethorphan and FDIc dihydrogen galactonate, dextromethorphan and FDIc dihydrogen glucarate, dextromethorphan and FDIc di hydrogen saccharate, dextromethorphan and FDIc dihydrogen mannonate, dextromethorphan and FDIc dihydrogen mucate, dextromethorphan and FDIc dihydrogen rhamnonate, and dextromethorphan and FDIc dihydrogen tartrate.

Compound 231-233

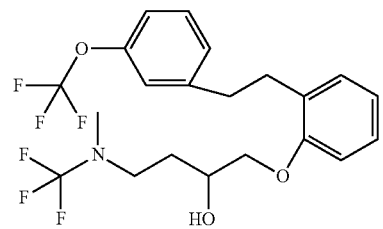

Compound 234-236

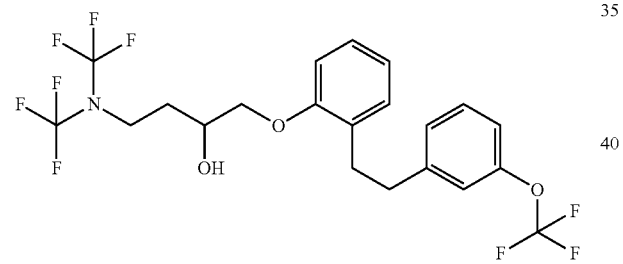

Compound 237-9

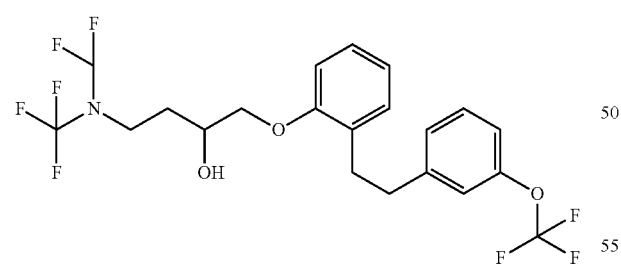

Compound 240-2

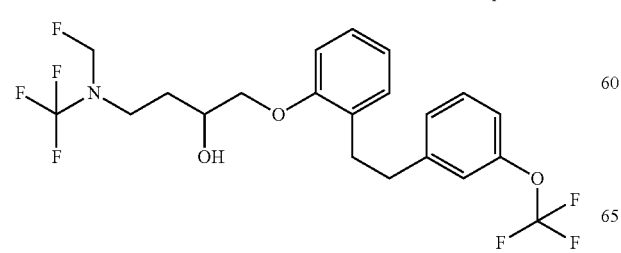

-continued

Compound 243-5

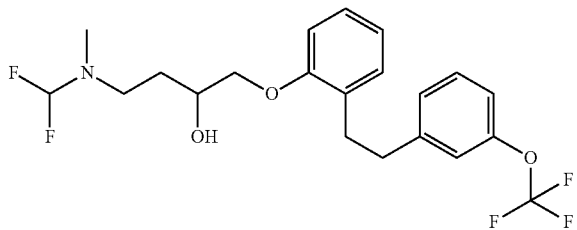

Compound 246-8

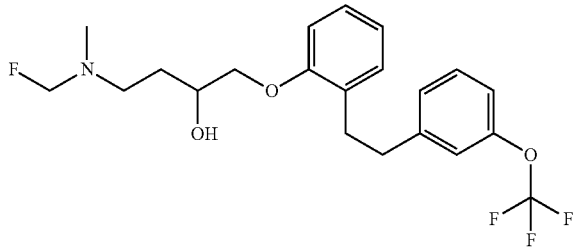

Compound 249-251

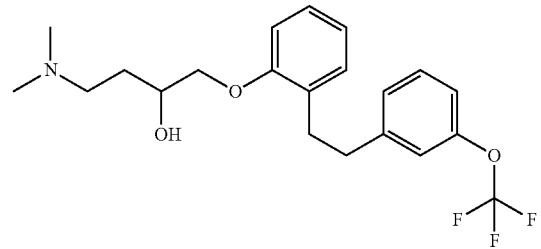

Compound 252-4

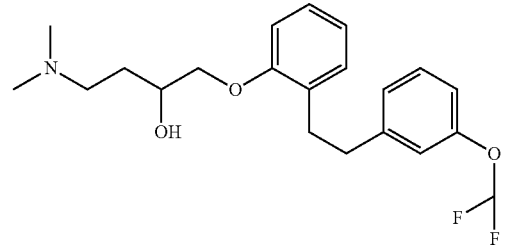

Compound 255-7

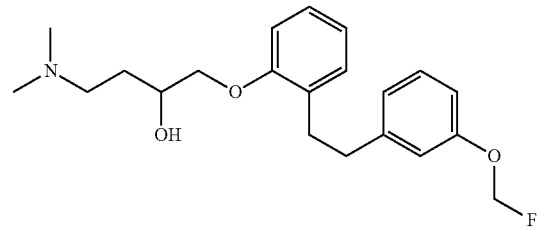

Compound 258-60
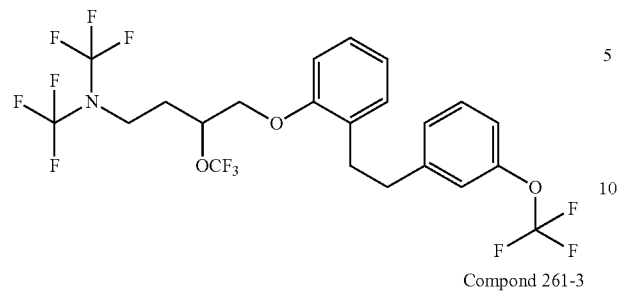
Compound 261-3
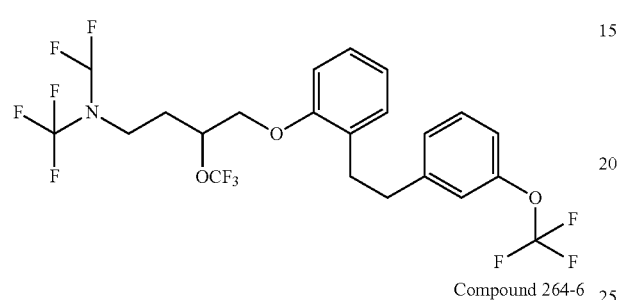
Compound 264-6
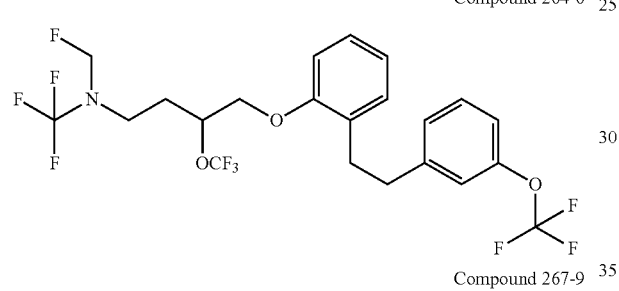
Compound 267-9
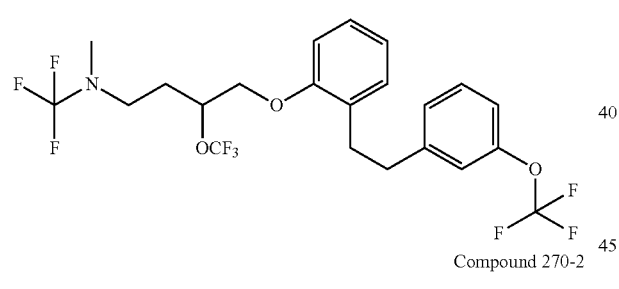
Compound 270-2
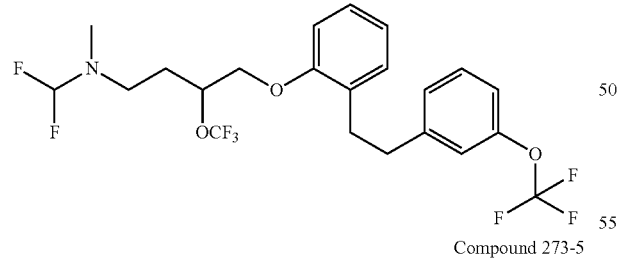
Compound 273-5
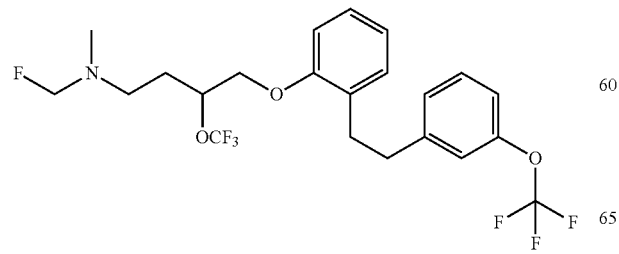
Compound 276-278
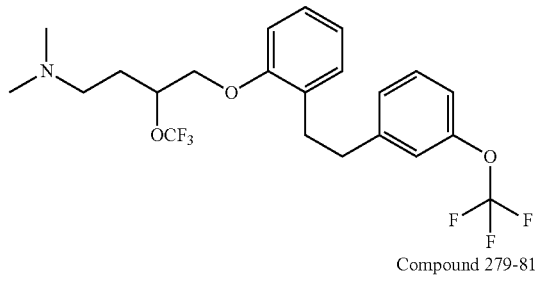
Compound 279-81
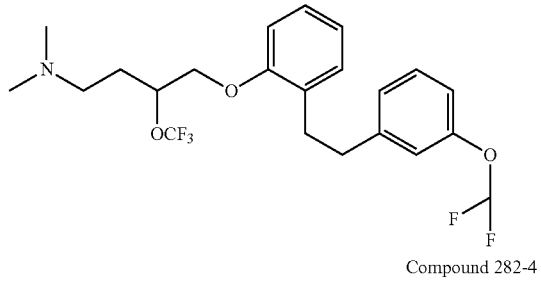
Compound 282-4
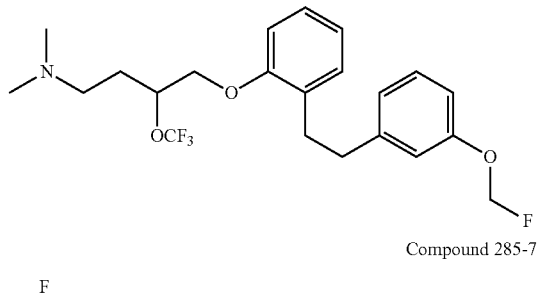
Compound 285-7
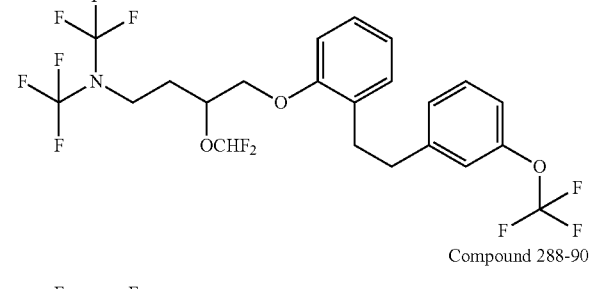
Compound 288-90
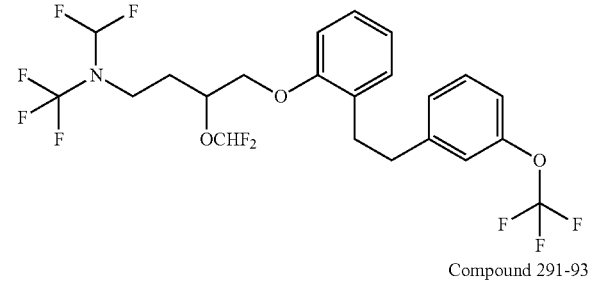
Compound 291-93
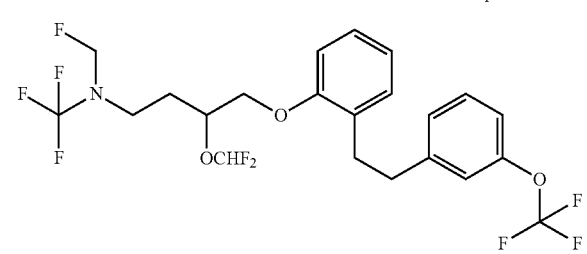

Compound 294-96
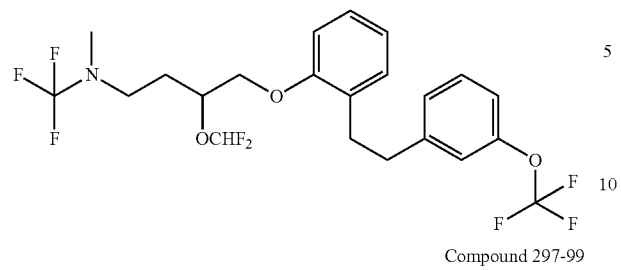
Compound 297-99
Compound 300-2
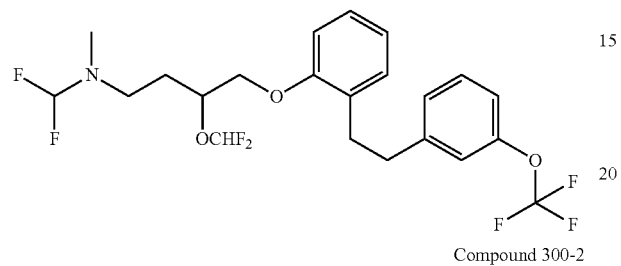
Compound 303-5
Compound 306-8
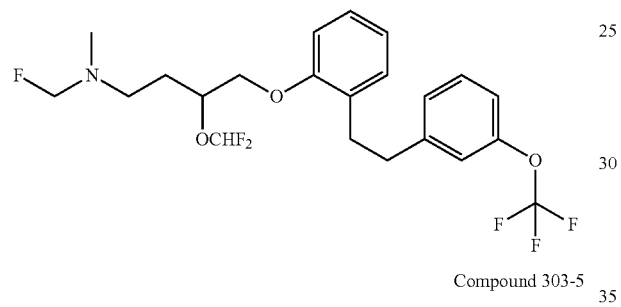
Compound 309-11
Compound 312-14
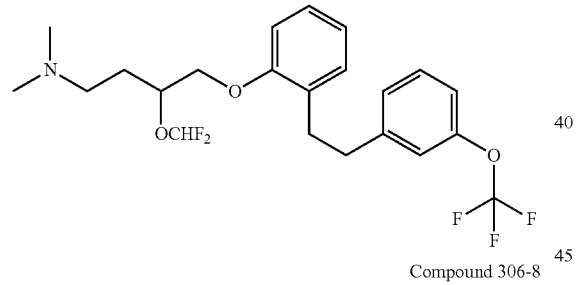
Compound 315-7
Compound 318-20
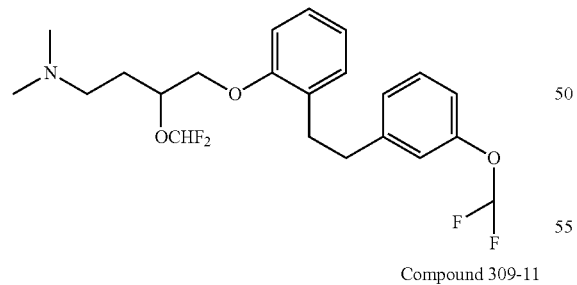
Compound 321-3
Compound 324-326
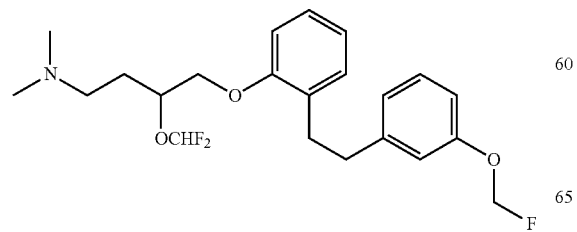
Compound 327-329

Compound 330-32
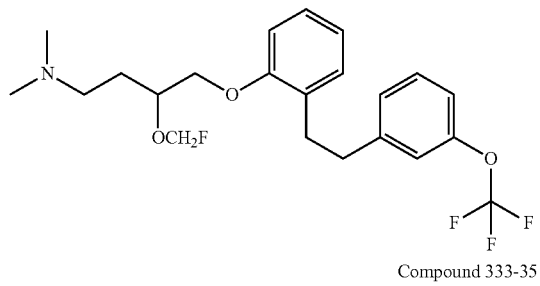
Compound 348-350
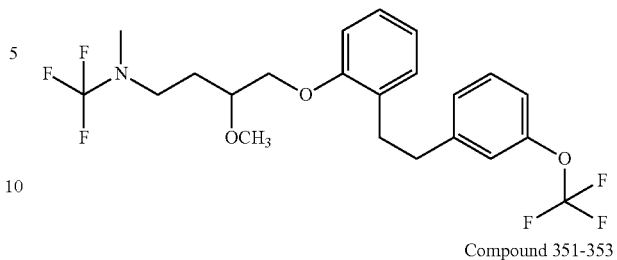
Compound 333-35
Compound 351-353
Compound 336-8
Compound 354-356
Compound 239-41
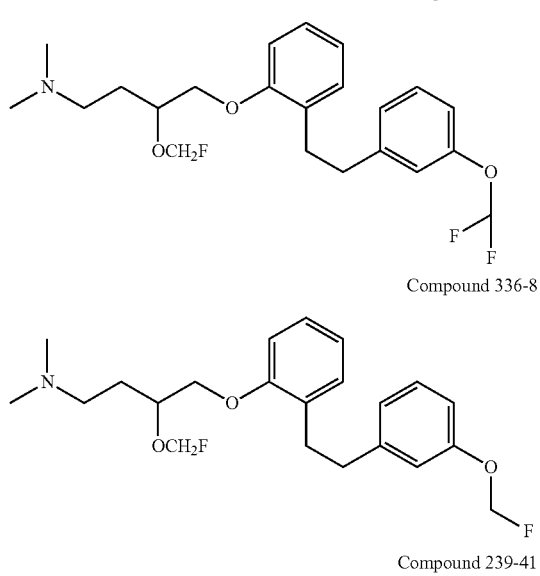
Compound 357-359
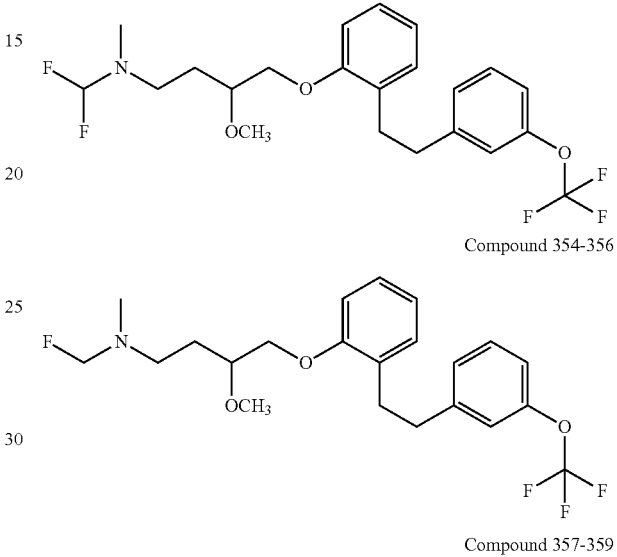
Compound 342-4
Compound 360-362
Compound 345-347
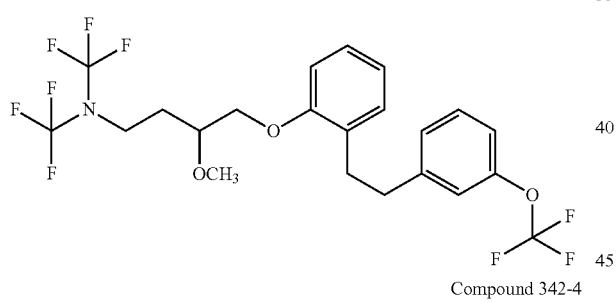
Compound 363-365
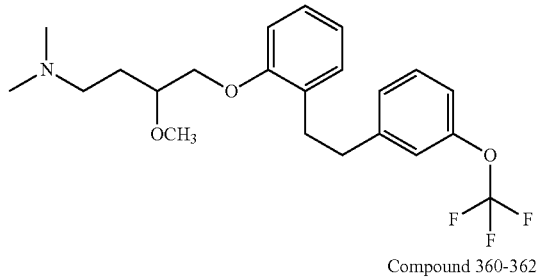
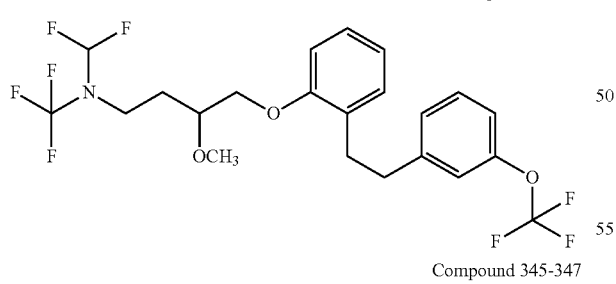
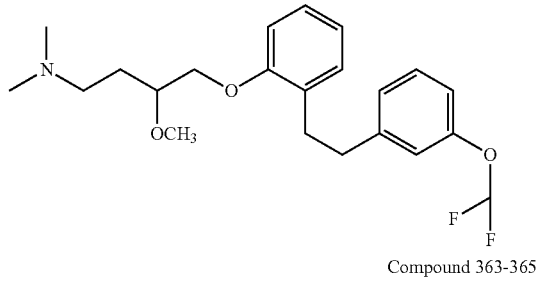
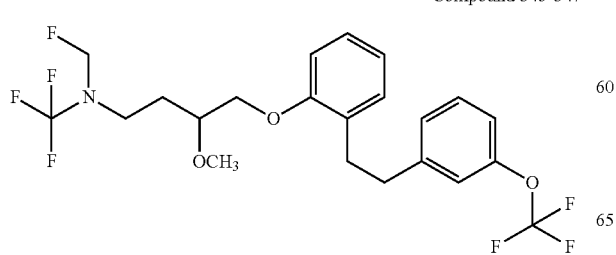
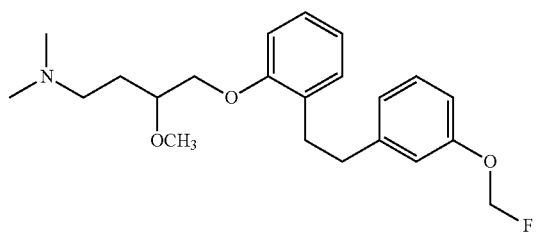

Another embodiment is a composition comprising an acid addition salt of dextromethorphan and FDId selected from: dextromethorphan and FDId dihydrogen adipate, dextromethorphan and FDId dihydrogen aspartate, dextromethorphan and FDId dihydrogen fumarate, dextromethorphan and FDId dihydrogen glutamate, dextromethorphan and FDId dihydrogen glutarate, dextromethorphan and FDId dihydrogen isophthallate, dextromethorphan and FDId dihydrogen maleate, dextromethorphan and FDId dihydrogen malonate, dextromethorphan and FDId dihydrogen oxalate, dextromethorphan and FDId dihydrogen pimelate, dextromethorphan and FDId dihydrogen phthallate, dextromethorphan and FDId dihydrogen sebacate, dextromethorphan and FDId dihydrogen succinate, dextromethorphan and FDId dihydrogen terephthallate, dextromethorphan and FDId dihydrogen N-acyl-aspartate, dextromethorphan and FDId dihydrogen N-acyl-glutamate, dextromethorphan and FDId dihydrogen citrate, dextromethorphan and FDId dihydrogen galactonate, dextromethorphan and FDId dihydrogen glucarate, dextromethorphan and FDId di hydrogen saccharate, dextromethorphan and FDId dihydrogen mannonate, dextromethorphan and FDId dihydrogen mucate, dextromethorphan and FDId dihydrogen rhamnonate, and dextromethorphan and FDId dihydrogen tartrate.

In another aspect of the inventions, the compound is a compound of Formula I derivatives include the following compounds:

365-367

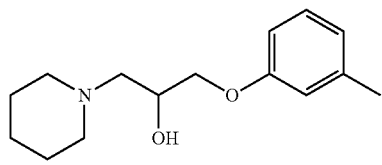

368-370

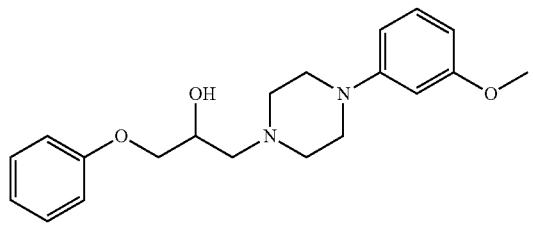

371-373

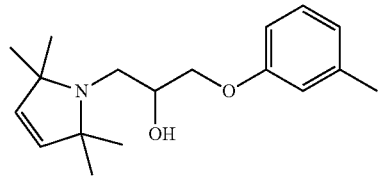

374-376

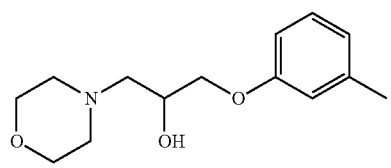

377-379

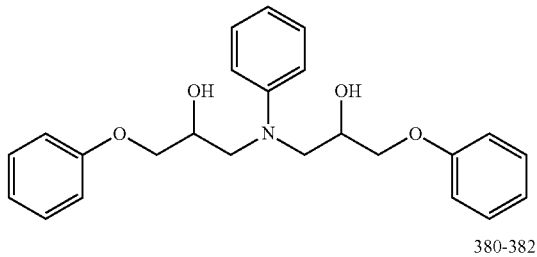

380-382

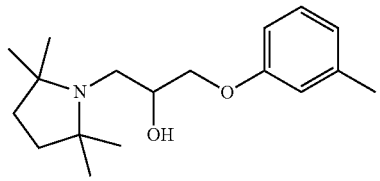

383-385

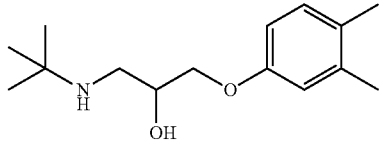

386-388

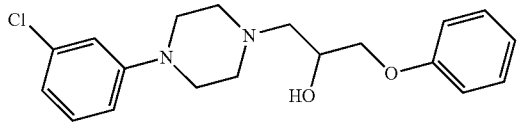

389-391

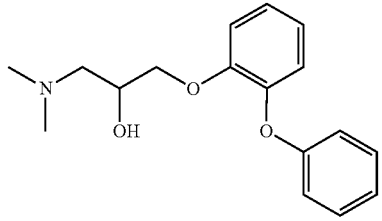

392-394

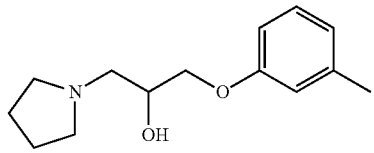

395-397

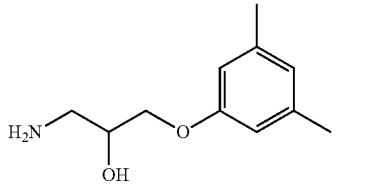

398-400

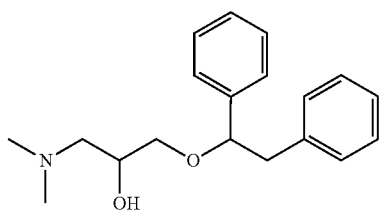

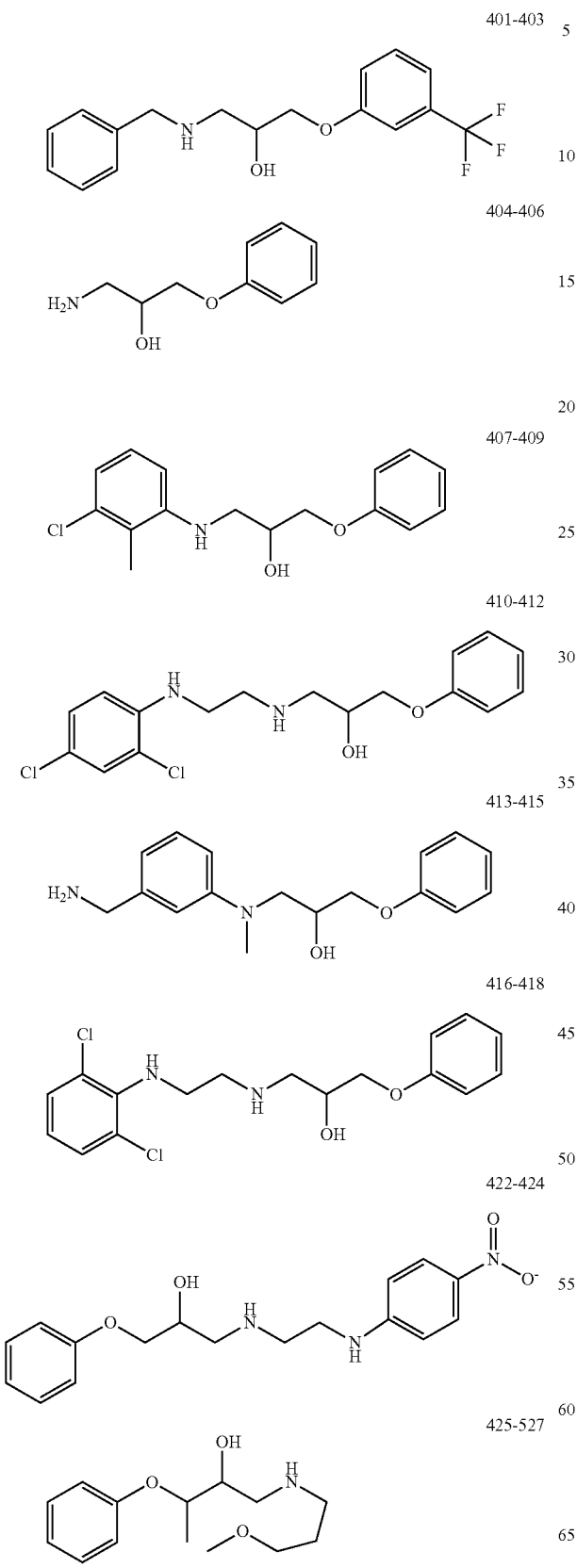
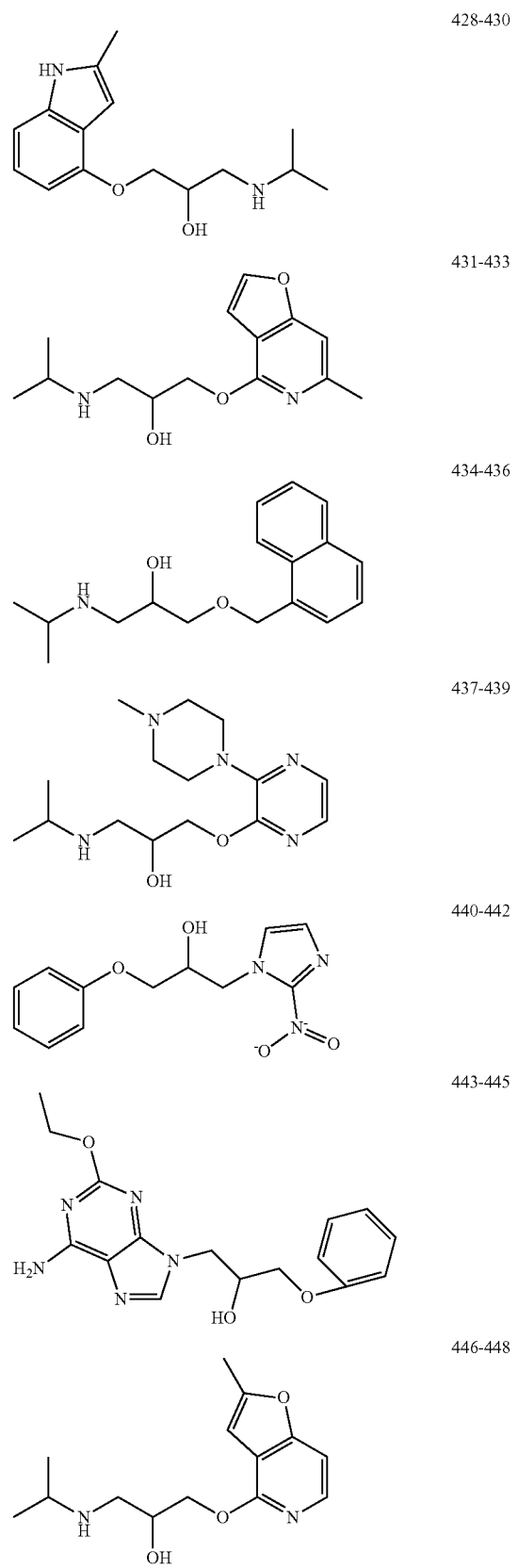

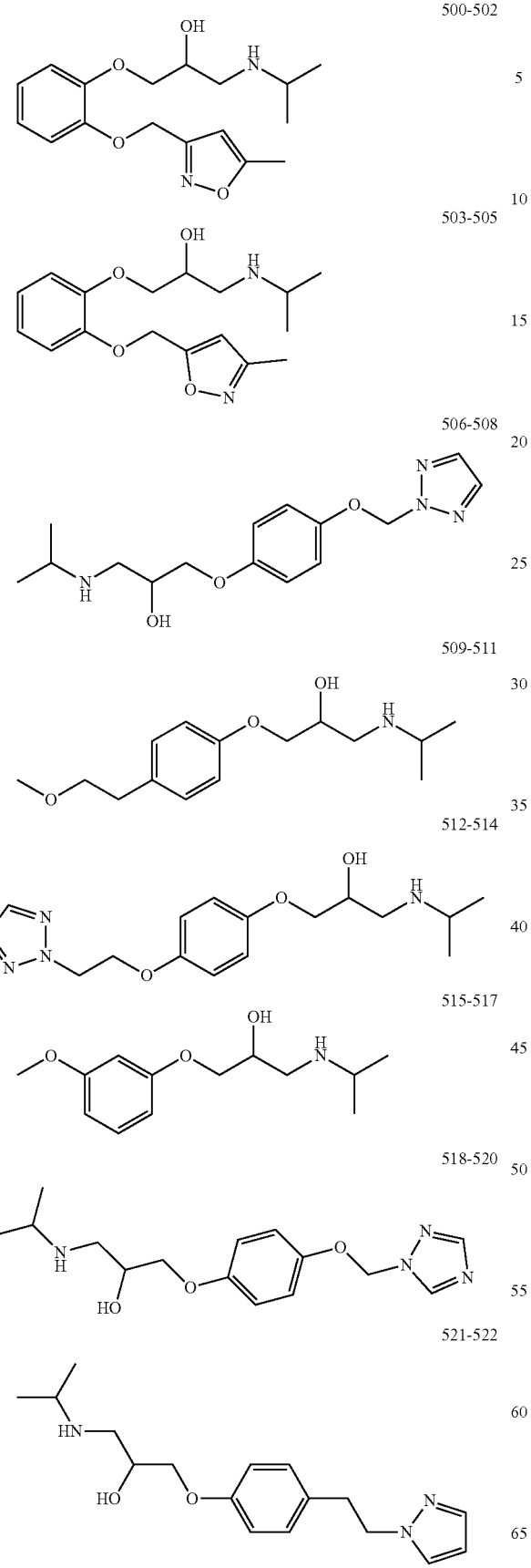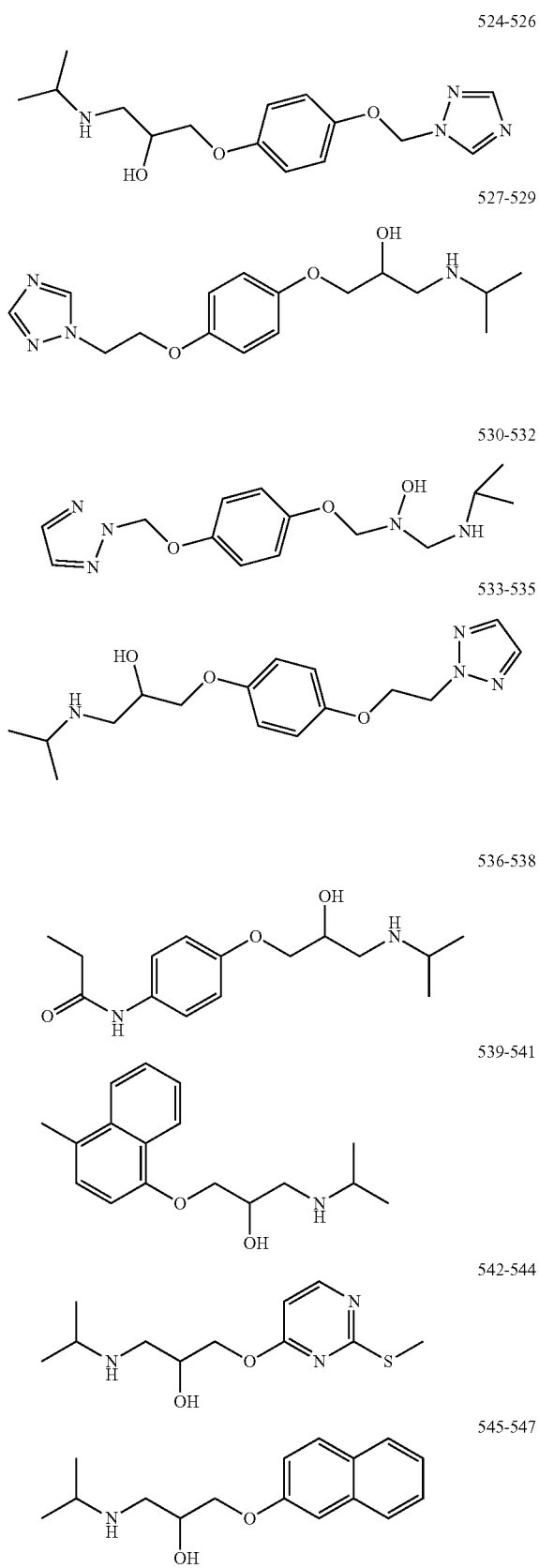

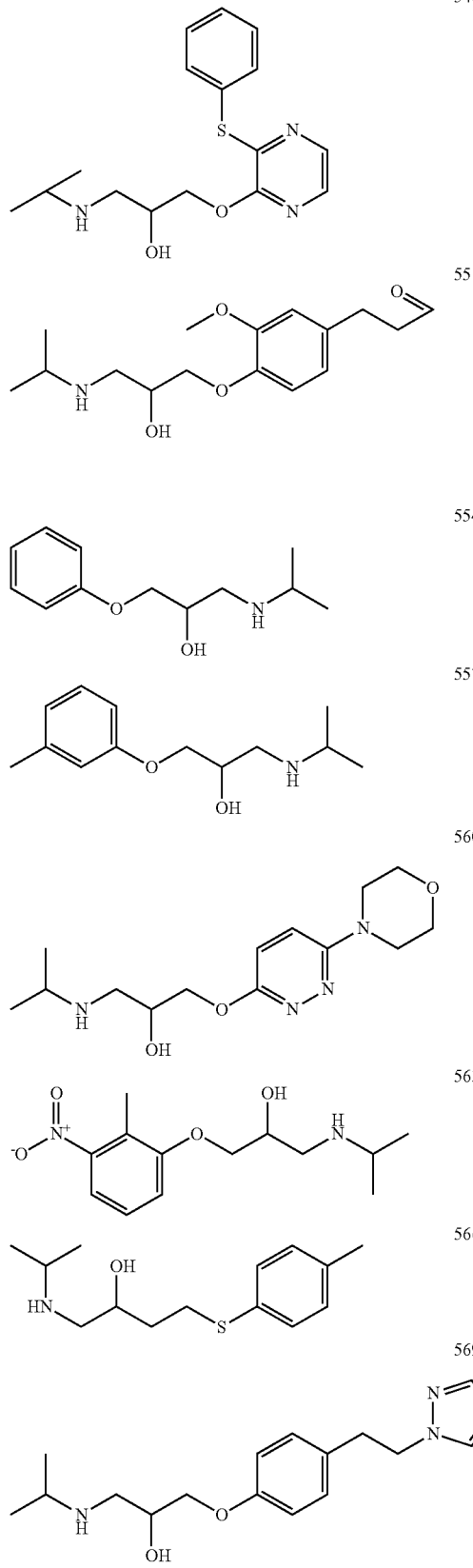
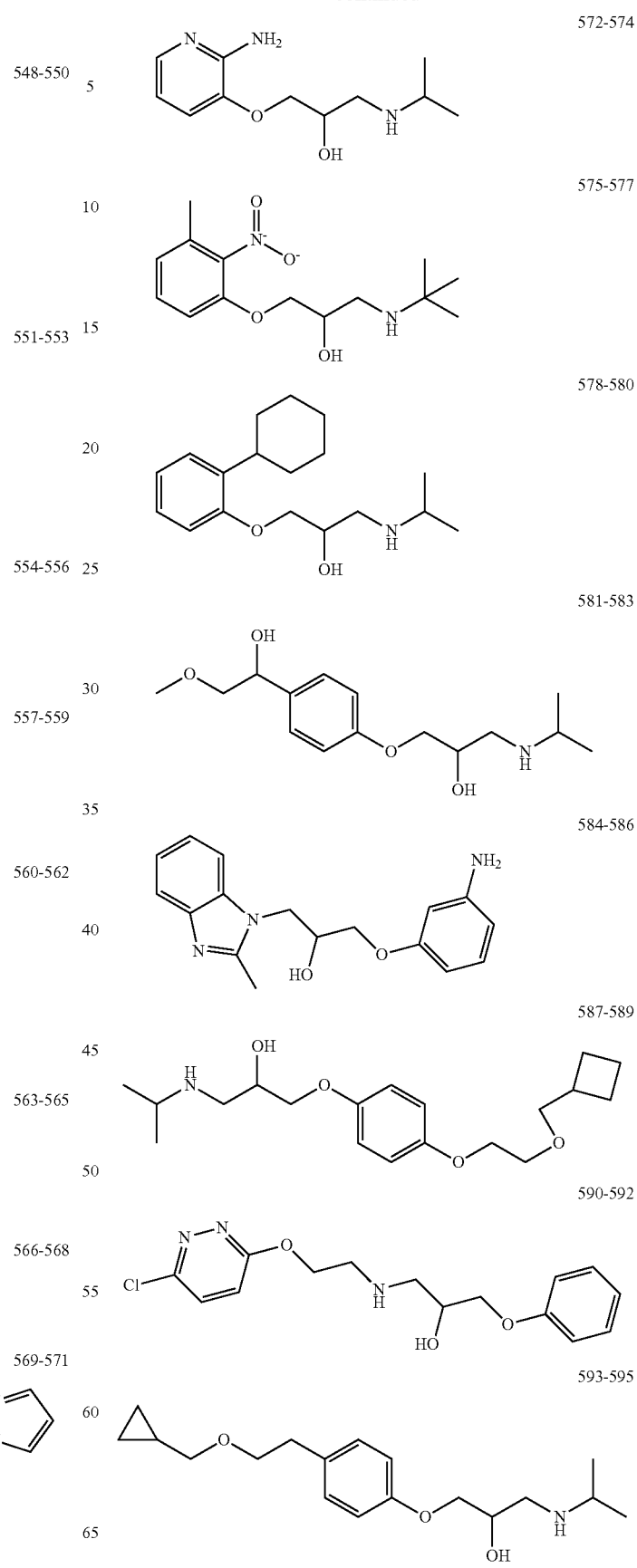

596-598
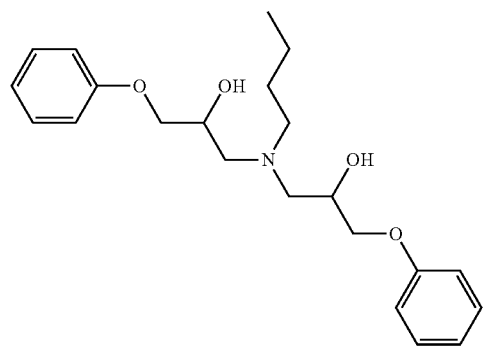
599-601
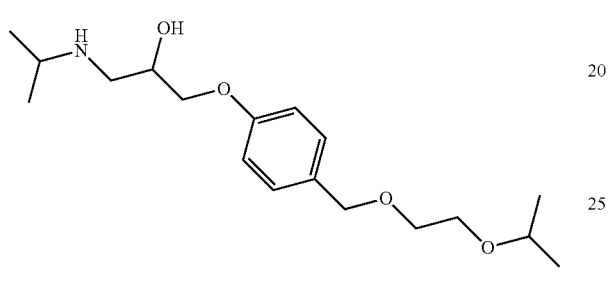
602-604
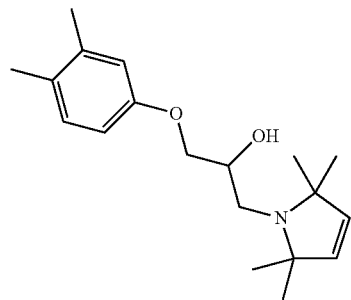
605-607
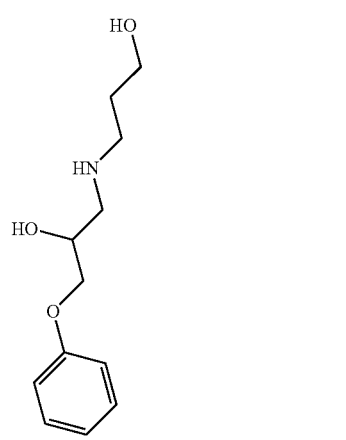
608-610
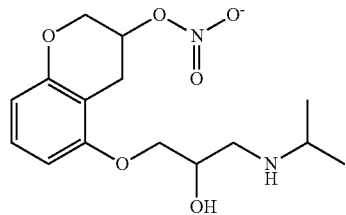
611-613
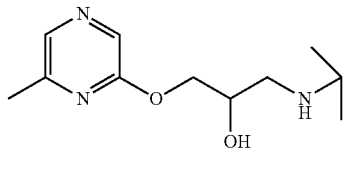
614-616
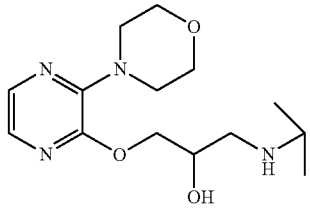
617-619
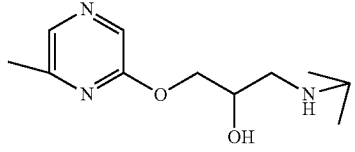
620-622
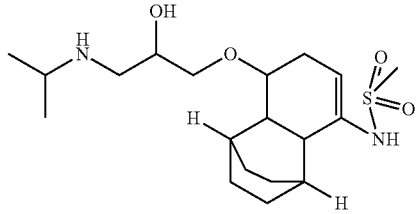
623-625
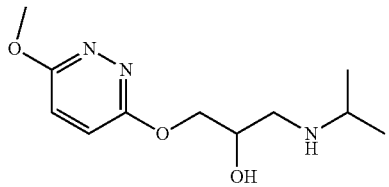
626-628
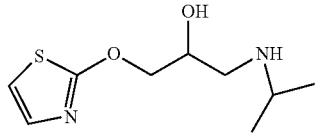
629-631
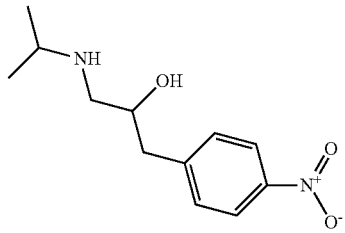
632-634
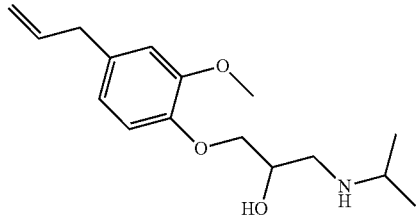

635-637
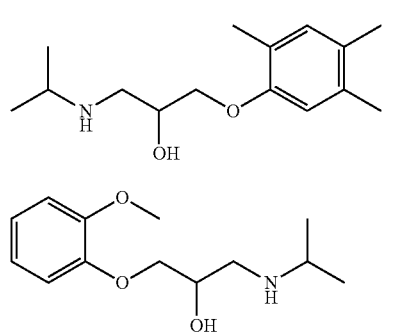
638-640
641-643
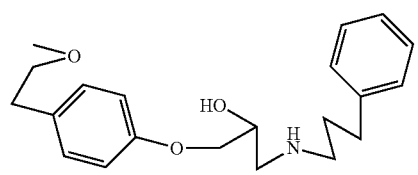
644-646
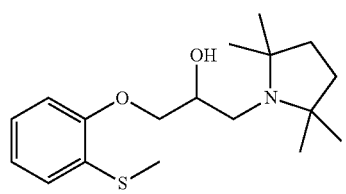
647-649
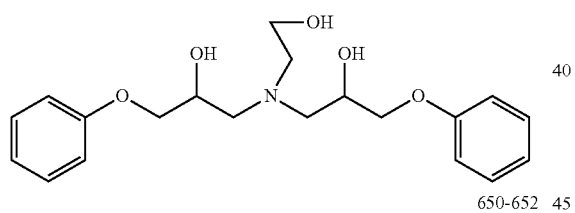
650-652
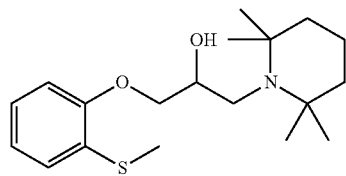
653-655
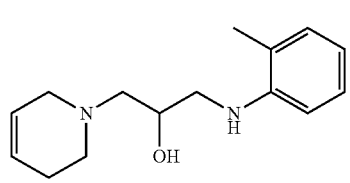
656-658
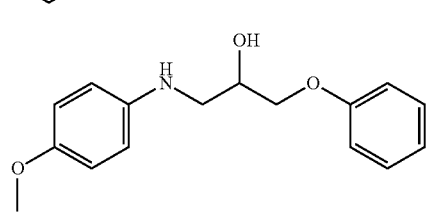
659-661
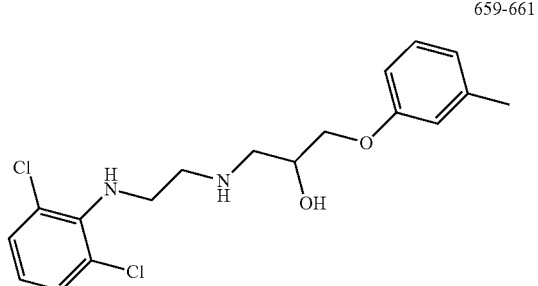
662-664
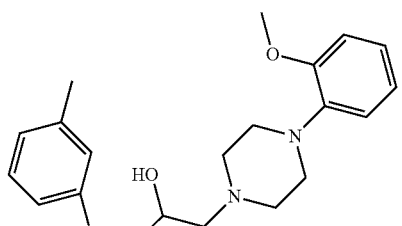
665-667
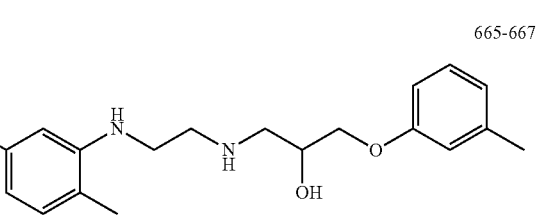
668-670
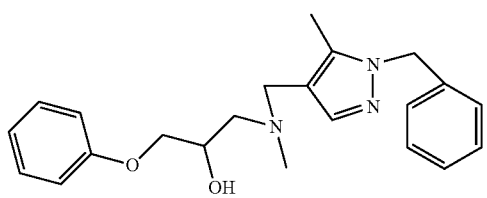
671-673
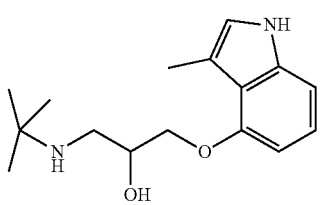
674-676
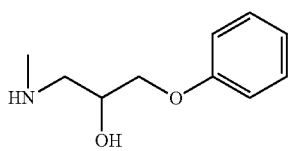
677-679
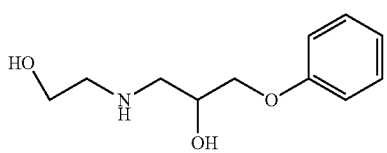

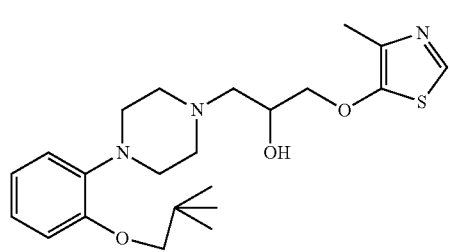 680-682
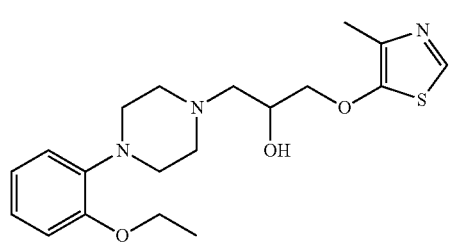 683-685
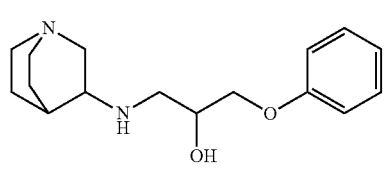 686-688
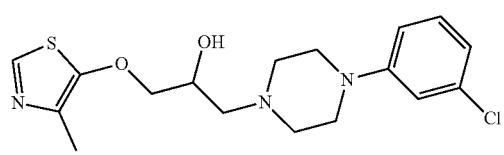 689-691
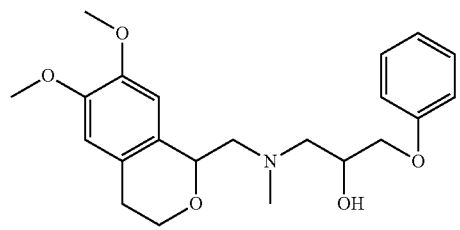 692-694
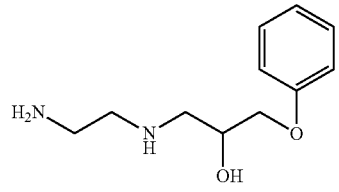 695-697
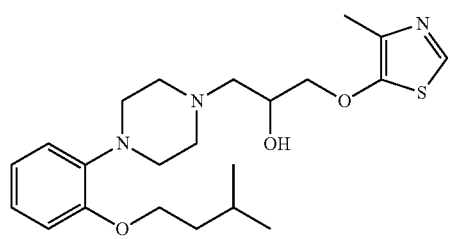 698-700
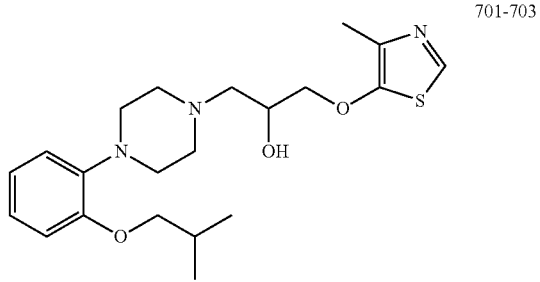 701-703
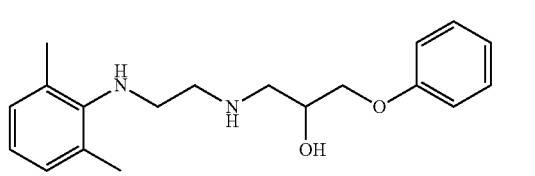 704-706
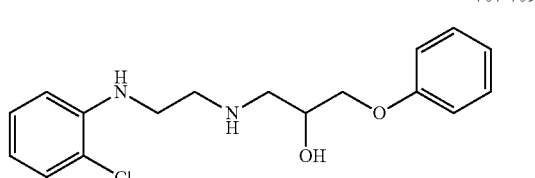 707-709
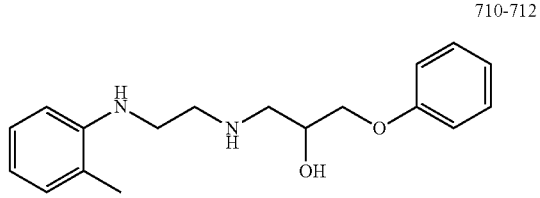 710-712
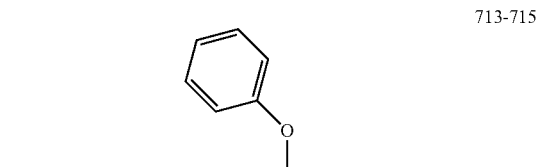 713-715
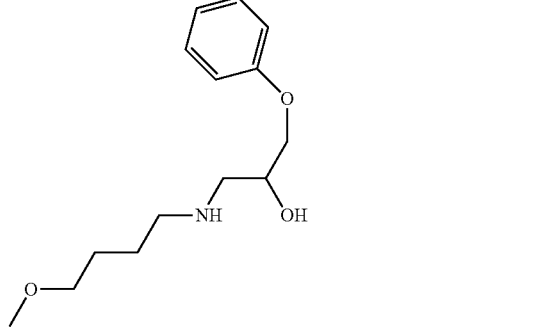
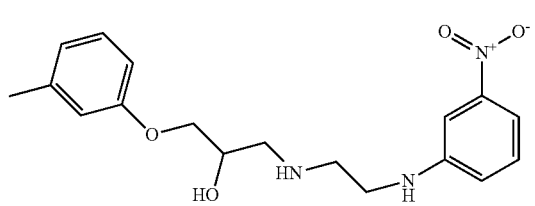 716-718
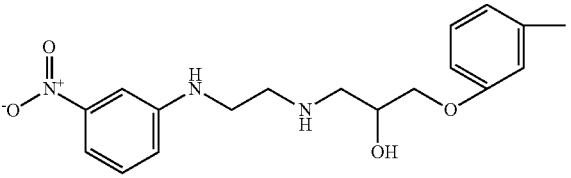 722-724

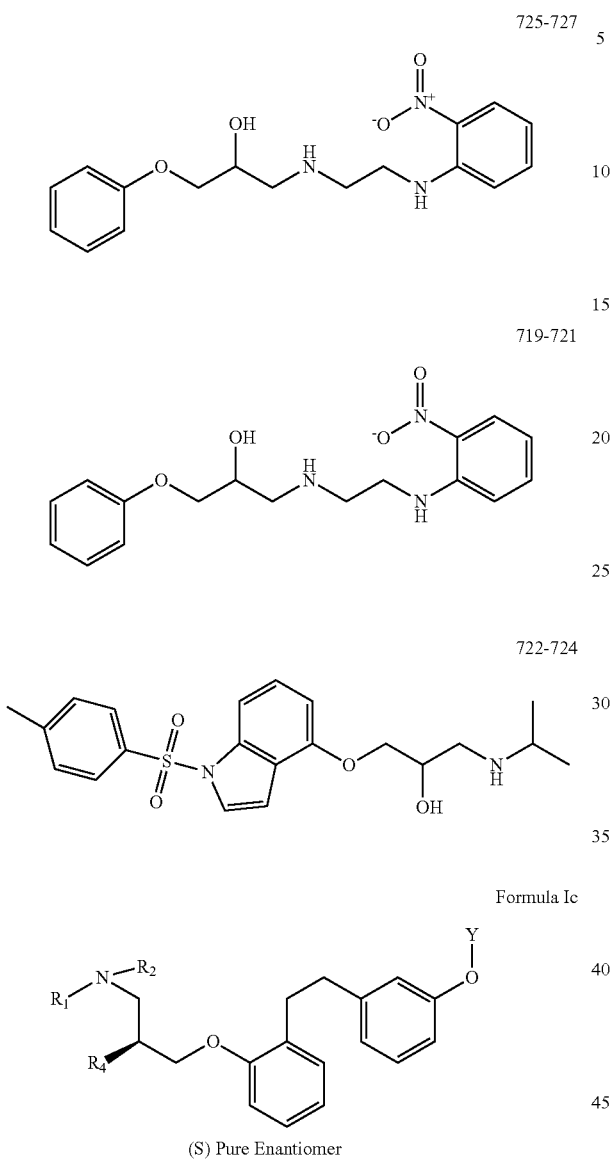

(S) Pure Enantiomer

Formula Id (R) Pure Enantiomer

In some embodiments, the compound of Formula I is Formula Ic or Formula Id:

In some embodiments, the compound of Formula Ic or Formula Id is M1, wherein, Y is CH₃; R4 is OH. In some embodiments, the compound of Formula Ic or Formula Id, as defined above is a fluoro derivative wherein R4 is OCF₃.

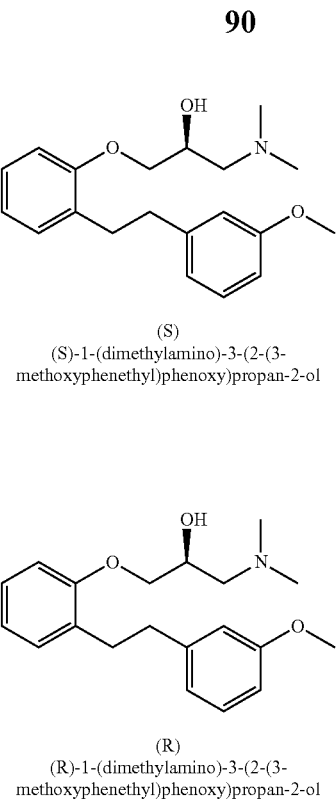

(S)
(S)-1-(dimethylamino)-3-(2-(3-methoxyphenethyl)phenoxy)propan-2-ol

M1

(R)
(R)-1-(dimethylamino)-3-(2-(3-methoxyphenethyl)phenoxy)propan-2-ol

M1

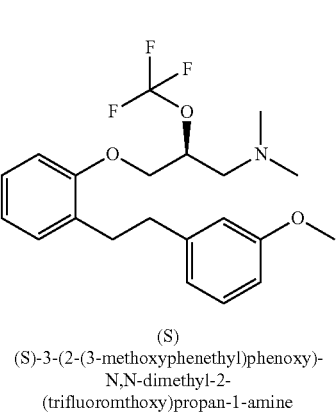

(S)
(S)-3-(2-(3-methoxyphenethyl)phenoxy)-N,N-dimethyl-2-(trifluoromthoxy)propan-1-amine Compound 219

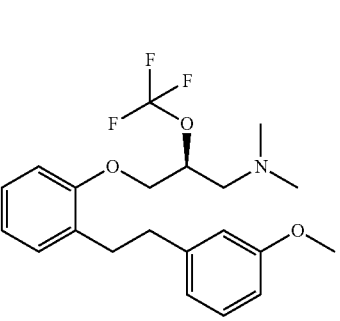

(R)
(S)-3-(2-(3-methoxyphenethyl)phenoxy)-N,N-dimethyl-2-(trifluoromthoxy)propan-1-amine Compound 220

In an embodiment of the invention is a composition comprising a compound having a Formula I,

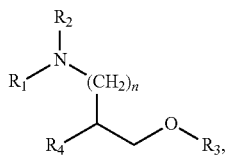

Formula I wherein $R_3$ is a bicyclic system and the rest of the Formula I represented by $R_7$: as shown in Formula If

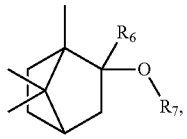

Formula If wherein, $R_6$ is H, substituted or unsubstituted —$C_{1-10}$ alkyl, substituted or unsubstituted —$C_{3-10}$ cycloalkyl, substituted or unsubstituted —$C_{5-10}$ aryl, substituted or unsubstituted —$C_{1-10}$ alkyl-$C_{5-10}$ aryl, substituted or unsubstituted —$C_{5-10}$ heteroaryl, or substituted or unsubstituted —$C_{1-10}$ alkyl-$C_{5-10}$ heteroaryl; $R_7$ is

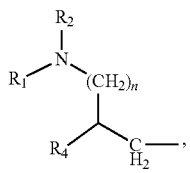

—$C_{1-10}$alkyl-X—(Y), —$C_{3-10}$ cycloalkyl-X—(Y)$_m$, —$C_{5-10}$ aryl-X—(Y)$_m$, or —$C_{5-10}$ heteroaryl-X—(Y)$_m$; wherein X is a bond, N, O, S, —$C_{1-10}$ alkyl, —$C_{3-10}$ cycloalkyl, —$C_{5-10}$ aryl, —CO—$C_{1-10}$ alkyl, —CO—$C_{3-10}$ cycloalkyl, —COC$_{5-10}$ aryl, —CO—$C_{5-10}$ heteroaryl, —CO—NH—$C_{1-10}$ alkyl, —CO—NH—$C_{3-10}$ cycloalkyl, —CO—NH—$C_{5-10}$ aryl, or —CO—NH—$C_{5-10}$ heteroaryl; Y is H, $C_{1-10}$ alkyl, $C_{3-10}$ cycloalkyl, $C_{5-10}$ aryl, —CO—$C_{1-10}$ alkyl, —CO—$C_{3-10}$ cycloalkyl, —COC$_{5-10}$ aryl, CO—$C_{5-10}$ heteroaryl, —CO—NH—$C_{1-10}$ alkyl, —CO—NH—$C_{3-10}$ cycloalkyl, —CO—NH—$C_{5-10}$ aryl, or —CO—NH—$C_{5-10}$ heteroaryl; and m is an integer 1 or 2; or pharmaceutically acceptable salts or N-oxides thereof; or prodrugs thereof.

In certain embodiments, the compound is a compound of Formula If wherein $R_6$ is an aryl, and $R_7$ is substituted or unsubstituted —$C_{1-10}$ alkyl-X—(Y)$_n$. In certain embodiments, $R_6$ is substituted or unsubstituted $C_{1-10}$ alkyl-$C_{5-10}$ aryl, and $R_7$ is substituted or unsubstituted —$C_{1-10}$ alkyl-X—(Y)$_n$. In certain embodiments, $R_6$ is phenyl, $R_7$ is —$C_{1-10}$ alkyl-N—($C_{1-10}$ alkyl)$_2$.

In an embodiment, the compound of Formula I includes, but not limited to, the following examples: RS4-((4-(dimethylamino)-1-(2-(3-methoxyphenethyl)phenoxy)butan-2-yl)oxy)-3,3-difluoro-4-oxobutanoic acid; S4-((4-(dimethylamino)-1-(2-(3-methoxyphenethyl)phenoxy)butan-2-yl)oxy)-3,3-difluoro-4-oxobutanoic acid; R4-((4-(dimethylamino)-1-(2-(3-methoxyphenethyl) phenoxy) butan-2-yl)oxy)-3,3-difluoro-4-oxobutanoic acid; RS4-((4-(dimethylamino)-1-(2-(3-methoxyphenethyl)phenoxy) butan-2-yl)oxy)-2,2-difluoro-4-oxobutanoic acid; S4-((4-(dimethylamino)-1-(2-(3-methoxyphenethyl)phenoxy)butan-2-yl)oxy)-2,2-difluoro-4-oxobutanoic acid; R4-((4-(dimethylamino)-1-(2-(3-methoxyphenethyl) phenoxy)butan-2-yl)oxy-2,2-difluoro-4-oxobutanoic acid; RS4-((4-(dimethylamino)-1-(2-(3-methoxyphenethyl) phenoxy) butan-2-yl)oxy)-2,2,3-trifluoro-4-oxobutanoic acid; S4-((4-(dimethylamino)-1-(2-(3-methoxyphenethyl)phenoxy) butan-2-yl)oxy)-2,2,3-trifluoro-4-oxobutanoic acid; R4-((4-(dimethylamino)-1-(2-(3-methoxyphenethyl) phenoxy)butan-2-yl)oxy)-2,2,3-trifluoro-4-oxobutanoic acid; RS4-((4-(dimethylamino)-1-(2-(3-methoxyphenethyl) phenoxy) butan-2-yl)oxy)-2,3,3-trifluoro-4-oxobutanoic acid; S4-((4-(dimethylamino)-1-(2-(3-methoxyphenethyl) phenoxy) butan-2-yl)oxy)-2,3,3-trifluoro-4-oxobutanoic acid; R4-((4-(dimethylamino)-1-(2-(3-methoxyphenethyl)phenoxy) butan-2-yl)oxy)-2,3,3-trifluoro-4-oxobutanoic acid; RS4-((4-(dimethylamino)-1-(2-(3-methoxyphenethyl) phenoxy) butan-2-yl)oxy)-2,3-difluoro-4-oxobutanoic acid; S4-((4-(dimethylamino)-1-(2-(3-methoxyphenethyl)phenoxy)butan-2-yl)oxy)-2,3-difluoro-4-oxobutanoic acid; R4-((4-(dimethylamino)-1-(2-(3-methoxyphenethyl) phenoxy)butan-2-yl)oxy)-2,3-difluoro-4-oxobutanoic acid; RS4-((4-(dimethylamino)-1-(2-(3-methoxyphenethyl) phenoxy) butan-2-yl)oxy)-2,2,3,3-tetrafluoro-4-oxobutanoic acid; S4-((4-(dimethylamino)-1-(2-(3-methoxyphenethyl)phenoxy) butan-2-yl)oxy)-2,2,3,3-tetrafluoro-4-oxobutanoic acid; R4-((4-(dimethylamino)-1-(2-(3-methoxyphenethyl)phenoxy) butan-2-yl) oxy)-2,2,3,3-tetrafluoro-4-oxobutanoic acid; RS5-((4-(dimethylamino)-1-(2-(3-methoxyphenethyl)phenoxy)butan-2-yl)oxy)-4,4-difluoro-5-oxopentanoic acid; S5-((4-(dimethylamino)-1-(2-(3-methoxyphenethyl) phenoxy)butan-2-yl)oxy)-4,4-difluoro-5-oxopentanoic acid; R5-((4-(dimethylamino)-1-(2-(3-methoxyphenethyl) phenoxy) butan-2-yl)oxy)-4,4-difluoro-5-oxopentanoic acid; RS5-((4-(dimethylamino)-1-(2-(3-methoxyphenethyl)phenoxy)butan-2-yl)oxy)-4,4-difluoro-5-oxopentanoic acid; S5-((4-(dimethylamino)-1-(2-(3-methoxyphenethyl) phenoxy) butan-2-yl)oxy)-4,4-difluoro-5-oxopentanoic acid; R5-((4-(dimethylamino)-1-(2-(3-methoxyphenethyl) phenoxy) butan-2-yl)oxy)-4,4-difluoro-5-oxopentanoic acid; RS5-((4-(dimethylamino)-1-(2-(3-methoxyphenethyl) phenoxy) butan-2-yl)oxy)-2,2-difluoro-5-oxopentanoic acid; S5-((4-(dimethylamino)-1-(2-(3-methoxyphenethyl) phenoxy) butan-2-yl) oxy)-2,2-difluoro-5-oxopentanoic acid; R5-((4-(dimethylamino)-1-(2-(3-methoxyphenethyl) phenoxy) butan-2-yl) oxy)-2,2-difluoro-5-oxopentanoic acid; RS4-(dimethylamino)-1-(2-(3-methoxyphenethyl) phenoxy)butan-2-yl 2,2-difluoroacetate; S4-(dimethylamino)-1-(2-(3-methoxyphenethyl) phenoxy)butan-2-yl 2,2-difluoroacetate; R4-(dimethylamino)-1-(2-(3-methoxyphenethyl) phenoxy)butan-2-yl 2,2-difluoroacetate; RS4-(dimethylamino)-1-(2-(3-methoxyphenethyl) phenoxy)butan-2-yl 2,2,2-trifluoroacetate; S4-(dimethylamino)-1-(2-(3-methoxyphenethyl) phenoxy)butan-2-yl 2,2,2-trifluoroacetate; R4-(dimethylamino)-1-(2-(3-methoxyphenethyl) phenoxy) butan-2-yl 2,2,2-trifluoroacetate; RS4-((difluoromethyl) (trifluoromethyl)amino)-1-(2-(3-(trifluoromethoxy) phenethyl)phenoxy) butan-2-ol; S4-((difluoromethyl) (trifluoromethyl) amino)-1-(2-(3-(trifluoromethoxy)phenethyl) phenoxy)butan-2-ol; R4-((difluoromethyl) (trifluoromethyl) amino)-1-(2-(3-(trifluoromethoxy) phenethyl) phenoxy)butan-2-ol; RS4-((fluoromethyl) (trifluoromethyl) amino)-1-(2-(3-(trifluoromethoxy) phenethyl)phenoxy)butan-2-ol; S4-((fluoromethyl) (trifluoromethyl) amino)-1-(2-(3-(trifluoromethoxy) phenethyl)phenoxy) butan-2-ol; R4-((fluoromethyl) (trifluoromethyl)amino)-1-(2-(3-(trifluoromethoxy) phenethyl)phenoxy)butan-2-ol; RS4-(methyl (trifluoromethyl) amino)-1-(2-(3-(trifluoromethoxy) phenethyl) phenoxy) butan-2-ol; S4-(methyl (trifluoromethyl) amino)-1-(2-(3-(trifluoromethoxy) phenethyl)phenoxy)butan-2-ol; R4-(methyl(trifluoromethyl)amino)-1-(2-(3-(trifluoromethoxy) phenethyl)phenoxy) butan-2-ol; RS4-((difluoromethyl) (methyl)amino)-1-(2-(3-(trifluoromethoxy) phenethyl) phenoxy) butan-2-ol; S4-((difluoromethyl)(methyl)amino)-1-(2-(3-(trifluoromethoxy) phenethyl) phenoxy) butan-2-ol; R4-((difluoromethyl) (methyl)amino)-1-(2-(3-(trifluoromethoxy) phenethyl)phenoxy) butan-2-ol; RS4-((fluoromethyl) (methyl)amino)-1-(2-(3-(trifluoromethoxy) phenethyl) phenoxy) butan-2-ol; S4-((fluoromethyl)(methyl)amino)-1-(2-(3-(trifluoromethoxy) phenethyl) phenoxy)butan-2-ol; R4-((fluoromethyl) (methyl)amino)-1-(2-(3-(trifluoromethoxy)phenethyl)phenoxy) butan-2-ol; RS4-(dimethylamino)-1-(2-(3-(trifluoromethoxy) phenethyl) phenoxy) butan-2-ol; S4-(dimethylamino)-1-(2-(3-(trifluoromethoxy) phenethyl) phenoxy) butan-2-ol; R4-(dimethylamino)-1-(2-(3-(trifluoromethoxy) phenethyl) phenoxy) butan-2-ol; R S1-(2-(3-(difluoromethoxy) phenethyl) phenoxy)-4-(dimethylamino) butan-2-ol; S1-(2-(3-(difluoromethoxy)phenethyl)phenoxy)-4-(dimethylamino)butan-2-ol; R1-(2-(3-(difluoromethoxy)phenethyl)phenoxy)-4-(dimethylamino)butan-2-ol; RS4-(dimethylamino)-1-(2-(3-(fluoromethoxy) phenethyl) phenoxy) butan-2-ol; S4-(dimethylamino)-1-(2-(3-(fluoromethoxy) phenethyl) phenoxy)butan-2-ol; R4-(dimethyl amino)-1-(2-(3-(fluoromethoxy)phenethyl)phenoxy)butan-2-ol; RS3-(trifluoro methoxy)-4-(2-(3-(trifluoromethoxy) phenethyl) phenoxy)-N,N-bis(trifluoromethyl) butan-1-amine; S3-(trifluoromethoxy)-4-(2-(3-(trifluoromethoxy) phenethyl)phenoxy)-N,N-bis (trifluoro methyl) butan-1-amine; R3-(trifluoromethoxy)-4-(2-(3-(trifluoromethoxy)phenethyl) phenoxy)-N,N-bis(trifluoromethyl)butan-1-amine; RSN-(difluoromethyl)-3-(trifluoromethoxy)-4-(2-(3-(trifluoromethoxy)phenethyl)phenoxy)-N-(trifluoromethyl)butan-1-amine; SN-(difluoromethyl)-3-(trifluoromethoxy)-4-(2-(3-(trifluoromethoxy)phenethyl)phenoxy)-N-(trifluoromethyl)butan-1-amine; RN-(difluoromethyl)-3-(trifluoromethoxy)-4-(2-(3-(trifluoromethoxy)phenethyl) phenoxy)-N-(trifluoromethyl)butan-1-amine; RSN-(fluoromethyl)-3-(trifluoromethoxy)-4-(2-(3-(trifluoro methoxy) phenethyl)phenoxy)-N-(trifluoromethyl)butan-1-amine; SN-(fluoromethyl)-3-(trifluoro methoxy)-4-(2-(3-(trifluoromethoxy)phenethyl)phenoxy)-N-(trifluoromethyl) butan-1-amine; RN-(fluoro methyl)-3-(trifluoromethoxy)-4-(2-(3-(trifluoromethoxy)phenethyl)phenoxy)-N-(trifluoro methyl) butan-1-amine; RSN-methyl-3-(trifluoromethoxy)-4-(2-(3-(trifluoromethoxy) phenethyl) phenoxy)-N-(trifluoromethyl)butan-1-amine; SN-methyl-3-(trifluoromethoxy)-4-(2-(3-(trifluoromethoxy) phenethyl)phenoxy)-N-(trifluoromethyl)butan-1-amine; RN-methyl-3-(trifluoromethoxy)-4-(2-(3-(trifluoromethoxy)phenethyl) phenoxy)-N-(trifluoromethyl)butan-1-amine; RSN-(difluoromethyl)-N-methyl-3-(trifluoromethoxy)-4-(2-(3-(trifluoromethoxy) phenethyl)phenoxy)butan-1-amine; SN-(difluoromethyl)-N-methyl-3-(trifluoromethoxy)-4-(2-(3-(trifluoromethoxy)phenethyl)phenoxy)butan-1-amine; RN-(difluoromethyl)-N-methyl-3-(trifluoro methoxy)-4-(2-(3-(trifluoromethoxy)phenethyl)phenoxy)butan-1-amine; RSN-(fluoromethyl)-N-methyl-3-(trifluoromethoxy)-4-(2-(3-(trifluoromethoxy) phenethyl)phenoxy) butan-1-amine; SN-(fluoromethyl)-N-methyl-3-(trifluoromethoxy)-4-(2-(3-(trifluoromethoxy) phenethyl) phenoxy)butan-1-amine; RN-(fluoromethyl)-N-methyl-3-(trifluoromethoxy)-4-(2-(3-(trifluoromethoxy)phenethyl)phenoxy)butan-1-amine; RSN,N-dimethyl-3-(trifluoromethoxy)-4-(2-(3-(trifluoromethoxy) phenethyl)phenoxy)butan-1-amine; SN,N-dimethyl-3-(trifluoromethoxy)-4-(2-(3-(trifluoromethoxy)phenethyl)phenoxy)butan-1-amine; RN,N-dimethyl-3-(trifluoromethoxy)-4-(2-(3-(trifluoromethoxy)phenethyl)phenoxy)butan-1-amine; RS4-(2-(3-(difluoromethoxy)phenethyl)phenoxy)-N,N-dimethyl-3-(trifluoromethoxy)butan-1-amine; S4-(2-(3-(difluoromethoxy)phenethyl)phenoxy)-N,N-dimethyl-3-(trifluoromethoxy)butan-1-amine; R4-(2-(3-(difluoromethoxy) phenethyl)phenoxy)-N,N-dimethyl-3-(trifluoromethoxy) butan-1-amine; RS4-(2-(3-(fluoromethoxy) phenethyl)phenoxy)-N,N-dimethyl-3-(trifluoromethoxy) butan-1-amine; S4-(2-(3-(fluoromethoxy) phenethyl)phenoxy)-N,N-dimethyl-3-(trifluoromethoxy) butan-1-amine; R4-(2-(3-(fluoromethoxy)phenethyl)phenoxy)-N,N-dimethyl-3-(trifluoromethoxy)butan-1-amine; RS3-(difluoromethoxy)-4-(2-(3-(trifluoromethoxy) phenethyl) phenoxy)-N,N-bis(trifluoromethyl)butan-1-amine; S3-(difluoromethoxy)-4-(2-(3-(trifluoro methoxy) phenethyl)phenoxy)-N,N-bis(trifluoromethyl)butan-1-amine; R3-(difluoromethoxy)-4-(2-(3-(trifluoromethoxy)phenethyl)phenoxy)-N,N-bis(trifluoromethyl)butan-1-amine; RS3-(difluoromethoxy)-N-(difluoromethyl)-4-(2-(3-(trifluoromethoxy)phenethyl) phenoxy)-N-(trifluoromethyl) butan-1-amine; S3-(difluoromethoxy)-N-(difluoromethyl)-4-(2-(3-(trifluoromethoxy) phenethyl)phenoxy)-N-(trifluoromethyl)butan-1-amine; R(–(difluoromethoxy)-N-(difluoromethyl)-4-(2-(3-(trifluoromethoxy)phenethyl)phenoxy)-N-(trifluoromethyl)butan-1-amine; RS3-(difluoromethoxy)-N-(fluoromethyl)-4-(2-(3-(trifluoromethoxy)phenethyl)phenoxy)-N-(trifluoromethyl) butan-1-amine; S3-(difluoromethoxy)-N-(fluoromethyl)-4-(2-(3-(trifluoromethoxy)phenethyl)phenoxy)-N-(trifluoromethyl)butan-1-amine; R3-(difluoromethoxy)-N-(fluoromethyl)-4-(2-(3-(trifluoromethoxy)phenethyl) phenoxy)-N-(trifluoromethyl)butan-1-amine; RS3-(difluoromethoxy)-N-methyl-4-(2-(3-(trifluoromethoxy) phenethyl) phenoxy)-N-(trifluoromethyl) butan-1-amine; S3-(difluoromethoxy)-N-methyl-4-(2-(3-(trifluoromethoxy) phenethyl)phenoxy)-N-(trifluoromethyl) butan-1-amine; R3-(difluoromethoxy)-N-methyl-4-(2-(3-(trifluoromethoxy)phenethyl)phenoxy)-N-(trifluoromethyl)butan-1-amine; RS3-(difluoro methoxy)-N-(difluoromethyl)-N-methyl-4-(2-(3-(trifluoromethoxy)phenethyl)phenoxy) butan-1-amine; S3-(difluoromethoxy)-N-(difluoromethyl)-N-methyl-4-(2-(3-(trifluoromethoxy) phenethyl) phenoxy) butan-1-amine; R3-(difluoromethoxy)-N-(difluoromethyl)-N-methyl-4-(2-(3-(trifluoromethoxy)phenethyl)phenoxy) butan-1-amine; RS3-(difluoromethoxy)-N-(fluoromethyl)-N-methyl-4-(2-(3-(trifluoromethoxy)phenethyl)phenoxy) butan-1-amine; S3-(difluoro methoxy)-N-(fluoromethyl)-N-methyl-4-(2-(3-(trifluoromethoxy)phenethyl) phenoxy) butan-1-amine; R3-(difluoromethoxy)-N-(fluoromethyl)-N-methyl-4-(2-(3-(trifluoromethoxy) phenethyl) phenoxy) butan-1-amine; RS3-(difluoromethoxy)-N,N-dimethyl-4-(2-(3-(trifluoromethoxy)phenethyl)phenoxy)butan-1-amine; S3-(difluoromethoxy)-N,N-dimethyl-4-(2-(3-(trifluoromethoxy) phenethyl)phenoxy)butan-1-amine; R3-(difluoromethoxy)-N,N-dimethyl-4-(2-(3-(trifluoromethoxy)phenethyl)phenoxy)butan-1-amine; RS3-(difluoromethoxy)-4-(2-(3-(difluoromethoxy) phenethyl)phenoxy)-N,N-dimethylbutan-1-amine S3-(difluoromethoxy)-4-(2-(3-(difluoromethoxy)phenethyl)phenoxy)-N,N-dimethylbutan-1-amine; R3-(difluoromethoxy)-4-(2-(3-(difluoromethoxy) phenethyl)phenoxy)-N,N-dimethylbutan-1-amine; RS3-(difluoromethoxy)-4-(2-(3-(fluoromethoxy)phenethyl)phenoxy)-N,N-dimethylbutan-1-amine; S3-(difluoromethoxy)-

4-(2-(3-(fluoromethoxy)phenethyl) phenoxy)-N,N-dimethyl butan-1-amine; R3-(difluoromethoxy)-4-(2-(3-(fluoromethoxy)phenethyl)phenoxy)-N,N-dimethylbutan-1-amine; RS3-(fluoromethoxy)-4-(2-(3-(trifluoromethoxy) phenethyl)phenoxy)-N,N-bis(trifluoromethyl)butan-1-amine; S3-(fluoro methoxy)-4-(2-(3-(trifluoromethoxy) phenethyl)phenoxy)-N,N-bis(trifluoromethyl)butan-1-amine; R3-(fluoromethoxy)-4-(2-(3-(trifluoromethoxy) phenethyl)phenoxy)-N,N-bis (trifluoromethyl) butan-1-amine; RSN-(difluoromethyl)-3-(fluoromethoxy)-4-(2-(3-(trifluoro methoxy) phenethyl)phenoxy)-N-(trifluoromethyl)butan-1-amine; SN-(difluoromethyl)-3-(fluoromethoxy)-4-(2-(3-(trifluoromethoxy)phenethyl)phenoxy)-N-(trifluoromethyl)butan-1-amine; RN-(difluoromethyl)-3-(fluoromethoxy)-4-(2-(3-(trifluoromethoxy)phenethyl)phenoxy)-N-(trifluoro methyl) butan-1-amine; RS3-(fluoromethoxy)-N-(fluoromethyl)-4-(2-(3-(trifluoromethoxy) phenethyl)phenoxy)-N-(trifluoromethyl) butan-1-amine; S3-(fluoromethoxy)-N-(fluoromethyl)-4-(2-(3-(trifluoromethoxy)phenethyl)phenoxy)-N-(trifluoromethyl)butan-1-amine; R3-(fluoromethoxy)-N-(fluoromethyl)-4-(2-(3-(trifluoromethoxy)phenethyl) phenoxy)-N-(trifluoromethyl)butan-1-amine; RS3-(fluoromethoxy)-N-methyl-4-(2-(3-(trifluoromethoxy) phenethyl) phenoxy)-N-(trifluoromethyl) butan-1-amine; S3-(fluoromethoxy)-N-methyl-4-(2-(3-(trifluoromethoxy) phenethyl)phenoxy)-N-(trifluoromethyl)butan; R3-(fluoromethoxy)-N-methyl-4-(2-(3-(trifluoromethoxy) phenethyl)phenoxy)-N-(trifluoromethyl)butan-1-amine; RSN-(difluoromethyl)-3-(fluoromethoxy)-N-methyl-4-(2-(3-(trifluoromethoxy)phenethyl) phenoxy)butan-1-amine; SN-(difluoromethyl)-3-(fluoromethoxy)-N-methyl-4-(2-(3-(trifluoromethoxy) phenethyl) phenoxy)butan-1-amine; RN-(difluoromethyl)-3-(fluoromethoxy)-N-methyl-4-(2-(3-(trifluoromethoxy)phenethyl)phenoxy)butan-1-amine; RS3-(fluoromethoxy)-N-(fluoromethyl)-N-methyl-4-(2-(3-(trifluoromethoxy)phenethyl)phenoxy)butan-1-amine; S3-(fluoromethoxy)-N-(fluoromethyl)-N-methyl-4-(2-(3-(trifluoromethoxy)phenethyl)phenoxy) butan-1-amine; R3-(fluoromethoxy)-N-(fluoromethyl)-N-methyl-4-(2-(3-(trifluoromethoxy) phenethyl) phenoxy) butan-1-amine; RS3-(fluoromethoxy)-N,N-dimethyl-4-(2-(3-(trifluoromethoxy) phenethyl) phenoxy)butan-1-amine; S3-(fluoromethoxy)-N,N-dimethyl-4-(2-(3-(trifluoromethoxy)phenethyl)phenoxy)butan-1-amine; R3-(fluoromethoxy)-N,N-dimethyl-4-(2-(3-(trifluoromethoxy)phenethyl)phenoxy) butan-1-amine; RS4-(2-(3-(difluoromethoxy) phen ethyl) phenoxy)-3-(fluoromethoxy)-N,N-dimethylbutan-1-amine; S4-(2-(3-(difluoro methoxy) phenethyl)phenoxy)-3-(fluoromethoxy)-N,N-dimethyl butan-1-amine; R4-(2-(3-(difluoro methoxy) phenethyl) phenoxy)-3-(fluoromethoxy)-N,N-dimethylbutan-1-amine; RS3-methoxy-4-(2-(3-(trifluoromethoxy)phenethyl)phenoxy)-N,N-bis (trifluoromethyl)butan-1-amine; S3-methoxy-4-(2-(3-(trifluoromethoxy) phenethyl)phenoxy)-N,N-bis (trifluoromethyl)butan-1-amine; R3-methoxy-4-(2-(3-(trifluoromethoxy)phenethyl)phenoxy)-N,N-bis (trifluoromethyl) butan-1-amine; RSN-(difluoromethyl)-3-methoxy-4-(2-(3-(trifluoromethoxy) phenethyl) phenoxy)-N-(trifluoromethyl)butan-1-amine; SN-(difluoromethyl)-3-methoxy-4-(2-(3-(trifluoromethoxy) phenethyl) phenoxy)-N-(trifluoromethyl)butan-1-amine; RN-(difluoromethyl)-3-methoxy-4-(2-(3-(trifluoromethoxy) phenethyl) phenoxy)-N-(trifluoromethyl)butan-1-amine RSN-(fluoromethyl)phenoxy)-N-(trifluoro methyl) butan-1-amine; SN-(fluoromethyl)-3-methoxy-4-(2-(3-(trifluoromethoxy) phenethyl) phenoxy)-N-(trifluoromethyl) butan-1-amine; RN-(fluoromethyl)-3-methoxy-4-(2-(3-(trifluoromethoxy) phenethyl) phenoxy)-N-(trifluoromethyl)butan-1-amine; RS3-methoxy-N-methyl-4-(2-(3-(trifluoromethoxy)phenethyl)phenoxy)-N-(trifluoromethyl)butan-1-amine; S3-methoxy-N-methyl-4-(2-(3-(trifluoromethoxy)phenethyl)phenoxy)-N-(trifluoromethyl)butan-1-amine; R3-methoxy-N-methyl-4-(2-(3-(trifluoromethoxy)phenethyl)phenoxy)-N-(trifluoro methyl) butan-1-amine; RS4-(2-(3-(difluoromethoxy)phenethyl)phenoxy)-3-methoxy-N,N-dimethylbutan-1-amine; S4-(2-(3-(difluoromethoxy) phenethyl)phenoxy)-3-methoxy-N,N-dimethylbutan-1-amine; R4-(2-(3-(difluoromethoxy)phenethyl)phenoxy)-3-methoxy-N,N-dimethylbutan-1-amine; RSN-(fluoromethyl)-3-methoxy-N-methyl-4-(2-(3-(trifluoromethoxy) phenethyl) phenoxy) butan-1-amine; SN-(fluoromethyl)-3-methoxy-N-methyl-4-(2-(3-(trifluoromethoxy)phenethyl)phenoxy)butan-1-amine; RN-(fluoromethyl)-3-methoxy-N-methyl-4-(2-(3-(trifluoromethoxy)phenethyl)phenoxy)butan-1-amine; RS4-(2-(3-(difluoromethoxy) phen ethyl) phenoxy)-3-methoxy-N,N-dimethylbutan-1-amine; S4-(2-(3-(difluoromethoxy) phen ethyl)phenoxy)-3-methoxy-N,N-dimethylbutan-1-amine; R4-(2-(3-(difluoromethoxy) phenethyl) phen oxy)-3-methoxy-N,N-dimethylbutan-1-amine; RS4-(2-(3-(fluoromethoxy) phen ethyl)phenoxy)-3-methoxy-N,N-dimethylbutan-1-amine; S4-(2-(3-(fluoromethoxy) phen ethyl) phenoxy)-3-methoxy-N,N-dimethylbutan-1-amine; R4-(2-(3-(fluoromethoxy) phenethyl) phenoxy)-3-methoxy-N,N-dimethylbutan-1-amine; RS4-(2-(3 (fluoromethoxy) phenethyl) phenoxy)-3-methoxy-N,N-dimethylbutan-1-amine; S4-(2-(3-(fluoromethoxy) phenethyl)phenoxy)-3-methoxy-N,N-dimethylbutan-1-amine; R4-(2-(3-(fluoromethoxy) phenethyl) phenoxy)-3-methoxy-N,N-dimethylbutan-1-amine; RS1-(piperidin-1-yl)-3-(m-tolyl oxy) propan-2-ol; S1-(piperidin-1-yl)-3-(m-tolyloxy)propan-2-ol; R1-(piperidin-1-yl)-3-(m-tolyloxy) propan-2-ol; RS1-(4-(3-methoxyphenyl)piperazin-1-yl)-3-phenoxypropan-2-ol S1-(4-(3-methoxyphenyl) piperazin-1-yl)-3-phenoxypropan-2-ol; R1-(4-(3-methoxyphenyl) piperazin-1-yl)-3-phenoxypropan-2-ol; RS1-(2,2,5,5-tetramethyl-2,5-dihydro-1H-pyrrol-1-yl)-3-(m-tolyloxy)propan-2-ol; S1-(2,2,5,5-tetramethyl-2,5-dihydro-1H-pyrrol-1-yl)-3-(m-tolyloxy) propan-2-ol; R1-(2,2,5,5-tetramethyl-2,5-dihydro-1H-pyrrol-1-yl)-3-(m-tolyloxy) propan-2-ol; RS1-morpholino-3-(m-tolyloxy) propan-2-ol; S1-morpholino-3-(m-tolyloxy) propan-2-ol; R1-morpholino-3-(m-tolyloxy)propan-2-ol; RS3,3'-(phenylazanediyl)bis(1-phenoxypropan-2-ol); S3,3'-(phenylazanediyl)bis(1-phenoxypropan-2-ol); R3,3'-(phenylazanediyl) bis(1-phenoxypropan-2-ol); RS1-(2,2,5,5-tetramethylpyrrolidin-1-yl)-3-(m-tolyloxy)propan-2-ol; S1-(2,2,5,5-tetramethylpyrrolidin-1-yl)-3-(m-tolyloxy)propan-2-ol; R1-(2,2,5,5-tetramethyl pyrrolidine-1-yl)-3-(m-tolyloxy) propan-2-ol; RS1-(tert-butylamino)-3-(3,4-dimethylphenoxy) propan-2-ol; S1-(tert-butylamino)-3-(3,4-dimethylphenoxy)propan-2-ol; R1-(tert-butylamino)-3-(3,4-dimethylphenoxy) propan-2-ol; RS1-(4-(3-chlorophenyl) piperazin-1-yl)-3-phenoxypropan-2-ol; S1-(4-(3-chlorophenyl) piperazin-1-yl)-3-phenoxypropan-2-ol; R1-(4-(3-chlorophenyl) piperazin-1-yl)-3-phenoxypropan-2-ol; RS1-(dimethylamino)-3-(2-phenoxy phenoxy) propan-2-ol; S1-(dimethylamino)-3-(2-phenoxyphenoxy)propan-2-ol; R1-(dimethyl amino)-3-(2-phenoxy phenoxy) propan-2-ol; RS1-(pyrrolidin-1-yl)-3-(m-tolyloxy)propan-2-ol; S1-(pyrrolidin-1-yl)-3-(m-tolyloxy)propan-2-ol; R1-(pyrrolidin-1-yl)-3-(m-tolyloxy)propan-2-ol; RS1-amino-3-(3,5-dimethylphenoxy)propan-2-ol; S1-amino-3-(3,5-dimethylphenoxy)propan-2-ol; R1-amino-3-(3,5- dimethylphenoxy)propan-2-ol; RS1-(dimethylamino)-3-(2-phenethylphenoxy)propan-2-ol; S1-(dimethylamino)-3-(2-phenethylphenoxy)propan-2-ol; R1-(dimethyl amino)-3-(2-phenethyl phenoxy) propan-2-ol; RS1-(benzylamino)-3-(3-(trifluoromethyl) phenoxy) propan-2-ol; S1-(benzylamino)-3-(3-(trifluoromethyl) phenoxy) propan-2-ol; R1-(benzylamino)-3-(3-(trifluoromethyl)phenoxy)propan-2-ol; RS1-amino-3-phenoxypropan-2-ol; S 1-amino-3-phenoxy propan-2-ol; R1-amino-3-phenoxypropan-2-ol; RS1-((3-chloro-2-methylphenyl) amino)-3-phenoxy propan-2-ol; S1-((3-chloro-2-methylphenyl)amino)-3-phenoxypropan-2-ol; R1-((3-chloro-2-methylphenyl) amino)-3-phenoxypropan-2-ol; RS1-((2-((2,4-dichloro phenyl)amino) ethyl)amino)-3-phenoxypropan-2-ol; S1-((2-((2,4-dichlorophenyl) amino) ethyl)amino)-3-phenoxypropan-2-ol; R1-((2-((2,4-dichlorophenyl)amino)ethyl)amino)-3-phenoxypropan-2-ol; RS1-((3-(aminomethyl)phenyl)(methyl)amino)-3-phenoxypropan-2-ol; S1-((3-(aminomethyl) phenyl) (methyl)amino)-3-phenoxypropan-2-ol; R1-((3-(aminomethyl)phenyl)(methyl)amino)-3-phenoxypropan-2-ol; RS1-((2-((2,6-dichlorophenyl)amino)ethyl)amino)-3-phenoxypropan-2-ol; S1-((2-((2,6-dichlorophenyl)amino)ethyl)amino)-3-phenoxypropan-2-ol; R1-((2-((2,6-dichloro phenyl) amino) ethyl)amino)-3-phenoxypropan-2-ol; RS1-((2-((4-nitrophenyl)amino) ethyl)amino)-3-phenoxypropan-2-ol; S1-((2-((4-nitrophenyl)amino)ethyl) amino)-3-phenoxy propan-2-ol; R1-((2-((4-nitrophenyl)amino)ethyl)amino)-3-phenoxypropan-2-ol; RS1-((3-methoxy propyl) amino)-3-phenoxybutan-2-ol; S1-((3-methoxypropyl) amino)-3-phenoxybutan-2-ol; R1-((3-methoxypropyl) amino)-3-phenoxybutan-2-ol; RS1-(isopropylamino)-3-((2-methyl-1H-indol-4-yl)oxy) propan-2-ol; S1-(isopropylamino)-3-((2-methyl-1H-indol-4-yl)oxy)propan-2-ol; R1-(isopropylamino)-3-((2-methyl-1H-indol-4-yl)oxy)propan-2-ol; RS1-(isopropylamino)-3-((6-methylfuro[3,2-c]pyridin-4-yl)oxy)propan-2-ol; S1-(isopropylamino)-3-((6-methylfuro[3,2-c]pyridin-4-yl)oxy) propan-2-ol; R1-(isopropylamino)-3-((6-methylfuro[3,2-c]pyridin-4-yl)oxy) propan-2-ol; RS1-(isopropylamino)-3-(naphthalen-1-ylmethoxy)propan-2-ol; S1-(isopropyl amino)-3-(naphthalen-1-ylmethoxy) propan-2-ol; R1-(isopropylamino)-3-(naphthalen-1-ylmethoxy) propan-2-ol; RS1-(isopropylamino)-3-((3-(4-methylpiperazin-1-yl) pyrazin-2-yl)oxy)propan-2-ol; S1-(isopropylamino)-3-((3-(4-methylpiperazin-1-yl)pyrazin-2-yl)oxy) propan-2-ol; R1-(isopropylamino)-3-((3-(4-methylpiperazin-1-yl)pyrazin-2-yl)oxy) propan-2-ol; RS1-(2-nitro-1H-imidazol-1-yl)-3-phenoxypropan-2-ol; S1-(2-nitro-1H-imidazol-1-yl)-3-phenoxypropan-2-ol; R1-(2-nitro-1H-imidazol-1-yl)-3-phenoxypropan-2-ol; RS1-(6-amino-2-ethoxy-9H-purin-9-yl)-3-phenoxypropan-2-ol; S1-(6-amino-2-ethoxy-9H-purin-9-yl)-3-phenoxy propan-2-ol; R1-(6-amino-2-ethoxy-9H-purin-9-yl)-3-phenoxypropan-2-ol; RS1-(isopropylamino)-3-((2-methylfuro[3,2-c]pyridin-4-yl)oxy) propan-2-ol; S1-(isopropylamino)-3-((2-methylfuro [3,2-c] pyridin-4-yl)oxy)propan-2-ol; R1-(isopropylamino)-3-((2-methylfuro[3,2-c]pyridin-4-yl)oxy) propan-2-ol; RS1-(isopropylamino)-3-(p-tolyloxy)propan-2-ol; S1-(isopropylamino)-3-(p-tolyloxy)propan-2-ol; R1-(isopropylamino)-3-(p-tolyloxy)propan-2-ol; RS1-(isopropylamino)-3-((5-methyl-3-morpholinopyrazin-2-yl)oxy)propan-2-ol; S1-(isopropylamino)-3-((5-methyl-3-morpholinopyrazin-2-yl)oxy) propan-2-ol; R1-(isopropylamino)-3-((5-methyl-3-morpholinopyrazin-2-yl)oxy)propan-2-ol; RS1-(4-(2-chlorophenyl) piperazin-1-yl)-3-phenoxy propan-2-ol; S1-(4-(2-chlorophenyl) piperazin-1-yl)-3-phenoxypropan-2-ol; R1-(4-(2-chloro phenyl) piperazin-1-yl)-3-phenoxypropan-2-ol; RS1-(isopropylamino)-3-((2-methylthieno [3,2-c]pyridin-4-yl)oxy)propan-2-ol; S1-(isopropyl amino)-3-((2-methylthieno[3,2-c]pyridin-4-yl)oxy) propan-2-ol; R-(isopropylamino)-3-((2-methylthieno[3,2-c]pyridin-4-yl)oxy)propan-2-ol; RS1-(isopropylamino)-3-(pyrimidin-2-yloxy)propan-2-ol; S1-(isopropylamino)-3-(pyrimidin-2-yloxy)propan-2-ol; R1-(isopropylamino)-3-(pyrimidin-2-yloxy)propan-2-ol; RS1-((3,4-dimethoxyphenethyl)amino)-3-phenoxypropan-2-ol; S1-((3,4-dimethoxyphenethyl)amino)-3-phenoxypropan-2-ol; R1-((3,4-dimethoxyphenethyl)amino)-3-phenoxypropan-2-ol; RS1-(4-(3-(1H-1,2,4-triazol-1-yl)propoxy)phenoxy)-3-(isopropylamino)propan-2-ol; S1-(4-(3-(1H-1,2,4-triazol-1-yl)propoxy)phenoxy)-3-(isopropylamino)propan-2-ol; R1-(4-(3-(1H-1,2,4-triazol-1-yl)propoxy)phenoxy)-3-(isopropylamino)propan-2-ol; RS1-(isopropylamino)-3-phenoxypropan-2-ol; S1-(isopropylamino)-3-phenoxypropan-2-ol; R1-(isopropylamino)-3-phenoxypropan-2-ol; RS1-(4-(3-(1H-1,2,4-triazol-1-yl)propoxy)phenoxy)-3-(isopropylamino)propan-2-ol; S1-(4-(3-(1H-1,2,4-triazol-1-yl)propoxy)phenoxy)-3-(isopropylamino)propan-2-ol; R1-(4-(3-(1H-1,2,4-triazol-1-yl)propoxy)phenoxy)-3-(isopropylamino)propan-2-ol; RS1-(isopropylamino)-3-(o-tolyloxy)propan-2-ol; S1-(isopropylamino)-3-(o-tolyloxy)propan-2-ol; R1-(isopropylamino)-3-(o-tolyloxy)propan-2-ol; RS2-(isopropylamino)-1-(4-methoxyphenoxy)ethan-1-ol; S2-(isopropylamino)-1-(4-methoxyphenoxy)ethan-1-ol; R2-(isopropylamino)-1-(4-methoxyphenoxy)ethan-1-ol; RS(Z)-1-(isopropylamino)-3-(2-methoxy-4-(prop-1-en-1-yl) phenoxy) propan-2-ol; S(Z)-1-(isopropylamino)-3-(2-methoxy-4-(prop-1-en-1-yl)phenoxy) propan-2-ol; R(Z)-1-(isopropylamino)-3-(2-methoxy-4-(prop-1-en-1-yl)phenoxy) propan-2-ol; RS1-(isopropylamino)-3-(4-(2-(methylthio)ethoxy)phenoxy)propan-2-ol; S1-(isopropylamino)-3-(4-(2-(methylthio)ethoxy)phenoxy) propan-2-ol; R1-(isopropylamino)-3-(4-(2-(methylthio) ethoxy) phenoxy)propan-2-ol; RS(E)-1-(isopropylamino)-3-(2-methoxy-4-(prop-1-en-1-yl)phenoxy)propan-2-ol; S(E)-1-(isopropylamino)-3-(2-methoxy-4-(prop-1-en-1-yl)phenoxy)propan-2-ol; R(E)-1-(isopropylamino)-3-(2-methoxy-4-(prop-1-en-1-yl)phenoxy)propan-2-ol; RS1-(isopropylamino)-3-(mesityloxy)propan-2-ol; S1-(isopropylamino)-3-(mesityloxy)propan-2-ol; R1-(isopropylamino)-3-(mesityloxy)propan-2-ol; RS1-(isopropylamino)-3-(4-((1-(methyl thio)propan-2-yl)oxy) phenoxy)propan-2-ol; S1-(isopropylamino)-3-(4-((1-(methylthio)propan-2-yl)oxy) phenoxy) propan-2-ol; R1-(isopropylamino)-3-(4-((1-(methylthio)propan-2-yl)oxy) phenoxy) propan-2-ol; RS1-(isopropylamino)-3-(4-(3-methyl-1H-indol-2-yl)phenoxy)propan-2-ol; S1-(isopropylamino)-3-(4-(3-methyl-1H-indol-2-yl)phenoxy)propan-2-ol; R1-(isopropyl amino)-3-(4-(3-methyl-1H-indol-2-yl) phenoxy)propan-2-ol; RS1-(isopropylamino)-3-(2-((5-methylisoxazol-3-yl)methoxy)phenoxy)propan-2-ol; S1-(isopropylamino)-3-(2-((5-methyl isoxazol-3-yl) methoxy) phenoxy)propan-2-ol; R1-(isopropylamino)-3-(2-((5-methyl isoxazol-3-yl)methoxy)phenoxy)propan-2-ol; RS1-(isopropylamino)-3-(2-((3-methylisoxazol-5-yl)methoxy) phenoxy)propan-2-ol; S1-(isopropylamino)-3-(2-((3-methylisoxazol-5-yl)methoxy) propan-2-ol; R1-(isopropylamino)-3-(2-((3-methylisoxazol-5-yl)methoxy)phenoxy)propan-2-ol; RS1-(4-((2H-1,2,3-triazol-2-yl)methoxy)phenoxy)-3-(isopropylamino)propan-2-ol; S1-(4-((2H-1,2,3-triazol-2-yl)methoxy)phenoxy)-3-(isopropylamino) propan-2-ol; R1-(4-((2H-1,2,3-triazol-2-yl)methoxy)phenoxy)-3-(isopropylamino)propan-2-ol; RS1-(isopropylamino)-3-(4-(2-methoxyethyl)phenoxy)propan-2- ol; S1-(isopropylamino)-3-(4-(2-methoxyethyl)phenoxy) propan-2-ol; R1-(isopropylamino)-3-(4-(2-methoxyethyl) phenoxy) propan-2-ol; RS1-(4-(2-(2H-1,2,3-triazol-2-yl) ethoxy)phenoxy)-3-(isopropylamino)propan-2-ol; S1-(4-(2-(2H-1,2,3-triazol-2-yl)ethoxy)phenoxy)-3-(isopropylamino) propan-2-ol; R1-(4-(2-(2H-1,2,3-triazol-2-yl)ethoxy) phenoxy)-3-(isopropylamino)propan-2-ol; RS1-(isopropylamino)-3-(3-methoxyphenoxy) propan-2-ol; S1-(isopropylamino)-3-(3-methoxyphenoxy)propan-2-ol; R1-(isopropylamino)-3-(3-methoxy phenoxy)propan-2-ol; RS1-(4-(2-(1H-1,2,4-triazol-1-yl)ethyl)phenoxy)-3-(isopropylamino) propan-2-ol; S1-(4-(2-(1H-1,2,4-triazol-1-yl) ethyl)phenoxy)-3-(isopropylamino) propan-2-ol; R1-(4-(2-(1H-1,2,4-triazol-1-yl)ethyl)phenoxy)-3-(isopropyl amino) propan-2-ol; RS1-(4-(2-(1H-pyrazol-1-yl)ethyl)phenoxy)-3-(isopropylamino) propan-2-ol; S1-(4-(2-(1H-pyrazol-1-yl) ethyl)phenoxy)-3-(isopropylamino)propan-2-ol; R1-(4-(2-(1H-pyrazol-1-yl)ethyl)phenoxy)-3-(isopropylamino) propan-2-ol; RS1-(4-(2-(1H-1,2,4-triazol-1-yl)ethyl) phenoxy)-3-(isopropylamino)propan-2-ol; S1-(4-(2-(1H-1, 2,4-triazol-1-yl)ethyl) phenoxy)-3-(isopropylamino)propan-2-ol; R1-(4-(2-(1H-1,2,4-triazol-1-yl)ethyl)phenoxy)-3-(isopropylamino)propan-2-ol; RS1-(4-(2-(1H-1,2,4-triazol-1-yl)ethoxy)phenoxy)-3-(isopropyl amino) propan-2-ol; S1-(4-(2-(1H-1,2,4-triazol-1-yl)ethoxy)phenoxy)-3-(isopropylamino) propan-2-ol; R1-(4-(2-(1H-1,2,4-triazol-1-yl)ethoxy)phenoxy)-3-(isopropylamino)propan-2-ol RS1-(4-((2H-1,2,3-triazol-2-yl)methoxy)phenoxy)-3-(isopropylamino)propan-2-ol; S1-(4-((2H-1,2,3-triazol-2-yl)methoxy)phenoxy)-3-(isopropylamino)propan-2-ol; R1-(4-((2H-1,2,3-triazol-2-yl)methoxy)phenoxy)-3-(isopropylamino)propan-2-ol; RS1-(4-(2-(2H-1,2,3-triazol-2-yl)ethoxy) phenoxy)-3-(isopropylamino)propan-2-ol; S1-(4-(2-(2H-1,2,3-triazol-2-yl) ethoxy)phenoxy)-3-(isopropylamino) propan-2-ol; R1-(4-(2-(2H-1,2,3-triazol-2-yl) ethoxy)phenoxy)-3-(isopropylamino) propan-2-ol; RSN-(4-(2-hydroxy-3-(isopropylamino) propoxy)phenyl) propionamide; SN-(4-(2-hydroxy-3-(isopropylamino) propoxy)phenyl)propionamide; RN-(4-(2-hydroxy-3-(isopropylamino)propoxy)phenyl)propionamide; RS1-(isopropylamino)-3-((4-methylnaphthalen-1-yl)oxy)propan-2-ol; S1-(isopropylamino)-3-((4-methylnaphthalen-1-yl)oxy)propan-2-ol; R1-(isopropylamino)-3-((4-methylnaphthalen-1-yl)oxy)propan-2-ol; RS1-(isopropylamino)-3-((2-(methylthio)pyrimidin-4-yl)oxy)propan-2-ol; S-(isopropylamino)-3-((2-(methylthio)pyrimidin-4-yl)oxy)propan-2-ol; R1-(isopropylamino)-3-((2-(methylthio)pyrimidin-4-yl)oxy) propan-2-ol; RS1-(isopropylamino)-3-(naphthalen-2-yloxy) propan-2-ol; S 1-(isopropylamino)-3-(naphthalen-2-yloxy) propan-2-ol; R1-(isopropylamino)-3-(naphthalen-2-yloxy) propan-2-ol; RS1-(isopropylamino)-3-((3-(phenylthio) pyrazin-2-yl)oxy)propan-2-ol; S1-(isopropylamino)-3-((3-(phenylthio)pyrazin-2-yl)oxy)propan-2-ol; R1-(isopropylamino)-3-((3-(phenylthio)pyrazin-2-yl)oxy) propan-2-ol; RS3-(4-(2-hydroxy-3-(isopropylamino) propoxy)-3-methoxyphenyl)propanal; S3-(4-(2-hydroxy-3-(isopropylamino)propoxy)-3-methoxyphenyl) propanal; R3-(4-(2-hydroxy-3-(isopropylamino)propoxy)-3-methoxyphenyl) propanal; RS1-(isopropylamino)-3-phenylpropan-2-ol; S1-(isopropylamino)-3-phenylpropan-2-ol; R1-(isopropylamino)-3-phenylpropan-2-ol; RS1-(isopropylamino)-3-(m-tolyloxy)propan-2-ol; S 1-(isopropylamino)-3-(m-tolyloxy)propan-2-ol; R1-(isopropylamino)-3-(m-tolyloxy) propan-2-ol; RS1-(isopropylamino)-3-((6-morpholinopyridazin-3-yl)oxy)propan-2-ol; S-(isopropylamino)-3-((6-morpholinopyridazin-3-yl)oxy) propan-2-ol; R1-(isopropylamino)-3-((6-morpholino pyridazin-3-yl)oxy)propan-2-ol; RS1-(isopropylamino)-3-(2-methyl-3-nitrophenoxy)propan-2-ol S1-(isopropylamino)-3-(2-methyl-3-nitrophenoxy)propan-2-ol; R1-(isopropylamino)-3-(2-methyl-3-nitrophenoxy)propan-2-ol; RS1-(isopropylamino)-4-(p-tolylthio)butan-2-ol; S1-(isopropyl amino)-4-(p-tolylthio)butan-2-ol; R1-(isopropylamino)-4-(p-tolylthio)butan-2-ol; RS1-(4-(2-(1H-pyrazol-1-yl)ethyl)phenoxy)-3-(isopropylamino)propan-2-ol; S1-(4-(2-(1H-pyrazol-1-yl)ethyl)phenoxy)-3-(isopropylamino) propan-2-ol; R1-(4-(2-(1H-pyrazol-1-yl)ethyl)phenoxy)-3-(isopropylamino)propan-2-ol; RS1-((2-aminopyridin-3-yl) oxy)-3-(isopropylamino)propan-2-ol S1-((2-aminopyridin-3-yl)oxy)-3-(isopropylamino)propan-2-ol; R1-((2-aminopyridin-3-yl)oxy)-3-(isopropylamino)propan-2-ol; RS1-(tert-butylamino)-3-(3-methyl-2-nitrophenoxy)propan-2-ol S1-(tert-butylamino)-3-(3-methyl-2-nitrophenoxy)propan-2-ol; R1-(tert-butylamino)-3-(3-methyl-2-nitrophenoxy)propan-2-ol; RS1-(2-cyclohexylphenoxy)-3-(isopropylamino)propan-2-ol S1-(2-cyclohexylphenoxy)-3-(isopropylamino)propan-2-ol; R1-(2-cyclohexylphenoxy)-3-(isopropylamino)propan-2-ol; RS1-(4-(1-hydroxy-2-methoxyethyl)phenoxy)-3-(isopropylamino) propan-2-ol; S1-(4-(1-hydroxy-2-methoxyethyl)phenoxy)-3-(isopropylamino) propan-2-ol; R1-(4-(1-hydroxy-2-methoxyethyl) phenoxy)-3-(isopropylamino) propan-2-ol; RS1-(3-amino phenoxy)-3-(2-methyl-1H-benzo[d]imidazol-1-yl)propan-2-ol; S1-(3-aminophenoxy)-3-(2-methyl-H-benzo[d]imidazol-1-yl)propan-2-ol; R1-(3-aminophenoxy)-3-(2-methyl-1H-benzo[d]Imidazol-1-yl)propan-2-ol; RS1-(4-(2-(cyclobutylmethoxy)ethoxy)phenoxy)-3-(isopropyl amino) propan-2-ol; S1-(4-(2-(cyclobutylmethoxy)ethoxy)phenoxy)-3-(isopropylamino) propan-2-ol; R1-(4-(2-(cyclobutylmethoxy)ethoxy)phenoxy)-3-(isopropyl amino)propan-2-ol; RS1-((2-((6-chloropyridazin-3-yl)oxy)ethyl) amino-3-phenoxy propan-2-ol; S1-((2-((6-chloropyridazin-3-yl)oxy)ethyl)amino)-3-phenoxypropan-2-ol; R1-((2-((6-chloropyridazin-3-yl)oxy)ethyl)amino)-3-phenoxypropan-2-ol; RS1-(4-(2-(cyclo propyl methoxy)ethyl)phenoxy)-3-(isopropylamino)propan-2-ol; S1-(4-(2-(cyclopropyl methoxy) ethyl)phenoxy)-3-(isopropylamino)propan-2-ol; R1-(4-(2-(cyclopropylmethoxy) ethyl)phenoxy)-3-(isopropylamino)propan-2-ol; RS3,3'-(butylazanediyl)bis (1-phenoxypropan-2-ol); S3,3'-(butylazanediyl)bis(1-phenoxypropan-2-ol); R3,3'-(butylazanediyl)bis(1-phenoxypropan-2-ol); RS1-(4-((2-isopropoxyethoxy)methyl)phenoxy)-3-(isopropylamino)propan-2-ol; S1-(4-((2-iso propoxyethoxy) methyl)phenoxy)-3-(isopropylamino)propan-2-ol; R1-(4-((2-isopropoxyethoxy) methyl) phenoxy)-3-(isopropylamino)propan-2-ol; RS1-(3,4-dimethylphenoxy)-3-(2,2,5, 5-tetra methyl-2,5-dihydro-H-pyrrol-1-yl)propan-2-ol; S1-(3,4-dimethyl phenoxy)-3-(2,2,5,5-tetra methyl-2,5-dihydro-H-pyrrol-1-yl)propan-2-ol; R1-(3,4-dimethyl phenoxy)-3-(2,2,5,5-tetra methyl-2,5-dihydro-1H-pyrrol-1-yl)propan-2-ol; RS3-((2-hydroxy-3-phenoxypropyl) amino) propan-1-ol; S3-((2-hydroxy-3-phenoxypropyl)amino)propan-1-ol; R3-((2-hydroxy-3-phenoxypropyl)amino)propan-1-ol; RS5-(2-hydroxy-3-(isopropylamino)propoxy)chroman-3-yl nitrate; S5-(2-hydroxy-3-(isopropylamino) propoxy)chroman-3-yl nitrate; R5-(2-hydroxy-3-(isopropylamino)propoxy)chroman-3-yl nitrate; RS1-(isopropylamino)-3-((6-methylpyrazin-2-yl)oxy)propan-2-ol; S1-(isopropylamino)-3-((6-methylpyrazin-2-yl)oxy) propan-2-ol; R1-(isopropylamino)-3-((6-methylpyrazin-2-yl)oxy)propan-2-ol; RS1-(isopropylamino)-3-((3-morpholinopyrazin-2-yl)oxy)propan-2-ol; S1-(isopropylamino)-3-((3-morpholinopyrazin-2-yl)oxy) propan-2-ol; R1-(isopropylamino)-3-((3- morpholinopyrazin-2-yl)oxy)propan-2-ol; RS1-(isopropylamino)-3-((6-methylpyrazin-2-yl)oxy)propan-2-ol; S1-(isopropylamino)-3-((6-methylpyrazin-2-yl)oxy)propan-2-ol; R1-(isopropylamino)-3-((6-methylpyrazin-2-yl)oxy)propan-2-ol; RSN-(8-(2-hydroxy-3-(isopropylamino)propoxy)-1,2,3,4,4a,7,8,8a-octahydro-1,4-ethanonaphthalen-5-yl)methanesulfonamide; SN-(8-(2-hydroxy-3-(isopropylamino)propoxy)-1,2,3,4,4a,7,8,8a-octahydro-1,4-ethanonaphthalen-5-yl)methane sulfonamide; RN-(8-(2-hydroxy-3-(isopropylamino)propoxy)-1,2,3,4,4a,7,8,8a-octahydro-1,4-ethanonaphthalen-5-yl)methanesulfonamide; RS1-(isopropylamino)-3-((6-methoxy pyridazin-3-yl)oxy)propan-2-ol; S1-(isopropylamino)-3-((6-methoxypyridazin-3-yl)oxy)propan-2-ol; R1-(isopropylamino)-3-((6-methoxypyridazin-3-yl)oxy)propan-2-ol; RS1-(isopropylamino)-3-(thiazol-2-yloxy)propan-2-ol; S1-(isopropylamino)-3-(thiazol-2-yloxy) propan-2-ol; R1-(isopropylamino)-3-(thiazol-2-yloxy)propan-2-ol; RS1-(isopropylamino)-3-(4-nitrophenyl) propan-2-ol; S1-(isopropylamino)-3-(4-nitrophenyl)propan-2-ol; R1-(isopropylamino)-3-(4-nitrophenyl)propan-2-ol; RS1-(isopropylamino)-3-(4-nitrophenyl)propan-2-ol; S 1-(isopropylamino)-3-(4-nitrophenyl)propan-2-ol; R1-(isopropylamino)-3-(4-nitrophenyl)propan-2-ol; RS1-(4-allyl-2-methoxyphenoxy)-3-(isopropylamino)propan-2-ol; S1-(4-allyl-2-methoxy phenoxy)-3-(isopropylamino)propan-2-ol; R1-(4-allyl-2-methoxyphenoxy)-3-(isopropyl amino) propan-2-ol; RS1-(isopropylamino)-3-(2,4,5-trimethylphenoxy)propan-2-ol; S1-(isopropylamino)-3-(2,4,5-trimethylphenoxy)propan-2-ol; R1-(isopropylamino)-3-(2,4,5-trimethylphenoxy) propan-2-ol; RS1-(isopropylamino)-3-(2-methoxyphenoxy)propan-2-ol; S1-(isopropylamino)-3-(2-methoxyphenoxy)propan-2-ol; R1-(isopropylamino)-3-(2-methoxyphenoxy)propan-2-ol; RS1-(4-(2-methoxyethyl)phenoxy)-3-((3-phenylpropyl)amino)propan-2-ol; S1-(4-(2-methoxyethyl)phenoxy)-3-((3-phenylpropyl)amino)propan-2-ol; R1-(4-(2-methoxyethyl) phenoxy)-3-((3-phenylpropyl)amino)propan-2-ol; RS1-(2-(methylthio)phenoxy)-3-(2,2,5,5-tetramethylpyrrolidin-1-yl) propan-2-ol; S1-(2-(methylthio)phenoxy)-3-(2,2,5,5-tetramethylpyrrolidin-1-yl)propan-2-ol R1-(2-(methylthio)phenoxy)-3-(2,2,5,5-tetramethylpyrrolidin-1-yl)propan-2-ol; RS3,3'-((2-hydroxyethyl)azanediyl)bis(1-phenoxypropan-2-ol); S3,3'-((2-hydroxyethyl)azanediyl) bis(1-phenoxy propan-2-ol); R3,3'-((2-hydroxyethyl)azanediyl)bis(1-phenoxypropan-2-ol); RS1-(2-(methylthio)phenoxy)-3-(2,2,6,6-tetramethylpiperidin-1-yl)propan-2-ol; S1-(2-(methylthio) phenoxy)-3-(2,2,6,6-tetramethylpiperidin-1-yl)propan-2-ol; R1-(2-(methylthio)phenoxy)-3-(2,2,6,6-tetramethyl piperidin-1-yl)propan-2-ol; RS1-(3,6-dihydropyridin-1 (2H)-yl)-3-(o-tolyloxy)propan-2-ol; S1-(3,6-dihydropyridin-1(2H)-yl)-3-(o-tolyloxy)propan-2-ol; R1-(3,6-dihydropyridin-1 (2H)-yl)-3-(o-tolyloxy)propan-2-ol; RS1-((4-methoxyphenyl)amino)-3-phenoxypropan-2-ol; S1-((4-methoxyphenyl)amino)-3-phenoxypropan-2-ol; R1-((4-methoxyphenyl) amino)-3-phenoxypropan-2-ol; RS1-((2-((2,6-dichlorophenyl)amino)ethyl)amino)-3-(m-tolyloxy)propan-2-ol; S1-((2-((2,6-dichlorophenyl)amino)ethyl)amino)-3-(m-tolyloxy)propan-2-ol; R1-((2-((2,6-dichlorophenyl)amino)ethyl)amino)-3-(m-tolyloxy)propan-2-ol; RS1-(4-(2-methoxyphenyl)piperazin-1-yl)-3-(m-tolyloxy)propan-2-ol; S1-(4-(2-methoxyphenyl)piperazin-1-yl)-3-(m-tolyloxy)propan-2-ol; R1-(4-(2-methoxyphenyl)piperazin-1-yl)-3-(m-tolyloxy)propan-2-ol; RS1-((2-((2,5-dimethylphenyl)amino)ethyl)amino)-3-(m-tolyloxy)propan-2-ol; S1-((2-((2,5-dimethylphenyl)amino)ethyl)amino)-3-(m-tolyloxy)propan-2-ol; R1-((2-((2,5-dimethyl phenyl)amino) ethyl)amino)-3-(m-tolyloxy)propan-2-ol; RS1-(((1-benzyl-3,5-dimethyl-1H-pyrazol-4-yl)methyl)(methyl)amino)-3-phenoxypropan-2-ol; S1-(((1-benzyl-3,5-dimethyl-1H-pyrazol-4-yl)methyl)(methyl)amino)-3-phenoxypropan-2-ol; R1-(((1-benzyl-3,5-dimethyl-1H-pyrazol-4-yl)methyl) (methyl)amino)-3-phenoxypropan-2-ol; RS1-(tert-butylamino)-3-((3-methyl-1H-indol-4-yl)oxy)propan-2-ol; S1-(tert-butylamino)-3-((3-methyl-1H-indol-4-yl)oxy)propan-2-ol; R1-(tert-butylamino)-3-((3-methyl-1H-indol-4-yl)oxy)propan-2-ol; RS1-(methyl amino)-3-phenoxypropan-2-ol; S1-(methylamino)-3-phenoxypropan-2-ol; R1-(methyl amino)-3-phenoxypropan-2-ol; RS1-((2-hydroxyethyl)amino)-3-phenoxypropan-2-ol; S1-((2-hydroxyethyl)amino)-3-phenoxypropan-2-ol; R1-((2-hydroxyethyl)amino)-3-phenoxypropan-2-ol; RS1-((4-methylthiazol-5-yl)oxy)-3-(4-(2-(neopentyloxy)phenyl)piperazin-1-yl)propan-2-ol; S1-((4-methylthiazol-5-yl)oxy)-3-(4-(2-(neopentyloxy)phenyl)piperazin-1-yl)propan-2-ol; R1-((4-methylthiazol-5-yl)oxy)-3-(4-(2-(neopentyloxy)phenyl)piperazin-1-yl)propan-2-ol; RS1-(4-(2-ethoxyphenyl)piperazin-1-yl)-3-((4-methylthiazol-5-yl)oxy)propan-2-ol; S1-(4-(2-ethoxyphenyl) piperazin-1-yl)-3-((4-methylthiazol-5-yl)oxy)propan-2-ol; R1-(4-(2-ethoxyphenyl) piperazin-1-yl)-3-((4-methylthiazol-5-yl)oxy)propan-2-ol; RS1-phenoxy-3-(quinuclidin-3-ylamino)propan-2-ol; S1-phenoxy-3-(quinuclidin-3-ylamino)propan-2-ol; R1-phenoxy-3-(quinuclidin-3-ylamino)propan-2-ol; RS1-(4-(3-chlorophenyl)piperazin-1-yl)-3-((4-methylthiazol-5-yl)oxy)propan-2-ol; S1-(4-(3-chlorophenyl)piperazin-1-yl)-3-((4-methylthiazol-5-yl)oxy) propan-2-ol; R1-(4-(3-chlorophenyl)piperazin-1-yl)-3-((4-methylthiazol-5-yl)oxy)propan-2-ol; RS1-(((6,7-dimethoxyisochroman-1-yl)methyl)(methyl)amino)-3-phenoxypropan-2-ol; S1-(((6,7-dimethoxyisochroman-1-yl)methyl)(methyl)amino)-3-phenoxypropan-2-ol; R1-(((6,7-dimethoxy isochroman-1-yl)methyl)(methyl)amino)-3-phenoxypropan-2-ol; RS1-((2-aminoethyl)amino)-3-phenoxy propan-2-ol; S1-((2-aminoethyl)amino)-3-phenoxypropan-2-ol; R1-((2-aminoethyl)amino)-3-phenoxypropan-2-ol; RS1-(4-(2-(isopentyloxy)phenyl)piperazin-1-yl)-3-((4-methylthiazol-5-yl)oxy)propan-2-ol; S1-(4-(2-(isopentyloxy)phenyl)piperazin-1-yl)-3-((4-methyl thiazol-5-yl)oxy)propan-2-ol; R1-(4-(2-(isopentyloxy)phenyl)piperazin-1-yl)-3-((4-methyl thiazol-5-yl)oxy)propan-2-ol; RS1-(4-(2-isobutoxyphenyl)piperazin-1-yl)-3-((4-methyl thiazol-5-yl)oxy)propan-2-ol; S1-(4-(2-isobutoxyphenyl)piperazin-1-yl)-3-((4-methylthiazol-5-yl)oxy) propan-2-ol; R1-(4-(2-isobutoxyphenyl)piperazin-1-yl)-3-((4-methylthiazol-5-yl)oxy) propan-2-ol; RS1-((2-((2,6-dimethylphenyl)amino)ethyl)amino)-3-phenoxypropan-2-ol; S1-((2-((2,6-dimethyl phenyl)amino)ethyl)amino)-3-phenoxypropan-2-ol; R1-((2-((2,6-dimethylphenyl) amino)ethyl)amino)-3-phenoxypropan-2-ol; RS1-((2-((2-chlorophenyl)amino)ethyl)amino)-3-phenoxypropan-2-ol; S1-((2-((2-chlorophenyl)amino)ethyl)amino)-3-phenoxypropan-2-ol; R1-((2-((2-chlorophenyl)amino)ethyl)amino)-3-phenoxypropan-2-ol; RS1-phenoxy-3-((2-(o-tolylamino)ethyl)amino)propan-2-ol; S1-phenoxy-3-((2-(o-tolylamino)ethyl)amino)propan-2-ol R1-phenoxy-3-((2-(o-tolylamino)ethyl)amino)propan-2-ol; RS1-((4-methoxybutyl)amino)-3-phenoxypropan-2-ol; S1-((4-methoxybutyl)amino)-3-phenoxypropan-2-ol; R1-((4-methoxybutyl)amino)-3-phenoxypropan-2-ol; RS1-((2-((3-nitrophenyl)amino)ethyl)amino)-3-(m-tolyloxy)propan-2-ol; S1-((2-((3-nitrophenyl)amino)ethyl)amino)-3-(m-tolyloxy)propan-2-ol R1-((2-((3-nitrophenyl)amino)ethyl)amino)-3-(m-tolyloxy)propan-2-ol; RS1-((2-((3- nitrophenyl) amino) ethyl)amino)-3-(m-tolyloxy)propan-2-ol; S1-((2-((3-nitrophenyl)amino)ethyl)amino)-3-(m-tolyloxy)propan-2-ol; R1-((2-((3-nitrophenyl)amino)ethyl)amino)-3-(m-tolyloxy)propan-2-ol; RS1-((2-((2-nitrophenyl)amino)ethyl)amino)-3-phenoxypropan-2-ol; S1-((2-((2-nitrophenyl) amino) ethyl)amino)-3-phenoxypropan-2-ol; R1-((2-((2-nitrophenyl)amino)ethyl)amino)-3-phenoxypropan-2-ol; RS1-((2-((2-nitrophenyl)amino)ethyl) amino)-3-phenoxypropan-2-ol; S1-((2-((2-nitrophenyl)amino)ethyl)amino)-3-phenoxypropan-2-ol; R 1-((2-((2-nitrophenyl)amino) ethyl)amino)-3-phenoxypropan-2-ol; RS1-(isopropylamino)-3-((1-tosyl-1H-indol-4-yl)oxy) propan-2-ol; S1-(isopropylamino)-3-((1-tosyl-1H-indol-4-yl)oxy)propan-2-ol; R1-(isopropylamino)-3-((1-tosyl-1H-indol-4-yl)oxy)propan-2-ol.

Another embodiment is a compound of Formula If, wherein $R_6$ and $R_7$ are independently substituted with one, two or three halogens, wherein the halogen is F, Cl, or Br. Examples of halogenated compounds of Formula I include, but not limited to:

N-methyl-N-(trifluoromethyl)-2-((1,7,7-trimethyl-2-phenylbicyclo[2.2.1]heptan-2-yl)oxy) ethan-1-amine,
N,N-bis(trifluoromethyl)-2-((1,7,7-trimethyl-2-phenylbicyclo [2.2.1]heptan-2-yl)oxy)ethan-1-amine,
2-((1,7-dimethyl-2-phenyl-7-(trifluoromethyl)bicyclo [2.2.1]heptan-2-yl)oxy)-N,N-bis (trifluoromethyl)ethan-1-amine,
2-((1-methyl-2-phenyl-7,7-bis(trifluoromethyl)bicyclo [2.2.1]heptan-2-yl)oxy)-N,N-bis(trifluoromethyl)ethan-1-amine,
N-methyl-2-((1-methyl-2-phenyl-7,7-bis(trifluoromethyl) bicyclo [2.2.1]heptan-2-yl)oxy)-N-(trifluoromethyl)ethan-1-amine,
N,N-dimethyl-2-((1-methyl-2-phenyl-7,7-bis (trifluoromethyl)bicyclo [2.2.1]heptan-2-yl)oxy)ethan-1-amine,
2-((1,7-dimethyl-2-phenyl-7-(trifluoromethyl)bicyclo [2.2.1]heptan-2-yl)oxy)-N,N-dimethylethan-1-amine, and
N,N-dimethyl-2-((1,7,7-trimethyl-2-(4-(trifluoromethoxy) phenyl)bicyclo[2.2.1]heptan-2-yl)oxy)ethan-1-amine.

Another embodiment is a composition comprising a compound of Formula If listed below:

2-phenyl-2-(3'-dimethylaminopropoxy)-1,7,7-trimethylbicyclo[2,2,1]heptane;
2-phenyl-2-(3'-diethylaminopropoxy)-1,7,7-trimethylbicyclo[2,2,1]heptane;
2-(p-methoxy-phenyl)-2-(3'-dimethylaminopropoxy)-1,7,7-trimethyl-bicyclo(2,2,1) heptane; 2-benzyl-2-(3'-dimethylaminopropoxy)-1,7,7-trimethylbicyclo [2,2,1]heptane;
2-benzyl-2-(3'-dimethylamino-2'-methylpropoxy)-1,7,7-trimethyl-bicyclo[2,2,1]heptane;
2-benzyl-2-(2-diisopropylaminoethoxy)-1,7,7-trimethyl-bicyclo[2,2,1]heptane;
2-benzyl-2-1'-(4'-benzylpiperazinyl)-propoxy 1,7,7-trimethylbicyclo [2,2,1]heptane;
2-benzyl-2-(3'-diisopropylaminopropoxy)-1,7,7-trimethylbicyclo[2,2,1]heptane;
2-benzyl-2-(3'-diethylaminopropoxy)-1,7,7-trimethylbicyclo [2,2,1]heptane;
2-benzyl-2-(3'-dimethylaminopropoxy)-1,7,7-trimethyl-bicyclo [2,2,1]heptane;
2-benzyl-2-(2'-diethylaminoethoxy)-1,7,7-trimethylbicyclo [2,2,1]heptane;
2-benzyl-2-(3'-dimethylamino propoxy)-1,7,7-trimethylbicyclo[2,2,1]heptane;
2-(3'-dimethylaminopropoxy)-2-(4'-methoxyphenyl)-1,7,7-trimethylbicyclo[2,2,1]heptane;
2-(p-chloro-benzyl)-2-(3'-dimethylaminopropoxy)-1,7,7-trimethylbicyclo[2,2,1]heptane;
2-(p-chloro-benzyl)-2-(2'-dimethylaminoethoxy)-1,7,7-trimethylbicyclo [2,2,1]heptane;
2-(3'-dimethylamino-2'-methyl)-propoxy-2-(p-chloro-phenyl)-1,7,7-trimethylbicyclo [2,2,1]heptane;
2-(3'-dimethylaminopropoxy)-2-phenyl-1,7,7-trimethylbicyclo[2,2,1]heptane;
2-(2'-dimethylaminoethoxy)-2-phenyl-1,7,7-trimethylbicyclo[2,2,1]heptane;
2-(3-diethylaminopropoxy)-2-phenyl-1,7,7-trimethylbicyclo[2,2,1]heptane;
2-(2'-diethylaminoethoxy)-2-(2'-thienyl)-1,7,7-trimethylbicyclo[2,2,1]heptane;
2-(3'-dimethylaminopropoxy)-2-(2'-thienyl)-1,7,7-trimethylbicyclo[2,2,1]heptane;
2-(3'-diethylaminopropoxy)-2-(2'-thienyl)-1,7,7-trimethylbicyclo[2,2,1]heptane;
2-benzyl-2-3'-(N-cyclohexyl-N-methyl)aminopropoxy]-1,7,7-trimethylbicyclo[2,2,1]heptane;
2-(p-methoxyphenyl)-2-(3'-dimethylaminopropoxy)-1,7,7-trimethylbicyclo[2,2,1]heptane;
(1R,2S,4R)-(−)-2-[(2'-{N,N-dimethylamino}-ethoxy)]-2-[phenyl]-1,7,7-trimethylbicyclo [2,2,1]heptane;
(1R,2S,4R)-(−)-2-benzyl-2-(3'-dimethylaminopropoxy)-1,7,7-trimethylbicyclo[2,2,1]heptane;
(1R,2S,4R)-(−)-2-benzyl-2-(2'-methyl-3'-dimethylaminopropoxy)-1,7,7-trimethylbicyclo [2,2,1]heptane;
(1RS,2RS,4RS)-2-phenyl-2-(2'-dimethylaminoethoxy)-1,7,7 trimethylbicyclo[2,2,1]heptane;
(1S,2R,4S)-(+)-2-phenyl-2-(2'-dimethylaminoethoxy)-1,7,7-trimethylbicyclo[2,2,1]heptane;
N,N-dimethyl-2-[[(1R,3S,4R)-4,7,7-trimethyl-3-phenyl-3-bicyclo[2.2.1] heptanyl] oxy]ethanamine (deramciclane);
N-methyl-N-(trifluoromethyl)-2-((1,7,7-trimethyl-2-phenylbicyclo [2.2.1]heptan-2-yl)oxy) ethan-1-amine,
N,N-bis(trifluoromethyl)-2-((1,7,7-trimethyl-2-phenylbicyclo[2.2.1]heptan-2-yl)oxy)ethan-1-amine,
2-((1,7-dimethyl-2-phenyl-7-(trifluoromethyl)bicyclo [2.2.1]heptan-2-yl)oxy)-N,N-bis(trifluoromethyl)ethan-1-amine,
2-((1-methyl-2-phenyl-7,7-bis(trifluoromethyl)bicyclo [2.2.1]heptan-2-yl)oxy)-N,N-bis(trifluoromethyl)ethan-1-amine,
N-methyl-2-((1-methyl-2-phenyl-7,7-bis(trifluoroethyl)bicyclo[2.2.1]heptan-2-yl)oxy)-N-(trifluoromethyl)ethan-1-amine,
N,N-dimethyl-2-((1-methyl-2-phenyl-7,7-bis(trifluoromethyl)bicyclo[2.2.1]heptan-2-yl)oxy)ethan-1-amine,
2-((1,7-dimethyl-2-phenyl-7-(trifluoromethyl)bicyclo [22.1] heptan-2-yl)oxy)-N,N-dimethylethan-1-amine, and
N,N-dimethyl-2-((1,7,7-trimethyl-2-(4-(trifluoromethoxy) phenyl)bicyclo[2.2.1]heptan-2-yl)oxy)ethan-1-amine.

Another embodiment is a composition comprising an acid addition salt of a compound of Formula If comprising hydrogen acetate, hydrogen acetyl salicylate, hydrogen adipate, hydrogen aspartate, hydrogen butyrate, hydrogen caprate, hydrogen caproate, hydrogen caprylate, hydrogen enanthate, hydrogen formate, hydrogen fumarate, hydrogen glutarate, hydrogen isophthallate, hydrogen maleate, hydrogen malonate, hydrogen oxalate, hydrogen pelargonate, hydrogen pimelate, hydrogen propionate, hydrogen phthallate, hydrogen salicylate, hydrogen sebacate, hydrogen succinate, hydrogen terephthallate, hydrogen tyrosinate, hydrogen tryptophanate, hydrogen methionate; hydrogen N-acyl-methionate; and hydrogen valerate.

Another embodiment is a composition comprising an acid addition salt of N,N-dimethyl-2-[[(1R,3S,4R)-4,7,7-trimethyl-3-phenyl-3-bicyclo[2.2.1]heptanyl]oxy]ethanamine (deramciclane) comprising deramciclane hydrogen acetate, deramciclane hydrogen acetyl salicylate, deramciclane hydrogen adipate, deramciclane hydrogen aspartate, deramciclane hydrogen butyrate, deramciclane hydrogen caprate, deramciclane hydrogen caproate, deramciclane hydrogen caprylate, deramciclane hydrogen enanthate, deramciclane hydrogen formate, deramciclane hydrogen fumarate, deramciclane hydrogen glutarate, deramciclane hydrogen isophthallate, deramciclane hydrogen maleate, deramciclane hydrogen malonate, deramciclane hydrogen oxalate, deramciclane hydrogen pelargonate, deramciclane hydrogen pimelate, deramciclane hydrogen propionate, deramciclane hydrogen phthallate, deramciclane hydrogen salicylate, deramciclane hydrogen sebacate, deramciclane hydrogen succinate, deramciclane hydrogen terephthallate, deramciclane hydrogen tyrosinate, deramciclane hydrogen tryptophanate, deramciclane hydrogen methionate; deramciclane hydrogen N-acyl-methionate; or deramciclane hydrogen valerate.

An embodiment of the invention is a composition comprising dextromethorphan or its acid addition salt and a compound of Formula I selected from the group consisting of:
2-phenyl-2-(2-dimethylaminoethoxy)-1,7,7-trimethylbicyclo[2,2,1]heptane;
2-phenyl-2-(3'-dimethylaminopropoxy)-1,7,7-trimethylbicyclo[2,2,1]heptane;
2-phenyl-2-(3'-diethylaminopropoxy)-1,7,7-trimethylbicyclo[2,2,1]heptane;
2-(p-methoxy-phenyl)-2-(3'-dimethylaminopropoxy)-1,7,7-trimethylbicyclo[2,2,1]heptane;
2-benzyl-2-(3'-dimethylaminopropoxy)-1,7,7-trimethylbicyclo[2,2,1]heptane;
2-benzyl-2-(3'-dimethylamino-2'-methylpropoxy)-1,7,7-trimethyl-bicyclo[2,2,1]heptane;
2-benzyl-2-(2-diisopropylaminoethoxy)-1,7,7-trimethyl-bicyclo[2,2,1]heptane;
2-benzyl-2-1'-(4'-benzylpiperazinyl)-propoxy1,7,7-trimethylbicyclo [2,2,1]heptane;
2-benzyl-2-(3'-diisopropylaminopropoxy)-1,7,7-trimethylbicyclo[2,2,1]heptane;
2-benzyl-2-(3'-diethylaminopropoxy)-1,7,7-trimethylbicyclo [2,2,1]heptane;
2-benzyl-2-(3'-dimethylaminopropoxy)-1,7,7-trimethyl-bicyclo[2,2,1]heptane;
2-benzyl-2-(2'-diethylaminoethoxy)-1,7,7-trimethylbicyclo [2,2,1]heptane;
2-benzyl-2-(3'-dimethylaminopropoxy)-1,7,7-trimethylbicyclo[2,2,1]heptane;
2-(3'-dimethylaminopropoxy)-2-(4'-methoxyphenyl)-1,7,7-trimethylbicyclo[2,2,1]heptane;
2-(p-chloro-benzyl)-2-(3'-dimethylaminopropoxy)-1,7,7-trimethylbicyclo[2,2,1]heptane;
2-(p-chloro-benzyl)-2-(2'-dimethylaminoethoxy)-1,7,7-trimethylbicyclo [2,2,1]heptane;
2-(3'-dimethylamino-2'-methyl)-propoxy-2-(p-chloro-phenyl)-1,7,7-trimethylbicyclo[2,2,1]heptane;
2-(3'-dimethylaminopropoxy)-2-phenyl-1,7,7-trimethylbicyclo[2,2,1]heptane;
2-(2'-dimethylaminoethoxy)-2-phenyl-1,7,7-trimethylbicyclo[2,2,1]heptane;
2-(3-diethylaminopropoxy)-2-phenyl-1,7,7-trimethylbicyclo [2,2,1]heptane;
2-(2'-diethylaminoethoxy)-2-(2'-thienyl)-1,7,7-trimethylbicyclo[2,2,1]heptane;
2-(3'-dimethylaminopropoxy)-2-(2'-thienyl)-1,7,7-trimethylbicyclo[2,2,1]heptane;
2-(3'-diethylaminopropoxy)-2-(2'-thienyl)-1,7,7-trimethylbicyclo[2,2,1]heptane;
2-benzyl-2-3'-(N-cyclohexyl-N-methyl)aminopropoxy]-1,7,7-trimethylbicyclo[2,2,1]heptane;
2-(p-methoxyphenyl)-2-(3'-dimethylaminopropoxy)-1,7,7-trimethylbicyclo[2,2,1]heptane;
(1R,2S,4R)-(−)-2-[(2'-{N,N-dimethylamino}-ethoxy)]-2-[phenyl]-1,7,7-trimethylbicyclo [2,2,1]heptane;
(1R,2S,4R)-(−)-2-benzyl-2-(3'-dimethylaminopropoxy)-1,7,7-trimethylbicyclo[2,2,1]heptane;
(1R,2S,4R)-(−)-2-benzyl-2-(2'-methyl-3'-dimethylaminopropoxy)-1,7,7-trimethylbicyclo [2,2,1]heptane;
(1RS,2RS,4RS)-2-phenyl-2-(2'-dimethylaminoethoxy)-1,7,7 trimethylbicyclo[2,2,1]heptane;
(1S,2R,4S)-(+)-2-phenyl-2-(2'-dimethylaminoethoxy)-1,7,7-trimethylbicyclo[2,2,1]heptane; N,N-dimethyl-2-[[(1R,3S,4R)-4,7,7-trimethyl-3-phenyl-3-bicyclo[2.2.1]heptanyl]oxy]ethanamine (deramciclane); or an acid addition salt thereof.

An embodiment of the invention is a composition comprising dextromethorphan or its acid addition salt, and deramciclane, deramciclane acetate, deramciclane acetyl salicylate, deramciclane adipate, deramciclane butyrate, deramciclane caprate, deramciclane caproate, deramciclane caprylate, deramciclane enanthate, deramciclane formate, deramciclane fumarate, deramciclane glutarate, deramciclane isophthallate, deramciclane maleate, deramciclane malonate, deramciclane oxalate, deramciclane pelargonate, deramciclane pimelate, deramciclane propionate, deramciclane phthallate, deramciclane salicylate, deramciclane sebacate, deramciclane succinate, deramciclane terephthallate, deramciclane tyrosinate, deramciclane tryptophanate, or deramciclane valerate; or a combination thereof.

In some embodiments, the compound of Formula II is a fluoro-derivative such as, but not limited to: (4bS,8aS,9S)-11-methyl-3-(trifluoromethoxy)-6,7,8,8a,9,10-hexahydro-5H-9,4b-(epiminoethano)phenanthrene; (4bS,8aS,9S)-3-(trifluoromethoxy)-11-(trifluoromethyl)-6,7,8,8a,9,10-hexahydro-5H-9,4b-(epiminoethano)phenanthrene; (4bS,8aS,9S)-3-methoxy-11-(trifluoromethyl)-6,7,8,8a,9,10-hexahydro-5H-9,4b-(epiminoethano)phenanthrene.

In some embodiments, the compound of Formula II is an acid addition salt selected from acetate, acetyl salicylate, adipate, aspartate, butyrate, caprate, caproate, caprylate, enanthate, formate, fumarate, glutamate glutarate, isophthallate, maleate, malonate, methionate, oxalate, pelargonate, pimelate, propionate, phthallate, salicylate, sebacate, succinate, terephthallate, tyrosinate, tryptophanate, valerate, N-acyl-aspartate, N-acyl-glutamate, N-acyl-tyrosinate, N-acyl-tryptophanate, N-acyl-methionate, citrate, galactonate, glucaric acid (saccharic acid), mannonate, mucate, rhamnonate, and tartrate.

In another embodiment, dextromethorphan or a compound of Formula II as defined above, and a derivative of a compound of Formula I, wherein the derivative is an acid addition salts selected from: acetate, acetyl salicylate, adipate, aspartate, butyrate, caprate, caproate, caprylate, enanthate, formate, fumarate, glutamate glutarate, isophthallate, maleate, malonate, methionate, oxalate, pelargonate, pimelate, propionate, phthallate, salicylate, sebacate, succinate, terephthallate, tyrosinate, tryptophanate, valerate, N-acyl-aspartate, N-acyl-glutamate, N-acyl-tyrosinate, N-acyl-tryptophanate, N-acyl-methionate, citrate, galactonate, glucaric acid (saccharic acid), mannonate, mucate, rhamnonate, and tartrate.

In some embodiments, the compound of Formula II is an acid addition salt selected from N-acyl-aspartate, N-acyl-glutarate, N-acyl-tyrosinate, N-acyl-tryptophanate, and N-acyl-methionate.

Examples include addition salts of base of formula II represented by dextromethorphan, such as dextromethorphan hydrogen acetate, dextromethorphan hydrogen acetyl salicylate, dextromethorphan hydrogen adipate, dextromethorphan hydrogen aspartate, dextromethorphan hydrogen butyrate, dextromethorphan hydrogen caprate, dextromethorphan hydrogen caproate, dextromethorphan hydrogen caprylate, dextromethorphan hydrogen enanthate, dextromethorphan hydrogen formate, dextromethorphan hydrogen fumarate, dextromethorphan hydrogen glutarate, dextromethorphan hydrogen isophthallate, dextromethorphan hydrogen maleate, dextromethorphan hydrogen malonate, dextromethorphan hydrogen oxalate, dextromethorphan hydrogen pelargonate, dextromethorphan hydrogen pimelate, dextromethorphan hydrogen propionate, dextromethorphan hydrogen phthallate, dextromethorphan hydrogen salicylate, dextromethorphan hydrogen sebacate, dextromethorphan hydrogen succinate, dextromethorphan hydrogen terephthallate, dextromethorphan hydrogen tyrosinate, dextromethorphan hydrogen tryptophanate, and dextromethorphan hydrogen valerate.

Another embodiment of the invention is a composition comprising an acid addition salt of compound of Formula I and an acid addition salt of a compound of Formula II. Another embodiment of the invention is a composition comprising an acid addition salt of deramciclane and an acid addition salt of dextromethorphan.

Another embodiment of the invention is a composition comprising an acid addition salt of a halogenated compound of Formula I and an acid addition salt of dextromethorphan. Another embodiment is a composition comprising the halogenated compound of Formula I is trifluoromethyl derivative of M1.

aspartate, benzenesulfonate, besylate, benzoate, bicarbonate, bitartrate, bromide, camphor sulfonate, camsylate, chloride, citrate, decanoate, edetate, lauryl sulfate, estolate, ethanesulfonate, esylate, fumarate, gluceptate, gluconate, glutamate, glycolate, glycollylarsanilate, hexanoate, hexylresorcinol, hydroxynaphthoate, isethionate, iodide, lactate, galactopyranosyl-d-gluconate, lactobionate, malate, maleate, mandelate, mesylate, methylbromide, methylnitrate, methylsulfate, mucate, napsylate, nitrate, octanoate, oleate, pamoate, 4,4'-methylenebis(3-hydroxy-2-naphthoate, pantothenate, phosphate, polygalacturonate, propionate, salicylate, stearate, succinate, sulfate, tartrate, teoclate, 8-chloro-1,3-dimethyl-7h-purine-2,6-dione, tosylate, malate, methionate, phthallate, malonate, tyrosinate, tryptophanate, maleate, fumarate, An embodiment of the invention is an addition salt of Formula I, wherein with organic acid such as aspartic acid, benzenesulfonic acid, besylic acid, benzoic acid, bicarbonic acid, tartaric acid, bromide, camphor sulfonic acid, camsylic acid, chloride, citric acid, decanoic acid, edetate, lauryl sulfonic acid, estolic acid, ethanesulfonic acid, esylic acid, fumaric acid, gluceptic acid, gluconic acid, glutamic acid, glycolic acid, glycollylarsanilic acid, hexanoic acid, hexylresorcinol, hydroxynaphthoic acid, isethionic acid, iodide, lactic acide, galactopyranosyl-d-gluconic acid, lactobionic acid, malic acid, maleic acid, mandelic acid, methanesulfonic acid, methylbromide, methylnitric acid, methylsulfonic acid, mucic acid, napsylic acid, nitric acid, octanoic acid, oleic acid, pamoic acid, 4,4'-methylenebis(3-hydroxy-2-naphthonic acid, pantothenic acid, phosphoric acid, polygalacturonic acid, propionic acid, salicylic acid, stearic acid, succinic acid, sulfuric acid, tartaric acid, teoclic acid, 8-chloro-1,3-dimethyl-7h-purine-2,6-dione, tosylic acid, malic acid, methionic acid, phthallic acid, malonic acid, tyrosine, tryptophan, maleic acid, fumaric acid, succinic acid, glutaric acid, adipic acid, pimelic acid, sebacic acid, formic acid, acetic acid, propionic acid, butyric acid, valeric acid, caproic acid, enanthic acid, caprylic acid, pelargonic acid, capric acid, oxalic acid, isophthallic acid, terephthallic acid, salicylic acid, difluorosuccinic acid, trifluorosuccinic acid, tetrafluorosuccinic acid, difluoroglutaric acid, difluoroacetic acid, trifluoroacetic acid; and dextromethorphan; or a combination thereof.

In some aspects of the invention, the compound of Formula I is a prodrug according to wherein the compound is an ester or an addition formed from the following acids: 3-(nitrooxy)propanoic acid (Vendors: AKos (AKOS006377427), and 1717 CheMall (OR235109)), 4-nitrooxybutanoic acid (Vendors: AKos (AKOS006378268) and iChemical (EBD3415162)), 3-(nitrooxy)butanoic acid (AKos (AKOS006376331, AKOS016035558), MolMall (21929)). Examples include, but not limited to, 3-nitrooxy derivatives of Compounds 71-73, 4-nitrooxy derivatives of Compounds 74-76, and 3-nitrooxy derivatives of Compounds 74-76. In some embodiments, the compounds of Formula I form addition salts of 3-(nitrooxy)propanoic acid, 3-(nitrooxy)butanoic acid, and 4-(nitrooxy)butanoic acid. In another embodiment, the acid addition salt is of 3-(nitrooxy)propanoic acid, 3-(nitrooxy)butanoic acid, and 4-(nitrooxy)butanoic acid.

In another embodiment, the pharmaceutically acceptable acid addition salts of the compounds of the Formula I can be formed with inorganic acids such as hydrochloric acid, hydrogen bromide, sulfuric acid, phosphoric acid and nitric acid.

Other anion salts of compounds of Formulas I and II include the salts formed from the following acidic groups:

Aspartate

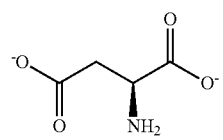

Benzenesulfonate
(Beslate)

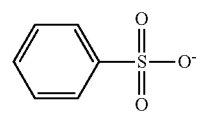

-continued
| | |
|---|---|
| Benzoate | 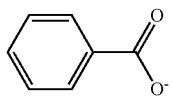 |
| Bicarbonate | 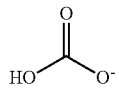 |
| Bitartrate | 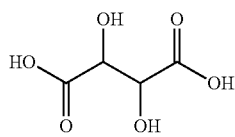 |
| Bromide | Br$^-$ |
| Camphor sulfonic acid (Camsylate) | 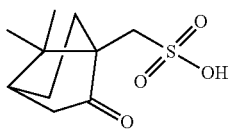 |
| Chloride | Cl$^-$ |
| Citrate | 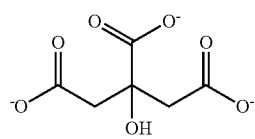 |
| Decanoate | 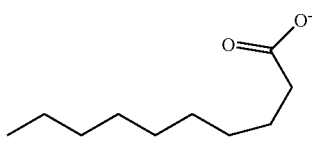 |
| Edetate | 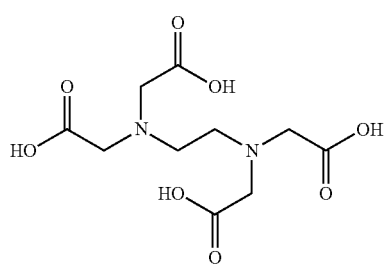 [SMILES: O=C(O)CN(CCN(CC(=O)O)CC(=O)O)CC(=O)O] |
| Lauryl sulfate (Estolate) | 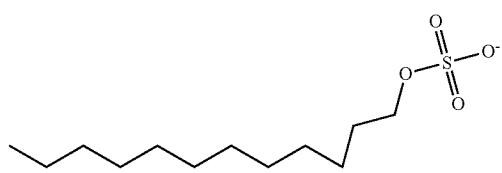 [SMILES: CCCCCCCCCCCCOS(=O)(=O)[O-]] |
| Ethanesulfonate (Esylate) | 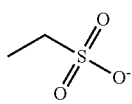 |
| Fumarate | 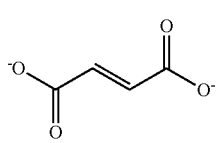 |

-continued
| | |
|---|---|
| Gluceptate | 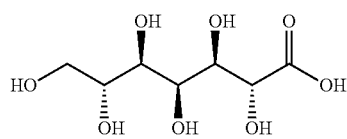 [SMILES: O=C(O)[C@H](O)[C@H](O)[C@@H](O)[C@H](O)[C@H](O)CO] |
| Gluconate | 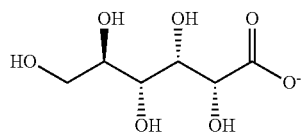 |
| Glutamate | 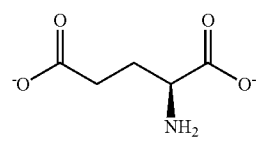 |
| Glycolate | 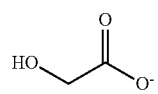 |
| Glycollylarsanilate | 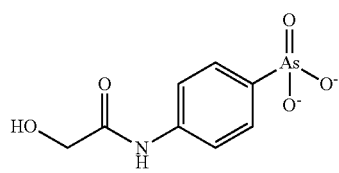 |
| Hexanoate | 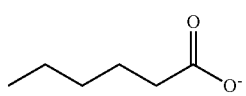 |
| Hexylresorcinol | 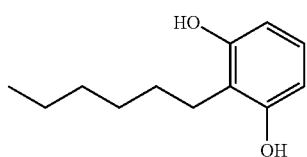 |
| Hydroxynaphthoate | 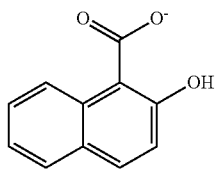 [SMILES: O=C([O-])c1c(O)ccc2ccccc12] |
| Isethionate | 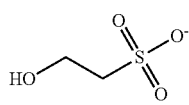 |
| Iodide | I$^-$ |
| Lactate | 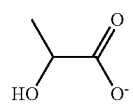 |

| | |
|---|---|
| Galactopyranosyl-D-gluconic acid (Lactobionate) | 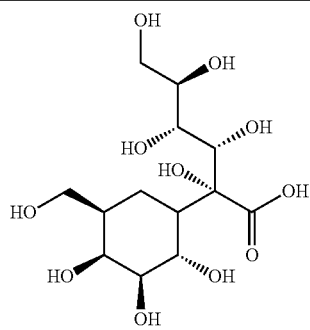 |
| Malate | 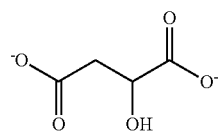 |
| Maleate | 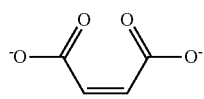 |
| Mandelate | 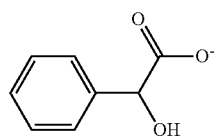 [SMILES: O=C([O-])C(O)c1ccccc1] |
| Mesylate | 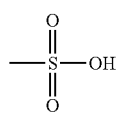 |
| Methylbromide | —Br |
| Methylnitrate | 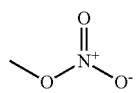 |
| Methylsulfate | 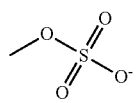 |
| Galactaric Acid (Mucate) | 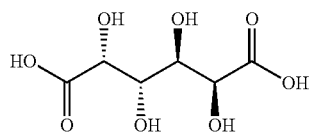 |
| Napsylate | 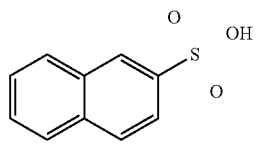 |
| Nitrate | 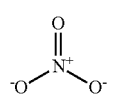 |
| Octanoate | 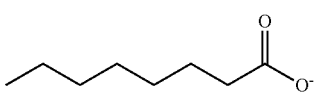 |

-continued
| | |
|---|---|
| Oleate | 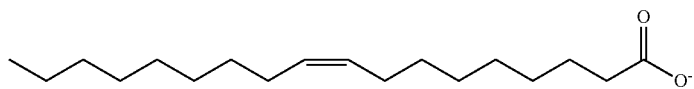 [SMILES: CCCCCCCC/C=C\CCCCCCCC(=O)[O-]] |
| Pamoate (4,4'-methylenebis(3-hydroxy-2-naphthoate)) | 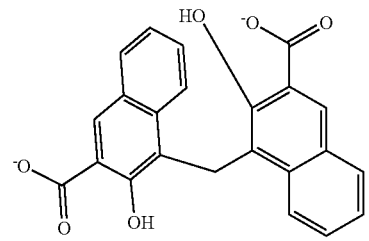 |
| Pantothenate | 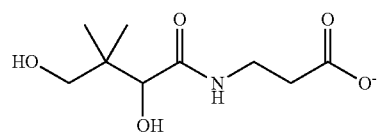 |
| Phosphate polygalacturonate | 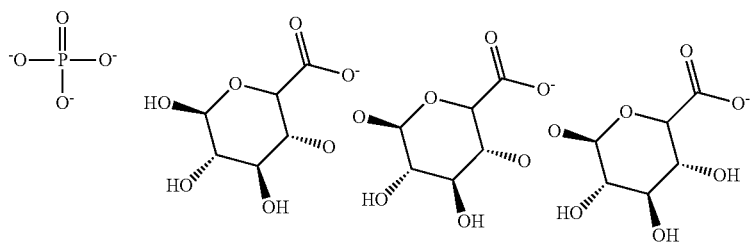 |
| Propionate | 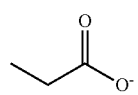 |
| Salicylate | 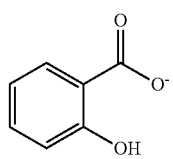 |
| Stearate | 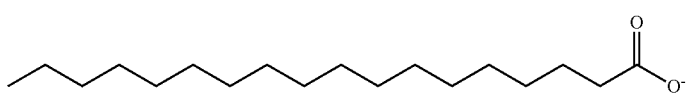 [SMILES: CCCCCCCCCCCCCCCCCC(=O)[O-]] |
| Succinate | 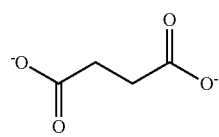 |
| Sulfate | 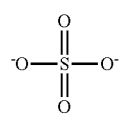 |
| Tartrate | 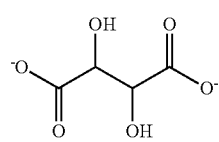 |

| | |
|---|---|
| Teoclate (8-chloro-1,3-dimethyl-7H-purine-2,6-dione) | 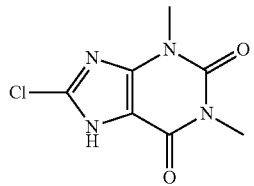 |
| Tosylate | 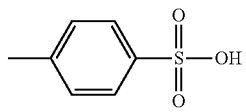 |

Acid addition salts of Formula I described represented below formulae:

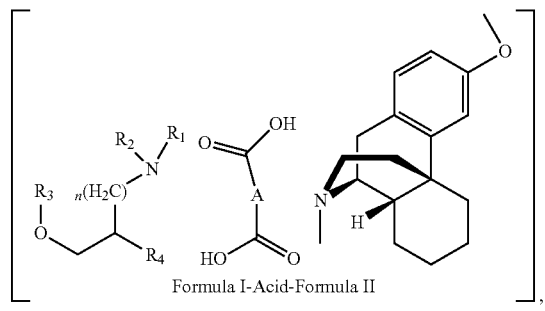

Formula I-Acid-Formula II

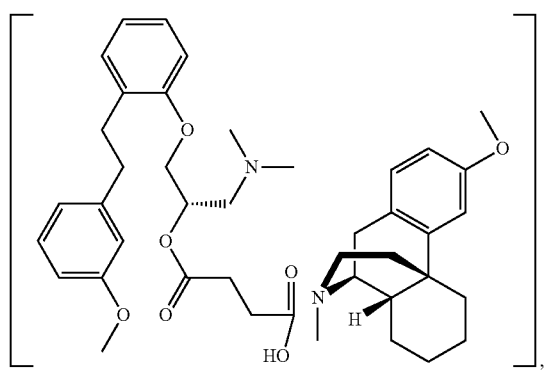

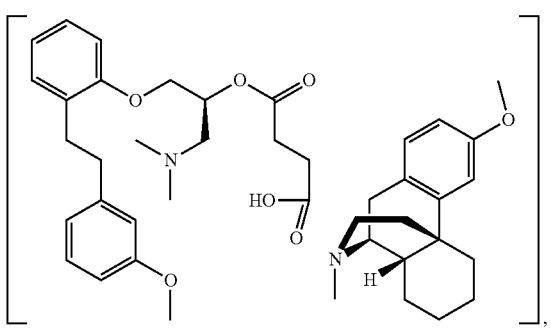

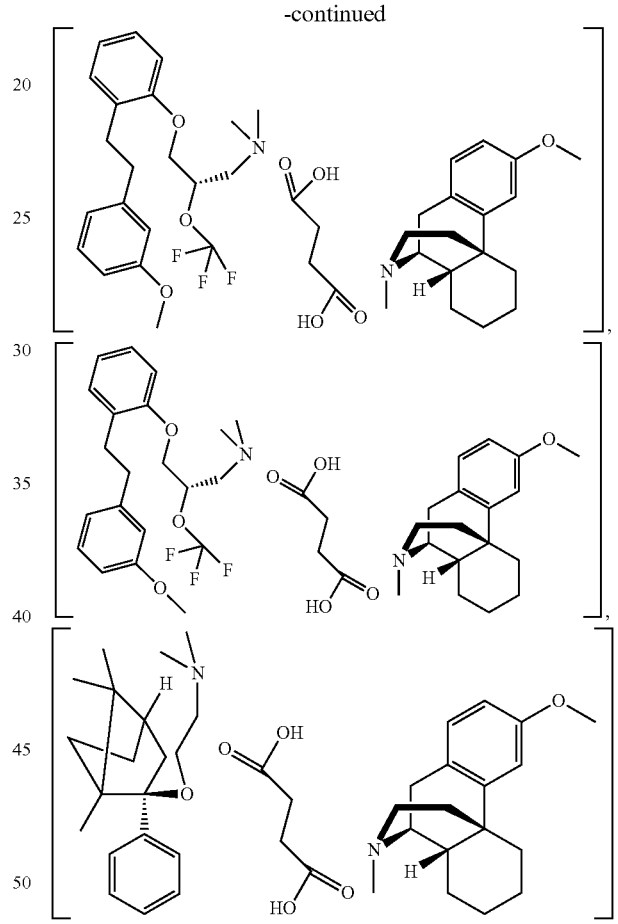

Another embodiment is a composition comprising a compound of Formula I, and at least one compound selected from thioridazine, perphenazine, fluphenazine, zuclopenthixol, risperidone, sertindole, nortriptyline, amitriptyline, imipramine, fluoxetine, paroxetine, ajmaline, amiodarone, amitriptyline, aprindine, azelastine, celecoxib, chlorpheniramine, chlorpromazine, diphenhydramine, doxorubicin, fluphenazine, fluvastatin, haloperidol, imipramine, indinavir, lasoprazole, levomepromazine, lopinavir, loratadine, mequitazine, methadone, metoclopramide, mibefradil, moclobemide, nelfinavir, nevirapine, nicardipine, norfluoxetine, perphenazine, pimozide, terfenadine, thioridazine, cimetidine, quinidine, cisapride, citalopram, clozapine, cocaine, desipramine, ranitidine, risperidone, ritonavir, saquinavir, sertraline, terbinafine, ticlopidine, trifluperidol, yohimbine, clomipramine, doxepin, mianserin, imipramine, 2-chloroimipramine, amitriptyline, amoxapine, protriptyline, trimipramine, nortriptyline, maprotiline, phenelzine, isocarboxazid, tranylcypromine, trazodone, citalopram, sertraline, aryloxy indanamine, benactyzine, escitalopram, fluvoxamine, venlafaxine, desvenlafaxine, duloxetine, mirtazapine, nefazodone, selegiline, sibutramine, milnacipran, tesofensine, brasofensine, moclobemide, rasagiline, nialamide, iproniazid, iproclozide, toloxatone, butriptyline, dosulepin, dibenzepin, iprindole, lofepramine, opipramol, and dapoxetine.

Another embodiment of the invention is a composition comprising a compound of Formula I, a compound of Formula II, and at least one compound selected from thioridazine, perphenazine, fluphenazine, zuclopenthixol, risperidone, sertindole, nortriptyline, amitriptyline, imipramine, fluoxetine, paroxetine, ajmaline, amiodarone, amitriptyline, aprindine, azelastine, celecoxib, chlorpheniramine, chlorpromazine, diphenhydramine, doxorubicin, fluphenazine, fluvastatin, haloperidol, imipramine, indinavir, lasoprazole, levomepromazine, lopinavir, loratadine, mequitazine, methadone, metoclopramide, mibefradil, moclobemide, nelfinavir, nevirapine, nicardipine, norfluoxetine, perphenazine, pimozide, terfenadine, thioridazine, cimetidine, quinidine, cisapride, citalopram, clomipramine, clozapine, cocaine, ranitidine, risperidone, ritonavir, saquinavir, sertraline, terbinafine, ticlopidine, trifluperidol, yohimbine, doxepin, mianserin, imipramine, 2-chloroimipramine, amitriptyline, amoxapine, desipramine, protriptyline, trimipramine, nortriptyline, maprotiline, phenelzine, isocarboxazid, tranylcypromine, trazodone, citalopram, sertraline, aryloxy indanamine, benactyzine, escitalopram, fluvoxamine, venlafaxine, desvenlafaxine, duloxetine, mirtazapine, nefazodone, selegiline, sibutramine, milnacipran, tesofensine, brasofensine, moclobemide, rasagiline, nialamide, iproniazid, iproclozide, toloxatone, butriptyline, dosulepin, dibenzepin, iprindole, lofepramine, opipramol, and dapoxetine.

Figure 13:
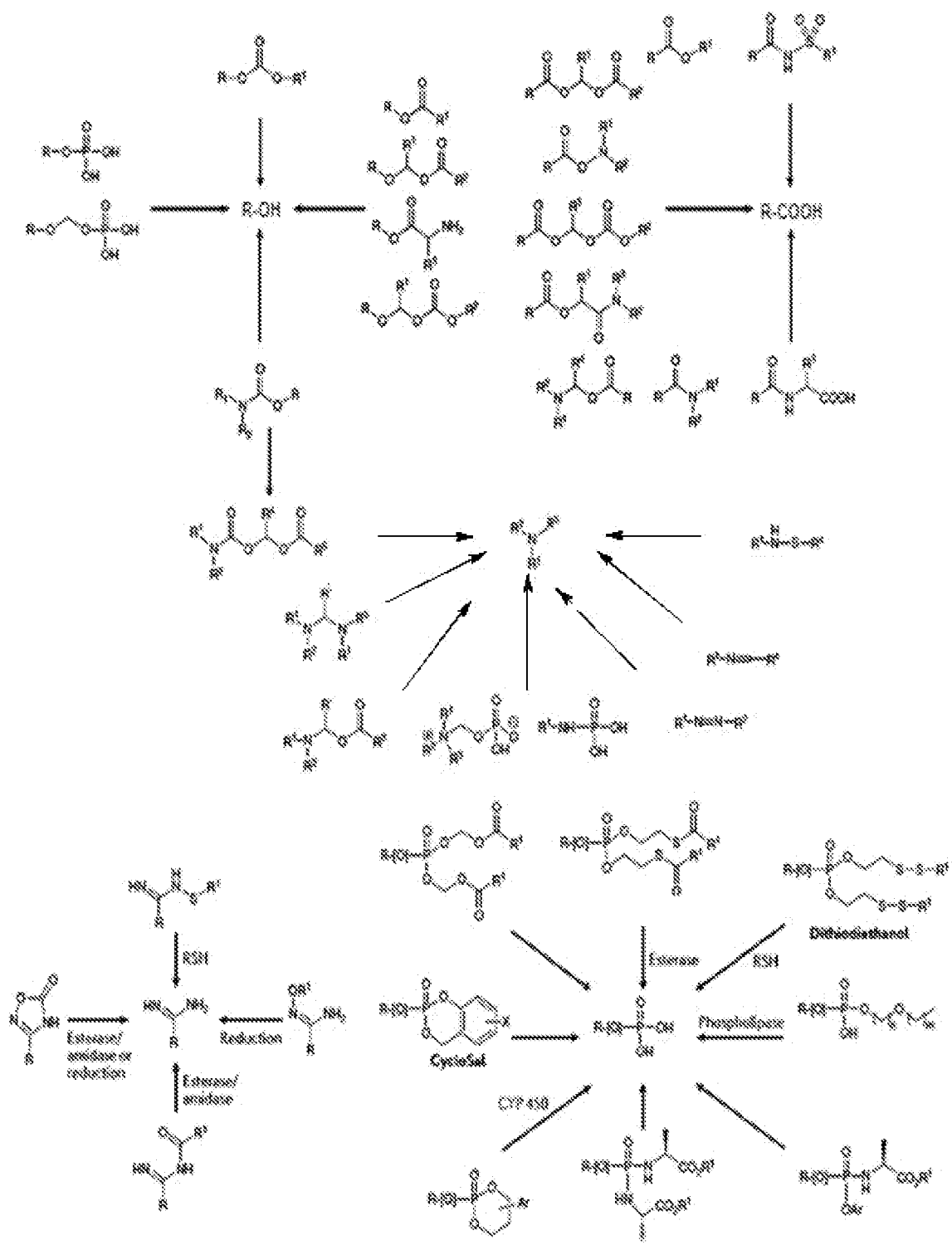
FIG. 13 shows prodrug strategies for the most common functional groups on parent drug compounds of Formula I and II represented by R with general schemes representing various embodiments of prodrugs of compounds of Formulae I and II.

In one embodiment, the composition comprises a compound of Formula I, wherein the compound wherein R3 is a conjugate or covalent compound formed either by etherification or esterification with derivatives of one or more of AChIs such as 2-((l-Benzylpiperidin-4-yl)methyl)-5,6-dimethoxy-2,3-dihydro-1H-inden-1-one (Donepezil), (S)-3-(1-(dimethylamino)ethyl)phenyl ethyl(methyl) carbamate (Rivastigmine), dimethyl (2,2,2-trichloro-1-hydroxyethyl) phosphonate (Metrifonate), (4aS,6R,8aS)-3-methoxy-11-methyl-4a,5,9,10,11,12-hexahydro-6H-benzo[2,3]benzofuro[4,3-cd]azepin-6-ol (Galantamine), and 1,2,3,4-tetrahydroacridin-9-amine (Tacrine), O,S-dimethyl acetylphosphoramidothioate, O,O-dimethyl S-((4-oxobenzo[d][1,2,3]triazin-3(4H)-yl)methyl) phosphorodithioate, 2,2-dimethyl-2,3-dihydrobenzofuran-7-yl methylcarbamate, S-(((4-chlorophenyl)thio)methyl) O,O-diethyl phosphorodithioate, 2-chloro-1-(2,4-dichlorophenyl)vinyl diethyl phosphate, O,O-diethyl O-(3,5,6-trichloropyridin-2-yl) phosphorothioate, 0-(3-chloro-4-methyl-2-oxo-2H-chromen-7-yl) O,O-diethyl phosphorothioate, 1-phenylethyl (E)-3-((dimethoxyphosphoryl)oxy)but-2-enoate,4-(tert-butyl)-2-chlorophenyl methyl methylphosphoramidate, O,O-diethyl O-(2-(ethylthio)ethyl) phosphorothioate, O,O-diethyl S-(2-(ethylthio)ethyl) phosphorothioate, O,O-diethyl O -(2-isopropyl-6-methylpyrimidin-4-yl) phosphorothioate, 2,2-dichlorovinyl dimethyl phosphate, (E)-4-(dimethylamino)-4-oxobut-2-en-2-yl dimethyl phosphate, O,O-dimethyl S-(2-(methylamino)-2-oxoethyl) phosphorodithioate, S,S'-(1,4-dioxane-2,3-diyl) O,O,O',O'-tetraethyl bis(phosphorodithioate), O,O-diethyl S-(2-(ethylthio)ethyl) phosphorodithioate, O-ethyl O -(4-nitrophenyl) phenylphosphonothioate, O,O, O',O'-tetraethyl S,S'-methylene bis(phosphorodithioate), O-ethyl S,S-dipropyl phosphorodithioate, 0-(4-(N,N-dimethylsulfamoyl)phenyl) O,O-dimethyl phosphorothioate, 0-(4-(N,N-dimethylsulfamoyl)phenyl) O,O-dimethyl phosphorothioate, ethyl (3-methyl-4-(methylthio)phenyl) isopropylphosphoramidate, O,O-dimethyl O -(3-methyl-4-nitrophenyl) phosphorothioate, O-ethyl S-phenyl ethylphosphonodithioate, isopropyl 2-((ethoxy(isopropylamino)phosphorothioyl)oxy)benzoate, diethyl 2-((dimethoxyphosphorothioyl)thio)succinate, O,S-dimethyl phosphoramidothioate, O,S-dimethyl phosphoramidothioate, S-((5-methoxy-2-oxo-1,3,4-thiadiazol-3(2H)-yl)methyl) O,O-dimethyl phosphorodithioate, methyl 3-((dimethoxyphosphoryl)oxy)but-2-enoate, (E)-dimethyl (4-(methylamino)-4-oxobut-2-en-2-yl) phosphate, 1,2-dibromo-2,2-dichloroethyl dimethyl phosphate, isopropyl (S)-methylphosphonofluoridate, 3,3-dimethylbutan-2-yl (S)-methylphosphonofluoridate, O,O-diethyl O -(4-nitrophenyl) phosphorothioate, S-(2-(ethylsulfinyl)ethyl) O,O-dimethyl phosphorothioate, O,O-diethyl S-((ethylthio)methyl) phosphorodithioate, S-((6-chloro-2-oxobenzo[d]oxazol-3(2H)-yl)methyl) O,O-diethyl phosphorodithioate, S-((1,3-dioxoisoindolin-2-yl)methyl) O,O-dimethyl phosphorodithioate, (E)-3-chloro-4-(diethylamino)-4-oxobut-2-en-2-yl dimethyl phosphate, 0,0,0',0'-tetramethyl O,O'-(thiobis(4,1-phenylene)) bis(phosphorothioate), tetraethyl diphosphate, S-((tert-butylthio)methyl) O,O-diethyl phosphorodithioate, 2-chloro-1-(2,4,5-trichlorophenyl)vinyl dimethyl phosphate, and dimethyl (2,2,2-trichloro-1-hydroxy ethyl)phosphonate, or pharmaceutically acceptable derivatives, metabolites, analogs, or salts thereof, prepared using prodrug strategies described in FIG. 13 wherein the parent drug compounds of Formula I and II are represented by R with general schemes representing various embodiments of prodrugs of compounds of Formula I and II (see for example, Rautio et al., The expanding role of prodrugs in contemporary drug design and development, Nature Reviews Drug Discovery, published online at DX DOI.ORG (27 Apr. 2018); Stella, Prodrugs: Some thoughts and current issues. J. Pharm. Sci. 99, 4755-4765 (2010); Clas et al., Chemistry-enabled drug delivery (prodrugs): recent progress and challenges. Drug Discov. Today 19, 79-87 (2014); Rautio et al., Prodrugs—Recent approvals and a glimpse of the pipeline. Eur. J. Pharm. Sci. 109, 146-161 (2017); Rautio et al. Prodrugs: design and clinical applications. Nat. Rev. Drug Discov. 7, 255-270 (2008); Stella et al., Prodrug strategies to overcome poor water solubility. Adv. Drug Deliv. Rev. 59, 677-694 (2007); Kumpulainen et al. Synthesis, in vitro and in vivo characterization of novel ethyl dioxy phosphate prodrug of propofol. Eur. J. Pharm. Sci. 34, 110-117 (2008); Hale et al. Phosphorylated morpholine acetal human neurokinin-1 receptor antagonists as water-soluble prodrugs. J. Med. Chem. 43, 1234-1241 (2000); Ishikawa et al. TAK-599, a novel N-phosphono type prodrug of anti-MRSA cephalosporin T-91825: synthesis, physicochemical and pharmacological properties. Bioorg. Med. Chem. 11, 2427-2437 (2003); Mehellou et al., Aryloxy phosphoramidate triesters: a technology for delivering monophosphorylated nucleosides and sugars into cells. Chem Med Chem 4, 1779-1791 (2009); Thornton et al., Nucleoside phosphate and phosphonate prodrug clinical candidates. J. Med. Chem. 59, 10400-10410 (2016); Pradere et al., Synthesis of nucleoside phosphate and phosphonate prodrugs. Chem. Rev. 114, 9154-9218 (2014); Starrett et al. Synthesis and in vitro evaluation of a phosphonate prodrug: bis(pivaloyloxymethyl) 9-(2-phosphonylmethoxyethyl) adenine. Antiviral Res. 19, 267-273 (1992); Starrett et al. Synthesis, oral bioavailability determination, and in vitro evaluation of prodrugs of the antiviral agent 9-[2-(phosphonomethoxy) ethyl]adenine (PMEA). J. Med. Chem. 37, 1857-1864 (1994); McGuigan et al. Synthesis, anti-human immunodeficiency virus activity and esterase lability of some novel carboxylic ester-modified phosphoramidate derivatives of stavudine (d4T). Antivir. Chem. Chemother. 9, 473-479 (1998); McGuigan et al., Synthesis and anti-HIV activity of some novel chain-extended phosphoramidate derivatives of d4T (stavudine): esterase hydrolysis as a rapid predictive test for antiviral potency. Antivir. Chem. Chemother. 9, 109-115 (1998); Erion et al. Design, synthesis, and characterization of a series of cytochrome P(450) 3A-activated prodrugs (HepDirect prodrugs) useful for targeting phosph(on)ate-based drugs to the liver. J. Am. Chem. Soc. 126, 5154-5163 (2004); Yuan et al., Evaluation of in vitro models for screening alkaline phosphatase-mediated bioconversion of phosphate ester prodrugs. DrugMetab. Dispos. 37, 1443-1447 (2009); Heimbach et al., Absorption rate limit considerations for oral phosphate prodrugs. Pharm. Res. 20, 848-856 (2003); Kadow et al., Inhibitors of human immunodeficiency virus type 1 (HIV-1) attachment 6. Preclinical and human pharmacokinetic profiling of BMS-663749, a phosphonooxymethyl prodrug of the HIV-1 attachment inhibitor 2-(4-benzoyl-1-piperazinyl)-1-(4,7-dimethoxy-1H-pyrrolo[2,3-c]pyridin-3-yl)-2-oxo ethanone (BMS-488043). J. Med. Chem. 55, 2048-2056 (2012); Heimbach et al., Enzyme-mediated precipitation of parent drugs from their phosphate prodrugs. Int. J. Pharm. 261, 81-92 (2003); all of which are incorporated herein by reference in their entirety).

P-1

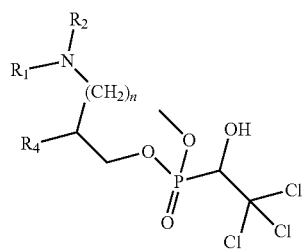

P-2

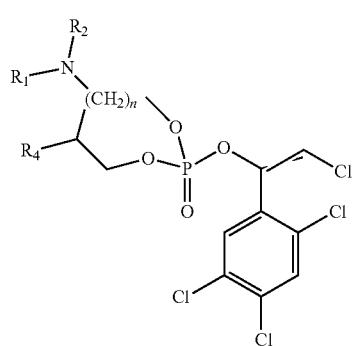

-continued

P-3

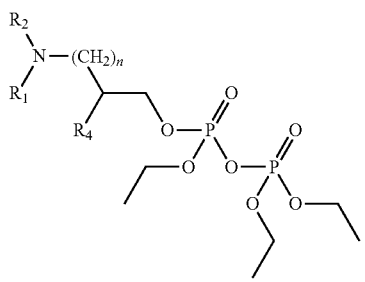

P-4

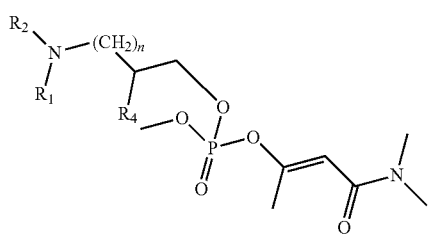

P-5

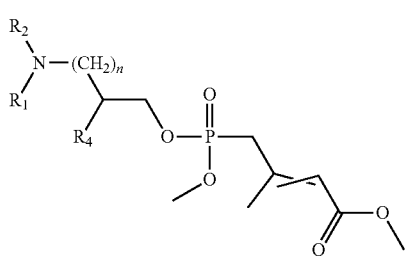

P-6

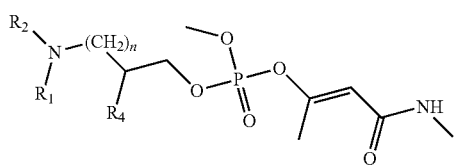

P-7

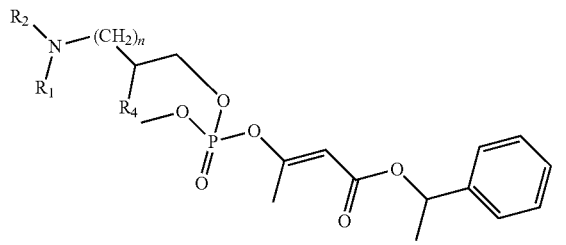

P-8

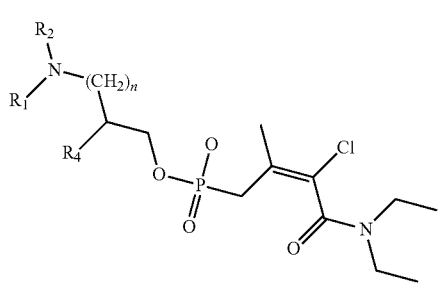

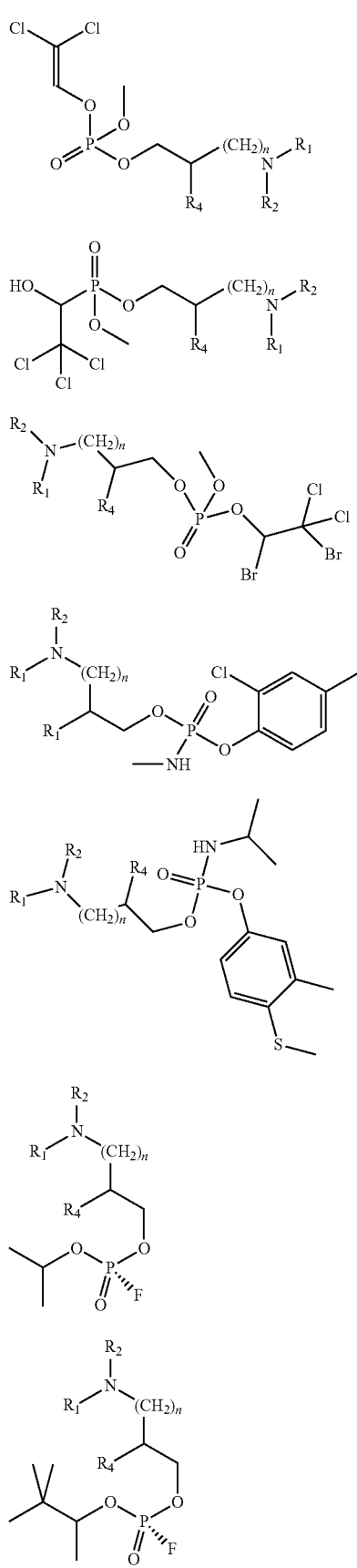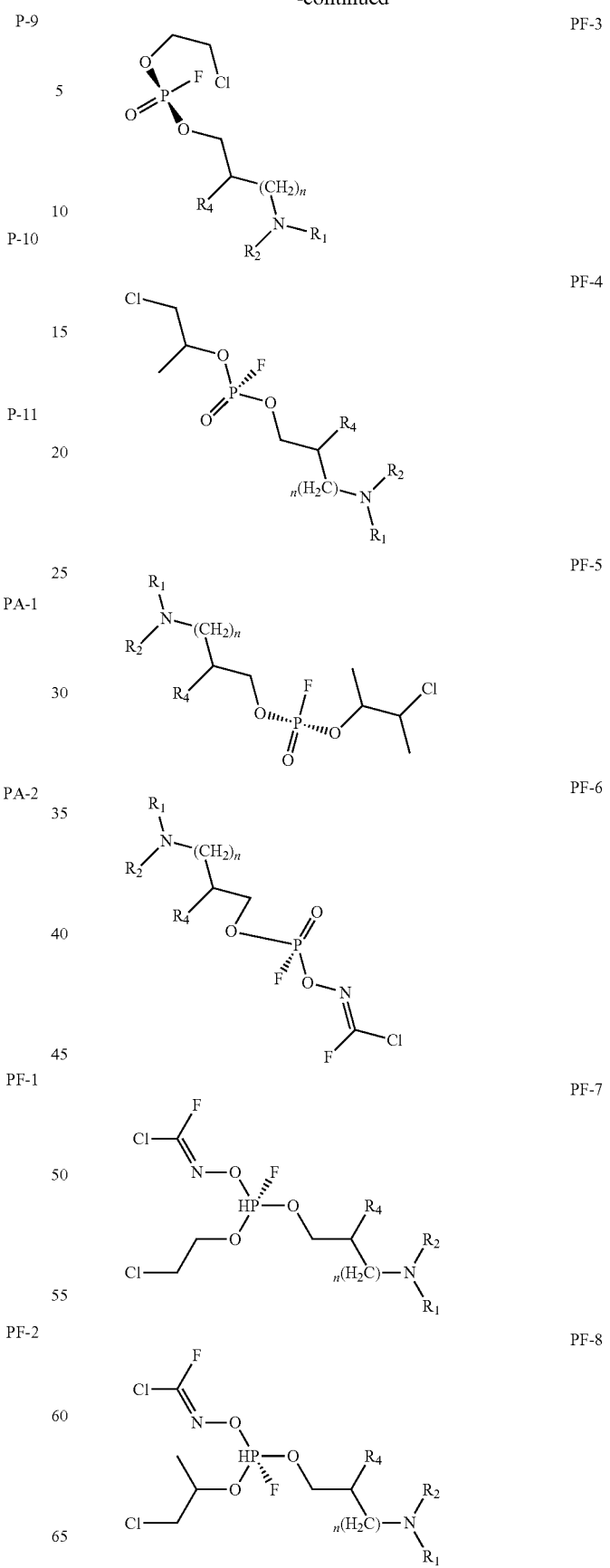

-continued
PF-9
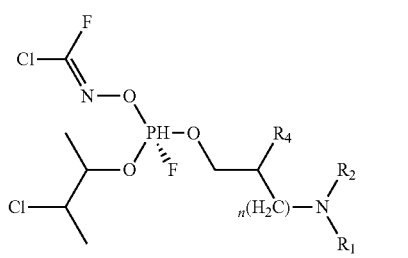
PT-1
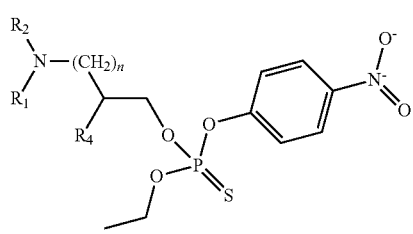
PT-2
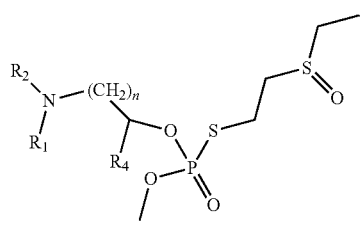
PT-3
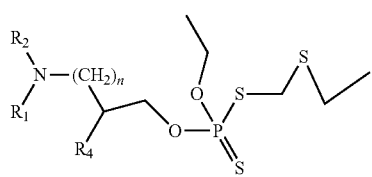
PT-4
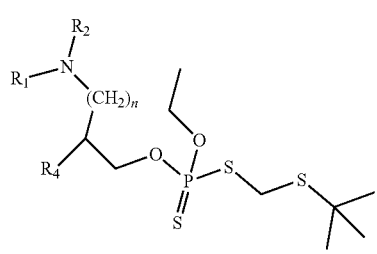
PT-5
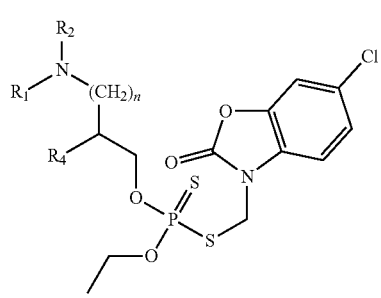
-continued
PT-6
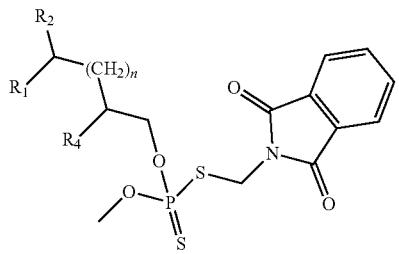
PT-7
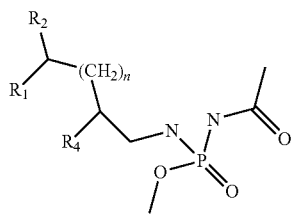
PT-8
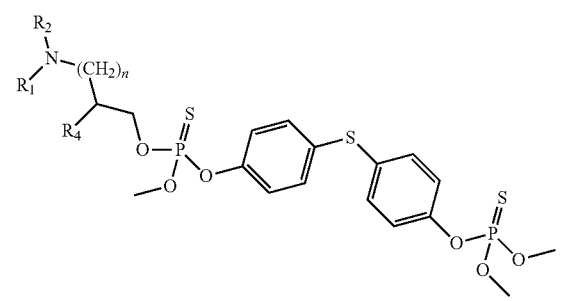
PT-9
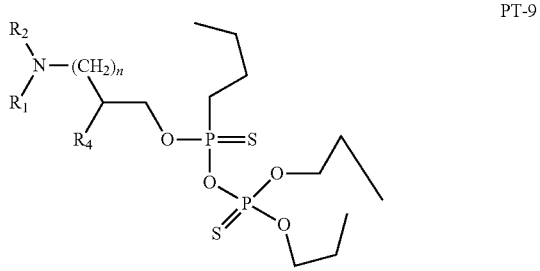
PT-10
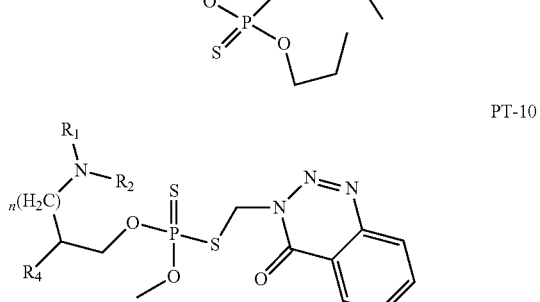
PT-11
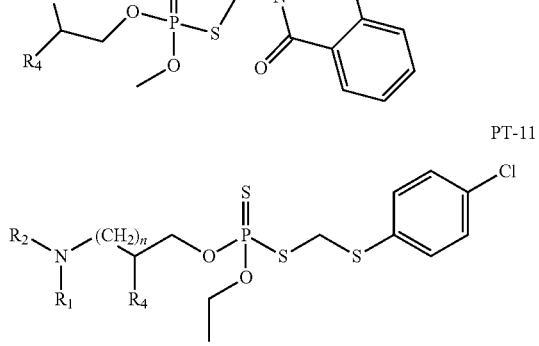

PT-12
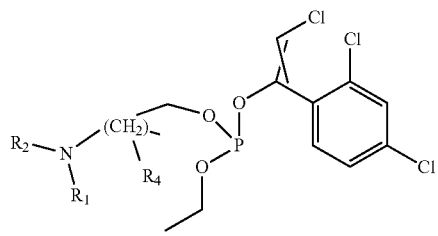
PT-13
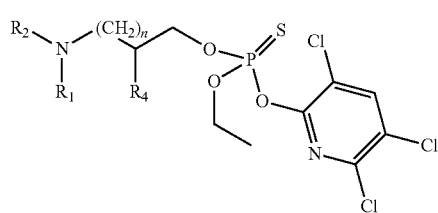
PT-14
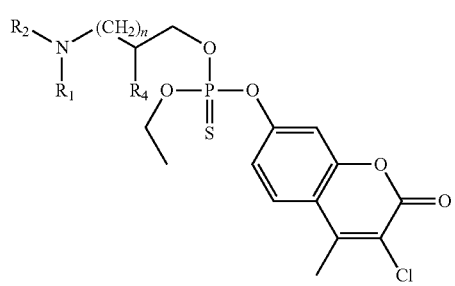
PT-15
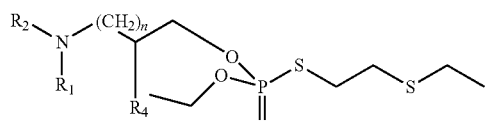
PT-16
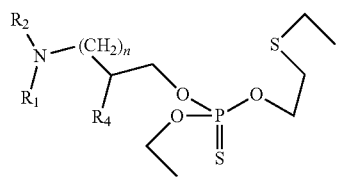
PT-17
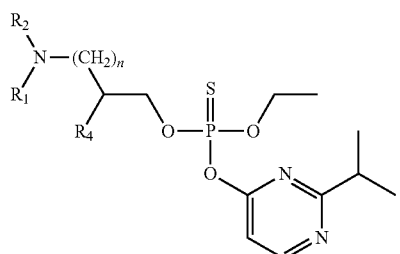
PT-18
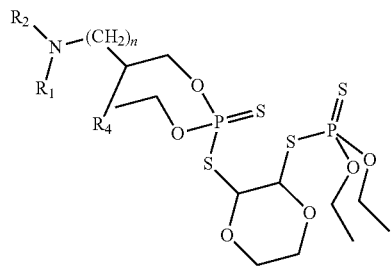
PT-19
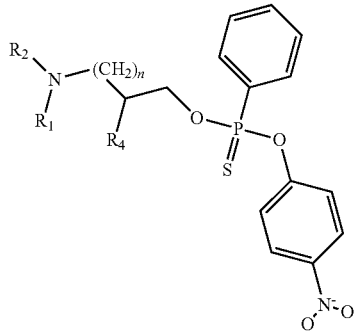
PT-20
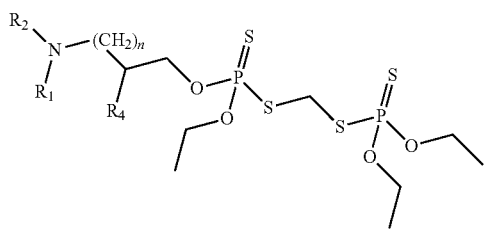
PT-21
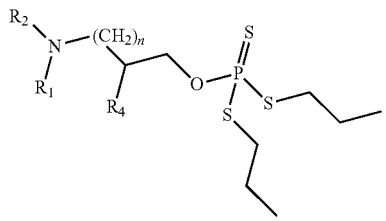
PT-22
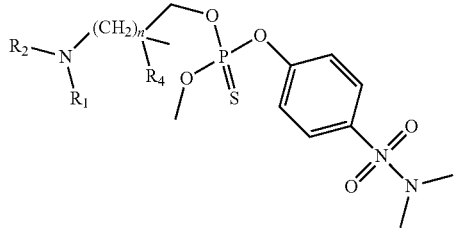
PT-23
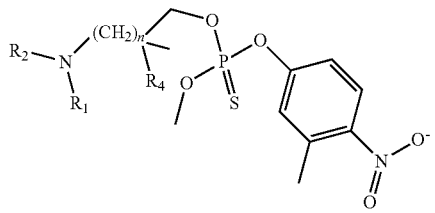
PT-24
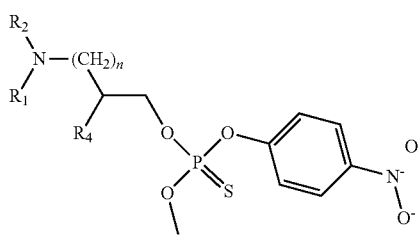

PT-25
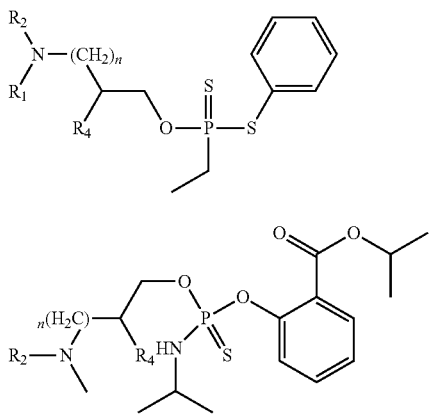
PT-26
PT-27
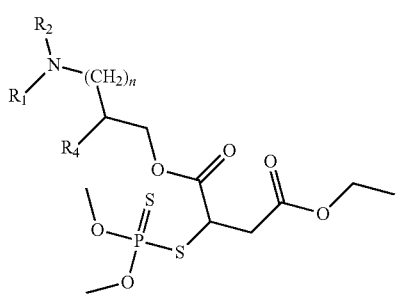
PT-28
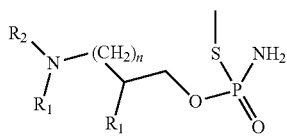
PT-29
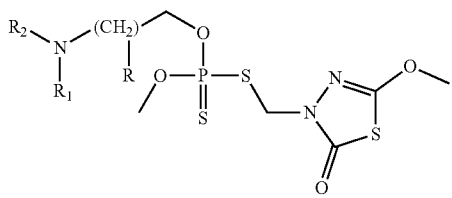
PT-30
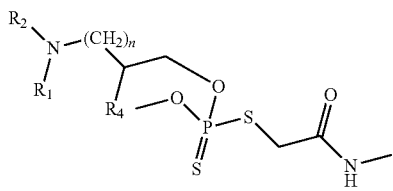
PT-31
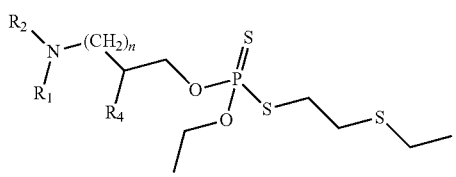
PT-32
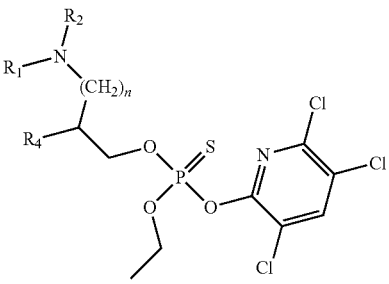
PT-33
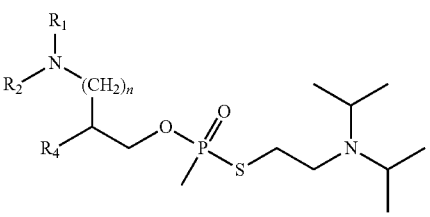
PT-34
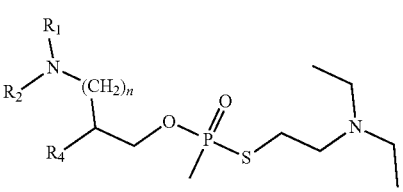
P = Phosphate
PA = PhosphorAmidate
PF = PhosphonoFluoridate
PT = PhosphoroThiate
In another embodiment, the prodrug compounds of Formula I include, but not limited to:
Compound 901
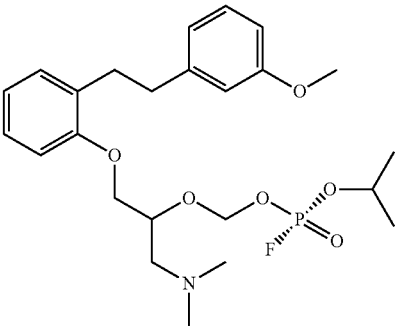
Compound 902
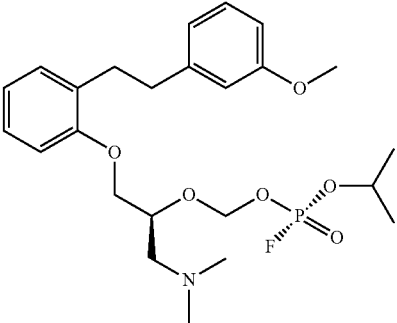

Compound 903
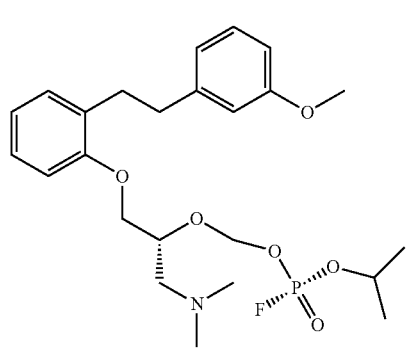
Compound 904
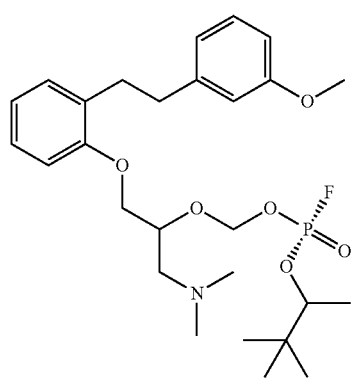
Compound 905
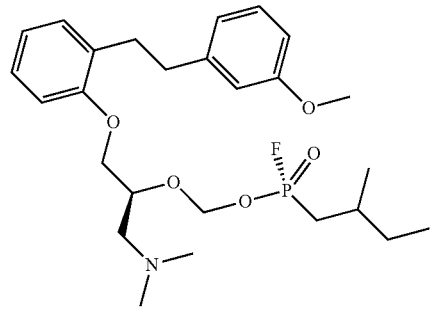
Compound 906
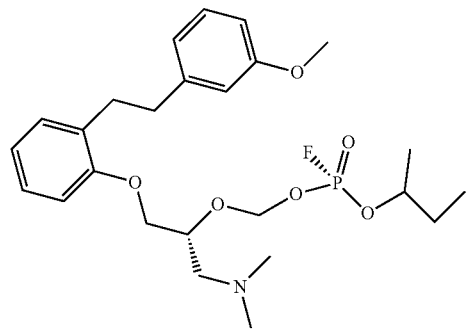
Compound 907
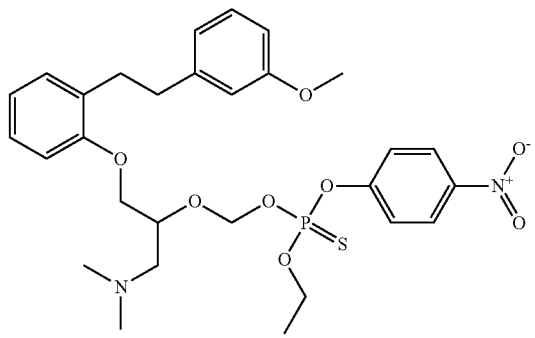
Compound 908
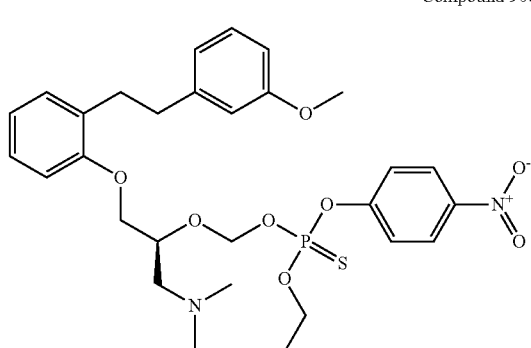
Compound 909
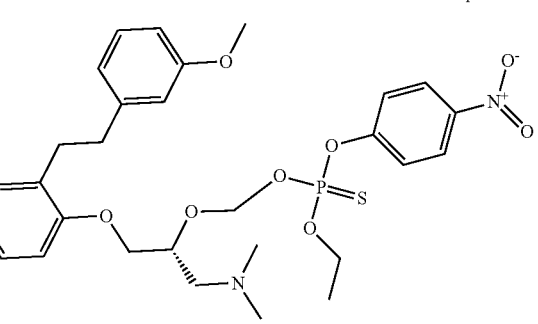
Compound 910
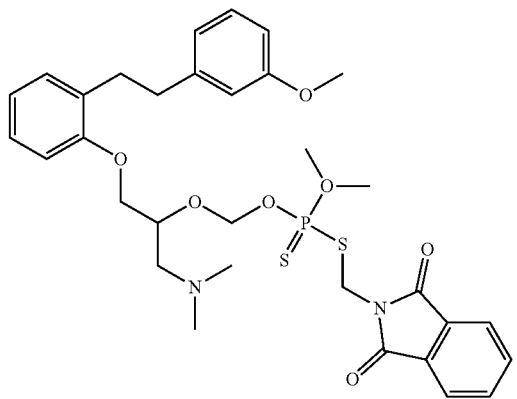

Compound 911
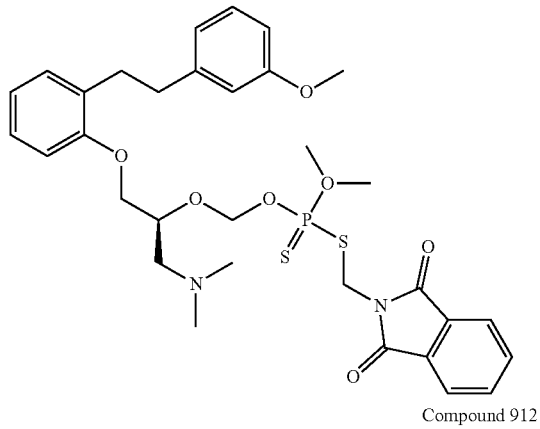
Compound 912
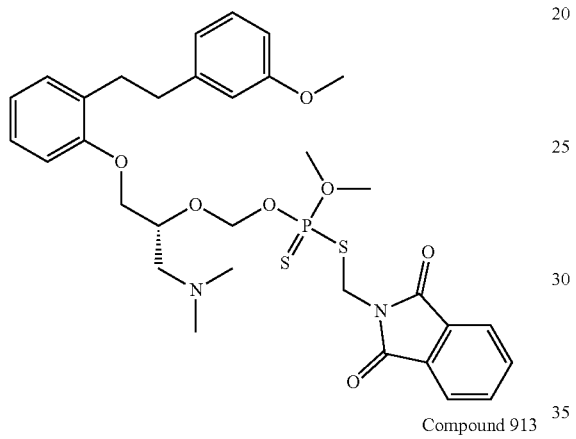
Compound 913
Compound 914
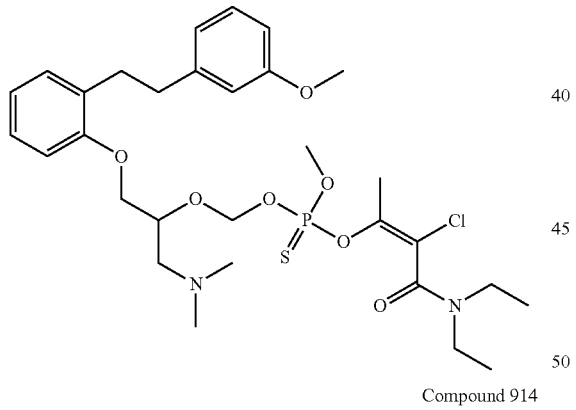
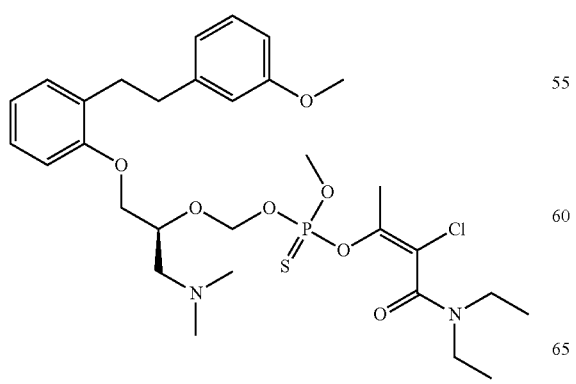
Compound 915
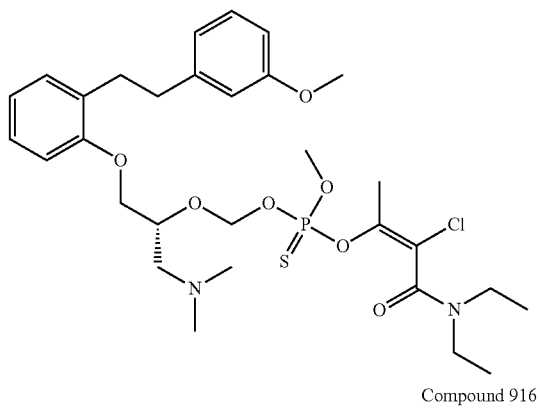
Compound 916
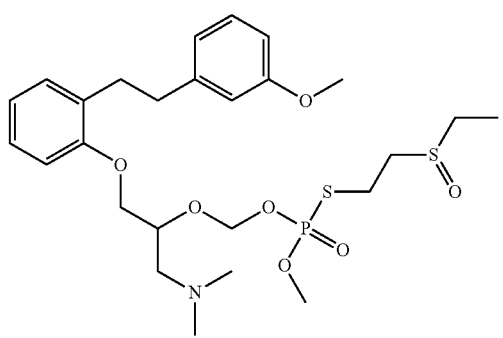
Compound 917
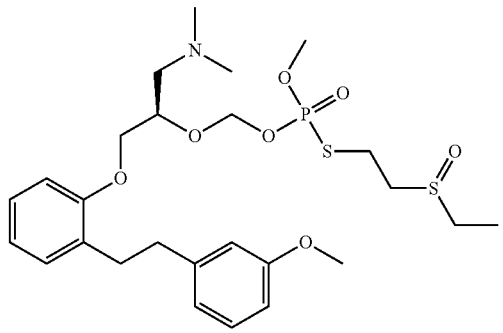
Compound 918
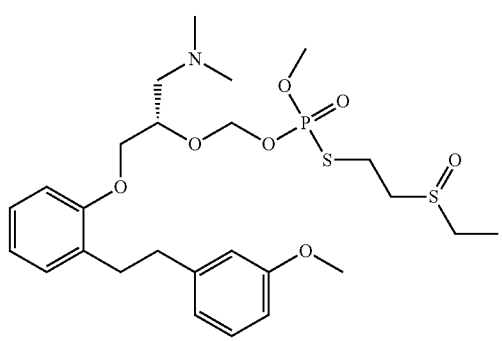

Compound 919
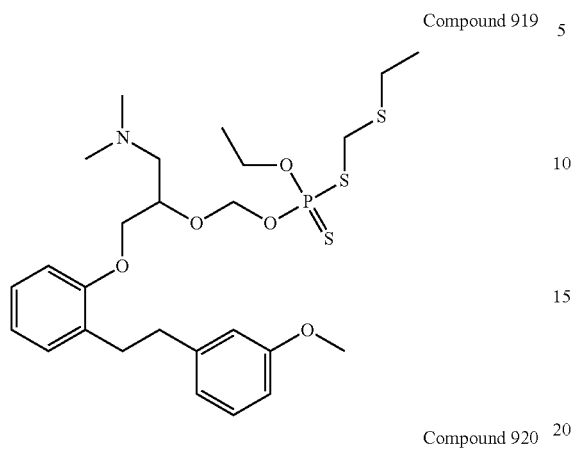
Compound 920
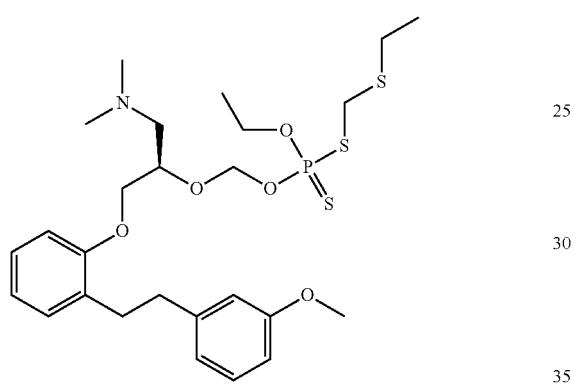
Compound 921
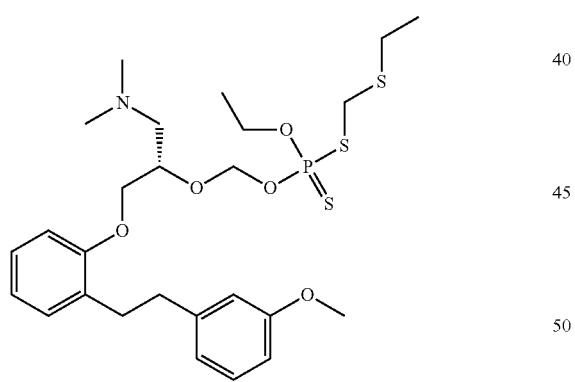
Compound 922
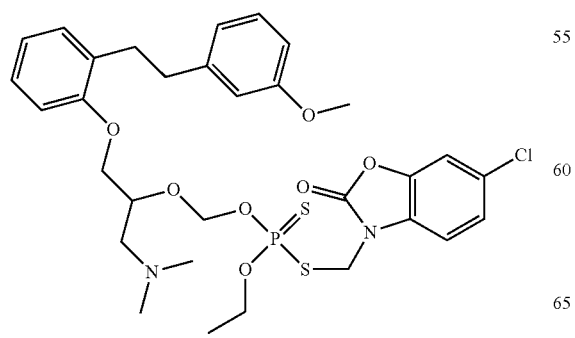
Compound 923
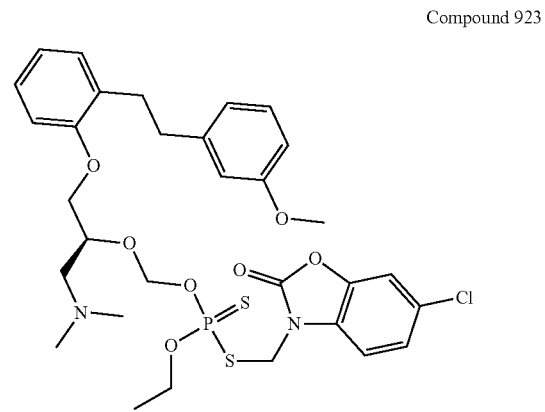
Compound 924
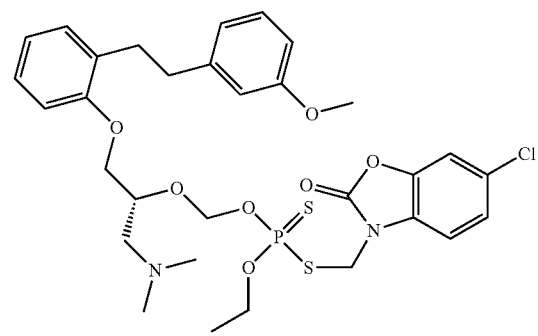
Compound 925
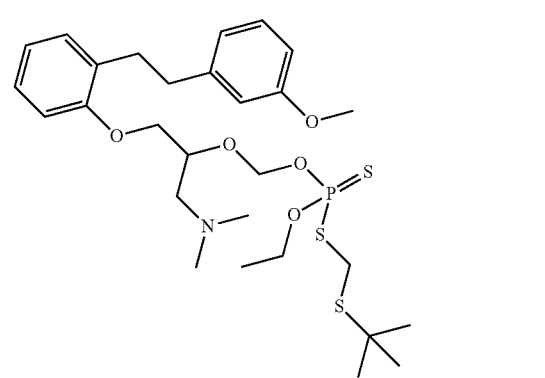
Compound 926
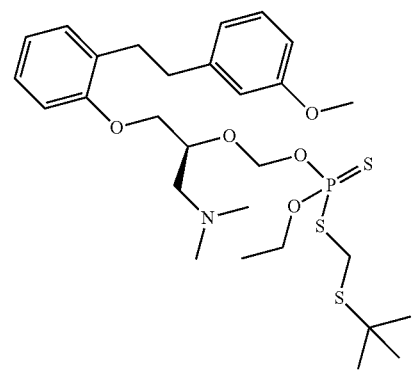

137
-continued
Compound 927
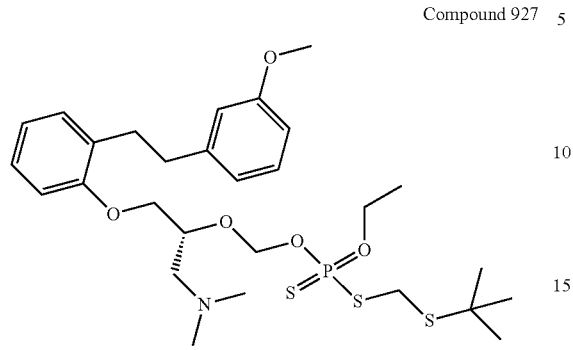
Compound 928
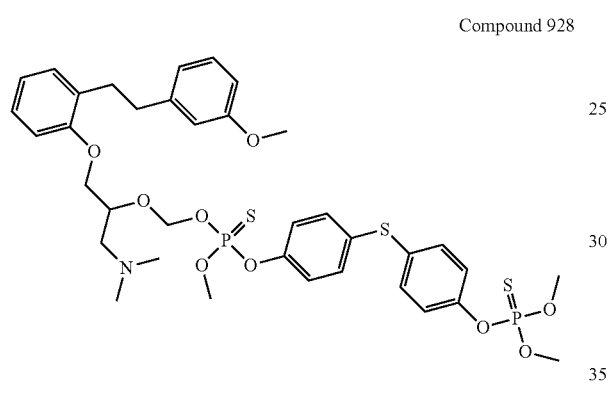
Compound 929
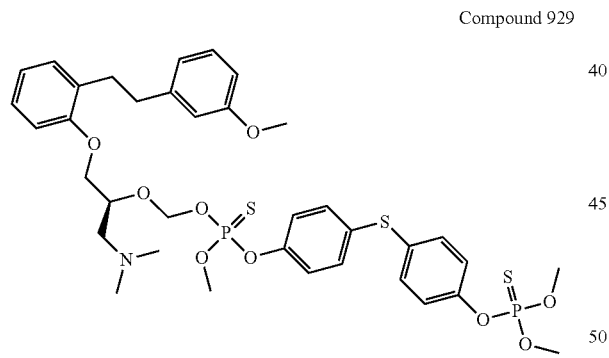
Compound 930
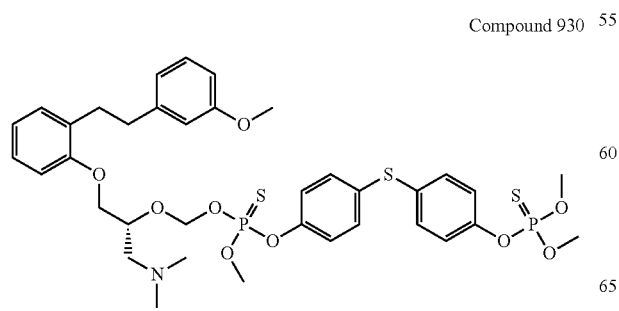
138
-continued
Compound 931
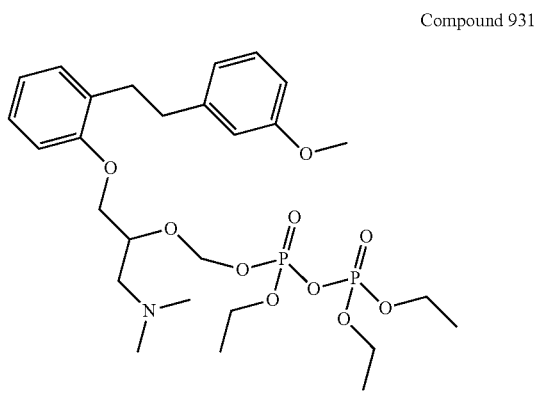
Compound 932
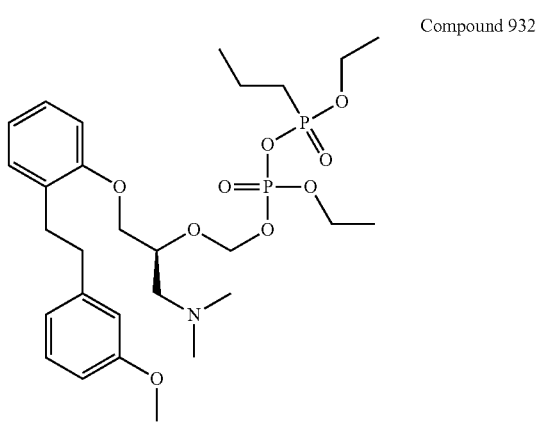
Compound 933
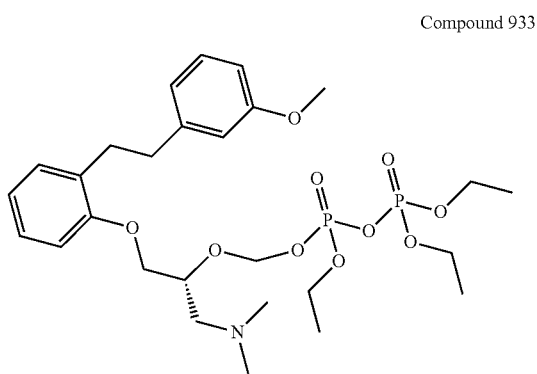
Compound 934
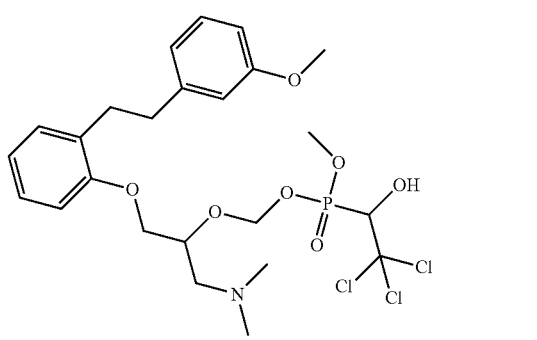

Compound 935
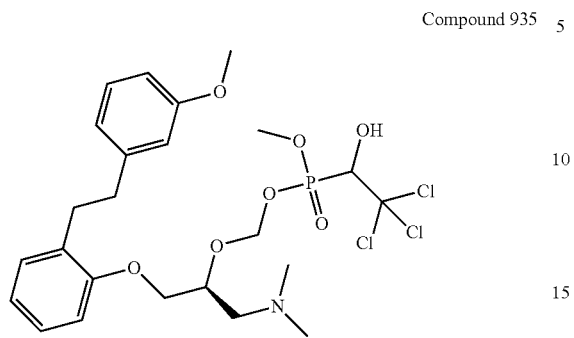
Compound 939
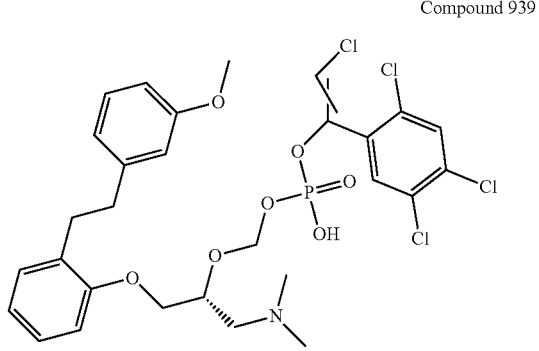
Compound 936
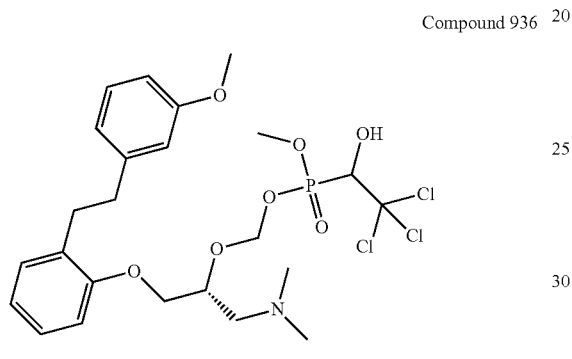
Compound 940
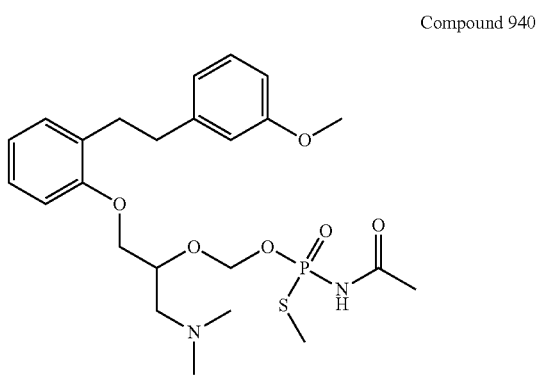
Compound 937
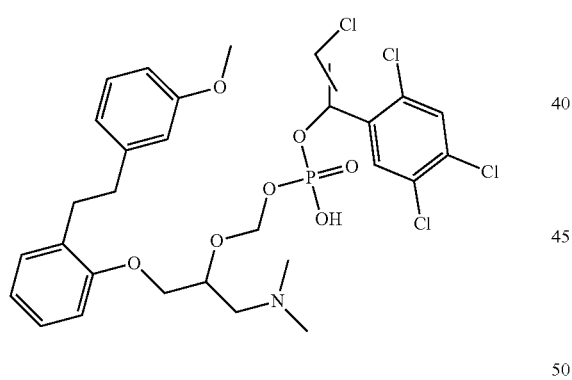
Compound 941
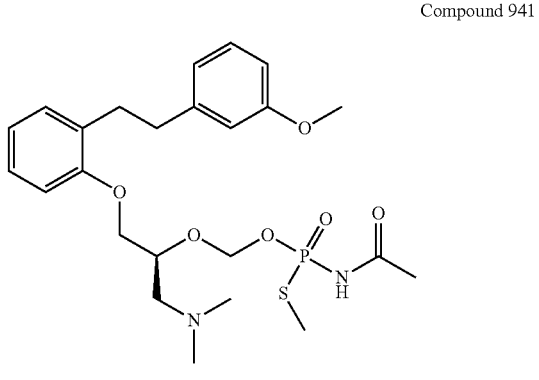
Compound 938
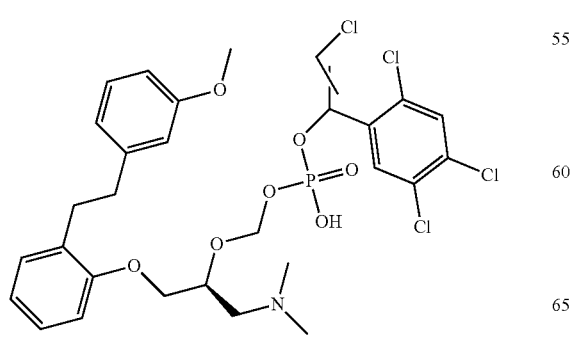
Compound 942
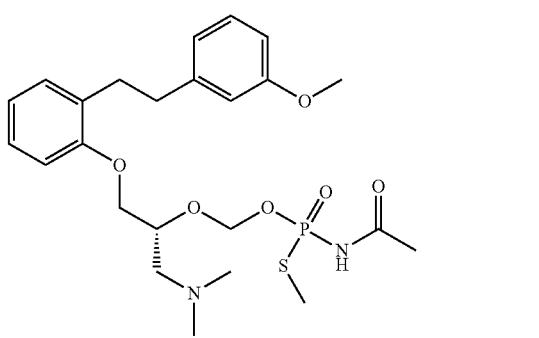

Compound 943
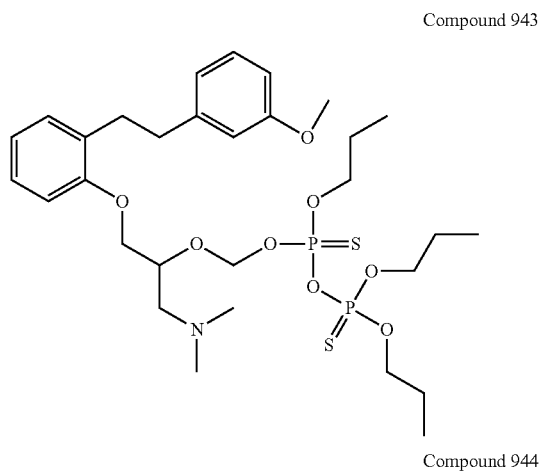
Compound 944
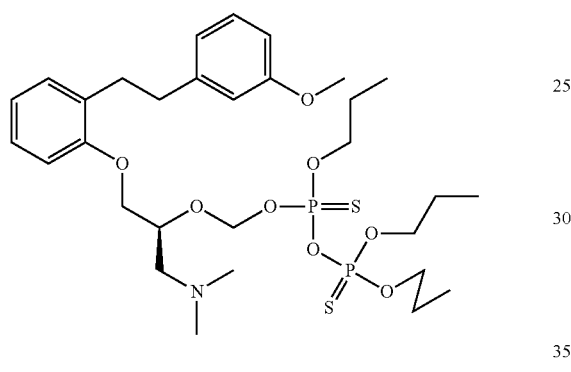
Compound 945
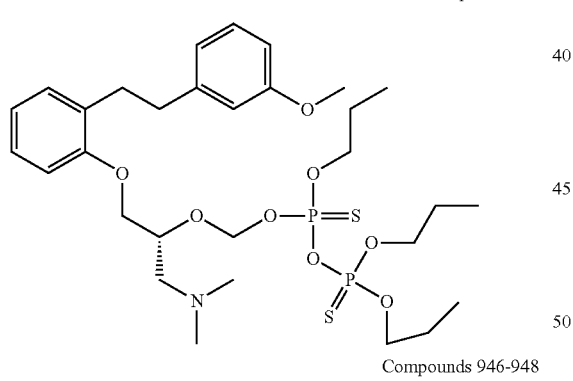
Compounds 946-948
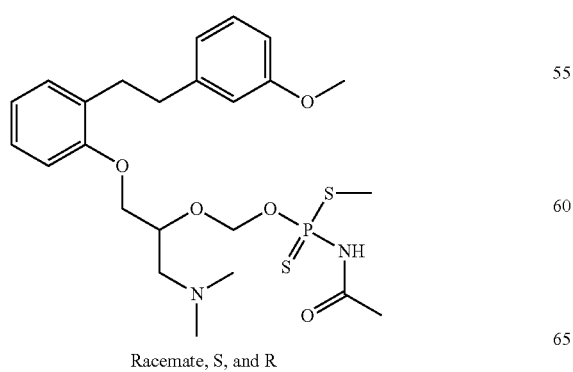
Racemate, S, and R
Compounds 949-951
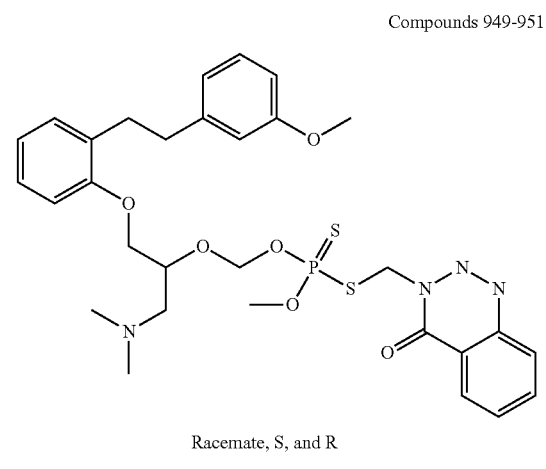
Racemate, S, and R
Compounds 952-954
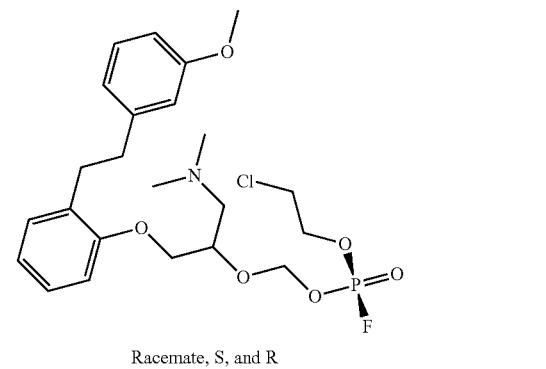
Racemate, S, and R
Compounds 955-957
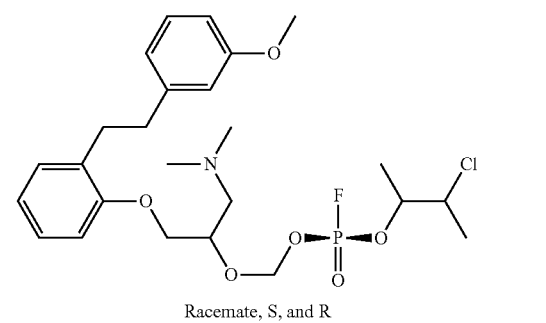
Racemate, S, and R
Compounds 958-960
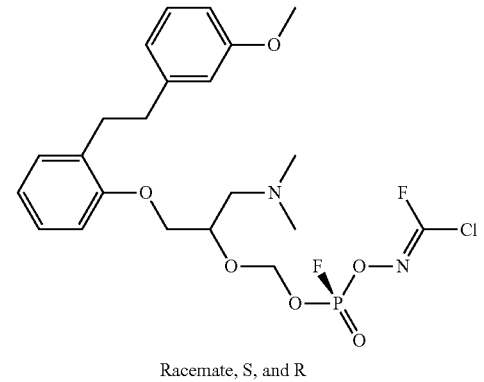
Racemate, S, and R

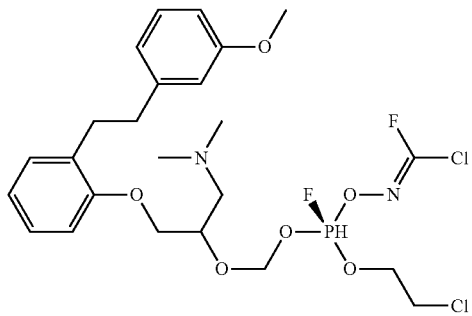

Compounds 961-963
Racemate, S, and R

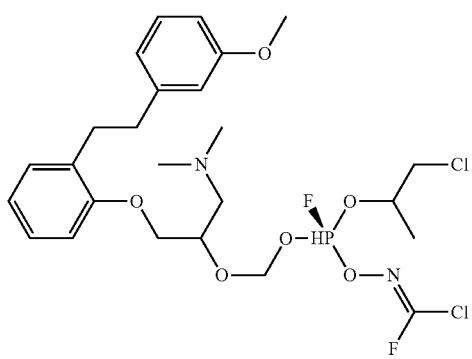

Compound 964-966
Racemate, S, and R

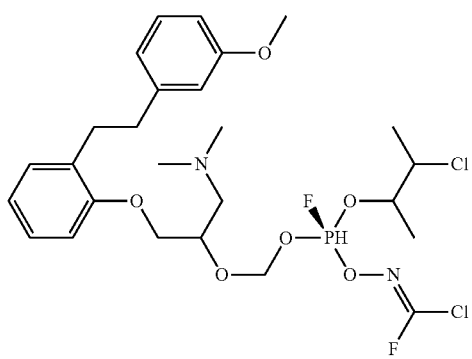

Compound 967-969
Racemate, S, and R

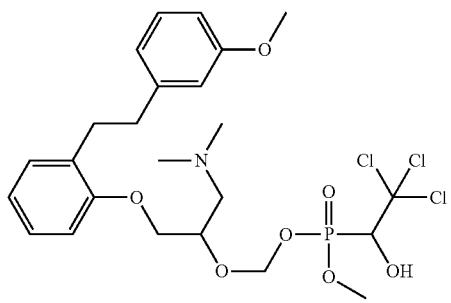

Compound 970-972
Racemate, S, and R

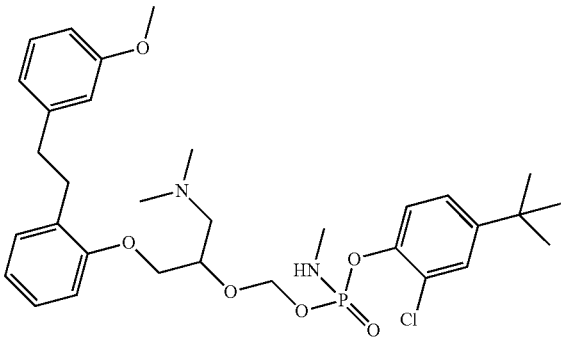

Compound 973-975
Racemate, S, and R

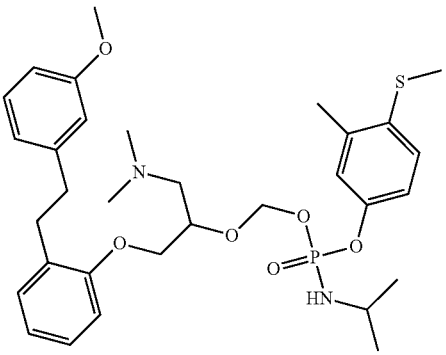

Compound 976-978
Racemate, S, and R

In another embodiment, the prodrugs of Formula I, exemplified by, but not limited to, compounds 901-978 representing Formulas P1-P11, PA-1 and 2, PF-1 to PF9, PT-1 to PT34, wherein P=Phosphate, PA=PhosphorAmidate, PF=PhosphonoFluoridate, and PT=PhosphoroThioate, are also acetylcholinesterase inhibitors due to the phosphate, phorphoramidate, phosphofuoridate, and phosphothioate moieties that confer such activity (McGleenon et al., Acetylcholinesterase inhibitors in Alzheimer's disease, Br J Clin Pharmacol, 48, 471-480 (1999); Acetylcholinesterase Inhibitors and Memantine, Acetylcholinesterase Inhibitors for the Treatment of Mild to Moderate Dementia, and Memantine for the Treatment of Moderate to Severe Dementia in Alzheimer's disease (AD) (June 2013), available at FIFEADTC SCOT NHS UK).

Methods of Use

The five most costly brain disorders (€ million) were: dementia: €22,164; psychotic disorders: €16,717; mood disorders: €19,238; addiction: €11,719; anxiety disorders: €11,687. Apart from psychosis, these five disorders ranked amongst those with the lowest direct medical expenditure per subject (<€3000) (Feinberg et al., The size, burden and cost of disorders of the brain in the UK, J Psychopharmacol. 27(9): 761-770 (2013 September); Projections of the Cost of Cancer Care in the United States: 2010-2020, J Natl Cancer Inst. 103(2): 117-128 (2011 Jan. 19) incorporated in entirety by reference). It was estimated that the total cost of bipolar disorder (BP), also known as manic-depressive illness, made more than a decade ago was as high as $45 billion per year. Most of this cost is accounted for by indirect costs related to reduced functional capacity and lost work. Patients with BP have higher rates of utilization of healthcare resources compared with the general population and compared with patients with other types of psychiatric conditions. Comorbidity contributes to the heavy burden that BP imposes on society. Brain diseases represent a considerable social and economic burden in Europe. With yearly costs of about 800 billion euros and an estimated 179 million people afflicted in 2010, brain diseases are an unquestionable emergency and a grand challenge for neuroscientists. The global cost of mental health conditions alone was estimated at US$2.5 trillion in 2010, with a projected increase to over US $6 trillion in 2030. Glioblastoma multiform is the most common malignant primary brain tumor in adults, with an estimated incidence of 4.43 per 100,000 person-years in the United States and a median age at presentation of 64 years. Symptoms often include headaches; nausea and vomiting; and progressive memory, personality, or neurologic deficits. While Alzheimer and other dementias are projected to show a 66% increase from 2005 to 2030. In the United States, depression is the second highest source of disability among women, and antidepressant non-responders are among the heaviest users of health care resources. Despite the clear decrease in quality of life and decreased productivity associated with depression, it is often underdiagnosed and inadequately treated.

Drug and alcohol dependence is a severe public health problem. It is estimated that between 26.4 million and 36 million people abuse opioids worldwide (UNODC, World Drug Report 2012), with an estimated 2.1 million people in the United States suffering from substance use disorders related to prescription opioid pain relievers in 2012 and an estimated 467,000 addicted to heroin (Substance Abuse and Mental Health Services Administration, Results from the 2012 National Survey on Drug Use and Health: Summary of National Findings, NSDUH Series H-46, HHS Publication No. (SMA) 13-4795. Rockville, Md.: Substance Abuse and Mental Health Services Administration, 2013; incorporated by reference in its entirety). The number of unintentional overdose deaths from prescription pain relievers has soared in the United States, more than quadrupled since 1999. There is also growing evidence to suggest a relationship between increased non-medical use of opioid analgesics and heroin abuse in the United States (Pradip et al., Associations of Nonmedical Pain Reliever Use and Initiation of Heroin Use in the US, Center for Behavioral Health Statistics and Quality Data Review, SAMHSA (2013); incorporated by reference in its entirety).

Links between a chronic diabetic metabolic situation and the risk and emergence of AD pathophysiology have long been suspected and substantiated in the recent years (Goldwaser et al., Breakdown of the Cerebrovasculature and Blood-Brain Barrier: A Mechanistic Link between Diabetes Mellitus and Alzheimer's Disease. *J Alzheimers Dis.* (2016 Aug. 1); incorporated by reference in its entirety). In several large post-mortem series, more than a third of all subjects clinically diagnosed with typical AD showed evidence of cerebrovascular disease and had to be re-classified as mixed dementia (Grandal et al., Prevalence and concordance between the clinical and the post-mortem diagnosis of dementia in a psychogeriatric clinic, Neurologia (2016); incorporated by reference in its entirety). From a clinical perspective, it is therefore desirable to extend AD therapy beyond currently approved drugs and mechanisms, and also address the cognitive impairment by optimizing a latent diabetic metabolic situation or the fairly frequent Type 2 diabetes in the elderly subjects. Indeed, glycemic control is thought to have an impact on the severity of cognitive impairment (Zilliox et al., Diabetes and Cognitive Impairment. *Curr Diab Rep,* 16 (9):87 (2016); incorporated by reference in its entirety). Due to the specific anti-diabetic actions of a compound of Formula I described above, in one embodiment, the present invention provides benefit on both, symptoms and disease progression in AD, and in cognitive impairment of mainly vascular origin (multi-infarct dementia, vascular dementia, vascular cognitive impairment, etc.).

In Parkinson's Disease, the anticholinergic effects of neuroleptics are highly unwanted as they inevitably worsen, in addition the motor condition and symptoms of the vegetative nervous system. In all dementias, lowering the seizure threshold is another infrequent but highly unwanted potential adverse effect of neuroleptics. About 10 million people worldwide have Parkinson's disease. Parkinson's disease is a synucleinopathy resulting in progressive neurodegeneration marked by motor dysfunction and non-motor symptoms including psychosis. More than 50% of patients with Parkinson's disease have psychosis at some time. Psychosis affects up to 75% of patients with Parkinson's disease dementia, and symptoms are more intractable in this group. Such psychosis is expressed primarily as hallucinations and delusions, which can cause great distress for patients and their caregivers. These episodes present a major challenge for treatment and care, increase the likelihood of placement in nursing homes, and are associated with increased mortality. Best-practice treatment guidelines promote initial consideration of comorbidities and reduction of dopaminergic therapy. However, these approaches are often insufficient, and few other therapeutic options exist.

The morbidity and mortality associated with depression are considerable and continue to increase. Depression currently ranks fourth among the major causes of disability worldwide, after lower respiratory infections, perinatal conditions, and HIV/AIDS. Seventeen percent of people will suffer from depression during their lifetime; making matters worse, people already suffering either from acute or chronic illness are even more likely to suffer from depression, where the incidence of depression may be 30% to 50% in patients depending on the specific medical condition.

The monoamine hypothesis has been the prevailing hypothesis of depression over the last several decades. It states that depression is associated with reduced monoamine function. Hence efforts to increase monoamine transmission by inhibiting serotonin (5-HT) and norepinephrine (NE) transporters has been a central theme in depression research since the 1960s. The selective 5-HT reuptake inhibitors (SSRIs) and 5-HT and NE reuptake inhibitors (SNRIs) that have emerged from this line of research are currently first line treatment options for major depressive disorder (MDD). One of the recent trends in antidepressant research has been to refine monoaminergic mechanisms by targeting monoaminergic receptors and additional transporters (e.g. with multimodal drugs and triple re-uptake inhibitors) or by adding atypical antipsychotics to SSRI or SNRI treatment. In addition, several other hypotheses of depression have been brought forward in pre-clinical and clinical research based on biological hallmarks of the disease and efficacy of pharmacological interventions. A central strategy has been to target glutamate receptors (for example, with intravenous infusions of the N-methyl-D-aspartate (NMDA) receptor antagonist ketamine). Other strategies have been based on modulation of cholinergic and gamma-aminobutyric acid (GABA)ergic transmission, neuronal plasticity, stress/hypothalamic pituitary adrenal (HPA)-axis, the reward system and neuroinflammation. Thus, there is a need to develop novel medications with complex pharmacological profiles derived from targeting several neurotransmitter and neuromodulator systems simultaneously.

BP frequently occurs together with other psychiatric disorders, especially anxiety disorders and substance abuse. In addition, BP has been associated with a variety of general medical conditions, which further complicate management of the psychiatric disorder (*Am J Manag Care,* 11: S85-S90 (2005); incorporated by reference in its entirety).

BP is a brain disorder that causes unusual shifts in mood, energy, activity levels, and the ability to carry out day-to-day tasks. BP is characterized by a dysregulation of mood, impulsivity, risky behavior and interpersonal problems. BP is a recurrent and often chronic psychiatric illness, associated with functional impairment, elevated suicide rates and utilization of mental health systems. BP is commonly under-recognized and as many as 40% of patients with BPs are initially misdiagnosed, resulting in increased risk for suicide, mania and chronic psychosocial suffering. When correctly diagnosed, successful treatment is possible <50% of diagnosed patients and as many as 10-15% of patients eventually die as a result of suicide (NIMH 2002).

While the pharmacological guidelines for treatment are well established, treatment for BP remains less than ideal. Most individuals still have breakthrough episodes or significant residual symptoms while on medication (NIMH 2002). In addition, functional deficits often remain even when patients are in remission (NIMH 2002). Because many patients with BP remain symptomatic, even while fully adherent to their medication regimens, the need for greater understanding of the pathogenesis of this illness from the research on the pharmacological mechanisms of bipolar medications is all the more urgent. The major medication therapy of BPs is mood stabilizers unless the pharmacology mechanisms are not clear yet. Common neuroprotective effects of mood stabilizers play a role of brain cell dysfunction in BP, and the dysfunction may eventually cause neuron loss. Volumetric neuroimaging, now increasingly assessing potential involvement of different brain structures in mood regulation, could be applied to test neuroanatomical models of mood disorders. Imaging studies suggested that ongoing neuronal atrophy accompanies BP. For instance, PET images of the cerebral blood flow and the rate of glucose metabolism regarding as brain activity detected the reduced activity in the subgenual prefrontal cortex during the bipolar depression. This decrement in activity was, in part, at least explained by a corresponding reduction of cortical volume, as same as magnetic resonance imaging demonstration of the mean gray matter volume. In BP, abnormalities of the third ventricle, frontal lobe, cerebellum, and possibly the temporal lobe are also noted.

Brain tumors are formed by abnormal growths and can appear in different areas of the brain. Benign (not cancerous) tumors may grow and press on nearby areas of the brain, but rarely spread into other tissues. Malignant (cancerous) tumors are likely to grow quickly and spread into other brain tissue. A tumor that grows into or presses on an area of the brain may stop that part of the brain from working the way it should, whether the tumor itself is benign or malignant, and will then require treatment. The most common type of brain tumor seen does not originate from the brain tissue itself, but rather are metastases from extracranial cancers such as lung cancer and breast cancer. Brain tumors include neurofibromatosis type 1 or 2, von Hippel-Lindau disease, tuberous sclerosis, Li-Fraumeni syndrome, Turcot syndrome type 1 and type 2, Klinefelter syndrome, and Nevoid basal cell carcinoma syndrome. Neuroblastoma is cancer found in developing nerve cells, usually in children under 10 years of age. Almost 90% of cases are diagnosed by the age of 5. Different factors can affect the type of neuroblastoma a child has and their prognosis.

Specific treatment for neurological cancer is based on several factors including a patient's overall health and medical history; the type, location, and size of the tumor; the extent of the condition; and other individual factors. Generally, treatment for patients with cancer of the brain or spinal cord includes surgery, chemotherapy, radiation therapy, and/or steroids to treat and prevent swelling, especially in the brain; anti-seizure medication to treat and prevent seizures associated with intracranial pressure; placement of a shunt (to help drain excess fluid in the brain); lumbar puncture/spinal tap (to measure pressure in the spinal cord and brain); bone marrow transplantation; rehabilitation (to regain lost motor skills and muscle strength); and/or antibiotics (to treat and prevent infections). Chemotherapy is the use of anticancer drugs to treat cancerous cells. In most cases, chemotherapy works by interfering with the cancer cell's ability to grow or reproduce. These drugs may be given into a vein or by mouth, as a tablet.

Neuropsychiatric symptoms are a common burden in patients suffering from Alzheimer's disease (AD), Parkinson's disease dementia (PDD), and many other neurodegenerative disorders, including but not limited to dementia with Lewy bodies (DLB), vascular dementia (VaD), and frontotemporal lobar degeneration (FTLD) (Kazui H et al. Differences of Behavioral and Psychological Symptoms of Dementia in Disease Severity in Four Major Dementias. PLoS ONE 11(8): e0161092 (2016); Van der Schyf C J. Psychotropic Drug Development Strategies that Target Neuropsychiatric Etiologies in Alzheimer's and Parkinson's Diseases. Drug Dev Res. 77: 458-468 (2016)).

Many neuropsychiatric symptoms manifest very early in neurodegenerative disease stages, and are even considered prodromal indicators or indicators for disease progression (Kazui H et al. Differences of Behavioral and Psychological Symptoms of Dementia in Disease Severity in Four Major Dementias. PLoS ONE 11(8): e0161092 (2016); Peters M E et al. Neuropsychiatric Symptoms as Predictors of Progression to Severe Alzheimer's Dementia and Death: The Cache County Dementia Progression Study. Am J Psychiatry 172: 460-465 (2015)).

Behavioral and psychological symptoms of dementia (BPSD), also known as neuropsychiatric symptoms, in neurodegenerative diseases and disease states including but not limited to AD have a multifactorial origin (McClam T D et al. Interventions for neuropsychiatric symptoms in neurocognitive impairment due to Alzheimer's disease: a review of the literature. Harv Rev Psychiatry 23: 377-393 (2015)). Therefore, a strategy aimed at simultaneously targeting multiple etiologies of a disease (hence, multiple drug targets) constitutes the best approach in the development of treatment strategies for a range of diseases including but not limited to AD (Nikolic K et al. Drug design for CNS diseases: polypharmacological profiling of compounds using cheminformatic, 3D-QSAR and virtual screening methodologies. Front Neurosci 10: 265 (2015)).

Individual BPSD symptoms may appear as mutually exclusive but can nevertheless share the underlying mechanisms. This shared mechanism similarity can occur at the neurochemical and/or neuroanatomical levels and serves as a basis for developing targeted, but not mechanism-specific therapies addressing more than one BPSD symptom.

Shared mechanisms are illustrated by similar neurochemical organizations of the projections from cortical areas to basal ganglia to thalamus and back to the cortex. For example, the dorsolateral prefrontal cortex projects to the dorsolateral caudate which in turn targets lateral dorsomedial parts of internal globus pallidus that sends projections to the principal part of the ventral anterior or mediodorsal thalamus which returns projections to the cortex. In contrast, the orbitofrontal cortex projects to the ventromedial caudate that projects to medial dorsomedial parts of internal globus pallidus that sends projections to the magnocellular part of ventral anterior or mediodorsal thalamus which returns projections to the cortex. Thus, different parts of cortex may be responsible for different functions but there are common principles according to which cortical networks operate (Aouizerate B et al. Pathophysiology of obsessive-compulsive disorder: a necessary link between phenomenology, neuropsychology, imagery and physiology. Prog Neurobiol 72(3):195-221 (2004)). Therefore, impairments in different circuits underlie the emergence of different BPSD symptoms. Heterogeneity of the clinical presentations of neurodegenerative disorders is determined by the predominant location of the pathology (i.e. by affected networks). For example, the dorsal anterior cingulate cortex and dorsolateral prefrontal cortex are more affected in apathetic patients, and the medial orbital frontal cortex in disinhibited patients with bvFTLD (e.g., Massimo et al. Dement Geriatr Cogn Disord 27:96-104 (2009)).

For 5-$HT_{2A}$ receptors that are targeted by compounds of Formula I, it is well established that serotonin via 5-$HT_{2A}$ receptors increases glutamatergic spontaneous excitatory postsynaptic currents in apical dendrites of layer V pyramidal cells of prefrontal cortex (Aghajanian G K, Marek G J. Serotonin, via 5-HT2A receptors, increases EPSCs in layer V pyramidal cells of prefrontal cortex by an asynchronous mode of glutamate release. Brain Res 825:161-71 (1999)). Such excessive asynchronous transmission may be functionally expressed in a variety of forms dependent on which part of the cerebral cortex is affected—from auditory or visual hallucinations to disinhibition and apathy—but in most cases, will be sensitive to manipulations involving 5-$HT_{2A}$ receptors that are present across various cortical areas (van Dyck C H et al. PET quantification of 5-$HT_{2A}$ receptors in the human brain: a constant infusion paradigm with [18F]altanserin. J Nucl Med 41(2):234-41 (2000)).

For glutamatergic signaling that is targeted by dextromethorphan and memantine, it is well established that it mediates thalamocortical signaling, causing the activation of corresponding areas of the cortex (Kharazia V N, Weinberg R J. Glutamate in thalamic fibers terminating in layer IV of primary sensory cortex. J Neurosci 14(10):6021-6032 (1994); Sherman S M. Thalamus plays a central role in ongoing cortical functioning. Nat Neurosci 19(4):533-41 (2016)).

Diseases like Alzheimer's disease are characterized by systematic, progressive, probably trans-synaptic spread of neurodegeneration. That does not only mean more cell loss in a certain area of the brain but also spreading of the pathology to other brain areas. As different brain areas have different functional roles, this explains why more advanced stages of the disease are accompanied by a wider spectrum of symptoms (Kazui et al. Differences of Behavioral and Psychological Symptoms of Dementia in Disease Severity in Four Major Dementias. PLoS ONE 11(8): e0161092 (2016)).

Behavioral and psychological symptoms of dementia, also known as neuropsychiatric symptoms, are commonly studied in the clinic using research tools such as the Neuropsychiatric Inventory (NPI; Cummings J L. The Neuropsychiatric Inventory: Assessing psychopathology in dementia patients. Neurology 48:S10-S16 (1997)). The NPI scale recognizes 12 sub-domains of behavioral functioning: delusions, hallucinations, agitation/aggression, dysphoria, anxiety, euphoria, apathy, disinhibition, irritability/lability, aberrant motor activity, night-time behavioral disturbances, and appetite and eating abnormalities.

Patients rarely display each and every of these NPI symptoms at once as there are NPI items like euphoria that are rare, even at a CDR score of 3. Conversely, clinical experience indicates that there is rarely a patient showing just one specific item, and none of the rest. Instead, BPSD symptoms occurs in various combinations or clusters. For example, a frequent AD cluster could e.g. be aggression, agitation, wandering, repetitiveness, while a frequent Vascular Dementia cluster could e.g. be confusion and restlessness, but the frequency and severity of NPI items is subject to change, e.g. from day to day, but especially during disease progression (Kazui et al. Differences of Behavioral and Psychological Symptoms of Dementia in Disease Severity in Four Major Dementias. PLoS ONE 11(8): e0161092 (2016); Johnson D K et al. Neuropsychiatric profiles in dementia. Alzheimer Dis Assoc Disord 25(4): 326-332 (2011)). As a given patient may present such a cluster of several symptoms of clinical relevance at once, there is a high medical need in treatments that can target various clusters of symptoms or the entire range of BPSD symptoms, irrespective of any currently prevailing pathophysiological hypothesis on the disease.

The prevalence of delusions is rather low in general population, in people with normal cognitive aging (0.4-2.4%) but is increased in subjects with mild cognitive impairment (MCI; 3.1-3.4%) and markedly increased in dementia (18.0-31.0%) (Geda Y E et al. The Prevalence of Neuropsychiatric Symptoms in Mild Cognitive Impairment and Normal Cognitive Aging: A Population-Based Study. Arch Gen Psychiatry 65(10): 1193-1198 (2008); Lyketsos C G et al. Prevalence of neuropsychiatric symptoms in dementia and mild cognitive impairment: results from the cardiovascular health study. JAMA 288(12):1475-83 (2002); Zhao Q F et al. The prevalence of neuropsychiatric symptoms in Alzheimer's disease: Systematic review and meta-analysis. J Affect Disord 190:264-71 (2016)). Prevalence of hallucinations is also low in the general population, in people with normal cognitive aging (0.4-0.6%) but is increased in subjects with MCI (0.6-1.3%) and dementia (10.5-16.0%) (Geda Y E et al. The Prevalence of Neuropsychiatric Symptoms in Mild Cognitive Impairment and Normal Cognitive Aging: A Population-Based Study. Arch Gen Psychiatry 65(10): 1193-1198 (2008); Lyketsos C G et al. Prevalence of neuropsychiatric symptoms in dementia and mild cognitive impairment: results from the cardiovascular health study. JAMA 288(12):1475-83 (2002); Zhao Q F et al. The prevalence of neuropsychiatric symptoms in Alzheimer's disease: Systematic review and meta-analysis. J Affect Disord 190: 264-71(2016)).

Both delusions and hallucinations are part or symptoms of psychosis in various neurological and psychiatric diseases and disease states. Neuroleptics have traditionally been used off-label to treat such symptoms faute-de-mieux in dementia; however, with very few exceptions both "typical" and "atypical" neuroleptics increase the incidence of CV adverse events and showed a markedly increased death rate when used off-label in dementia. Hence, the FDA issued a "black box" warning against their off-label use outside schizophrenia which leaves little therapeutic options to treat such BPSD symptoms in dementia. On this background, a completely different class, namely 5-$HT_{2A}$ receptor antagonists and inverse agonists demonstrated an antipsychotic-like efficacy profile in preclinical studies (Weiner et al. 5-hydroxytryptamine2A receptor inverse agonists as antipsychotics. J Pharmacol Exp Ther 299(1):268-76 (2001)). Several 5-HT$_{2A}$ receptor antagonists and inverse agonists have been in development for neuropsychiatric indications and there were reports of beneficial antipsychotic effects obtained with compounds such as eplivanserin (Meltzer H Y et al. Placebo-controlled evaluation of four novel compounds for the treatment of schizophrenia and schizoaffective disorder. Am J Psychiatry 161: 975-84 (2004)). 5-HT$_{2A}$ receptor inverse agonist pimavanserin significantly reduced psychotic symptoms, which includes hallucinations and delusions, in patients with moderate to severe Parkinson's disease (Cummings J et al. Pimavanserin for patients with Parkinson's disease psychosis: a randomised, placebo-controlled phase 3 trial. Lancet 383: 533-40 (2014)) and has been FDA approved specifically for the treatment of these symptoms in PDD. In patients with Alzheimer's disease dementia, HTR2A T102C polymorphism is a significant risk factor for psychosis with an allelic OR of 2.191 for C allele that increased to 5.143 for the homozygous CC genotype (Ramanathan S, Glatt S J. Serotonergic system genes in psychosis of Alzheimer dementia: meta-analysis. Am J Geriatr Psychiatry 17(10):839-46 (2009)).

Dextromethorphan has NMDA receptor channel blocking properties and NMDA receptor channel blockers such as phencyclidine or ketamine are known to possess psychotomimetic rather than antipsychotic properties. There are reports of psychosis induced by dextromethorphan in humans (Miller S C. Dextromethorphan psychosis, dependence and physical withdrawal. Addict Biol 10(4):325-7 (2005)). These psychoactive properties of dextromethorphan may be a function of its metabolic degradation resulting in production of dextrorphan (Zawertailo L A et al. Effect of metabolic blockade on the psychoactive effects of dextromethorphan. Hum Psychopharmacol 25(1):71-9 (2010)). Psychoactive effects of dextromethorphan observed in some subjects do not exclude a possibility that dextromethorphan also has antipsychotic properties under certain circumstances. Indeed, dextromethorphan, but not its metabolite dextrorphan, was reported to attenuate phencyclidine-induced motor behaviors in rats (Székely J I et al. Induction of phencyclidine-like behavior in rats by dextrorphan but not dextromethorphan. Pharmacol Biochem Behav 40(2):381-6 (1991)). Meta-analysis of the randomized controlled studies of another NMDA receptor channel blocker, memantine, in patients with Alzheimer's disease indicated that memantine induces significant improvement in delusions (Kishi T et al. The effects of memantine on behavioral disturbances in patients with Alzheimer's disease: a meta-analysis. Neuropsychiatr Dis Treatment 13: 1909-1928 (2017)).

Agitation and aggression are grouped together as one item on the NPI scale. Prevalence of agitation and aggression is low in general population, in people with normal cognitive aging (2.8-2.9%) but is increased in subjects with MCI (9.1-11.3%) and dementia (30.3-40%) (Geda Y E et al. The Prevalence of Neuropsychiatric Symptoms in Mild Cognitive Impairment and Normal Cognitive Aging: A Population-Based Study. Arch Gen Psychiatry 65(10): 1193-1198 (2008); Lyketsos C G et al. Prevalence of neuropsychiatric symptoms in dementia and mild cognitive impairment: results from the cardiovascular health study. JAMA 288(12): 1475-83 (2002); Zhao Q F et al. The prevalence of neuropsychiatric symptoms in Alzheimer's disease: Systematic review and meta-analysis. J Affect Disord 190:264-71 (2016)). So this NPI item is one the most prevalent and at the same time difficult to treat clinical BPSD symptom.

Preclinical studies indicate that blockade of 5-HT2A receptors reduces aggression in laboratory rodents (Sakaue M et al. Modulation by 5-hT2A receptors of aggressive behavior in isolated mice. Jpn J Pharmacol 89(1):89-92 (2002)). Human genetics data indicate that scores on three out of four subscales of the Buss-Perry Aggression Questionnaire (Hostility, Anger and Physical Aggression) show significant association with HTR2A rs7322347 T allele (Banlaki Z et al. Polymorphism in the serotonin receptor 2a (HTR2A) gene as possible predisposal factor for aggressive traits. PLoS One 10(2):e0117792 (2015)). In a case-control study in Chinese subjects with AD, aggression in AD was significantly associated with 5-HT$_{2A}$ receptor polymorphism such as T102C (Lam L C et al. 5-HT2A T102C receptor polymorphism and neuropsychiatric symptoms in Alzheimer's disease. Int J Geriatr Psychiatry 19(6):523-6 (2004)).

Various NMDA receptor channel blockers have been shown to attenuate aggressive behaviors in mice and these effects may be difficult to separate from sedative action (Belozertseva I V, Bespalov A Y. Effects of NMDA receptor channel blockade on aggression in isolated male mice. Aggr Behav 25:381-396 (1999)). In patients with probable Alzheimer disease and clinically significant agitation, dextromethorphan-quinidine combination reduced Agitation/Aggression scores of the NPI (Cummings J L et al. Effect of Dextromethorphan-Quinidine on Agitation in Patients With Alzheimer Disease Dementia: A Randomized Clinical Trial. JAMA 314(12):1242-54 (2015))). A meta-analysis of randomized controlled studies of another nonselective NMDA receptor channel blocker, memantine, in patients with Alzheimer's disease indicated that also memantine induces significant improvement in agitation/aggression (Kishi T et al. The effects of memantine on behavioral disturbances in patients with Alzheimer's disease: a meta-analysis. Neuropsychiatr Dis Treatment 13: 1909-1928 (2017)).

The prevalence of dysphoria/depression is moderate in general population, in people with normal cognitive aging (7.2-11.4%) but is increased in subjects with MCI (20.1-27.0%) and it is one of the most prevalent problems in dementia (32.3-42%) (Geda Y E et al. The Prevalence of Neuropsychiatric Symptoms in Mild Cognitive Impairment and Normal Cognitive Aging: A Population-Based Study. Arch Gen Psychiatry 65(10): 1193-1198 (2008); Lyketsos C G et al. Prevalence of neuropsychiatric symptoms in dementia and mild cognitive impairment: results from the cardiovascular health study. JAMA 288(12):1475-83 (2002); Zhao Q F et al. The prevalence of neuropsychiatric symptoms in Alzheimer's disease: Systematic review and meta-analysis. J Affect Disord 190:264-71 (2016)).

Preclinical studies using brain stimulation reward indicated that 5-HT2A receptor antagonism may counteract dysphoria induced by conventional neuroleptics such as haloperidol (Benaliouad F et al. Blockade of 5-HT2a receptors reduces haloperidol-induced attenuation of reward. Neuropsychopharmacology 32(3):551-61 (2007)). 5-HT2A receptor antagonists exert antidepressant-like effects in preclinical models sensitive to clinically used antidepressant drugs (Marek G J et al. The selective 5-HT2A receptor antagonist M100907 enhances antidepressant-like behavioral effects of the SSRI fluoxetine. Neuropsychopharmacology 30: 2205-2215 (2005); Patel J G et al. The highly selective 5-hydroxytryptamine (5-HT)2A receptor antagonist, EMD 281014, significantly increases swimming and decreases immobility in male congenital learned helpless rats in the forced swim test. Synapse 52: 73-75 (2004)).

NMDA receptor channel blockers such as dextromethorphan have been shown to possess antidepressant-like properties in preclinical models (Sakhaee E et al. The role of NMDA receptor and nitric oxide/cyclic guanosine monophosphate pathway in the antidepressant-like effect of dextromethorphan in mice forced swimming test and tail suspension test. Biomed Pharmacother 85:627-634 (2017)). Of the NMDA receptor channel blockers, ketamine, is proven to have rapid and robust antidepressant activity in patients with treatment-resistant major depressive disorder (Singh J B et al. A Double-Blind, Randomized, Placebo-Controlled, Dose-Frequency Study of Intravenous Ketamine in Patients With Treatment-Resistant Depression. Am J Psychiatry 173 (8):816-26 (2016)). Dextromethorphan given in combination with quinidine also exerts antidepressant action in humans (Murrough J W et al. Dextromethorphan/quinidine pharmacotherapy in patients with treatment resistant depression: A proof of concept clinical trial. J Affect Disord 218:277-283 (2017)). Dextromethorphan is not a selective NMDA receptor channel blocker and is more potent at serotonin and norephinephrine transporters as well as sigma-1 receptors that may contribute to therapeutic effects of dextromethorphan (Stahl S M. Mechanism of action of dextromethorphan/quinidine: comparison with ketamine. CNS Spectrums 18: 225-227 (2013)). While monoamine transporters are targeted by most currently used antidepressants, sigma-1 receptors have also been found to contribute to antidepressant-like effects of dextromethorphan in laboratory animals (Nguyen L et al. Involvement of sigma-1 receptors in the antidepressant-like effects of dextromethorphan. PLoS One 9(2):e89985 (2014)).

The prevalence of apathy is low in general population, in people with normal cognitive aging (3.2-4.8%) but is increased in subjects with MCI (14.7-18.5%) and dementia (35.9-49%) (Geda Y E et al. The Prevalence of Neuropsychiatric Symptoms in Mild Cognitive Impairment and Normal Cognitive Aging: A Population-Based Study. Arch Gen Psychiatry 65(10): 1193-1198 (2008); Lyketsos C G et al. Prevalence of neuropsychiatric symptoms in dementia and mild cognitive impairment: results from the cardiovascular health study. JAMA 288(12):1475-83 (2002); Zhao Q F et al. The prevalence of neuropsychiatric symptoms in Alzheimer's disease: Systematic review and meta-analysis. J Affect Disord 190:264-71 (2016)). In a case-control study in Chinese subjects with AD, apathy in AD was significantly associated with 5-HT2A receptor polymorphism such as T102C (Lam L C et al. 5-HT2A T102C receptor polymorphism and neuropsychiatric symptoms in Alzheimer's disease. Int J Geriatr Psychiatry 19(6):523-6 (2004)). Apathy is a symptom frequently seen in patients with schizophrenia and belongs to the group of negative symptoms. $5\text{-HT}_{2A}$ receptor antagonists reduce the severity of negative symptoms in patients with schizophrenia (Davidson M et al. Efficacy and Safety of MIN-101: A 12-Week Randomized, Double-Blind, Placebo-Controlled Trial of a New Drug in Development for the Treatment of Negative Symptoms in Schizophrenia. Am J Psychiatry DOI: 10.1176/appi.ajp.2017. Ser. No. 17/010,122 (2017); Meltzer H Y et al. Placebo-controlled evaluation of four novel compounds for the treatment of schizophrenia and schizoaffective disorder. Am J Psychiatry 161(6):975-84 (2004)).

NMDA receptor channel blockers such as memantine are reported to reduce apathy in certain patients with neurodegenerative diseases (Links K A et al. A case of apathy due to frontotemporal dementia responsive to memantine. Neurocase 19(3):256-61 (2013)) or with the negative symptoms in schizophrenia (Paraschakis A. Tackling negative symptoms of schizophrenia with memantine. Case Rep Psychiatry 2014:384783 (2014)).

The prevalence of anxiety is low in general population, in people with normal cognitive aging (5.0-5.8%) but is increased in subjects with MCI (9.9-14.1%) and dementia (21.5-39%) (Geda Y E et al. The Prevalence of Neuropsychiatric Symptoms in Mild Cognitive Impairment and Normal Cognitive Aging: A Population-Based Study. Arch Gen Psychiatry 65(10): 1193-1198 (2008); Lyketsos C G et al. Prevalence of neuropsychiatric symptoms in dementia and mild cognitive impairment: results from the cardiovascular health study. JAMA 288(12):1475-83 (2002); Zhao Q F et al. The prevalence of neuropsychiatric symptoms in Alzheimer's disease: Systematic review and meta-analysis. J Affect Disord 190:264-71 (2016)).

$5\text{-HT}_{2A}$ receptor antagonists exert anxiolytic in various preclinical models, particularly models of conditioned fear (Adamec R et al. Prophylactic and therapeutic effects of acute systemic injections of EMD 281014, a selective serotonin 2A receptor antagonist on anxiety induced by predator stress in rats. Eur J Pharmacol 504(1-2):79-96 (2004); Millan M J. The neurobiology and control of anxious states. Progr Neurobiol 70: 83-244 (2003)). In humans, $5\text{-HT}_{2A}$ receptor blockade attenuates emotional processing in the orbitofrontal cortex involved in the evaluation of socially relevant stimuli (Hornboll B et al. Pharmacological blockade of 5-HT2A receptors reduces orbitofrontal activation during processing of fearful and angry faces in healthy subjects. NeuroImage 47: S39-S41 (2009)). 5-HT2 receptor antagonist serazepine (CGS-15040A) has shown efficacy in clinical trials in patients with generalized anxiety disorder (Katz R J et al. Serotonergic (5-HT2) mediation of anxiety-therapeutic effects of serazepine in generalized anxiety disorder. Biol Psychiatry 34: 41-44 (1993)).

Like other members of the NMDA receptor antagonist class (Chojnacka-Wójcik E et al. Glutamate receptor ligands as anxiolytics. Curr Opin Investig Drugs 2(8):1112-9 (2001)), dextromethorphan was observed to induce anxiolytic-like effects in laboratory animals within a certain dose range (Dere E et al. NMDA-receptor antagonism via dextromethorphan and ifenprodil modulates graded anxiety test performance of C57BL/6 mice. Behav Pharmacol 14(3): 245-9 (2003)). Preclinical anxiolytic effects of dextromethorphan may be related not only to the inhibition of NMDA receptor function but also to interaction with the sigma-1 receptors (Kamei H et al. (+)-SKF-10,047 and dextromethorphan ameliorate conditioned fear stress through the activation of phenytoin-regulated sigma 1 sites. Eur J Pharmacol 299(1-3):21-8 (1996)). In patients with AD, treatment with another nonselective NMDA receptor channel blocker, memantine, significantly decreases in the scores of NPI subscale for anxiety (Ishikawa I et al. The effect of memantine on sleep architecture and psychiatric symptoms in patients with Alzheimer's disease. Acta Neuropsychiatr 28(3): 157-64 (2016)).

The prevalence of euphoria/elation is very low in general population, and in people with normal cognitive aging (0.3-0.4%) but is increased in subjects with MCI (0.6-1.3%) and dementia (3.1-7%) (Geda Y E et al. The Prevalence of Neuropsychiatric Symptoms in Mild Cognitive Impairment and Normal Cognitive Aging: A Population-Based Study. Arch Gen Psychiatry 65(10): 1193-1198 (2008); Lyketsos C G et al. Prevalence of neuropsychiatric symptoms in dementia and mild cognitive impairment: results from the cardiovascular health study. JAMA 288(12):1475-83 (2002); Zhao Q F et al. The prevalence of neuropsychiatric symptoms in Alzheimer's disease: Systematic review and meta-analysis. J Affect Disord 190:264-71 (2016)).

Human PET studies have established a positive correlation of the psychostimulant drug-induced-induced changes in euphoria analog scale scores with decreases in [11C] raclopride receptor binding potential (BP) in the caudate nucleus and putamen consistent with an increase in endogenous dopamine (Drevets W C. Amphetamine-induced dopamine release in human ventral striatum correlates with euphoria. Biol Psychiatry 49(2):81-96 (2001)). A nonselective 5-HT2A receptor agonist psilocybin significantly reduced [11C]raclopride BP in the ventral striatum that correlated with depersonalization associated with euphoria (Vollenweider F X et al. 5-HT modulation of dopamine release in basal ganglia in psilocybin-induced psychosis in man—a PET study with [11C]raclopride. Neuropsychopharmacology 20(5):424-33 (1999)). Preclinical data have indicated that the majority of prefrontal cortical pyramidal neurons that project to the dorsal raphe nuclei and ventral tegmental area express 5-HT2A receptors (Vazquez-Borsetti P. et al. Pyramidal neurons in rat prefrontal cortex projecting to ventral tegmental area and dorsal raphe nucleus express $5\text{-HT}_{2A}$ receptors. Cereb Cortex 19:1678-86 (2009)). Consequently, blockade of prefrontal $5\text{-HT}_{2A}$ receptors may modulate pyramidal neurons projecting to the midbrain and thereby inhibit the dopaminergic system in the midbrain (Erbdrup B H et al. Serotonin 2A receptor antagonists for treatment of schizophrenia. Expert Opin Investig Drugs 20(9):1211-1223 (2011)). DOpaminergic midbrain system is also under control of cholinergic projections such as those originating in habenula and activity of these projections are modulated by α3β4-containing nicotinic acetylcholine receptors (McCallum S E et al. α3β4 nicotinic acetylcholine receptors in the medial habenula modulate the mesolimbic dopaminergic response to acute nicotine in vivo. Neuropharmacology 63(3):434-40 (2012)). Antagonism at α3β4-containing nicotinic acetylcholine receptors is associated with various effects ascribed to reduced dopamine tone (Maisonneuve I M, Glick S D. Anti-addictive actions of an iboga alkaloid congener: a novel mechanism for a novel treatment. Pharmacol Biochem Behav 75(3):607-18 (2003)). α3β4-containing nicotinic acetylcholine receptors are one of the main targets of dextromethorphan (Taylor C P et al. Pharmacology of dextromethorphan: Relevance to dextromethorphan/quinidine (Nuedexta®) clinical use. Pharmacol Ther 164:170-82 (2016)).

The prevalence of disinhibition is low in general population, in people with normal cognitive aging (0.9-1.6%) but is increased in subjects with MCI (3.1-4.7%) and dementia (12.7-17%) (Geda Y E et al. The Prevalence of Neuropsychiatric Symptoms in Mild Cognitive Impairment and Normal Cognitive Aging: A Population-Based Study. Arch Gen Psychiatry 65(10): 1193-1198 (2008); Lyketsos C G et al. Prevalence of neuropsychiatric symptoms in dementia and mild cognitive impairment: results from the cardiovascular health study. JAMA 288(12):1475-83 (2002); Zhao Q F et al. The prevalence of neuropsychiatric symptoms in Alzheimer's disease: Systematic review and meta-analysis. J Affect Disord 190:264-71 (2016)).

Alterations in the balance of functional activity within the 5-HT system underlie impulse control and preclinical studies suggest that the $5\text{-HT}_{2A}$ receptor regulates impulsive behavior, including both inherent and induced behavioral disinhibition (Anastasio N C et al. Serotonin (5-hydroxytryptamine) 5-HT(2A) receptor: association with inherent and cocaine-evoked behavioral disinhibition in rats. Behav Pharmacol 22(3):248-61 (2011)).

In humans, there are significant associations found between high levels of behavioral impulsivity and certain 5-HT2A polymorphisms such as the C/C genotype of rs6313 (Jakubczyk A et al. The CC genotype in HTR2A T102C polymorphism is associated with behavioral impulsivity in alcohol-dependent patients. J Psychiatr Res 46(1):44-9 (2012)). Humans with the A/A genotype of the HTR2A 1438A/G polymorphism have higher scores of maladaptive impulsivity (Tomson K et al. Effect of a human serotonin 5-HT2A receptor gene polymorphism on impulsivity: Dependence on cholesterol levels. J Affect Disord 206:23-30 (2016)). From a neuroanatomical perspective, neocortex is known to be rich in $5\text{-HT}_{2A}$ receptors and behavioral disinhibition in neurodegenerative diseases such as behavioral variant frontotemporal dementia is correlated with the cortical thickness of the right parahippocampal gyrus, right orbitofrontal cortex and right insula (Santillo A F et al. Grey and White Matter Clinico-Anatomical Correlates of Disinhibition in Neurodegenerative Disease. PLoS One 11(10): e0164122 (2016)).

Combination of dextromethorphan and quinidine has positive therapeutic effects in patients with pseudobulbar affect (PBA), (Pioro E P. Review of Dextromethorphan 20 mg/Quinidine 10 mg (NUEDEXTA®) for Pseudobulbar Affect. Neurol Ther 17; 3(1):15-28 (2014)). PBA may occur in association with a variety of neurological diseases such as amyotrophic lateral sclerosis, extrapyramidal and cerebellar disorders, multiple sclerosis, traumatic brain injury, Alzheimer's disease, stroke, and brain tumors. PBA is a disinhibition syndrome, in which pathways involving serotonin and glutamate are disrupted (Ahmed A, Simmons Z. Pseudobulbar affect: prevalence and management. Ther Clin Risk Manag 9:483-9 (2013)). Meta-analysis of the randomized controlled studies of another nonselective NMDA receptor channel blocker, memantine, in patients with Alzheimer's disease indicated that memantine induces significant improvement in disinhibition (Kishi T et al. The effects of memantine on behavioral disturbances in patients with Alzheimer's disease: a meta-analysis. Neuropsychiatr Dis Treatment 13: 1909-1928 (2017)).

The prevalence of irritability/lability is low in general population, in people with normal cognitive aging (4.6-7.6%) but is increased in subjects with MCI (14.7-19.4%) and dementia (27-36%) (Geda Y E et al. The Prevalence of Neuropsychiatric Symptoms in Mild Cognitive Impairment and Normal Cognitive Aging: A Population-Based Study. Arch Gen Psychiatry 65(10): 1193-1198 (2008); Lyketsos C G et al. Prevalence of neuropsychiatric symptoms in dementia and mild cognitive impairment: results from the cardiovascular health study. JAMA 288(12):1475-83 (2002); Zhao Q F et al. The prevalence of neuropsychiatric symptoms in Alzheimer's disease: Systematic review and meta-analysis. J Affect Disord 190:264-71 (2016)).

Animal and human functional magnetic resonance studies have pointed to a specific involvement of the $5\text{-HT}_{2A}$ receptor in the prefrontal cortical (PFC) feedback regulatory projection onto the amygdala. As this receptor is highly expressed in the prefrontal cortex areas, it affects inhibitory control of emotion-based and emotion-controlled actions, such as various impulse-related behaviors (Aznar S, Klein A B. Regulating prefrontal cortex activation: an emerging role for the $5\text{-HT}_2\text{A}$ serotonin receptor in the modulation of emotion-based actions? Mol Neurobiol 48(3):841-53 (2013)).

Combination of dextromethorphan and quinidine has positive therapeutic effects in patients with pseudobulbar affect that is characterized by emotional lability, uncontrolled crying or laughing which may be disproportionate or inappropriate to the social context (Pioro E P. Review of Dextromethorphan 20 mg/Quinidine 10 mg (NUEDEXTA®) for Pseudobulbar Affect. Neurol Ther 17; 3(1): 15-28 (2014)). In patients with AD, treatment with another nonselective NMDA receptor channel blocker, memantine, significantly decreases the scores of NPI item for irritability/lability (Ishikawa I et al. The effect of memantine on sleep architecture and psychiatric symptoms in patients with Alzheimer's disease. Acta Neuropsychiatr 28(3):157-64 (2016)). Meta-analysis of the randomized controlled studies of memantine in patients with Alzheimer's disease indicated that memantine was superior to control in irritability/lability (Kishi T et al. The effects of memantine on behavioral disturbances in patients with Alzheimer's disease: a meta-analysis. Neuropsychiatr Dis Treatment 13: 1909-1928 (2017)).

The prevalence of aberrant motor activity is low in general population, in people with normal cognitive aging (0.4-0.6%) but is increased in subjects with MCI (1.3-3.8%) and dementia (16-32%) (Geda Y E et al. The Prevalence of Neuropsychiatric Symptoms in Mild Cognitive Impairment and Normal Cognitive Aging: A Population-Based Study. Arch Gen Psychiatry 65(10): 1193-1198 (2008); Lyketsos C G et al. Prevalence of neuropsychiatric symptoms in dementia and mild cognitive impairment: results from the cardiovascular health study. JAMA 288(12):1475-83 (2002); Zhao Q F et al. The prevalence of neuropsychiatric symptoms in Alzheimer's disease: Systematic review and meta-analysis. J Affect Disord 190:264-71 (2016)).

Aberrant motor behavior in AD is found to be significantly associated with 5-HT2A receptor polymorphism such as T102C (Lam L C et al. 5-HT2A T102C receptor polymorphism and neuropsychiatric symptoms in Alzheimer's disease. Int J Geriatr Psychiatry 19(6):523-6 (2004); Pritchard A L et al. Role of 5HT 2A and 5HT 2C polymorphisms in behavioural and psychological symptoms of Alzheimer's disease. Neurobiol Aging 29(3):341-7 (2008)).

Aberrant motor behavior in various neurological disease state such as Parkinson's disease are due to abnormal plasticity processes in basal ganglia that may be expressed as behavioral sensitization that is sensitive to glutamate/NMDA receptor blockade (Chase T N et al. Striatal glutamatergic mechanisms and extrapyramidal movement disorders. Neurotox Res 5(1-2):139-46 (2003)) and antagonism at α3β4-containing receptors (Maisonneuve I M, Glick S D. Anti-addictive actions of an iboga alkaloid congener: a novel mechanism for a novel treatment. Pharmacol Biochem Behav 75(3):607-18 (2003)), two of the receptor targets of dextromethorphan (Taylor C P et al. Pharmacology of dextromethorphan: Relevance to dextromethorphan/quinidine (Nuedexta®) clinical use. Pharmacol Ther 164:170-82 (2016)).

The prevalence of night-time behavioral disturbances is moderate in general population, in people with normal cognitive aging (10.9%) but is increased in subjects with MCI (13.8-18.3%) and dementia (27.4-39%) (Geda Y E et al. The Prevalence of Neuropsychiatric Symptoms in Mild Cognitive Impairment and Normal Cognitive Aging: A Population-Based Study. Arch Gen Psychiatry 65(10): 1193-1198 (2008); Lyketsos C G et al. Prevalence of neuropsychiatric symptoms in dementia and mild cognitive impairment: results from the cardiovascular health study. JAMA 288(12):1475-83 (2002); Zhao Q F et al. The prevalence of neuropsychiatric symptoms in Alzheimer's disease: Systematic review and meta-analysis. J Affect Disord 190:264-71 (2016)).

$5-HT_{2A}$ receptors play a major role in regulation of sleep (Vanover K E, Davis R E. Role of 5-HT2A receptor antagonists in the treatment of insomnia. Nat Sci Sleep 2:139-50 (2010)). In a clinical trial assessing safety and efficacy of 5-HT2A receptor inverse agonist pimavanserin in patients with moderate to severe Parkinson's disease, participants reported improvements on night-time sleep and daytime wakefulness for pimavanserin compared with placebo (Cummings J et al. Pimavanserin for patients with Parkinson's disease psychosis: a randomised, placebo-controlled phase 3 trial. Lancet 383: 533-40 (2014)). Another 5-HT2A receptor inverse agonist, eplivanserin, has demonstrated clinical efficacy in patients with insomnia (European Medicines Agency. Withdrawal Assessment Report for Sliwens (Eplivanserin), Mar. 18, 2010, London. EMA/CHMP/90435/2010).

Meta-analysis of the randomized controlled studies of another nonselective NMDA receptor channel blocker, memantine, in patients with Alzheimer's disease indicated that memantine induces significant improvement in night-time disturbance/diurnal rhythm disturbances (Kishi T et al. The effects of memantine on behavioral disturbances in patients with Alzheimer's disease: a meta-analysis. Neuropsychiatr Dis Treatment 13: 1909-1928 (2017)). In patients with AD, memantine was effective in reducing fragmented sleep and polysomnography revealed longer total sleep, increases in sleep efficiency and time spent in stage II, and decreases in nocturnal awakening, the periodic limb movement index, and time spent in stage I (Ishikawa I et al. The effect of memantine on sleep architecture and psychiatric symptoms in patients with Alzheimer's disease. Acta Neuropsychiatr 28(3):157-64 (2016)).

The prevalence of appetite and eating abnormalities is low in general population, in people with normal cognitive aging (5.3%) but is increased in subjects with MCI (10.4-10.7%) and dementia (19.6-34%) (Geda Y E et al. The Prevalence of Neuropsychiatric Symptoms in Mild Cognitive Impairment and Normal Cognitive Aging: A Population-Based Study. Arch Gen Psychiatry 65(10): 1193-1198 (2008); Lyketsos C G et al. Prevalence of neuropsychiatric symptoms in dementia and mild cognitive impairment: results from the cardiovascular health study. JAMA 288(12):1475-83 (2002); Zhao Q F et al. The prevalence of neuropsychiatric symptoms in Alzheimer's disease: Systematic review and meta-analysis. J Affect Disord 190:264-71(2016)).

Serotonin plays a major role in emergence and maintenance of various types of eating disorders (Steiger H. Eating disorders and the serotonin connection: state, trait and developmental effects. J Psychiatry Neurosci 29(1):20-9 (2004)). The gene encoding 5-HT2A receptor (HTR2A) has been implicated as a functional candidate in many neuropsychiatric phenotypes including eating disorders (Norton N, Owen M J. HTR2A: association and expression studies in neuropsychiatric genetics. Ann Med 37(2):121-9 (2005)). Eating behavior and appetite are also modulated by one of the receptor target's of dextromethorphan, serotonin transporter, that is affected in patients with eating disorders (Spies M et al. The serotonin transporter in psychiatric disorders: insights from PET imaging. Lancet Psychiatry 2(8):743-55 (2015)).

Thus, current evidence suggests that pathophysiology of neurodegenerative diseases such as Alzheimer's disease is complex, involves multiple neuroanatomic substrates, neurochemical and neuropharmacological mechanism resulting in the following: i) one Therapeutic Mode of Action (TMA) may be used to treat more than one clinically diagnosable BPSD item (e.g. an NPI symptom or symptom cluster); ii) one TMA may be used to treat symptoms of two or more clinically distinct neurodegenerative diseases (e.g. AD, PD, DLB, FTLD, etc.) as illustrated by the emerging efficacy profile of Nuplazid®; iii) a single TMA is unlikely to ever cover the full spectrum of BPSD symptoms; iv) a single TMA may not produce a maximally possible therapeutic benefit against even a single BPSD symptom or symptom cluster.

Thus, in contrast to the limited clinical efficacy exerted by a single-MTA therapy with pimavanserin (Nuplazid®; Ballard C et al. Evaluation of the safety, tolerability, and efficacy of pimavanserin versus placebo in patients with Alzheimer's disease psychosis: a phase 2, randomised, placebo-controlled, double-blind study. Lancet Neurology (2018) 17: 213-22), combination therapy comprising several MTAs represented by compounds of Formula I and compounds of Formula II delivers both a broader and stronger efficacy profile.

An embodiment is a method of treating behavioral and psychological symptoms of dementia in a patient in need thereof comprising the step of administering a pharmaceutical composition comprising a compound of Formula II (DEX) and one or more agents selected from the group comprising 5-HT2A receptor antagonist, 5-HT2A receptor inverse agonist, and CYP2D6 inhibitor. In another embodiment, the agent is a Dual Agent (DA) having properties of both 5-HT2A receptor antagonist and CYP2D6 inhibitor. In another embodiment, the agent is a DA having properties of both 5-HT2A receptor inverse agonist and CYP2D6 inhibitor. In another embodiment, the DA is a compound of Formula I.

DEX is an agonist of the 02 receptor, an N-methyl-D-aspartate (NMDA) antagonist, and an α3β4 nicotinic receptor antagonist. Uptake of norepinephrine and serotonin are also inhibited. Several neuropsychiatric diseases and syndromes such as Alzheimer's disease and behavioral and psychological symptoms of dementia involve dis-regulation of glutamatergic, cholinergic, serotoninergic and norepinephrinergic neurotransmitter systems. Accordingly, In another embodiment, the composition comprises an NMDA receptor antagonist such as ketamine, methadone, memantine, amantadine, dextropropoxyphene, ketobemidone and dextromethorphan (Jamero et al., The Emerging Role of NMDA Antagonists in Pain Management, US Pharm. 36(5): HS4-HS8 (2011); Sang, NMDA-receptor antagonists in neuropathic pain: experimental methods to clinical trials, J Pain Symptom Manage. 19 (1 Suppl) S21-5 (2000); incorporated in entirety herein by reference). In another embodiment, the composition is a combination of a compound of Formula I, and ketamine, methadone, memantine, amantadine, dextropropoxyphene, ketobemidone, or dextromethorphan. The compound of Formula I forms the combination as mixture, complex, conjugate, compound with covalent bond, or a salt.

In another embodiment, the pharmaceutical composition comprises a compound of formula I and a compound of formula II (exemplified by SARPODEX™, DERADEX™, or DERAPHAN™). Another embodiment is a method of treatment of a patient in need thereof comprising the step of administering a pharmaceutical composition comprising comprises SARPODEX™, DERADEX™, or DERAPHAN™.

Psychological symptoms of dementia involve disregulation of glutamatergic, cholinergic, serotoninergic and norepinephrinergic neurotransmitter systems. Therefore, an embodiment is a method of treating behavioral and psychological symptoms of dementia. Another embodiment is a treatment of a person in need thereof comprising administering a composition comprising a compound of Formula I and a compound of Formula II to improve EEG abnormalities, behavior, cognition, and reduce seizures, as well as improve breathing abnormalities, motor capabilities, bone density, and GI dysfunction. Another embodiment is the treatment of a person in need thereof comprising administering a composition comprising DERATINE™, SARPOTINE™, SARPODEX™, DERADEX™, or DERAPHAN™ to improve EEG abnormalities, behavior, cognition, and reduce seizures, as well as improve breathing abnormalities, motor capabilities, bone density, and GI dysfunction. Another embodiment is a treatment of a person in need thereof comprising administering a composition comprising DERATINE™, SARPOTINE™, SARPODEX™, DERADEX™, or DERAPHAN™ in the treatment of other diseases and conditions, including involuntary emotional expression disorder (IEED) or pseudobulbar affect (PBA), neurodegenerative diseases, neuropathic pain, and brain injuries.

Another embodiment is a composition comprising a compound of DERATINE™, SARPOTINE™, SARPODEX™, DERADEX™, or DERAPHAN™ alone or in combination with other drugs such as analgesics (e.g. acetaminophen), antihistamines (e.g. chlorpheniramine), decongestants (e.g., pseudoephedrine) and/or expectorants (e.g., guaifenesin).

Dextromethorphan is metabolized into active metabolites in the liver starting with O- and N-demethylation to form primary metabolites DO and 3-methoxy-morphinan are further N- and O-demethylated respectively to 3-hydroxy-morphinan. A major metabolic catalyst is the cytochrome P450 enzyme 2D6 (CYP2D6), which is responsible for the O-demethylation reactions of dextromethorphan and 3-methoxymorphinan. N-demethylation of dextromethorphan and DO are catalyzed by enzymes in the related CYP3A family. Conjugates of DO and 3-hydroxymorphinan can be detected in human plasma and urine within hours of its ingestion. DO is a substance most notable for its psychoactive effects.

SGL is a 5-HT2A receptor inverse agonist and CYP2D6 inhibitor. SGL inhibits responses to 5-HT mediated by 5-HT2A receptors such as platelet aggregation, vasoconstriction and vascular smooth muscle proliferation. SGL (MCI-9042) was shown to have the same affinity as ritanserin for 5-HT2A receptors (Nishio et al., Binding affinity of a compound of formula I or sarpogrelate, a new antiplatelet agent, and its metabolite for serotonin receptor subtypes. *Arch Int Pharmacodyn Ther.* 331(2):189-202 (1996 March-April); incorporated by reference in entirety). The blockade of 5-HT2A receptors can inhibit thrombus formation, suppresses platelet aggregation and inhibits vascular smooth muscle cell proliferation (Pertz et al., In-vitro pharmacology of a compound of Formula I and the enantiomers of its major metabolite: 5-HT2A receptor specificity, stereoselectivity and modulation of ritanserin-induced depression of 5-HT contractions in rat tail artery. *J Pharm Pharmacol.* 47(4): 310-6 (1995 April); incorporated by reference in entirety). Accordingly, an embodiment is a method of treatment of a patient in need thereof comprising administering a composition comprising a compound of Formula I and a compound of Formula II, or DERATINE™, SARPOTINE™, SARPODEX™, DERADEX™, or DERAPHAN™.

Another embodiment is the method of treatment wherein the patient is suffering from a disease or disorder comprising peripheral arterial disease, e.g., Raynaud's Disease and claudicatio intermittens; pulmonary hypertension (Saini et al., 2004; incorporated by reference in entirety), angina pectoris (Kinugawa et al., 2002; incorporated by reference in entirety), and/or diabetes mellitus (Pietraszek et al., 1993; Ogawa et al., 1999; incorporated by reference in entirety). In another embodiment, the method of treatment of a patient after coronary stenting comprising a compound of Formula I, to and is useful in restenosis (Doggrell, sarpogrelate: cardiovascular and renal clinical potential, Expert Opinion on Investigational Drugs, Volume 13, Issue 7 (2004); incorporated by reference in entirety).

DO is a substance most notable for its psychoactive effects that likely arise from blockade of NMDA receptors. DO has a substantially higher affinity for NMDA receptors compared to that of DEX. Adverse psychoactive effects of DEX have been associated with its metabolism to DO (Taylor et al., Pharmacology of dextromethorphan: Relevance to dextromethorphan/quinidine (Nuedexta®) clinical use. *Pharmacol Ther.* 164:170-82 (2016 August); incorporated by reference in its entirety). Therefore, another embodiment is a method of reducing adverse effects of DEX during treatment of a patient in need thereof comprising the step of administering a pharmaceutical composition comprising DEX and one or more agents selected from the group comprising 5-HT2A receptor antagonist/inverse agonist, and CYP2D6 inhibitor. In another embodiment, the agent is an agent having properties of both 5-HT2A receptor antagonist/inverse agonist and CYP2D6 inhibitor. In another embodiment, the agent is an agent having properties of both 5-HT2A receptor inverse agonist and CYP2D6 inhibitor. In another embodiment, the agent is a compound of Formula I and a compound of Formula II, or DERATINE™, SARPOTINE™, SARPODEX™, DERADEX™, or DERAPHAN™.

Another embodiment is a composition comprising (6)-1-{2-[2-(3-methoxyphenil) ethyl]-phenoxy}-3-(dimethylamino)-2-propanol (M–1) (Nagatomo et al., 2004; Saini et al., 2004; incorporated by reference in entirety), a 5-HT2A receptor inverse agonist and CYP2D6 inhibitor.

The genetically polymorphic cytochrome CYP2D6 has been implicated in the metabolism of many antipsychotic agents, including thioridazine, perphenazine, chlorpromazine, fluphenazine, haloperidol, zuclopenthixol, risperidone, and sertindole (Michalets, 1998). This enzyme is also important in the metabolism of other drugs that are commonly prescribed to patients with psychiatric disorders, e.g., tricyclic antidepressants (nortriptyline, desipramine, amitriptyline, imipramine, and clomipramine) and selective serotonin reuptake inhibitors, including fluoxetine and paroxetine (Taylor and Lader, 1996; Sproule et al., 1997; incorporated by reference in entirety). Drugs that inhibit these enzymes would be expected to cause increases in the plasma concentration of co-administered antipsychotic drugs (Goff, 1993; Ereshefsky, 1996; Michalets, 1998; incorporated by reference in entirety). These increases may, in turn, lead to the development or aggravation of antipsychotics-induced side effects including cardiac toxicity, anticholinergic side effects, or orthostatic hypotension (Ereshefsky, 1996; Desta et al., 1999; incorporated by reference in entirety).

Many antipsychotic drugs inhibited CYP2D6-catalyzed DEX O-demethylation. Among the antipsychotic drugs tested, thioridazine and perphenazine were the most potent inhibitors and decreased the DO formation rate to 26.5 and 19.7% of control activity at 10 microM, and 11.4 and 10.7% of control activity at 25 micro M, respectively. The inhibitory potency of these drugs on DEX O-demethylation was comparable to the inhibitory effect of 10 to 25 microM quinidine. The estimated mean IC50 values for thioridazine and perphenazine were 2.7±0.5 and 1.5±0.3 micro M, respectively. The IC50 of quinidine, a potent CYP2D6 inhibitor, was estimated to be 0.52±0.2 micro M under these conditions. The estimated IC50s of chlorpromazine, fluphenazine, and haloperidol were 9.7, 16.3, and 14.4 micro M, respectively. Cisthiothixene, clozapine, and risperidone exhibited weaker inhibition than the other drugs tested, with mean $IC_{50}$s estimated to be 136.6, 92.2, and 39.1 micro M, respectively (Shin et al., Effect Of Antipsychotic Drugs on Human Liver Cytochrome P-450 (Cyp) Isoforms in Vitro: Preferential Inhibition of CYP2D6, Drug Metabolism And Disposition, Vol. 27, No. 9 (1999); incorporated by reference in its entirety).

In one embodiment, the pharmaceutical composition of the invention comprise one or more of the CYP2D6 inhibitors such as, but are not limited to, Ajmaline, Amiodarone, Amitriptyline, Aprindine, Azelastine, Celecoxib, Chlorpheniramine, Chlorpromazine, Diphenhydramine, Doxorubicin, Fluoxetine, Fluphenazine, Fluvastatin, Fluvoxamine, Haloperidol, Imipramine, Indinavir, Lasoprazole, Levomepromazine, Lopinavir, Loratadine, Mequitazine, Methadone, Metoclopramide, Mibefradil, Moclobemide, Nelfinavir, Nevirapine, Nicardipine, Norfluoxetine, Paroxetine, Perphenazine, Pimozide, Terfenadine, Thioridazine, Cimetidine, Quinidine, Cisapride, Citalopram, Clomipramine, Clozapine, Cocaine, Desipramine, Ranitidine, Risperidone, Ritonavir, Saquinavir, Sertraline, Terbinafine, Ticlopidine, Trifluperidol, Venlafaxine, and Yohimbine.

In one embodiment, the invention is a combination of a 5HT2A receptor antagonist and a CYP2D6 inhibitor providing a therapeutic advantage of the simultaneous 5HT2A receptor antagonism and 2D6 inhibition. In another embodiment, the invention is a combination of a 5HT2A receptor inverse agonist and a CYP2D6 inhibitor providing a therapeutic advantage of the simultaneous 5HT2A receptor inverse agonism and 2D6 inhibition. A compound of Formula I and a compound of Formula II; or DERATINE™, SARPOTINE™, SARPODEX™, DERADEX™, or DERAPHAN™ provides a unique therapeutic advantage by combining both CYP2D6 inhibition and 5HT2A receptor inverse agonism to improve the magnitude of the therapeutic response to DEX. Thus, Formula I and a compound of Formula II; or DERATINE™, SARPOTINE™, SARPODEX™, DERADEX™, or DERAPHAN™ avoids potential health risks associated with the concomitant use of an anti-arrhythmic drug quinidine with DEX. Accordingly, an embodiment is a composition comprising Formula I and a compound of Formula II; or DERATINE™, SARPOTINE™, SARPODEX™, DERADEX™, or DERAPHAN™.

Some embodiments include a method of decreasing the number of doses and/or total daily dose of dextromethorphan, a metabolite, a derivative or a prodrug thereof (DEX) that can be administered while increasing efficacy and safeguarding tolerability and safety, comprising orally administering an effective amount of a compound of Formula I and a compound of Formula II; or DERATINE™, SARPOTINE™, SARPODEX™, DERADEX™, or DERAPHAN™.

Some embodiments include a method of reducing an adverse event associated with treatment comprising co-administering a compound of Formula I and a compound of Formula II; or, DERATINE™, SARPOTINE™, SARPODEX™, DERADEX™, or DERAPHAN™ to a subject in need of DEX and/or a compound of Formula I, DERA- TINE™, SARPOTINE™, SARPODEX™, DERADEX™, or DERAPHAN™ treatment, wherein the subject is at risk of experiencing the adverse event as a result being treated with DEX and/or a compound of Formula I, DERATINE™, SARPOTINE™, SARPODEX™, DERADEX™, or DERAPHAN™.

Some embodiments include a method of decreasing DO plasma levels comprising co-administering a compound of Formula I and a compound of Formula II; or DERATINE™, SARPOTINE™, SARPODEX™, DERADEX™, or DERAPHAN™ to a subject in need of treatment with DEX, wherein the compound of Formula I and a compound of Formula II; or DERATINE™, SARPOTINE™, SARPODEX™, DERADEX™, or DERAPHAN™ is administered on the first day of at least two days of treatment with DEX, wherein a decrease in the DO plasma level occurs on the first day that a compound of Formula I and a compound of Formula II; or DERATINE™, SARPOTINE™, SARPODEX™, DERADEX™, or DERAPHAN™ are administered, as compared to the same amount of DEX administered without a compound of Formula I.

Another embodiment is a method of decreasing DO plasma levels comprising co-administering a compound of Formula I and a compound of Formula II; or DERATINE™, SARPOTINE™, SARPODEX™, DERADEX™, or DERAPHAN™, for at least eight consecutive days, to a subject in need of treatment with DEX, wherein, on the eighth day, the DO plasma level is lower than the DO plasma level that would have been achieved by administering the same amount of DEX administered without a compound of Formula I for eight consecutive days.

5-HT2A receptor antagonist/inverse agonists, such as a compound of Formula I and a compound of Formula II; or DERATINE™, SARPOTINE™, SARPODEX™, DERADEX™, or DERAPHAN™, can be used to improve the therapeutic properties of DEX, such as in the treatment of neurological disorders. A compound of Formula I and a compound of Formula II; or DERATINE™, SARPOTINE™, SARPODEX™, DERADEX™, or DERAPHAN™ regardless of stereochemistry, can be effective in inhibiting or reducing the metabolism of DEX in some subjects, accomplished by co-administering a compound of Formula I and a compound of Formula II; or DERATINE™, SARPOTINE™, SARPODEX™, DERADEX™, or DERAPHAN™.

Another embodiment is a method of treating a neurological disorder comprising administering a 5-HT2A receptor antagonist/inverse agonist and DEX to a subject in need thereof, wherein the subject is an extensive metabolizer of DEX.

Another embodiment is a method of treating a neurological disorder comprising administering a 5-HT2A receptor inverse agonist, antagonist, and DEX to a subject in need thereof, wherein the subject is an extensive metabolizer of DEX.

Another embodiment is a method of increasing DEX plasma levels in a subject in need of treatment with DEX, wherein the subject is an extensive metabolizer of DEX, comprising co-administering a compound of Formula I and a compound of Formula II; or DERATINE™, SARPOTINE™, SARPODEX™, DERADEX™, or DERAPHAN™ to the subject.

Another embodiment is a method of inhibiting the metabolism of DEX, comprising administering a compound of formula I, or a compound of Formula I and a compound of Formula II; or DERATINE™, SARPOTINE™, SARPODEX™, DERADEX™, or DERAPHAN™, to a subject, wherein the subject is an extensive metabolizer of DEX, and wherein DEX is present in the body of the subject at the same time as a compound of Formula I.

Another embodiment is a method of increasing the metabolic lifetime of DEX, comprising administering a compound of Formula I and a compound of Formula II; or DERATINE™, SARPOTINE™, SARPODEX™, DERADEX™, or DERAPHAN™ to a subject in need of treatment with DEX, wherein the subject is an extensive metabolizer of DEX, and wherein DEX is present in the body of the subject at the same time as a compound of Formula I.

Another embodiment is a method of correcting extensive metabolism of DEX, comprising administering a compound of Formula I and a compound of Formula II; or DERATINE™, SARPOTINE™, SARPODEX™, DERADEX™, or DERAPHAN™, to a subject in need thereof.

Another embodiment is a method of improving the antitussive properties of DEX comprising administering a compound of Formula I and a compound of Formula II; or DERATINE™, SARPOTINE™, SARPODEX™, DERADEX™, or DERAPHAN™ in conjunction with administration of DEX to a subject in need of treatment for a cough.

Another embodiment is a method of treating cough comprising administering a combination of a compound of Formula I and a compound of Formula II; or DERATINE™, SARPOTINE™, SARPODEX™, DERADEX™, or DERAPHAN™ to a subject in need thereof.

Another embodiment is a method of treating a neurological disorder comprising administering a compound of Formula I and a compound of Formula II; or DERATINE™, SARPOTINE™, SARPODEX™, DERADEX™, or DERAPHAN™ to a subject in need thereof, wherein the compound of Formula I and a compound of Formula II; or DERATINE™, SARPOTINE™, SARPODEX™, DERADEX™, or DERAPHAN™ are administered at least once a day for at least eight days.

Another embodiment is a method of treating a neurological disorder comprising administering about 5 mg/day to about 600 mg/day, about 5 mg/day to about 300 mg/day, about 5 mg/day to about 400 mg/day, about 5 mg/day to about 500 mg/day, about 5 mg/day to about 600 mg/day, about 5 mg/day to about 1,000 mg/day, about 50 mg/day to about 1000 mg/day, about 100 mg/day to about 1000 mg/day, about 150 mg/day to about 1000 mg/day, about 150 mg/day to about 5000 mg/day, about 150 mg/day to about 300 mg/day, or about 150 mg/day to about 100 mg/day, or an amount as required of a compound of Formula I and about 0.1 mg/day to about 1 mg/day, about 0.5 mg/day to about 15 mg/day, about 15 mg/day to about 60 mg/day, about 15 mg/day to about 120 mg/day, about 0.1 mg/day to about 200 mg/day, or an amount as required of DEX to a subject in need thereof.

Another embodiment is a method of increasing DEX plasma levels in a subject in need of treatment with DEX, wherein the subject is an extensive metabolizer of DEX, comprising co-administering a compound of Formula I with DEX to the subject.

Another embodiment is a method of inhibiting the metabolism of DEX, comprising administering a compound of Formula I, to a subject, wherein the subject is an extensive metabolizer of DEX, and wherein DEX is present in the body of the subject at the same time as a compound of Formula I.

Another embodiment is a method of increasing the metabolic lifetime of DEX, comprising administering a compound of formula I, to a subject in need of treatment with DEX, wherein the subject is an extensive metabolizer of DEX, and wherein DEX is present in the body of the subject at the same time as a compound of formula I.

Another embodiment is a method of increasing DEX plasma levels comprising co-administering a compound of formula I and DEX to a subject in need of treatment with DEX, wherein the compound of formula I is administered on the first day of at least two days of co-administration of a compound of formula I, with DEX, wherein an increase in the DEX plasma level occurs on the first day that a compound of formula I and DEX are co-administered, as compared to the same amount of DEX administered without a compound of formula I.

Another embodiment is a method of increasing DEX plasma levels comprising co-administering a compound of formula I and DEX for at least five consecutive days, to a subject in need of treatment with DEX, wherein, on the fifth day, the DEX plasma level is higher than the DEX plasma level that would have been achieved by administering the same amount of DEX administered without a compound of formula I, for five consecutive days.

Another embodiment is a method of increasing DEX plasma levels comprising co-administering a compound of formula I and DEX for at least six consecutive days, to a subject in need of treatment with DEX, wherein, on the sixth day, the DEX plasma level is higher than the DEX plasma level that would have been achieved by administering the same amount of DEX administered without a compound of formula I, for six consecutive days.

Another embodiment is a method of reducing a trough effect of DEX comprising, co-administering a compound of formula I, with DEX to a subject in need of treatment with DEX, wherein DEX has a plasma level 12 hours after co-administering a compound of formula I, with DEX that is at least twice the plasma level that would be achieved by administering the same amount of DEX without a compound of formula I.

Another embodiment is a method of reducing a trough effect of DEX comprising, co-administering a compound of formula I, with DEX to a subject in need of treatment with DEX, wherein DEX has a plasma level 12 hours after co-administering a compound of formula I, with DEX that is at least twice the plasma level that would be achieved by administering the same amount of DEX without a compound of Formula I.

Another embodiment is a method of reducing a trough effect of DEX comprising, co-administering a compound of formula I, with DEX to a subject in need of treatment with DEX, wherein DEX has a plasma level 12 hours after co-administering a compound of formula I, with DEX that is at least twice the plasma level that would be achieved by administering the same amount of DEX without a compound of Formula I.

Another embodiment is a method of reducing an adverse event or other unwanted consequences such as addiction associated with treatment by DEX, comprising co-administering a compound of Formula I, and DEX to a subject in need of DEX treatment, wherein the subject is at risk of experiencing the adverse event as a result of being treated with DEX.

Another embodiment is a method of reducing an adverse event associated with treatment by a compound of formula I, comprising co-administering DEX and a compound of formula I, to a subject in need of a compound of Formula I, treatment, wherein the subject is at risk of experiencing the adverse event as a result of being treated with a compound of formula I.

Another embodiment is a method of improving antitussive properties of DEX comprising administering a compound of formula I, in conjunction with administration of DEX to a subject in need of treatment for cough.

Another embodiment is a method of treating cough comprising administering a combination of a compound of formula I and DEX to a subject in need thereof.

Another embodiment is a method of treating a neurological disorder comprising administering a compound of formula I and DEX to a subject in need thereof, wherein the compound of formula I and DEX are administered at least once a day for at least 8 days.

Another embodiment is a method of treating a neurological disorder comprising administering a composition comprising DEX, Formula I, DERATINE™, SARPOTINE™, SARPODEX™, DERADEX™, or DERAPHAN™ to a subject in need thereof, wherein the DEX, Formula I, DERATINE™, SARPOTINE™, SARPODEX™, DERADEX™, or DERAPHAN™ is administered at least once a day for at least 8 days.

Another embodiment is a method of treating a neurological disorder comprising administering a composition comprising DEX, Formula I, DERATINE™, SARPOTINE™, SARPODEX™, DERADEX™, or DERAPHAN™ to a subject in need thereof, wherein the compound of formula I and DEX are administered at least once a day for at least 8 days.

Another embodiment is an oral sustained release delivery system for DEX, comprising a composition comprising DEX, Formula I, DERATINE™, SARPOTINE™, SARPODEX™, DERADEX™, or DERAPHAN™, and a vehicle.

Another embodiment is a method of decreasing the number of doses of DEX that can be administered without loss of efficacy, comprising orally administering an effective amount of a composition comprising DEX and Formula I, or DERATINE™, SARPOTINE™, SARPODEX™, DERADEX™, or DERAPHAN™ to a subject in need of treatment with DEX.

Another embodiment is a pharmaceutical composition, dosage form, or medicament comprising a therapeutically effective amount of DEX, a therapeutically effective amount of a compound of formula I and a pharmaceutically acceptable excipient.

In an aspect, provided is a method of increasing the metabolic lifetime of DEX, comprising administering 5-HT2A receptor antagonist/inverse agonist to a subject in need of treatment with DEX, wherein 5-HT2A receptor antagonist/inverse agonist is an inhibitor of a CYP2D6 enzyme and wherein DEX is present in the body of the subject at the same time as the inhibitor of a CYP2D6. In another embodiment, the composition comprises DEX and Formula I, or DERATINE™, SARPOTINE™, SARPODEX™, DERADEX™, or DERAPHAN™.

In another aspect, provided is a method of preventing adverse events associated with treatment by DEX, comprising co-administering 5-HT2A receptor antagonist/inverse agonist or such as a compound of formula I, to a subject in need of treatment with DEX, wherein the subject is at risk of experiencing the adverse event as a result of being treated with DEX.

In another aspect, provided is a method for using 5HT2A receptor antagonists such as a compound of formula I, to improve the therapeutic properties of DEX in the treatment of neurological disorders.

In another aspect, provided is a method of treating a disorder or disease comprising administering a composition comprising 5HT2A receptor antagonist and DEX to a subject in need thereof. In another embodiment, the composition comprises DEX and Formula I, or DERATINE™, SARPOTINE™, SARPODEX™, DERADEX™, or DERAPHAN™.

In another aspect, provided is a method for selecting a 5-HT2A receptor antagonist/inverse agonist for the use in combination with DEX in a subject in need thereof.

Another embodiment, NMDA receptor antagonists reduce the physical aspects of the expression of morphine dependence as measured by naloxone-precipitated withdrawal (Bristow et al., Competitive and glycine: NMDA receptor antagonists attenuate withdrawal-induced behaviors and increased hippocampal acetylcholine efflux in morphine-dependent rats. *Neuropharmacology.* 36: 241-250 (1997); Popik et al., Inhibition of reinforcing effects of morphine and motivational aspects of naloxone-precipitated opioid withdrawal by N-methyl-D-aspartate receptor antagonist, memantine. *J. Pharmacol. Exp. Ther.* 280: 854-865 (1997); Popik et al., Inhibition of reinforcing effects of morphine and naloxone-precipitated opioid withdrawal by novel glycine site and uncompetitive NMDA receptor antagonists. *Neuropharmacology.* 37: 1033-1042 (1998); incorporated by reference in its entirety) and may attenuate not only the physical but also affective and motivational components of abstinence states, as well as craving (Cornish et al. A randomized, double-blind, placebo-controlled safety study of high-dose dextromethorphan in methadone-maintained male inpatients. *Drug & Alcohol Dependence.* 67(2): 177-83(2002); incorporated by reference in entirety). By reducing withdrawal symptoms, such medications should be beneficial for the patients during the acute detoxification phase of treatment for opioid dependence (Cornish et al., A randomized, double-blind, placebo-controlled safety study of high-dose dextromethorphan in methadone-maintained male inpatients. *Drug & Alcohol Dependence.* 67(2): 177-83 (2002); incorporated by reference in entirety).

Accordingly, an embodiment is a method of treating a subject in need of treatment for disorders or diseases associated with addiction and substance abuse comprising administration of DEX and Formula I, or DERATINE™, SARPOTINE™, SARPODEX™, DERADEX™, or DERAPHAN™.

Chronic exposure to morphine results in a number of biochemical adaptations of the glutamatergic receptor system in the limbic system (Fitzgerald et al., Drugs of abuse and stress increase the expression of GluR1 and NMDAR1 glutamate receptor subunits in the rat ventral tegmental area: common adaptations among cross-sensitizing agents. *J. Neurosci.* 16: 274-282 (1996); incorporated by reference in entirety). Excitatory amino acids are involved in the mediation of many neurochemical and behavioral effects resulting from chronic exposure to abusing drugs, some of which can be prevented or reversed using glutamatergic antagonists (Inturrisi, Preclinical evidence for a role of glutamatergic systems in opioid tolerance and dependence. *Semin. Neurosci.* 9: 110-119 (1997); incorporated by reference in entirety). Continued self-administration of abusive drugs, including opioid, results in an overstimulation of dopamine in the brain reward centers and an increased release of excitatory amino acids including glutamate leading to the development of tolerance and dependence which could be blocked by glutamate antagonists (Herman et al., Clinical medication development for opiate addiction: focus on nonopioids and opioid antagonists for the amelioration of opiate withdrawal symptoms and relapse prevention. *Semin. Neurosci.* 9: 158-172 (1997); incorporated by reference in entirety). Accordingly, an embodiment is a method of treating a subject in need of treatment for disorders or diseases associated with addiction and substance abuse resulting from opioid tolerance and dependence by amelioration of opiate withdrawal symptoms and relapse prevention comprising administration of DEX and Formula I, or DERATINE™, SARPOTINE™, SARPODEX™, DERADEX™, or DERAPHAN™.

DEX affords neuroprotection on dopamine neurons in several inflammation-based animal Parkinson's disease models (Li et al., Protective effect of dextromethorphan against endotoxic shock in mice. *Biochemical Pharmacology.* 69(2): 233-40 (2005); Liu et al., Dextromethorphan protects dopaminergic neurons against inflammation-mediated degeneration through inhibition of microglial activation. *Journal of Pharmacology & Experimental Therapeutics.* 305(1):212-8 (2003); Zhang et al., Neuroprotective effect of dextromethorphan in the MPTP Parkinson's disease model: role of NADPH oxidase. *FASEB Journal.* 18(3): 589-91 (2004); Zhang et al., 3-hydroxymorphinan is neurotrophic to dopaminergic neurons and is also neuroprotective against LPS-induced neurotoxicity. *FASEB Journal.* 19(3): 395-7 (2005); incorporated by reference in entirety). 1-10 micro M DEX protected dopamine neurons against lipopolysaccharide (LPS)-induced reduction of dopamine uptake in rat primary mixed mesencephalic neuron-glia cultures. Morphologically, in LPS-treated cultures, besides the reduction of an abundance of dopamine neurons, the dendrites of the remaining dopamine neurons were significantly less elaborative than those in the controls. In cultures pretreated with DEX (10 micro M) before LPS stimulation, dopamine neurons were significantly more numerous and the dendrites less affected. Significant neuroprotection was observed in cultures with DEX added up to 60 minutes after the addition of LPS. Thus, DEX significantly protects monoamine neurons not only with pretreatment but also with post-treatment (Zhang et al., Neuroprotective effect of dextromethorphan in the MPTP Parkinson's disease model: role of NADPH oxidase. *FASEB Journal,* 18(3): 589-91 (2004); incorporated by reference in entirety). Animal studies using both LPS and MPTP PD models also show potent protective effect of DEX (Zhang et al., Neuroprotective effect of dextromethorphan in the MPTP Parkinson's disease model: role of NADPH oxidase. *FASEB Journal,* 18(3): 589-91 (2004); incorporated by reference in entirety). Accordingly, an embodiment is a method of treating a subject in need of a treatment for Parkinson's disease comprising administration of DEX and Formula I, or DERATINE™, SARPOTINE™, SARPODEX™, DERADEX™, or DERAPHAN™.

The neuroprotective effect of DEX is associated with the inhibition of microglia over-activation by inhibition of superoxide anion production from NADPH-oxidase, and this neuroprotective effect of DEX is not associated with its NMDA receptor antagonist property. There is A correlation was observed between the anti-inflammatory potency and neuroprotection of NMDA receptor antagonists, such as MK801, AP5, and memantine, suggesting that the dopamine neuroprotection provided by DEX in the inflammation-related neurodegenerative models is not mediated through the NMDA receptor. This conclusion is not in conflict with previous reports, indicating that NMDA receptor blockade is associated with the neuroprotective effects of DEX in the acute glutamate-induced excitotoxicity models. Accordingly, an embodiment is a method of treating a subject in need of treatment for a disorder or disease thereof comprising administration of DEX and Formula I, or DERATINE™, SARPOTINE™, SARPODEX™, DERADEX™, or DERAPHAN™ wherein the disorder or disease is an inflammation-related neurodegenerative disorder.

GC-dependent effects of morphine activate the hypothalamic-pituitary-adrenal (HPA) axis. The activation of the HPA axis increases the products of GC as potent immunomodulatory hormones (Freier et al., A mechanism of action for morphine-induced immunosuppression: corticosterone mediates morphine-induced suppression of natural killer cell activity. *J Pharmacol Exp Ther* 270(3): 1127-33 (1994); Mellon et al., Role of central opioid receptor subtypes in morphine-induced alterations in peripheral lymphocyte activity. *Brain Res* 789(1): 56-67 (1998); incorporated by reference in entirety). Accordingly, an embodiment is a method of treating a subject in need of treatment for a disorder or disease thereof comprising administration of DEX and Formula I, or DERATINE™, SARPOTINE™, SARPODEX™, DERADEX™, or DERAPHAN™ wherein the disorder or disease is opioid dependence. The dosage of up to about 500 mg/day DEX is suggested, including doses of 120, 240, and 480 mg/day of DEX for heroin addicts undergoing withdrawal. DEX at high doses caused mild elevations of heart rate, blood pressure, temperature, and plasma bromide (Cornish et al., A randomized, double-blind, placebo-controlled safety study of high-dose dextromethorphan in methadone-maintained male inpatients. *Drug & Alcohol Dependence*. 67(2): 177-83 (2002); incorporated by reference in entirety). Particularly among Han Chinese in Taiwan, DEX has been reported to have quite different "dextromethorphan metabolic enzyme CYP2D6" from that of Western population (Yeh et al., Analysis of pharmacokinetic parameters for assessment of dextromethorphan metabolic phenotypes. *J. Biomed. Sci.* 10: 552-564 (2003); incorporated by reference in entirety).

Significantly higher interleukin-6, interleukin-8, and TNF-alpha levels are manifested in bipolar disorder (BP) patients during manic and depressive episodes than normal controls (Kim et al., Alexithymia and Stress Response Patterns among Patients with Depressive Disorders in Korea. *Psychiatry Investig.* 6(1): 13-8 (2009); O'Brien et al., Cytokine profiles in bipolar affective disorder: focus on acutely ill patients. *J Affect Disord.* 90(2-3): 263-7 (2006); Brietzke et al., Comparison of cytokine levels in depressed, manic and euthymic patients with bipolar disorder. *J Affect Disord.* 116(3): 214-7 (2009); incorporated by reference in entirety).

In postmortem frontal cortex from BP patients, the significantly higher protein and mRNA levels of IL-1 beta receptor and neuroinflammatory markers inducible nitric oxide synthase (iNOS) and c-fos were found (Rao et al., Increased excitotoxicity and neuroinflammatory markers in postmortem frontal cortex from bipolar disorder patients. *Mol. Psychiatry.* 15(4): 384-92 (2010); incorporated by reference in entirety). Taken together, the imbalance of the immune system, subsequently leading to the neuronal inflammatory response, might be related to the progression of the brain atrophy and aggravated BP symptoms. BP treatment with immune-targeted therapies showed antidepressant effects. For example, open-label acetylsalicylic acid when added to fluoxetine led to increased remission rates in individuals with major depression who were previously non-responsive to fluoxetine monotherapy (Mendlewicz et al., Shortened onset of action of antidepressants in major depression using acetylsalicylic acid augmentation: a pilot open-label study. *Int. Clin. Psychopharmacol.* 21(4): 227-31 (2006); incorporated by reference in entirety).

Thus, using an anti-inflammatory agent combined with a mood stabilizer improves the treatment effect on BP. Mood stabilizers have been shown to activate interconnected intracellular signaling pathways that promote neurogenesis and synaptic plasticity. A reduction in brain volume in BP patients was found to be largely suppressed by chronic treatment with Valproate (VPA) resulting in neuroprotective effects, as VPA renders neurons less susceptible to a variety of insults (Chen et al., Valproate protects dopaminergic neurons in midbrain neuron/glia cultures by stimulating the release of neurotrophic factors from astrocytes. Mol Psychiatry. 11(12):1116-1125 (December 2006); incorporated by reference in entirety) and even stimulates neurogenesis in the adult rodent brain. VPA induces cytoprotective proteins like Bcl-2, glucose-regulated protein 78 (Grp78), brain-derived neurotrophic factor (BDNF) and heat shock protein 70. Moreover, VPA promotes neurite outgrowth, while VPA at therapeutic levels was reported to inhibit histone deacetylase (HDAC), an enzyme that catalyzes the removal of the acetyl group from lysine residues of histones, promoting local, neuronal BDNF biosynthesis. Accordingly, an embodiment is a method of treating a subject in need of treatment for a disorder or disease thereof comprising administration of DEX and a compound of Formula I, or DERATINE™, SARPOTINE™ SARPODEX™, DERADEX™, or DERAPHAN™, wherein the disorder or disease is BP.

Another embodiment is a method of reducing adverse events of DEX in a subject in need thereof comprising:
a. administering DEX; and
b. administering a compound of Formula I, to the subject.

Some embodiments include a method of treating neuropsychiatric disorders comprising administering a therapeutically effective amount of DEX and a therapeutically effective amount of a compound of formula I, to a person in need thereof.

Some embodiments include a method of enhancing the therapeutic properties of DEX in treating neuropsychiatric disorders, comprising co-administering DEX and a compound of formula I.

Some embodiments include a method of increasing DEX plasma levels in a subject that is an extensive metabolizer of DEX, comprising co-administering a 5-HT2A receptor antagonist/inverse agonist, such as a compound of formula I and DEX to the subject.

Some embodiments include a method of inhibiting the metabolism of DEX, comprising administering a 5-HT2A receptor antagonist/inverse agonist, such as a compound of formula I to a subject, wherein the subject is an extensive metabolizer of DEX, and wherein DEX is present in the body of the subject at the same time as the 5-HT2A receptor antagonist/inverse agonist.

Some embodiments include a method of increasing the metabolic lifetime of DEX, including increasing the elimination half-life ($T_{1/2}$) of DEX. These embodiments may comprise administering a 5-HT2A receptor antagonist/inverse agonist, such as a compound of formula I to a subject, wherein the subject is an extensive metabolizer of DEX, and wherein DEX is present in the body of the subject at the same time as the 5-HT2A receptor antagonist/inverse agonist.

Some embodiments include a method of correcting extensive metabolism of DEX, comprising administering a 5-HT2A receptor antagonist/inverse agonist, such as a compound of formula I to a subject in need thereof, such as a subject in need of treatment for pain.

Some embodiments include a method of improving the therapeutic properties of DEX in treating neuropsychiatric disorders comprising administering a 5-HT2A receptor antagonist/inverse agonist, such as a compound of formula I in conjunction with administration of DEX to a subject in need of treatment for a neuropsychiatric disorder.

Some embodiments include a method of treating neuropsychiatric disorders comprising administering a combination of a 5-HT2A receptor antagonist/inverse agonist, such as a compound of formula I and DEX to a subject in need thereof.

DEX is used as a cough suppressant. According to the FDA's DEX product labeling requirement under the OTC Monograph [21CFR341.74], DEX should be dosed 6 times a day (every 4 hours), 4 times a day (every 6 hours), or 3 times a day (every 8 hours).

DEX is rapidly metabolized in the human liver. This rapid hepatic metabolism may limit systemic drug exposure in individuals who are extensive metabolizers. Subjects can be: 1) extensive metabolizers of DEX—those who rapidly metabolize DEX; 2) poor metabolizers of DEX—those who only poorly metabolize DEX; or 3) intermediate metabolizers of DEX—those whose metabolism of DEX is somewhere between that of an extensive metabolizer and a poor metabolizer. Extensive metabolizers can also be ultra-rapid metabolizers. Extensive metabolizers of DEX are a significant portion of the human population. DEX can, for example, be metabolized to DO.

When given the same oral dose of DEX, plasma levels of DEX are significantly higher in poor metabolizers or intermediate metabolizers as compared to extensive metabolizers of DEX. The low plasma concentrations of DEX can limit its clinical utility as a single agent for extensive metabolizers, and possibly intermediate metabolizers, of DEX. Some antidepressants, such as a compound of Formula I inhibit the metabolism of DEX, and can thus improve its therapeutic efficacy. Similarly, antidepressants may allow DEX to be given less often, such as once a day instead of twice a day, once a day instead of three times a day, once a day instead of four times a day, twice a day instead of three times a day, or twice a day instead of four times a day, without loss of therapeutic efficacy.

Pain or other neuropsychiatric disorders may be treated by a method comprising administering a therapeutically effective amount of DEX and a therapeutically effective amount of a 5-HT2A receptor antagonist/inverse agonist, such as a compound of formula I to a person in need thereof.

Examples of neuropsychiatric disorders that may be treated, or that may be treated with increased efficacy, by a combination of DEX and a 5-HT2A receptor antagonist/inverse agonist a compound of formula I include, but are not limited to: affective disorders, psychiatric disorders, cerebral function disorders, movement disorders, dementias, traumatic brain injury, chronic traumatic encephalopathy, PTSD, motor neuron diseases, neurodegenerative diseases, seizure disorders, and headaches.

Affective disorders that may be treated by a combination of DEX and a 5-HT2A receptor antagonist/inverse agonist a compound of formula I include, but are not limited to, depression, major depression, treatment-resistant depression and treatment-resistant bipolar depression, BPs including cyclothymia, seasonal affective disorder, mania, anxiety disorders, attention deficit disorder (ADD), attention deficit disorder with hyperactivity (ADDH), and attention deficit/hyperactivity disorder (AD/HD), bipolar and manic conditions, obsessive-compulsive disorder, bulimia, anorexia, obesity or weight gain, narcolepsy, chronic fatigue syndrome, premenstrual syndrome, substance addiction or abuse, nicotine addiction, psycho-sexual dysfunction, pseudobulbar affect, and emotional lability.

Depression may be manifested by changes in mood, feelings of intense sadness, despair, mental slowing, sleep disturbances, loss of concentration, pessimistic worry, agitation, and self-depreciation. Physical symptoms of depression may include insomnia, anorexia, weight loss, decreased energy and libido, apathy, and abnormal hormonal circadian rhythms.

Psychiatric disorders that may be treated by a combination of DEX and a 5-HT2A receptor antagonist/inverse agonist such as a compound of formula I include, but are not limited to, anxiety disorders, including but not limited to, phobias, generalized anxiety disorder, social anxiety disorder, panic disorder, agoraphobia, obsessive-compulsive disorder, and post-traumatic stress disorder (PTSD); mania, manic depressive illness, hypomania, unipolar depression, depression, stress disorders, somatoform disorders, personality disorders, psychosis, schizophrenia, delusional disorder, schizoaffective disorder, schizotypy, aggression, aggression in Alzheimer's disease, agitation, and apathy in Alzheimer's disease.

Apathy, or loss of motivation, is the most common change in behavior in Alzheimer's disease (AD). It is common throughout the spectrum of cognitive decline from mild cognitive impairment to severe Alzheimer's disease (AD), as well as in a variety of other neuropsychiatric disorders. Apathy represents a form of executive cognitive dysfunction. Patients with apathy suffer from decreased daily function and specific cognitive deficits and rely on families to provide more care, which results in increased stress for families. Apathy is one of the primary syndromes associated with frontal and subcortical pathology, and apathy in AD appears to have multiple neuroanatomical correlates that implicate components of frontal subcortical networks. Despite the profound effects of this common syndrome, only a few instruments have been designed to specifically assess apathy, and these instruments have not been directly compared. Assessment of apathy in AD requires clinicians to distinguish loss of motivation from loss of ability due to cognitive decline. Although apathy may be misdiagnosed as depression because of an overlap in symptoms, current research has shown apathy to be a discrete syndrome. Distinguishing apathy from depression has important treatment implications because these disorders respond to different interventions.

The Apathy Inventory (IA), a rating scale for global assessment of apathy and separate assessment of emotional blunting, lack of initiative, and lack of interest, is a reliable method for assessing in demented and non-demented elderly subjects several dimensions of the apathetic syndrome, and also the subject's awareness of these symptoms. The IA assesses apathy as effectively as the Neuro Psychiatric Inventory apathy domain (Robert et al., The Apathy Inventory: assessment of apathy and awareness in Alzheimer's disease, Parkinson's disease and mild cognitive impairment, the Journal of Geriatric Psychiatry, Volume 17, Issue 12, Pages 1099-1105 (December 2002); Landes et al., Apathy in Alzheimer's Disease, the Journal of American Geriatric Society, Volume 49, Issue 12, Pages 1700-1707 (December 2001); Malloy et al., Apathy and Its Treatment in Alzheimer's Disease and Other Dementias, Psychiatric Times, Vol. XXII, Issue 13 (Nov. 1, 2005); incorporated by reference in entirety). Apathy can be the result of damage to one or more areas of the brain such as the frontal cortex, the thalamus, striatum and the amygdala. In most cases direct damage to the frontal lobes or the subcortical nuclei that have connections to the frontal lobes, cause apathy. Apathy associated with Alzheimer's disease is very difficult to treat. Antidepressants, SSRIs, psychostimulants, acetylcholinesterase inhibitors etc. alleviated apathy only to some degree.

Accordingly, an embodiment of the invention is a combination of DEX and Formula I, or DERATINE™, SARPOTINE™, SARPODEX™, DERADEX™, or DERAPHAN™; and one or more of antidepressants, SSRIs, psychostimulants, acetylcholinesterase inhibitors, dopaminergic agents. Another embodiment is a combination of DEX and Formula I, or DERATINE™, SARPOTINE™, SARPODEX™, DERADEX™, or DERAPHAN™ and one or more of donepezil, memantine, amantanidine, bupropion, ropinirole, methylphenidate, amphetamine, modafinil, metrifonate, tacrine, galantamine, rivastigmine, nefiracetam, *Ginkgo biloba* extract, etc. (Ruthirakuhan et al., Pharmacological interventions for apathy in Alzheimer's disease (Protocol), Cochran Database of Systemic Studies, 2016, Issue 5. Art. No.: CD012197, Published by John Wiley & Sons, Ltd.; Pharmacological and Nonpharmacological Treatment for Apathy in Alzheimer Disease: A Systematic Review Across Modalities, Journal of Geriatric Psychiatry and Neurology, Vol 30, Issue 1, 2017; references are incorporated by reference in entirety).

Acetylcholinesterase is one of the most prominent constituents of central cholinergic pathways. It terminates the synaptic action of acetylcholine through hydrolysis and yields the choline moiety that is necessary for transmitter recycling. The pathogenesis of Alzheimer's disease (AD) has been linked to a deficiency in the brain neurotransmitter acetylcholine. The efficacy of acetylcholinesterase inhibitors (AChEIs) is attained through their augmentation of acetylcholine-medicated neuron to neuron transmission. This is accomplished by increasing the concentration of acetylcholine through reversible inhibition of its hydrolysis by acetylcholinesterase. (USFDA Reference ID: 3096907; Guidance on Donepezil Hydrochloride, Finalized August 2017, incorporated by reference in entirety).

Accordingly, in one embodiment, the composition comprises AChIs such as 2-((1-Benzylpiperidin-4-yl)methyl)-5,6-dimethoxy-2,3-dihydro-H-inden-1-one (Donepezil), (S)-3-(1-(dimethylamino)ethyl)phenyl ethyl(methyl) carbamate (Rivastigmine), dimethyl (2,2,2-trichloro-1-hydroxyethyl)phosphonate (Metrifonate), dimethyl (2,2,2-trichloro-1-hydroxyethyl)phosphonate (Metrifonate), (4aS,6R,8aS)-3-methoxy-11-methyl-4a,5,9,10,11,12-hexahydro-6H-benzo[2,3]benzofuro[4,3-cd]azepin-6-ol (Galantamine), and 1,2,3,4-tetrahydroacridin-9-amine (Tacrine), O,S-dimethyl acetylphosphoramidothioate, O,O-dimethyl S-((4-oxobenzo[d][1,2,3]triazin-3(4H)-yl)methyl) phosphorodithioate, 2,2-dimethyl-2,3-dihydrobenzofuran-7-yl methylcarbamate, S-(((4-chlorophenyl)thio)methyl) O,O-diethyl phosphorodithioate, 2-chloro-1-(2,4-dichlorophenyl)vinyl diethyl phosphate, O,O-diethyl O-(3,5,6-trichloropyridin-2-yl) phosphorothioate, O-(3-chloro-4-methyl-2-oxo-2H-chromen-7-yl) O,O-diethyl phosphorothioate, 1-phenylethyl (E)-3-((dimethoxyphosphoryl)oxy)but-2-enoate,4-(tert-butyl)-2-chlorophenyl methyl methylphosphoramidate, O,O-diethyl O-(2-(ethylthio)ethyl) phosphorothioate, O,O-diethyl S-(2-(ethylthio)ethyl) phosphorothioate, O,O-diethyl O-(2-isopropyl-6-methylpyrimidin-4-yl) phosphorothioate, 2,2-dichlorovinyl dimethyl phosphate, (E)-4-(dimethylamino)-4-oxobut-2-en-2-yl dimethyl phosphate, O,O-dimethyl S-(2-(methylamino)-2-oxoethyl) phosphorodithioate, S,S'-(1,4-dioxane-2,3-diyl) O,O,O',O'-tetraethyl bis(phosphorodithioate), O,O-diethyl S-(2-(ethylthio)ethyl) phosphorodithioate, O-ethyl O-(4-nitrophenyl) phenylphosphonothioate, O,O,O',O'-tetraethyl S,S'-methylene bis(phosphorodithioate), O-ethyl S,S-dipropyl phosphorodithioate, O-(4-(N,N-dimethylsulfamoyl)phenyl) O,O-dimethyl phosphorothioate, O-(4-(N,N-dimethylsulfamoyl)phenyl) O,O-dimethyl phosphorothioate, ethyl (3-methyl-4-(methylthio)phenyl) isopropylphosphoramidate, O,O-dimethyl O-(3-methyl-4-nitrophenyl) phosphorothioate, O-ethyl S-phenyl ethylphosphonodithioate, isopropyl 2-((ethoxy(isopropylamino)phosphorothioyl)oxy)benzoate, diethyl 2-((dimethoxyphosphorothioyl)thio)succinate, O,S-dimethyl phosphoramidothioate, O,S-dimethyl phosphoramidothioate, S-((5-methoxy-2-oxo-1,3,4-thiadiazol-3(2H)-yl)methyl) O,O-dimethyl phosphorodithioate, methyl 3-((dimethoxyphosphoryl)oxy)but-2-enoate, (E)-dimethyl (4-(methylamino)-4-oxobut-2-en-2-yl) phosphate, 1,2-dibromo-2,2-dichloroethyl dimethyl phosphate, isopropyl (S)-methylphosphonofluoridate, 3,3-dimethylbutan-2-yl (S)-methylphosphonofluoridate, O,O-diethyl O-(4-nitrophenyl) phosphorothioate, S-(2-(ethylsulfinyl)ethyl) O,O-dimethyl phosphorothioate, O,O-diethyl S-((ethylthio)methyl) phosphorodithioate, S-((6-chloro-2-oxobenzo[d]oxazol-3(2H)-yl)methyl) O,O-diethyl phosphorodithioate, S-((1,3-dioxoisoindolin-2-yl)methyl) O,O-dimethyl phosphorodithioate, (E)-3-chloro-4-(diethylamino)-4-oxobut-2-en-2-yl dimethyl phosphate, O,O,O',O'-tetramethyl O,O'-(thiobis(4,1-phenylene)) bis(phosphorothioate), tetraethyl diphosphate, S-((tert-butylthio)methyl) O,O-diethyl phosphorodithioate, 2-chloro-1-(2,4,5-trichlorophenyl)vinyl dimethyl phosphate, and dimethyl (2,2,2-trichloro-1-hydroxyethyl)phosphonate, or pharmaceutically acceptable derivatives, metabolites, analogs, or salts thereof.

Substance abuse and addiction that may be treated by a combination of DEX and a 5-HT2A receptor antagonist/inverse agonist such as a compound of formula I includes, but is not limited to, drug dependence, addiction to cocaine, psychostimulants (e.g., crack, cocaine, speed, meth), nicotine, alcohol, opioids, anxiolytic and hypnotic drugs, *cannabis* (marijuana), amphetamines, hallucinogens, phencyclidine, volatile solvents, and volatile nitrites. Nicotine addiction includes nicotine addiction of all known forms, such as smoking cigarettes, cigars and/or pipes, and addiction to chewing tobacco.

Cerebral function disorders that may be treated by a combination of DEX and a 5-HT2A receptor antagonist/inverse agonist such as a compound of formula I include, but are not limited to, disorders involving intellectual deficits such as vascular dementia, Alzheimer's type dementia, Lewy Body Dementia, Fronto-Temporal Lobar Degeneration, memory loss, amnesia/amnestic syndrome, epilepsy, disturbances of consciousness, coma, lowering of attention, speech disorders, voice spasms, Parkinson's disease, Lennox-Gastaut syndrome, autism, hyperkinetic syndrome, and schizophrenia. Cerebral function disorders also include disorders caused by cerebrovascular diseases including, but not limited to, stroke, cerebral infarction, cerebral bleeding, cerebral arteriosclerosis, cerebral venous thrombosis, head injuries, and the like where symptoms include disturbance of consciousness, dementia, coma, lowering of attention, apathy, and speech disorders.

Movement disorders that may be treated by a combination of DEX and a 5-HT2A receptor antagonist/inverse agonist such as a compound of formula I include, but are not limited to, akathisia, akinesia, associated movements, athetosis, ataxia, ballismus, hemiballismus, bradykinesia, cerebral palsy, chorea, Huntington's disease, rheumatic chorea, Sydenham's chorea, dyskinesia, tardive dyskinesia, dystonia, blepharospasm, spasmodic torticollis, dopamine-responsive dystonia, Parkinson's disease, restless legs syndrome (RLS), tremor, essential tremor, Tourette's syndrome, and Wilson's disease.

Dementias that may be treated by a combination of DEX and a 5-HT2A receptor antagonist/inverse agonist such as a compound of formula I include, but are not limited to, Alzheimer's disease, Parkinson's disease, vascular dementia, dementia with Lewy bodies, mixed dementia, frontotemporal dementia, Creutzfeldt-Jakob disease, normal pressure hydrocephalus, Huntington's disease, Wernicke-Korsakoff Syndrome, and Fronto-Temporal Lobar Degeneration (FTLD).

Motor neuron diseases that may be treated by a combination of DEX and a 5-HT2A receptor antagonist/inverse agonist such as a compound of formula I include, but are not limited to, amyotrophic lateral sclerosis (ALS), progressive bulbar palsy, primary lateral sclerosis (PLS), progressive muscular atrophy, post-polio syndrome (PPS), spinal muscular atrophy (SMA), spinal motor atrophies, Tay-Sach's disease, Sandhoff disease, and hereditary spastic paraplegia.

Neurodegenerative diseases that may be treated by a combination of DEX and a 5-HT2A receptor antagonist/inverse agonist such as a compound of formula I include, but are not limited to Alzheimer's disease, prion-related diseases, cerebellar ataxia, spinocerebellar ataxia (SCA), spinal muscular atrophy (SMA), bulbar muscular atrophy, Friedrich's ataxia, Huntington's disease, Lewy body disease, Parkinson's disease, amyotrophic lateral sclerosis (ALS or Lou Gehrig's disease), multiple sclerosis (MS), multiple system atrophy, Shy-Drager syndrome, corticobasal degeneration, progressive supranuclear palsy, Wilson's disease, Menkes disease, adrenoleukodystrophy, cerebral autosomal dominant arteriopathy with subcortical infarcts and leukoencephalopathy (CADASIL), muscular dystrophies, Charcot-Marie-Tooth disease (CMT), familial spastic paraparesis, neurofibromatosis, olivopontine cerebellar atrophy or degeneration, striatonigral degeneration, Guillain-Barré syndrome, and spastic paraplegia.

Seizure disorders that may be treated by a combination of DEX and a 5-HT2A receptor antagonist/inverse agonist such as a compound of formula I include, but are not limited to, epileptic seizures, nonepileptic seizures, epilepsy, febrile seizures; partial seizures including, but not limited to, simple partial seizures, Jacksonian seizures, complex partial seizures, and epilepsia partialis continua; generalized seizures including, but not limited to, generalized tonic-clonic seizures, absence seizures, atonic seizures, myoclonic seizures, juvenile myoclonic seizures, and infantile spasms; and status epilepticus.

Types of headaches that may be treated by a combination of DEX and a 5-HT2A receptor antagonist/inverse agonist such as a compound of formula I include, but are not limited to, migraine, trigeminal cephalgia, tension, and cluster headaches including Bing-Horton-Syndrome.

Other neurological disorders that may be treated by a combination of DEX and a 5-HT2A receptor antagonist/inverse agonist such as a compound of formula I, a derivative, a metabolite or prodrug of any of these compounds include, Rett Syndrome, autism, tinnitus, disturbances of consciousness disorders, sexual dysfunction, intractable coughing, narcolepsy, cataplexy; voice disorders due to uncontrolled laryngeal muscle spasms, including, but not limited to, abductor spasmodic dysphonia, adductor spasmodic dysphonia, muscular tension dysphonia, and vocal tremor; diabetic neuropathy, chemotherapy-induced neurotoxicity, such as methotrexate neurotoxicity; incontinence including, but not limited, stress urinary incontinence, urge urinary incontinence, and fecal incontinence; and erectile dysfunction.

Pain relieving properties of DEX may be enhanced by a method comprising co-administering DEX and a 5-HT2A receptor antagonist/inverse agonist, such as a compound of formula I, a metabolite, a derivative, or prodrug of any of these compounds, with DEX.

Pain relieving properties of a compound of formula I, may be enhanced by a method comprising co-administering DEX with a compound of formula I.

These methods may be used to treat or provide relief to, any pain including, but not limited to, musculoskeletal pain, neuropathic pain, cancer-related pain, acute pain, nociceptive pain, etc.

Examples of musculoskeletal pain include low back pain (i.e. lumbosacral pain), primary dysmenorrhea, and arthritic pain, such as pain associated with rheumatoid arthritis, juvenile rheumatoid arthritis, osteoarthritis, osteoarthosis, axial spondyloarthritis including ankylosing spondylitis, etc.

In some embodiments, a combination of DEX and a 5-HT2A receptor antagonist/inverse agonist, such as a compound of formula I, is used for treating chronic musculoskeletal pain.

Examples of neuropathic pain include idiopathic and diabetic peripheral neuropathy, post-herpetic neuralgia, trigeminal neuralgia, monoradiculopathies, phantom limb pain, central pain, etc. Other causes of neuropathic pain include cancer-related pain, lumbar nerve root compression, spinal cord injury, post-stroke pain, central multiple sclerosis pain, HIV-associated neuropathy, and radio- or chemotherapy associated neuropathy, etc.

The term "treating" or "treatment" includes the diagnosis, cure, mitigation, treatment, or prevention of disease in man or other animals, or any activity that otherwise affects the structure or any function of the body of man or other animals.

Any 5-HT2A receptor antagonist/inverse agonist may be used in combination with DEX to improve the therapeutic properties of DEX. DEX and the 5-HT2A receptor antagonist/inverse agonist may be administered in separate compositions or dosage forms, or may be administered in a single composition or dosage form comprising both.

5-HT2A receptor antagonist/inverse agonists that can be co-administered with DEX include, but are not limited to, a compound of formula I, clomipramine, doxepin, fluoxetine, mianserin, imipramine, 2-chloroimipramine, amitriptyline, amoxapine, desipramine, protriptyline, trimipramine, nortriptyline, maprotiline, phenelzine, isocarboxazid, tranylcypromine, paroxetine, trazodone, citalopram, sertraline, aryloxy indanamine, benactyzine, escitalopram, fluvoxamine, venlafaxine, desvenlafaxine, duloxetine, mirtazapine, nefazodone, selegiline, sibutramine, milnacipran, tesofensine, brasofensine, moclobemide, rasagiline, nialamide, iproniazid, iproclozide, toloxatone, butriptyline, dosulepin, dibenzepin, iprindole, lofepramine, opipramol, norfluoxetine, dapoxetine, etc., or a metabolite or prodrug of any of these compounds, or a pharmaceutically acceptable salt of any of these compounds.

Combining a compound of formula I, with DEX may provide greater efficacy, such as greater pain relief, than would otherwise be achieved by administering either component alone. In extensive metabolizers, DEX can be rapidly and extensively metabolized, yielding low systemic exposure even at high doses. A compound of formula I, besides possessing antidepressant and analgesic properties, is an inhibitor of DEX metabolism. Metabolites of a compound of formula I, which include a compound of formula I, a derivative, a metabolite are also inhibitors of DEX metabolism. Thus, a compound of formula I, including a form of a compound of formula I, that is rapidly converted in the body (such as a salt, hydrate, solvate, polymorph, etc.), is a prodrug of a compound of formula I.

As explained above, this inhibition may augment DEX plasma levels, resulting in additive or synergistic efficacy such as relief of neurological disorders including pain, depression, smoking cessation, etc. Thus, while inhibition of DEX metabolism is only one of many potential benefits of the combination, co-administration of DEX with a compound of formula I may thereby enhance the efficacy of a compound of formula I, for many conditions. Co-administration of DEX with a compound of formula I may enhance the analgesic properties of a compound of formula I for many conditions. Co-administration of DEX with a compound of formula I may also enhance the antidepressant properties of a compound of formula I for many conditions, including faster onset of action.

Another potential benefit of co-administration of DEX and a compound of formula I is that it may be useful to reduce the potential for an adverse event, such as drowsiness or confusion, associated with treatment by DEX. This may be useful, for example, in subjects at risk of experiencing an adverse event as a result being treated with DEX.

Another potential benefit of co-administration of DEX and a compound of formula I is that it may be useful to reduce the potential for an adverse event, such as seizure, associated with treatment by a compound of Formula I. This may be useful, for example, in subjects at risk of experiencing the adverse event as a result being treated with a compound of formula I.

With respect to DEX, a compound of formula I, co-administration may reduce a central nervous system adverse event, a gastrointestinal event, or another type of adverse event associated with any of these compounds. Central nervous system (CNS) adverse events include, but are not limited to, nervousness, dizziness, sleeplessness, light-headedness, tremor, hallucinations, convulsions, CNS depression, fear, anxiety, headache, increased irritability or excitement, tinnitus, drowsiness, dizziness, sedation, somnolence, confusion, disorientation, lassitude, incoordination, fatigue, euphoria, nervousness, insomnia, sleeping disturbances, convulsive seizures, excitation, catatonic-like states, hysteria, hallucinations, delusions, paranoia, headaches and/or migraine, and extrapyramidal symptoms such as oculogyric crisis, torticollis, hyperexcitability, increased muscle tone, ataxia, and tongue protrusion.

Gastrointestinal adverse events include, but are not limited to, nausea, vomiting, abdominal pain, dysphagia, dyspepsia, diarrhea, abdominal distension, flatulence, peptic ulcers with bleeding, loose stools, constipation, stomach pain, heartburn, gas, loss of appetite, feeling of fullness in stomach, indigestion, bloating, hyperacidity, dry mouth, gastrointestinal disturbances, and gastric pain.

Co-administering DEX and a 5-HT2A receptor antagonist/inverse agonist, such as a compound of formula I does not necessarily require that the two compounds be administered in the same dosage form. For example, the two compounds may be administered in a single dosage form, or they may be administered in two separate dosage forms. Additionally, the two compounds may be administered at the same time, but this is not required. The compounds can be given at different times as long as both are in a human body at the same time for at least a portion of the time that treatment by co-administration is being carried out.

In some embodiments, co-administration of a combination of a compound of formula I and DEX results in pain relieving properties. For example, the combination may have improved pain-relieving properties as compared to a compound of formula I alone or compared to DEX alone, including potentially faster onset of action.

In some embodiments, the combination may have improved pain relieving properties of at least about 0.5%, at least about 1%, at least about 10%, at least about 20%, at least about 30%, at least about 50%, at least 100%, up to about 500% or up to 1000%, about 0.5% to about 1000%, about 10% to about 20%, about 20% to about 30%, about 30% to about 40%, about 40% to about 50%, about 50% to about 60%, about 60% to about 70%, about 70% to about 80%, about 80% to about 90%, about 90% to about 100%, about 100% to about 110%, about 110% to about 120%, about 120% to about 130%, about 130% to about 140%, about 140% to about 150%, about 150% to about 160%, about 160% to about 170%, about 170% to about 180%, about 180% to about 190%, about 190% to about 200%, or any amount of pain relief in a range bounded by, or between, any of these values, as compared to a compound of formula I alone.

In some embodiments, the combination may have improved pain relieving properties of at least about 0.5%, at least about 1%, at least about 10%, at least about 20%, at least about 30%, at least about 50%, at least 100%, up to about 500% or up to 1000%, about 0.5% to about 1000%, about 10% to about 20%, about 20% to about 30%, about 30% to about 40%, about 40% to about 50%, about 50% to about 60%, about 60% to about 70%, about 70% to about 80%, about 80% to about 90%, about 90% to about 100%, about 100% to about 110%, about 110% to about 120%, about 120% to about 130%, about 130% to about 140%, about 140% to about 150%, about 150% to about 160%, about 160% to about 170%, about 170% to about 180%, about 180% to about 190%, about 190% to about 200%, or any amount of pain relief in a range bounded by, or between, any of these values, as compared to as compared to DEX alone.

Unless otherwise indicated, any reference to a compound herein, such as DEX, a compound of Formula I by structure, name, or any other means, includes pharmaceutically acceptable salts; alternate solid forms, such as polymorphs, solvates, hydrates, etc.; tautomers; deuterium-modified compounds, such as deuterium-modified DEX and a compound of formula I; or any chemical species that may rapidly convert to a compound described herein under conditions in which the compounds are used as described herein. Examples of deuterium modified DEX and a compound of formula I, include, but are not limited to, those shown below.

A dosage form or a composition may be a blend or mixture of DEX and a compound that inhibits the metabolism of DEX, such as a compound of formula I, either alone or within a vehicle. For example, DEX and a compound of formula I, may be dispersed within each other or dispersed together within a vehicle. A dispersion may include a mixture of solid materials wherein small individual particles are substantially one compound, but the small particles are dispersed within one another, such as might occur if two powders of two different drugs are blended with a solid vehicle material, and the blending is done in the solid form. In some embodiments, DEX and a compound of formula I, may be substantially uniformly dispersed within a composition or dosage form. Alternatively, DEX and a compound of formula I, may be in separate domains or phases in a composition or dosage form. For example, one drug may be in a coating, and another drug may be in a core within the coating. For example, one drug may be formulated for sustained release and another drug may be formulated for immediate release.

Some embodiments include administration of a tablet that contains a compound of formula I in a form that provides sustained release and DEX in a form that provides immediate release or vice versa. While there are many ways that sustained release of a compound of formula I, may be achieved, in some embodiments, a compound of formula I is combined with hydroxypropyl methylcellulose. For example, particles of a compound of formula I hydrochloride could be blended with microcrystalline cellulose and hydroxypropyl methylcellulose (e.g., METHOCEL™) to form an admixture of blended powders. This could then be combined with immediate release DEX in a single tablet.

DEX and/or a 5-HT2A receptor antagonist/inverse agonist such as a compound of formula I may be combined with a pharmaceutical carrier selected on the basis of the chosen route of administration and standard pharmaceutical practice as described, for example, in Remington's Pharmaceutical Sciences, 2005. The relative proportions of active ingredient and carrier may be determined, for example, by the solubility and chemical nature of the compounds, chosen route of administration and standard pharmaceutical practice.

Therapeutic compounds may be administered by any means that may result in the contact of the active agent(s) with the desired site or site(s) of action in the body of a patient. The compounds may be administered by any conventional means available for use in conjunction with pharmaceuticals, either as individual therapeutic agents or in a combination of therapeutic agents. For example, they may be administered as the sole active agents in a pharmaceutical composition, or they can be used in combination with other therapeutically active ingredients.

Therapeutic compounds may be administered to a subject in a variety of forms adapted to the chosen route of administration, e.g., orally or parenterally. Parenteral administration in this respect includes administration by the following routes: intravenous, intramuscular, subcutaneous, intraocular, intrasynovial, transepithelial, including transdermal, ophthalmic, sublingual and buccal; topically including ophthalmic, dermal, ocular, rectal and nasal inhalation via insufflation, aerosol and rectal systemic.

The ratio of DEX to a compound of formula I may vary. In some embodiments, the weight ratio of DEX to a compound of formula I, may be about 0.1 to about 10, about 0.1 to about 2, about 0.2 to about 1, about 0.1 to about 0.5, about 0.1 to about 0.3, about 0.2 to about 0.4, about 0.3 to about 0.5, about 0.5 to about 0.7, about 0.8 to about 1, about 0.2, about 0.3, about 0.4, about 0.45, about 0.6, about 0.9, or any ratio in a range bounded by, or between, any of these values. A ratio of 0.1 indicates that the weight of DEX is 1/10 that of a compound of formula I. A ratio of 10 indicates that the weight of DEX is 10 times that of a compound of formula I.

The amount of DEX in a therapeutic composition may vary. For example, some liquid compositions may comprise about 0.0001% (w/v) to about 50% (w/v), about 0.01% (w/v) to about 20% (w/v), about 0.01% (w/v) to about 10% (w/v), about 0.001% (w/v) to about 1% (w/v), about 0.1% (w/v) to about 0.5% (w/v), about 1% (w/v) to about 3% (w/v), about 3% (w/v) to about 5% (w/v), about 5% (w/v) to about 7% (w/v), about 7% (w/v) to about 10% (w/v), about 10% (w/v) to about 15% (w/v), about 15% (w/v) to about 20% (w/v), about 20% (w/v) to about 30% (w/v), about 30% (w/v) to about 40% (w/v), or about 40% (w/v) to about 50% (w/v) of DEX.

Some liquid dosage forms may contain about 10 mg to about 500 mg, about 30 mg to about 350 mg, about 50 mg to about 200 mg, about 50 mg to about 70 mg, about 20 mg to about 50 mg, about 30 mg to about 60 mg, about 40 mg to about 50 mg, about 40 mg to about 42 mg, about 42 mg to about 44 mg, about 44 mg to about 46 mg, about 46 mg to about 48 mg, about 48 mg to about 50 mg, about 80 mg to about 100 mg, about 110 mg to about 130 mg, about 170 mg to about 190 mg, about 45 mg, about 60 mg, about 90 mg, about 120 mg, or about 180 mg of DEX, or any amount of DEX in a range bounded by, or between, any of these values.

Some solid compositions may comprise at least about 5% (w/w), at least about 10% (w/w), at least about 20% (w/w), at least about 50% (w/w), at least about 70% (w/w), at least about 80%, about 10% (w/w) to about 30% (w/w), about 10% (w/w) to about 20% (w/w), about 20% (w/w) to about 30% (w/w), about 30% (w/w) to about 50% (w/w), about 30% (w/w) to about 40% (w/w), about 40% (w/w) to about 50% (w/w), about 50% (w/w) to about 80% (w/w), about 50% (w/w) to about 60% (w/w), about 70% (w/w) to about 80% (w/w), or about 80% (w/w) to about 90% (w/w) of DEX.

Some solid dosage forms may contain about 10 mg to about 500 mg, about 30 mg to about 350 mg, about 20 mg to about 50 mg, about 30 mg to about 60 mg, about 40 mg to about 50 mg, about 40 mg to about 42 mg, about 42 mg to about 44 mg, about 44 mg to about 46 mg, about 46 mg to about 48 mg, about 48 mg to about 50 mg, about 50 mg to about 200 mg, about 50 mg to about 70 mg, about 80 mg to about 100 mg, about 110 mg to about 130 mg, about 170 mg to about 190 mg, about 60 mg, about 90 mg, about 120 mg, or about 180 mg of DEX, or any amount of DEX in a range bounded by, or between, any of these values.

The amount of a compound of formula I, in a therapeutic composition may vary. If increasing the plasma level of DEX is desired, a compound of formula I should be administered in an amount that increases the plasma level of DEX. For example, a compound of formula I, may be administered in an amount that results in a plasma concentration of DEX in the subject, on day 8, that is at least about 2 times, at least about 5 times, at least about 10 times, at least about 15 times, at least about 20 times, at least about 30 times, at least about 40 times, at least about 50 times, at least about 60 times, at least about 70 times, or at least about 80 times, the plasma concentration of the same amount of DEX administered without a compound of formula I.

In some embodiments, a compound of formula I, may administered to a subject in an amount that results in a 12 hour area under the curve from the time of dosing ($AUC_{0-12}$), or average plasma concentration in the subject for the 12 hours following dosing ($C_{avg}$) of DEX, on day 8, that is at least about 2 times, at least about 5 times, at least about 10 times, at least about 15 times, at least about 20 times, at least about 30 times, at least about 40 times, at least about 50 times, at least about 60 times, at least about 70 times, or at least about 80 times the plasma concentration of the same amount of DEX administered without a compound of formula I.

In some embodiments, a compound of formula I, may administered to a subject in an amount that results in a maximum plasma concentration ($C_{max}$) of DEX in the subject, on day 8, that is at least about 2 times, at least about 5 times, at least about 10 times, at least about 15 times, at least about 20 times, at least about 30 times, or at least about 40 times the plasma concentration of the same amount of DEX administered without a compound of formula I.

For co-administration of a compound of formula I, an increase in the DEX plasma level can occur on the first day that a compound of formula I is administered, as compared to the same amount of DEX administered without a compound of formula I. For example, the DEX plasma level on the first day that a compound of formula I is administered may be at least about 1.5 times, at least about at least 2 times, at least about 2.5 times, at least about 3 times, at least about 4 times, at least about 5 times, at least about 6 times at least about 7 times, at least about 8 times, at least about 9 times, or at least about 10 times the level that would be achieved by administering the same amount of DEX without a compound of formula I.

In some embodiments, the DEX AUC on the first day that a compound of formula I is administered may be at least twice the AUC that would be achieved by administering the same amount of DEX without a compound of formula I.

In some embodiments, the DEX $C_{max}$ on the first day that a compound of formula I is administered may be at least twice the $C_{max}$ that would be achieved by administering the same amount of DEX without a compound of formula I.

In some embodiments, the DEX trough level (e.g., plasma level 12 hours after administration) on the first day that a compound of formula I is administered may be at least twice the trough level that would be achieved by administering the same amount of DEX without a compound of formula I.

In some embodiments, a compound of formula I is administered on the first day of at least two days of treatment with DEX, wherein a decrease in the DO plasma level occurs on the first day that a compound of formula I and DEX are co-administered, as compared to the same amount of DEX administered without a compound of formula I. For example, the DO plasma level on the first day may be reduced by at least 5% as compared to the DO plasma level that would be achieved by administering the same amount of DEX without a compound of formula I.

In some embodiments, a compound of formula I and DEX are co-administered for at least five consecutive days, to a subject in need of treatment with DEX, wherein, on the fifth day, the DEX plasma level is higher than the DEX plasma level that would have been achieved by administering the same amount of DEX administered without a compound of formula I, for five consecutive days. For example, the DEX plasma level on the fifth day (for example at 0 hours, 1 hour, 3 hours, 6 hours, or 12 hours after administration) may be at least 5 times, at least 10 times, at least 20 times, at least 40 times, at least 50 times, at least 60 times, at least 65 times, or up to about 500 times, the level that would be achieved by administering the same amount of DEX without a compound of formula I, for five consecutive days.

In some embodiments, a compound of formula I and DEX are co-administered for at least six consecutive days, to a subject in need of treatment with DEX, wherein, on the sixth day, the DEX plasma level is higher than the DEX plasma level that would have been achieved by administering the same amount of DEX administered without a compound of formula I, for six consecutive days. For example, the DEX plasma level on the sixth day (for example at 0 hours, 1 hour, 3 hours, 6 hours, or 12 hours after administration) may be at least 5 times, at least 10 times, at least 20 times, at least 30 times, at least 50 times, at least 60 times, at least 70 times, at least 75 times, or up to about 500 times, the level that would be achieved by administering the same amount of DEX without a compound of formula I, for six consecutive days.

In some embodiments, a compound of formula I and DEX are co-administered for at least seven consecutive days, to a subject in need of treatment with DEX, wherein, on the seventh day, the DEX plasma level is higher than the DEX plasma level that would have been achieved by administering the same amount of DEX administered without a compound of formula I, for seven consecutive days. For example, the DEX plasma level on the seventh day (for example at 0 hours, 1 hour, 3 hours, 6 hours, or 12 hours after administration) may be at least 5 times, at least 10 times, at least 20 times, at least 30 times, at least 50 times, at least 70 times, at least 80 times, at least 90 times, or up to about 500 times, the level that would be achieved by administering the same amount of DEX without a compound of formula I, for seven consecutive days.

In some embodiments, a compound of formula I and DEX are co-administered for at least eight consecutive days, wherein, on the eighth day, DEX has a plasma level, for example at 0 hours, 1 hour, 3 hours, 6 hours, or 12 hours, after co-administering a compound of formula I with DEX that is at least 5 times, at least 10 times, at least 20 times, at least 30 times, at least 50 times, at least 60 times, at least 70 times, at least 80 times, at least 90 times, at least 100 times, or up to about 1,000 times, the plasma level that would be achieved by administering the same amount of DEX without a compound of formula I for eight consecutive days.

In some embodiments, a compound of formula I and DEX are co-administered for at least eight consecutive days, to a subject in need of treatment with DEX, wherein, on the eighth day, the DO plasma level is lower than the DO plasma level that would have been achieved by administering the same amount of DEX administered without a compound of Formula I for eight consecutive days. For example, the DO plasma level on the eighth day (for example at 0 hours, 1 hour, 3 hours, 6 hours, or 12 hours after administration) may be reduced by at least 10%, at least 20%, at least 30%, at least 40%, or at least 50%, as compared to the DO plasma level that would be achieved by administering the same amount of DEX without a compound of formula I for eight consecutive days.

In some embodiments, a compound of formula I may be administered to a subject in an amount that results in an $AUC_{0-12}$ of a compound of formula I in the subject, on day 8, that is at least about 100 nghr/mL, at least about 200 nghr/mL, at least about 500 nghr/mL, at least about 600 nghr/mL, at least about 700 nghr/mL, at least about 800 nghr/mL, at least about 900 nghr/mL, at least about 1,000 nghr/mL, at least about 1,200 nghr/mL, at least 1,600 nghr/mL, or up to about 15,000 nghr/mL.

In some embodiments, a compound of formula I may be administered to a subject in an amount that results in a $C_{avg}$ of a compound of formula I in the subject, on day 8, that is at least about 10 ng/mL, at least about 20 ng/mL, at least about 40 ng/mL, at least about 50 ng/mL, at least about 60 ng/mL, at least about 70 ng/mL, at least about 80 ng/mL, at least about 90 ng/mL, at least about 100 ng/mL, at least 120 ng/mL, or up to about 1,500 ng/mL.

Some liquid compositions may comprise about 0.0001% (w/v) to about 50% (w/v), about 0.01% (w/v) to about 20% (w/v), about 0.01% to about 10% (w/v), about 1% (w/v) to about 3% (w/v), about 3% (w/v) to about 5% (w/v), about 5% (w/v) to about 7% (w/v), about 5% (w/v) to about 15% (w/v), about 7% (w/v) to about 10% (w/v), about 10% (w/v) to about 15% (w/v), about 15% (w/v) to about 20% (w/v), about 20% (w/v) to about 30% (w/v), about 30% (w/v) to about 40% (w/v), or about 40% (w/v) to about 50% (w/v) of a compound of Formula I or any amount of a compound of Formula I, in a range bounded by, or between, any of these values.

Some liquid dosage forms may contain about 10 mg to about 1000 mg, about 50 mg to about 1000 mg, about 10 mg to about 50 mg, about 50 mg to about 100 mg, about 40 mg to about 90 mg, about 200 mg to about 300 mg, about 70 mg to about 95 mg, about 100 mg to about 200 mg, about 105 mg to about 200 mg, about 110 mg to about 140 mg, about 180 mg to about 220 mg, about 280 mg to about 320 mg, about 200 mg, about 150 mg, or about 300 mg of a compound of Formula I, or any amount of a compound of Formula I, in a range bounded by, or between, any of these values.

Some solid compositions may comprise at least about 5% (w/w), at least about 10% (w/w), at least about 20% (w/w), at least about 50% (w/w), at least about 70% (w/w), at least about 80%, about 10% (w/w) to about 30% (w/w), about 10% (w/w) to about 20% (w/w), about 20% (w/w) to about 30% (w/w), about 30% (w/w) to about 50% (w/w), about 30% (w/w) to about 40% (w/w), about 40% (w/w) to about 50% (w/w), about 50% (w/w) to about 80% (w/w), about 50% (w/w) to about 60% (w/w), about 70% (w/w) to about 80% (w/w), or about 80% (w/w) to about 90% (w/w) of a compound of Formula I, or any amount of a compound of Formula I, in a range bounded by, or between, any of these values.

Some solid dosage forms may contain about 10 mg to about 1000 mg, about 50 mg to about 1000 mg, about 10 mg to about 50 mg, about 50 mg to about 100 mg, about 40 mg to about 90 mg, about 200 mg to about 300 mg, about 70 mg to about 95 mg, about 100 mg to about 200 mg, about 105 mg to about 200 mg, about 110 mg to about 140 mg, about 50 mg to about 150 mg, about 180 mg to about 220 mg, about 280 mg to about 320 mg, about 200 mg, about 150 mg, or about 300 mg of a compound of Formula I, or any amount of a compound of Formula I, in a range bounded by, or between, any of these values.

In some embodiments, a compound of Formula I is administered at a dose that results in a a compound of Formula I, plasma level of about 0.1 μM to about 10 μM, about 0.1 μM to about 5 μM, about 0.2 μM to about 3 μM, 0.1 μM to about 1 μM, about 0.2 μM to about 2 μM, 1 μM to about 10 μM, about 1 μM to about 5 μM, about 2 μM to about 3 μM, or about 2.8 μM to about 3 μM, about 1.5 μM to about 2 μM, about 4.5 μM to about 5 μM, about 2.5 μM to about 3 μM, about 1.8 μM, about 4.8 μM, about 2.9 μM, about 2.8 μM, or any plasma level in a range bounded by, or between, any of these values.

In some embodiments, a compound of Formula I may be administered to a subject in an amount that results in an $AUC_{0-12}$ of a compound of Formula I in the subject, on day 8, that is at least about 200 ngh/mL, at least about 400 ngh/mL, at least about 700 ngh/mL, at least about 1,000 ngh/mL, at least about 3,000 ngh/mL, at least about 7,000 ngh/mL, at least about 10,000 ngh/mL, at least about 15,000 ngh/mL, at least about 20,000 ngh/mL, at least about 30,000 ngh/mL, up to about 50,000 ngh/mL, up to about 150,000 ngh/mL, or any AUC in a range bounded by, or between, any of these values.

In some embodiments, a compound of Formula I is administered to a subject in an amount that results in a $C_{max}$ of a compound of Formula I in the subject, on day 8, that is at least about 20 ng/mL, at least about 60 ng/mL, at least about 90 ng/mL, at least about 100 ng/mL, at least about 150 ng/mL, at least about 200 ng/mL, at least about 300 ng/mL, up to about 1,000 ng/mL, at least about 4,000 ng/mL, up to about 10,000 ng/mL, up to about 50,000 ng/mL, or any $C_{max}$ in a range bounded by, or between, any of these values.

In some embodiments, a compound of Formula I is administered to a subject in an amount that results in a $C_{avg}$ of a compound of Formula I in the subject, on day 8, that is at least about 20 ng/mL, at least about 30 ng/mL, at least about 50 ng/mL, at least about 80 ng/mL, at least about 90 ng/mL, at least about 100 ng/mL, at least about 150 ng/mL, at least about 200 ng/mL, at least about 300 ng/mL, up to about 1,000 ng/mL, up to about 5,000 ng/mL, up to about 30,000 ng/mL, or any $C_{avg}$ in a range bounded by, or between, any of these values.

For compositions comprising both DEX and a compound of Formula I some liquids may comprise about 0.0001% (w/v) to about 50% (w/v), about 0.01% (w/v) to about 20% (w/v), about 0.01% to about 10% (w/v), about 1% (w/v) to about 3% (w/v), about 3% (w/v) to about 5% (w/v), about 5% (w/v) to about 7% (w/v), about 5% (w/v) to about 15% (w/v), about 7% (w/v) to about 10% (w/v), about 10% (w/v) to about 15% (w/v), about 15% (w/v) to about 20% (w/v), about 20% (w/v) to about 30% (w/v), about 30% (w/v) to about 40% (w/v), about 40% (w/v) to about 50% (w/v) of DEX and a compound of Formula I combined, or any amount in a range bounded by, or between, any of these values. Some solid compositions may comprise at least about 5% (w/w), at least about 10% (w/w), at least about 20% (w/w), at least about 50% (w/w), at least about 70% (w/w), at least about 80%, about 10% (w/w) to about 30% (w/w), about 10% (w/w) to about 20% (w/w), about 20% (w/w) to about 30% (w/w), about 30% (w/w) to about 50% (w/w), about 30% (w/w) to about 40% (w/w), about 40% (w/w) to about 50% (w/w), about 50% (w/w) to about 80% (w/w), about 50% (w/w) to about 60% (w/w), about 70% (w/w) to about 80% (w/w), about 80% (w/w) to about 90% (w/w) of DEX and a compound of Formula I combined, or any amount in a range bounded by, or between, any of these values. In some embodiments, the weight ratio of DEX to a compound of Formula I in a single composition or dosage form may be about 0.1 to about 2, about 0.2 to about 1, about 0.1 to about 0.3, about 0.2 to about 0.4, about 0.3 to about 0.5, about 0.5 to about 0.7, about 0.8 to about 1, about 0.2, about 0.3, about 0.4, about 0.45, about 0.6, about 0.9, or any ratio in a range bounded by, or between, any of these values.

A therapeutically effective amount of a therapeutic compound may vary depending upon the circumstances. For example, a daily dose of DEX may in some instances range from about 0.1 mg to about 1000 mg, about 40 mg to about 1000 mg, about 20 mg to about 600 mg, about 60 mg to about 700 mg, about 100 mg to about 400 mg, about 15 mg to about 20 mg, about 20 mg to about 25 mg, about 25 mg to about 30 mg, about 30 mg to about 35 mg, about 35 mg to about 40 mg, about 40 mg to about 45 mg, about 45 mg to about 50 mg, about 50 mg to about 55 mg, about 55 mg to about 60 mg, about 20 mg to about 60 mg, about 60 mg to about 100 mg, about 100 mg to about 200 mg, about 100 mg to about 140 mg, about 160 mg to about 200 mg, about 200 mg to about 300 mg, about 220 mg to about 260 mg, about 300 mg to about 400 mg, about 340 mg to about 380 mg, about 400 mg to about 500 mg, about 500 mg to about 600 mg, about 15 mg, about 30 mg, about 60 mg, about 120 mg, about 180 mg, about 240 mg, about 360 mg, or any daily dose in a range bounded by, or between, any of these values. DEX may be administered once daily; or twice daily or every 12 hours, three times daily, four times daily, or six times daily in an amount that is about half, one-third, one-quarter, or one-sixth, respectively, of the daily dose.

A daily dose of a compound of Formula I may in some instances range from about 10 mg to about 1000 mg, about 50 mg to about 600 mg, about 100 mg to about 2000 mg, about 50 mg to about 100 mg, about 70 mg to about 95 mg, about 100 mg to about 200 mg, about 105 mg to about 200 mg, about 100 mg to about 150 mg, about 150 mg to about 300 mg, about 150 mg to about 200 mg, about 200 mg to about 250 mg, about 250 mg to about 300 mg, about 200 mg about 300 mg, about 300 mg to about 400 mg, about 400 mg to about 500 mg, about 400 mg to about 600 mg, about 360 mg to about 440 mg, about 560 mg to about 640 mg, or about 500 mg to about 600 mg, about 100 mg, about 150 mg, about 200 mg, about 300 mg, about 400 mg, about 600 mg, or any daily dose in a range bounded by, or between, any of these values. a compound of Formula I may be administered once daily; or twice daily or every 12 hours, or three times daily in an amount that is about half or one-third, respectively, of the daily dose.

In some embodiments: 1) about 50 mg/day to about 100 mg/day, about 100 mg/day to about 150 mg/day, about 150 mg/day to about 300 mg/day, about 150 mg/day to about 200 mg/day, about 200 mg/day to about 250 mg/day, about 250 mg/day to about 300 mg/day of a compound of Formula I or about 300 mg/day to about 500 mg/day of a compound of Formula I; and/or 2) about 15 mg/day to about 60 mg/day, about 15 mg/day to about 30 mg/day, about 30 mg/day to about 45 mg/day, about 45 mg/day to about 60 mg/day, about 60 mg/day to about 100 mg/day, about 80 mg/day to about 110 mg/day, about 100 mg/day to about 150 mg/day, or about 100 mg/day to about 300 mg/day of DEX, are administered to a subject in need thereof.

In some embodiments, about 150 mg/day of a compound of Formula I and about 30 mg/day of DEX, about 150 mg/day of a compound of Formula I and about 60 mg/day of DEX, about 150 mg/day of a compound of Formula I and about 90 mg/day of DEX, about 150 mg/day of a compound of Formula I and about 120 mg/day of DEX, about 200 mg/day of a compound of Formula I and about 30 mg/day of DEX, about 200 mg/day of a compound of Formula I and about 60 mg/day of DEX, about 200 mg/day of a compound of Formula I and about 90 mg/day of DEX, about 200 mg/day of a compound of Formula I and about 120 mg/day of DEX, about 300 mg/day of a compound of Formula I and about 30 mg/day of DEX, about 300 mg/day of a compound of Formula I and about 60 mg/day of DEX, about 300 mg/day of a compound of Formula I and about 90 mg/day of DEX, or about 300 mg/day of a compound of Formula I and about 120 mg/day of DEX is administered to the subject.

In some embodiments, about 100 mg/day of a compound of Formula I and about 15 mg/day of DEX is administered to the subject for 1, 2, or 3 days, followed by about 200 mg/day of a compound of Formula I and about 30 mg/day of DEX. In some embodiments, about 100 mg/day of a compound of Formula I and about 30 mg/day of DEX is administered to the subject for 1, 2, or 3 days, followed by about 200 mg/day of a compound of Formula I and about 60 mg/day of DEX.

In some embodiments, about 75 mg/day of a compound of Formula I and about 15 mg/day of DEX is administered to the subject for 1, 2, or 3 days, followed by about 150 mg/day of a compound of Formula I and about 30 mg/day of DEX. In some embodiments, about 75 mg/day of a compound of Formula I and about 30 mg/day of DEX is administered to the subject for 1, 2, or 3 days, followed by about 150 mg/day of a compound of Formula I and about 60 mg/day of DEX.

A 5-HT2A receptor antagonist/inverse agonist, such as a compound of Formula I may be administered for as long as needed to treat a neurological condition, such as pain, depression or cough. In some embodiments, a 5-HT2A receptor antagonist/inverse agonist, such as a compound of Formula I and DEX are administered at least once a day, such as once daily or twice daily, for at least 1 day, at least 3 days, at least 5 days, at least 7 days, at least 8 days, at least 14 days, at least 30 days, at least 60 days, at least 90 days, at least 180 days, at least 365 days, or longer.

Therapeutic compounds may be formulated for oral administration, for example, with an inert diluent or with an edible carrier, or it may be enclosed in hard or soft shell gelatin capsules, compressed into tablets, or incorporated directly with the food of the diet. For oral therapeutic administration, the active compound may be incorporated with an excipient and used in the form of ingestible tablets, buccal tablets, troches, capsules, elixirs, suspensions, syrups, wafers, and the like.

Tablets, troches, pills, capsules and the like may also contain one or more of the following: a binder such as gum tragacanth, acacia, cornstarch, or gelatin; an excipient, such as dicalcium phosphate; a disintegrating agent such as corn starch, potato starch, alginic acid, and the like; a lubricant such as magnesium stearate; a sweetening agent such as sucrose, lactose, or saccharin; or a flavoring agent such as peppermint, oil of wintergreen, or cherry flavoring. When the dosage unit form is a capsule, it may contain, in addition to materials of the above type, a liquid carrier. Various other materials may be present as coating, for instance, tablets, pills, or capsules may be coated with shellac, sugar or both. A syrup or elixir may contain the active compound, sucrose as a sweetening agent, methyl and propylparabens as preservatives, a dye and flavoring, such as cherry or orange flavor. It may be desirable for material in a dosage form or pharmaceutical composition to be pharmaceutically pure and substantially nontoxic in the amounts employed.

Some compositions or dosage forms may be a liquid or may comprise a solid phase dispersed in a liquid.

Therapeutic compounds may be formulated for parenteral or oral administration. Solutions of the active compounds as free bases or pharmacologically acceptable salts can be prepared in water suitably mixed with a surfactant, such as hydroxypropylcellulose. A dispersion can also have an oil dispersed within, or dispersed in, glycerol, liquid polyethylene glycols, and mixtures thereof. Under ordinary conditions of storage and use, these preparations may contain a preservative to prevent the growth of microorganisms.

Although dementias such as Alzheimer's disease (AD) are characterized by cognitive deficits, neuropsychiatric symptoms (behavioral and psychological symptoms of dementia, BPSD) are among the main drivers for caregiver burden and hospitalization. Frequency of BPSD symptoms increases with the disease progression (e.g. up to 60% in mild and moderate AD and up to 90% in severe AD).

Currently marketed dementia therapies leave much room for improvement when it comes to treat BPSD but also other non-cognitive areas of concern. In the continued absence of a disease-modifying therapy, this is of increasing importance, as symptoms like hostility, aggression, wandering, sexually inappropriate behavior or incontinence pose major problems to caregivers and families, and are predictors for (costly) nursing home placement.

It is common global practice to prescribe (typical or atypical) neuroleptics to facilitate nursing and caregiving. However, the FDA has determined that off-label prescription of neuroleptics poses a major threat to the health of demented subjects, and has issued a black box warning, citing severe cardiovascular adverse events and an increased risk for death. EU approval of risperidone allows for short-term use in moderate-severe AD patients only in case of harm to self or others. In Parkinson's Disease, the anticholinergic effects of neuroleptics are highly unwanted as they inevitably worsen, in addition, the motor condition and symptoms of the vegetative nervous system. In all dementias, lowering the seizure threshold is another infrequent but highly unwanted potential adverse effect of neuroleptics. These concerns about the use of neuroleptic drugs in dementias result in decreased use of neuroleptics in this category of patients leaving BPSD symptoms in the vast majority of mild-to-moderate AD patients essentially untreated.

Accordingly, several embodiments are novel compositions and methods useful in the symptomatic and disease-modifying treatment of neurodegenerative diseases and brain injuries including sequelae thereof like organic brain syndrome and chronic traumatic encephalopathies; chronic or intractable pain, ophthalmologic indications associated with retinopathies, anxiety disorders, post-traumatic stress disorder, depression, diabetes mellitus and it's complications like peripheral neuropathies with or without neuropathic pain, Buerger's disease, Raynaud's disease, coronary artery disease, angina pectoris, atherosclerosis including CNS like multi-infarct dementia, Vascular Cognitive Impairment, Vascular Dementia or Binswanger's Disease, and nephropathies.

In a first aspect, provided is a method of increasing the metabolic lifetime of DEX, comprising administering 5-HT2A receptor antagonist/inverse agonist of Formula I to a subject in need of treatment with DEX, wherein 5-HT2A receptor antagonist/inverse agonist is an inhibitor of a CYP2D6 enzyme and wherein DEX is present in the body of the subject at the same time as M1.

In a second aspect, provided is a method of preventing adverse events associated with treatment by DEX, comprising co-administering 5-HT2A receptor antagonist/inverse agonist of Formula I to a subject in need of treatment with DEX, wherein the subject is at risk of experiencing the adverse event as a result of being treated with DEX.

In a third aspect, provided is a method for using 5HT2A receptor antagonists of Formula I to improve the therapeutic properties of DEX in the treatment of neuropsychiatric disorders.

In a fourth aspect, provided is a method of treating a neuropsychiatric disorder comprising administering a 5HT2A receptor antagonist of Formula I and DEX to a subject in need thereof.

In an embodiment of the first, second, third and fourth aspects, 5-HT2A receptor antagonist/inverse agonist is a prodrug of M1 such as a compound of Formula I or pharmaceutically acceptable salts thereof.

In an embodiment of the first, second and third aspects, 5-HT2A receptor antagonist/inverse agonist is an enantiomer of M1 such as (R)-1-(dimethylamino)-3-(2-(3-methoxyphenethyl) phenoxy) propan-2-ol) or (S)-1-(dimethylamino)-3-(2-(3-methoxyphenethyl)phenoxy)propan-2-ol), or pharmaceutically acceptable salts thereof.

In an embodiment of the third and fourth aspects, the neuropsychiatric disorder is Alzheimer's disease.

In a fifth aspect, provided is a method for selecting a 5-HT2A receptor antagonist/inverse agonist for the use in combination with DEX in subjects in need thereof.

In an embodiment of the fifth aspect, a specific enantiomer of a 5HT2A receptor antagonist with potent CYP2D6 inhibitory activity has higher blood-brain barrier penetration.

In an embodiment of the fifth aspect, a specific enantiomer of an 5HT2A receptor antagonist with potent CYP2D6 inhibitory activity has a better ratio of central vs peripheral effects when administered in combination with DEX, wherein central effects are assessed by direct or indirect 5HT2A receptor engagement methods while peripheral effects are assessed by methods based on blood glucose measurement.

In an embodiment of the fifth aspect, DEX and the selected 5-HT2A antagonist are administered in a combined dose, and wherein the amount of DEX administered comprises from about 20 mg/day to about 80 mg/day.

In an embodiment of the fifth aspect, DEX is administered in a combined dose with a selected enantiomer of M1, wherein the amount of the M1 enantiomer administered comprises from about 0.1 mg/day to about 1000 mg/day.

An embodiment of the invention is a method to augment therapeutic properties of DEX by administering it with a 5HT2A receptor antagonist that has potent CYP2D6 inhibitory activity, and multiple therapeutic benefits of its own.

Some embodiments include a method of treating a disease or disorder comprising administering about 5 mg/day to about 600 mg/day, about 5 mg/day to about 300 mg/day, about 5 mg/day to about 400 mg/day, about 5 mg/day to about 500 mg/day, about 5 mg/day to about 600 mg/day, about 5 mg/day to about 1,000 mg/day, about 50 mg/day to about 1000 mg/day, about 100 mg/day to about 1000 mg/day, about 150 mg/day to about 1000 mg/day, about 150 mg/day to about 5000 mg/day, about 150 mg/day to about 300 mg/day, or about 150 mg/day to about 100 mg/day, or an amount as required of a compound of Formula I and about 0.1 mg/day to about 1 mg/day, about 0.5 mg/day to about 15 mg/day, about 15 mg/day to about 60 mg/day, about 15 mg/day to about 120 mg/day, about 0.1 mg/day to about 200 mg/day, or any amount of a compound of Formula I in a range bounded by, or between, any of these values, or an amount as required of DEX to a subject in need thereof.

Borodkin, Book chapter: Ion-exchange resin delivery system, in "Polymers for Controlled Drug Delivery", Tarcha, P J, Ed., CRC Press, Boca Raton, 1990; incorporated by reference in its entirety). The composition of the present invention can be formulated into any pharmaceutical dosage forms for oral, topical, rectal, vaginal, nasal, or ophthalmic administration, and include syrups and suspensions, using commonly known ingredients and procedures and methods (U.S. Pat. Nos. 4,221,778, 4,762,709, 4,788,055, 4,959,219, 4,996,047, 5,071,646, and 5,186,930; Borodkin, Book chapter: Ion-exchange resin delivery system, in "Polymers for Controlled Drug Delivery", Tarcha, P J, Ed., CRC Press, Boca Raton, 1990; incorporated by reference in entirety) can be used to formulate the compositions of the invention.

The present invention can be formulated into any pharmaceutical dosage forms for oral, topical, rectal, vaginal, nasal, or ophthalmic administration, and include syrups and suspensions, and commonly known ingredients and procedures to formulate pharmaceutical composition are within the purview of a person skilled in the art, including various known methods (U.S. Pat. Nos. 4,221,778, 4,762,709, 4,788,055, 4,959,219, 4,996,047, 5,071,646, 4,221,778, and 5,186,930; incorporated herein in their entirety by reference) can be used to formulate the composition of the invention.

The oral formulations and the tablet formulations include enteric coating layered formulations that comprise a separating layer to separate the acidic enteric coating material from omeprazole being an acid susceptible substance. HPC or other suitable polymers disclosed herein may be used in a layer that separates the core material from the enteric coating layer in the described formulations.

Synthetic Methods

SGL hydrochloride (CAS NO.: 135159-51-2), with its systematic name of Butanedioic acid, mono(2-(dimethylamino)-1-((2-(2-(3-methoxyphenyl) ethyl) phenoxy) methyl) ethyl) ester, hydrochloride, could be produced through many synthetic methods (Chen et al., A practical synthesis of sarpogrelate hydrochloride and in vitro platelet aggregation inhibitory activities of its analogues, Chinese Chemical Letters, Volume 21, Issue 3, March 2010, Pages 287-28; J Med Chem 33(6) (1990); CN103242179 A; WO2015008973; incorporated by reference in entirety).

The reaction of 2-hydroxy-3'-methoxybibenzyl with epichlorohydrin by means of a base in a suitable solvent gives 2-(2,3-epoxypropoxy)-3'-methoxybibenzyl, which by reaction with dimethylamine in refluxing in a suitable solvent yields 2-[3-(dimethylamino)-2-hydroxypropoxy]-3'-methoxybibenzyl. Finally, this compound is treated with succinic anhydride while refluxing in a suitable solvent with an acid.

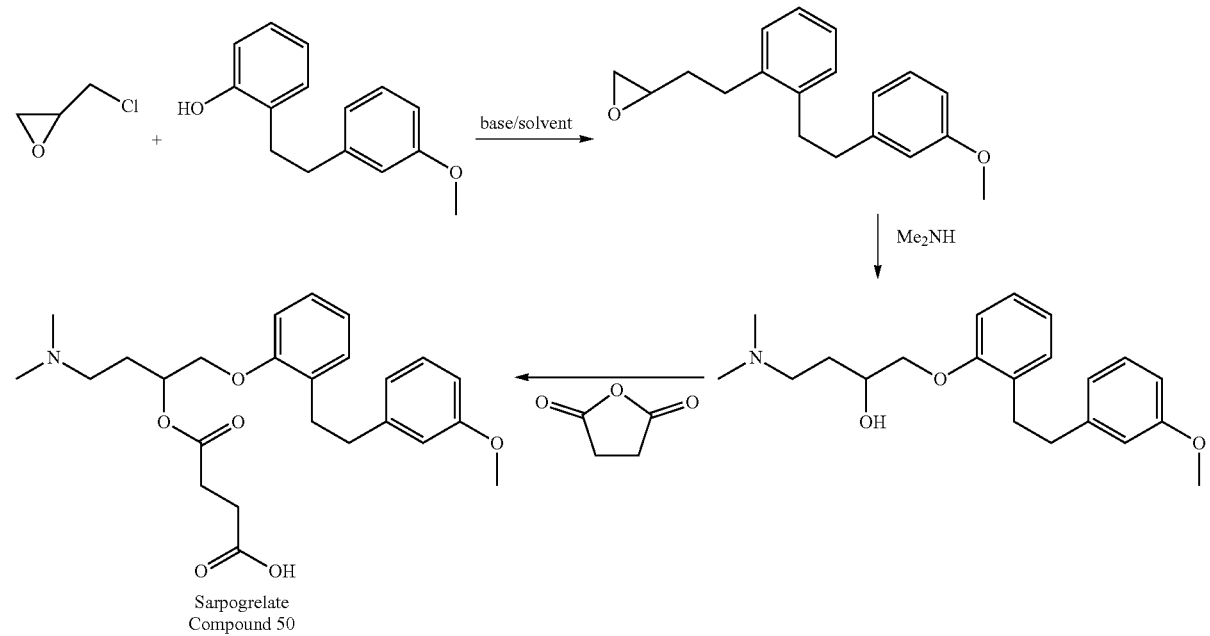

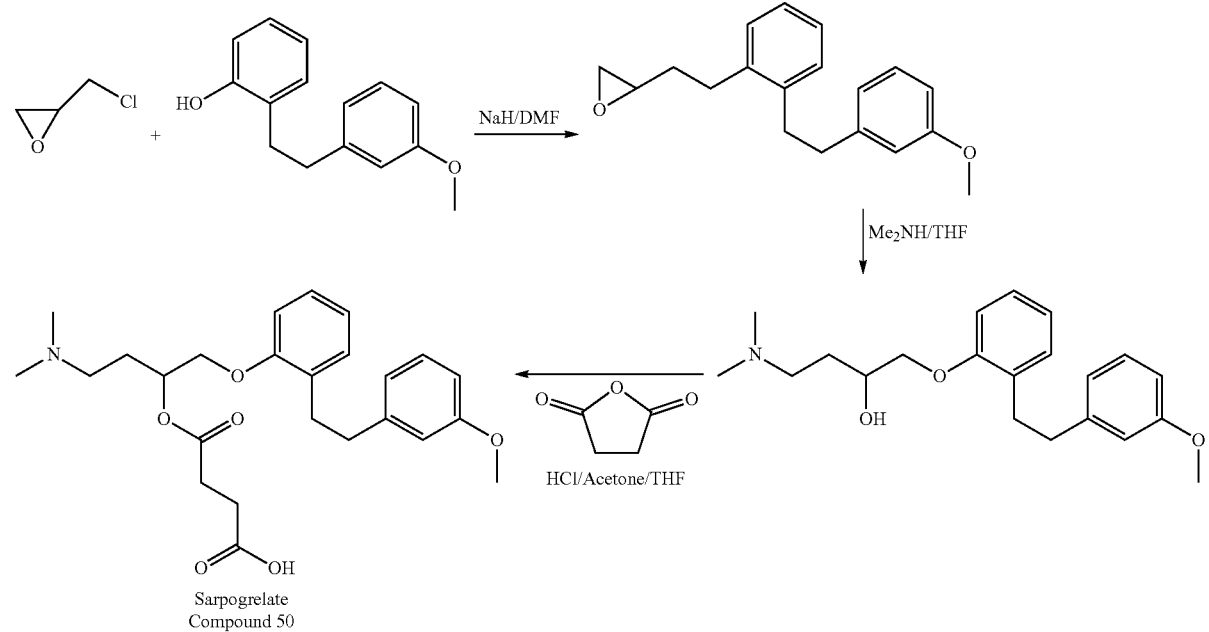

As shown in the scheme below, the reaction of 2-hydroxy-3'-methoxybibenzyl with epichlorohydrin by means of a base NaH in DMF gives 2-(2,3-epoxypropoxy)-3'-methoxybibenzyl, which by reaction with dimethylamine in refluxing THF yields 2-[3-(dimethylamino)-2-hydroxypropoxy]-3'-methoxybibenzyl. Finally, this compound is treated with succinic anhydride in refluxing THF and with HCl in acetone (*J Med Chem* 33(6) (1990), incorporated by reference herein).

SGL hydrochloride was synthesized with about 46% overall yield from salicylicaldehyde via benzyl protection, reduction, chlorination, Arbuzov reaction, Wittig-Horner reaction, catalytic hydrogenation to give 2-2-(3-methoxyphenyl)ethyl phenol, which was subjected to react with epichlorohydrin, amination, esterification and salt formation.

SGL hydrochloride drug substance used in the preparation SGL hydrochloride tablets needed to achieve acceptable purity, single hetero content must meet the corresponding requirements. U.S. Pat. No. 4,485,258 discloses a synthesis method of the first SGL hydrochloride, and recrystallized from acetone to obtain, but the experiments show that SGL hydrochloride poor solubility in acetone, acetone, hydrochloric acid is not suitable as a recrystallization solvent SGL. CN101239920A disclosed as acetonitrile, propionitrile, 1,4-dioxane, tetrahydrofuran, dimethyl formamide, dimethyl acetamide, sulfolane, dimethyl sulfoxide or a mixture of more than two kinds thereof with methanol, ethanol, acetone, ethyl acetate, diethyl ether, diisopropyl ether or the like can be used as the recrystallization solvent SGL hydrochloride, the purity of the product can reach 98%. And $C_{2-10}$ alkanes, $C_{3-10}$ ketones, $C_{2-10}$ carboxylic acid esters, $C_{1-10}$ halogenated alkanes, aromatic hydrocarbons or aromatic derivative at room temperature to the reflux temperature of the hydrochloric acid solubility is small should not alone SGL as a recrystallization solvent, SGL hydrochloride, and water as a recrystallization solvent or an organic solvent, an aqueous 5% or more cannot be obtained a high purity product. Existing literature does not mention the issue of a single impurity content control.

Enantiomerically pure form of SGL can be produced using chiral ligands to induce formation of a single enantiomer of choice as shown below:

Scheme II

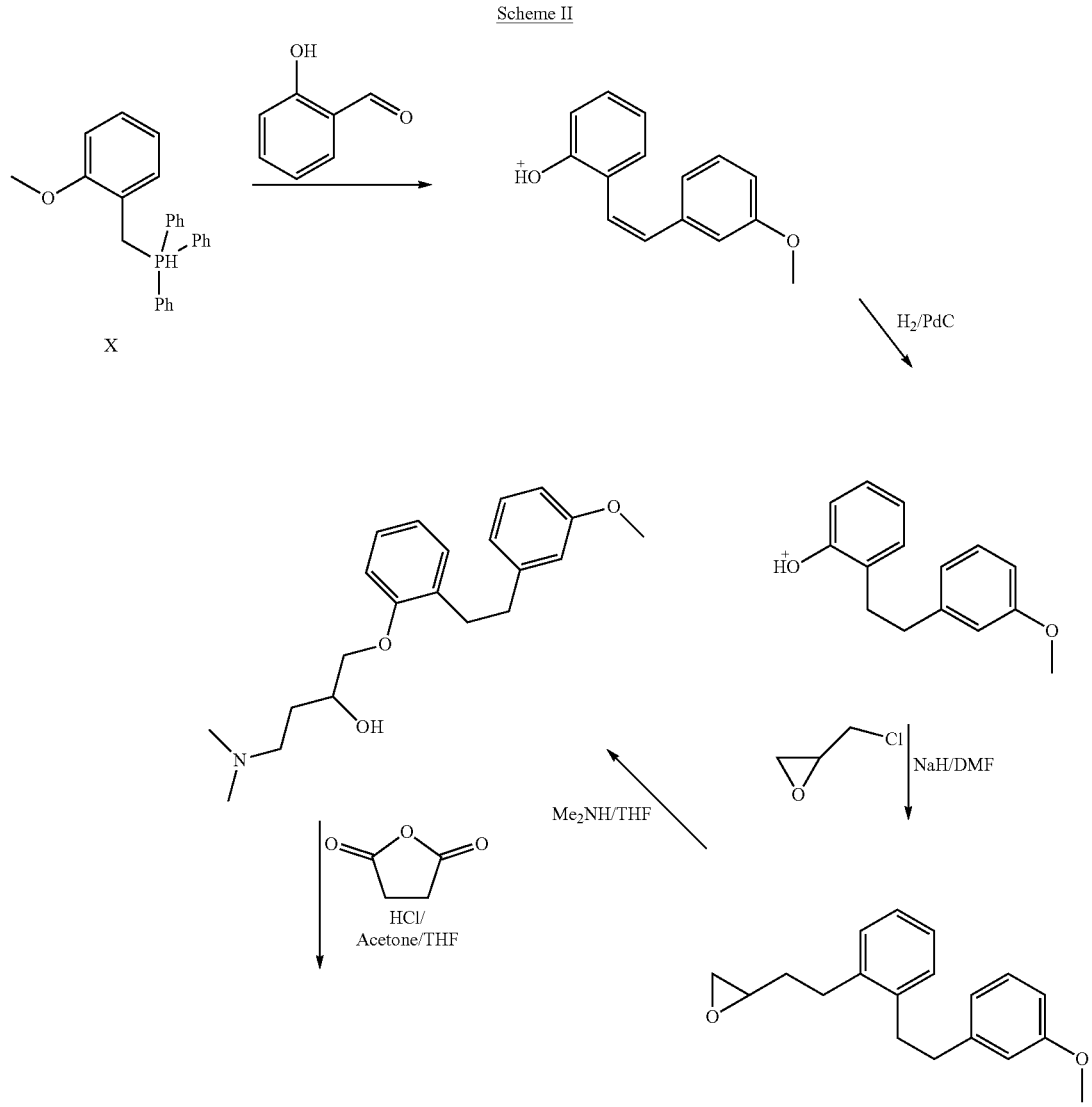

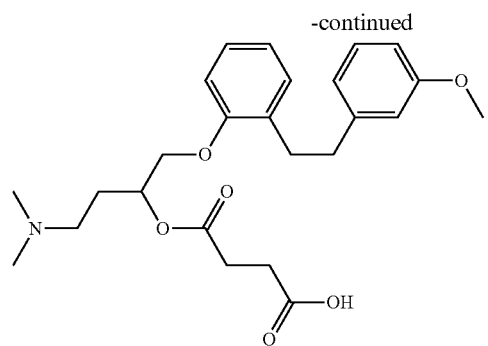
Sarpogrelate
Compound 50
Scheme III
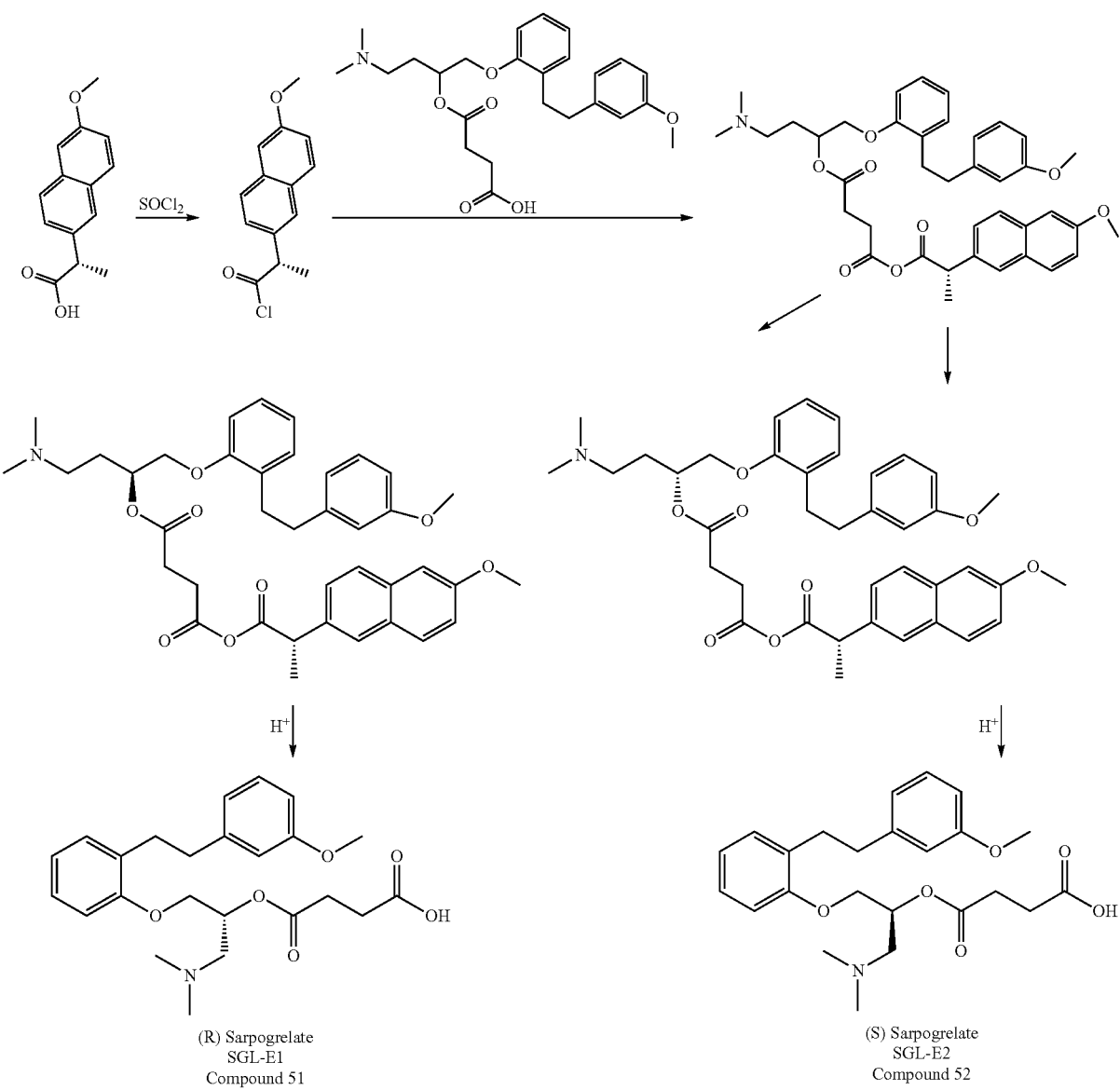
(R) Sarpogrelate
SGL-E1
Compound 51
(S) Sarpogrelate
SGL-E2
Compound 52

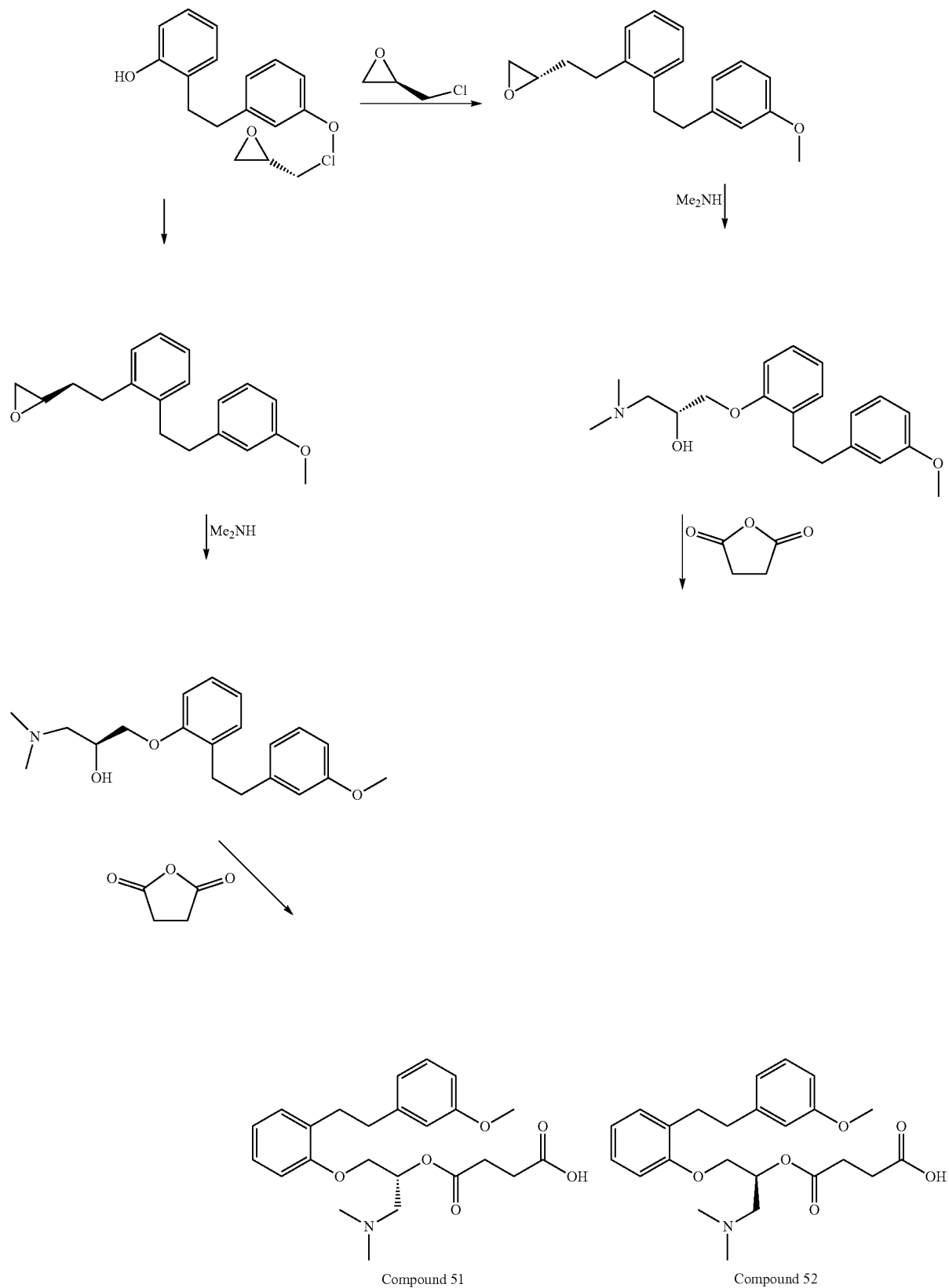

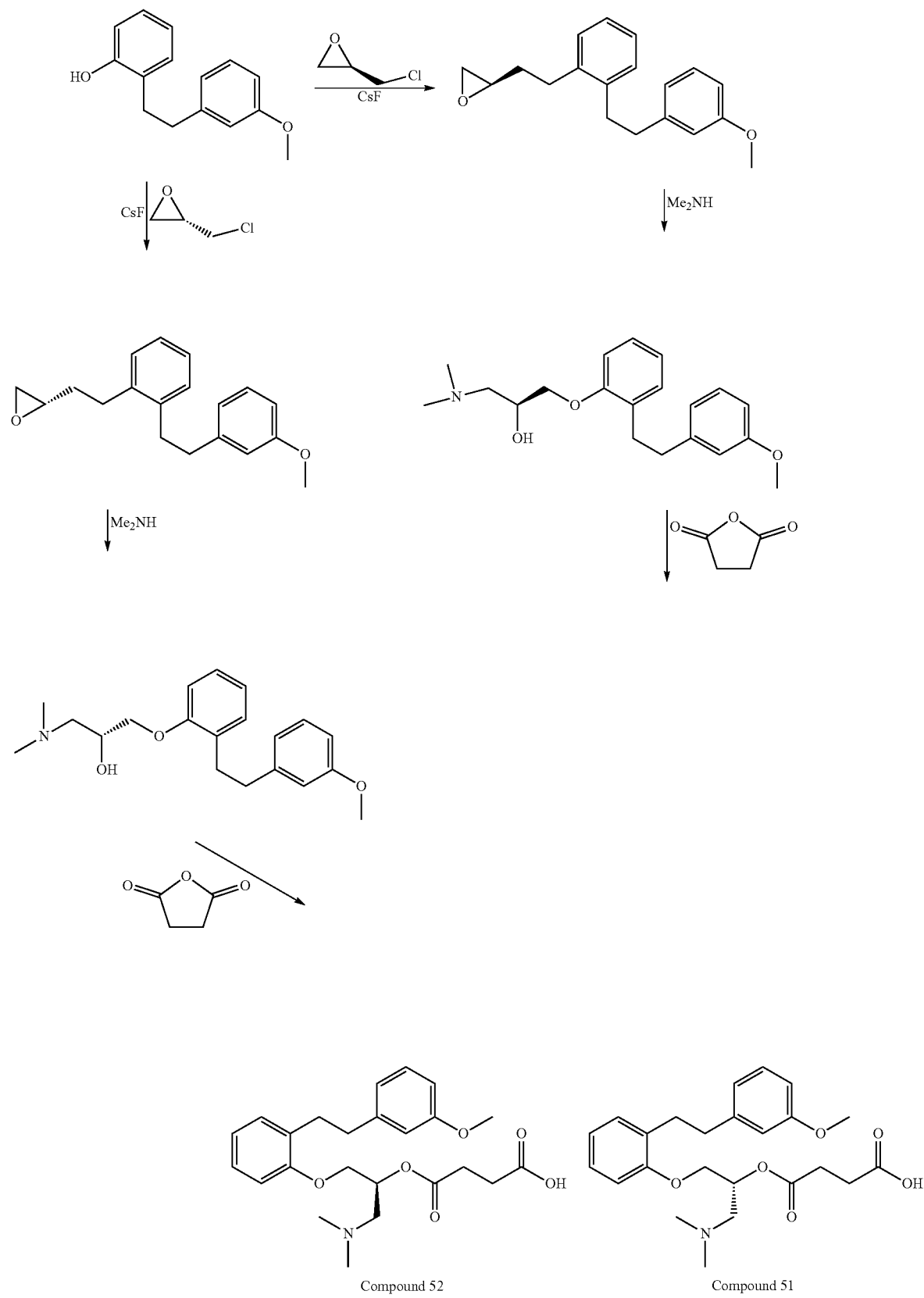

Scheme VI
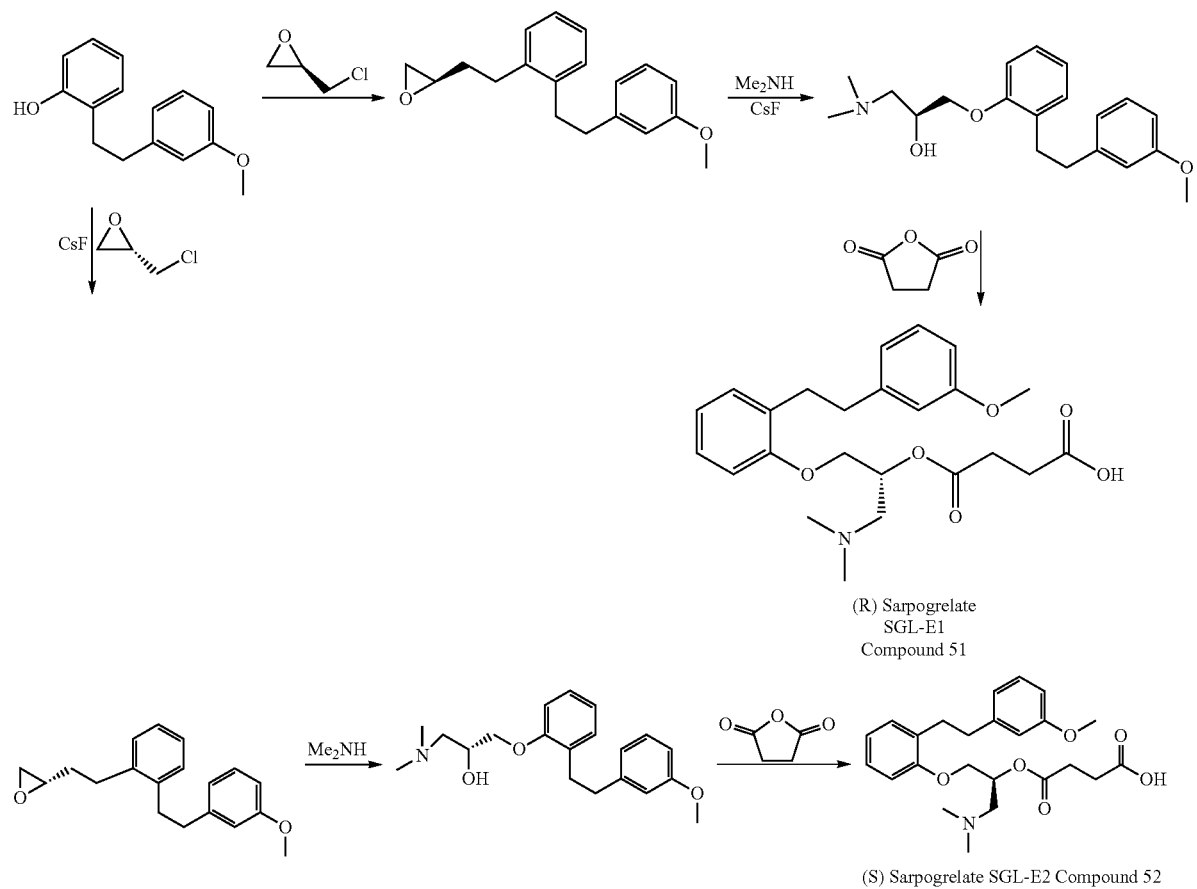
Scheme VII
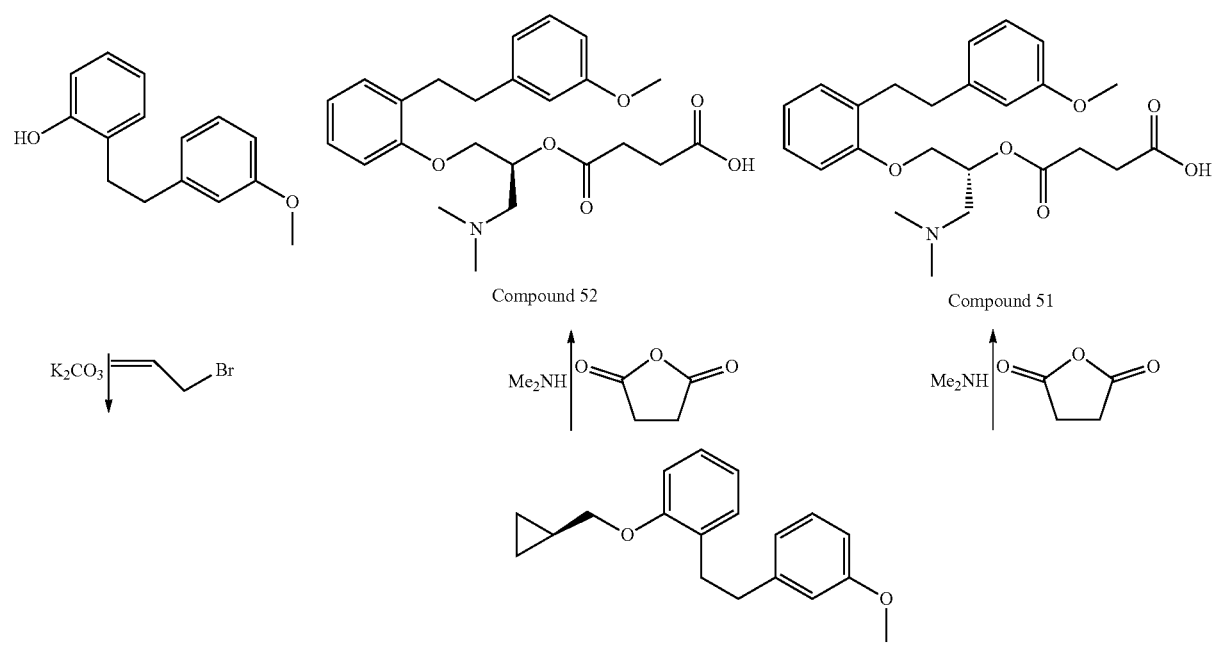

201 202
-continued
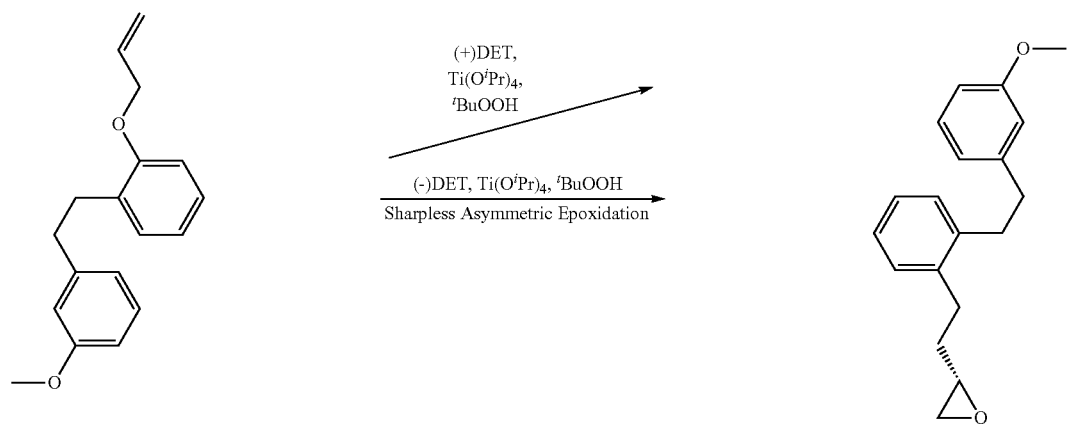
Scheme VIII
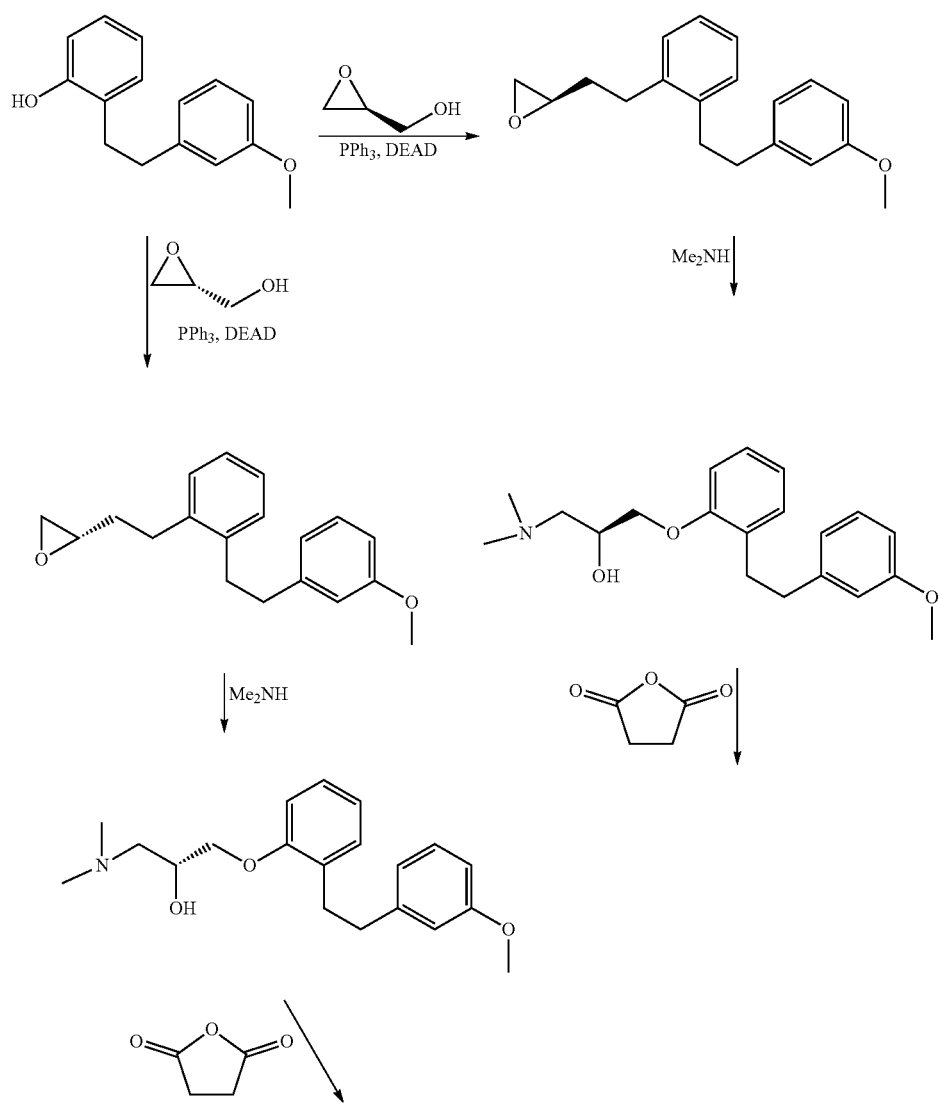

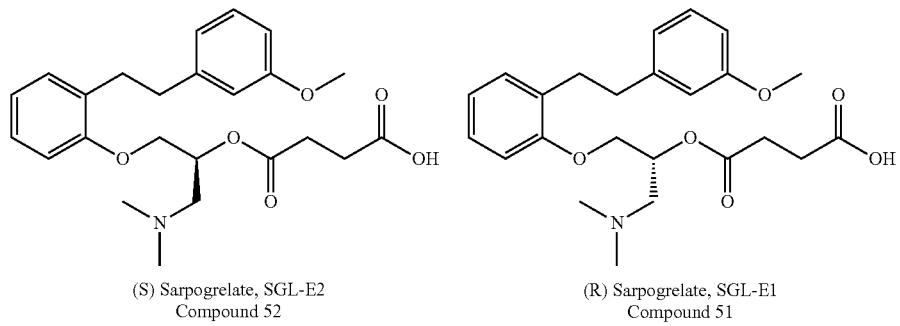
(S) Sarpogrelate, SGL-E2
Compound 52
(R) Sarpogrelate, SGL-E1
Compound 51
Scheme VIIIa
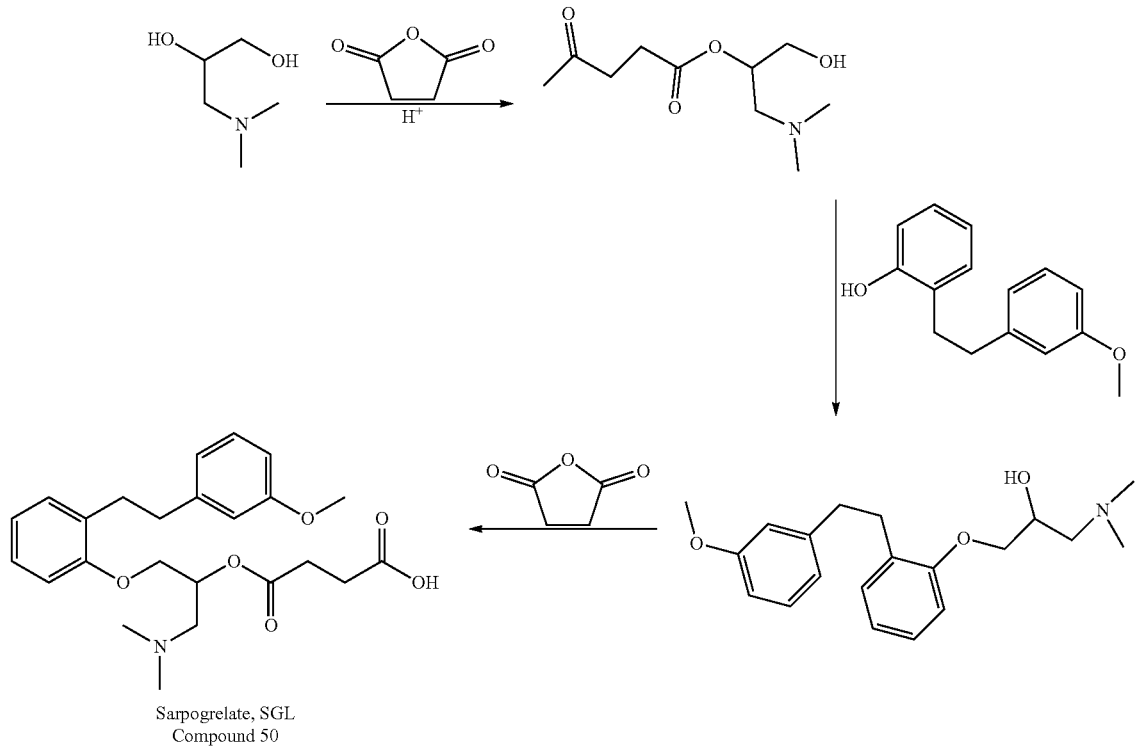
Sarpogrelate, SGL
Compound 50
Scheme VIIIb
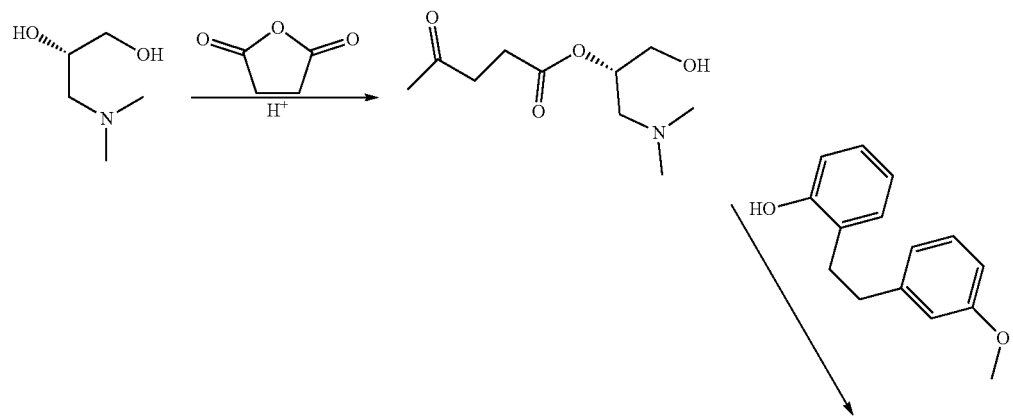

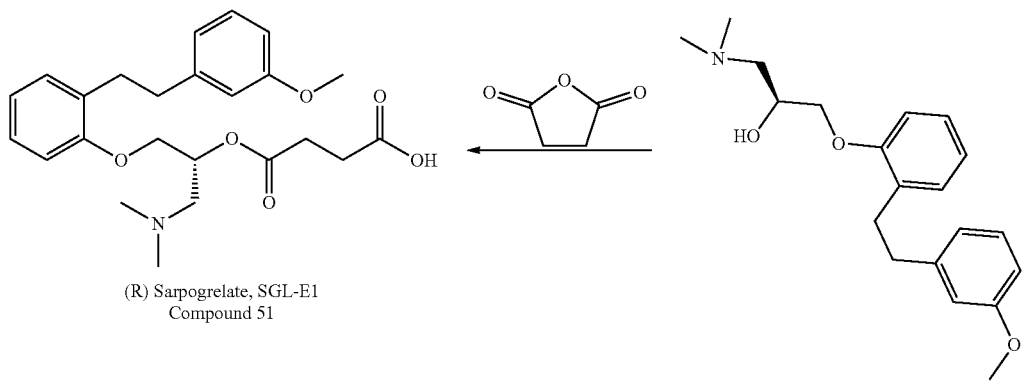
(R) Sarpogrelate, SGL-E1
Compound 51
Scheme VIIIc
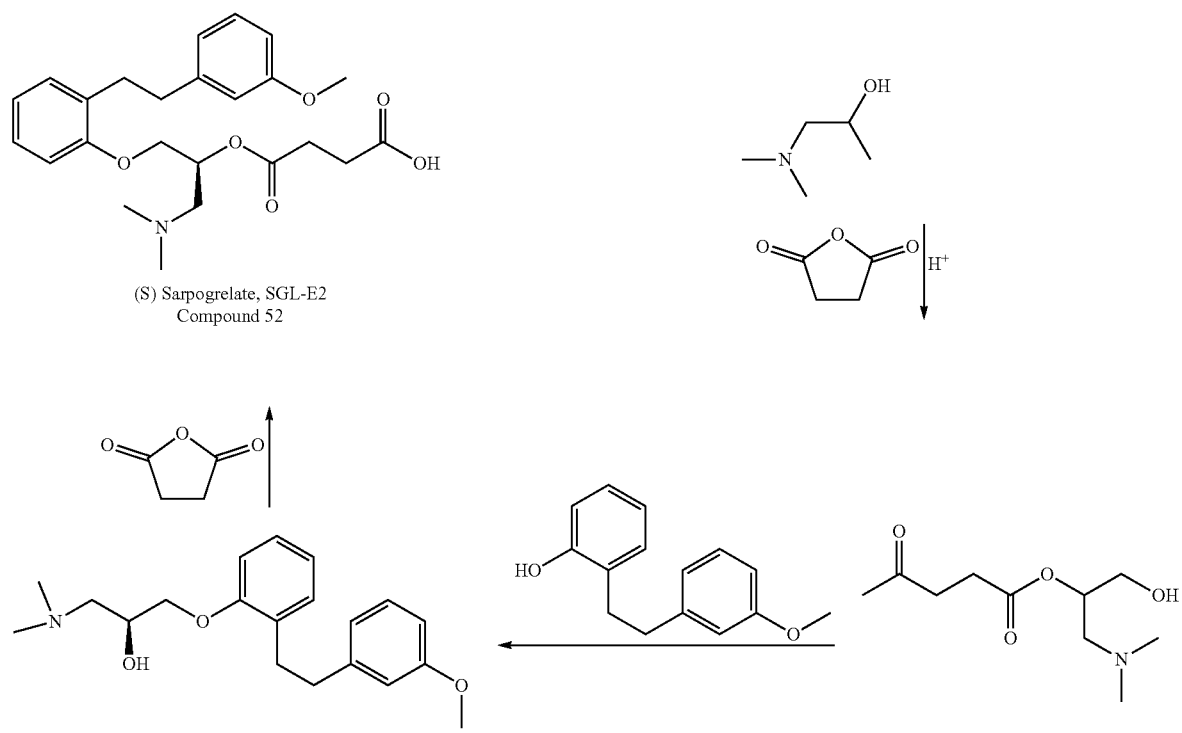
(S) Sarpogrelate, SGL-E2
Compound 52
Scheme IX
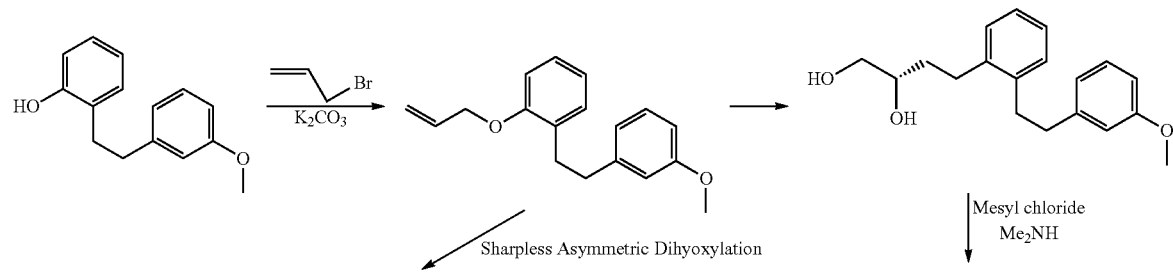
Sharpless Asymmetric Dihyoxylation
Mesyl chloride
Me₂NH

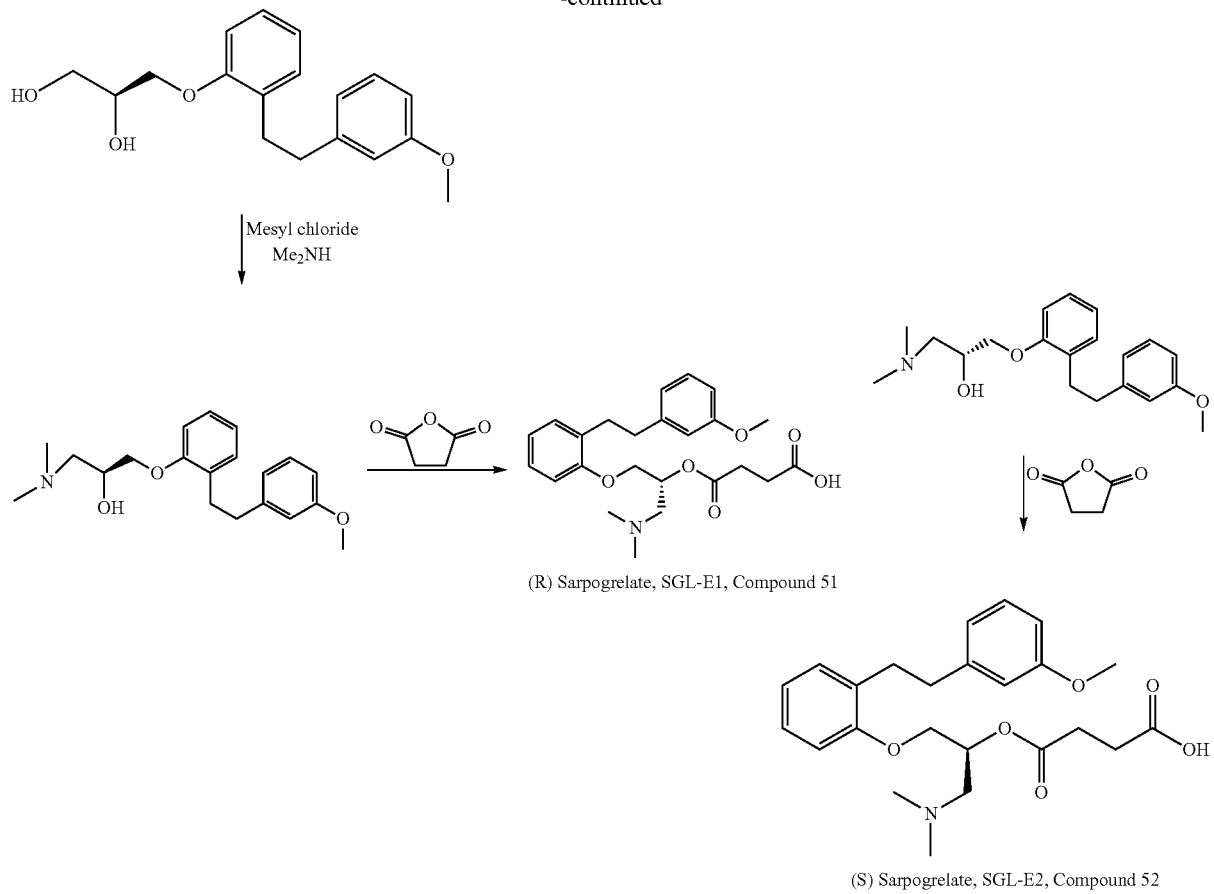

(R) Sarpogrelate, SGL-E1, Compound 51

(S) Sarpogrelate, SGL-E2, Compound 52

Chiral organic compounds play an important role in pharmaceuticals, agrochemicals and other materials which possess useful biological activity. Enzymes and other natural binding sites recognize substrates with particular chirality to generate a variety of biological functions. These enzymes or receptor sites are specific in their action, because the enantiomers may exhibit different properties due to the chirality. Hence for biologically active compounds, it is possible that only one of the enantiomer is active and the other is devoid of activity, both enantiomers are active but they have different potencies or both the enantiomers have similar or equal activities. Therefore, the production of enantiomerically pure molecules of drugs is of interest and the methodology has three basic strategies, 1) resolution (2) use of chiral building blocks and (3) asymmetric synthesis. Asymmetric synthesis provides by far the most efficient use of one chiral material to prepare another.

The preparation of enantiomerically pure molecules of biological interest can be effectively achieved by asymmetric synthesis. This method involves the creation of one or more chiral centers from prochiral starting materials under the influence of chiral substrates. The preparation of enantiomerically pure compounds involves use of chiral auxiliaries, chiral reagents or chiral catalysts, or a combination thereof.

In another embodiment, the compounds of the disclosure can be prepared from (2R)-3-(dimethylamino)-1,2-propanediol and (2S)-3-(dimethylamino)-1,2-propanediol (Scheme VIII).

Various versatile and convenient chiral carboxylic acid ligands are available in the literature such as mandelic acid, 2-metylmandelic acid, 2-chloromandelic acid, 3-chloromandelic acid, 4-methoxymandelic acid, O-acetylmandelic acid, α-methoxyphenylacetic acid, malic acid, tartaric acid, etc. The chiral ligands can be prepared from readily available building blocks. (Moloney et al., Chiral carboxylic acid ligands derived from camphoric acid, Tetrahedron: Asymmetry, Volume 7, Issue 9, September 1996, Pages 2551-2562; U.S. Pat. No. 7,230,135 B2; Product: (S)-2-Amino-1,2,3,4-tetrahydro-6-methoxy-naphthalene, Chiral Quest Corp; Ager (Ed), CHAPTER I Chiral Hydroxy Compounds As Ligands In Asymmetric Synthesis, Handbook of Chiral Chemicals, Second Edition; Hu et al., Adventure in Asymmetric Hydrogenation: Synthesis of Chiral Phosphorus Ligands and Asymmetric Hydrogenation of Heteroaromatics, Top Organomet Chem 36:313-354 (2011); Ishihara et al., An extremely simple, convenient, and selective method for acetylating primary alcohols in the presence of secondary alcohols, J. Org. Chem., 58 (15), pp 3791-3793 (1993); Edwards et al., The stereoselective replacement of hydroxyl groups by chlorine, using the mesyl chloride-N,N-dimethylformamide reagent, Carbohydrate Research, Volume 35, Issue 1, Pages 111-129 (July 1974); incorporated by reference in entirety).

Formation of the diastereomeric compounds and salts is carried out in a suitable reaction medium. Suitable reaction media include water, methanol, ethanol, 1-propanol, 2-propanol, diethyl ether, methyl tert-butyl ether, tetrahydrofuran, acetic acid, methyl acetate, ethyl acetate, isopropyl acetate, butyl acetate, acetone, methyl ethyl ketone, methyl isobutyl ketone, acetonitrile, methylene chloride, chloroform, 1,2-dichloroethane, benzene, toluene and xylenes, and/or mixtures thereof.

Sarpodexter™ and Sarpodexamide™

Amidation/Acylation (WO1998043961).

Linkers that can be used in the synthesis of SARPODEX-AMIDE™ Derivatives in the above scheme include, but not limited to, linkers (described in Simplicio et al., Prodrugs for Amines, Molecules 13, 519-547 (2008); Mahato et al., Prodrugs for Improving Tumor Targetability and Efficiency, Adv Drug Deliv Rev. 63(8): 659-670 (2011 Jul. 18); Jornada et al., The Prodrug Approach: A Successful Tool for Improving Drug Solubility, Molecules 21, 42 (2016); Jain et al., Mutual prodrugs containing bio-cleavable and drug releasable disulfide linkers, Bioorganic Chemistry 49C:40-48 (July 2013); US20130053301, WO2011089216A1; WO2006136586 A2; U.S. Pat. No. 7,932,294; US 20060046967 A1; U.S. Pat. Nos. 8,357,723; 8,349,901; 8,354,455; 9,550,734; US20160220694; US20160002167; US20150328323; U.S. Pat. No. 9,090,563; US20140058063; US20130158271; U.S. Pat. No. 8,288,557; US20110274695; WO1998043961; incorporated by reference in entirety).

Esterification

Esters are derived from carboxylic acids. A carboxylic acid contains the —COOH group, and in an ester the hydrogen in this group is replaced by a hydrocarbon group R' such as an alkyl, cycloalkyl, an aryl, and a hetero-aryl group. Esters are produced when carboxylic acids are heated with alcohols in the presence of an acid catalyst. The catalyst is an acid, usually concentrated sulfuric acid. Dry hydrogen chloride gas can be used in some cases. TsOH (tosic acid) is also often used.

The esterification reaction is both slow and reversible. The equation for the reaction between an acid RCOOH and an alcohol R'OH (where R and R' can be the same or different) is:

Scheme XI

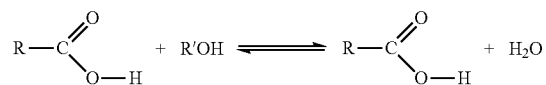

The alcohol is generally used as solvent so is present in large excess. (WO 1998043961).

Sarpodexter™

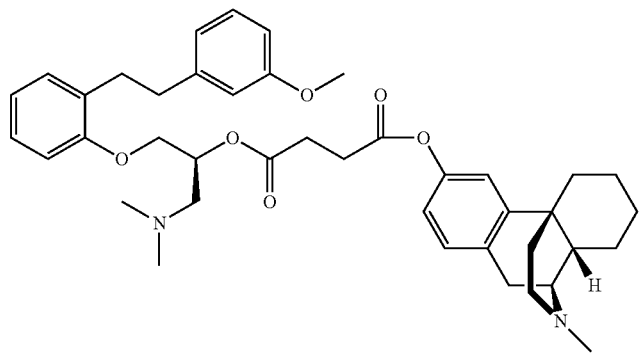

Compound 165
Diatereomer Sarpodex-amide
(S)-1-(dimethylamino)-3-(2-(3-methoxyphenethyl)phenoxy)propan-2-yl((4bS,8aS,9S)-11-methyl-6,7,8,8a,9,10-hexahydro-5H-9,4b-(epiminoethano)phenanthren-3-yl) succinate

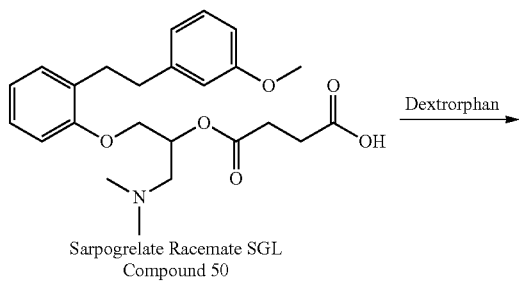

Sarpogrelate Racemate SGL
Compound 50

Dextrorphan →

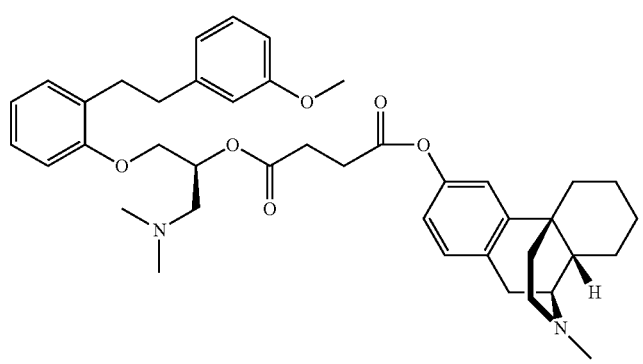

Compound 166
Diatereomer Sarpodex-amide
(S)-1-(dimethylamino)-3-(2-(3-methoxyphenethyl)phenoxy)propan-2-yl(((4bS,8aS,9S)-11-methyl-6,7,8,8a,9,10-hexahydro-5H-9,4b-(epiminoethano)phenanthren-3-yl) succinate In another embodiment of preparation of the compositions of the application, the diastereomerically pure SARPODEXTER can be obtained by reacting the racemic sarpogrelate with optically pure dextrorphan (DO-H₃, compound 151) under mild esterification conditions to obtain a mixture of diastereomeric esters, compounds 165-166, which can be separated by crystallization and chromatographic techniques mentioned above and the techniques described in this specification to obtain diastereomerically pure SARPODEXTERs 165 and 166.

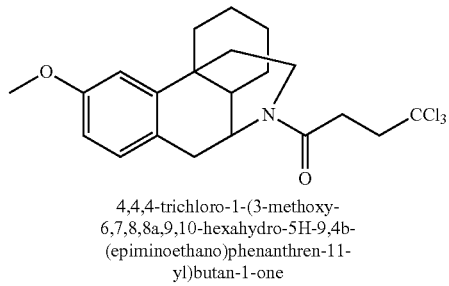

4,4,4-trichloro-1-(3-methoxy-6,7,8,8a,9,10-hexahydro-5H-9,4b-(epiminoethano)phenanthren-11-yl)butan-1-one The trichloroethoxycarbonyl above can be converted to N-desmethyl dextromethorphan by heating to reflux in presence of powdered zinc in glacial acetic acid.

The N-desmethyl dextromethorphan obtained as described above or purchased (CAS Number: 125-71-3) can be treated with trifluoromethansulfonic anhydride and pyridine at room temperature (as described in Liebigs Ann. Chem. 1986, 336, and WO1998043961, incorporated herein in its entirety).

Optically Pure Sarpodexamide

EXAMPLES

Preparation of Sarpodexamide™ Derivatives

A compound of Formula I or Sarpodexamide™ derivatives can be obtained by reacting dextromethorphan either as a single isomer or a mixture thereof with 2,2,2-trichloroethyl chloroformate in refluxing toluene thus obtaining the N-demethylated compound.

Scheme XIII

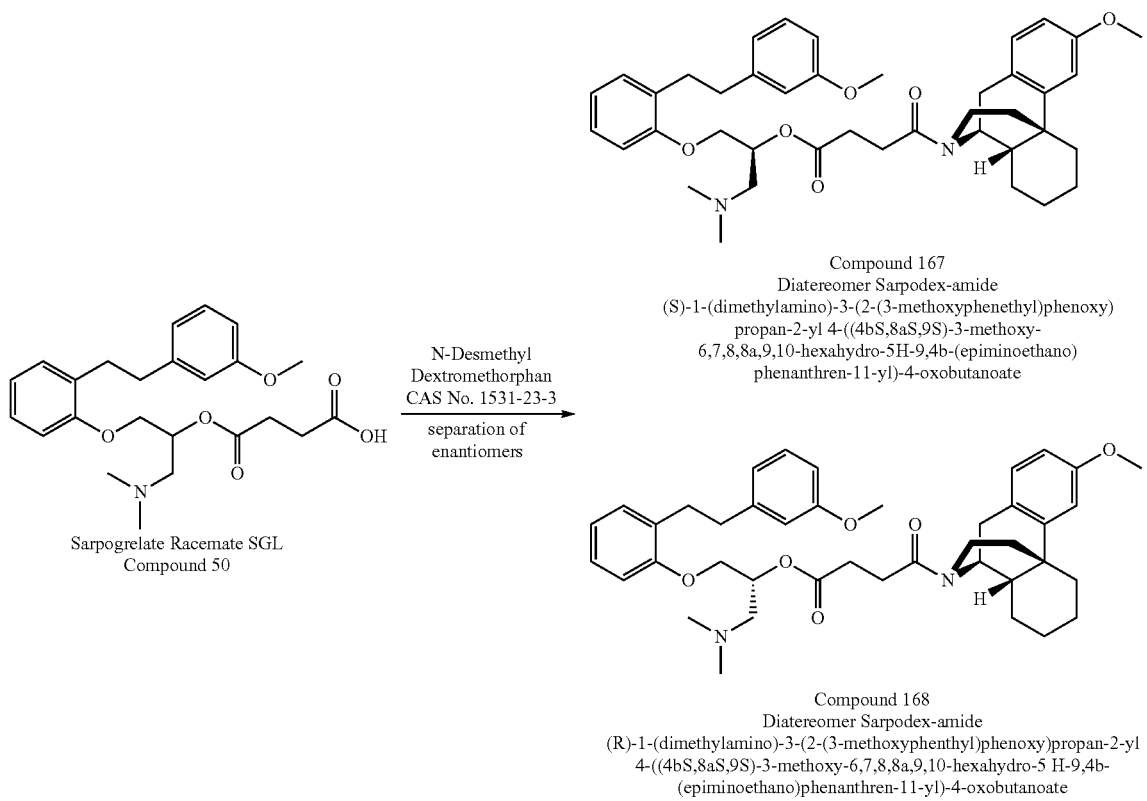

Compound 167
Diatereomer Sarpodex-amide
(S)-1-(dimethylamino)-3-(2-(3-methoxyphenethyl)phenoxy)propan-2-yl 4-((4bS,8aS,9S)-3-methoxy-6,7,8,8a,9,10-hexahydro-5H-9,4b-(epiminoethano)phenanthren-11-yl)-4-oxobutanoate Sarpogrelate Racemate SGL
Compound 50

N-Desmethyl Dextromethorphan
CAS No. 1531-23-3
separation of enantiomers

Compound 168
Diatereomer Sarpodex-amide
(R)-1-(dimethylamino)-3-(2-(3-methoxyphenthyl)phenoxy)propan-2-yl 4-((4bS,8aS,9S)-3-methoxy-6,7,8,8a,9,10-hexahydro-5 H-9,4b-(epiminoethano)phenanthren-11-yl)-4-oxobutanoate As shown in Scheme XIII, amides (S)-1-(dimethyl-amino)-3-(2-(3-methoxyphenethyl) phenoxy) propan-2-yl 4-((4bS,8aS,9S)-3-methoxy-6,7,8,8a,9,10-hexahydro-5H-9,4b-(epiminoethano) phenanthren-11-yl)-4-oxobutanoate (Compound 167) and (R)-1-(dimethylamino)-3-(2-(3-methoxyphenethyl)phenoxy)propan-2-yl 4-((4bS,8aS,9S)-3-methoxy-6,7,8,8a,9,10-hexahydro-5H-9,4b-(epimino-ethano)phenanthren-11-yl)-4-oxo butanoate (compound 168) can be obtained from sarpogrelate by amidation with N-desmethyl dextromethorphan using HBTU in combination with Hünig's base in 1-2 h. Reagents such as uronium salt (1-cyano-2-ethoxy-2-oxoethylidenaminooxy) dimethyl-amino morpholino carbenium hexafluorophosphate (COMU), ethyl 2-cyano-2-(2-nitrobenzenesulfonyloxy-imino) acetate (o-NosylOXY), EDCI and NaHCO$_3$, B(OCH$_2$CF$_3$)$_3$, trimethylaluminium, Lanthanum trifluo-romethanesulfonate, ZrOCl$_2$.8 H$_2$O, methanesulfonyl chloride and N-methylimidazole, N,N'-carbonyldiimidazole (CDI), etc. can be used.

Optically Pure Dex, Formula I, Sarpodex™, Deradex™, or Deraphan™ Salt

In one embodiment, this separation process may be performed on a compound containing a mixture of at least one pair of diastereomers, and the diastereomers may be separated by contacting the mixture with at least one ionic liquid in which one of the diastereomers is soluble to a greater extent than the other diastereomer, and separating the lower-solubility diastereomer from the mixture. The inventions disclosed herein thus include processes for the separation of diastereomers, the use of such processes, and the products obtained and obtainable by such processes.

In another embodiment, this separation process may be performed on a compound such as a diastereomeric mixture of DERATINE™, SARPOTINE™, SARPODEX™, DERADEX™, or DERAPHAN™ salt wherein, the diastereomers are separated by contacting the mixture with at least one ionic liquid in which one of the diastereomers is soluble to a greater extent than the other diastereomer, and separating the lower-solubility diastereomer from the mixture.

In yet another embodiment, there is provided a process for separating the erythro or threo diastereomers of DERATINE™, SARPOTINE™, SARPODEX™, DERADEX™, Scheme XIV

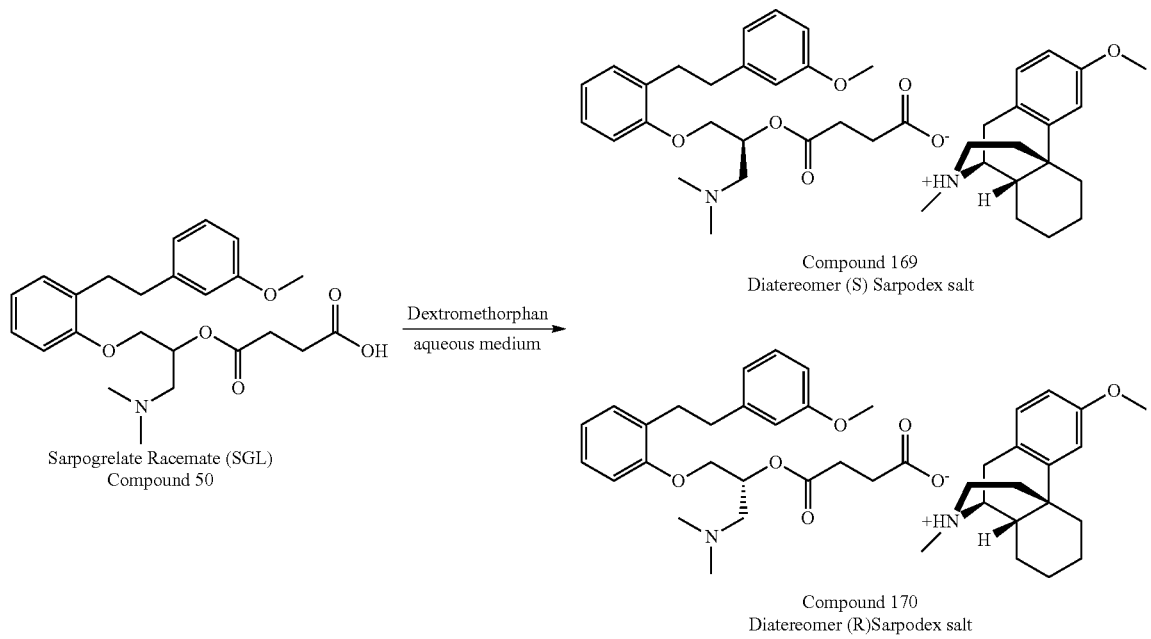

Compound 50 and compound 149 form a diastereomeric salt mixture of dextromethorphan (S)-4-((1-(dimethyl-amino)-3-(2-(3-methoxyphenethyl)phenoxy)propan-2-yl) oxy)-4-oxobutanoate (S-SARPODEX™) salt and dextromethorphan (R)-4-((1-(dimethylamino)-3-(2-(3-methoxyphenethyl)phenoxy)propan-2-yl)oxy)-4-oxobutanoate (R-SARPODEX™) salt in chloroform or other suitable solvents such as dichloromethane, DMF, etc., which can be separated by crystallization and recrystallization in suitable solvents such DMF and/or chromatographic techniques referred to and described in this specification.

In one embodiment, provided is a process for separating the diastereomers of a compound by using an ionic liquid to increase separation efficiency. When the diastereomers are separated, for example, by a process such as liquid-liquid extraction, one or more ionic liquids may be used as the extractant.

or DERAPHAN™ from a mixture comprising both diastereomers by liquid-liquid extraction using at least one ionic liquid as an extractive solvent.

Another embodiment is a process for performing an industrial operation selected from the group consisting of a calibration operation, a cleaning operation, a rinsing operation, a drying operation, a particulate removal operation, a solvent operation, a dispersion operation, a heat transfer operation, and an insulating operation, comprising contacting a mixture comprising a pair of diastereomers of DERATINE™, SARPOTINE™, SARPODEX™, DERADEX™, or DERAPHAN™ with at least one ionic liquid in which one of the diastereomers is soluble to a greater extent than the other diastereomer, separating the lower-solubility diastereomer from the mixture, and employing the separated diastereomer in the operation.

Another embodiment is a process for separating one diastereomer from another diasteromer in a pair of diastereomers in a compound. In such a process, an ionic liquid is used to facilitate the separation, and the diastereomers may be separated by contacting the mixture with at least one ionic liquid in which one of the diastereomers is soluble to a greater extent than the other diastereomer, and separating the lower-solubility diastereomer from the mixture.

The term "ionic liquid" is defined as an organic salt that is fluid at or below about 100° C.

"Liquid-liquid extraction" is a process for separating components in solution by their distribution between two immiscible liquid phases. Liquid-liquid extraction involves the transfer of mass from one liquid phase into a second immiscible liquid phase, and is carried out using an extractant or solvent.

Components in a liquid mixture can be separated by a process such as liquid-liquid extraction using a single equilibrium (or theoretical) stage, or using multiple stages. An equilibrium, or theoretical, stage is a device that allows intimate mixing of a feed with an immiscible liquid such that concentrations approach equilibrium, followed by physical separation of the two immiscible liquid phases. A single stage device can be a separatory funnel, or an agitated vessel, which allows for intimate mixing of the feed with the immiscible extractant. Following intimate mixing, one or both of the liquid phases can be recovered, for example, by decantation.

Multiple stage devices for liquid separation can be crosscurrent or countercurrent devices. In a multiple stage device, the feed enters a first equilibrium stage and is contacted with an extractant. The two liquid phases are mixed, with droplets of one phase suspended in the second phase, and then the two phases are separated, and DERATINE™, SARPOTINE™, SARPODEX™, DERADEX™, or DERAPHAN™ from the first stage is contacted with additional extractant, and the separation process is repeated. The process of (1) contacting DERATINE™, SARPOTINE™, DERADEX™, DERAPHAN™, or SARPODEX™ with extractant, (2) allowing for equilibrium concentrations to be approached, and (3) separating the liquid phases is repeated until the desired purity of the component of interest is achieved. The number of equilibrium stages will depend on the desired purity, as well as the solubility of the components in the extractant and the flow rates of the feed and extractant.

In a crosscurrent system (or device), the feed is initially contacted with extractant in a first equilibrium stage. DEX, Formula I, DERATINE™, SARPOTINE™, SARPODEX™, DERADEX™, or DERAPHAN™ from this stage then cascades down through one or more additional stages. At each stage, the composition is contacted with fresh extractant, and further purification of the desired component in the composition is achieved. An example of a crosscurrent system where the threo isomer of the composition is purified using the ionic liquid 1-butyl-3-methylimidazolium tetrafluoroborate ([BMIM][BF$_4$] as the extractant. In a countercurrent system or device, the extractant enters at the stage farthest from the feed, and the two phases are passed through and across each other, coming from the two different (e.g. opposite) directions.

Equipment used for liquid-liquid extraction can be classified as "stagewise" or "continuous (differential) contact" equipment. Stagewise equipment is also referred to as "mixer-settlers". Mixing the liquids occurs by contacting the feed with the extractant, and the resultant dispersion is settled as the two phases separate. Mixing can occur with the use of baffles or impellers, and the separation process may be carried out in batch fashion or with continuous flow. Settlers can be simple gravity settlers, such as decanters, or can be cyclones or centrifuges, which enhance the rate of settling.

Continuous contact equipment is typically arranged for multistage countercurrent contact of the immiscible liquids, without repeated separation of the liquids from each other between stages. Instead, the liquids remain in continuous contact throughout their passage through the equipment. Countercurrent flow is maintained by the difference in densities of the liquids and either the force of gravity (vertical towers) or centrifugal force (centrifugal extractors). Gravity-operated extractors can be classified as spray towers, packed towers or perforated-plate (sieve-plate) towers. Gravity-operated towers also include towers with rotating stirrers and pulsed towers as is known in the art.

When the diastereomers of a compound of the composition, and in particular the threo and erythro isomers of 2,3-dihydrodecafluoropentane, are separated by a process such as liquid-liquid extraction, any of the equipment described above can be used to perform the separation. In one preferred embodiment, the separation is carried out using a vertical tower with perforated plates. After separation of the phase containing the lower-solubility diastereomer from the phase containing the extractant and the higher-solubility diastereomer, the higher solubility diastereomer may be separated from the extractant by a process such as distillation.

The transfer of mass from one liquid phase into a separate immiscible phase by liquid-liquid extraction, and equipment for use therein, is discussed further in sources such as Robbins and Cusack, "Liquid-Liquid Extraction Operations and Equipment" in Perry's Chemical Engineers' Handbook, 7$^{th}$ Ed., (McGraw-Hill, 1997, Section 15), incorporated by reference. Known liquid-liquid extraction processes that operate on principles that are the same as or similar to those applicable to the separations described herein include the recovery of acetic acid from water using ethyl ether or ethyl acetate as the extractant (Brown, Chem. Engr. Prog. (1963) 59:65), and the recovery of phenolics from water with methyl isobutyl ketone as the extractant as described by Scheibel in "Liquid-Liquid Extraction" (Perry and Weissburg (eds), Separation and Purification, 3$^{rd}$ Ed. (1978) Chapter 3, John Wiley & Sons, Inc., Hoboken, N.J.), incorporated by reference.

The dielectrical constant of the solvent (if solvent is used at the resolutions) changes the formation, composition and enantiomer recognition of the crystalls (Sakai et al., Tetrahedron: Asymmetry, 14, 3716 (2003); incorporated by reference in entirety). The composition of crystalline diastereoisomers is also influenced by the pH of the reaction mixture (Fogassy et al., J. Chem. Res., S 11, 346 (1981); Fogassy et al., J. Chem. Soc. Perkin Trans. 2. (1988), incorporated by reference in entirety). The purity (de) of the diastereoisomer can be improved using a mixture of structurally related resolving agents. It is often referred as "Dutch resolution" in the literature (Kellogg et al., Synthesis, 1626 (2003), incorporated by reference). If the diastereoisomeric salt cannot be separated by fractionated precipitation, it is feasible to get its crystalline solvate by fractionated precipitation from a solvate forming solution (Schindler et al., Chirality, 19, 239 (2007), incorporated by reference). When the solvent, unsuitable for separation of the diastereoisomers, contains structurally partly similar compounds to the solvate forming solution (U.S. Pat. Nos. 214720, Chem. Abs. 124, 117097 (1995); U.S. Pat. No. 2,133,894; Chem. Abs. 139, 90595 (2001), incorporated by reference), the separation of enantiomers became feasible by fractionated precipitation of the diastereoisomeric salt (Pálovics et al., Separation of the Mixtures of Chiral Compounds by Crystallization, Advances in Crystallization Processes, pp 1-37 (2012), incorporated by reference).

At the crystallization of melts of racemate forming enantiomeric mixtures the eutectic composition usually determinates the composition of the crystallized mixture and the oily residue. That eutectic composition can be known from the binary melting point phase diagram. When the initial isomeric composition (ee0) is higher than the eutectic composition, the pure optical isomer cam be crystallized.

An ionic liquid, or a mixture of two or more thereof, may be used in a process hereof to separate the diastereomers of a compound. When, for example, the diastereomers of DERATINE™, SARPOTINE™, SARPODEX™, DERADEX™, or DERAPHAN™ are separated by a process such as liquid-liquid extraction, the extractant used may be an ionic liquid or a mixture of two or more ionic liquids. Ionic liquids are organic compounds that are liquid at room temperature (approximately 25° C.). They differ from most salts in that they have very low melting points, and they generally tend to be liquid over a wide temperature range. They also generally tend to not be soluble in non-polar hydrocarbons; to be immiscible with water (depending on the anion); and to be highly ionizing (but have a low dielectric strength). Ionic liquids have essentially no vapor pressure, most are air and water stable, and they can either be neutral, acidic or basic.

A cation or anion of an ionic liquid useful herein can in principle be any cation or anion such that the cation and anion together form an organic salt that is liquid at or below about 100° C. The properties of an ionic liquid can, however, be tailored by varying the identity of the cation and/or anion. For example, the acidity of an ionic liquid can be adjusted by varying the molar equivalents and type and combinations of Lewis acids used.

Many ionic liquids are formed by reacting a nitrogen-containing heterocyclic ring, preferably a heteroaromatic ring, with an alkylating agent (for example, an alkyl halide) to form a quaternary ammonium salt, and performing ion exchange or other suitable reactions with various Lewis acids or their conjugate bases to form the ionic liquid. Examples of suitable heteroaromatic rings include substituted pyridines, imidazole, substituted imidazole, pyrrole and substituted pyrroles. These rings can be alkylated with virtually any straight, branched or cyclic $C_{1-20}$ alkyl group, but preferably, the alkyl groups are $C_{1-16}$ groups, since groups larger than this may produce low melting solids rather than ionic liquids. Various triarylphosphines, thioethers and cyclic and non-cyclic quaternary ammonium salts may also been used for this purpose. Counter ions that may be used include chloroaluminate, bromoaluminate, gallium chloride, tetrafluoroborate, tetrachloroborate, hexafluorophosphate, nitrate, trifluoromethane sulfonate, methylsulfonate, p-toluenesulfonate, hexafluoroantimonate, hexafluoroarsenate, tetrachloroaluminate, tetrabromoaluminate, perchlorate, hydroxide anion, copper dichloride anion, iron trichloride anion, zinc trichloride anion, as well as various lanthanum, potassium, lithium, nickel, cobalt, manganese, and other metal-containing anions.

Ionic liquids may also be synthesized by salt metathesis, by an acid-base neutralization reaction or by quaternizing a selected nitrogen-containing compound; or they may be obtained commercially from several companies such as Merck (Darmstadt, Germany) or BASF (Mount Olive, N.J.).

Representative examples of useful ionic liquids are described in sources such as J. Chem. Tech. Biotechnol., 68:351-356 (1997); Chem. Ind., 68:249-263 (1996); J. Phys. Condensed Matter, 5: (supp 34B):B99-B 106 (1993); Chemical and Engineering News, Mar. 30, 1998, 32-37; J. Mater. Chem., 8:2627-2636 (1998); Chem. Rev., 99:2071-2084 (1999); and US 2004/0133058; all of which are incorporated by reference.

In one embodiment, a library of ionic liquids may be prepared, for example, by preparing various alkyl derivatives of a particular cation (such as the quaternary ammonium cation), and varying the associated anions (US 20090131728A1, incorporated in entirety by reference). In another embodiment, the diastereomers of the invention can be separated efficiently by cation exchange with mixed-mode sorbent in the solid phase extraction (SPE) procedure.

In one embodiment, diastereomers can be separated by extractive distillation, wherein an auxiliary which changes the partial pressure of the various diastereomers to be separated to a different degree allowing easier separation of the diastereomers by distillation in a good yield. Separation can be accomplished using fractionating columns, and preferably under reduced pressure of about $10^{-3}$ bar to about 1 bar (U.S. Pat. No. 4,874,473 A, US 20070225505 A1, incorporated in entirety by reference).

In one embodiment, reversed (RP-HPLC) and normal phase chromatographic (NP-HPLC) separations can be used to separate the diastereomers of the invention Columns that can be used in the separation of enantiomers can be Primesep C, NUCLEOSIL, cellulose based chiral HPLC columns, SHISEIDO Chiral CD-Ph, etc. (Fekete et al., Compative Study Separation of Diastereomers by HPLC, Chromatographia, 57, No. ¾ (2003 February), U.S. Pat. No. 7,119,211 B2, incorporated in entirety by reference).

Adamantanylamino-4-Oxobutanoate Derivatives

Using the above protocols for amide and ester formation, the derivatives of compounds 50-52 cn be prepared to obtain amide compounds 1001-1006, and ester compounds 1007-1009:

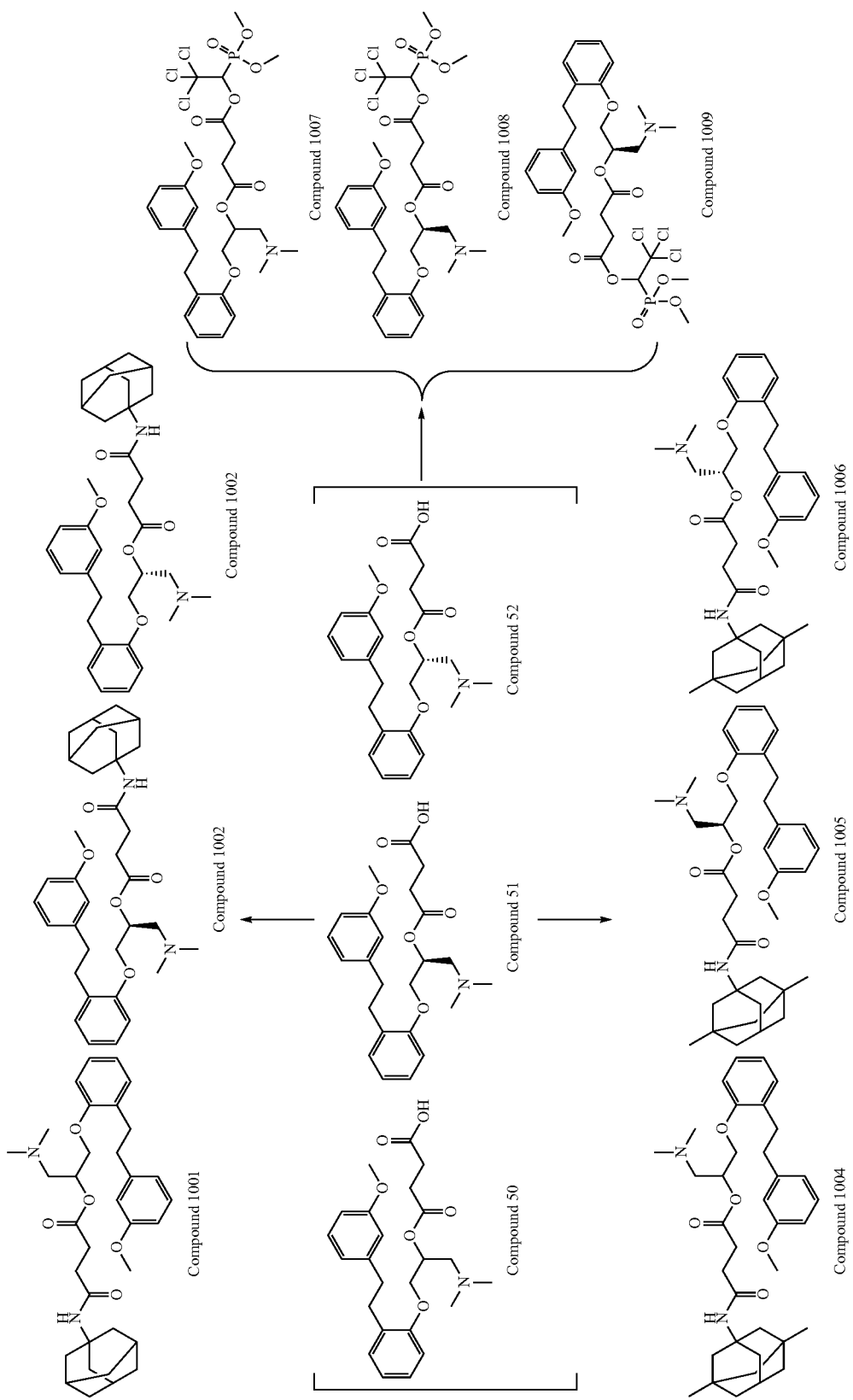

Compound 1001 1-(dimethylamino)-3-(2-(3-methoxyphenethyl)phenoxy)propan-2-yl 4-(adamantan-1-ylamino)-4-oxobutanoate;
Compound 1002 (S)-1-(dimethylamino)-3-(2-(3-methoxy phenethyl) phenoxy) propan-2-yl 4-(adamantan-1-ylamino)-4-oxobutanoate;
Compound 1003 (R)-1-(dimethylamino)-3-(2-(3-methoxyphenethyl) phenoxy) propan-2-yl 4-(adamantan-1-ylamino)-4-oxobutanoate;
Compound 1004 (R)-1-(dimethylamino)-3-(2-(3-methoxyphenethyl) phenoxy) propan-2-yl 4-((3,5-dimethyl adamantan-1-yl) amino)-4-oxo butanoate;
Compound 1005 1-(dimethylamino)-3-(2-(3-methoxyphenethyl) phenoxy) propan-2-yl 4-((3,5-dimethyl adamantan-1-yl)amino)-4-oxobutanoate;
Compound 1006 (S)-1-(dimethylamino)-3-(2-(3-methoxyphenethyl) phenoxy) propan-2-yl 4-((3,5-dimethyl adamantan-1-yl) amino)-4-oxobutanoate;
Compound 1007 1-(dimethylamino)-3-(2-(3-methoxyphenethyl)phenoxy)propan-2-yl (2,2,2-trichloro-1-(dimethoxyphosphoryl)ethyl) succinate;
Compound 1008 (S)-1-(dimethylamino)-3-(2-(3-methoxyphenethyl)phenoxy)propan-2-yl (2,2,2-trichloro-1-(dimethoxyphosphoryl)ethyl) succinate; and
Compound 1008 (R)-1-(dimethylamino)-3-(2-(3-methoxyphenethyl)phenoxy)propan-2-yl (2,2,2-trichloro-1-(dimethoxyphosphoryl)ethyl) succinate.

Pharmaceutical Formulations

The compositions of this invention can be prepared by adding a compound of Formula I, DERATINE™, SARPOTINE™, SARPODEX™, DERADEX™, or DERAPHAN™ to, and dissolved in, a suitable solvent. The solution, thus obtained, is added to the complex magnesium aluminum silicate to form a paste-like mass. While the foregoing steps are carried out at about room temperature, elevated temperatures can be employed if desired. Subsequently, sodium chloride and sodium saccharin are added to, and uniformly distributed throughout, the paste. Edible coloring and: flavoring materials can be incorporated into the system at any stage of the preparative method. In another embodiment, soluble ingredients are added to a compound of Formula I, DERATINE™, SARPOTINE™, SARPODEX™, DERADEX™, or DERAPHAN™ solution which is prepared in the first step. The paste which is thus obtained can be incorporated readily into a conventional hard candy-forming mass, which mass, in turn, can be worked up, by conventional procedures, into attractive, pleasant-tasting lozenges each containing therapeutically effective quantities of a compound of Formula I, DERATINE™, SARPOTINE™, SARPODEX™, DERADEX™, or DERAPHAN™ uniformly distributed throughout.

Variations in the preparative methods presented here are within the scope of the present invention. For example, in producing the compositions of the invention, one can mix racemate or enatiomerically pure compound of Formula I, DERATINE™, SARPOTINE™, SARPODEX™, DERADEX™, or DERAPHAN™ and the complex magnesium aluminum silicate and subsequently add a suitable solvent thereto to form a paste therewith. Sodium chloride and sodium saccharin can be added to the dextromethorphan-complex magnesium aluminum silicate mixture prior to forming the mixture into a paste. In the alternative, sodium chloride and sodium saccharin can be added to the paste. Furthermore, suitable flavoring agents and coloring agents can be added either to the dry mixture or to the paste. In carrying out this invention, any medicinally acceptable organic solvent which is suitable for pharmaceutical use and in which a compound of Formula I, DERATINE™, SARPOTINE™, SARPODEX™, DERADEX™, or DERAPHAN™ is soluble can be employed. Thus, for example, organic solvents, such as propylene glycol, glycerine, 1,3-butylene glycol, benzyl alcohol, etc., can be used. In an embodiment of compositions of the invention, benzyl alcohol is employed as the solvent for the Saprodex™.

Edible coloring agents and edible flavoring agents can be used in preparing the present compositions. Flavoring agents which are suitable for use include, for example, licorice, ginger, natural fruit extracts, etc. As the coloring agent one can use any color which is suitable for use in foods and drugs. The quantity of coloring and the quantity of flavoring agents used in formulating the composition of this invention is variable.

In an embodiment, the formulation contains about 0.3 g to about 1.5 g, about 1.0 g, of thickener; about 1 g to about 10 g, about 2.5 g, of 1,2-propylen glycol as a dissolving agent; about 0.12 g to about 0.19 g, or 0.15 g, of at least one paraben preservative such as methyl paraben; about 0.05 g to about 0.2 g, or about 0.1 g, of sorbic acid; about 30 g to about 60 g, or 40 g of a sugar alcohol solution; about 0.05 to about 0.2 g, or 0.1 g of an artificial sweetener; a compound of Formula I, DERATINE™, SARPOTINE™, SARPODEX™, DERADEX™, or DERAPHAN™-resin complex in an amount to yield a desired strength of about 2.10 g (the amount of a 1:6 complex needed to deliver equivalent to 60 mg of a compound of Formula I, DERATINE™, SARPOTINE™, SARPODEX™, DERADEX™, or DERAPHAN™ in a 20 ml adult 12 hour dose); and sufficient water to bring the volume up to 100 ml.

In another embodiment, suitable thickeners include: tragacanth; bentonite; acacia and lower alkyl ethers of cellulose (including the hydroxy and carboxy derivatives of the cellulose ethers). Exemplary paraben preservatives are $C_1$-$C_4$ alkyl parabens namely methyl, ethyl, propyl, and butyl parabens. In one embodiment, both methyl and propyl paraben are present in the formulation in a ratio of methyl paraben to propyl paraben of from about 2.5:1 to about 7.5:1. In another embodiment the methyl and propyl paraben ratio is 4:1.

In one embodiment, the artificial sweetener is a form of saccharin or aspartame. In one embodiment, saccharin is sacharin sodium. In other embodiments, equivalent sweetening amounts of other known sweetening agents such as the sugar alcohol sorbitol may be substituted therefor.

In another embodiment, the formulation comprises an amount of resinate sufficient to deliver, when administered at one dose every 12 hours, an antitussive effective amount of a compound of Formula I, DERATINE™, SARPOTINE™, SARPODEX™, DERADEX™, or DERAPHAN™ over a period of approximately 12 hours to a patient in need of such administration.

In an embodiment, the formulation comprises an adult dose of 20 ml contains approximately 420 mg of resinate, to deliver equivalent to 60 mg of a compound of Formula I, DERATINE™, SARPOTINE™, SARPODEX™, DERADEX™, or DERAPHAN™ when the drug to resin ratio is 1:6 and 2.10 g of resinate are present per 100 ml of formulation. The dosage can be altered analogously to that known for the administration of dextromethorphan which has not been complexed with resin, i.e. the typical 15 mg-30 mg/dose of dextromethorphan hydrobromide 1 to 4 times daily, becomes S-20 ml once to twice daily.

In another embodiment, the formulation comprises the nontoxic substances that block the NMDA receptor in accordance with this invention are dextromethorphan ((+)-3- hydroxy-Nmethylmorphinan), a compound of Formula I, DERATINE™, SARPOTINE™, SARPODEX™, DERADEX™, or DERAPHAN™ or derivatives thereof, and Saprodexter™, mixtures and pharmaceutically acceptable salts thereof.

In another embodiment, the formulation comprises substances that block the NMDA receptor include dizocilpine (5-methyl-10,11-dihydro-5H-5,10-epiminodibenzo[ad][7] annulene), ketamine (2-(2-chlorophenyl)-2-(methylamino)cyclohexan-1-one), magnesium, selfotel ((2S,4R)-4-(phosphonormethyl)piperidine-2-carboxylic acid), aptiganel ((E)-1-(3-ethylphenyl)-1-methyl-2-(naphthalen-1-yl)guanidine), felbamate (2-phenylpropane-1,3-diyl dicarbamate), phencyclidine (1-(1-phenylcyclohexyl)piperidine), amantadine (1-aminoadamantine), memantine (3,5 dimethylaminoadamantone), pyrroloquinoline quinone (PQQ, 4,5-dioxo-4,5-dihydro-1H-pyrrolo[2,3-f]quinoline-2,7,9-tricarboxylic acid), (R)-(E)-4-(3-phosphonoprop-2-enyl)piperazine-2-carboxylic acid, (R)-2-amino-5-phosphonopentanoate, (S) and (R) 6-(1HTetrazol-5-ylmethyl)decahydroisoquinoline-3-carboxylic acid, (S)-a-amino-5-(phosphonomethyl)[1,19-biphenyl]-3-propanoic acid, (S) and (R) (6)-cis-4-(4-phenylbenzoyl) piperazine-2,3-dicarboxylic acid, cis-4-phosphonomethyl-2-piperidine carboxylic acid, 2R,4R,5S-(2-amino-4,5-(1,2-cyclohexyl)-7-phosphonoheptanoic acid), and cis-4-(phosphonomethyl)-2-piperidinecarboxylic acid, mixtures and pharmaceutically acceptable salts thereof. (U.S. Pat. No. 5,891,885, Christie et al., Native N-Methyl-D-aspartate Receptors Containing NR2A and NR2B Subunits Have Pharmacologically Distinct Competitive Antagonist Binding Sites, The Journal Of Pharmacology And Experimental Therapeutics, Vol. 292, No. 3, pp 1169-74 (2000), incorporated by reference in entirety).

In another embodiment, the therapeutic composition comprises at least one other pharmacologically active substance e.g., caffeine (a stimulant), an antiemetic drug such as metoclopramide, domperidone, belladonna alkaloids and phenothiazines such as chlorpromazine, prochlorperazine, and promethazine, a nonnarcotic analgesic, e.g., acetaminophen or a nonsteroidal anti-inflammatory drug such as aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, nabumetone, naproxen, oxaprozin, phenylbutazone, piroxicam, sulindac, tolmetin, zomepirac, and the like.

Synthesis of Compounds of the Invention

All reactions were performed under an argon atmosphere with dry solvents, unless otherwise stated. Dry chloroform ($CH_3Cl$), methylene chloride ($CH_2Cl_2$), tetrahydrofuran (THF), ethyl acetate, DMF, DMSO, methanol, ethanol, and acetonitrile ($CH_3CN$) were purchased or prepared. All commercially available reagents were purchased and used without further purification. Reactions were monitored by thin-layer chromatography (TLC) on silica gel plates (Merck TLC Silica Gel 60 F254) using UV light, PMA (an ethanolic solution of phosphomolybdic acid) or ANIS (an ethanolic solution of para-anisaldehyde) as visualizing agent. Purification of products was conducted by column chromatography through silica gel 60 (0.060-0.200 mm). NMR spectra were obtained on Bruker AVANCE III 500 MHz (Bruker Corporation, Billerica, Mass., USA) using residual undeuterated solvent or TMS (tetramethylsilane) as an internal reference. High-resolution mass spectra (HR-MS) were recorded on a JEOL JMS-700 (JEOL, Tokyo, Japan) using E1 (electron impact).

Example 1

Dextromethorphan has been synthesized from a benzylisoquinoline (with a planar structure) by Grewe's cyclization to give the corresponding morphinan, wherein the 1,2,3,4,5,6,7,8-octahydro-1-(4-methoxybenzyl)isoquinoline is converted into the N-formyl derivative, cyclized to the N-formyl normorphinan, and the formyl group reduced to an N-methyl group, to give 3-methoxy-17-methylmorphinan. Dextromethorphan is freely soluble in ethanol 96% and essentially insoluble in water. Dextromethorphan can be monohydrated hydrobromide salt or bound to an ion exchange resin based on polystyrene sulfonic acid. Dextrometorphan's specific rotation in water is +27.6° (20° C., Sodium D-line).

Example 2

Equimolar sarpogrelate (429.506 g/mol) and dextromethorphan (271.40 g/mol) were mixed in a suitable solvent, agitated and let crystallize. The compound of Formula I and dextromethorphan positive cation would form hydrogen bond to form a complex and crystallize.

Example 3

To a solution of 54.28 g of dextromethorphan in one liter of chloroform is added a solution of 85.9 g of sarpogrelate in chloroform at 70° C. The salt is precipitated from the hot solution by the addition of ethyl acetate. After cooling the salt is collected, washed with ethyl acetate and dried to yield d-3-methoxy-N-methylmorphinan 4-[1-dimethylamino-3-[2-[2-(3-methoxyphenyl) ethyl]phenoxy]propan-2-yl] oxy-4-oxobutanoate salt and recrystallized from aqueous dimethylformamide (DMF) to yield of 135 g of the compound of Formula I, DERATINE™, SARPOTINE™, SARPODEX™, DERADEX™, or DERAPHAN™.

Example 4

Ingredients: 15 g of a compound of Formula I, DERATINE™, SARPOTINE™, SARPODEX™, DERADEX™, or DERAPHAN™; 15 g Glyceryl tristearate; 100 ml Carbon tetrachloride. Preparation: Glyceryl tristearate is dissolved in the warm carbon tetrachloride at 55-60° C. A compound of formula I, derivative thereof, SARPODEX™ or derivative thereof is then added and suspended in the solution. The suspension is then spray dried using an inlet temperature of 90° C. and an outlet temperature of 40° C. The resulting coated a compound of Formula I, DERATINE™, SARPOTINE™, SARPODEX™, DERADEX™, or DERAPHAN™ having an average particle size of from about 10 to about 200 microns is then suspended in the following aqueous vehicle.

Ingredients:

10.00 g Tragacanth, USP; 1.20 g Methylparaben, USP; 0.20 g Propylparaben, USP; 0.30 g Saccharin sodium, USP; 3.00 g Sucaryl sodium, USP; 250.00 mL Sorbic acid; 1.00 g Methyl cellulose, 15 cps; 2.00 mL Imitation black currant; and 1000.00 mL Distilled water.

The parabens, saccharin sodium, sucaryl sodium and sorbic acid are dissolved in a portion of the distilled water which has been heated to 85° C. The tragacanth is then added to this solution and dispersed uniformly. The dispersion is again heated, cooled and the sorbitol solution, a solution of the methyl cellulose in water and the imitation black currant are then added with mixing to form the vehicle. The coated a compound of Formula I, DERATINE™, SARPOTINE™, SARPODEX™, DERADEX™, or DERAPHAN™ is then added to the above vehicle and mixed until the particles are thoroughly wetted and uniformly dispersed.

The controlled drug-release composition of the present invention is characterized by comprising 100 parts by weight of an organic polymeric material which is soluble in an organic solvent and insoluble in water; 5 to 60 parts by weight of a lipid-soluble, low molecular weight release auxiliary agent; and 1 to 70 parts by weight of a drug.

In one embodiment, the polymeric material is biodegradable or biocompatible, or both, for example, biodegradable aliphatic polyester, or an aliphatic poly(carbonate), poly(lactic acid), lactic acid-glycolic acid copolymer, poly(caprolactone), poly(hydroxybutyric acid) and the like.

In one embodiment, the release auxiliary agent is a carboxylic acid ester, a monoester or diester of glycerin. In another embodiment, the release auxiliary agent is an ester of an organic acid selected from succinic acid, citric acid, tartaric acid, malic acid or the like, or monoacetate ester or diacetate ester of glycerin.

In one embodiment, the composition may further comprise a cell adhesion material or an endothelialization promoting agent on a surface of a medical device.

In one embodiment, in invention is a drug-releasable medical device characterized by containing the compositions of the present disclosure. The drug-releasable medical device forms a layer of the composition on the surface, and contacts with a living body, or is incorporated or indwelled in a living body. The device includes a stent, a catheter, a clip, an organ replacement medical device, a capsule sensor or an artificial organ. The stent in one embodiment is used for treating coronary artery stenosis and gradually releasing the composition from the surface. The release rate is $1/10^3$ mu g/mm$^2$/h to 1 mu g/mm$^2$/h on 21 days after indwelling the stent. In addition, the stent of the present invention is characterized in that the drug to be gradually released is carried in a polymeric material coated on the surface of a metal forming the stent or in a porous stent substrate.

The polymeric material coated on the surface of the stent is amorphous. The polymeric material coated on the surface of the stent is an amorphous biodegradable polymeric material. The polymeric material is a poly(lactic acid) or a lactic acid-glycolic acid copolymer, which is biodegradable. The polymeric material further comprises a release auxiliary agent that promotes the release of a drug to be carried. The auxiliary agent that promotes the release of a drug is a tartrate ester or a malate ester, or a monoester or diester of glycerin. The surface of the metal forming the stent may be a porous body and the above-mentioned drug to be gradually released may be carried in the porous body. In one embodiment, the porous body has a pore size of 0.01 nm to 300 nm in diameter.

Example 5: Optically Pure Sarpomalate

Malic acid is a component of many of the foods that we eat daily. Although it is found as a naturally occurring organic compound in various fruits, many choose to take malic acid supplements to increase their overall health, as well as treat various maladies. Today, the acid is most commonly used as a food additive and preservative. It is a mild and relatively harmless acid when used in appropriate amounts. As a food supplement, it is generally considered beneficial for health and is present in large amounts in apple juices. As when taking any supplement, however, you should not exceed the recommended amounts for consumption (Malic-Acid-Benefits-Health-Supplements at NEWS-MAX.COM). Natural organic compounds having asymmetric carbon usually exist as an optically active material and exhibit physiological activity markedly different from that of enantiomers.

Malic acid (0.55 mmol, 1.1 equiv.), dicyclohexylcarbodiimide (DCC, 0.55 mmol, 1.1 equiv.) and 4-dimethylaminopyridine at 0° C. are added to a stirred solution of racemate or enantiomerically pure M1 (0.50 mmol, 1.0 equiv.) in CH$_2$Cl$_2$ (5 mL), heated over 30 min to 25° C., stirred the mixture at 25° C. for 18 to 24 h, and diluted with CH$_2$Cl$_2$ (50 mL) and sat. aq. NaHCO$_3$ (30 mL). The organic layer is separated, dried (Na$_2$SO$_4$), filtered, and concentrated under reduced pressure. The crude residue is purified by column chromatography (silica gel, hexanes:EtOAc) to yield racemic or diasteriomerically pure sarpomalate, respectively depending upon the M1 and malic acid used (compounds 25-29). Racemic sarpomalate can be purified by crystallization and/or chiral chromatography to obtain diasteriomerically pure sarpomalate.

Example 6: Optically Pure Sarpomethionate

Methionine (0.55 mmol, 1.1 equiv.), dicyclohexylcarbodiimide (DCC, 0.55 mmol, 1.1 equiv.) and 4-dimethylaminopyridine at 0° C. are added to a stirred solution of racemate or enantiomerically pure M1 (0.50 mmol, 1.0 equiv.) in CH$_2$Cl$_2$ (5 mL), heated over 30 min to 25° C., stirred the mixture at 25° C. for 18 to 24 h, and diluted with CH$_2$Cl$_2$ (50 mL) and sat. aq. NaHCO$_3$ (30 mL). The organic layer is separated, dried (Na$_2$SO$_4$), filtered, and concentrated under reduced pressure. The crude residue is purified by column chromatography (silica gel, hexanes:EtOAc) to yield racemic or diasteriomerically pure sarpomethionate, respectively depending upon the M1 and methionine used (compounds 30-34). Racemic sarpomethionate can be purified by crystallization and/or chiral chromatography to obtain diasteriomerically pure sarpomethionate.

Example 7: Optically Pure Sarpophthallate

Phthallic acid (0.55 mmol, 1.1 equiv.), dicyclohexylcarbodiimide (DCC, 0.55 mmol, 1.1 equiv.) and 4-dimethylaminopyridine at 0° C. are added to a stirred solution of racemate or enantiomerically pure M1 (0.50 mmol, 1.0 equiv.) in CH$_2$Cl$_2$(5 mL), heated over 30 min to 25° C., stirred the mixture at 25° C. for 18 to 24 h, and diluted with CH$_2$Cl$_2$ (50 mL) and sat. aq. NaHCO$_3$(30 mL). The organic layer is separated, dried (Na$_2$SO$_4$), filtered, and concentrated under reduced pressure. The crude residue is purified by column chromatography (silica gel, hexanes:EtOAc) to yield racemic or optically pure sarpophthallate, respectively depending upon the M1 and phthallic acid used to yield compounds 35-37. Racemic sarpophthallate can be purified by crystallization and/or chiral chromatography to obtain diasteriomerically pure sarpomalate.

Example 8: Optically Pure Sarpomalonate

Malonic acid (0.55 mmol, 1.1 equiv.), dicyclohexylcarbodiimide (DCC, 0.55 mmol, 1.1 equiv.) and 4-dimethylaminopyridine at 0° C. are added to a stirred solution of racemate or enantiomerically pure M1 (0.50 mmol, 1.0 equiv.) in CH$_2$Cl$_2$ (5 mL), heated over 30 min to 25° C., stirred the mixture at 25° C. for 18 to 24 h, and diluted with CH$_2$Cl$_2$ (50 mL) and sat. aq. NaHCO$_3$ (30 mL). The organic layer is separated, dried (Na$_2$SO$_4$), filtered, and concentrated under reduced pressure. The crude residue is purified by column chromatography (silica gel, hexanes:EtOAc) to yield racemic or optically pure sarpomalonate, respectively depending upon the M1 to yield compounds 38-40. Racemic sarpomalonate can be purified by crystallization and/or chiral chromatography to obtain optically pure sarpomalonate.

Example 9: Optically Pure Sarpotyrosinate

Tyrosine (0.55 mmol, 1.1 equiv.), dicyclohexylcarbodiimide (DCC, 0.55 mmol, 1.1 equiv.) and 4-dimethylaminopyridine at 0° C. are added to a stirred solution of racemate or enantiomerically pure M1 (0.50 mmol, 1.0 equiv.) in $CH_2Cl_2$ (5 mL), heated over 30 min to 25° C., stirred the mixture at 25° C. for 18 to 24 h, and diluted with $CH_2Cl_2$ (50 mL) and sat. aq. $NaHCO_3$ (30 mL). The organic layer is separated, dried ($Na_2SO_4$), filtered, and concentrated under reduced pressure. The crude residue is purified by column chromatography (silica gel, hexanes:EtOAc) to yield racemic or optically pure sarpotyrosinate, respectively depending upon the M1 to yield compounds 41-43. Racemic sarpotyrosinate can be purified by crystallization and/or chiral chromatography to obtain optically pure sarpotyrosinate.

Example 10: Optically Pure Sarpotryptophanate

Tryptophan (0.55 mmol, 1.1 equiv.), dicyclohexylcarbodiimide (DCC, 0.55 mmol, 1.1 equiv.) and 4-dimethylaminopyridine at 0° C. are added to a stirred solution of racemate or enantiomerically pure M1 (0.50 mmol, 1.0 equiv.) in $CH_2Cl_2$ (5 mL), heated over 30 min to 25° C., stirred the mixture at 25° C. for 18 to 24 h, and diluted with $CH_2Cl_2$ (50 mL) and sat. aq. $NaHCO_3$ (30 mL). The organic layer is separated, dried ($Na_2SO_4$), filtered, and concentrated under reduced pressure. The crude residue is purified by column chromatography (silica gel, hexanes:EtOAc) to yield racemic or optically pure sarpotryptophanate, respectively depending upon the M1 to yield compounds 44-46. Racemic sarpotryptophanate can be purified by crystallization and/or chiral chromatography to obtain optically pure sarpotryptophanate.

Example 11: Optically Pure Sarpomaleate

Maleic acid (0.55 mmol, 1.1 equiv.), dicyclohexylcarbodiimide (DCC, 0.55 mmol, 1.1 equiv.) and 4-dimethylaminopyridine at 0° C. are added to a stirred solution of racemate or enantiomerically pure M1 (0.50 mmol, 1.0 equiv.) in $CH_2Cl_2$ (5 mL), heated over 30 min to 25° C., stirred the mixture at 25° C. for 18 to 24 h, and diluted with $CH_2Cl_2$ (50 mL) and sat. aq. $NaHCO_3$ (30 mL). The organic layer is separated, dried ($Na_2SO_4$), filtered, and concentrated under reduced pressure. The crude residue is purified by column chromatography (silica gel, hexanes:EtOAc) to yield racemic or optically pure sarpomaleate, respectively depending upon the M1 to yield compounds 47-49. Racemic sarpomaleate can be purified by crystallization and/or chiral chromatography to obtain optically pure sarpomaleate.

Example 12: Optically Pure Sarpogrelate

Succinic acid (0.55 mmol, 1.1 equiv.), dicyclohexylcarbodiimide (DCC, 0.55 mmol, 1.1 equiv.) and 4-dimethylaminopyridine at 0° C. are added to a stirred solution of racemate or enantiomerically pure M1 (0.50 mmol, 1.0 equiv.) in $CH_2Cl_2$ (5 mL), heated over 30 min to 25° C., stirred the mixture at 25° C. for 18 to 24 h, and diluted with $CH_2Cl_2$ (50 mL) and sat. aq. $NaHCO_3$ (30 mL). The organic layer is separated, dried ($Na_2SO_4$), filtered, and concentrated under reduced pressure. The crude residue is purified by column chromatography (silica gel, hexanes:EtOAc) to yield racemic or optically pure sarpogrelate, respectively depending upon the M1 to yield compounds 50-52. Racemic sarpogrelate can be purified by crystallization and/or chiral chromatography to obtain optically pure sarpogrelate.

Example 13: Optically Pure Sarpoglutarate

Glutaric acid (0.55 mmol, 1.1 equiv.), dicyclohexylcarbodiimide (DCC, 0.55 mmol, 1.1 equiv.) and 4-dimethylaminopyridine at 0° C. are added to a stirred solution of racemate or enantiomerically pure M1 (0.50 mmol, 1.0 equiv.) in $CH_2Cl_2$ (5 mL), heated over 30 min to 25° C., stirred the mixture at 25° C. for 18 to 24 h, and diluted with $CH_2Cl_2$ (50 mL) and sat. aq. $NaHCO_3$ (30 mL). The organic layer is separated, dried ($Na_2SO_4$), filtered, and concentrated under reduced pressure. The crude residue is purified by column chromatography (silica gel, hexanes:EtOAc) to yield racemic or optically pure sarpoglutarate, respectively depending upon the M1 to yield compounds 53-55. Racemic sarpoglutarate can be purified by crystallization and/or chiral chromatography to obtain optically pure sarpoglutarate.

Example 14: Optically Pure Sarpoadipate

Adipic acid (0.55 mmol, 1.1 equiv.), dicyclohexylcarbodiimide (DCC, 0.55 mmol, 1.1 equiv.) and 4-dimethylaminopyridine at 0° C. are added to a stirred solution of racemate or enantiomerically pure M1 (0.50 mmol, 1.0 equiv.) in $CH_2Cl_2$ (5 mL), heated over 30 min to 25° C., stirred the mixture at 25° C. for 18 to 24 h, and diluted with $CH_2Cl_2$ (50 mL) and sat. aq. $NaHCO_3$ (30 mL). The organic layer is separated, dried ($Na_2SO_4$), filtered, and concentrated under reduced pressure. The crude residue is purified by column chromatography (silica gel, hexanes:EtOAc) to yield racemic or optically pure sarpoadipate, respectively depending upon the M1 to yield compounds 56-58. Racemic sarpoadipnate can be purified by crystallization and/or chiral chromatography to obtain optically pure sarpoadipate.

Example 15: Optically Pure Sarpopimelate

Pimelic acid (0.55 mmol, 1.1 equiv.), dicyclohexylcarbodiimide (DCC, 0.55 mmol, 1.1 equiv.) and 4-dimethylaminopyridine at 0° C. are added to a stirred solution of racemate or enantiomerically pure M1 (0.50 mmol, 1.0 equiv.) in $CH_2Cl_2$ (5 mL), heated over 30 min to 25° C., stirred the mixture at 25° C. for 18 to 24 h, and diluted with $CH_2Cl_2$ (50 mL) and sat. aq. $NaHCO_3$ (30 mL). The organic layer is separated, dried ($Na_2SO_4$), filtered, and concentrated under reduced pressure. The crude residue is purified by column chromatography (silica gel, hexanes:EtOAc) to yield racemic or optically pure sarpopimelate, respectively depending upon the M1 to yield compounds 59-61. Racemic sarpopimelate can be purified by crystallization and/or chiral chromatography to obtain optically pure sarpopimelate.

Example 16: Optically Pure Sarposebacate

Sebacic acid (0.55 mmol, 1.1 equiv.), dicyclohexylcarbodiimide (DCC, 0.55 mmol, 1.1 equiv.) and 4-dimethylaminopyridine at 0° C. are added to a stirred solution of racemate or enantiomerically pure M1 (0.50 mmol, 1.0 equiv.) in CH$_2$Cl$_2$(5 mL), heated over 30 min to 25° C., stirred the mixture at 25° C. for 18 to 24 h, and diluted with CH$_2$Cl$_2$ (50 mL) and sat. aq. NaHCO$_3$ (30 mL). The organic layer is separated, dried (Na$_2$SO$_4$), filtered, and concentrated under reduced pressure. The crude residue is purified by column chromatography (silica gel, hexanes:EtOAc) to yield racemic or optically pure sarposebacate, respectively depending upon the M1 to yield compounds 62-64. Racemic sarposebacate can be purified by crystallization and/or chiral chromatography to obtain optically pure sarposebacate.

Example 17: Optically Pure Sarpoformate

Formic acid (0.55 mmol, 1.1 equiv.), dicyclohexylcarbodiimide (DCC, 0.55 mmol, 1.1 equiv.) and 4-dimethylaminopyridine at 0° C. are added to a stirred solution of racemate or enantiomerically pure M1 (0.50 mmol, 1.0 equiv.) in CH$_2$Cl$_2$ (5 mL), heated over 30 min to 25° C., stirred the mixture at 25° C. for 18 to 24 h, and diluted with CH$_2$Cl$_2$ (50 mL) and sat. aq. NaHCO$_3$ (30 mL). The organic layer is separated, dried (Na$_2$SO$_4$), filtered, and concentrated under reduced pressure. The crude residue is purified by column chromatography (silica gel, hexanes:EtOAc) to yield racemic or optically pure sarpoformate, respectively depending upon the M1 to yield compounds 65-67. Racemic sarpoformate can be purified by crystallization and/or chiral chromatography to obtain optically pure sarpoformate.

Example 18: Optically Pure Sarpoacetate

Acetic acid (0.55 mmol, 1.1 equiv.), dicyclohexylcarbodiimide (DCC, 0.55 mmol, 1.1 equiv.) and 4-dimethylaminopyridine at 0° C. are added to a stirred solution of racemate or enantiomerically pure M1 (0.50 mmol, 1.0 equiv.) in CH$_2$Cl$_2$ (5 mL), heated over 30 min to 25° C., stirred the mixture at 25° C. for 18 to 24 h, and diluted with CH$_2$Cl$_2$ (50 mL) and sat. aq. NaHCO$_3$ (30 mL). The organic layer is separated, dried (Na$_2$SO$_4$), filtered, and concentrated under reduced pressure. The crude residue is purified by column chromatography (silica gel, hexanes:EtOAc) to yield racemic or optically pure sarpoacetate, respectively depending upon the M1 to yield compounds 68-70. Racemic sarpoacetate can be purified by crystallization and/or chiral chromatography to obtain optically pure sarpoacetate.

Example 19: Optically Pure Sarpopropionate

Propionic acid (0.55 mmol, 1.1 equiv.), dicyclohexylcarbodiimide (DCC, 0.55 mmol, 1.1 equiv.) and 4-dimethylaminopyridine at 0° C. are added to a stirred solution of racemate or enantiomerically pure M1 (0.50 mmol, 1.0 equiv.) in CH$_2$Cl$_2$(5 mL), heated over 30 min to 25° C., stirred the mixture at 25° C. for 18 to 24 h, and diluted with CH$_2$Cl$_2$ (50 mL) and sat. aq. NaHCO$_3$(30 mL). The organic layer is separated, dried (Na$_2$SO$_4$), filtered, and concentrated under reduced pressure. The crude residue is purified by column chromatography (silica gel, hexanes:EtOAc) to yield racemic or optically pure sarpopropionate, respectively depending upon the M1 to yield compounds 71-73. Racemic sarpopriopionate can be purified by crystallization and/or chiral chromatography to obtain optically pure sarpopropionate.

Example 20: Optically Pure Sarpobutyrate

Butyric acid (0.55 mmol, 1.1 equiv.), dicyclohexylcarbodiimide (DCC, 0.55 mmol, 1.1 equiv.) and 4-dimethylaminopyridine at 0° C. are added to a stirred solution of racemate or enantiomerically pure M1 (0.50 mmol, 1.0 equiv.) in CH$_2$Cl$_2$ (5 mL), heated over 30 min to 25° C., stirred the mixture at 25° C. for 18 to 24 h, and diluted with CH$_2$Cl$_2$ (50 mL) and sat. aq. NaHCO$_3$ (30 mL). The organic layer is separated, dried (Na$_2$SO$_4$), filtered, and concentrated under reduced pressure. The crude residue is purified by column chromatography (silica gel, hexanes:EtOAc) to yield racemic or optically pure sarpobutyrate, respectively depending upon the M1 to yield compounds 74-76. Racemic sarpobutyrate can be purified by crystallization and/or chiral chromatography to obtain optically pure sarpobutyrate.

Example 21: Optically Pure Sarpovalerate

Valeric acid (0.55 mmol, 1.1 equiv.), dicyclohexylcarbodiimide (DCC, 0.55 mmol, 1.1 equiv.) and 4-dimethylaminopyridine at 0° C. are added to a stirred solution of racemate or enantiomerically pure M1 (0.50 mmol, 1.0 equiv.) in CH$_2$Cl$_2$(5 mL), heated over 30 min to 25° C., stirred the mixture at 25° C. for 18 to 24 h, and diluted with CH$_2$Cl$_2$ (50 mL) and sat. aq. NaHCO$_3$(30 mL). The organic layer is separated, dried (Na$_2$SO$_4$), filtered, and concentrated under reduced pressure. The crude residue is purified by column chromatography (silica gel, hexanes:EtOAc) to yield racemic or optically pure sarpovalerate, respectively depending upon the M1 to yield compounds 77-79. Racemic sarpovalerate can be purified by crystallization and/or chiral chromatography to obtain optically pure sarpovalerate.

Example 22: Optically Pure Sarpocaproate

Caproic acid (0.55 mmol, 1.1 equiv.), dicyclohexylcarbodiimide (DCC, 0.55 mmol, 1.1 equiv.) and 4-dimethylaminopyridine at 0° C. are added to a stirred solution of racemate or enantiomerically pure M1 (0.50 mmol, 1.0 equiv.) in CH$_2$Cl$_2$ (5 mL), heated over 30 min to 25° C., stirred the mixture at 25° C. for 18 to 24 h, and diluted with CH$_2$Cl$_2$ (50 mL) and sat. aq. NaHCO$_3$ (30 mL). The organic layer is separated, dried (Na$_2$SO$_4$), filtered, and concentrated under reduced pressure. The crude residue is purified by column chromatography (silica gel, hexanes:EtOAc) to yield racemic or optically pure sarpocaproate, respectively depending upon the M1 to yield compounds 80-82. Racemic sarpocaproate can be purified by crystallization and/or chiral chromatography to obtain optically pure sarpocaproate.

Example 23: Optically Pure Sarpoenanthate

Enanthoic (heptanoic) acid (0.55 mmol, 1.1 equiv.), dicyclohexylcarbodiimide (DCC, 0.55 mmol, 1.1 equiv.) and 4-dimethylaminopyridine at 0° C. are added to a stirred solution of racemate or enantiomerically pure M1 (0.50 mmol, 1.0 equiv.) in CH$_2$Cl$_2$ (5 mL), heated over 30 min to 25° C., stirred the mixture at 25° C. for 18 to 24 h, and diluted with CH$_2$Cl$_2$ (50 mL) and sat. aq. NaHCO$_3$ (30 mL). The organic layer is separated, dried (Na$_2$SO$_4$), filtered, and concentrated under reduced pressure. The crude residue is purified by column chromatography (silica gel, hexanes: EtOAc) to yield racemic or optically pure sarpoenanthoate, respectively depending upon the M1 to yield compounds 62-64. Racemic sarpoenanthoate can be purified by crystallization and/or chiral chromatography to obtain optically pure sarpoenanthoateate.

Example 24: Optically Pure Sarpocaprylate

Caprylic acid (0.55 mmol, 1.1 equiv.), dicyclohexylcarbodiimide (DCC, 0.55 mmol, 1.1 equiv.) and 4-dimethylaminopyridine at 0° C. are added to a stirred solution of racemate or enantiomerically pure M1 (0.50 mmol, 1.0 equiv.) in CH$_2$Cl$_2$(5 mL), heated over 30 min to 25° C., stirred the mixture at 25° C. for 18 to 24 h, and diluted with CH$_2$Cl$_2$ (50 mL) and sat. aq. NaHCO$_3$(30 mL). The organic layer is separated, dried (Na$_2$SO$_4$), filtered, and concentrated under reduced pressure. The crude residue is purified by column chromatography (silica gel, hexanes:EtOAc) to yield racemic or optically pure sarpocaprylate, respectively depending upon the M1 to yield compounds 86-88. Racemic sarpocaprylate can be purified by crystallization and/or chiral chromatography to obtain optically pure sarpocaprylate.

Example 25: Optically Pure Sarpopelargonate

Pelargonic acid (0.55 mmol, 1.1 equiv.), dicyclohexylcarbodiimide (DCC, 0.55 mmol, 1.1 equiv.) and 4-dimethylaminopyridine at 0° C. are added to a stirred solution of racemate or enantiomerically pure M1 (0.50 mmol, 1.0 equiv.) in CH$_2$Cl$_2$ (5 mL), heated over 30 min to 25° C., stirred the mixture at 25° C. for 18 to 24 h, and diluted with CH$_2$Cl$_2$ (50 mL) and sat. aq. NaHCO$_3$ (30 mL). The organic layer is separated, dried (Na$_2$SO$_4$), filtered, and concentrated under reduced pressure. The crude residue is purified by column chromatography (silica gel, hexanes:EtOAc) to yield racemic or optically pure sarpopelargonate, respectively depending upon the M1 to yield compounds 89-91. Racemic sarpopelargonate can be purified by crystallization and/or chiral chromatography to obtain optically pure sarpopelargonate.

Example 26: Optically Pure Sarpocaprate

Capric acid (0.55 mmol, 1.1 equiv.), dicyclohexylcarbodiimide (DCC, 0.55 mmol, 1.1 equiv.) and 4-dimethylaminopyridine at 0° C. are added to a stirred solution of racemate or enantiomerically pure M1 (0.50 mmol, 1.0 equiv.) in CH$_2$Cl$_2$ (5 mL), heated over 30 min to 25° C., stirred the mixture at 25° C. for 18 to 24 h, and diluted with CH$_2$Cl$_2$ (50 mL) and sat. aq. NaHCO$_3$ (30 mL). The organic layer is separated, dried (Na$_2$SO$_4$), filtered, and concentrated under reduced pressure. The crude residue is purified by column chromatography (silica gel, hexanes:EtOAc) to yield racemic or optically pure sarpocaprate, respectively depending upon the M1 to yield compounds 92-94. Racemic sarpocaprate can be purified by crystallization and/or chiral chromatography to obtain optically pure sarpocaprate.

Example 27: Optically Pure Sarpooxalate

Oxalic acid (0.55 mmol, 1.1 equiv.), dicyclohexylcarbodiimide (DCC, 0.55 mmol, 1.1 equiv.) and 4-dimethylaminopyridine at 0° C. are added to a stirred solution of racemate or enantiomerically pure M1 (0.50 mmol, 1.0 equiv.) in CH$_2$Cl$_2$ (5 mL), heated over 30 min to 25° C., stirred the mixture at 25° C. for 18 to 24 h, and diluted with CH$_2$Cl$_2$ (50 mL) and sat. aq. NaHCO$_3$ (30 mL). The organic layer is separated, dried (Na$_2$SO$_4$), filtered, and concentrated under reduced pressure. The crude residue is purified by column chromatography (silica gel, hexanes:EtOAc) to yield racemic or optically pure sarpooxalate, respectively depending upon the M1 to yield compounds 95-97. Racemic sarpooxalate can be purified by crystallization and/or chiral chromatography to obtain optically pure sarpooxalate.

Example 28: Optically Pure Sarpoisophthallate

Isophthallic acid (0.55 mmol, 1.1 equiv.), dicyclohexylcarbodiimide (DCC, 0.55 mmol, 1.1 equiv.) and 4-dimethylaminopyridine at 0° C. are added to a stirred solution of racemate or enantiomerically pure M1 (0.50 mmol, 1.0 equiv.) in CH$_2$Cl$_2$ (5 mL), heated over 30 min to 25° C., stirred the mixture at 25° C. for 18 to 24 h, and diluted with CH$_2$Cl$_2$ (50 mL) and sat. aq. NaHCO$_3$ (30 mL). The organic layer is separated, dried (Na$_2$SO$_4$), filtered, and concentrated under reduced pressure. The crude residue is purified by column chromatography (silica gel, hexanes:EtOAc) to yield racemic or optically pure sarpoisophthallate, respectively depending upon the M1 to yield compounds 98-100. Racemic sarpoisophthallate can be purified by crystallization and/or chiral chromatography to obtain optically pure sarpoisophthallate.

Example 29: Optically Pure Sarpoterephthallate

Terephthallic acid (0.55 mmol, 1.1 equiv.), dicyclohexylcarbodiimide (DCC, 0.55 mmol, 1.1 equiv.) and 4-dimethylaminopyridine at 0° C. are added to a stirred solution of racemate or enantiomerically pure M1 (0.50 mmol, 1.0 equiv.) in CH$_2$Cl$_2$ (5 mL), heated over 30 min to 25° C., stirred the mixture at 25° C. for 18 to 24 h, and diluted with CH$_2$Cl$_2$ (50 mL) and sat. aq. NaHCO$_3$ (30 mL). The organic layer is separated, dried (Na$_2$SO$_4$), filtered, and concentrated under reduced pressure. The crude residue is purified by column chromatography (silica gel, hexanes:EtOAc) to yield racemic or optically pure sarpoterephthallate, respectively depending upon the M1 to yield compounds 101-103. Racemic sarpoterephthallate can be purified by crystallization and/or chiral chromatography to obtain optically pure sarpoterephthallate.

Example 30: Optically Pure Sarposalicilate

Salicilic acid (0.55 mmol, 1.1 equiv.), dicyclohexylcarbodiimide (DCC, 0.55 mmol, 1.1 equiv.) and 4-dimethylaminopyridine at 0° C. are added to a stirred solution of racemate or enantiomerically pure M1 (0.50 mmol, 1.0 equiv.) in CH$_2$Cl$_2$ (5 mL), heated over 30 min to 25° C., stirred the mixture at 25° C. for 18 to 24 h, and diluted with CH$_2$Cl$_2$ (50 mL) and sat. aq. NaHCO$_3$ (30 mL). The organic layer is separated, dried (Na$_2$SO$_4$), filtered, and concentrated under reduced pressure. The crude residue is purified by column chromatography (silica gel, hexanes:EtOAc) to yield racemic or optically pure sarposalicilate, respectively depending upon the M1 to yield compounds 104-106. Racemic sarposalicilate can be purified by crystallization and/or chiral chromatography to obtain optically pure sarposalicilate.

Example 31: Optically Pure Sarpoacetylsalicilate

Acetylsalicilic acid (0.55 mmol, 1.1 equiv.), dicyclohexylcarbodiimide (DCC, 0.55 mmol, 1.1 equiv.) and 4-dimethylaminopyridine at 0° C. are added to a stirred solution of racemate or enantiomerically pure M1 (0.50 mmol, 1.0 equiv.) in CH$_2$Cl$_2$ (5 mL), heated over 30 min to 25° C., stirred the mixture at 25° C. for 18 to 24 h, and diluted with CH$_2$Cl$_2$ (50 mL) and sat. aq. NaHCO$_3$ (30 mL). The organic layer is separated, dried (Na$_2$SO$_4$), filtered, and concentrated under reduced pressure. The crude residue is purified by column chromatography (silica gel, hexanes:EtOAc) to yield racemic or optically pure sarpoacetylsalicilate, respectively depending upon the M1 to yield compounds 107-109. Racemic sarpoacetylsalicilate can be purified by crystallization and/or chiral chromatography to obtain optically pure sarpoacetylsalicilate. (Park et al., Aspirination of α-Aminoalcohol (Sarpogrelate M1), Molecules 21(9), 1126 (2016); incorporated in entirety by reference).

Example 32

To a stirred solution of M1 (0.50 mmol, 1.0 equiv.) in $CH_2Cl_2$ (5 mL) or $CH_3CN$ (5 mL) was added aspirin (0.55 mmol, 1.1 equiv.) and 1,1'-carbonyldiimidazole (CDI, 0.60 mmol, 1.2 equiv.) at 25° C. The mixture was stirred for 12 h, and diluted with $CH_2Cl_2$ (40 mL) and sat. aq. $NH_4Cl$ (25 mL). The organic layer was separated, dried ($Na_2SO_4$), filtered, and concentrated under reduced pressure. The crude residue was purified by column chromatography (silica gel, hexanes:EtOAc) to obtain compound 107. Racemic sarpoacetylsalicilate compound 107 can be purified by crystallization and/or chiral chromatography to obtain optically pure sarpoacetylsalicilates 108 and 109.

Example 33

To a stirred solution of M1 (0.50 mmol, 1.0 equiv.) in THF (5 mL) was added acetylsalicylic acid (0.75 mmol, 1.5 equiv.), triphenylphosphine (0.75 mmol, 1.5 equiv.) and diisopropyl azodicarboxylate (DIAD, 0.75 mmol, 1.5 equiv.) at 0° C. The mixture was stirred at the same temperature for 1 h, and the solvent was removed under reduced pressure. The residue was diluted with EtOAc (30 mL) and sat. aq. $NH_4Cl$ (15 mL). The organic layer was separated, dried ($Na_2SO_4$), filtered, and concentrated under reduced pressure. The crude residue was purified by column chromatography (silica gel, hexanes:EtOAc) to obtain compound 107. Racemic sarpoacetylsalicilate compound 107 can be purified by crystallization and/or chiral chromatography to obtain optically pure sarpoacetylsalicilates 108 and 109.

Example 34

To a stirred solution of acetyl salicylate (1.00 mmol, 2.0 equiv.) in $CH_2Cl_2$ (5 mL) was added oxalyl chloride (2 M in $CH_2Cl_2$, 0.60 mL, 1.20 mmol, 2.4 equiv.) and dimethylformamide (DMF, 8.0 µL, 0.10 mmol, 0.2 equiv.) at 0° C. Then, the temperature was gradually raised to 25° C. The mixture was stirred at the same temperature for 12 h. Then, to another stirred solution of M1 3 (0.50 mmol, 1.0 equiv.) in $CH_2Cl_2$ (5 mL) was added pyridine (0.24 mL, 3.0 mmol, 6.0 equiv.) and the previously prepared aspirinyl chloride solution. The mixture was stirred for another 12 h, and diluted with $CH_2Cl_2$ (50 mL) and sat. aq. $NaHCO_3$ (30 mL). The organic layer was separated, dried ($Na_2SO_4$), filtered, and concentrated under reduced pressure. The crude residue was purified by column chromatography (silica gel, hexanes: EtOAc) to obtain compound 107. Racemic sarpoacetylsalicilate compound 107 can be purified by crystallization and/or chiral chromatography to obtain optically pure sarpoacetylsalicilates 108 and 109.

Example 35

To a stirred solution of salicylate ester (241 mg, 0.536 mmol, 1.0 equiv.) in pyridine (2 mL) was added $Ac_2O$ (76 µL, 0.81 mmol, 1.5 equiv.) at 0° C. The temperature was raised to 25° C. The mixture was stirred at the same temperature for 12 h. Then, the mixture was concentrated under reduced pressure and diluted with ethyl acetate (30 mL) and washed with $H_2O$ (10 mL). The organic layer was separated, dried ($Na_2SO_4$), filtered, and concentrated under reduced pressure. The crude residue was purified by column chromatography (silica gel, hexanes: EtOAc=1:2) to afford compound 107 (239 mg, 90% yield). Racemic sarpoacetylsalicilate compound 107 can be purified by crystallization and/or chiral chromatography to obtain optically pure sarpoacetylsalicilates 108 and 109.

Example 36

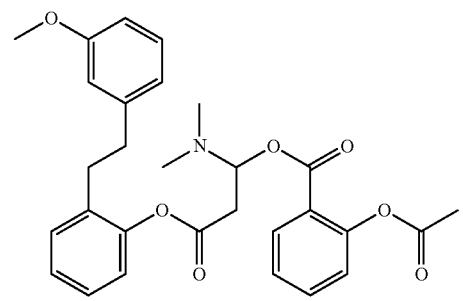

1-(dimethylamino)-3-(2-(3-methoxyphenethyl)phenoxy)-3-oxopropyl 2-acetoxybenzoate 1-(Dimethylamino)-3-(2-(3-methoxyphenethyl)phenoxy) propan-2-yl 2-acetoxy benzoate (compound 163): colorless oil; $R_f$=0.25 (silica gel, hexanes: EtOAc 1:1); $^1$H-NMR (500 MHz, $CDCl_3$): δ=7.99 (dd, $J_1$=1.6 Hz, $J_2$=7.9 Hz, 1H), 7.53-7.50 (m, 1H), 7.18 (ddd, $J_1$=1.1 Hz, $J_2$=7.9 Hz, $J_3$=7.9 Hz, 1H), 7.18-7.14 (m, 2H), 7.10-7.06 (m, 2H), 6.89-6.86 (m, 2H), 6.77 (d, J=7.7 Hz, 1H), 6.72-6.71 (m, 2H), 5.56-5.51 (m, 1H), 4.28-4.22 (m, 2H), 3.75 (s, 3H), 2.92-2.71 (m, 6H), 2.32 (s, 6H), 2.30 (s, 3H) ppm; $^{13}$C-NMR (125 MHz, $CDCl_3$): δ=169.7, 163.9, 159.7, 156.5, 150.9, 144.1, 134.0, 131.9, 130.5, 130.3, 129.3, 127.4, 126.1, 123.9, 123.4, 121.0, 120.9, 114.2, 111.39, 111.37, 71.2, 67.6, 59.4, 55.2, 46.4, 36.5, 32.8, 21.1 ppm; HRMS (EI): calcd for $C_{29}H_{33}NO_6$ [M$^+$]: 491.2308, found 491.2310.

Example 37

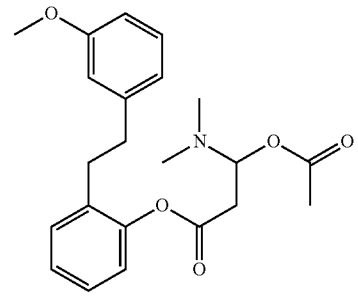

2-(3-methoxyphenethyl)phenyl 3-acetoxy-3-(dimethylamino)propanoate 1-(Dimethylamino)-3-(2-(3-methoxyphenethyl)phenoxy) propan-2-ylacetate (compound 164): colorless oil; $R_f$=0.19 (silica gel, hexanes:EtOAc 1:2); $^1$H-NMR (500 MHz, $CDCl_3$): δ=7.21 (t, J=7.8 Hz, 1H), 7.16 (ddd, $J_1$=1.7 Hz, $J_2$=7.8 Hz, $J_3$=7.8 Hz, 1H), 7.11 (dd, $J_1$=1.7 Hz, $J_2$=7.4 Hz, 1H), 6.87 (ddd, $J_1$=1.0 Hz, $J_2$=7.4 Hz, $J_3$=7.4 Hz, 1H), 6.84 (t, J=8.9 Hz, 2H), 6.78 (t, J=1.9 Hz, 1H), 6.76-6.73 (m, 1H), 5.39-5.34 (m, 1H), 4.19-4.09 (m, 2H), 3.80 (s, 3H), 2.91-

2.84 (m, 4H), 2.69-2.61 (m, 2H), 2.30 (s, 6H), 2.05 (s, 3H) ppm; $^{13}$C-NMR (125 MHz, CDCl$_3$): δ=170.8, 159.7, 156.5, 144.2, 130.5, 130.3, 129.4, 127.4, 121.0, 120.9, 114.3, 111.3, 111.2, 70.4, 67.7, 59.7, 55.3, 46.4, 36.6, 33.2, 21.4 ppm; HRMS (EI): calcd for C$_{22}$H$_{29}$NO$_4$ [M$^+$]: 371.2097, found 371.2095.

Example 38

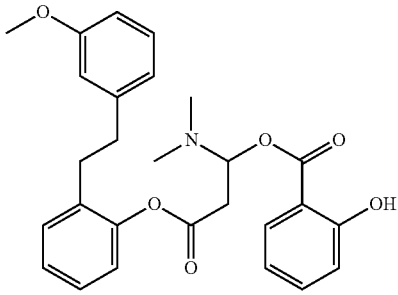

1-(dimethylamino)-3-(2-(3-methoxyphenethyl)phenoxy)-3-oxopropyl 2-hydroxybenzoate 1-(Dimethylamino)-3-(2-(3-methoxyphenethyl)phenoxy)propan-2-yl-2-hydroxy benzoate (compound 165) colorless oil; R$_f$=0.23 (silica gel, hexanes:EtOAc 2:1); $^1$H-NMR (500 MHz, CDCl$_3$): δ=10.69 (s, 1H), 7.83 (dd, J$_1$=1.7 Hz, J$_2$=8.0 Hz, 1H), 7.44-7.41 (m, 1H), 7.20-7.16 (m, 2H), 7.11 (dd, J$_1$=1.6 Hz, J$_2$=7.4 Hz, 1H), 6.96 (dd, J$_1$=0.9 Hz, J$_2$=8.4 Hz, 1H), 6.91-6.88 (m, 2H), 6.81-6.77 (m, 1H), 6.76-6.72 (m, 3H), 5.70-5.66 (m, 1H), 4.30-4.29 (m, 2H), 3.76 (s, 3H), 2.91-2.82 (m, 6H), 2.40 (s, 6H) ppm; $^{13}$C-NMR (125 MHz, CDCl$_3$): δ=169.6, 161.8, 159.7, 156.3, 144.0, 136.0, 130.5, 130.4, 130.1, 129.4, 127.4, 121.2, 120.9, 119.4, 117.8, 114.3, 112.5, 111.3, 111.2, 71.2, 67.6, 59.4, 55.2, 46.1, 36.5, 32.8 ppm; HRMS (EI): calcd for C$_{27}$H$_{31}$NO$_5$ [M$^+$]: 449.2202, found 449.2200.

Example 39

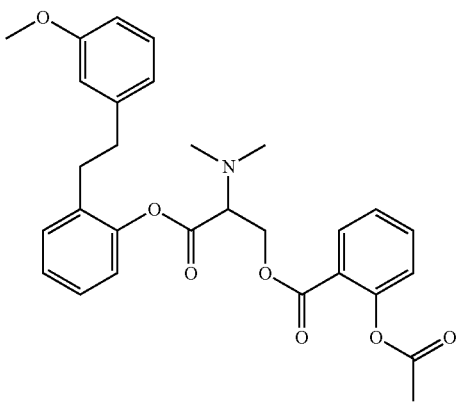

2-(dimethylamino)-3-(2-(3-methoxyphenethyl)phenoxy)-3-oxopropyl 2-acetoxybenzoate 2-(Dimethylamino)-3-(2-(3-methoxyphenethyl)phenoxy)propyl2-acetoxybenzoate (Compound 166): colorless oil; R$_f$=0.20 (silica gel, hexanes:EtOAc 1:1); $^1$H-NMR (500 MHz, CDCl$_3$): δ=7.98 (dd, J$_1$=1.6 Hz, J$_2$=7.8 Hz, 1H), 7.55 (ddd, J$_1$=1.7 Hz, J$_2$=7.8 Hz, J$_3$=7.8 Hz, 1H), 7.28 (ddd, J$_1$=1.1 Hz, J$_2$=7.7 Hz, J$_3$=7.7 Hz, 1H), 7.21-7.17 (m, 2H), 7.13 (dd, J$_1$=1.5 Hz, J$_2$=7.4 Hz, 1H), 7.11 (dd, J$_1$=1.0 Hz, J$_2$=8.1 Hz, 1H), 6.92-6.88 (m, 2H), 6.81 (d, J=7.7 Hz, 1H), 6.75-6.73 (m, 2H), 4.62-4.53 (m, 2H), 4.20-4.12 (m, 2H), 3.77 (s, 3H), 3.29-3.24 (m, 1H), 2.95-2.85 (m, 4H), 2.51 (s, 6H), 2.31 (s, 3H) ppm; $^{13}$C-NMR (125 MHz, CDCl$_3$): δ=169.9, 164.3, 159.7, 156.5, 150.9, 144.0, 134.1, 131.7, 130.4, 130.3, 129.4, 127.4, 126.1, 124.0, 123.2, 121.0, 120.9, 114.2, 111.4, 111.1, 65.7, 62.8, 62.0, 55.2, 42.6, 36.6, 32.6, 21.1 ppm; HRMS (EI): calcd for C$_{29}$H$_{33}$NO$_6$ [M$^+$]: 491.2308, found 491.2309.

Example 40: Deuteration of H-Compound to form D-Compound

The H-compound (a compound of the invention, about 1.25 mmol) is dissolved in 3 mL of 100 mM pH=7 deuterated phosphate-buffered saline (D-PBS) diluted with 9.00 mL D$_2$O to a final concentration of 25 mM. 100 mM D-PBS pH=7 (pH paper) buffer is prepared by dissolving 259.5 mg of K$_3$PQ$_4$ in D$_2$O (12.00 mL) and adding 264 µL 20% DCl in D$_2$O. The reaction mixture is shaken at room temperature for 11 days while monitoring for completion of hydrogen/deuterium (H/D) exchange by LC/MS.

A small scale workup is performed to prepare the hydrochloride salt of the deuterated compound. Thus a 1.2 mL aliquot of the reaction mixture (10% of total volume) is diluted with 5 mL saturated NaHCO$_3$ and extracted with EtOAc (3×5 mL). The organic layer is dried over Na2S04 and filtered. Evaporation of the solvent gave 20 mg of a colorless oil which is converted to the HCl salt by addition of a few drops of 4M HCl in dioxane. The salt is triturated with ether and the solvents were evaporated to give deuterated compound HCl salt. A 9.6 mL aliquot (80% of total volume) is diluted with 40 mL saturated NaHCO$_3$ and extracted once with EtOAc (200 mL). The organic layer is quickly dried over Na$_2$SO$_4$. Evaporation of the solvent gives the compound which is stored in a freezer.

Example 41: Preparation of Crude Sarpogrelate Hydrochloride 1-dimethylamino-3-[2-[2-(3-methoxyphenyl)ethyl]phenoxy]-2-propanol hydrochloride A 250 ml 13.7 g and water 25 ml were taken in a single-neck flask and stirred to dissolve. The solution is treated with 20% aqueous sodium hydroxide to a pH about 9 to about 14, and was extracted with 30 ml of toluene, and the organic layer was concentrated at 50° C. under reduced pressure to give a brown oil, which was dissolved in 30 mL of tetrahydrofuran. Then, butyryl anhydride 4.5 g was added and heated to reflux with stirring for about 1 to about 4 hours, and concentrated to dryness under reduced pressure at 40° C. Ethyl acetate (25 mL) is added to dissolve the residue and saturated hydrogen chloride in ethyl acetate solution is added dropwise to adjust PH 1 or lower while stirring for about 50-60 min to obtain sarpogrelate hydrochloride crude wet product, and dried under reduced pressure (−0.08~−0.1 MPa) at 45 to 55° C. to yield crude sarpogrelate hydrochloride 14.7 g, yield 86%, HPLC purity 98.6%.

Example 42: Purification of the Crude Hydrochloride Sarpogrelate

The crude sarpogrelate hydrochloride 5 g was dissolved in butanone (20 mL), heated while stirring until dissolved, refluxed for 20-30 min, cooled to 25-35° C., continued stirring 40-60 min, filtered, and the filter cake was rinsed with a small amount of methyl ethyl ketone to give a white loose solid, 55-65° C. and dried under reduced pressure to 24 h, to give sarpogrelate hydrochloride 4.6 g, yield 92%, HPLC purity of 99.9%.

Example 43: Purification of the Crude Hydrochloride Sarpogrelate

The crude sarpogrelate hydrochloride 5 g in butanone 30 ml was heated with stirring until dissolved and refluxed 20-30 min, cooling to 25-35° C., incubated with stirring 40-60 min, filtered, and the filter cake was rinsed with a small amount of methyl ethyl ketone to give a white loose solid, 55-65° C. and dried under reduced pressure to 24 h, to give 4.55 sarpogrelate hydrochloride, yield 91%, HPLC purity 99.7%.

Example 44: Purification of the Crude Hydrochloride Sarpogrelate

The crude sarpogrelate hydrochloride 5 g in butanone 40 ml is heated with stirring until dissolved and refluxed 20-30 min, cooling to 25-35° C., incubated with stirring 40-60 min, filtered, and the filter cake was rinsed with a small amount of methyl ethyl ketone to give a white solid, 55-65° C. and dried under reduced pressure to 24 h, to give sarpogrelate hydrochloride 4.5 g, yield 90%, HPLC purity 99.8%.

Example 45: Purification of the Crude Hydrochloride Sarpogrelate

The crude product was sarpogrelate hydrochloride 5 g, join butanone 20 ml, heated with stirring until dissolved and refluxed 20-30 min, cooled slowly with stirring to room temperature, at −10° C. stand for crystallization, filtration, The filter cake was rinsed with a small amount of methyl ethyl ketone to give a white fluffy solid, 55-65° C. and dried under reduced pressure to 24 h, to give the hydrochloride sarpogrelate 4.62 g, yield 92.4%, HPLC purity 99.2%, largest single matter content of 0.09%.

Sarpogrelate Enantiomers:

Enantiomers of compounds described here can be separated using chromatographic techniques. The preparative separation of enantiomers by chromatography on chiral stationary phases (CSPs) has been recognized as being a useful alternative to the more conventional approaches such as enantioselective synthesis and enzymatically catalyzed transformations (Francotte, Enantioselective chromatography as a powerful alternative for the preparation of drug enantiomers, Journal of Chromatography A, Volume 906, Issues 1-2, Pages 379-397 (12 Jan. 2001); Rajendran, et al., Simulated moving bed chromatography for the separation of enantiomers, Journal of Chromatography A, Volume 1216, Issue 4, Pages 709-738 (23 Jan. 2009); Maier et al., Separation of enantiomers: needs, challenges, perspectives, Journal of Chromatography A, Volume 906, Issues 1-2, Pages 3-33 (12 Jan. 2001); Miller et al., Chromatographic resolution of the enantiomers of a pharmaceutical intermediate from the milligram to the kilogram scale, Journal of Chromatography A, Volume 849, Issue 2, Pages 309-317 (23 Jul. 1999); Andersson et al., Preparative chiral chromatographic resolution of enantiomers in drug discovery, Journal of Biochemical and Biophysical Methods, Volume 54, Issues 1-3, Pages 11-23 (31 Dec. 2002); Pirkle et al., Chapter 6 Separation of Enantiomers by Liquid Chromatographic Methods, Asymmetric Synthesis, pp 87-124, in Volume 1: Analytical Methods covers the major analytical methods used to determine enantiomeric ratios, by Morrison (ed), Elsevier, (Dec. 2, 2012); incorporated in entirety by reference). Racemates of the invention can be resolved from an analytical to a preparative scale by this technique.

Simulated moving-bed chromatography can be used for the separation of the enantiomers of the compounds of the invention, feasible at all production scales, from laboratory to pilot to production plant (Juza et al., Simulated moving-bed chromatography and its application to chirotechnology, Trends in Biotechnology, Volume 18, Issue 3, Pages 108-118 (1 Mar. 2000), incorporated in entirety by reference).

Example 46: Separation of Enantiomers of Sarpogrelate Hydrochloride ((−)-4-((1-(dimethylamino)-3-(2-(3-ethoxyphenethyl) phenoxy)propan-2-yloxy)-4-oxobutanoic Acid Hydrochloride)

Sarpogrelate hydrochloride was separated with the XBridge® C18 3.5 m, 2.1×50 mm column, using a mobile phase: gradient elution from 10% MeCN in 0.01% TFA to 95% MeCN in 0.01% TFA, with a flow rate of 0.5 ml/min, at UV 254 nm, to yield 5.30 mg of enantiomer (99% HPLC purity). NMR: 400 MHz 1H-NMR (C0300, ppm) 7.20-7.14 (m, 2H) 7.11 (dd, J=7.4, 1.6 Hz, 1H) 6.94-6.87 (m, 2H) 6.79-6.71 (m, 3H) 5.70-5.62 (m, 1H) 4.18 (dd, J=10.6, 4.1 Hz, 1H) 4.15 (dd, J=10.6, 4.7 Hz, 1H) 3.75 (S, 3H) 3.70 (dd, J=13.8, 10.1 Hz, 1H) 3.54 (dd, J=13.8, 2.3 Hz, 1H) 2.98 (s, 6H) 2.96-2.77 (m, 4H) 2.76-2.53 (m, 4H). ESI-MS, m/z): 429 [M+H]+. Melting point (° C.): 155-156. Optical rotation, alpha [D]: −20.0 (c 0.33, MeOH).

Example 47: Dextromethorphan Malate

Dissolve the free base dextromethorphan (0.05 mole) in 20 ml of acetone, add the solution to a solution of the malic acid (0.05 mole) in 60 ml of hot water, and then cool the reaction mixture to separate crystals by filtration and dry.

Example 48: Dextromethorphan Methionate

Dissolve the free base dextromethorphan (0.05 mole) in 20 ml of acetone, add the solution to a solution of the methionine or N-acyl methionine (0.05 mole) in 60 ml of hot water, and then cool the reaction mixture to separate crystals by filtration and dry.

Example 49: Dextromethorphan Phthallate

Dissolve the free base dextromethorphan (0.05 mole) in 20 ml of acetone, add the solution to a solution of the phthallic acid (0.05 mole) in 60 ml of hot water, and then cool the reaction mixture to separate crystals by filtration and dry.

Example 50: Dextromethorphan Malonate

Dissolve the free base dextromethorphan (0.05 mole) in 20 ml of acetone, add the solution to a solution of the malonic acid (0.05 mole) in 60 ml of hot water, and then cool the reaction mixture to separate crystals by filtration and dry.

Example 51: Dextromethorphan Tyrosinate

Dissolve the free base dextromethorphan (0.05 mole) in 20 ml of acetone, add the solution to a solution of the tyrosine or N-acyl tyrosine (0.05 mole) in 60 ml of hot water, and then cool the reaction mixture to separate crystals by filtration and dry.

Example 52: Dextromethorphan Tryptophanate

Dissolve the free base dextromethorphan (0.05 mole) in 20 ml of acetone, add the solution to a solution of the tryptophan or N-acyl tryptophan (0.05 mole) in 60 ml of hot water, and then cool the reaction mixture to separate crystals by filtration and dry.

Example 53: Dextromethorphan Maleate

Dissolve the free base dextromethorphan (0.05 mole) in 20 ml of acetone, add the solution to a solution of the maleic acid (0.05 mole) in 60 ml of hot water, and then cool the reaction mixture to separate crystals by filtration and dry.

Example 54: Dextromethorphan Succinate

Dissolve the free base dextromethorphan (0.05 mole) in 20 ml of acetone, add the solution to a solution of the succinic acid (0.05 mole) in 60 ml of hot water, and then cool the reaction mixture to separate crystals by filtration and dry.

Example 55: Dextromethorphan Glutarate/Glutamate

Dissolve the free base dextromethorphan (0.05 mole) in 20 ml of acetone, add the solution to a solution of the glutaric acid, glutamic acid or N-acyl glutamic acid (0.05 mole) in 60 ml of hot water, and then cool the reaction mixture to separate crystals by filtration and dry.

Example 56: Dextromethorphan Adipate

Dissolve the free base dextromethorphan (0.05 mole) in 20 ml of acetone, add the solution to a solution of the adiptic acid (0.05 mole) in 60 ml of hot water, and then cool the reaction mixture to separate crystals by filtration and dry.

Example 57: Dextromethorphan Pimelate

Dissolve the free base dextromethorphan (0.05 mole) in 20 ml of acetone, add the solution to a solution of the pimelic acid (0.05 mole) in 60 ml of hot water, and then cool the reaction mixture to separate crystals by filtration and dry.

Example 58: Dextromethorphan Sebacate

Dissolve the free base dextromethorphan (0.05 mole) in 20 ml of acetone, add the solution to a solution of the sebacic acid (0.05 mole) in 60 ml of hot water, and then cool the reaction mixture to separate crystals by filtration and dry.

Example 59: Dextromethorphan Formate

Dissolve the free base dextromethorphan (0.05 mole) in 20 ml of acetone, add the solution to a solution of the formic acid (0.05 mole) in 60 ml of hot water, and then cool the reaction mixture to separate crystals by filtration and dry.

Example 60: Dextromethorphan Acetate

Dissolve the free base dextromethorphan (0.05 mole) in 20 ml of acetone, add the solution to a solution of the acetic acid (0.05 mole) in 60 ml of hot water, and then cool the reaction mixture to separate crystals by filtration and dry.

Example 61: Dextromethorphan Propionate

Dissolve the free base dextromethorphan (0.05 mole) in 20 ml of acetone, add the solution to a solution of the propionic acid (0.05 mole) in 60 ml of hot water, and then cool the reaction mixture to separate crystals by filtration and dry.

Example 62: Dextromethorphan Butyrate

Dissolve the free base dextromethorphan (0.05 mole) in 20 ml of acetone, add the solution to a solution of the butyric acid (0.05 mole) in 60 ml of hot water, and then cool the reaction mixture to separate crystals by filtration and dry.

Example 63: Dextromethorphan Valerate

Dissolve the free base dextromethorphan (0.05 mole) in 20 ml of acetone, add the solution to a solution of the valeric acid (0.05 mole) in 60 ml of hot water, and then cool the reaction mixture to separate crystals by filtration and dry.

Example 64: Dextromethorphan Caproate

Dissolve the free base dextromethorphan (0.05 mole) in 20 ml of acetone, add the solution to a solution of the caproic acid (0.05 mole) in 60 ml of hot water, and then cool the reaction mixture to separate crystals by filtration and dry.

Example 65: Dextromethorphan Enanthate

Dissolve the free base dextromethorphan (0.05 mole) in 20 ml of acetone, add the solution to a solution of the enanthoic (heptanoic) acid (0.05 mole) in 60 ml of hot water, and then cool the reaction mixture to separate crystals by filtration and dry.

Example 66: Dextromethorphan Caprylate

Dissolve the free base dextromethorphan (0.05 mole) in 20 ml of acetone, add the solution to a solution of the caprylic acid (0.05 mole) in 60 ml of hot water, and then cool the reaction mixture to separate crystals by filtration and dry.

Example 67: Dextromethorphan Pelargonate

Dissolve the free base dextromethorphan (0.05 mole) in 20 ml of acetone, add the solution to a solution of the pelargonic acid (0.05 mole) in 60 ml of hot water, and then cool the reaction mixture to separate crystals by filtration and dry.

Example 68: Dextromethorphan Caprate

Dissolve the free base dextromethorphan (0.05 mole) in 20 ml of acetone, add the solution to a solution of the capric acid (0.05 mole) in 60 ml of hot water, and then cool the reaction mixture to separate crystals by filtration and dry.

Example 69: Dextromethorphan Oxalate

Dissolve the free base dextromethorphan (0.05 mole) in 20 ml of acetone, add the solution to a solution of the oxalic acid (0.05 mole) in 60 ml of hot water, and then cool the reaction mixture to separate crystals by filtration and dry.

Example 70: Dextromethorphan Isophthallate

Dissolve the free base dextromethorphan (0.05 mole) in 20 ml of acetone, add the solution to a solution of the isophthalic acid (0.05 mole) in 60 ml of hot water, and then cool the reaction mixture to separate crystals by filtration and dry.

Example 71: Dextromethorphan Terephthallate

Dissolve the free base dextromethorphan (0.05 mole) in 20 ml of acetone, add the solution to a solution of the terephthalic acid (0.05 mole) in 60 ml of hot water, and then cool the reaction mixture to separate crystals by filtration and dry.

Example 72: Dextromethorphan Salicylate

Dissolve the free base (0.05 mole) in 20 ml of acetone, add the solution to a solution of the salicylic acid (0.05 mole) in 60 ml of hot water, and then cool the reaction mixture to separate crystals by filtration and dry.

Example 73: Dextromethorphan Acetylsalicylate

Dissolve the free base (0.05 mole) in 20 ml of acetone, add the solution to a solution of the acetyl salicylic acid (0.05 mole) in 60 ml of hot water, and then cool the reaction mixture to separate crystals by filtration and dry.

Example 74-96: Diacid Addition Salt of Dextromethorphan and a Compound Selected from Formula I Compounds Comprising FDIc and FDId (Compounds 219-269)

Dissolve the free base (FDIc or FDId) (0.25 mole) and dextromethorphan (0.25 mole) in 20 ml of acetone, add the solution to a solution of a di or tri acid (0.05 mole) in 60 ml of hot water, and then cool the reaction mixture to separate crystals by filtration and dry. The di and tri acids include, but not limited to adipic acid, aspartic acid, N-acyl aspartic acid, citric acid, fumaric acid, galactonic acid, glutaric acid, glutamic acid, N-acyl glutamic acid, glucaric acid (saccharic acid), malic acid, maleic acid, mannonic acid, mucic acid, oxalic acid, pimelic acid, phthallic acid, isophthallic acid, terephthallic acid, rhamnonic acid, sebacic acid, succinic acid, and tartaric acid. Thus, forming addition salts such as:

Example 74

Adipic acid addition salt of (FDIc or FDId) and dextromethorphan

Example 75

Aspartic acid addition salt of (FDIc or FDId) and dextromethorphan

Example 76

N-Acyl aspartic acid, addition salt of (FDIc or FDId) and dextromethorphan

Example 77

Citric acid addition salt of (FDIc or FDId) and dextromethorphan

Example 78

Fumaric acid addition salt of (FDIc or FDId) and dextromethorphan

Example 79

Galactonic acid addition salt of (FDIc or FDId) and dextromethorphan

Example 80

Glutaric acid addition salt of (FDIc or FDId) and dextromethorphan

Example 81

Glutamic acid addition salt of (FDIc or FDId) and dextromethorphan

Example 82

N-Acyl glutamic acid addition salt of (FDIc or FDId) and dextromethorphan

Example 83

Glucaric acid (saccharic acid) addition salt of (FDIc or FDId) and dextromethorphan Example 84

Malic acid addition salt of (FDIc or FDId) and dextromethorphan

Example 85

Maleic acid addition salt of (FDIc or FDId) and dextromethorphan

Example 86

Mannonic acid addition salt of (FDIc or FDId) and dextromethorphan

Example 87

Mucic acid addition salt of (FDIc or FDId) and dextromethorphan

Example 88

Oxalic acid addition salt of (FDIc or FDId) and dextromethorphan

Example 89

Pimelic acid addition salt of (FDIc or FDId) and dextromethorphan

Example 90

Phthallic acid addition salt of (FDIc or FDId) and dextromethorphan

Example 91

Isophthallic acid addition salt of (FDIc or FDId) and dextromethorphan

Example 92

Terephthallic acid addition salt of (FDIc or FDId) and dextromethorphan

Example 93

Rhamnonic acid addition salt of (FDIc or FDId) and dextromethorphan,

Example 94

Sebacic acid addition salt of (FDIc or FDId) and dextromethorphan

Example 95

Succinic acid addition salt of (FDIc or FDId) and dextromethorphan

Example 96

Tartaric acid addition salt of (FDIc or FDId) and dextromethorphan

Example 97

Compound 901 ((1-(dimethylamino)-3-(2-(3-methoxyphenethyl)phenoxy) propan-2-yl)oxy)methyl isopropyl (S)-phosphorofluoridate;

Example 98

Compound 902 (((S)-1-(dimethylamino)-3-(2-(3-methoxyphenethyl) phenoxy) propan-2-yl)oxy) methyl isopropyl (S)-phosphorofluoridate;

Example 99

Compound 903 (((R)-1-(dimethylamino)-3-(2-(3-methoxyphenethyl) phenoxy) propan-2-yl)oxy)methyl isopropyl (S)-phosphorofluoridate;

Example 100

Compound 904 ((1-(dimethylamino)-3-(2-(3-methoxyphenethyl) phenoxy) propan-2-yl)oxy)methyl (3,3-dimethylbutan-2-yl) (R)-phosphorofluoridate;

Example 101

Compound 905 sec-butyl ((((S)-1-(dimethylamino)-3-(2-(3-methoxy phenethyl) propan-2-yl)oxy)methyl) (R)-phosphorofluoridate;

Example 102

Compound 906 sec-butyl ((((R)-1-(dimethylamino)-3-(2-(3-methoxyphenethyl) phenoxy)propan-2-yl)oxy)methyl) (R)-phosphorofluoridate;

Example 102

Compound 907 O-(((1-(dimethylamino)-3-(2-(3-methoxyphenethyl) phenoxy)propan-2-yl)oxy)methyl)O-ethyl O-(4-nitrophenyl) phosphorothioate;

Example 103

Compound 908 O—((((S)-1-(dimethylamino)-3-(2-(3-methoxyphenethyl) phenoxy)propan-2-yl)oxy)methyl)O-ethyl O-(4-nitrophenyl) phosphorothioate;

Example 104

Compound 909 O—((((R)-1-(dimethylamino)-3-(2-(3-methoxyphenethyl) phenoxy)propan-2-yl)oxy)methyl)O-ethyl O-(4-nitrophenyl) phosphorothioate;

Example 105

Compound 910 O-(((1-(dimethylamino)-3-(2-(3-methoxyphenethyl) phenoxy)propan-2-yl)oxy)methyl)S-((1,3-dioxoisoindolin-2-yl)methyl) (dimethyl-13-oxidaneyl) phosphonodithioate;

Example 106

Compound 911 O—((((S)-1-(dimethylamino)-3-(2-(3-methoxyphenethyl)phenoxy)propan-2-yl)oxy)methyl)S-((1,3-dioxoisoindolin-2-yl)methyl) (dimethyl-13-oxidaneyl) phosphonodithioate;

Example 107

Compound 912 O—((((R)-1-(dimethylamino)-3-(2-(3-methoxyphenethyl) phenoxy)propan-2-yl)oxy)methyl)S-((1,3-dioxoisoindolin-2-yl)methyl) (dimethyl-13-oxidaneyl) phosphonodithioate;

Example 108

Compound 913 (E)-3-chloro-4-(diethylamino)-4-oxobut-2-en-2-yl (((1-(dimethylamino)-3-(2-(3-methoxyphenethyl) phenoxy)propan-2-yl)oxy)methyl) methyl phosphate;

Example 109

Compound 914 (E)-3-chloro-4-(diethylamino)-4-oxobut-2-en-2-yl ((((S)-1-(dimethylamino)-3-(2-(3-methoxyphenethyl)phenoxy)propan-2-yl)oxy)methyl) methyl phosphate;

Example 110

Compound 915 (E)-3-chloro-4-(diethylamino)-4-oxobut-2-en-2-yl ((((R)-1-(dimethylamino)-3-(2-(3-methoxyphenethyl)phenoxy)propan-2-yl)oxy)methyl) methyl phosphate

Example 111

Compound 916 O-(((1-(dimethylamino)-3-(2-(3-methoxyphenethyl) phenoxy)propan-2-yl)oxy) methyl)S-(2-(ethylsulfinyl)ethyl)O-methyl phosphorothioate;

Example 112

Compound 917 O—((((S)-1-(dimethylamino)-3-(2-(3-methoxyphenethyl) phenoxy)propan-2-yl) oxy) methyl)S-(2-(ethylsulfinyl)ethyl)O-methyl phosphorothioate;

Example 113

Compound 918 O—((((R)-1-(dimethylamino)-3-(2-(3-methoxyphenethyl) phenoxy)propan-2-yl) oxy) methyl)S-(2-(ethylsulfinyl)ethyl)O-methyl phosphorothioate;

Example 114

Compound 919 O-(((1-(dimethylamino)-3-(2-(3-methoxyphenethyl) phenoxy) propan-2-yl)oxy) methyl)O-ethyl S-((ethyl thio)methyl) phosphorodithioate;

Example 115

Compound 920 O-(((1-(dimethylamino)-3-(2-(3-methoxyphenethyl) phenoxy)propan-2-yl) oxy) methyl)O-ethyl S-((ethylthio)methyl) phosphorodithioate;

Example 116

Compound 921 O-(((1-(dimethylamino)-3-(2-(3-methoxyphenethyl) phenoxy)propan-2-yl) oxy) methyl)O-ethyl S-((ethylthio)methyl) phosphorodithioate;

Example 117

Compound 922 S-((6-chloro-2-oxobenzo[d]oxazol-3(2H)-yl)methyl)O-(((1-(dimethylamino)-3-(2-(3-methoxyphenethyl)phenoxy)propan-2-yl)oxy)methyl)O-ethyl phosphorodithioate;

Example 118

Compound 923 S-((6-chloro-2-oxobenzo[d]oxazol-3(2H)-yl)methyl)O—((((S)-1-(dimethylamino)-3-(2-(3-methoxyphenethyl)phenoxy)propan-2-yl)oxy)methyl)O-ethyl phosphorodithioate;

Example 119

Compound 924 S-((6-chloro-2-oxobenzo[d]oxazol-3(2H)-yl)methyl)O—((((R)-1-(dimethylamino)-3-(2-(3-methoxyphenethyl)phenoxy)propan-2-yl)oxy)methyl) O-ethyl phosphorodithioate;

Example 120

Compound 925 S-((tert-butylthio)methyl) O-(((1-(dimethylamino)-3-(2-(3-methoxy phenethyl) phenoxy)propan-2-yl)oxy)methyl)O-ethyl phosphorodithioate;

Example 121

Compound 926 S-((tert-butyl thio) methyl)O—((((S)-1-(dimethyl amino)-3-(2-(3-methoxy phen ethyl) phenoxy) propan-2-yl)oxy)methyl)O-ethyl phosphorodithioate;

Example 122

Compound 927 S-((tert-butylthio) methyl)O—((((R)-1-(dimethyl amino)-3-(2-(3-methoxy phen ethyl) phenoxy) propan-2-yl)oxy)methyl)O-ethyl phosphorodithioate;

Example 123

Compound 928 O-(4-((4-(((((1-(dimethyl amino)-3-(2-(3-methoxyphenethyl) phenoxy) propan-2-yl) oxy) methoxy) (methoxy) phosphorothioyl) oxy) phenyl) thio) phenyl) O,O-dimethyl phosphorothioate;

Example 124

Compound 929 O-(4-((4-((((((S)-1-(dimethylamino)-3-(2-(3-methoxy phenethyl) phenoxy) propan-2-yl) oxy) methoxy) (methoxy) phosphorothioyl) oxy) phenyl) thio) phenyl) O,O-dimethyl phosphorothioate;

Example 125

Compound 930 O-(4-((4-((((((R)-1-(dimethylamino)-3-(2-(3-methoxyphenethyl) phenoxy)propan-2-yl)oxy) methoxy) (methoxy) phosphorothioyl) oxy) phenyl) thio) phenyl) O,O-dimethyl phosphorothioate;

Example 126

Compound 931 ((1-(dimethylamino)-3-(2-(3-methoxyphenethyl) phenoxy) propan-2-yl)oxy) methyl triethyl diphosphate;

Example 127

Compound 932 (((S)-1-(dimethylamino)-3-(2-(3-methoxyphenethyl) phenoxy) propan-2-yl) oxy) methyl triethyl diphosphate;

Example 128

Compound 933 (((R)-1-(dimethylamino)-3-(2-(3-methoxyphenethyl) phenoxy) propan-2-yl) oxy) methyl triethyl diphosphate;

Example 129

Compound 934 ((1-(dimethylamino)-3-(2-(3-methoxyphenethyl) phenoxy) propan-2-yl) oxy) methyl methyl (2,2,2-trichloro-1-hydroxyethyl)phosphonate;

Example 130

Compound 935 (((S)-1-(dimethylamino)-3-(2-(3-methoxyphenethyl) phenoxy) propan-2-yl)oxy) methyl methyl (2,2,2-trichloro-1-hydroxyethyl)phosphonate;

Example 131

Compound 936 (((R)-1-(dimethylamino)-3-(2-(3-methoxyphenethyl) phenoxy) propan-2-yl)oxy) methyl methyl (2,2,2-trichloro-1-hydroxyethyl)phosphonate;

Example 132

Compound 937 2-chloro-1-(2,4,5-trichlorophenyl) vinyl (((1-(dimethylamino)-3-(2-(3-methoxy phenethyl) phenoxy) propan-2-yl)oxy) methyl) hydrogen phosphate;

Example 133

Compound 938 2-chloro-1-(2,4,5-trichlorophenyl) vinyl ((((S)-1-(dimethyl amino)-3-(2-(3-methoxy phenethyl) phenoxy) propan-2-yl) oxy) methyl) hydrogen phosphate;

Example 134

Compound 939 2-chloro-1-(2,4,5-trichlorophenyl) vinyl ((((R)-1-(dimethyl amino)-3-(2-(3-methoxy phenethyl) phenoxy) propan-2-yl) oxy) methyl) hydrogen phosphate;

Example 135

Compound 940 O-(((1-(dimethylamino)-3-(2-(3-methoxyphenethyl) phenoxy) propan-2-yl)oxy) methyl)S-methyl acetylphosphoramidothioate;

Example 136

Compound 941 O—((((S)-1-(dimethylamino)-3-(2-(3-methoxyphenethyl) phenoxy) propan-2-yl) oxy) methyl)S-methyl acetyl phosphoramidothioate;

Example 137

Compound 942 O—((((R)-1-(dimethylamino)-3-(2-(3-methoxyphenethyl) phenoxy) propan-2-yl)oxy) methyl)S-methyl acetylphosphoramidothioate;

Example 138

Compound 943 (O-(((1-(dimethylamino)-3-(2-(3-methoxyphenethyl) phenoxy)propan-2-yl)oxy)methyl)O-propyl phosphorothioic) (O,O-dipropyl phosphorothioic) anhydride;

Example 139

Compound 944 (O—((((S)-1-(dimethylamino)-3-(2-(3-methoxyphenethyl) phenoxy)propan-2-yl) oxy) methyl)O-propyl phosphorothioic) (O,O-dipropyl phosphorothioic) anhydride;

Example 140

Compound 945 (O—((((R)-1-(dimethyl amino)-3-(2-(3-methoxy phenethyl) phenoxy) propan-2-yl) oxy) methyl)O-propyl phosphorothioic) (O,O-dipropyl phosphorothioic) anhydride;

Example 141

Compound 946 O-(((1-(dimethylamino)-3-(2-(3-methoxyphenethyl) phenoxy)propan-2-yl) oxy) methyl)S-methyl acetylphosphoramidothioate;

Example 142

Compound 947 O—((((S)-1-(dimethylamino)-3-(2-(3-methoxyphenethyl) phenoxy)propan-2-yl) oxy) methyl)S-methyl acetylphosphoramidothioate;

Example 143

Compound 948 O—((((R)-1-(dimethylamino)-3-(2-(3-methoxy phenethyl)phenoxy)propan-2-yl) oxy) methyl)S-methyl acetylphosphoramidothioate;

Example 144

Compound 949 O-(((1-(dimethylamino)-3-(2-(3-methoxyphenethyl) phenoxy)propan-2-yl)oxy)methyl)O-methyl S-((4-oxobenzo[d][1,2,3]triazin-3(4H)-yl)methyl) phosphorodithioate compound with methane (1:1);

Example 145

Compound 950 O—((((S)-1-(dimethylamino)-3-(2-(3-methoxyphenethyl) phenoxy)propan-2-yl)oxy)methyl)O-methyl S-((4-oxobenzo[d][1,2,3]triazin-3(4H)-yl)methyl) phosphorodithioate compound with methane (1:1);

Example 146

Compound 951 O—((((R)-1-(dimethylamino)-3-(2-(3-methoxyphenethyl) phenoxy)propan-2-yl)oxy)methyl)O-methyl S-((4-oxobenzo[d][1,2,3]triazin-3(4H)-yl)methyl) phosphorodithioate compound with methane (1:1);

Example 147

Compound 952 2-chloroethyl (((1-(dimethylamino)-3-(2-(3-methoxyphenethyl) phenoxy)propan-2-yl)oxy)methyl) (R)-phosphorofluoridate;

Example 148

Compound 953 2-chloroethyl ((((S)-1-(dimethylamino)-3-(2-(3-methoxyphenethyl) phenoxy)propan-2-yl)oxy)methyl) (R)-phosphorofluoridate;

Example 149

Compound 954 2-chloroethyl ((((R)-1-(dimethylamino)-3-(2-(3-methoxy phenethyl) phenoxy)propan-2-yl)oxy)methyl) (R)-phosphorofluoridate;

Example 150

Compound 955 3-chlorobutan-2-yl (((1-(dimethylamino)-3-(2-(3-methoxy phenethyl) phenoxy)propan-2-yl)oxy)methyl) (R)-phosphorofluoridate;

Example 151

Compound 956 3-chlorobutan-2-yl ((((S)-1-(dimethylamino)-3-(2-(3-methoxy phenethyl) phenoxy)propan-2-yl)oxy)methyl) (R)-phosphorofluoridate;

Example 152

Compound 957 3-chlorobutan-2-yl ((((R)-1-(dimethylamino)-3-(2-(3-methoxy phenethyl) phenoxy)propan-2-yl)oxy)methyl) (R)-phosphorofluoridate;

Example 153

Compound 958 ((1-(dimethylamino)-3-(2-(3-methoxyphenethyl)phenoxy) propan-2-yl)oxy)methyl (S)-((((E)-chlorofluoromethylene)amino)oxy)phosphonofluoridate;

Example 154

Compound 959 ((((S)-1-(dimethylamino)-3-(2-(3-methoxyphenethyl)phenoxy) propan-2-yl)oxy)methyl (S)-((((E)-chlorofluoromethylene)amino)oxy)phosphonofluoridate;

Example 156

Compound 960 ((((R)-1-(dimethylamino)-3-(2-(3-methoxyphenethyl)phenoxy) propan-2-yl)oxy)methyl (S)-((((E)-chlorofluoromethylene)amino)oxy)phosphonofluoridate;

Example 157

Compound 961 2-chloroethyl (((1-(dimethylamino)-3-(2-(3-methoxyphenethyl)phenoxy) propan-2-yl)oxy)methyl) (E)-(((chlorofluoromethylene) amino)oxy)phosphorofluoridate;

Example 158

Compound 962 2-chloroethyl ((((S)-1-(dimethylamino)-3-(2-(3-methoxyphenethyl) phenoxy) propan-2-yl)oxy)methyl) (E)-(((chlorofluoromethylene)amino) oxy)phosphorofluoridate;

Example 159

Compound 963 2-chloroethyl ((((R)-1-(dimethylamino)-3-(2-(3-methoxyphenethyl) phenoxy) propan-2-yl)oxy)methyl) (E)-(((chlorofluoromethylene)amino) oxy)phosphorofluoridate;

Example 160

Compound 964 1-chloropropan-2-yl (((1-(dimethylamino)-3-(2-(3-methoxyphenethyl) phenoxy) propan-2-yl)oxy)methyl) (E)-(((chlorofluoromethylene)amino)oxy) phosphorofluoridate;

Example 161

Compound 965 1-chloropropan-2-yl ((((S)-1-(dimethylamino)-3-(2-(3-methoxyphenethyl) phenoxy) propan-2-yl)oxy)methyl) (E)-(((chlorofluoromethylene) amino)oxy) phosphoro fluoridate;

Example 162

Compound 966 1-chloropropan-2-yl ((((R)-1-(dimethylamino)-3-(2-(3-methoxy phenethyl) phenoxy) propan-2-yl)oxy)methyl) (E)-(((chlorofluoro methylene) amino) oxy) phosphoro fluoridate;

Example 163

Compound 967 3-chlorobutan-2-yl (((1-(dimethylamino)-3-(2-(3-methoxyphenethyl)phenoxy) propan-2-yl)oxy)methyl) (E)-(((chlorofluoromethylene)amino) oxy)phosphorofluoridate;

Example 164

Compound 968 3-chlorobutan-2-yl ((((S)-1-(dimethylamino)-3-(2-(3-methoxyphenethyl) phenoxy) propan-2-yl)oxy)methyl) (E)-(((chlorofluoromethylene)amino) oxy) phosphoro fluoridate;

Example 165

Compound 969 3-chlorobutan-2-yl ((((R)-1-(dimethylamino)-3-(2-(3-methoxyphenethyl) phenoxy) propan-2-yl)oxy)methyl) (E)-(((chlorofluoromethylene) amino)oxy) phosphoro fluoridate.

Example 166

Compound 970 ((1-(dimethylamino)-3-(2-(3-methoxyphenethyl) phenoxy) propan-2-yl)oxy) methyl methyl (2,2,2-trichloro-1-hydroxyethyl)phosphonate.

Example 167

Compound 971 ((((S)-1-(dimethylamino)-3-(2-(3-methoxyphenethyl) phenoxy) propan-2-yl)oxy) methyl methyl (2,2,2-trichloro-1-hydroxyethyl)phosphonate;

Example 168

Compound 972 ((((R)-1-(dimethylamino)-3-(2-(3-methoxyphenethyl) phenoxy) propan-2-yl)oxy)methyl methyl (2,2,2-trichloro-1-hydroxyethyl)phosphonate.

Example 169

Compound 973 4-(tert-butyl)-2-chlorophenyl (((1-(dimethylamino)-3-(2-(3-methoxyphenethyl) phenoxy)propan-2-yl)oxy)methyl) methylphosphoramidate compound with methane (1:1);

Example 170

Compound 974 4-(tert-butyl)-2-chlorophenyl ((((S)-1-(dimethylamino)-3-(2-(3-methoxy phenethyl) phenoxy)propan-2-yl)oxy)methyl) methylphosphoramidate compound with methane (1:1).

Example 171

Compound 975 4-(tert-butyl)-2-chlorophenyl ((((R)-1-(dimethylamino)-3-(2-(3-methoxy phenethyl) phenoxy)propan-2-yl)oxy)methyl) methylphosphoramidate compound with methane (1:1).

Example 172

Compound 976 ((1-(dimethylamino)-3-(2-(3-methoxyphenethyl) phenoxy) propan-2-yl) oxy) methyl (3-methyl-4-(methylthio) phenyl) isopropylphosphoramidate;

Example 173

Compound 977 ((((S)-1-(dimethylamino)-3-(2-(3-methoxyphenethyl) phenoxy) propan-2-yl)oxy) methyl (3-methyl-4-(methylthio)phenyl) isopropylphosphoramidate.

Example 174

Compound 978 ((((R)-1-(dimethylamino)-3-(2-(3-methoxyphenethyl) phenoxy) propan-2-yl)oxy) methyl (3-methyl-4-(methylthio)phenyl) isopropylphosphoramidate.

Example 175

Compound 829 ((2,(−)-[1R,2S,4R]-2-(2-dimethyl amino ethoxy)-2-phenyl-1,7,7-trimethyl bicyclo [2.2.1]heptane)

fumarate (U.S. Pat. No. 4,342,762 A; Ladányi L et al., Stereochemistry and enantiomeric purity of a novel anxiolytic agent, deramciclane fumarate. Chirality 11:689-93 (1999), incorporated by reference). Fumarate of compound 829 can be prepared by a three-step synthesis scheme using readily available and low-cost starting materials (camphor) with very high enantiomeric purity (>99.9%). 3.9 g (0.1 g atom) of potassium metal are added to 100 ml of anhydrous xylene, and the mixture is reacted with 23.04 g (0.1 mole) of (+)-2-phenyl-1,7,7-trimethyl-bicyclo(2,2,1)heptan-2-ol under vigorous stirring. When the formation of hydrogen gas has ceased, a solution of 10.3 g (0.11 moles) of 1-dimethylamnino-2-chloro-ethaJie in 30 ml of anhydrous xylene is introduced, under further stirring. The reaction mixture is kept at 100° C. for 6 hours, then washed thrice with 50 ml of water, and extracted with a solution of 15 g (0.1 mole) of tartaric acid in 80 ml of water or with 0.11 mole of diluted aqueous hydrochloric acid. The aqueous phase is made alkaline to pH 10 with an aqueous solution of potassium hydroxide of 20% under cooling (at 0 to 5° C.). The base separated as an oil is extracted with ether. After distilling off the solvent the residue is either purified with fractionated distillation under vacuo or used for salt formation. Yield: 25.2 g (D.6%) of a pale yellow oil, BP: 131°–135° C./26.7 Pa, Hydrogen fumarate, m.p.: 180°-182° C. The enantiomneric separation is accomplished by HPLC on Chiralcel OD (250×4.6 mm; 10 μm) and hexane-ethanol (99.5:0.5) as mobile phase at room temperature. Chemical Formula: C24H35NO5. Molecular Weight: 417.55. Elemental Analysis: Calculated: C, 69.03%; H, 8.45%; N, 3.35%. Found: C, 69.05%; H, 8.59%; N, 3.44%.

Compound 829 is a dual $5\text{-}HT_{2A}/5\text{-}HT_2C$ receptors inverse agonist at clinically relevant doses and does not induce down-regulation of these receptors (Pilvimiiki E P et al., Deramciclane, a putative anxiolytic drug, is a serotonin 5-HT2C receptor inverse agonist but fails to induce 5-HT2C receptor down-regulation. Psychopharmacology (1998) 136: 99-104). Deramciclane is at least 10-fold selective against dopamine $D_2$ receptors (Gacsályi I et al., Receptor binding profile and anxiolytic-type activity of deramciclane (EGIS-3886) in animal models. Drug Dev Res (1997) 40:333-348). Extensive evaluation of Compound 829 in dopaminergic models has not revealed any functional significance of these receptor binding data. Compound 829 was not found to elevate prolactin—at least within the dose-range that covers therapeutically relevant exposures (Laine K et al., Effect of the novel anxiolytic drug deramciclane on the pharmacokinetics and pharmacodynamics of the CYP3A4 probe drug buspirone. Eur J Clin Pharmacol (2003) 59: 761-766).

Compound 829 has been extensively characterized preclinically and a large body of evidence indicate CNS target(s) for the pharmacodynamic activity of deramciclane. Gacsályi and colleagues (Gacsályi I et al., Receptor binding profile and anxiolytic-type activity of deramciclane (EGIS-3886) in animal models. Drug Dev Res (1997) 40:333-348) described a profile of effects induced by deramciclane that are typical for $5\text{-}HT_{2A}/5\text{-}HT_{2C}$ receptor inverse agonists. N-desmethylderivative of compound 829 is a biologically active metabolite having a profile similar to that of to Compound 829.

Ability of Compound 829 to target $5\text{-}HT_{2A}$ receptors in the CNS has been directly demonstrated in both animals (Pilvimiki E P et al., Deramciclane, a putative anxiolytic drug, is a serotonin 5-HT2C receptor inverse agonist but fails to induce 5-HT2C receptor down-regulation. Psychopharmacology (1998) 136:99-104) and humans (Kanerva H et al., Brain 5-HT2A receptor occupancy of deramciclane in humans after a single oral administration—a positron emission tomography study. Psychopharmacology (1999) 145: 76-81).

Ability of Compound 829 to target 5-HT2A receptors in the CNS has been directly demonstrated in rats using [3H]mesulergine binding to choroid plexus (Pilvimiiki E P et al., Deramciclane, a putative anxiolytic drug, is a serotonin 5-HT2C receptor inverse agonist but fails to induce 5-HT2C receptor down-regulation. Psychopharmacology (1998) 136: 99-104). Doses of Compound 829 that produce near-maximal inhibition of [3H]mesulergine binding (0.5 mg/kg) are at the lower range of doses producing efficacy in animal models (Gacsályi I et al., Receptor binding profile and anxiolytic-type activity of deramciclane (EGIS-3886) in animal models. Drug Dev Res (1997) 40:333-348). Therefore, Compound 829 is expected to produce in humans antidepressant, anxiolytic, appetite-stimulating and other effects, all of which are therapeutically relevant in patients with dementia (Jensen N H et al., Therapeutic potential of 5-HT2C receptor ligands. Scientific World Journal. 2010 Sep. 14; 10:1870-85; Meltzer H Y et al., Serotonin receptors as targets for drugs useful to treat psychosis and cognitive impairment in schizophrenia. Curr Pharm Biotechnol. 2012 June; 13(8):1572-86).

For Compound 829, there is evidence on therapeutic effects from clinical studies in patients with generalized anxiety disorder (Naukkarinen H et al., Deramciclane in the treatment of generalized anxiety disorder: a placebo-controlled, double-blind, dose-finding study. Eur Neuropsychopharmacol (1999) 15:617-23), strengthening the claim that Compound 829 is a CNS-active compound that is capable of engaging its target(s). In the intent-to-treat population (n=208), both deramciclane 30 mg/day and 60 mg/day doses provided clinically relevant improvements in Hamilton Anxiety Rating scale HAM-A total score after 8 weeks of treatment, reaching statistical significance compared with placebo (n=51) in the 60 mg/day dose group (p=0.024, n=54) and a clear trend in the 30 mg/day group (p=0.059, n=53), but not in the 10 mg/day group (n=54). On the HAM-A psychic anxiety factor, significant improvements were seen in patients in the deramciclane 30 mg/day and 60 mg/day treatment groups compared with those in the placebo group.

Compound 829 is also a CYP 2D6 inhibitor based on studies in humans using desipramine as a substrate. In this randomized double-blind, cross-over study, fifteen healthy subjects received either 60 mg/day Compound 829 or placebo for 8 days. On day 8 of each study phase, the subjects received a 100-mg single dose of desipramine. Repeated administration of Compound 829 doubled the AUC of desipramine (Laine K et al., Effect of the novel anxiolytic drug deramciclane on cytochrome P(450) 2D6 activity as measured by desipramine pharmacokinetics. Eur J Clin Pharmacol (2004) 59:893-898, incorporated by reference).

Example 176 Compound 1001 1-(dimethylamino)-3-(2-(3-methoxyphenethyl) phenoxy) propan-2-yl 4-(adamantan-1-ylamino)-4-oxobutanoate Chemical Formula: C34H46N2O5; Exact Mass: 562.34; Molecular Weight: 562.75; m/z: 562.34 (100.0%), 563.34 (36.8%), 564.35 (3.9%), 564.35 (2.7%), 564.34 (1.0%); Elemental Analysis: C, 72.57; H, 8.24; N, 4.98; O, 14.21. Boiling Point: 1300.87 [K]; Melting Point: 890.75 [K]; Critical Temp: 1176.29 [K]; Critical Pres: 8.99 [Bar]; Critical Vol: 1685.5 [cm3/mol]; Gibbs Energy: 126.8 [kJ/mol]; Log P: 5.06; MR: 160.74 [cm3/mol]; Henry's Law: 16.03;

Heat of Form: −719.51 [kJ/mol]; tPSA: 77.1; CLogP: 6.5154; CMR: 16.1393; LogS: −6.845; pKa: 8.362.

Example 177 Compound 1002 (S)-1-(dimethylamino)-3-(2-(3-methoxy phenethyl) phenoxy) propan-2-yl 4-(adamantan-1-ylamino)-4-oxobutanoate Chemical Formula: C34H46N2O5; Exact Mass: 562.34; Molecular Weight: 562.75; m/z: 562.34 (100.0%), 563.34 (36.8%), 564.35 (3.9%), 564.35 (2.7%), 564.34 (1.0%); Elemental Analysis: C, 72.57; H, 8.24; N, 4.98; O, 14.21. Boiling Point: 1300.87 [K]; Melting Point: 890.75 [K]; Critical Temp: 1176.29 [K]; Critical Pres: 8.99 [Bar]; Critical Vol: 1685.5 [cm3/mol]; Gibbs Energy: 126.8 [kJ/mol]; Log P: 5.06; MR: 160.74 [cm3/mol]; Henry's Law: 16.03; Heat of Form: −719.51 [kJ/mol]l tPSA: 77.1; CLogP: 6.5154; CMR: 16.1393; LogS: −6.845; pKa: 8.362.

Example 178 Compound 1003 (R)-1-(dimethylamino)-3-(2-(3-methoxyphenethyl) phenoxy) propan-2-yl 4-(adamantan-1-ylamino)-4-oxobutanoate Chemical Formula: C34H46N2O5; Exact Mass: 562.34; Molecular Weight: 562.75; m/z: 562.34 (100.0%), 563.34 (36.8%), 564.35 (3.9%), 564.35 (2.7%), 564.34 (1.0%); Elemental Analysis: C, 72.57; H, 8.24; N, 4.98; 0, 14.21. Boiling Point: 1300.87 [K]; Melting Point: 890.75 [K]; Critical Temp: 1176.29 [K]; Critical Pres: 8.99 [Bar]; Critical Vol: 1685.5 [cm3/mol]; Gibbs Energy: 126.8 [kJ/mol]; Log P: 5.06; MR: 160.74 [cm3/mol]; Henry's Law: 16.03; Heat of Form: −719.51 [kJ/mol]l tPSA: 77.1; CLogP: 6.5154; CMR: 16.1393; LogS: −6.845; pKa: 8.362.

Example 179 Compound 1004 (R)-1-(dimethylamino)-3-(2-(3-methoxyphenethyl) phenoxy) propan-2-yl 4-((3,5-dimethyl adamantan-1-yl)amino)-4-oxo butanoate Chemical Formula: C36H50N2O5; Exact Mass: 590.37; Molecular Weight: 590.81; m/z: 590.37 (100.0%), 591.38 (38.9%), 592.38 (7.4%), 592.38 (1.0%); Elemental Analysis: C, 73.19; H, 8.53; N, 4.74; O, 13.54. Boiling Point: 1347.11 [K]; Melting Point: 961.09 [K]; Critical Temp: 1191.88 [K]; Critical Pres: 8.46 [Bar]; Critical Vol: 1793.5 [cm3/mol]; Gibbs Energy: 132.66 [kJ/mol]; Log P: 6; MR: 169.53 [cm3/mol]; Henry's Law: 15.78; Heat of Form: −730.31 [kJ/mol]; tPSA: 77.1; CLogP: 7.5534; CMR: 17.0669; LogS: −7.773; pKa: 8.362.

Example 180 Compound 1005 1-(dimethylamino)-3-(2-(3-methoxyphenethyl) phenoxy) propan-2-yl 4-((3,5-dimethyl adamantan-1-yl)amino)-4-oxobutanoate Chemical Formula: C36H50N2O5; Exact Mass: 590.37; Molecular Weight: 590.81; m/z: 590.37 (100.0%), 591.38 (38.9%), 592.38 (7.4%), 592.38 (1.0%); Elemental Analysis: C, 73.19; H, 8.53; N, 4.74; O, 13.54. Boiling Point: 1347.11 [K]; Melting Point: 961.09 [K]; Critical Temp: 1191.88 [K]; Critical Pres: 8.46 [Bar]; Critical Vol: 1793.5 [cm3/mol]; Gibbs Energy: 132.66 [kJ/mol]; Log P: 6; MR: 169.53 [cm3/mol]; Henry's Law: 15.78; Heat of Form: −730.31 [kJ/mol]; tPSA: 77.1; CLogP: 7.5534; CMR: 17.0669; LogS: −7.773; pKa: 8.362.

Example 181 Compound 1005 (S)-1-(dimethylamino)-3-(2-(3-methoxyphenethyl) phenoxy) propan-2-yl 4-((3,5-dimethyl adamantan-1-yl) amino)-4-oxobutanoate Chemical Formula: C36H50N2O5; Exact Mass: 590.37; Molecular Weight: 590.81; m/z: 590.37 (100.0%), 591.38 (38.9%), 592.38 (7.4%), 592.38 (1.0%); Elemental Analysis: C, 73.19; H, 8.53; N, 4.74; O, 13.54. Boiling Point: 1347.11 [K]; Melting Point: 961.09 [K]; Critical Temp: 1191.88 [K]; Critical Pres: 8.46 [Bar]; Critical Vol: 1793.5 [cm3/mol]; Gibbs Energy: 132.66 [kJ/mol]; Log P: 6; MR: 169.53 [cm3/mol]; Henry's Law: 15.78; Heat of Form: −730.31 [kJ/mol]; tPSA: 77.1; CLogP: 7.5534; CMR: 17.0669; LogS: −7.773; pKa: 8.362

Example 182 Compound 1007 1-(dimethylamino)-3-(2-(3-methoxyphenethyl) phenoxy) propan-2-yl (2,2,2-trichloro-1-(dimethoxyphosphoryl)ethyl) Succinate Chemical Formula: C28H37Cl3NO9P; Exact Mass: 667.13; Molecular Weight: 668.93; m/z: 667.13 (100.0%), 669.12 (95.9%), 671.12 (30.6%), 668.13 (30.3%), 670.13 (29.0%), 672.12 (9.3%), 671.13 (4.2%), 673.12 (3.3%), 669.13 (2.7%), 669.13 (1.8%), 669.13 (1.7%), 671.13 (1.6%), 673.13 (1.4%); Elemental Analysis: C, 50.28; H, 5.58; Cl, 15.90; N, 2.09; O, 21.53; P, 4.63.

Example 183 Compound 1008 (S)-1-(dimethylamino)-3-(2-(3-methoxyphenethyl) phenoxy) propan-2-yl (2,2,2-trichloro-1-(dimethoxyphosphoryl) ethyl) Succinate Chemical Formula: C28H37Cl3NO9P; Exact Mass: 667.13; Molecular Weight: 668.93; m/z: 667.13 (100.0%), 669.12 (95.9%), 671.12 (30.6%), 668.13 (30.3%), 670.13 (29.0%), 672.12 (9.3%), 671.13 (4.2%), 673.12 (3.3%), 669.13 (2.7%), 669.13 (1.8%), 669.13 (1.7%), 671.13 (1.6%), 673.13 (1.4%); Elemental Analysis: C, 50.28; H, 5.58; Cl, 15.90; N, 2.09; O, 21.53; P, 4.63.

Example 184 Compound 1009 (R)-1-(dimethylamino)-3-(2-(3-methoxyphenethyl) phenoxy)propan-2-yl (2,2,2-trichloro-1-(dimethoxyphosphoryl)ethyl) Succinate Chemical Formula: C28H37Cl3NO9P; Exact Mass: 667.13; Molecular Weight: 668.93; m/z: 667.13 (100.0%), 669.12 (95.9%), 671.12 (30.6%), 668.13 (30.3%), 670.13 (29.0%), 672.12 (9.3%), 671.13 (4.2%), 673.12 (3.3%), 669.13 (2.7%), 669.13 (1.8%), 669.13 (1.7%), 671.13 (1.6%), 673.13 (1.4%); Elemental Analysis: C, 50.28; H, 5.58; Cl, 15.90; N, 2.09; O, 21.53; P, 4.63.

Biological Studies

Biological studies were conducted using compounds of Formula I exemplified by 4-((1-(dimethylamino)-3-(2-(3-methoxyphenethyl)phenoxy)propan-2-yl)oxy)-4-oxobutanoic acid (represented by compounds 50, 51, and 52); 1-(dimethylamino)-3-(2-(3-methoxyphenethyl)phenoxy) propan-2-ol (represented by compounds 146, 147, 148);

255 / 256

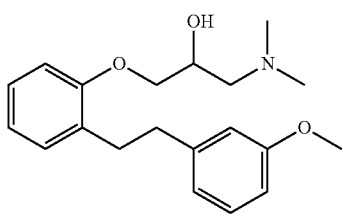

Racemate M1
1-(dimethylamino)-3-(2-(3-methoxyphenethyl)phenoxy)propan-2-ol

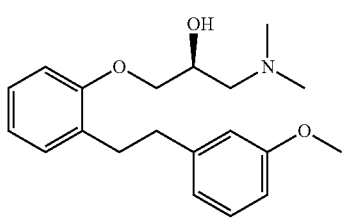

Enantiomer 1 (M1-E1)
(S)-1-(dimethylamino)-3-(2-(3-methoxyphenethyl)phenoxy)propan-2-ol

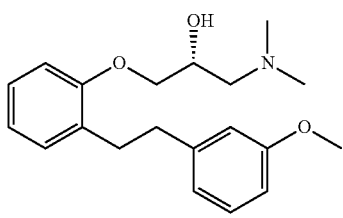

Enantiomer 2 (M1L-E2)
(R)-1-(dimethylamino)-3-(2-(3-methoxyphenethyl)phenoxy)propan-2-ol

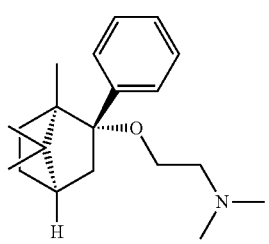

Enantiomer
N,N-dimethyl-2-(((1R,2S,4R)-1,7,7-trimethyl-2-phenylbicyclo[2.2.1]heptan-2-yl)oxy)ethan-1-amine Compound 146

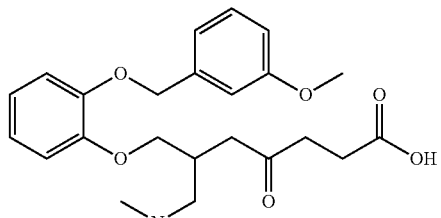

Sarpogrelate Racemate (SGL)
4-((1-(dimethylamino)-3-(2-(3-methoxyphenethyl)phenoxy)propan-2-yl)oxy)-4-oxobutanoic acid Compound 147

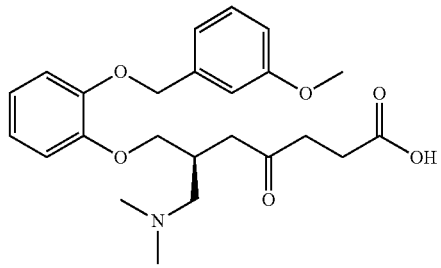

Sarpogrelate Enantiomer 1 (SGL-E1)
(S)-4-((1-(dimethylamino)-3-(2-(3-methoxyphenethyl)phenoxy)propan-2-yl)oxy)-4-oxobutanoic acid Compound 148

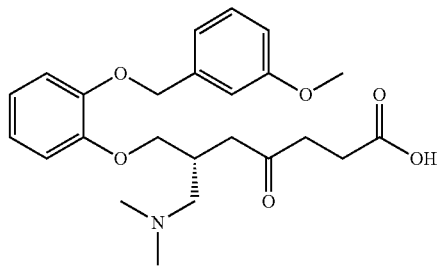

Sarpogrelate Enantiomer 2 (SGL-E2)
(R)-4-((1-(dimethylamino)-3-(2-(3-methoxyphenethyl)phenoxy)propan-2-yl)oxy)-4-oxobutanoic acid Compound 829

N,N-dimethyl-2-[[(1R,3S,4R)-4,7,7-trimethyl-3-phenyl-3-bicyclo[2.2.1] heptanyl] oxy]ethanamine or N,N-dimethyl-2-(((1R,2S,4S)-1,7,7-trimethyl-2-phenylbicyclo [2.2.1]heptan-2-yl)oxy)ethan-1-amine (Compound 829, deramciclane) and compounds of Formula II, exemplified by dextromethorphan, derivatives and metabolites thereof.

Example 185: Dex Metabolism and Central Effects of 5HT2A Receptor Blockade

Antipsychotic drugs attenuate locomotor hyperactivity induced by psychostimulant and psychotomimetic drugs in laboratory rodents. While hyperactivity induced by dopaminergic agents such as d-amphetamine is reversed by both typical and atypical antipsychotics that are currently in the clinic use, 5HT2A receptor antagonists are more effective against hyperactivity induced by NMDA receptor antagonists such as phencyclidine-like channel blockers (Carlsson et al., The 5-HT2A receptor antagonist M100907 is more effective in counteracting NMDA antagonist-than dopamine agonist-induced hyperactivity in mice, *J. Neural. Transm.* 106(2):123-9 (1999)). Pimavanserin (ACP-103) is an example of a 5HT2A receptor antagonist that was administered in mice in combination with 0.3 mg/kg MK-801 (i.p.) 15 min before the test session (Vanover et al., Pharmacological and behavioral profile of N-(4-fluorophenylmethyl)-N-(1-methylpiperidin-4-yl)-N'-(4-(2-methylpropyloxy) phenylmethyl) carbamide (2R,3R)-dihydroxybutanedioate (2:1) (ACP-103), a novel 5-hydroxytryptamine (2A) receptor inverse agonist, J Pharmacol Exp Ther. 317(2):910-8 (2006 May); incorporated by reference). Motor activity data were collected during a 15-min session in a lit room. Mice had no prior exposure to the motor cages. Immediately before placing the mice in the locomotor chambers, effects on myorelaxation/ataxia were determined by placing each of the mouse's forepaws in contact with a horizontal wire while holding the mouse by the base of the tail. Mice were required to bring at least one hindpaw in contact with the wire within 10 s to be scored as a "pass" and failure to do so was considered ataxic. Each dose or dose combination was tested in a separate group of mice. ACP-103 significantly attenuated MK-801-induced hyperactivity in mice at doses of 0.1 and 0.3 mg/kg s.c. [$F(7,63)=6.010$; $p<0.0001$], consistent with an antipsychotic-like effect.

When given in combination with quinidine in patients with neurological diseases (Schoedel et al., Evaluating the safety and efficacy of dextromethorphan/quinidine in the treatment of pseudobulbar affect. Neuropsychiatric Disease and Treatment 2014:10 1161-1174; incorporated by reference in its entirety), dextromethorphan is used at the dose of 10 mg that may be administered twice a day. Currently known clinical dose of Sarpogrelate is 100 mg that is typically given three times a day (Doggrell (2004) sarpogrelate: cardiovascular and renal clinical potential, Expert Opinion on *Investigational Drugs*, 13:7, 865-874; incorporated by reference in its entirety). Thus, current clinical dose of Sarpogrelate significantly exceeds that of dextromethorphan. Given that the molecular weight of sarpogrelate is about 429 and molecular weight of dextromethorphan is about 271, combined use of dextromethorphan and sarpogrelate at the current clinical doses does not result in a molar ratio of 1:1. However, such molar ratio of 1:1 is a pre-requisite for preparing and using sarpogrelate salts of dextromethorphan. As the current clinical use of sarpogrelate is for peripheral (non-CNS) indications (Doggrell (2004) sarpogrelate: cardiovascular and renal clinical potential, Expert Opinion on *Investigational Drugs*, 13:7, 865-874; incorporated by reference in its entirety), use of sarpogrelate for CNS indications may require lower doses and therefore enable co-administration with dextromethorphan as sarpogrelate salt of dextromethorphan or as a mixture in a molar ratio of 1:1. In laboratory animals, sarpogrelate is typically given at doses of 25 mg/kg and above to induce peripheral effects (Ma et al., Effective treatment with combination of peripheral 5-hydroxytryptamine synthetic inhibitor and 5-hydroxytryptamine 2 receptor antagonist on glucocorticoid-induced whole-body insulin resistance with hyperglycemia. J Diabetes Investig 7(6):833-844 (2016); incorporated by reference in its entirety). An example of higher CNS activity of sarpogrelate is provided by an example where sarpogrelate is given to Sprague-Dawley rats at the doses of 0.3, 1 and 3 mg/kg 30 min prior to a centrally acting 5-HT2A agonist DOI (3 mg/kg; (1(2,5-dimethoxy-4-iodophenyl)-2-aminopropane)hydrochloride) and frequency of DOI-induced head shakes is reduced by co-administration of a compound of Formula I, SARPODEX™, DERADEX™, or DERAPHAN™.

A compound of Formula I as well as both enantiomers of its primary metabolite M1 are 5HT2A receptor antagonists (Pertz et al., In-vitro pharmacology of a compound of Formula I and the enantiomers of its major metabolite: 5-HT2A receptor specificity, stereoselectivity and modulation of ritanserin-induced depression of 5-HT contractions in rat tail artery, J Pharm Pharmacol. 47(4):310-6 (1995 April); incorporated by reference in its entirety). To confirm the ability of M1 S- and R-enantiomers to reach 5HT2A receptors in the CNS, rats are pretreated with 0.1 mg/kg of MK801 and attenuation of MK801-stimulated locomotor hyperactivity is monitored across a range of doses of both a compound of Formula I during 120-min test session conducted using conventional motor activity monitors.

DEX acts at a number of receptors and one of its targets is the NMDA receptor (Taylor et al., Pharmacology of dextromethorphan: Relevance to dextromethorphan/quinidine (Nuedexta®) clinical use. Pharmacol Ther. 164:170-82 (2016 August); incorporated by reference in its entirety). However, DEX is a less potent NMDA receptor antagonist than its metabolite, DO. Accordingly, DEX is less likely to induce phencyclidine-like motor activity than DO. The behavioral effects of DEX, DO and phencyclidine (PCP) were compared in rats. DO (15-120 mg/kg) was similar to PCP (1.25-20 mg/kg) in inducing dose-dependent locomotor hyperactivity, stereotypy and ataxia. DEX (15-120 mg/kg) induced moderate hyperactivity only at the higher doses about 45 min after treatment. DEX and DO modified the locomotor facilitation induced by 10 mg/kg PCP in opposite directions. Pretreatment with DO facilitated, whereas DEX dose-dependently inhibited PCP-elicited hyperactivity (Székely et al., Induction of phencyclidine-like behavior in rats by DO but not DEX, Pharmacol Biochem Behav, 40(2):381-6 (1991 October); incorporated by reference in its entirety).

Example 186

A compound of Formula I as well as both enantiomers of its primary metabolite are CYP2D6 inhibitors. DEX is a commonly used substrate in in vitro metabolism studies to reveal 2D6 inhibitory activity of biologically active substances and drugs. In a dedicated set of studies, a compound of Formula I are administered prior to DEX and rats' locomotor activity is monitored for 120 min in order to demonstrate that a compound of Formula I prevents emergence of hyperactivity in DEX-treated subjects. These studies are paralleled by measurements plasma DEX levels. The combination of pharmacokinetic (plasma DEX concentration) and pharmacodynamic (MK-801- and DEX-induced hyperactivity) studies are used to identify the M1 enantiomer and the dose level(s) producing the most optimal ratio of anti-hyperactivity and DEX metabolism-suppressing effects.

Example 187: Blood Glucose and Insulin Sensitivity

In contrast to the sulfonylurea drugs, which result in significantly higher basal insulin secretion compared to vehicle treatment, DO and its prodrug DEX did not significantly alter basal insulin secretion from mouse or human islets or in vivo (Marquard et al., Characterization of pancreatic NMDA receptors as possible drug targets for diabetes treatment. Nat Med 21(4):363-72 (2015); incorporated by reference in its entirety). More specifically, application of DEX via drinking water (4 mg/ml) overnight changed neither basal plasma insulin nor fasting blood glucose concentrations in mice, but led to significantly higher glucose-induced plasma insulin concentrations and glucose tolerance than were seen in non-DEX-treated controls (glucose administered intraperitoneally at 1.5 mg/kg body weight).

Marguard et al. (2015) suggested that effects of DEX are mediated via NMDA receptor channel blocker and specifically pointed at the rapid metabolism of DEX into DO, a potent inhibitor of the NMDA receptors. To prove NMDA receptor involvement, Marguard et al. demonstrated that glucose-stimulated insulin secretion and glucose tolerance are not observed in mice genetically engineered to lack NMDA receptor function.

To test whether DEX could lead to higher serum insulin concentrations and lower blood glucose concentrations in people with type 2 diabetes mellitus (T2DM), a Phase 2a, Double-blinded, placebo-controlled, randomized, crossover, single-dose proof-of-concept study was performed (Marquard et al., Characterization of pancreatic NMDA receptors as possible drug targets for diabetes treatment. Nat Med 21(4):363-72 (2015); incorporated by reference in its entirety). Twenty males with T2DM on metformin monotherapy (age 59 (46-66) years (mean (range)); mean body mass index (BMI) 29.2 (25.2-34.1) kg m-2; glycated hemoglobin (HbA1c) 6.9 (6.5-7.4)%) were recruited. Each received a single oral dose of 60 mg DEX, 270 mg DEX, 100 mg amantadine or placebo, followed by an oral glucose tolerance test (OGTT) 1 h after drug intake on four treatment days, separated by a washout period of 7-14 days. Consistent with the results in mice, DEX led to neither higher fasting serum insulin concentrations nor lower fasting blood glucose concentrations compared to placebo and did not provoke any severe hypoglycemic events up to a dose of 270 mg. In contrast, following oral glucose intake, both 60 and 270 mg DEX dosages resulted in significantly ($P<0.05$) higher maximal serum insulin concentrations compared to those seen with placebo.

In addition, the primary endpoint was reached for 270 mg DEX; that is, the area under the curve of blood glucose concentrations within the first 2 h of the OGTT (glucose AUC1-3 h) was significantly ($P<0.05$) smaller in individuals who received 270 mg doses of DEX than in the same individuals receiving placebo on a different treatment day.

Blood glucose level is also under control of peripheral 5HT2A receptors (Yamada et al., Hyperglycemia induced by the 5-HT receptor agonist, 5-methoxytryptamine, in rats: involvement of the peripheral 5-HT2A receptor. *Eur J Pharmacol.* 323(2-3):235-40 (1997); incorporated by reference in its entirety). More specifically, administration of non-selective 5HT receptor agonist such as 5-methoxytryptamine induced hyperglycemia that is prevented by pretreatment with 5-HT2A receptor antagonist ketanserin as well as peripherally acting 5-HT2 receptor antagonist, xylamidine. These results suggested that 5-methoxytryptamine-induced hyperglycemia is mediated by the peripheral 5-HT2A receptors.

Second-generation antipsychotics with dual dopamine and serotonin receptor antagonism have been associated with an increased risk for impaired glucose tolerance and diabetes mellitus. Though this has been largely attributed to weight gain, there is also a direct, receptor-mediated effect of antipsychotics on glucose tolerance. Certain 5HT2A receptor antagonists such as ketanserin impair insulin sensitivity (Gilles et al., Antagonism of the serotonin (5-HT)-2 receptor and insulin sensitivity: implications for atypical antipsychotics. *Psychosom Med.* 67(5):748-51 (2005)); incorporated by reference in its entirety). In the study by Gilles et al., ten healthy male volunteers were included in a double-blind, placebo-controlled crossover study of a single dose of 40 mg of the 5-HT2 antagonist ketanserin versus placebo. Insulin sensitivity was measured by means of the euglycemic-hyperinsulinemic clamp technique. Subjects were treated with the alpha-1 adrenergic antagonist phenoxybenzamine in both parts of the study to control for ketanserin's effects at the level of this receptor. Compared with the placebo condition, subjects showed a significantly decreased insulin sensitivity after ketanserin (placebo: 9.4+/−3.6 mg/kg/min; ketanserin: 7.7+/−2.1 mg/kg/min; p=0.047).

Thus, combining DEX and 5-HT2A receptor antagonists may lead to synergistic effects on blood glucose and insulin sensitivity that may be undesired in case of a long-term treatment as it may have unwanted metabolic side-effects qualitatively similar to those observed in patients treated with antipsychotic drugs. These effects may limit the doses of DEX and 5-HT2A receptor antagonists that can be safely administered as a combination.

There are two approaches that are part of this invention and that enable therapeutic use of combinations of DEX and 5HT2A receptor antagonists while reducing the risks of peripheral metabolic adverse effects.

One approach is based on the use of 5HT2A receptor inverse agonist or antagonist that inhibits CYP2D6 and thereby reduces the conversion of DEX into DO. Both DEX and DO are NMDA receptor channel blockers, and NMDA receptor inhibition in pancreatic islets was suggested to be responsible for glucose-stimulated insulin secretion, and glucose intolerance enhanced by DEX and DO (Marquard et al., Characterization of pancreatic NMDA receptors as possible drug targets for diabetes treatment. Nat Med 21(4): 363-72 (2015); incorporated by reference in its entirety). Since DO is more potent NMDA receptor channel blocker than DEX (Pechnick et al., Comparison of the Effects of DEX, DO, and Levorphanol on the Hypothalamo-Pituitary-Adrenal Axis, The Journal Of Pharmacology and Experimental Therapeutics, 309:515-522 (2004); incorporated by reference in its entirety), inhibition of DEX metabolism via CYP2D6 may reduce the expression of effects of DEX on glucose-stimulated insulin secretion and glucose tolerance and, therefore, risks of metabolic side-effects.

The second approach is the selection of a 5HT2A receptor inverse agonist or antagonist that has the best ratio of central vs. peripheral 5HT2A receptor occupancy. Accordingly, a 5HT2A receptor inverse agonist or antagonist is chosen to produce therapeutically relevant central 5HT2A receptor occupancy at the doses that are at lowest risk of producing unwanted metabolic effects such as, but not limited to, glucose intolerance.

The compound of formula I is a 5HT2A receptor inverse agonist or antagonist that has 2D6 inhibitory properties. Acute and chronic effects of a compound of Formula I on glucose tolerance and insulin resistance have been examined (Takishita et al., Effect of sarpogrelate hydrochloride, a 5-HT2 blocker, on insulin resistance in Otsuka Long-Evans Tokushima fatty rats (OLETF rats), a type 2 diabetic rat model. J Cardiovasc Pharmacol 43(2):266-70 (2004); incorporated by reference in its entirety). In these studies, Otsuka Long-Evans Tokushima Fatty rats, a model of type 2 diabetes, were randomly assigned to 2 groups; those with 30 mg/kg BW/d a compound of Formula I treatment of 4 weeks (HTB group) and without (control group). The glucose infusion rate was significantly increased in the HTB group compared with the control group. The blood glucose levels after oral glucose tolerance test and levels of plasma insulin and lipids were significantly lower in the HTB group than in the control group. a compound of Formula I was shown to reverse insulin resistance induced by various means including glucocorticoid drug treatment (Ma et al., Effective treatment with a combination of peripheral 5-hydroxytryptamine synthetic inhibitor and 5-hydroxytryptamine-2 receptor antagonist on glucocorticoid-induced whole-body insulin resistance with hyperglycemia. *J Diabetes Investig* 7: 833-844 (2016); incorporated by reference in its entirety).

Synergistic effects of a compound of Formula I on blood glucose and insulin sensitivity have been shown for several drugs including carbidopa (Ma et al., Effective treatment with a combination of peripheral 5-hydroxytryptamine synthetic inhibitor and 5-hydroxytryptamine-2 receptor antagonist on glucocorticoid-induced whole-body insulin resistance with hyperglycemia *J Diabetes Investig* 7: 833-844 (2016); incorporated by reference in its entirety) and pioglitazone (Iizuka et al., Beneficial effects of a compound of sarpogrelate hydrochloride, a 5-HT2A receptor antagonist, supplemented with pioglitazone on diabetic model mice. *Endocr Res.* 34(1-2):18-30 (2009); incorporated by reference in its entirety).

Insulin-sensitizing effects of a compound of Formula I have also been confirmed in humans (Kokubu et al., Persistent insulin-sensitizing effects of sarpogrelate hydrochloride, a serotonin 2A receptor antagonist, in patients with peripheral arterial disease. *Circ J* 70(11):1451-6 (2006); incorporated by reference in its entirety). Indices of insulin resistance (fasting immunoreactive insulin) were measured before and after 2 weeks of a compound of Formula I administration (300 mg/day) in 24 patients (19 men, 76+/−9 years) with peripheral arterial disease. Sixteen of the 24 patients were also examined after 3 months of treatment. After 2 weeks of treatment, significant decreases in fasting immunoreactive insulin (p=0.03) were observed. After 3 months of treatment, significant decreases in fasting immunoreactive insulin (16.0+/−10.3 vs 9.2+/−2.0 microU/ml, p=0.03) were maintained.

A compound of Formula I is rapidly metabolized into metabolite that also has both 5HT2A receptor antagonist and 2D6 inhibitory properties. Both enantiomers of metabolite are biologically active and share the ability to block 5HT2A receptors and 2D6. To establish which of the enantiomers has the most optimal properties for being combined with DEX, effects of these substances alone and in combination with DEX on oral glucose tolerance are assessed (Taniguchi et al., Diabetes, 55, 2371-2378 (2006); incorporated by reference in its entirety). This method is based on the measurement of whole blood glucose and plasma insulin. Test substances are administered to male Sprague-Dawley rats (group size: 8 per group). Animals are tested after an overnight food deprivation and individually housed. Test substance is administered 60 minutes before glucose challenge, i.e. after baseline blood glucose measurement. Animals are challenged with glucose at 2 g/kg as an oral gavage at T0, after blood glucose measurement. Blood glucose is measured from a drop of blood collected from the cut tip of the tail, using a commercially available glucose-meter at 8 time-points: baseline (before treatment), T0 (before glucose) and then 15, 30, 60, 90, 120 and 180 minutes post-glucose challenge.

Example 188: Effects of Formula I Alone on AD Pathophysiology

Links between a chronic diabetic metabolic situation and the risk and emergence of AD pathophysiology have long been suspected and substantiated in the recent years (Goldwasser et al., Breakdown of the Cerebrovasculature and Blood-Brain Barrier: A Mechanistic Link between Diabetes Mellitus and Alzheimer's Disease. *J Alzheimers Dis* 54(2): 445-56 (2016 Aug. 1); incorporated by reference in its entirety). In several large post-mortem series, more than a third of all subjects clinically diagnosed with typical AD showed evidence of cerebrovascular disease and had to be re-classified as mixed dementia (Grandal Leiros et al., Prevalence and concordance between the clinical and the post-mortem diagnosis of dementia in a psychogeriatric clinic, Neurologia S0213-4853(16)30070-6 (2016); incorporated by reference in its entirety). From a clinical perspective, it is desirable to extend AD therapy beyond currently approved drugs and mechanisms, and also address the cognitive impairment by optimizing a latent diabetic metabolic situation or the fairly frequent Type 2 diabetes in the elderly subjects. Indeed, glycaemic control is thought to have an impact o the severity of cognitive impairment (Zilliox et al., Diabetes and Cognitive Impairment. *Curr Diab Rep*, 16 (9):87 (2016); incorporated by reference in its entirety).

Due to the specific anti-diabetic actions of a compound of Formula I described above, it is, therefore, conceivable to attempt an added benefit on both, symptoms and disease progression in AD, and in cognitive impairment of mainly vascular origin (multi-infarct dementia, vascular dementia, vascular cognitive impairment, etc.).

Based on the Japanese regulatory label, the incidence of adverse events with a compound of Formula I therapy in internal medicine is quite low as compared to placebo and the nature of AEs reported found to be acceptable; therefore, the benefit-risk ratio of added a compound of Formula I therapy seems defendable, also in an elderly, multimorbid population.

Example 189: Stereoselective Reversal of Psychostimulant-Induced Hyperactivity In Vivo by Compound Motor activity data were collected during a 15-min session in a lit room. Mice had no prior exposure to the motor cages. Immediately before placing the mice in the locomotor chambers, effects on myorelaxation/ataxia were determined by placing each of the mouse's forepaws in contact with a horizontal wire while holding the mouse by the base of the tail. Mice were required to bring at least one hindpaw in contact with the wire within 10 s to be scored as a "pass" and failure to do so was considered ataxic. Each dose or dose combination was tested in a separate group of mice. ACP-103 significantly attenuated MK-801-induced hyperactivity in mice at doses of 0.1 and 0.3 mg/kg s.c. [$F(7,63)=6.010$; $p<0.0001$], consistent with an antipsychotic-like effect.

HEK-293 cells expressing human recombinant 5HT2A receptor were used in the antagonist radioligand binding studies. A compound of Formula I such as Compound 50 racemate and both enantiomers were applied at concentrations ranging from 3.0E-11 M to 1.0E-07 M. M1 enantiomers were applied at concentrations ranging from 1.0E-11 M to 3.0E-08 M. The IC50 values (concentration causing a half-maximal inhibition of control specific binding) and Hill coefficients (nH) were determined by non-linear regression analysis of the competition curves generated with mean replicate values using Hill equation curve fitting. The inhibition constants (Ki) were calculated using the Cheng Prusoff equation. Both sarpogrelate enantiomers were potent inhibitors of [3H]ketanserin binding (Table 1). M1 enantiomers also potently bind to 5HT2A receptors with the Ki values that are approximately one order of magnitude higher than those of sarpogrelate enantiomers (Table 1). There are no meaningful differences between enantiomers in terms of 5-HT2A receptor binding for sarpogrelate or its main metabolite.

TABLE 3

Inhibitory effects of sarpogrelate (racemate and enantiomers) and M-1 enantiomers on 5-HT2A receptor binding

| Compound | IC50, nM | pKi |
|---|---|---|
| 50 | 9.6 | 8.3 |
| (+) 51 | 7.5 | 8.4 |
| (−) 52 | 11 | 8.2 |
| (+) 147 | 1.2 | 9.1 |
| (−) 148 | 1.3 | 9.2 |

Figure 7:
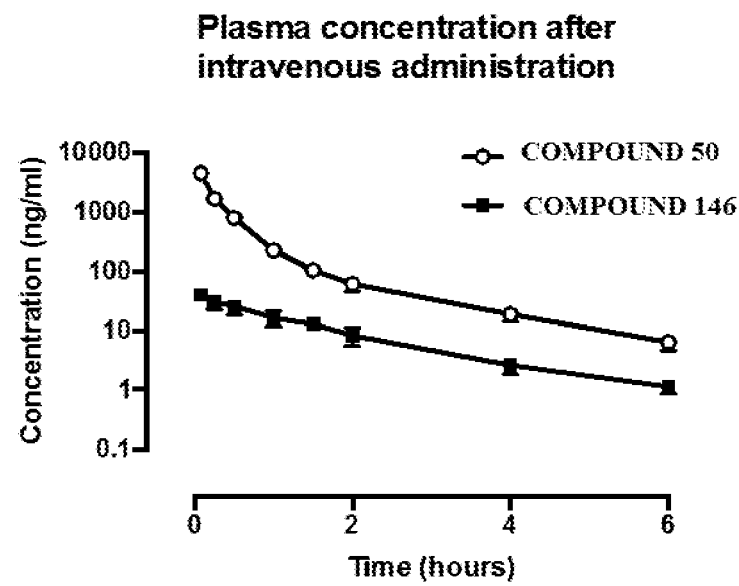
FIG. 7 shows plasma level curves of sarpogrelate and M1 in male Wistar rats after single intravenous administrations of sarpogrelate hydrochloride (2 mg/kg). Data are presented as mean (±SD) concentration (ng/ml). N=4.

To confirm the ability of M1 enantiomers to induce effects that are relevant to CNS diseases and that are known for 5-HT2A receptor agonists and inverse agonists, separate groups of female Wistar rats (n=6-9), housed 4-5 per cage under standard colony room conditions with free access to food and water, were pretreated intraperitoneally with varying doses of one of the two M1 enantiomers (0, 3 or 10 mg/kg) followed 15 minutes later by 0.1 mg/kg of MK801 or its vehicle and immediately thereafter placed into computer-controlled motor activity recording chambers (25× 35.5×34 cm, L×W×H; transparent Plexiglas walls and a non-transparent plastic floor; enclosed within sound-attenuating ventilated cubicles) for 60 minutes, during which infrared photocell interruptions (5 cm and 14 cm off the floor) were recorded as a measure of motor activity. MK-801 is a phencyclidine-like NMDA receptor channel blocked commonly used in psychopharmacology research on novel therapies including novel antipsychotics. Analysis of variance (ANOVA) has revealed main effects of the M1 dose and the interaction between M1 dose and MK-801 treatment factors for the (−) M1 enantiomer [$F(2,39)=6.154$; $p=0.0048$, $F(2,39)=4.613$; $p=0.0159$, respectively] and not for the (+) M1 enantiomer [$F(2,42)=0.5211$; $p=0.5977$, $F(2,42)=0.5229$; $p=0.5966$, respectively]. As shown in FIG. 7, both doses of the (−)M1 enantiomer as well as 3 mg/kg of a prototypical 5-HT2A receptor antagonist M-100,907 reduced hyperactivity induced by MK-801 (Dunnett's multiple comparisons test). Thus, despite no significant differences between M1 enantiomers in terms of binding to 5-HT2A receptors, surprisingly, only one of the enantiomers exerts efficacy in a preclinical model of psychomotor activation that is known to be sensitive to 5-HT2A receptor blockade.

Figure 8:
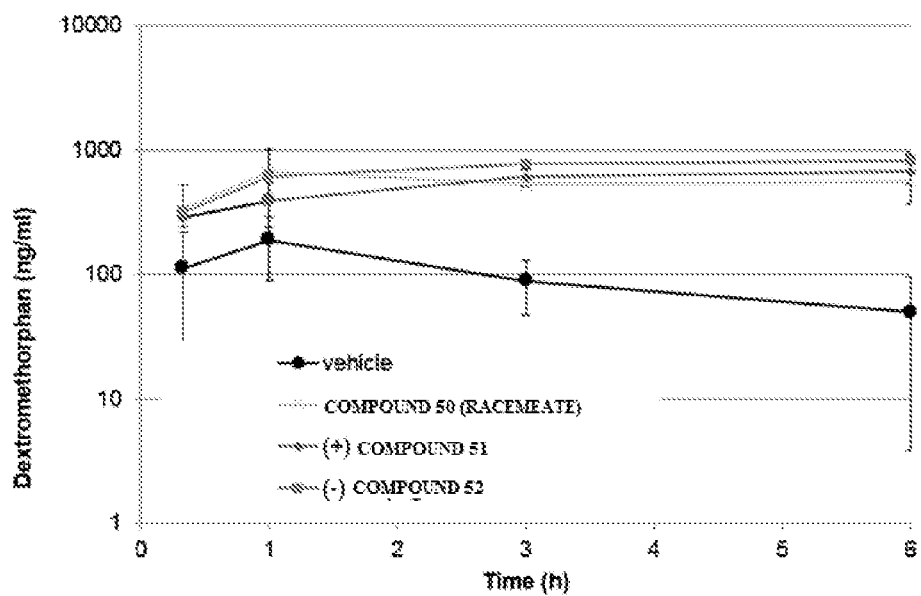
FIG. 8 shows plasma level curves of dextromethorphan in male Wistar rats that received dextromethorphan (50 mg/kg, per os) immediately followed by intravenous bolus injection of sarpogrelate (1, 3 or 10 mg/kg; racemate or one of the enantiomers) or vehicle via vascular access port at t=0 h. Data are presented as mean (±SD) concentration (ng/ml). N=2-3.

Example 190: Reversal of Motor Hyperactivity Induced by Olfactory Bulbectomy in Rats In a dedicated set of studies, adult male Sprague-Dawley rats (Charles River, Germany) were subjected to bilateral olfactory bulbectomy performed under ketamine/xylasine anesthesia. The animals were allowed to recover for 14 days following surgery while being handled daily to eliminate any aggressiveness that would otherwise arise. Sham-operated animals were treated in the same way but the olfactory bulbs were left intact. Drugs administration and locomotor activity testing were performed 4 times for each rat with 72 hours break between consecutive test sessions. Prior to each test session, animals were first treated with dextromethorphan (0, 15, 30 or 60 mg/kg. per os) followed 15 min later by sarpogrelate (1, 3 and 10 mg/kg, intraperitoneal) and another 15 min later were placed into Opto-Varimex cages for locomotor activity recording over 30 min. Hyperactivity in rats after olfactory bulbectomy is observed mostly during the early portion of the test sessions. FIG. 8 presents average activity counted over the first 15 min of the test when activity of the bulbectomized animals was significantly higher than that of the sham controls. ANOVA revealed a significant main effects of both surgery and sarpogrelate dose factors [$F(1,88)=5.04$, $p=0.0273$; $F(3,88)=5.02$, $p=0.0029$, respectively]. Post hoc pairwise comparisons (Sidak's multiple comparisons test) confirmed that significant differences between bulbectomized and sham-operated were observed only in rats that were pretreated prior to the test with vehicle instead of sarpogrelate. Bulbectomized rats pretreated with 3 or 10 mg/kg of sarpogrelate spent less time in ambulations compared with the respective controls that received vehicle instead of sarpogrelate. These anti-hyperactivity effects of sarpogrelate are observed at the doses that do not affect activity of sham-operated rats and therefore do not reflect a generalized non-specific impairment of motor capabilities. Thus, surprisingly, despite being previously referred to as a peripherally restricted 5-HT2A receptor antagonist with only minimal penetration across the blood-brain barrier (Obata H et al. Antinociception in rat by sarpogrelate, a selective 5-HT(2A) receptor antagonist, is peripheral. Eur J Pharmacol 404(1-2):95-102 (2000)), sarpogrelate is observed to exert behaviorally specific anti-hyperactivity effects in rats after olfactory bulbectomy, a model commonly used to study CNS drugs such as antidepressants.

Example 191: Inhibition of Dextromethorphan Metabolism In Vitro and In Vivo

Dextromethorphan O-demethylase activity was determined in human liver microsomes. Sarpogrelate (1.0E-8 M to 3.0E-5 M) or M−1 (concentration: 3.0E-9 M to 1.0E-5 M) and dextromethorphan were dissolved in acetonitrile and serially diluted with acetonitrile to the required concentrations to give a final organic solvent concentration of 1.0% in the incubation mixture. The incubation mixtures contained pooled human liver microsomes (final concentrations: 0.25 mg/ml), dextromethorphan, and a NADPH-generating system (1.3 mM NADP+, 3.3 mM glucose 6-phosphate, 3.3 mM MgCl2, and 0.4 U/ml glucose-6-phosphate dehydrogenase). After incubation and centrifugation, the supernatant was diluted 100-fold with acetonitrile and then injected into the LC-MS/MS system. All incubations were performed in triplicate, and mean values were used for analysis. The IC50 values (concentration causing a half-maximal inhibition of control specific binding) and Hill coefficients (nH) were determined by non-linear regression analysis of the competition curves generated with mean replicate values using Hill equation curve fitting. Both sarpogrelate enantiomers inhibited CYP2D6-mediated dextromethorphan O-demethylation (Table 4).

TABLE 4

Inhibitory effects of sarpogrelate (racemate and enantiomers) and M-1 enantiomers on CYP 2D6 activity.

| Compound | IC50, μM |
|---|---|
| 50 | 1.2 |
| (+) 51 | 0.58 |
| (−) 52 | 1.3 |

TABLE 4-continued

Inhibitory effects of sarpogrelate
(racemate and enantiomers) and M-1
enantiomers on CYP 2D6 activity.

| Compound | IC50, µM |
|---|---|
| (+) 147 | 0.038 |
| (−) 148 | 0.096 |

While both enantiomers of M1 markedly inhibited 2D6 activity with the IC50 values of 0.038-0.096 µM, sarpogrelate enantiomers were approximately 10-15 times less potent (Table 4). Based on previous in vivo studies, sarpogrelate was classified as a weak 2D6 inhibitor. This classification was based on a less than 2-fold increase in the substrate AUC (i.e. per guidance provided by the US Food and Drug Administration, Draft guidance for industry: drug interaction studies—study design, data analysis, implication for dosing and labeling recommendations. Center for Drug Evaluation and Research, US FDA (2012) (Guidance Compliance Regulatory Information at FDA.GOV).

Figure 9A:
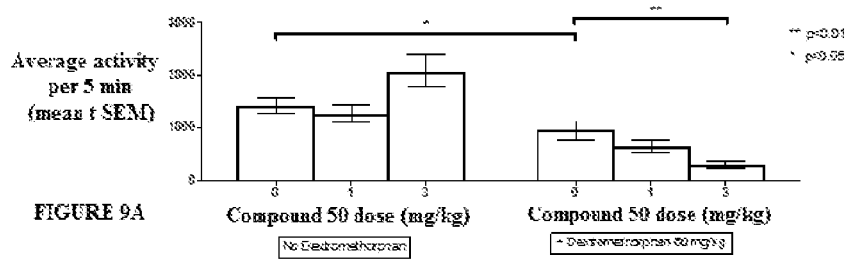
FIGS. 9A, 9B, and 9C show effects of a combination of dextromethorphan with Compound 50 racemate (upper panel), (−) Compound 51 (middle panel) or (+) Compound 52 on PCP-induced hyperactivity in rats.
Figure 9B:
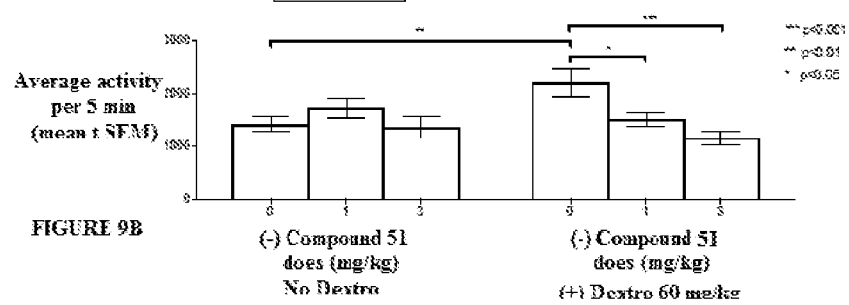
Figure 9C:
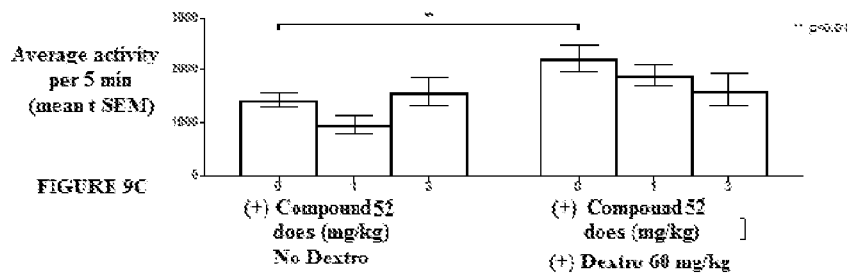

Pharmacokinetic study was performed in male Wistar rats equipped with the jugular vein cannulas. Sarpogrelate hydrochloride was formulated in Pharmasolv: PBS buffer (5:95) mixture and administered at the dose of 2 mg/kg intravenously. Blood samples were collected from the jugular vein using heparin as anticoagulant at the scheduled time-points: 5 min, 15 min, 30 min, 1 h, 1.5 h, 2 h, 4 h, and 6 h. An LC-MS/MS bioanalytical method was used for the simultaneous quantification of sarpogrelate and M1 in plasma samples. Following 2 mg/kg intravenous bolus administration the plasma level curves showed small inter-individual variability (FIG. 9). Apparent terminal elimination half-life was estimated at 1.21±0.159 h. Formation of M1 metabolite of sarpogrelate was rapid as the highest M1 concentrations were measured at the first sampling time points. In spite of the rapid formation, concentrations of the free M1 metabolite were orders of magnitude lower in the circulation than those of the parent compound (M1/sarpogrelate ratio of 2.98±0.597%). Thus, although M1 enantiomers are significantly more potent 2D6 inhibitors than the parent compound, potential impact of M1 is mitigated by low relative exposure to M1 suggested by the ratio of plasma AUC for M1 and sarpogrelate.

Example 192

In a separate set of studies, ability of sarpogrelate to inhibit dextromethorphan metabolism in vivo was studied in rats. Adult male Sprague Dawley rats (RjHan:SD) purchased from Janvier Labs (France) were housed in a climate-controlled room under a 12 h light/12 h dark cycle with ad libitum access to food and water. Two-three days prior to blood sampling, rats were provided with a catheter in the jugular vein and, thereafter, rats treated once with Carprofen (5 mg/kg) directly after surgery and catheters were rinsed daily with Heparin (500 IE/ml) (20 µl/rat/day). On the day of the experiment, dextromethorphan (50 mg/kg) was administered by oral gavage, immediately followed by intravenous bolus injection of sarpogrelate (1, 3 or 10 mg/kg; racemate or one of the enantiomers) or vehicle via vascular access port at t=0 h. Blood samples were collected at four time points until 6 hours post dextromethorphan administration. Sample size was 80 µl Li-heparin whole blood/time point, i.e. 40 µl Li-heparin plasma/time point. Whole blood samples were stored on ice until centrifugation (10 min at 3000 g, 4° C.). Plasma was prepared within 45 min after collection, frozen at −20° C. and stored at this temperature until processed for LC-MS analysis.

Figure 10:
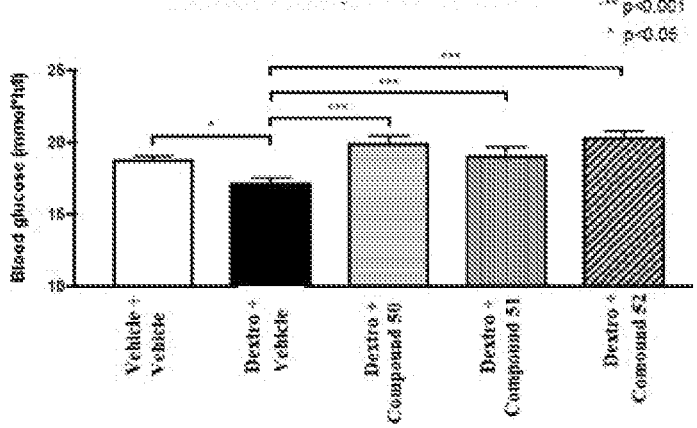
FIG. 10 shows effects of dextromethorphan and sarpogrelate racemate on blood glucose level. Data are presented as area under the curve (mean±SEM) for blood glucose level over the period of time 30-180 min after oral glucose (2 g/kg) challenge. N=8 per group.

As shown in FIG. 10, in rats treated with sarpogrelate (racemate or enantiomers) plasma levels of dextromethorphan continued to be high even at the later time points while, in vehicle-treated rats, dextromethorphan levels declined towards the 6-h time point.

Surprisingly, quantification of the AUC for dextromethorphan indicated that, at the highest tested dose of 10 mg/kg, sarpogrelate increased the dextromethorhan AUC 5.3-6.9 fold. Even at the lower dose of 3 mg/kg, dextromethorphan AUC was increased 2.7 (for the (−) enantiomer) to 3.3 fold (for the (+) enantiomer).

TABLE 5

Area under the curve (0-6 h) analysis of
dextromethorphan plasma concentration in rats
treated with sarpogrelate (racemate and enantiomers)

| Treatment | Sarpogrelate dose (mg/kg) | Dextromethorphan AUC (ng*hr/ml) | Fold increase (relative to vehicle) |
|---|---|---|---|
| Vehicle | — | 605.8 | — |
| Compound 50 | 1 | 2329.5 | 3.8 |
|  | 3 | 3356.1 | 5.5 |
|  | 10 | 3211.9 | 5.3 |
| (+)Compound 51 | 1 | 827.0 | 1.4 |
|  | 3 | 2021.5 | 3.3 |
|  | 10 | 4154.3 | 6.9 |
| (−)Compound 52 | 1 | 921.4 | 1.5 |
|  | 3 | 1649.5 | 2.7 |
|  | 10 | 3195.9 | 5.3 |

Example 193: Inhibition of Phencyclidine-Induced Hyperactivity in Rats Treated by a Combination of Sarpogrelate and Dextromethorphan The behavioral effects of DEX, DO and phencyclidine (PCP) were compared in rats. DO (15-120 mg/kg) was similar to PCP (1.25-20 mg/kg) in inducing dose-dependent locomotor hyperactivity, stereotypy and ataxia. DEX (15-120 mg/kg) induced moderate hyperactivity only at the higher doses about 45 min after treatment. DEX and DO modified the locomotor facilitation induced by 10 mg/kg PCP in opposite directions.

In a dedicated set of studies, Compound 50 racemate and enantiomers were co-administered with DEX to demonstrate the ability of such drug combination(s) to counteract psychomotor activation and hyperactivity. Male Sprague-Dawley rats were administered intraperitoneally Compound 50 (sarpogrelate racemate), (−) sarpogrelate, (+) sarpogrelate or vehicle as well as subcutaneous (racemate experiment) or oral (enantiomer experiments) dextromethorphan or vehicle (water) and were placed individually into the Opto-Varimex-4 auto-tracks. Fifteen minutes later rats were removed from the boxes, injected with phencyclidine (PCP; 5 mg/kg, subcutaneous) and returned to the auto-tracks for additional 105 min (i.e. until a total recording time of 120 min). Data analysis focused on the second half of the test (60-120 min). ANOVA has revealed significant interaction between the dose of sarpogrelate and the dose of dextromethorphan (FIG. 11, upper panel; $F(9,120)=2.38$, $P=0.015$).

Figure 11A:
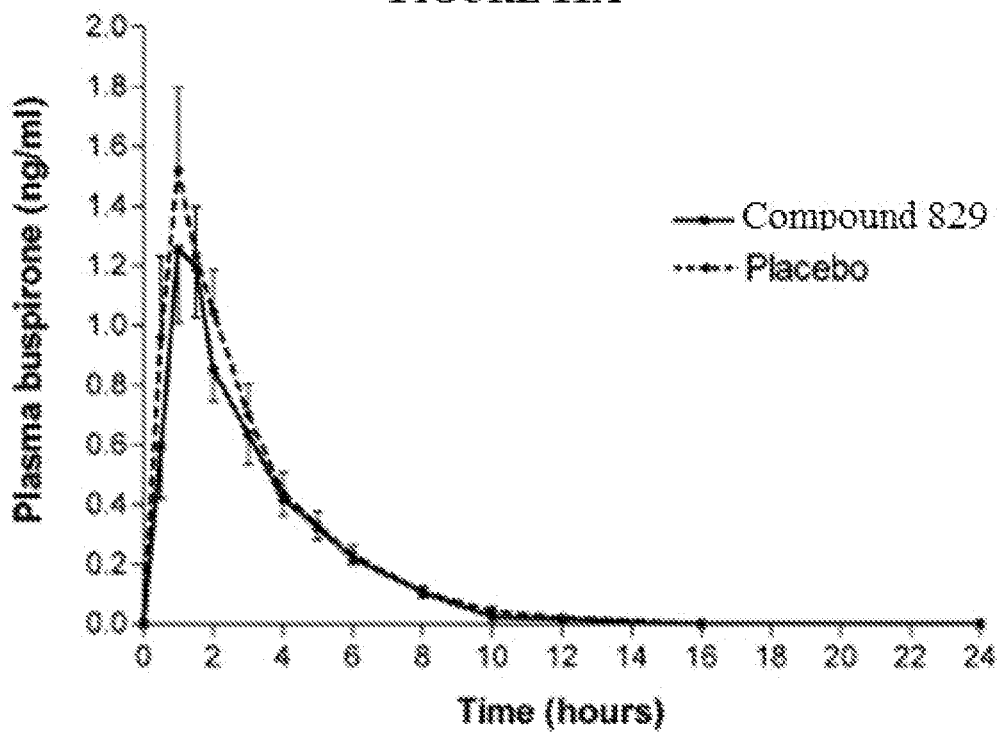
FIGS. 11A and 11B show the mean (SEM) concentrations of (a) buspirone and (b) 1-PP after administration of 20 mg buspirone after an 8-day pretreatment with either 60 mg Compound 829 (closed square; n=16) or placebo (closed circle; n=16) once daily.
Figure 11B:
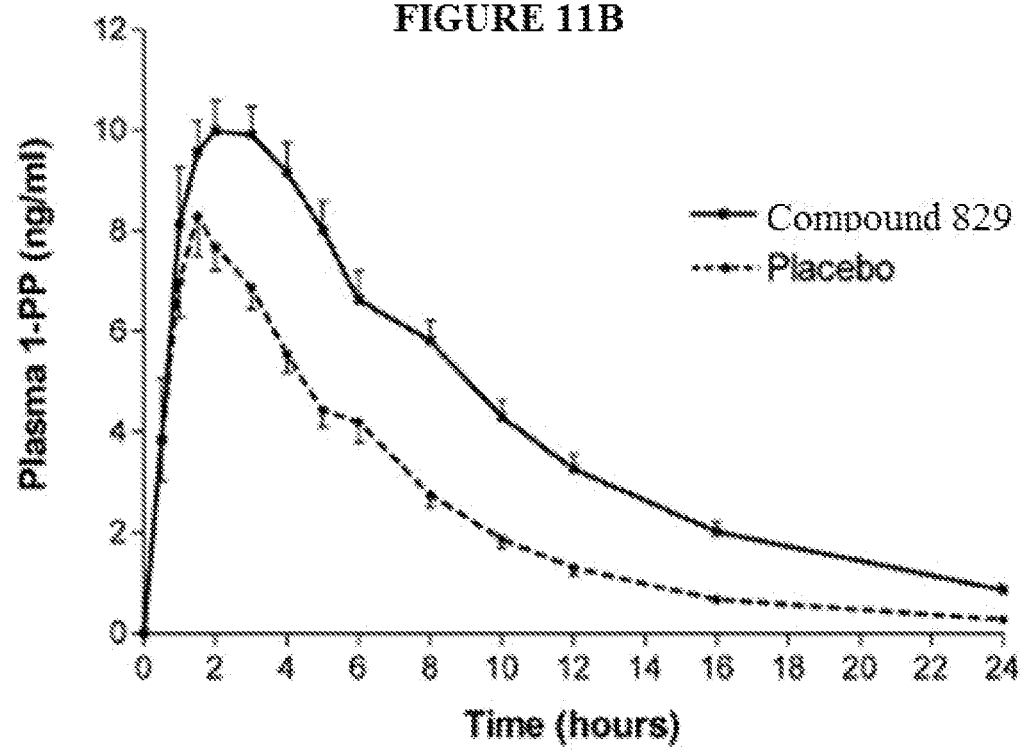

Similar statistically significant interaction with the dose of dextromethorphan was observed for (−) sarpogrelate (FIG. 11, middle panel; $F(9,141)=3.07$, $P=0.002$) but not for (+) sarpogrelate (FIG. 11, lower panel; $F(9,120)=1.65$, $P=0.1$).

The post-hoc analysis indicated that, in the presence of dextromethorphan, 3 mg/kg of sarpogrelate racemate as well as 1 mg/kg or 3 mg/kg of (−) sarpogrelate inhibited motor hyperactivity in PCP-treated rats (Dunnett's multiple comparisons test). This pattern of the results is surprising given that the (−) enantiomer of sarpogrelate is less potent than the (+) enantiomer in terms of inhibiting dextromethorphan metabolism both in vitro (Table 4) and in vivo (Table 5).

When given in the absence of dextromethorphan, neither sarpogrelate racemate nor sarpogrelate enantiomers reduced activity in PCP-treated rats. When given in combination with dextromethorphan, inhibitory effects of sarpogrelate were observed irrespective of whether dextromethorphan by itself reduced (subcutaneous administration, experiment with sarpogrelate racemate) or enhanced (oral administration, experiments with sarpogrelate enantiomers) motor activity in PCP-treated rats. Thus, presence of dextromethorphan may be required for sarpogrelate exert inhibitory effects in subjects with psychomotor activation such as rats with hyperactivity after exposure to a psychotomimetic drug PCP. Such pattern of supra-additive interactions between dextromethorphan and sarpogrelate is surprising.

Figure 12A:
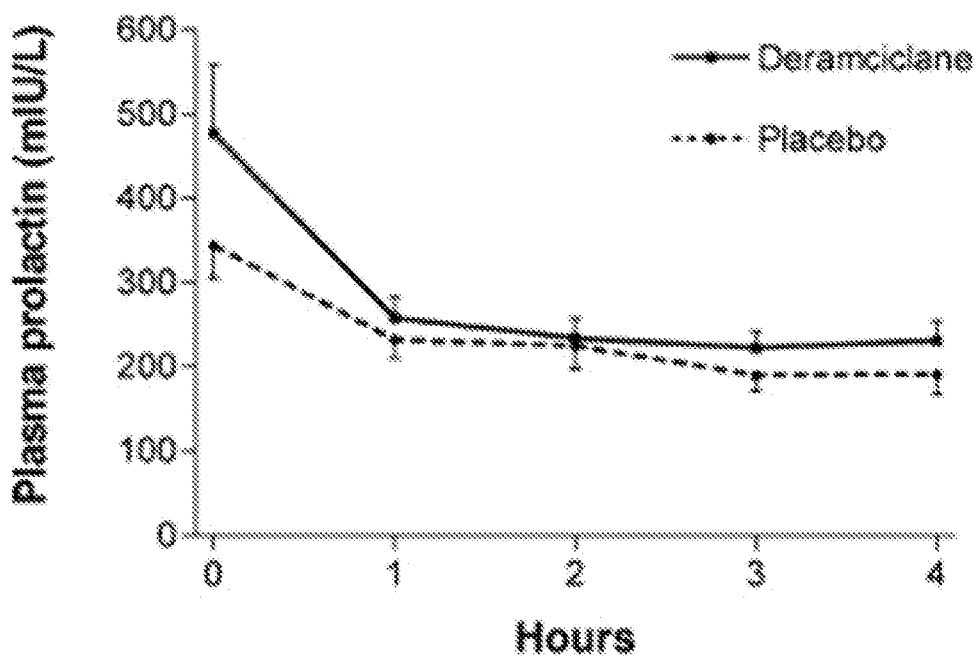
FIGS. 12A and 12B show the mean (SEM) plasma prolactin concentrations (a) after treatment with Compound 829 60 mg (closed square; n=16) or placebo (closed circle; n=16) once daily for 7 days and (b) after concomitant administration of 20 mg of buspirone after an 8-day pretreatment with either 60 mg Compound 829 (closed square; n=16) or placebo (closed circle; n=16) once daily.
Figure 12B:
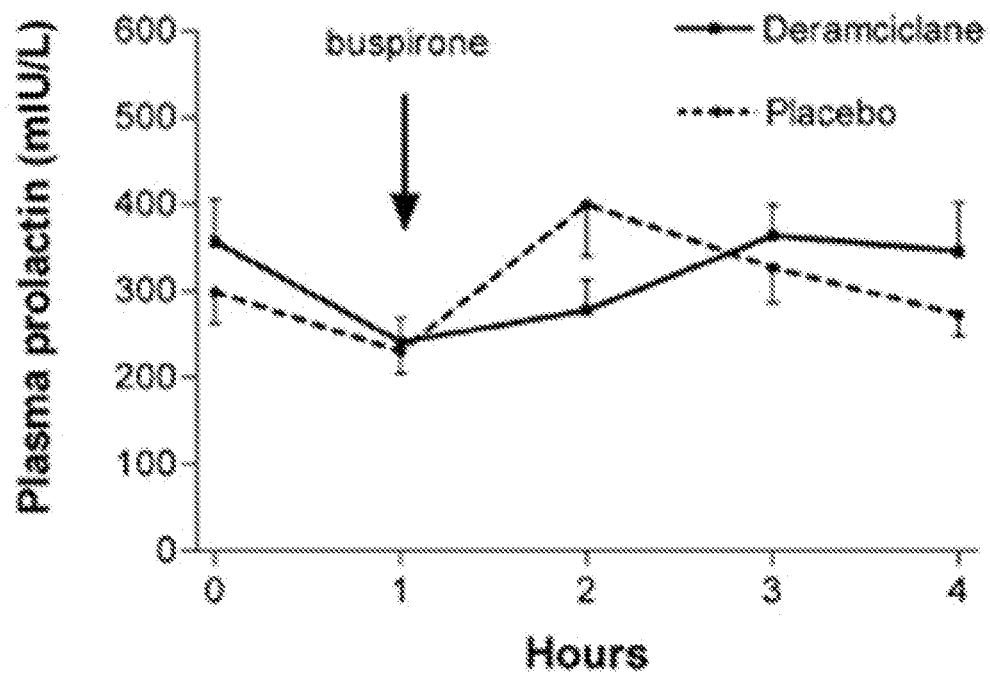

Example 194: Method of Assessment of Blood Glucose Levels and Oral Glucose Tolerance Test substances were administered to male Wistar (Han) rats (180-280 g at the beginning of the experiments; Janvier Labs) housed in groups under free access to food and water. After overnight food deprivation, the tip of the tail was cut, each rat was weighed, housed individually and left without stress in a quiet room. Approximately 1 hour later, baseline blood glucose was measured from a drop of blood collected from the tail tip, using a commercially available glucosemeter (OneTouch®, Lifescan) and then rats received intraperitoneal injection of sarpogrelate and/or dextromethorphan and 30 min later blood glucose was measured again and rats immediately challenged with glucose at 2 g/kg by oral gavage. Then, blood glucose was measured at 6 timepoints until 180 minutes post-glucose challenge. As shown in FIG. 12, there was a main effect of drug treatment ($F(4,59)=12.0$, $p<0.0001$). Post hoc pairwise group comparisons indicated that, when given alone, dextromethorphan has significantly reduced blood glucose level and this effect of dextromethorphan was reversed when it was administered in combination with sarpogrelate racemate or either of the enantiomers.

Example 195

52 Weeks of Chronic Toxicity Test and 5 Weeks of Recovery Test Using Beagle Dogs (Suzuki et al., Pharmacology & Therapeutics Vol 19 Supplement '91)

Compound 50 hydrochloride was given orally to beagle dogs at dose levels of 5, 20, 80 and 320 mg/kg/day for 52 consecutive weeks. No animal died or was sacrificed in extremis regardless of sex. As for general conditions, emesis was noted in males and females receiving 320 mg/kg/day and males receiving 80 mg/kg/day and salivation in females receiving 320 mg/kg/day. The body weight gain was inhibited in males and females receiving 320 mg/kg/day. Food consumption was inhibited in females receiving 80 mg/kg/day and over. Females receiving 320 mg/kg/day also showed an inhibition of water consumption. In the recovery period, the general conditions observed showed no difference between the control and treated groups. There was no treatment related change at electrocardiographic or ophthalmoscopic examination. In the urinalysis, an increase in protein was revealed in females receiving 320 mg/kg/day, in the hematological examination, an increase in a platelet count in males receiving 320 mg/kg/day, and in the biochemical examination, an increase in potassium in males receiving 80 mg/kg/day and over, and females receiving 320 mg/kg/day. These changes recovered after drug withdrawal. The relative weight of the thyroid and liver was increased in males receiving 80 mg/kg/day and over, but no treatment related change was seen in the histopathological examination. In the histopathological examination, fatty degeneration was revealed in the cortico-medullary border zone of the kidney in males receiving 320 mg/kg/day. In the recovery period however this change was not found. The no effect dose level of compound 50 hydrochloride in a 52-week study was estimated at 20 mg/kg.

While contain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention. It will be understood by those skilled in the art that various changes in form and details may be made therein without departing from the spirit and scope of the invention as set forth in the appended claims. Those skilled in the art will recognize or be able to ascertain using no more than routine experimentation, many equivalents to the specific embodiments of the invention described herein. Such equivalents are intended to be encompassed in the scope of the claims. Reasonable variations are not to be regarded as a departure from the scope of the invention. It will be obvious that the thus described invention may be varied and that various modifications, additions, substitutions, and variations to the illustrative examples set forth herein can be made without departing from the spirit of the invention and are, therefore, considered within the scope of the invention. All documents referenced above, including, but are not limited to, printed publications, and provisional and regular patent applications, are incorporated herein by reference in their entirety.

Example 196: Reversal of Motor Hyperactivity Induced by NMDA Receptor Blockade in Rats To confirm the ability of the present invention (a compound of Formula I) to induce antipsychotic-like effects that are relevant to efficacy against behavioral and psychological symptoms of dementia and that are known for 5-HT2A receptor agonists and inverse agonists, separate groups of rats, housed under standard colony room conditions with free access to food and water, are pretreated with varying doses of deramciclane (up to 30 mg/kg) followed by an NMDA receptor channel blocker or its vehicle and immediately thereafter placed into computer-controlled motor activity recording chambers. NMDA receptor channel blockers are commonly used in psychopharmacology research on novel therapies including novel antipsychotics. Analysis of variance (ANOVA) is applied to reveal main effects of the deramciclane dose and the interaction between the deramciclane dose and NMDA receptor treatment factors.

Example 197: Reversal of Motor Hyperactivity Induced by Olfactory Bulbectomy in Rats In a dedicated set of studies, adult male rats are subjected to bilateral olfactory bulbectomy, a model commonly used to study CNS drugs such as antidepressants. The animals are allowed to recover for at least 14 days following surgery. Sham-operated animals are treated in the same way but the olfactory bulbs are left intact. Prior to each test session, animals are treated with dextromethorphan (up to 60 mg/kg per os) combined with the compound of Formula I (up to 30 mg/kg) and later placed into activity monitors for locomotor activity recording. Hyperactivity in rats after olfactory bulbectomy is observed mostly during the early portion of the test sessions. Results are presented as average activity counted over the early portions of test session when activity of the bulbectomized animals is significantly higher than that of the sham controls. ANOVA is applied to reveal significant main effects of both surgery and treatment dose factors. The anti-hyperactivity effects of deramciclane are observed at the doses that do not affect activity of sham-operated rats and therefore do not reflect a generalized non-specific impairment of motor capabilities.

Example 198: Inhibition of Dextromethorphan Metabolism

Dextromethorphan O-demethylase activity is determined in human liver microsomes. The compound of Formula I (concentration: up to 3.0E-5 M) and dextromethorphan are dissolved in acetonitrile and serially diluted with acetonitrile to the required concentrations to give a final organic solvent concentration of about 1.0% in the incubation mixture. The incubation mixtures contain pooled human liver microsomes, dextromethorphan, and a NADPH-generating system. After incubation and centrifugation, the supernatant is diluted up to 100-fold with acetonitrile and then injected into the LC-MS/MS system. All incubations are performed in triplicate, and mean values are used for analysis. The IC50 values (concentration causing a half-maximal inhibition of control specific binding) and Hill coefficients (nH) are determined using methods such as non-linear regression analysis of the competition curves generated with mean replicate values using Hill equation curve fitting. Deramciclane is observed to inhibit CYP2D6-mediated dextromethorphan O-demethylation.

Based on previous human studies with desipramine as a substrate, the compound of Formula I can be classified as a weak 2D6 inhibitor (Laine K et al., Effect of the novel anxiolytic drug deramciclane on cytochrome P450 2D6 activity as measured by desipramine pharmacokinetics. Eur J Clin Pharmacol (2004) 59: 893-898). This classification was based on about 2-fold increase in the substrate AUC (i.e. per guidance provided by the US Food and Drug Administration, Draft guidance for industry: drug interaction studies—study design, data analysis, implication for dosing and labeling recommendations. Center for Drug Evaluation and Research, US FDA (2012), Guidance Compliance Regulatory Information at FDA.GOV).

In a pharmacokinetic study performed in rats, ability of the compound of Formula I to inhibit dextromethorphan metabolism is studied in vivo. Adult rats are housed in a climate-controlled room under a 12 h light/12 h dark cycle with ad libitum access to food and water. On the day of the experiment, dextromethorphan (50 mg/kg) is administered by oral gavage, immediately followed by deramciclane (up to 30 mg/kg) or vehicle (t=0 h). Blood samples are collected at multiple time points until 24 hours post dextromethorphan administration. Sample size is about 80 μl Li-heparin whole blood/time point, i.e. 40 μl Li-heparin plasma/time point. Whole blood samples are stored on ice until centrifugation (10 min at 3000 g, 4° C.). Plasma is prepared within 45 min after collection, frozen at −20° C. and stored at this temperature until processed for LC-MS analysis. In rats treated with the compound of Formula I, plasma levels of dextromethorphan continue to be high even at the later time points while, in vehicle-treated rats, dextromethorphan levels decline faster.

Example 199: Effects of the Compound of Formula I on Discriminative Stimulus Effects of Dextromethorphan and Memantine Drug discrimination is commonly used to assess interoceptive stimulus control produced by psychoactive drugs (Sukhotina I A et al., Effects of calcium channel blockers on behaviors induced by the N-methyl-D-aspartate receptor antagonist, dizocilpine, in rats. Pharmacol Biochem Behav (1999) 63:569-80). These methods are used to address ability of certain classes of CNS active drugs such as NMDA receptor channel blockers to produce adverse effects (Nicholson K L et al., Evaluation of the reinforcing and discriminative stimulus properties of the low-affinity N-methyl-D-aspartate channel blocker memantine. Behav Pharmacol (1998) 9:231-43).

Figure 1B:
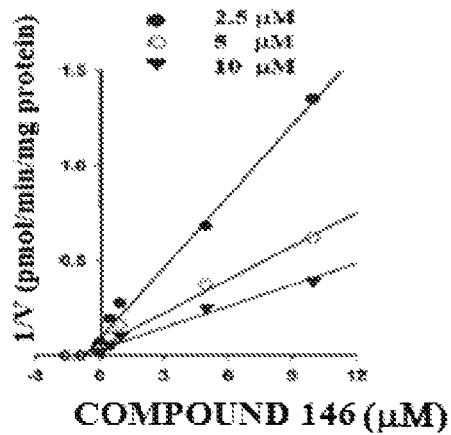
Figure 1C:
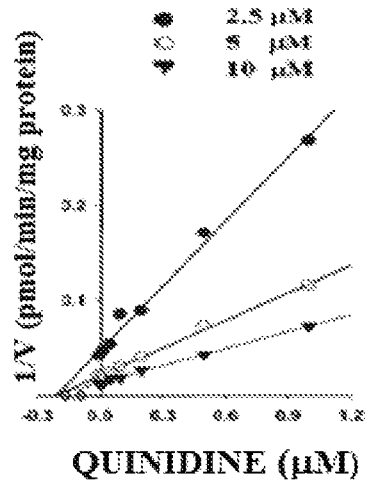
Figure 4A:
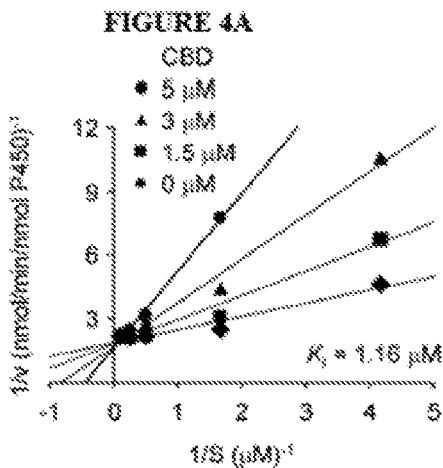
FIGS. 4A, 4B, and 4C represent Lineweaver-Burk plots for the inhibition of CYP2D6 and human liver microsomes (HLMs) by Compound 847 (canabiodiol, CBD). Recombinant CYP2D6 was incubated with (A) 3-[2-(N,N-Diethyl-N-methylammonium) ethyl]-7-methoxy-4-methylcoumarin (AMMC) in the presence of CBD (FIG. 4A), (B) dextromethorphan in the presence of CBD (FIG. 4B), and (C) in the absence of CBD (FIG. 4C), HLMs were incubated with dextromethorphan in the presence or absence of CBD. Each point is the mean of duplicate determinations.
Figure 4B:
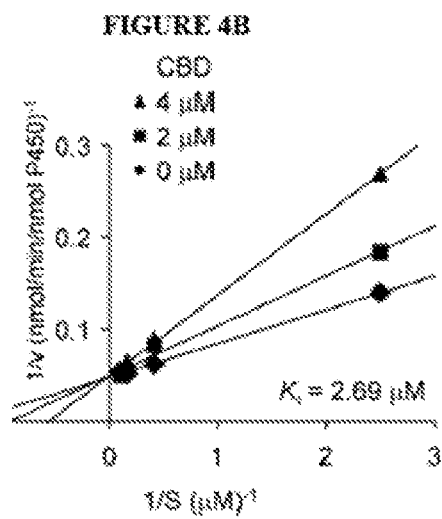
Figure 4C:
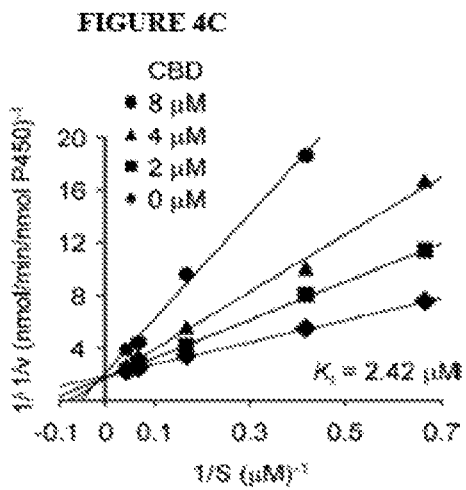
Figure 4D:
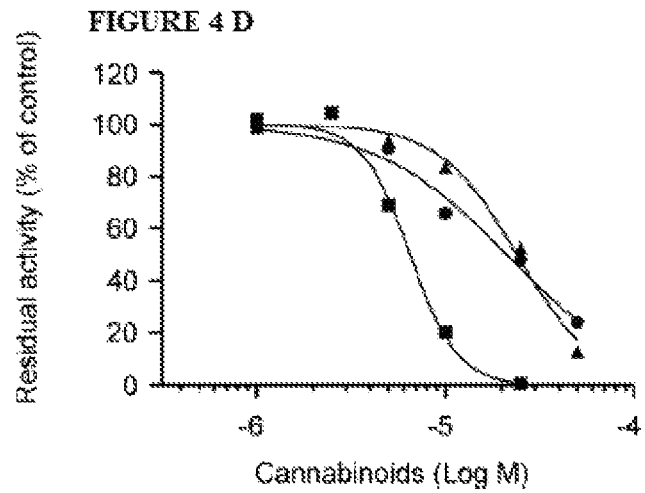
FIGS. 4D, 4E, and 4F represent effects of the major phytocannabinoids $\Delta^9$-tetrahydro cannabinol ($\Delta^9$-THC), CBD, and cannabinol (CBN) on AMMC and the dextromethorphan O-demethylase activities of CYP2D6 and HLMs. Recombinant CYP2D6 was incubated with (D) 0.6 µM AMMC (FIG. 4D), (E) 0.6 µM dextromethorphan (FIG. 4E) in the presence of various amounts of $\Delta^9$-THC, CBD, and CBN; and (F) HLMs were incubated with 4 µM dextromethorphan in the presence of various amounts of $\Delta^9$-THC, CBD, and CBN (FIG. 4F). Each point is the mean of two determinations (Yamaori et al., Cannabidiol, a Major Phytocannabinoid, As a Potent Atypical Inhibitor for CYP2D6, *Drug Metabolism and Disposition*, Vol. 39, No. 11 (2011) incorporated in entirety by reference).
Figure 4E:
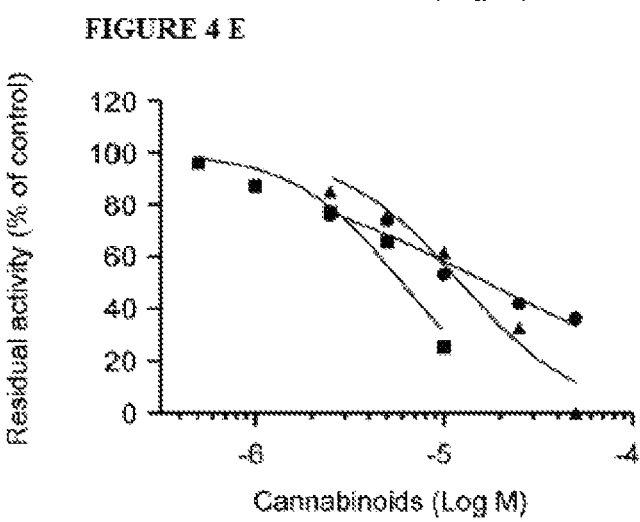
Figure 4F:
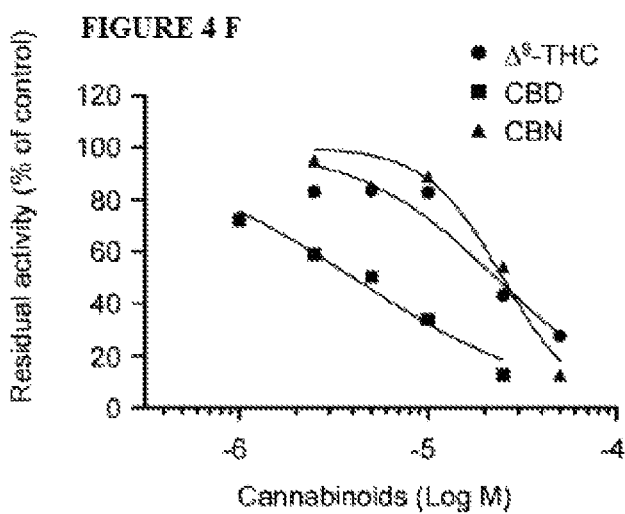
Figure 5:
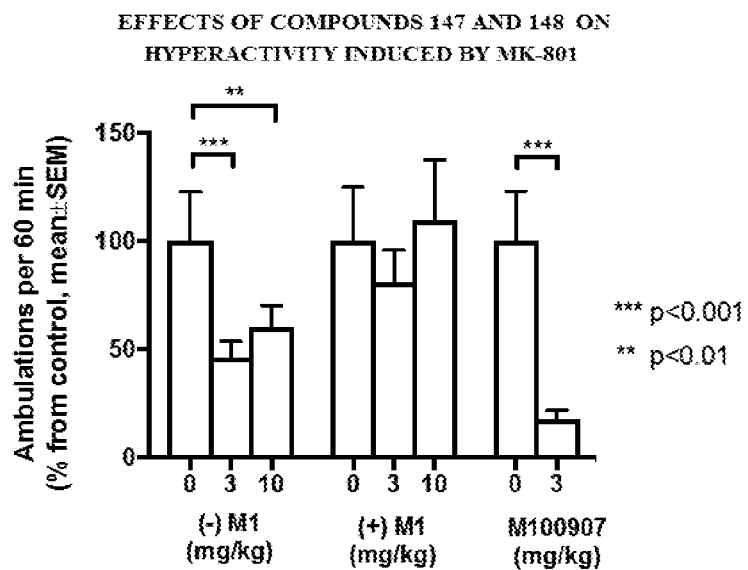
FIG. 5 shows effects of (−) and (+) enantiomers of M1 as well as M-100,907 on MK-801-induced hyperactivity in rats. Data are presented as mean (±SEM) average activity over a 60-min test session. N=5-9 per group.
Figure 6:
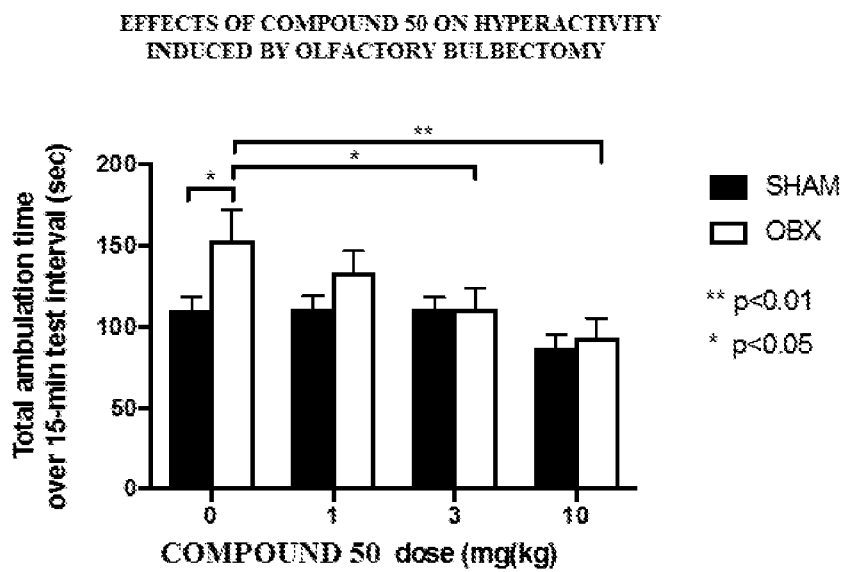
FIG. 6 shows effects of sarpogrelate on motor activity in rats after olfactory bulbectomy (OBX) or sham surgery (SHAM). Data are presented as mean (±SEM) average activity over a 5-min test session. N=12 per group.
Figure 14A:
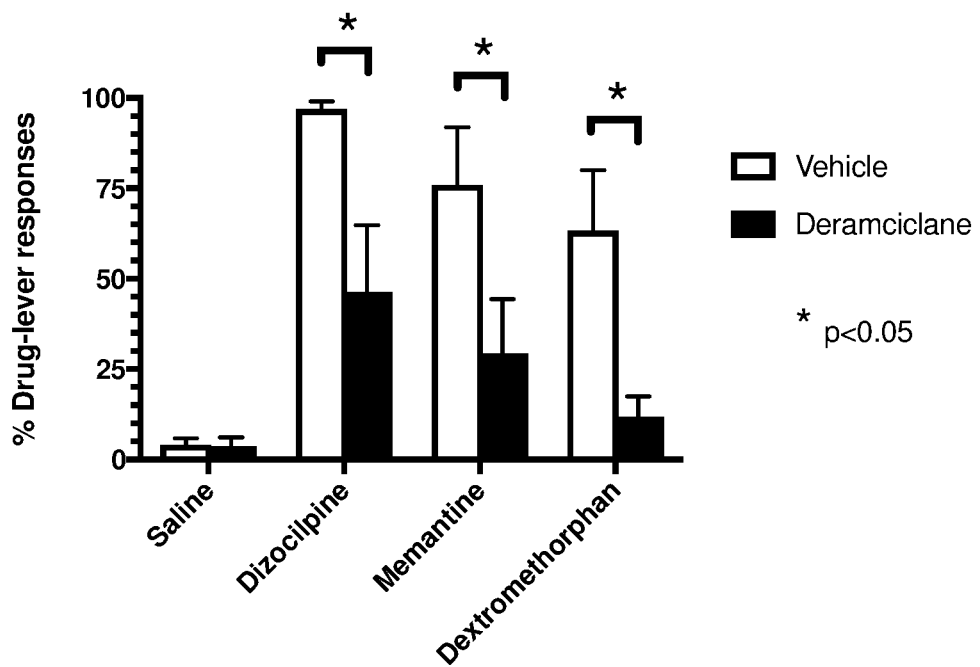
FIGS. 14A and 14B show the effect of compound 829 on discriminative stimulus effects of NMDA receptor channel blockers. Data are presented as mean (±S.E.M.) percent of drug-lever responses (upper panel) and response rate (responses per second; lower panel). N=6.
Figure 14B:
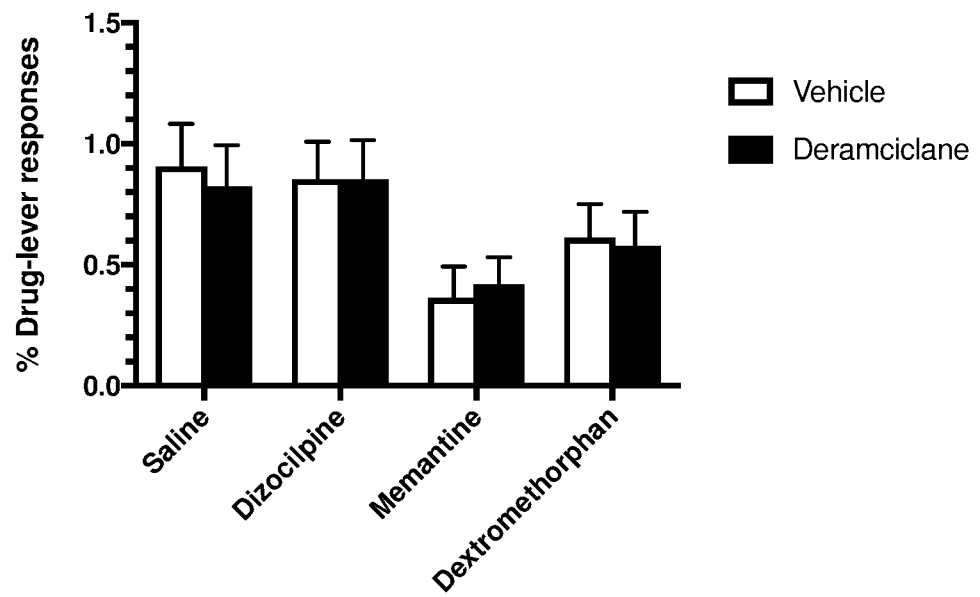

Adult male Wistar rats were housed individually with water available ad lib. Food consumption was restricted to 14-16 g/day given after behavioral testing to maintain a constant body weight (300-330 g). Behavioral training and testing was conducted using standard two-lever operant conditioning chambers connected to a microcomputer through an interface and controlled by MED-PC software. Each chamber was equipped with a food dispenser, which delivered 45-mg food pellets. At the start of each drug discrimination training session, rats were injected i.p. with either 0.056 mg/kg of dizocilpine or saline, returned to their home cages, and then 15 min later were placed into the operant chambers for a total of 15 min. During test sessions, 10 consecutive responses on either lever produced a pellet delivery. Prior to the test sessions, there were two injections given; one i.p. with deramciclane (3 mg/kg) or its vehicle (preinjection time 60 min) and one with dizocilpine (0.056 mg/kg), memantine (10 mg/kg), dextromethorphan (30 mg/kg) or saline (preinjection time 15 min). The percentage of responses on the dizocilpine-designated lever (DLR) and response rate (responses/s) were calculated for each test session to establish that deramciclane significantly reduces the intensity of discriminative stimulus effects of NMDA receptor channel blockers (FIG. 14A) at the dose that had not significantly impair operant performance (FIG. 14B). Reduced intensity of discriminative stimulus effects of memantine in the presence of deramciclane (FIG. 1, upper panel) indicates that deramciclane can control unwanted effects of NMDA receptor channel blockers such as dextromethorphan (Nicholson K L et al., Evaluation of the reinforcing properties and phencyclidine-like discriminative stimulus effects of dextromethorphan and dextrorphan in rats and rhesus monkeys. Psychopharmacology (1999) 146: 49-59) not only by inhibiting dextromethorphan's metabolism (Zawertailo L A et al., Effect of metabolic blockade on the psychoactive effects of dextromethorphan. Hum Psychopharmacol (2010) 25:71-9) but also by pharmacodynamic mechanisms. Thus, given the 2D6 inhibitory properties of deramciclane, deramciclane most efficiently controls subjective effects of NMDA receptor channel blockers that are metabolized via CYP 2D6 such as dextromethorphan.

Figure 15A:
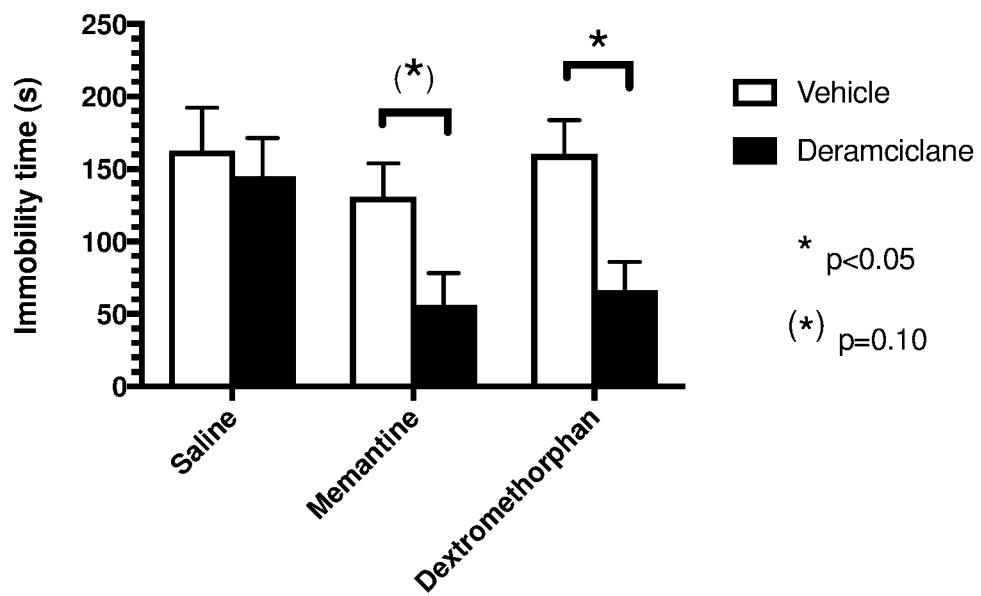
FIG. 15A shows the effect of compound 829 in combination with memantine and in combination dextromethorphan in the tail suspension test. Data are presented as mean (±S.E.M.) immobility time. N=8.
Figure 15B:
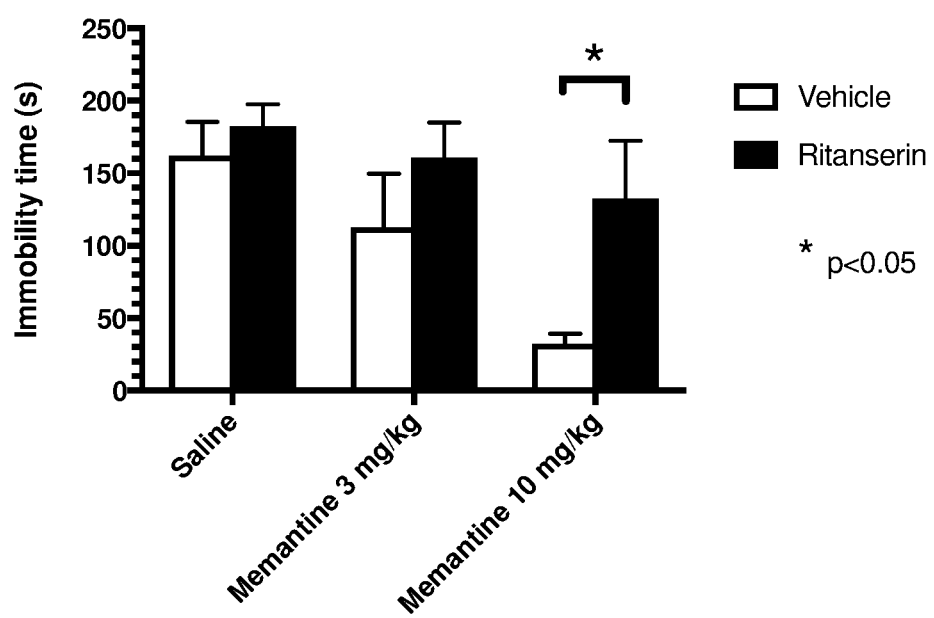
FIG. 15b shows the effect of ritanserin in combination with memantine in the tail suspension test. Data are presented as mean (±S.E.M.) immobility time. N=7-8.

Example 200: Antidepressant-Like Effects of the Compound of Formula I Given in Combination with an NMDA Receptor Channel Blocker Tail suspension is one of the classical tests used to study antidepressant drugs and was also applied to evaluate antidepressant-like effects of NMDA receptor channel blockers (Kos T et al., Effect of 5-HT3 receptor antagonist MDL 72222 on behaviors induced by ketamine in rats and mice. European Neuropsychopharmacology (2006) 16:297-310). Mice were transferred from the housing room to the testing area in their home cages and allowed to adapt to the new environment for at least 1 h before drug treatment. Immobility was induced by tail suspension whereby mice were attached individually on a paper adhesive tape, 65 cm above the table top. The tape was placed approximately 1 cm from the tip of the tail. Animals were suspended for 6 min and the duration of immobility was recorded. Mice were considered immobile only when they were completely motionless. Prior to the test sessions, there were two injections given; one i.p. with deramciclane (3 mg/kg) or its vehicle (preinjection time 60 min) and one with memantine (3 mg/kg), dextromethorphan (10 mg/kg) or saline (preinjection time 30 min). While given alone none of the treatments at these dose levels had statistically significant effects, combined administration of deramciclane with dextrimethorphan significantly reduced immobility time suggesting antidepressant-like potential of this combination (FIG. 15A). Combination of deramciclane with memantine also reduced immobility time by 57% (P=0.1). Surprisingly, when a subeffective dose of memantine (3 mg/kg) was given in a combination with another 5-HT2A/2C receptor antagonist, ritanserin (1 mg/kg), no reduction in immobility time was observed (FIG. 15B). Instead, ritanserin was able to reverse antidepressant-like effects of an effective dose of memantine (10 mg/kg). These results suggest that, when given in a combination with NMDA receptor channel blockers, deramciclane is capable of producing pharmacodynamic effects that distinguish it from at least some of the other representatives of the class of 5-HT2A/2C receptor antagonists and inverse agonists.

Example 201: Anxiolytic Effects of the Compound of Formula I Given in Combination with an NMDA Receptor Channel Blocker Conflict tests such as the Geller-Seifter test are commonly used to study anxiolytic effects of drugs and were also applied to evaluate anxiolytic effects of glutamate receptor antagonists (Pietraszek M et al., Anxiolytic-like effects of mGlu1 and mGlu5 receptor antagonists in rats. Eur J Pharmacol (2005) 514:25-34).

Figure 16A:
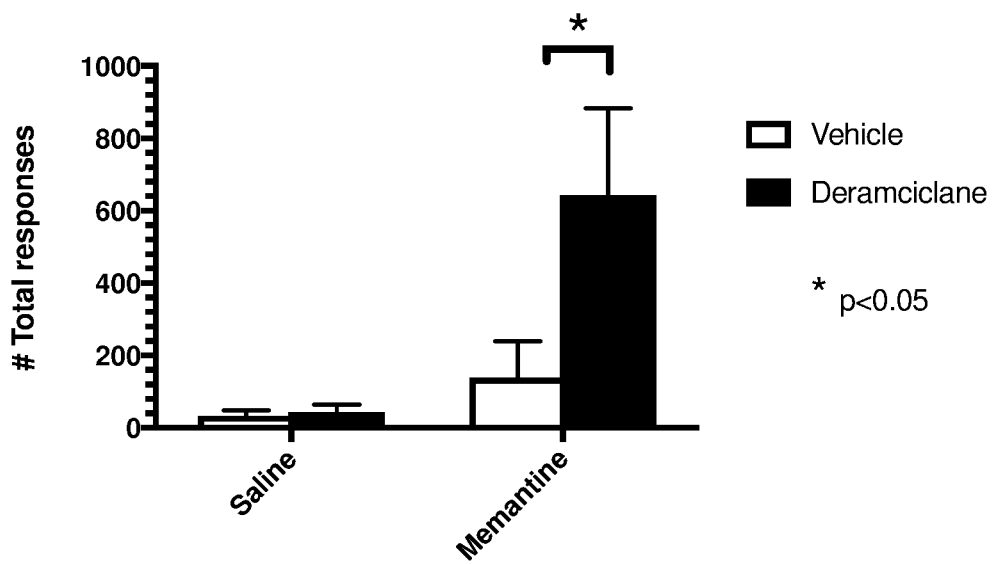
FIG. 16A shows the effect of compound 829 and memantine on punished responding in the Geller-Seiffer test. Data are presented as mean (±S.E.M.) number of responses per session. N=4.
Figure 16B:
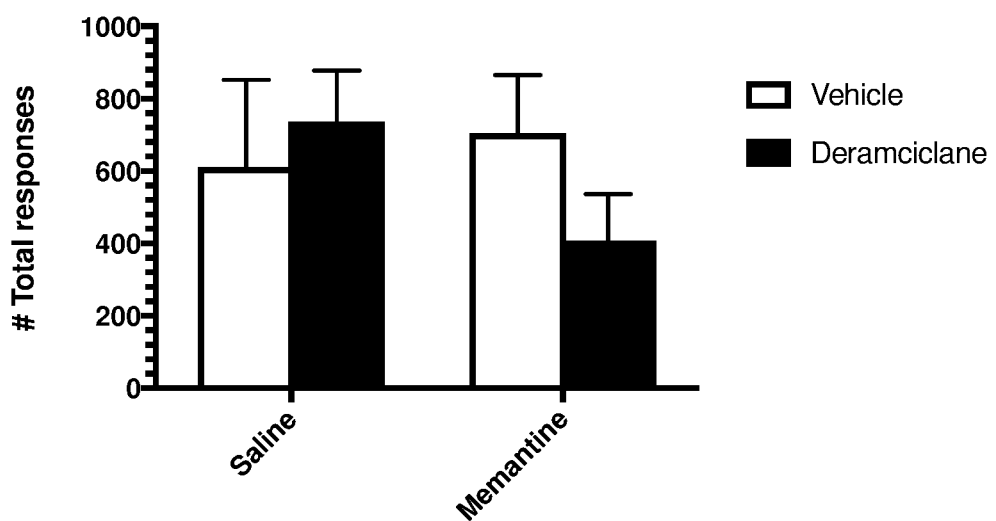
FIG. 16B shows the effect of compound 829 and memantine on unpunished responding in the Geller-Seiffer test. Data are presented as mean (±S.E.M.) number of responses per session. N=4.

Using standard operant conditioning chambers, connected to a computer through an interface and controlled by MED-PC software, rats were trained to lever press under a multiple fixed ratio (FR) 20 (food only), FR 20 (food and shock) schedule in which three 7-min unpunished components alternated with three 3-min punished components for a total session length of 30 min. Shock amperage and duration were adjusted for each individual rat. The data were analyzed as response rates (responses per second) during the punished and unpunished components of each session. For analysis purposes, the response rate data obtained during the drug tests were expressed as a response rate change relative to the 5-day baseline. Prior to the test sessions, there were two injections given; one i.p. with deramciclane (1 mg/kg) or its vehicle (preinjection time 60 min) and one with memantine (3 mg/kg) or saline (preinjection time 30 min). Both deramciclane and memantine were given at the dose levels that had on its own any appreciable effects on either punished or unpunished responding (FIGS. 16A and 16B). However, when subeffective doses of memantine and deramciclane were given in combination, rats were observed to emit significantly more punished responses, indicating synergistic interactions between deramciclane and memantine that result in reduced anxiety.

Figure 17:
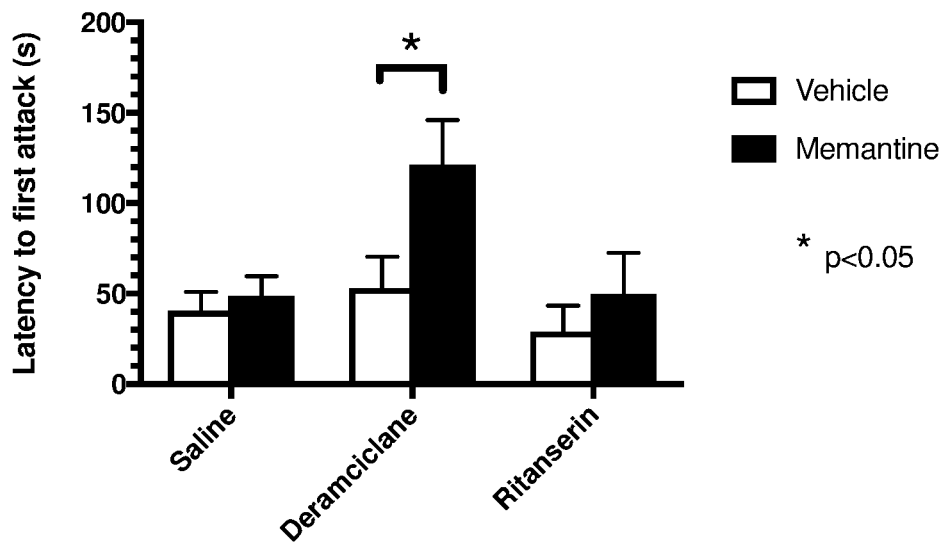
FIG. 17 shows the effect of compound 829 in combination with memantine, and ritanserin in combination with memantine on isolation-induced aggression. Data are presented as mean (±S.E.M.) latency to the first attack. N=7.
Figure 18:
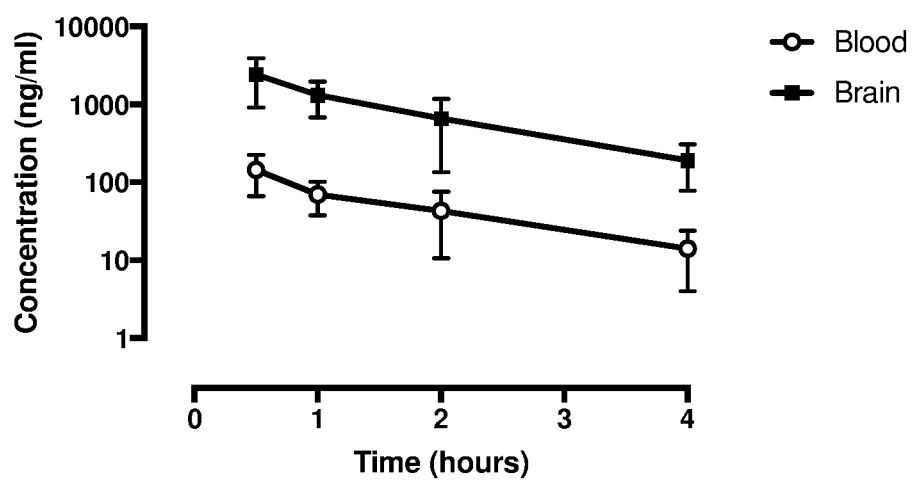
FIG. 18 shows the total concentration of compound 146 (M1) in plasma and brain tissue. The total brain and plasma concentration after intraperitonial administration of a composition of the invention comprising a compound of the Formula I, exemplified by Compound 146. Data are presented as mean (±S.E.M.) amount of compound in brain tissue extracts measured using the UPLC/MS analysis. N=4.

Example 202: Anti-Aggressive Effects of the Compound of Formula I Given in Combination with an NMDA Receptor Channel Blocker Male mice housed in isolation readily develop and demonstrate aggression towards intruders. Such paradigms have been applied to evaluate anti-aggressive of NMDA receptor channel blockers (Belozertseva I V, Bespalov A Y, Effects of NMDA receptor channel blockade on aggression in isolated male mice, Aggressive Behavior (1999) 25: 381-396). In these experiments, mice were housed individually and, starting after the first two weeks of isolation, were repeatedly (twice a week) allowed to attack for 4 min a group-housed stimulus intruder mouse. Only the resident mice that consistently exhibit attack behavior toward intruders were used for the drug tests. Drug tests began when resident mice demonstrated attacks toward the intruder in at least three consecutive tests and lived in isolation for at least 35 days. Intruder mice were housed in groups of five. Thirty minutes prior to the test, mice were treated with memantine (10 mg/kg) combined with deramciclane (3 mg/kg) or ritanserin (1 mg/kg). When given alone, none of the compounds at the chosen doses exerted any appreciable effects on agonistic behaviors (attacks, bites, threats, tail rattling, upright and sideways posturing, pushing, and retreating). However, when memantine was combined with deramciclane (but not ritanserin), mice were significantly less likely to attack in the absence of any visible ataxia (FIG. 17). Thus, while deramciclane or NMDA receptor antagonists may not be effective when given alone, they can produce robust anti-aggressive properties when given in a combination.

Example 203

The activity of dextromethorphan O-demethylation was measured (Yu et al., Comparative contribution to dextromethorphan metabolism by cytochrome P450 isoforms in vitro: can dextromethorphan be used as a dual probe for both CTP2D6 and CYP3A activities? Drug Metab Dispos, 29:1514-1520 (2001)) with minor modifications. Recombinant CYP2D6 (0.25 pmol) and HLMs (12.5 µg of protein) were used as enzyme sources. An incubation mixture consisted of an enzyme source, dextromethorphan, an NADPH-generating system (500 µM NADP, 10 mM glucose 6-phosphate, 10 mM magnesium chloride, and 1 unit/ml glucose 6-phosphate dehydrogenase), and 100 mM potassium phosphate buffer (pH 7.4) in a final volume of 200 µl. Incubations were performed at 37° C. for 10 min and were terminated by adding 10 µl of 70% (w/v) perchloric acid. After removal of protein by centrifugation, 50 µl of the supernatant was subjected to a high-performance liquid chromatography (D7500 integrator, L-7100 pump, L-7200 autosampler, L-7300 column oven, and L-7485 fluorescence detector) equipped with a Mightysil RP-18 GP column (4.6µ 250 mm, 5 µm). The mobile phase was the mixture of acetonitrile/methanol: 10 mM potassium phosphate buffer adjusted to pH 3.5 with phosphoric acid (200:160:630). Elution was performed at a flow rate of 1.0 ml/min. The formation of dextrorphan was monitored at an excitation of 280 nm and an emission of 310 nm.

The preincubation mixture contained recombinant CYP2D6 (2 pmol), each major cannabinoid (2.5-50 µM), an NADPH-generating system (8.2 µM NADP, 0.41 mM glucose 6-phosphate, 0.41 mM magnesium chloride, and 1 unit/ml glucose 6-phosphate dehydrogenase), and 100 mM potassium phosphate buffer (pH 7.4) in a final volume of 180 µl. After prewarming at 37° C. for 5 min, reactions were initiated by the addition of the NADPH-generating system. After a 20-min preincubation, 20 µl of AMMC solution was added to the preincubation mixture (final substrate concentration, 0.6 µM). Incubations were conducted under the same manner as described under Enzyme Assays for AMMC O-demethylase activity. Prediction of In Vivo Drug Interactions for CYP2D6. An estimate of in vivo inhibition potency was determined by the methods of Obach et al. (2006). The maximal unbound hepatic input concentration, Cmax, u, inlet, was determined using the following equation:

$$C_{max,u,inlet} = f_u \cdot (C_{max} + D \times F_a \times k_a / Q_h)$$

Cmax is defined as the maximal systemic concentration, fu is the fraction unbound in the blood, D is the oral dose, Fa is the fraction of the oral dose absorbed, ka is the first-order absorption rate constant, and Qh is the hepatic blood flow. In the case of marijuana smoking, absorption from the gastrointestinal tract is not taken into account. Thus, the Cmax, u, inlet for inhaled cannabinoids is equal to fu Cmax. The value of fu for cannabinoids is at most 0.05 because 95 to 99% of plasma THC is bound to plasma proteins, mainly lipoproteins (Grotenhermen, 2003). A ratio of the area under the curve (AUC) with inhibitor to control AUC could be estimated using the following equation:

$$AUC_{inhibited}/AUC_{control} = 1/\{[f_{m(CYP2D6)}/(1+[I]_{in\ vivo}/K_i)] + (1 - f_{m(CYP2D6)})\}$$

In the above equation, AUC inhibited is the area under the curve for a given substrate probe in the presence of an inhibitor, and $AUC_{control}$ is the area under the curve for the same probe substrate without inhibitor. The fraction of metabolism of the probe substrate by CYP2D6 and the magnitude of the potency of the inhibitor are represented by fm(CYP2D6) and Ki, respectively. The value of unity was used for the fm(CYP2D6) of dextromethorphan/dextrorphan urinary ratio (Obach et al., 2006). Thus, a ratio of $AUC_{inhibited}$ to $AUC_{control}$ of dextromethorphan is equal to $1+[I]_{in\ vivo}/K_i$.

Example 204

The time related distribution and pharmacokinetics of double-labelled compound 829 (compound 829-phenyl-C-14 and -ethyl-H-3) were studied in the plasma, hypophysis and 14 cerebral regions, including the spinal cord o f the rat after a single oral treatment (acute experiments) and after repeated administration of one dose daily for six days (subacute experiments). The tissue levels of compound 829 were calculated from the simultaneously determined dpm values and the specific activities of the two radioisomers present in the dose administered. EGIS-38 85 was rapidly absorbed from the gastrointestinal tract t(max)=1.0 h). The concentration-time curves in the tissues can be described by a two compartment open model. The H-3-activity could be measured during the whole period of the acute experiment (95 h), whereas C-14-radioactivity fell below the detection limit within 24 h. The AUC (0.96) values f or H-3 were 10 to 15 times higher than that for C-14. I, all samples examined, on the concentration time curves a peak characteristic of ent erohepatic cycle can be seen at 12 h. The studies indicated that intact molecules entered brain tissues from the circulation. The results of the subacute experiments indicate that the C-14-labelled compound 829, or its metabolite(s) carrying the tracer, reach an equilibrium as early as on the second to third day, whilst the level of H-3-radioactivity continually increases during the six days of repeated administration. In the subacute experiments the peak concentrations were reached at 0.5 h after the final treatment. However, their values for 3H were higher than in acute experiments. The last tendency was not observed in the case of C-14-tracer. The AUC values of H-3-labelled compound 829 determined in subacute experiments predominated over C-14; the ratios were 50 to 60 in all brain regions. The enterohepatic cycle, seen after a single dose, also operated after repeated dosage. The time related concentrations of compound 829 in the hypophysis were at least two times higher than that in the plasma and the brain tissues. No significant difference was seen in the concentrations of compound 829 in the symmetrical (left and right) regions of the brain (Magyar et al., Distribution Of Deramciclane In Rat-Brain Regions, European journal of drug metabolism and pharmacokinetics, 23(2), pp. 125-131 (1998), incorporated in entirety).

Example 205

5HT2a ASSAY: Evaluation of the affinity of compounds for the human 5-HT2A receptor in transfected HEK-293 cells determined in a radioligand binding assay. Cell membrane homogenates (30-50 µg protein) were incubated 15 min at 37° C. with 0.5 nM [3H]ketanserin in the absence or presence of the test compound in a buffer containing 50 mM Tris-HCl (pH 7.4). Nonspecific binding was determined in the presence of 1 µM ketanserin. Following incubation, the samples were filtered rapidly under vacuum through glass fiber filters presoaked with 0.3% PEI and rinsed several times with ice-cold 50 mM Tris-HCl using a 96-sample cell harvester. The filters were dried then counted for radioactivity in a scintillation counter using a scintillation cocktail (WO2005013952A1, EP1500391A1[ab1], incorporated in its entirety by reference).

Example 206

Male NMRI mice (20-25 g bodyweight) were dropped on a hot plate (56±0,5° C.) and the latency time elapsed until licking the forepaws was measured. The reaction time was tested twice before treatment. Animals were discarded if the first basal latency time >5 sec. or the difference between the two control measurements was greater than 3 sec. Mice were treated either with saline or with morphine HCl 1 mg/kg subcutaneously and at the same time either with vehicle or with deramciclane or buspirone, HCl 30 mg/kg intraperitoneally, respectively. After the treatment (15, 30, 45 and 60 min.) the reaction time was measured again. Animals were regarded as positive if they produced a 2.5-fold reaction time increase at least twice compared to their first control values. Administration of a combination of morphine and compound 129 showed statistically significant analgesic effect over administration of either of the compounds alone (EP1734940 B 1, incorporated in its entirety by reference).

Example 207: CNS Efficacy of the Compound of Formula I can be Mediated by a Biologically Active Metabolite Compound 50 is a peripherally acting 5-HT2A receptor antagonist (Obata H et al., Antinociception in rat by sarpogrelate, a selective 5-HT(2A) receptor antagonist, is peripheral. Eur J Pharmacol (2000) 404:95-102) and there is a direct evidence generated using [14C] labeled Compound 50 that sarpogrelate may not be able to cross the blood-brain barrier in the rat (Komatsu T et al., Studies on the Metabolic Fate of (+)-2(Dimethylamino)-1-CCo(m-methoxyphenethyl) phenoxyDmethyl]ethyl hydrogen siccinate hydrochloride (MCI-9042) (II): Absorption, Distribution, Metabolism and Excretion after a Single Administration to Rats).

Adult male SD rats were pretreated with the compound 146 or M1 (10 mg/kg intraperitoneally) and the brain and blood plasma were collected 30, 60, 120 and 240 min after M1 administration. The amount of compound in brain tissue extracts was measured using the UPLC/MS analysis. As shown in Figure XYZ, total brain concentration of M1 significantly exceeded the blood concentration. Thus, unlike Compound 50, M1 readily penetrates into the brain and may be responsible for surprising CNS effects of Compound 50.

We claim:
1. A composition comprising
   a) at least one compound selected from the group consisting of:
   2-phenyl-2-(2-dimethylaminoethoxy)-1,7,7-trimethylbicyclo[2,2,1]heptane (deramciclane);
   2-phenyl-2-(3'-dimethylaminopropoxy)-1,7,7-trimethylbicyclo[2,2,1]heptane;
   2-phenyl-2-(3'-diethylaminopropoxy)-1,7,7-trimethylbicyclo[2,2,1]heptane;
   2-(p-methoxy-phenyl)-2-(3'-dimethylaminopropoxy)-1,7,7-trimethylbicyclo[2,2,1]heptane;
   2-benzyl-2-(3'-dimethylaminopropoxy)-1,7,7-trimethylbicyclo[2,2,1]heptane;
   2-benzyl-2-(3'-dimethylamino-2'-methylpropoxy)-1,7,7-trimethyl-bicyclo[2,2,1]heptane;
   2-benzyl-2-(2-diisopropylaminoethoxy)-1,7,7-trimethylbicyclo[2,2,1]heptane;
   2-benzyl-2-1'-(4'-benzylpiperazinyl)-propoxy1,7,7-trimethylbicyclo[2,2,1]heptane;
   2-benzyl-2-(3'-diisopropylaminopropoxy)-1,7,7-trimethylbicyclo[2,2,1]heptane;
   2-benzyl-2-(3'-diethylaminopropoxy)-1,7,7-trimethylbicyclo[2,2,1]heptane;
   2-benzyl-2-(3'-dimethylaminopropoxy)-1,7,7-trimethylbicyclo[2,2,1]heptane;
   2-benzyl-2-(2'-diethylaminoethoxy)-1,7,7-trimethylbicyclo[2,2,1]heptane;
   2-benzyl-2-(3'-dimethylaminopropoxy)-1,7,7-trimethylbicyclo[2,2,1]heptane;
   2-(3'-dimethylaminopropoxy)-2-(4'-methoxyphenyl)-1,7,7-trimethylbicyclo[2,2,1]heptane;
   2-(p-chloro-benzyl)-2-(3'-dimethylaminopropoxy)-1,7,7-trimethylbicyclo[2,2,1]heptane;
   2-(p-chloro-benzyl)-2-(2'-dimethylaminoethoxy)-1,7,7-trimethylbicyclo[2,2,1]heptane;
   2-(3'-dimethylamino-2'-methyl)-propoxy-2-(p-chlorophenyl)-1,7,7-trimethylbicyclo[2,2,1]heptane;
   2-(3'-dimethylaminopropoxy)-2-phenyl-1,7,7-trimethylbicyclo[2,2,1]heptane;
   2-(2'-dimethylaminoethoxy)-2-phenyl-1,7,7-trimethylbicyclo[2,2,1]heptane;
   2-(3-diethylaminopropoxy)-2-phenyl-1,7,7-trimethylbicyclo[2,2,1]heptane;
   2-(2'-diethylaminoethoxy)-2-(2'-thienyl)-1,7,7-trimethylbicyclo[2,2,1]heptane;
   2-(3'-dimethylaminopropoxy)-2-(2'-thienyl)-1,7,7-trimethylbicyclo[2,2,1]heptane;
   2-(3'-diethylaminopropoxy)-2-(2'-thienyl)-1,7,7-trimethylbicyclo[2,2,1]heptane;
   2-benzyl-2-3'-(N-cyclohexyl-N-methyl)aminopropoxy]-1,7,7-trimethylbicyclo[2,2,1]heptane;
   2-(p-methoxyphenyl)-2-(3'-dimethylaminopropoxy)-1,7,7-trimethylbicyclo[2,2,1]heptane;
   (1R,2S,4R)-(−)-2-[(2'-{N,N-dimethylamino}-ethoxy)]-2-[phenyl]-1,7,7-trimethylbicyclo[2,2,1]heptane;
   (1R,2S,4R)-(−)-2-benzyl-2-(3'-dimethylaminopropoxy)-1,7,7-trimethylbicyclo[2,2,1]heptane;
   (1R,2S,4R)-(−)-2-benzyl-2-(2'-methyl-3'-dimethylaminopropoxy)-1,7,7-trimethylbicyclo [2,2,1]heptane;
   (1RS,2RS,4RS)-2-phenyl-2-(2'-dimethylaminoethoxy)-1,7,7-trimethylbicyclo[2,2,1]heptane;
   (1S,2R,4S)-(+)-2-phenyl-2-(2'-dimethylaminoethoxy)-1,7,7-trimethylbicyclo[2,2,1]heptane;
   N,N-dimethyl-2-[[(1R,3S,4R)-4,7,7-trimethyl-3-phenyl-3-bicyclo[2,2,1]heptanyl]oxy ethanamine;
   ((2,(−)-[1R,2S,4R]-2-(2-dimethyl amino ethoxy)-2-phenyl-1,7,7-trimethyl bicyclo [2,2,1]heptane) fumarate;
   1-(dimethylamino)-3-(2-(3-methoxyphenethyl)phenoxy) propan-2-yl 4-(adamantan-1-ylamino)-4-oxobutanoate;
   (S)-1-(dimethylamino)-3-(2-(3-methoxy phenethyl) phenoxy) propan-2-yl 4-(adamantan -1-ylamino)-4-oxobutanoate; and
   (R)-1-(dimethylamino)-3-(2-(3-methoxyphenethyl) phenoxy) propan-2-yl 4-(adamantan-1-ylamino)-4-oxobutanoate; or salts thereof selected from the group consisting of acetate, acetyl salicylate, adipate, aspartate, butyrate, caprate, caproate, caprylate, enanthate, formate, fumarate, glutamate glutarate, hydrobromide, hydrochloride, isophthallate, maleate, malonate, methionate, oxalate, pelargonate, pimelate, propionate, phthallate, salicylate, sebacate, succinate, terephthallate, tyrosinate, tryptophanate, valerate, N-acyl-aspartate, N-acyl-glutamate, N-acyl-tyrosinate, N-acyl-tryptophanate, N-acyl-methionate, citrate, galactonate, glucaric acid (saccharic acid), mannonate, mucate, rhamnonate, and tartrate; or a combination thereof;
   and
   b) at least one compound selected from the group consisting of:
   ketamine; methadone; memantine; amantadine; dextropropoxyphene; ketobemidone; dextromethorphan;
   (4bS,8aS,9S)-11-methyl-3-(trifluoromethoxy)-6,7,8,8a,9,10-hexahydro-5H-9,4b-(epiminoethano)phenanthrene;
   (4bS,8aS,9S)-3-(trifluoromethoxy)-11-(trifluoromethyl)-6,7,8,8a,9,10-hexahydro-5H-9,4b-(epiminoethano) phenanthrene; and
   (4bS,8aS,9S)-3-methoxy-11-(trifluoromethyl)-6,7,8,8a,9,10-hexahydro-5H-9,4b-(epiminoethano) phenanthrene; or salts thereof selected from the group consisting of acetate, acetyl salicylate, adipate, aspartate, butyrate, caprate, caproate, caprylate, enanthate, formate, fumarate, glutamate glutarate, hydrobromide, hydrochloride, isophthallate, maleate, malonate, methionate, oxalate, pelargonate, pimelate, propionate, phthallate, salicylate, sebacate, succinate, terephthallate, tyrosinate, tryptophanate, valerate, N-acyl-aspartate, N-acyl-glutamate, N-acyl-tyrosinate, N-acyl-tryptophanate, N-acyl-methionate, citrate, galactonate, glucaric acid (saccharic acid), mannonate, mucate, rhamnonate, and tartrate; or a combination thereof.

2. A composition comprising a) deramciclane and b) memantine; or salts thereof selected from the group consisting of acetate, acetyl salicylate, adipate, aspartate, butyrate, caprate, caproate, caprylate, enanthate, formate, fumarate, glutamate glutarate, hydrobromide, hydrochloride, isophthallate, maleate, malonate, methionate, oxalate, pelargonate, pimelate, propionate, phthallate, salicylate, sebacate, succinate, terephthallate, tyrosinate, tryptophanate, valerate, N-acyl-aspartate, N-acyl-glutamate, N-acyl-tyrosinate, N-acyl-tryptophanate, N-acyl-methionate, citrate, galactonate, glucaric acid (saccharic acid), mannonate, mucate, rhamnonate, and tartrate; or a combination thereof.

3. The composition of claim 1, wherein the composition further comprises: a. polymer, b. emulsifier, c. binder, d. a disintegrating agent, and/or e. a lubricant.

4. A pharmaceutical composition comprising a combination of:
deramciclane and dextromethorphan: or salts thereof selected from the group consisting of acetate, acetyl salicylate, adipate, aspartate, butyrate, caprate, caproate, caprylate, enanthate, formate, fumarate, glutamate glutarate, hydrobromide, hydrochloride, isophthallate, maleate, malonate, methionate, oxalate, pelargonate, pimelate, propionate, phthallate, salicylate, sebacate, succinate, terephthallate, tyrosinate, tryptophanate, valerate, N-acyl-aspartate, N-acyl-glutamate, N-acyl-tyrosinate, N-acyl-tryptophanate, N-acyl-methionate, citrate, galactonate, glucaric acid (saccharic acid), mannonate, mucate, rhamnonate, and tartrate; or a combination thereof.

5. The pharmaceutical composition of claim 4, wherein the composition further comprises: a. polymer, b. emulsifier, c. binder, d. a disintegrating agent, and/or e. a lubricant.

6. The composition of claim 1, further comprising ajmaline, amiodarone, amitriptyline, amoxapine, aprindine, azelastine, amphetamine, aryloxyindanamine, benactyzine, brasofensine, bupropion, butriptyline, celecoxib, 2-chloro-imipramine, chlorpheniramine, chlorpromazine, cimetidine, cisapride, citalopram, clomipramine, clozapine, cocaine, dapoxetine, desipramine, desvenlafaxine, dibenzepin, diphenhydramine, donepezil, dosulepin, doxorubicin, duloxetine, escitalopram, fluoxetine, fluphenazine, fluvastatin, fluvoxamine, galantamine, haloperidol, lmlpramme, indinavir, iprindole, iproclozide, iproniazid, isocarboxazid, lansoprazole, levomepromazine, lofepramine, lopinavir, loratadine, lurasidone, maprotiline, mequitazine, methadone, methylphenidate, metoclopramide, mianserin, mibefradil, milnacipran, mirtazapine, moclobemide, modafinil, nefazodone, nelfinavir, nevuapme, nialamide, nicardipine, norfluoxetine, nortriptyline, opipramol, perphenazine, phenelzine, pimozide, protriptyline, quinidine, rasagiline, risperidone, ritonavir, rivastigmine, saquinavir, selegiline, sertindole, sertraline, sibutramine, tacrine, terbinafine, terfenadine, tesofensine, thioridazine, ticlopidine, toloxatone, tranylcypromine, trazodone, trifluperidol, trimipramine, venlafaxine, yohimbine, or zuclopenthixol; or a combination thereof.

7. A method of treatment of a subject in need thereof comprising:
a) administering a therapeutically effective amount of the composition of claim 4, and
b) increasing dextromethorphan plasma levels, wherein the subject is an extensive metabolizer of dextromethorphan.

8. The method of claim 7, wherein the composition is administered once or twice a day, wherein the daily dose of dextromethorphan is about 0.1 mg to about 1000 mg, resulting in an $AUC_{0\text{-}12}$ of dextromethorphan that is greater than the $AUC_{0\text{-}12}$ of dextromethorphan that would be achieved by administering the same amount of dextromethorphan alone without deramciclane.

9. The method of claim 7, wherein the $AUC_{0\text{-}12}$ of deramciclane is at least about 10 ng/hr/mL, about 100 ng/hr/mL, 200 ng/hr/mL, about 300 ng/hr/mL, or about 400 ng/hr/ml, or about 500 ng/hr/mL, or about 600 ng/hr/mL, or about 700 ng/hr/mL, or about 800 ng/hr/mL, or about 900 ng/hr/mL, or about 1000 ng/hr/mL.

10. The method of claim 7, wherein the administration is cutaneous, oral, nasal, anal, rectal, vaginal, sublingual, buccal, sublabial, muscular, intramuscular, intravenous, peritoneal, epidural, intracerebral, intracerebroventricular, epicutaneous or topical, intraarticular, intracardiac, intracavernous, intradermal, intralesional, intramuscular, intraocular, intraosseous, intraperitoneal, intrathecal, intrauterine, intravaginal, intravesical, intravitreal, transdermal, or transmucosal.

11. A method of treatment comprising:
a) administering a therapeutically effective amount of the composition of claim 4;
b) targeting CYP2D6 enzyme, and NMDA, 5-HT2A, and 5HT2c receptors;
c) treating a neuropsychiatric or neurodegenerative disease or disorder, or brain injury, comprising behavioral and psychological symptoms of dementia (BPSD), in a patient in need thereof; and
d) producing a symptomatic relief and/or disease modification.

* * * * *